United States Patent
Zhao et al.

(10) Patent No.: US 11,998,584 B2
(45) Date of Patent: *Jun. 4, 2024

(54) CONJUGATE OF A TUBULYSIN ANALOG WITH BRANCHED LINKERS

(71) Applicant: Hangzhou DAC Biotech Co., Ltd., Hangzhou (CN)

(72) Inventors: Robert Yongxin Zhao, Lexington, MA (US); Qingliang Yang, Hangzhou (CN); Yuanyuan Huang, Hangzhou (CN); Linyao Zhao, Hangzhou (CN); Shun Gai, Hangzhou (CN); Hangbo Ye, Hangzhou (CN); Jun Lei, Hangzhou (CN); Yifang Xu, Hangzhou (CN); Mingjun Cao, Hangzhou (CN); Huihui Guo, Hangzhou (CN); Junxiang Jia, Hangzhou (CN); Qianqian Tong, Hangzhou (CN); Wenjun Li, Hangzhou (CN); Xiaomai Zhou, Hangzhou (CN); Hongsheng Xie, Hangzhou (CN); Lu Bai, Hangzhou (CN); Xiang Cai, Hangzhou (CN); Xiaotao Zhuo, Hangzhou (CN); Xiuzheng Zhang, Hangzhou (CN); Jun Zheng, Hangzhou (CN)

(73) Assignee: Hangzhou DAC Biotech Co., Ltd., Hangzhou (CN)

( * ) Notice: Subject to any disclaimer, the term of this patent is extended or adjusted under 35 U.S.C. 154(b) by 275 days.

This patent is subject to a terminal disclaimer.

(21) Appl. No.: 16/759,175

(22) PCT Filed: Dec. 31, 2017

(86) PCT No.: PCT/CN2017/120454
§ 371 (c)(1),
(2) Date: Apr. 24, 2020

(87) PCT Pub. No.: WO2019/127607
PCT Pub. Date: Jul. 4, 2019

(65) Prior Publication Data
US 2020/0276261 A1    Sep. 3, 2020

(51) Int. Cl.
A61K 38/07   (2006.01)
A61K 45/06   (2006.01)
C07K 5/117   (2006.01)

(52) U.S. Cl.
CPC .............. *A61K 38/07* (2013.01); *A61K 45/06* (2013.01); *C07K 5/1024* (2013.01)

(58) Field of Classification Search
CPC ..................................................... A61K 38/07
See application file for complete search history.

(56) References Cited

U.S. PATENT DOCUMENTS

| 2005/0249740 A1 | 11/2005 | Domling et al. |
| 2010/0048490 A1 | 2/2010 | Mahov et al. |

(Continued)

FOREIGN PATENT DOCUMENTS

| CA | 2 962 440 A1 | 3/2016 |
| CN | 101678124 A | 3/2010 |

(Continued)

OTHER PUBLICATIONS

Lyon et al. "Reducing hydrophobicity of homogeneous antibody-drug conjugates improves pharmacokinetics and therapeutic index," Nature Biotechnology, 2015, vol. 33, No. 7, pp. 733-735 (Year: 2015).*

(Continued)

*Primary Examiner* — Shengjun Wang
(74) *Attorney, Agent, or Firm* — BUCHANAN, INGERSOLL & ROONEY PC

(57) ABSTRACT

The present invention relates to the conjugation of a tubulysin analog compound to a cell-binding molecule with (Continued)

branched/side-chain linkers for having better delivery of the conjugate compound and targeted treatment of abnormal cells. It also relates to a branched-linkage method of conjugation of a tubulysin analog molecule to a cell-binding ligand, as well as methods of using the conjugate in targeted treatment of cancer, infection and autoimmune disease.

20 Claims, 63 Drawing Sheets

(56) References Cited

U.S. PATENT DOCUMENTS

| | | | |
|---|---|---|---|
| 2016/0339114 | A1 | 11/2016 | Gingipalli et al. |
| 2017/0007714 | A1* | 1/2017 | Kontermann ............ A61P 29/00 |
| 2017/0152274 | A1 | 6/2017 | Zhao et al. |
| 2020/0069814 | A1 | 3/2020 | Zhao et al. |
| 2023/0149502 | A1 | 5/2023 | Zhao et al. |
| 2023/0165930 | A1 | 6/2023 | Zhao et al. |
| 2023/0165931 | A1 | 6/2023 | Zhao et al. |

FOREIGN PATENT DOCUMENTS

| | | | | |
|---|---|---|---|---|
| EA | 201992081 | A1 | 1/2020 | |
| JP | 2017-506649 | A | 3/2017 | |
| WO | 2004005326 | A2 | 1/2004 | |
| WO | WO-2014009774 | A1 * | 1/2014 | ............ A61K 45/06 |
| WO | 2015/127685 | A1 | 9/2015 | |
| WO | 2015/151078 | A2 | 10/2015 | |
| WO | 2016/059622 | A2 | 4/2016 | |
| WO | 2017/046658 | A1 | 3/2017 | |
| WO | 2018/086139 | A1 | 5/2018 | |
| WO | 2018/185526 | A1 | 10/2018 | |

OTHER PUBLICATIONS

Drake et al. "An emerging playbook for antibody-drug conjugates: Lessons from the laboratory and clinic suggest a strategy for improving efficacy and safety ," Current Opinion in Chemical Biology, 2015, vol. 28, pp. 174-180 (Year: 2015).*
Office Action dated Jul. 14, 2021, by the Canadian Patent Office in corresponding Canadian Patent Application No. 3,085,634. (6 pages).
Extended European Search Report dated Dec. 16, 2020, by the European Patent Office in corresponding European Patent Application No. 17936036.7. (11 pages).
Examination Report No. 3 dated Jun. 14, 2022, by the Australian Patent Office in corresponding Australian Patent Application No. 2017445144. (3 pages).
Office Action dated Feb. 21, 2022, by the Canadian Patent Office in corresponding Canadian Patent Application No. 3,085,634. (13 pages).
Notice of Submission of Opinion dated May 27, 2022, by the Korean Patent Office in corresponding Korean Patent Application No. 10-2020-7019406 and an English translation of the Notice. (25 pages).
Notice of Reasons for Refusal dated Mar. 8, 2022, by the Japanese Patent Office in corresponding Japanese Patent Application No. 2020-535958 and an English translation of the Notice. (9 pages).
International Search Report (PCT/ISA/210) dated Sep. 27, 2018, by the State Intellectual Property Office of the P.R. China as the International Searching Authority for International Application No. PCT/CN2017/120454.
Written Opinion (PCT/ISA/237) dated Sep. 27, 2018, by the State Intellectual Property Office of the P.R. China as the International Searching Authority for International Application No. PCT/CN2017/120454.
Examination report No. 1 dated Jul. 23, 2021, by the Australian Patent Office in corresponding Australian Patent Application No. 2017445144. (4 pages).

Notice of Reasons for Refusal dated Aug. 10, 2021, by the Japanese Patent Office in corresponding Japanese Patent Application No. 2020-535958 and an English translation of the Notice. (22 pages).
Notification Concerning Transmittal of International Preliminary Report on Patentability and International Preliminary Report on Patentability dated Jun. 30, 2020, by the International Bureau of WIPO in corresponding International Patent Application No. PCT/CN2017/120454. (5 pages).
Examination report No. 2 dated Feb. 9, 2022, by the Australian Patent Office in corresponding Australian Patent Application No. 2017445144. (5 pages).
Office Action dated Jan. 24, 2022, by the Eurasian Patent Office in Eurasian Patent Application No. 202091217 and an English translation of the Action. (8 pages) .
Written Opinion dated Mar. 28, 2022, by the Intellectual Property Office of Singapore in corresponding Singaporean Patent Application No. 11202004801W. (8 pages) .
Examination report No. 4 dated Jul. 15, 2022, by the Australian Patent Office in corresponding Australian Patent Application No. 2017445144. (3 pages).
Examination report No. 5 dated Jul. 21, 2022, by the Australian Patent Office in corresponding Australian Patent Application No. 2017445144. (4 pages).
Examination report No. 6 dated Jul. 26, 2022, by the Australian Patent Office in corresponding Australian Patent Application No. 2017445144. (4 pages).
Notice of Reasons for Refusal dated Sep. 6, 2022, by the Japanese Patent Office in corresponding Japanese Patent Application No. 2020-535958 and an English translation of the Notice. (6 pages).
Office Action dated Oct. 31, 2022, by the Canadian Intellectual Property Office in corresponding Canadian Patent Application No. 3,085,634 (5 pages).
Office Action dated Mar. 31, 2023, by the Canadian Intellectual Property Office in corresponding Canadian Patent Application No. 3,085,634. (3 pages).
Office Action (Notice of Deficiencies) dated May 15, 2022, by the Israel Patent Office in corresponding Israel Patent Application No. 275274. (5 pages).
Office Action (Notice of Deficiencies) dated Mar. 7, 2023, by the Israel Patent Office in corresponding Israel Patent Application No. 275274. (5 pages).
Office Action (Decision to Grant a Patent) dated Mar. 7, 2023, by the Japan Patent Office in corresponding Japanese Patent Application No. 2020-535958 and an English translation of the Office Action. (6 pages).
Office Action (Notice of Final Rejection) dated Feb. 21, 2023, by the Korean Intellectual Property Office in corresponding Korean Patent Application No. 10-2020-7019406 and an English translation of the Office Action. (16 pages).
Office Action (Request for the Submission of an Opinion) dated Jun. 7, 2023, by the Korean Intellectual Property Office in corresponding Korean Patent Application No. 10-2020-7019406 and an English translation of the Office Action. (9 pages).
Examination Report No. 1 dated Sep. 19, 2023, by IP Australia in corresponding Australian Patent Application No. 2022205269 (3 pages).
Patent Examination Report 2 dated Aug. 8, 2023, by the New Zealand Intellectual Property Office in corresponding New Zealand Patent Application No. 764814 (6 pages).
Request for the Submission of an Opinion dated Aug. 12, 2023, by the Korean Intellectual Property Office in corresponding Korean Patent Application No. 10-2023-7017364, with English translation of the Request (16 pages).
Written Decision on Registration dated Aug. 16, 2023, by the Korean Intellectual Property Office in corresponding Korean Patent Application No. 10-2020-7019406, with English translation of the Decision (6 pages).
Office Action issued on Dec. 15, 2023, by the Korean Intellectual Property Office in corresponding Korean Patent Application No. 10-2023-7017364, and an English Translation of the Office Action. (6 pages).

(56) References Cited

OTHER PUBLICATIONS

Office Action (Patent Examination Report No. 3) issued on Nov. 27, 2023, by the New Zealand Intellectual Property Office in corresponding New Zealand Patent Application No. 764814. (5 pages).

* cited by examiner

CONJUGATE OF A TUBULYSIN ANALOG WITH BRANCHED LINKERS

FIELD OF THE INVENTION

The present invention relates to the conjugation of a tubulysin analog compound to a cell-binding molecule with branched (side-chain) linkers for having better pharmacokinetics in delivery of the conjugate compound, resulting in much precise targeted treatment of abnormal cells. It also relates to a branched-linkage method of conjugation of a tubulysin analog molecule to a cell-binding ligand, as well as methods of using the conjugate in targeted treatment of cancer, infection and autoimmune disease.

BACKGROUND OF THE INVENTION

Antibody-drug conjugates (ADCs) have become one of promising targeting therapies for cancer as evidenced by the clinical success of brentuximab vedotin (Adcetris) for relapsed/refractory Hodgkin lymphoma (Okeley, N., et al, Hematol Oncol. Clin. North. Am, 2014, 28, 13-25; Gopal, A., et al, Blood 2015, 125, 1236-43) and ado-trastuzumab emtansine for relapsed HER2+ breast cancer (Peddi, P. and Hurvitz, S., Ther. Adv. Med. Oncol. 2014, 6(5), 202-9; Lambert, J. and Chari, R., J. Med. Chem. 2014, 57, 6949-64). The three important components, monoclonal antibody, cytotoxic payload, and conditional linker of ADCs plus the sites where to link the linker-payload components are all important factors to make success of ADC (L. Ducry and B Stump, Bioconjugate Chem., 2010, 21, 5-13; G. S. Hamilton, Biologicals 2015, 43, 318-32).

It has be three decades to study each factor of the components of ADCs. However, linker technologies remain limited in scope, since drugs that are conjugated must contain certain reactive functional groups, ensure circulation stability, and facile drug release upon antigen binding and intracellular uptake, and importantly be not harming normal tissues once the linker-payload components are off-targeted during the circulation (Ponte, J. et al., Bioconj. Chem., 2016, 27(7), 1588-98; Dovgan, I., et al. Sci. Rep. 2016, 6, 30835; Ross, P. L. and Wolfe, J. L. J. Pharm. Sci. 105(2), 391-7; Chen, T. et al. J. Pharm. Biomed. Anal., 2016, 117, 304-10).

In early ADCs, the linkers which were particularly used for ADCs targeting of liquid tumor were too labile, and led to the release of free drug in the circulation and consequent off-target toxicity (Bander, N. H. et al, Clin. Adv. Hematol. Oncol., 2012, 10, 1-16). In the current generation of ADCs, the linkers are more stable, and the cytotoxic agents are significantly more potent (Behrens, C. R. and Liu, B., mAbs, 2014. 6, 46-53). However, the off-target toxicity so far is still the major challenge in development of ADC drugs (Roberts, S. A. et al, Regul. Toxicol. Pharmacol. 2013, 67, 382-91). For instance, in clinical practice Ado-trastuzumab emtansine (T-DM1, Kadcyla®) which is used stable (none-cleavable) MCC linker has shown great benefit to patients who have HER2-positive metastatic breast cancer (mBC) or who have already been treated for mBC or developed HER2 tumor recurrence within six months of adjuvant therapy (Peddi, P. and Hurvitz, S., Ther. Adv. Med. Oncol. 2014, 6(5), 202-209; Piwko C, et al, Clin Drug Investig. 2015, 35(8), 487-93; Lambert, J. and Chari, R., J. Med. Chem. 2014, 57, 6949-64). But, T-DM1 had failed in clinic trial as first-line treatment for patients with HER2 positive unresectable locally advanced or metastatic breast cancer and as the second line treatment of HER2-positive advanced gastric cancer due to a little benefit to patients when comparison the side toxicity to the efficacy (Ellis, P. A., et al, J. Clin. Oncol. 2015, 33, (suppl; abstr 507 of 2015 ASCO Annual Meeting); Shen, K. et al, Sci Rep. 2016; 6: 23262; de Goeij, B. E. and Lambert, J. M. Curr Opin Immunol 2016, 40, 14-23; Barrios, C. H. et al, J Clin Oncol 2016, 34, (suppl; abstr 593 of 2016 ASCO Annual Meeting).

To address issues of the off-target toxicity, research and development into ADC chemistry and design are now expanding the scopes of the linker-payload compartments and conjugate chemistry beyond the sole potent payloads, and especially to address activity of the linker-payload of ADCs toward targets/target diseases (Lambert, J. M. Ther Deliv 2016, 7, 279-82; Zhao, R. Y. et al, 2011, J. Med. Chem. 54, 3606-23). Nowadays many drug developers and academic institutions are highly focusing on establishing novel reliable specific conjugation linkers and methods for site-specific ADC conjugation, which seem to have longer circulation half-life, higher efficacy, potentially decreased off-target toxicity, and a narrow range of in vivo pharmacokinetic (PK) properties of ADCs as well as better batch-to-batch consistency in ADC production (Hamblett, K. J. et al, Clin. Cancer Res. 2004, 10, 7063-70; Adem, Y. T. et al, Bioconjugate Chem. 2014, 25, 656-664; Boylan, N. J. Bioconjugate Chem. 2013, 24, 1008-1016; Strop, P., et al 2013 Chem. Biol. 20, 161-67; Wakankar, A. mAbs, 2011, 3, 161-172). These specific conjugation methods reported so far include incorporation of engineered cysteines (Junutula, J. R. et al. Nat. Biotechnol. 2008, 26, 925-32; Junutula, J. R., et al 2010 Clin. Cancer Res. 16, 4769; U.S. Pat. Nos. 8,309,300; 7,855,275; 7,521,541; 7,723,485, WO2008/141044), selenocysteines (Hofer, T., et al. Biochemistry 2009, 48, 12047-57; Li, X., et al. Methods 2014, 65, 133-8; U.S. Pat. No. 8,916,159 for US National Cancer Institute), cysteine containing tag with perfluoroaromatic reagents (Zhang, C. et al. Nat. Chem. 2015, 8, 1-9), thiolfucose (Okeley, N. M., et al 2013 Bioconjugate Chem. 24, 1650), non-natural amino acids (Axup, J. Y., et al, Proc. Nat. Acad. Sci. USA. 2012, 109, 16101-6; Zimmerman, E. S., et al., 2014, Bioconjug. Chem. 25, 351-361; Wu, P., et al, 2009 Proc. Natl. Acad. Sci. 106, 3000-5; Rabuka, D., et al, Nat. Protoc. 2012, 7, 1052-67; U.S. Pat. No. 8,778,631 and US Pat Appl. 20100184135, WO2010/081110 for Sutro Biopharma; WO2006/069246, 2007/059312, U.S. Pat. Nos. 7,332,571, 7,696,312, and 7,638,299 for Ambrx; WO2007/130453, U.S. Pat. Nos. 7,632,492 and 7,829,659 for Allozyne), conjugation to reduced intermolecular disulfides by re-bridging dibromomalemides (Jones, M. W. et al. J. Am. Chem. Soc. 2012, 134, 1847-52), bis-sulfone reagents (Badescu, G. et al. Bioconjug. Chem. 2014, 25, 1124-36; WO2013/190272, WO2014/064424 for PolyTherics Ltd), dibromopyridazinediones (Maruani, A. et al. Nat. Commun. 2015, 6, 6645), galactosyl- and sialyltransferases (Zhou, Q. et al. Bioconjug. Chem. 2014, 25, 510-520; US Pat Appl 20140294867 for Sanofi-Genzyme), formylglycine generating enzyme (FGE) (Drake, P. M. et al. Bioconj. Chem. 2014, 25, 1331-41; Carrico, I. S. et al U.S. Pat. Nos. 7,985,783; 8,097,701; 8,349,910, and US Pat Appl 20140141025, 20100210543 for Redwood Bioscience), phosphopantetheinyl transferases (PPTases) (Grunewald, J. et al. Bioconjug. Chem. 2015, 26, 2554-62), sortase A (Beerli, R. R., et al. PLoS One 2015, 10, e0131177), genetically introduced glutamine tag with Streptoverticillium mobaraense transglutaminase (mTG) (Strop, P., Bioconj. Chem., 2014, 25, 855-62; Strop, P., et al., Chem. Biol. 2013, 20, 161-7; U.S. Pat. No. 8,871,908 for Rinat-Pfizer) or with microbial transglutaminase (MTGase) (Dennler, P., et al, 2014, Bioconjug. Chem. 25, 569-78; Siegmund, V. et al. Angew. Chemie—Int.

Ed. 2015, 54, 13420-4; US pat appl 20130189287 for Innate Pharma; U.S. Pat. No. 7,893,019 for Bio-Ker S.r.l. (IT)), an enzyme/bacterium forming an isopeptide bond-peptide bonds that form outside of the protein main chain (Kang, H. J., et al. Science 2007, 318, 1625-8; Zakeri, B. et al. Proc. Natl. Acad. Sci. USA 2012, 109, E690-7; Zakeri, B. & Howarth, M. J. Am. Chem. Soc. 2010, 132, 4526-7).

We have disclosed several conjugation methods of rebridging a pair of thiols of the reduced inter chain disulfide bonds of a native antibody, such as using bromo maleimide and dibromomaleimide linkers (WO2014/009774), 2,3-disubstituted succinic/2-monosubstituted/2,3-disubstituted fumaric or maleic linkers (WO2015/155753, WO20160596228), acetylenedicarboxylic linkers (WO2015/151080, WO20160596228) or hydrazine linkers (WO2015/151081). The ADCs made with these linkers and methods have demonstrated better therapeutic index windows than the traditionally unselective conjugation via the cysteine or lysine residues on an antibody. Here we disclose the invention of tubulysin conjugate containing a long side chain linker. The long side chain linker can prevent an antibody-drug conjugate from hydrolysis by a hydrolase, e.g. a proteinase or an esterase and lead to the conjugate more stable in the circulation.

Tubulysins as a potent cytotoxic agents are well known in the art and can be isolated from natural sources according to known methods or prepared synthetically according to known methods (e. g. Balasubramanian, R., et al. J. Med. Chem., 2009, 52, 238-40; Wipf, P., et al. Org. Lett., 2004, 6, 4057-60; Pando, O., et al. J. Am. Chem. Soc., 2011, 133, 7692-5; Reddy, J. A., et al. Mol. Pharmaceutics, 2009, 6, 1518-25; Raghavan, B., et al. J. Med. Chem., 2008, 51, 1530-33; Patterson, A. W., et al. J. Org. Chem., 2008, 73, 4362-9; Pando, O., et al. Org. Lett., 2009, 11 (24), 5567-9; Wipf, P., et al. Org. Lett., 2007, 9 (8), 1605-7; Friestad, G. K., Org. Lett., 2004, 6, 3249-52; Peltier, H. M., et al. J. Am. Chem. Soc., 2006, 128, 16018-9; Chandrasekhar, S., et al J. Org. Chem., 2009, 74, 9531-4; Liu, Y., et al. Mol. Pharmaceutics, 2012, 9, 168-75; Friestad, G. K., et al. Org. Lett., 2009, 11, 1095-8; Kubicek, K., et al., Angew Chem Int Ed Engl, 2010.49: 4809-12; Chai, Y., et al., Chem Biol, 2010, 17: 296-309; Ullrich, A., et al., Angew Chem Int Ed Engl, 2009, 48, 4422-5; Sani, M., et al. Angew Chem Int Ed Engl, 2007, 46, 3526-9; Domling, A., et al., Angew Chem Int Ed Engl, 2006, 45, 7235-9; Patent applications: Zanda, M., et al, Can. Pat. Appl. CA 2710693 (2011); Chai, Y., et al. Eur. Pat. Appl. 2174947 (2010), WO 2010034724; Leamon, C. et al, WO2010033733, WO 2009002993; Ellman, J., et al, PCT WO2009134279; WO 2009012958, US appl. 20110263650, 20110021568; Matschiner, G., et al, WO2009095447; Vlahov, I., et al, WO2009055562, WO 2008112873; Low, P., et al, WO2009026177; Richter, W., WO2008138561; Kjems, J., et al, WO 2008125116; Davis, M.; et al, WO2008076333; Diener, J.; et al, U.S. Pat. Appl. 20070041901, WO2006096754; Matschiner, G., et al, WO2006056464; Vaghefi, F., et al, WO2006033913; Doemling, A., Ger. Offen. DE102004030227, WO2004005327, WO2004005326, WO2004005269; Stanton, M., et al, U.S. Pat. Appl. Publ. 20040249130; Hoefle, G., et al, Ger. Offen. DE10254439, DE10241152, DE10008089; Leung, D., et al, WO2002077036; Reichenbach, H., et al, Ger. Offen. DE19638870; Wolfgang, R., US20120129779; Chen, H., US appl. 20110027274. We previously disclosed the construction of tubulysins conjugate (PCT/IB2012/053554) for targeted treatment of cancer, infection and autoimmune disease. The present invention of tubulysin conjugate containing a long branched (side-chain) linker can prolong the half-life of a conjugate during the targeted delivery and minimize exposure to non-target cells, tissues or organs during the blood circulation, resulting in less the off-target toxicity.

SUMMARY OF THE INVENTION

The present invention provides branched-linkage of a tubulysin analog to an antibody. It also provides a method of conjugation of a tubulysin analog to an antibody with the side chain-linker.

In one aspect of the present invention, a conjugate containing a side chain-linkage is represented by Formula (I):

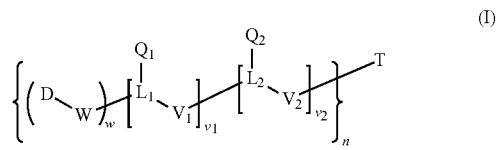

wherein

"—" represents a single bond; n is 1 to 30;

T is a cell-binding agent/molecule, selected from the group consisting of an antibody, a single chain antibody, an antibody fragment that binds to a target cell, a monoclonal antibody, a single chain monoclonal antibody, a monoclonal antibody fragment that binds to the target cell, a chimeric antibody, a chimeric antibody fragment that binds to the target cell, a domain antibody, a domain antibody fragment that binds to the target cell, an adnectin that mimics antibody, DARPins, a lymphokine, a hormone, a vitamin, a growth factor, a colony stimulating factor, a nutrient-transport molecule (a transferrin), and a binding peptide, protein, small molecule attached on albumin, a polymer, a dendrimer, a liposome, a nanoparticle, a vesicle, or a (viral) capsid;

$L_1$ and $L_2$ are a chain of atoms selected from C, N, O, S, Si, and P, preferably having 0-500 atoms, which covalently connects to W and $V_1$, and $V_1$ and $V_2$. The atoms used in forming the $L_1$ and $L_2$ may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination above thereof. Preferably $L_1$ and $L_2$ are, the same or different, independently selected from O, NH, N, S, P, NNH, NHNH, N($R_3$), N($R_3$)N($R_{3'}$), CH, CO, C(O)NH, C(O)O, NHC(O)NH, NHC(O)O, polyethyleneoxy unit of formula $(OCH_2CH_2)_pOR_3$, or $(OCH_2CH(CH_3))_pOR_3$, or $NH(CH_2CH_2O)_pR_3$, or $NH(CH_2CH(CH_3)O)_pR_3$, or $N[(CH_2CH_2O)_pR_3]$—$[(CH_2CH_2O)_pR_{3'}]$, or $(OCH_2CH_2)_pCOOR_3$, or $CH_2CH_2(OCH_2CH_2)_pCOOR_3$, wherein p and p' are independently an integer selected from 0 to about 1000, or combination thereof; $C_1$-$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or $(Aa)_r$, r=1-12(one to 12 amino acid units), which is composed from natural or unnatural amino acids, or the same or different sequences of dipeptide, tripeptide, tetrapeptide, pentapeptide, hexapeptide, heptapeptide, octapeptide, nonapeptide, decapeptide, undecapeptide or dodecapeptide unit;

W is a stretcher unit, normally a self-immolative spacer, a peptidic unit, a hydrazone, a disulfide, a thioether, an ester, or an amide bond; w is 1 or 2 or 3;

$V_1$ and $V_2$ are independently a spacer unit and selected from O, NH, S, $C_1$-$C_8$ alkyl, $C_2$-$C_8$ heteroalkyl, alkenyl, or alkynyl, $C_3$-$C_8$ aryl, heterocyclic, carbocyclic, cycloalkyl, alkylcycloalkyl, heterocycloalkyl, heteroaralkyl, heteroalkylcycloalkyl, or alkylcarbonyl, or $(Aa)_r$, r=1-12(one to 12 amino acid units), which is composed from a natural or unnatural amino acid, or the same or different sequences of dipeptide, tripeptide, tetrapeptide, pentapeptide, hexapeptide, heptapeptide, octapeptide, nonapeptide, decapeptide, undecapeptide or dodecapeptide unit; or $(CH_2CH_2O)_p$, p is 0-1000; and $v_1$ and $v_2$ are independently 0, 1 or 2, but $v_1$ and $v_2$ are 0 at the same time; when $v_1$ or $v_2$ is 0, it means that one of the side chain $Q_1$ or $Q_2$ fragment is absent.

$Q_1$ and $Q_2$ are independently represented by Formula (I-q1):

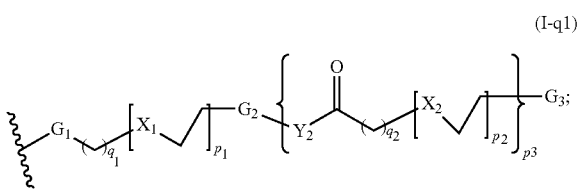

(I-q1)

$NH_2$, $CH_2S(O)_2NH_2$, $OS(O)_2OH$, $OS(O)_2OR_1$, $CH_2S(O)_2OR_1$, Ar, $ArR_1$, ArOH, $ArNH_2$, ArSH, $ArNHR_1$, or $(Aa)_{q1}$; $p_1$, $p_2$ and $p_3$ are independently 0-100 but are not 0 at the same time; $q_1$ and $q_2$ are independently 0-24;

Preferably $Q_1$ and $Q_2$ are independently a $C_2$-$C_{90}$ polycarboxylacid or a $C_2$-$C_{90}$ polyalkylamine, a $C_6$-$C_{90}$ oligosaccharide or polysaccharide, a $C_6$-$C_{90}$ zwitterionic betaines or zwitterionic poly(sulfobetaine)) (PSB)s that consist of a quaternary ammonium cation and a sulfonate anion, biodegradable polymer (such as composed of poly (lactic/glycolic) acid (PLGA), poly(acrylates), chitosan, copolymer of N-(2-hydroxypropyl)methacrylamide, poly[2-(methacryloyloxy)ethyl phosphorylcholine] (PMPC), poly-L-glutamic acid, poly(lactide-co-glycolide) (PLG), poly(lactide-co-glycolide), Poly(ethylene glycol)(PEG), poly(propylene glycol) (PPG), poly(lactide-co-glycolide), poly(ethylene glycol)-modified peptides, poly(ethylene glycol)-modified lipids, poly(ethylene glycol)-modified alkylcarboxic acid, poly (ethylene glycol)-modified alkylamine, poly(lactide-co-glycolide, hyaluronic acid (HA) (glycosaminoglycan), heparin/heparan sulfate (HSGAGs), chondroitin sulfate/dermatan sulfate (CSGAGs), poly(ethylene glycol)-modified alkylsulfate, poly(ethylene glycol)-modified alkylphosphate, or poly (ethylene glycol)-modified alkyl quaternary ammonium;

D is tubulysin analog having the following formula (II):

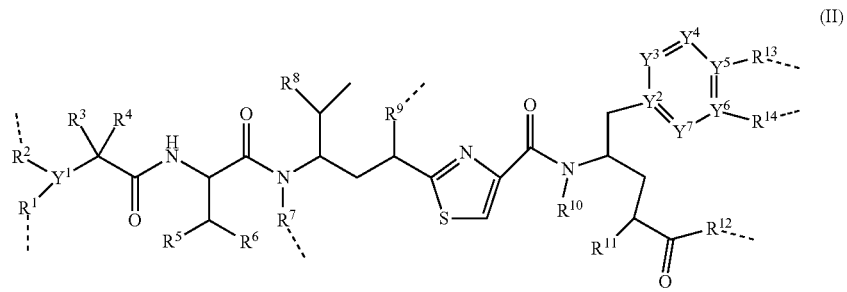

(II)

wherein ∿∿∿ is the site linked to $L_1$ or $L_2$; $G_1$ and $G_2$ are independently OC(O), NHC(O), C(O), $CH_2$, NH, OC(O)NH, NHC(O)NH, O, S, B, P(O)(OH), NHP(O)(OH), NHP(O)(OH)NH, $CH_2P(O)(OH)NH$, OP(O)(OH)O, $CH_2P(O)(OH)O$, $NHS(O)_2$, $NHS(O)_2NH$, $CH_2S(O)_2NH$, $OS(O)_2O$, $CH_2S(O)_2O$, Ar, $ArCH_2$, ArO, ArNH, ArS, $ArNR_1$, $(Aa)_r$, (r=1-12); $X_1$ and $X_2$ are independently O, $CH_2$, S, NH, $N(R_1)$, $^+NH(R_1)$, $^+N(R_1)(R_2)$, C(O), OC(O), OC(O)O, OC(O)NH, NHC(O)NH; $Y_2$ is O. NH, $NR_1$, $CH_2$. S. Ar; $G_3$ is OH, SH, $OR_1$, $SR_1$, $OC(O)R_1$, $NHC(O)R_1$, $C(O)R_1$, $CH_3$, $NH_2$, $NR_1$, $^+NH(R_1)$, $^+N(R_1)(R_2)$, C(O)OH, $C(O)NH_2$, NHC(O)$NH_2$, $BH_2$, $BR_1R_2$, P(O)(OH)$_2$, NHP(O)(OH)$_2$, NHP(O)(NH$_2$)$_2$, S(O)$_2$(OH), $(CH_2)_{q1}C(O)OH$, $(CH_2)_{q1}P(O)(OH)_2$, $C(O)(CH_2)_{q1}C(O)OH$, $OC(O)(CH_2)_{q1}C(O)OH$, NHC(O)$(CH_2)_{q1}C(O)OH$, $CO(CH_2)_{q1}P(O)(OH)_2$, NHC(O)O$(CH_2)_{q1}C(O)OH$, OC(O)NH$(CH_2)_{q1}C(O)OH$, NHCO$(CH_2)_{q1}P(O)(OH)_2$, NHC(O)(NH)$(CH_2)_{q1}C(O)OH$, CONH$(CH_2)_{q1}P(O)(OH)_2$, NHS(O)$_2(CH_2)_{q1}C(O)OH$, CO$(CH_2)_{q1}S(O)_2(OH)$, NHS(O)$_2NH(CH_2)_{q1}C(O)OH$, OS(O)$_2$NH$(CH_2)_{q1}C(O)OH$, NHCO$(CH_2)_{q1}S(O)_2(OH)$, NHP(O)(OH)(NH)$(CH_2)_{q1}C(O)OH$, CONH$(CH_2)_{q1}S(O)(OH)$, OP(O)(OH)$_2$, $(CH_2)_{q1}P(O)(NH_2)$, NHS(O)$_2$(OH), NHS(O)$_2$ or a pharmaceutically acceptable salt, hydrates, or hydrated salt; or a polymorphic crystalline structure; or an optical isomer, racemate, diastereomer or enantiomer thereof, wherein - - - - - is a linkage site that links to W independently;

wherein $R^1$, $R^2$, $R^3$, and $R^4$ are independently H, $C_1$~$C_8$ alkyl; $C_2$~$C_8$ heteroalkyl, or heterocyclic; $C_3$~$C_8$ aryl, Aralkyl, cycloalkyl, alkylcycloalkyl, heterocycloalkyl, heteroalkylcycloalkyl, carbocyclic, or alkylcarbonyl; or $R^1R_2$, $R^1R_3$, $R^2R^3$, $R^3R^4$, $R^5R^6$, $R^{11}R^{12}$ or $R^{13}R^{14}$ form a 3-7 membered carbocyclic, cycloalkyl, heterocyclic, heterocycloalkyl, aromatic or heteroaromatic ring system; $R^1$ and $R^2$ can be independently absent when they link to W independently or simultaneously, $Y^1$ is N or CH;

wherein $R^5$, $R^6$, $R^8$, $R^{10}$ and $R^{11}$ are independently H, or $C_1$~$C_4$ alkyl or heteroalkyl;

wherein $R^7$ is independently H, $R^{14}$, —$R^{14}C(=O)X^1R^{15}$; or —$R^{14}X^1R^{15}$; $X^1$ is O, S, S—S, NH, $CH_2$ or $NR^{14}$;

wherein $R^9$ is selected from H, OH, —O—, =O, —$OR^{14}$, —$OC(=O)R^{14}$, —$OC(=O)NHR^{14}$—, —$OC(=O)R^{14}SSR^{15}$—, $OP(=O)(OR^{14})$—, —$OC(=O)NR^{14}R^{15}$, $OP(=O)(OR^{14})$, or $OR^{14}OP(=O)(OR^{15})$;

wherein $R^{11}$ is independently H, $R^{14}$, —$R^{14}C(=O)R^{16}$, —$R^{14}X^2R^{16}$, —$R^{14}C(=O)X^2$, wherein $X^2$ is —O—, —S—, —NH—, —N($R^{14}$)—, —O—$R^{14}$—, —S—$R^{14}$—, —S(=O)—$R^{14}$—, or —NH$R^{14}$;

wherein $R^{12}$ is $R^{15}$, —OH, —SH, —NH$_2$, NH, NHNH$_2$, —NH($R^{15}$), —O$R^{15}$, —$R^{15}COR^{16}$, $R^{15}COOR^{16}$, —$R^{15}C(O)NH_2$, —$R^{15}C(O)NHR^{17}$, —SR$^{16}$, $R^{15}S(=O)R^{16}$, —$R^{15}P(=)(OR^{17})_2$, —$R^{15}OP(=O)(OR^{17})_2$, —CH$_2$OOP(=O)(OR$^{17}$)$_2$, —$R^{15}SO_2R^{17}$, —$R^{15}X^2R^{16}$, —$R^{15}C(=O)X^2$, where $X^2$ is —O—, OH, SH, —S—, NH$_2$, —NH—, —N($R^{15}$)—, —O—$R^{15}$—, —S—$R^{15}$—, —S(=O)—$R^{15}$—, CH$_2$ or —NH$R^{15}$—;

$R^{13}$ and $R^{14}$ are independently H, O, S, NH, N($R^{15}$), NHNH, —OH, —SH, —NH$_2$, NH, NHNH$_2$, —NH($R^{15}$), —OR$^{15}$, CO, —COX$^2$, —COX$^2$R$^{16}$, R$^{17}$, F, Cl, Br, I, SR$^{16}$, NR$^{16}$R$^{17}$, N=NR$^{16}$, N=R$^{16}$, NO$_2$, SOR$^{16}$R$^{17}$, SO$_2$R$^{16}$, SO$_3$R$^{16}$, OSO$_3$R$^{16}$, PR$^{16}$R$^{17}$, POR$^{16}$R$^{17}$, PO$_2$R$^{16}$R$^{17}$, OP(O)(OR$^{17}$)$_2$, OCH$_2$OP(O)(OR$^{17}$)$_2$, OC(O)R$^{17}$, OC(O)OP(O)(OR$^{17}$)$_2$, PO(OR$^{16}$)(OR$^{17}$), OP(O)(OR$^{17}$)OP(O)(OR$^{17}$)$_2$, OC(O)NHR$^{17}$; —O—(C$_4$-C$_{12}$ glycoside), —N—(C$_4$-C$_{12}$ glycoside); C$_1$-C$_8$ alkyl, heteroalkyl; C$_2$-C$_8$ of alkenyl, alkynyl, heteroalkyl, heterocycloalkyl; C$_3$-C$_8$ of aryl, Ar-alkyl, carbocyclic, cycloalkyl, heteroalkylcycloalkyl, alkylcarbonyl, heteroaryl, or 2-8 carbon atoms of esters, ether, or amide; or peptides containing 1-8 amino acids (NH(Aa)$_{1-8}$ or CO(Aa)$_{1-8}$ (N-terminal or C-terminal 1-8 the same or different amino acids), or polyethyleneoxy unit of formula (OCH$_2$CH$_2$)$_p$ or (OCH$_2$CH(CH$_3$))$_p$, wherein p is an integer from 0 to about 1000, or combination of above groups thereof; $X^2$ is O, S, S—S, NH, CH$_2$, OH, SH, NH$_2$, CHR$^{14}$ or NR$^{14}$;

$R^{15}$, $R^{16}$ and $R^{17}$ is independently H, C$_1$-C$_8$ alkyl, heteroalkyl; C$_2$-C$_8$ of alkenyl, alkynyl, heteroalkyl, heterocycloalkyl; C$_3$-C$_8$ of aryl, Ar-alkyl, carbocyclic, cycloalkyl, heteroalkylcycloalkyl, alkylcarbonyl, heteroaryl, alkylcarbonyl, or Na$^+$, K$^+$, Cs$^+$, Li$^+$, Ca$^{2+}$, Mg$^+$, Zn$^{2+}$, N$^+$(R$^1$)(R$^2$)(R$^3$)(R$^4$), HN$^+$(C$_2$H$_5$OH)$_3$ salt;

$Y^1$ and $Y^2$ are independently N or CH; q is 0 or 1; when q=0, $Y^3$ does not exist, $Y^4$, $Y^5$, $Y^6$ and $Y^7$ are independently CH, N, NH, O, S, or N (R1), thus $Y^2$, $Y^4$, $Y^5$, $Y^6$ and $Y^7$ form a heteroaromatic ring of furan, pyrrole thiophene, thiazole, oxazole and imidazole, pyrazole, triazole, tetrazole, thiadiazole; when q=1, $Y^3$, $Y^4$, $Y^5$, $Y^6$ and $Y^7$ are independently CH or N, thus $Y^2$, $Y^3$, $Y^4$, $Y^5$, $Y^6$ and $Y^7$ form aromatic ring of benzene, pyridine, pyridazine, pyrimidine, pyrazine, triazine, tetrazine, pentazine;

In another aspect of the present invention, a conjugate containing a side chain-linkage is represented by Formula (III):

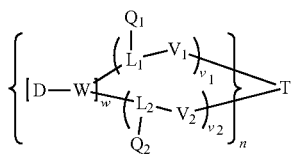

wherein D, W, w, L$_1$, L$_2$, Q$_1$, Q$_2$, V$_1$, V$_2$, v$_1$, v$_2$, n, T are defined the same as in Formula (I).

In another aspect of the present invention, the side chain-linkage compound is represented by Formula (IV), which can readily react to a cell-binding molecule T to form a conjugate of Formula (I):

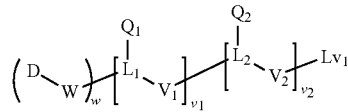

wherein D, W, w, L$_1$, L$_2$, Q$_1$, Q$_2$, V$_1$, V$_2$, v$_1$, v$_2$, and n, are defined the same as in Formula (I); Lv1 is a function group described below.

In another aspect of the present invention, the side chain-linkage compound is represented by Formula (V), which can readily react to a cell-binding molecule T to form a conjugate of Formula (III):

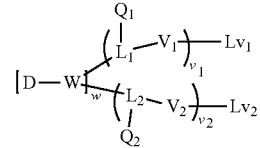

wherein D, W, w, L$_1$, L$_2$, Q$_1$, Q$_2$, V$_1$, V$_2$, v$_1$, v$_2$, and n, are defined the same as in Formula (I).

Lv$_1$ and Lv$_2$ represent the same or different reacting group that can be reacted with a thiol, amine, carboxylic acid, selenol, phenol or hydroxyl group on a cell-binding molecule. Lv$_1$ and Lv$_2$ are independently selected from OH; F; Cl; Br; I; nitrophenol; N-hydroxysuccinimide (NHS); phenol; dinitrophenol; pentafluorophenol; tetrafluorophenol; difluorophenol; mono-fluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions, or for Mitsunobu reactions.

The examples of condensation reagents are: EDC (N-(3-Dimethylaminopropyl)-N'-ethylcarbodiimide), DCC (Dicyclohexyl-carbodiimide), N,N'-Diisopropylcarbodiimide (DIC), N-Cyclohexyl-N'-(2-morpholino-ethyl)carbodiimide metho-p-toluenesulfonate (CMC, or CME-CDI), 1,1'-Carbonyldiimi-dazole (CDI), TBTU (O-(Benzotriazol-1-yl)-N,N,N',N'-tetramethyluronium tetrafluoroborate), N,N,N',N'-Tetramethyl-O-(1H-benzotriazol-1-yl)-uronium hexafluorophosphate (HBTU), (Benzotriazol-1-yloxy)tris(dimethylamino)-phosphonium hexafluorophosphate (BOP), (Benzotriazol-1-yloxy)tripyrrolidinophosphonium hexafluorophosphate (PyBOP), Diethyl cyanophosphonate (DEPC), Chloro-N,N,N',N'-tetramethylformamidiniumhexafluorophosphate, 1-[Bis(dimethylamino)methylene]-1H-1,2,3-triazolo[4,5-b]pyridinium 3-oxid hexafluorophosphate (HATU), 1-[(Dimethylami-no)(morpholino)methylene]-1H-[1,2,3]triazolo[4,5-b]pyridine-1-ium 3-oxide hexafluoro-phosphate (HDMA), 2-Chloro-1,3-dimethyl-imidazolidinium hexafluorophosphate (CIP), Chlorotripyrrolidinophosphonium hexafluorophosphate (PyCloP), Fluoro-N,N,N',N'-bis(tetramethylene)formamidinium hexafluorophosphate (BTFFH), N,N,N',N'-Tetramethyl-S-(1-oxido-2-pyridyl)thiuronium hexafluorophosphate, O-(2-Oxo-1 (2H)pyridyl)-N,N,N',N'-tetramethyluronium tetrafluoroborate (TPTU), S-(1-Oxido-2-pyridyl)-N,N,N',N'-tetramethylthiuronium tetrafluoroborate, O-[(Ethoxycarbonyl)-cyanomethylenamino]-N,N,N',N'-tetramethyluronium hexafluorophosphate (HOTU), (1-Cyano-2-ethoxy-2-oxoethylidenaminooxy) dimethylamino-morpholino-carbenium hexafluorophosphate (COMU), O-(Benzotriazol-1-yl)-N,N,N',N'-bis(tetramethylene)uronium hexafluorophosphate (HBPyU), N-Benzyl-N'-cyclohexyl-carbodiimide (with, or without polymer-bound), Dipyrrolidino(N-succinimidyl-oxy)carbenium hexafluorophosphate (HSPyU), Chlorodipyrrolidinocarbenium hexafluorophosphate (PyC1U), 2-Chloro-1,3-dimethylimidazolidinium tetrafluoroborate(CIB), (Benzotriazol-1-yloxy)dipiperidino-carbenium hexafluorophosphate (HBPipU), O-(6-Chlorobenzotriazol-1-yl)-N,N,N',N'-tetramethyluronium tetrafluoroborate (TCTU), Bromotris(dimethylamino)-phosphonium hexafluorophosphate (BroP), Propylphosphonic anhydride (PPACA, T3P®), 2-Morpholinoethyl isocyanide (MEI), N,N,N',N'-Tetramethyl-O—(N-succinimidyl)uronium hexafluorophosphate (HSTU), 2-Bromo-1-ethyl-pyridinium tetrafluoroborate (BEP), O-[(Ethoxycarbonyl)cyano-methylenamino]-N,N,N',N'-tetra-methyluronium tetrafluoroborate (TOTU), 4-(4,6-Dimethoxy-1,3,5-triazin-2-yl)-4-methylmorpholiniumchloride (MM™, DMTMM), N,N,N',N'-Tetramethyl-O—(N-succinimidyl)uronium tetrafluoroborate (TSTU), O-(3,4-Dihydro-4-oxo-1,2,3-benzotriazin-3-yl)-N,N,N',N'-tetramethyluronium tetrafluoro-borate (TDBTU),1,1'-(Azodicarbonyl)-dipiperidine (ADD), Di-(4-chlorobenzyl)azodicarboxylate (DCAD), Di-tert-butyl azodicarboxylate (DBAD), Diisopropyl azodicarboxylate (DIAD), Diethyl azodicarboxylate (DEAD). In addition, $Lv_1$ and $Lv_2$ can be an anhydride, formed by acid themselves or formed with other $C_1$~$C_8$ acid anhydrides;

The present invention further relates to a method of making a cell-binding molecule-drug conjugate of Formula (I) and Formula (III) as well the application of the conjugates of Formula (I) and Formula (III).

DETAILED DESCRIPTION OF THE INVENTION

Definitions

Figure 1:
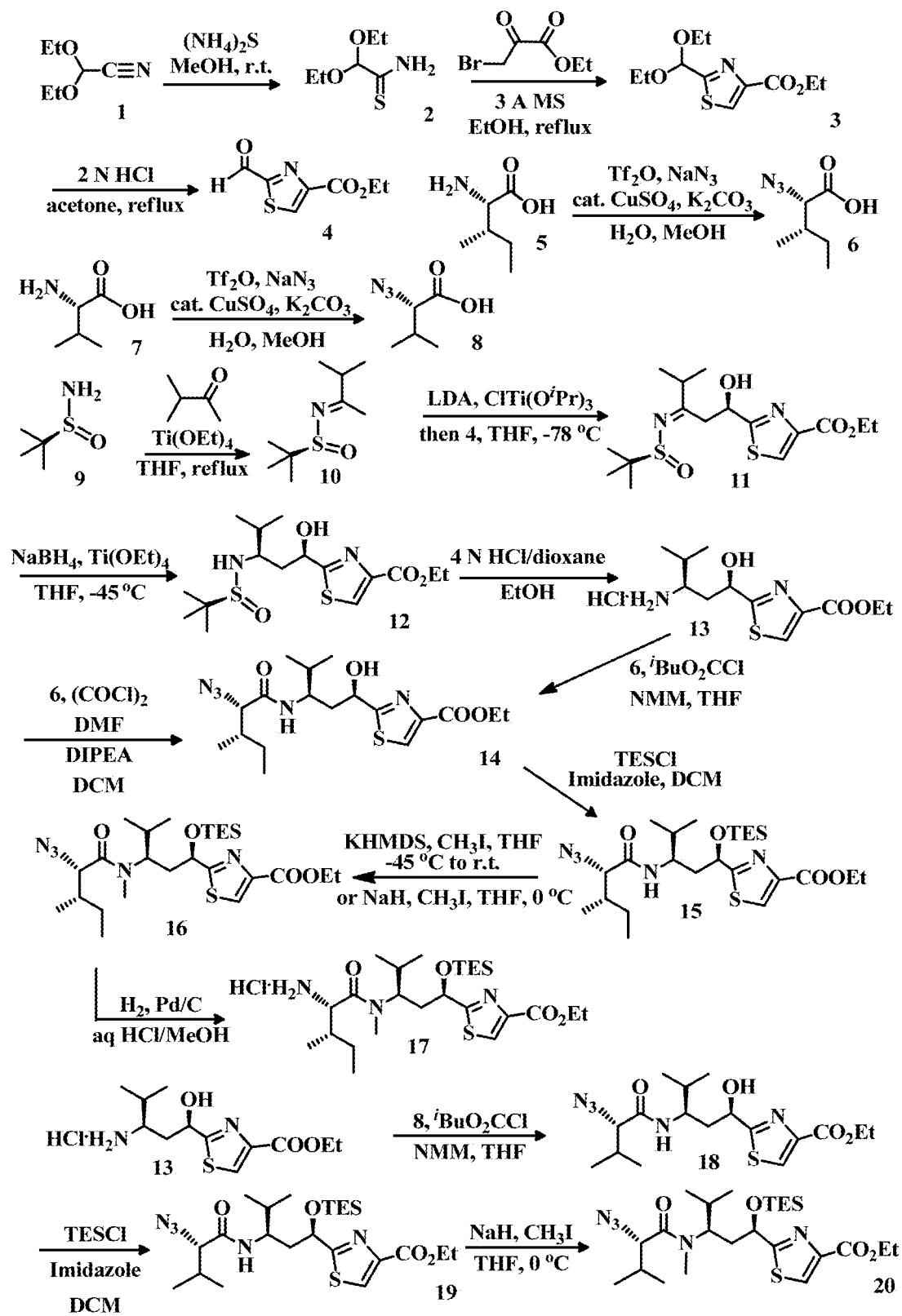
FIG. 1 shows the general synthesis of Tuv component of a Tubulysin analog.
Figure 2:
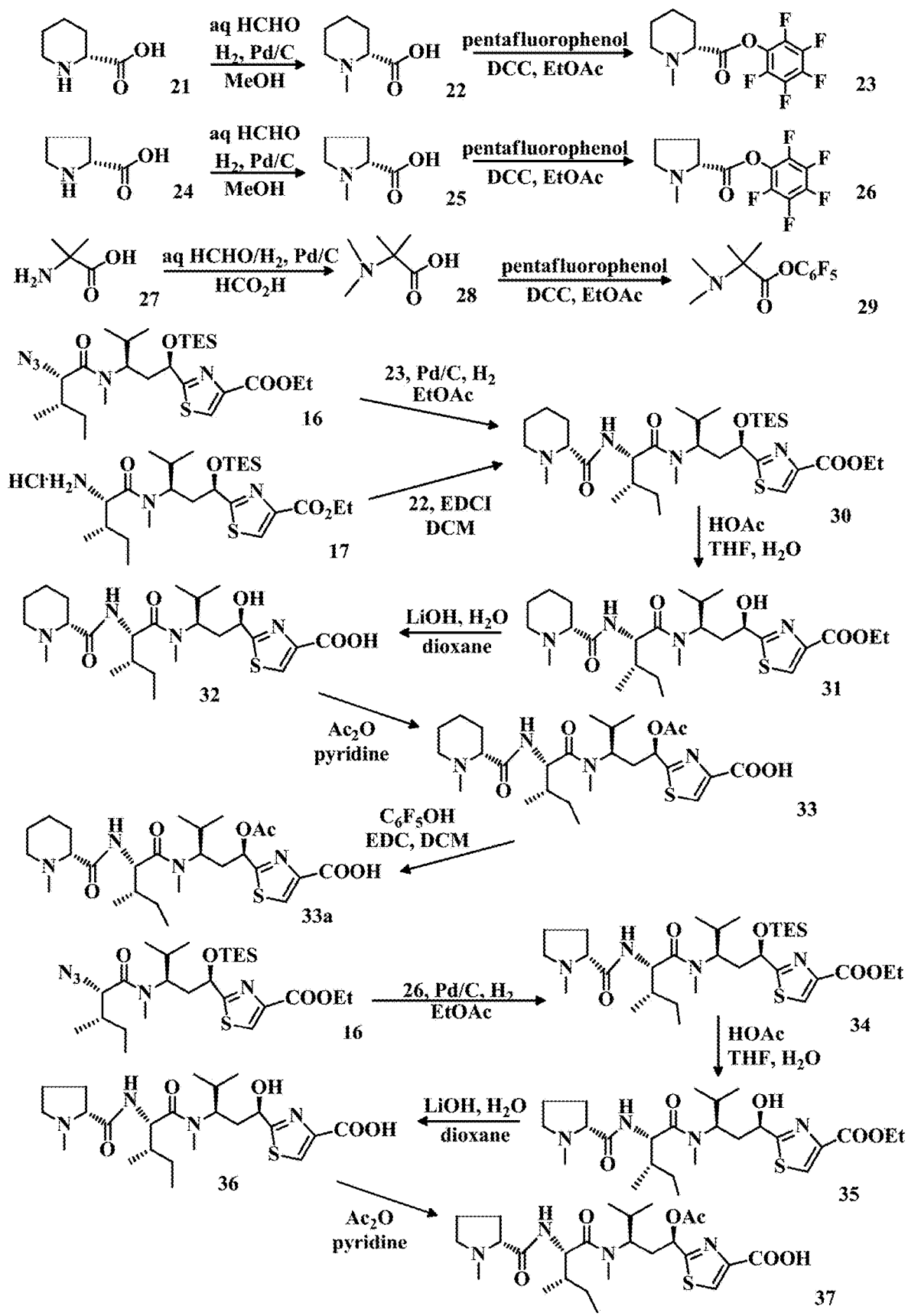
FIG. 2 shows the synthesis of tubulysin components.
Figure 3:
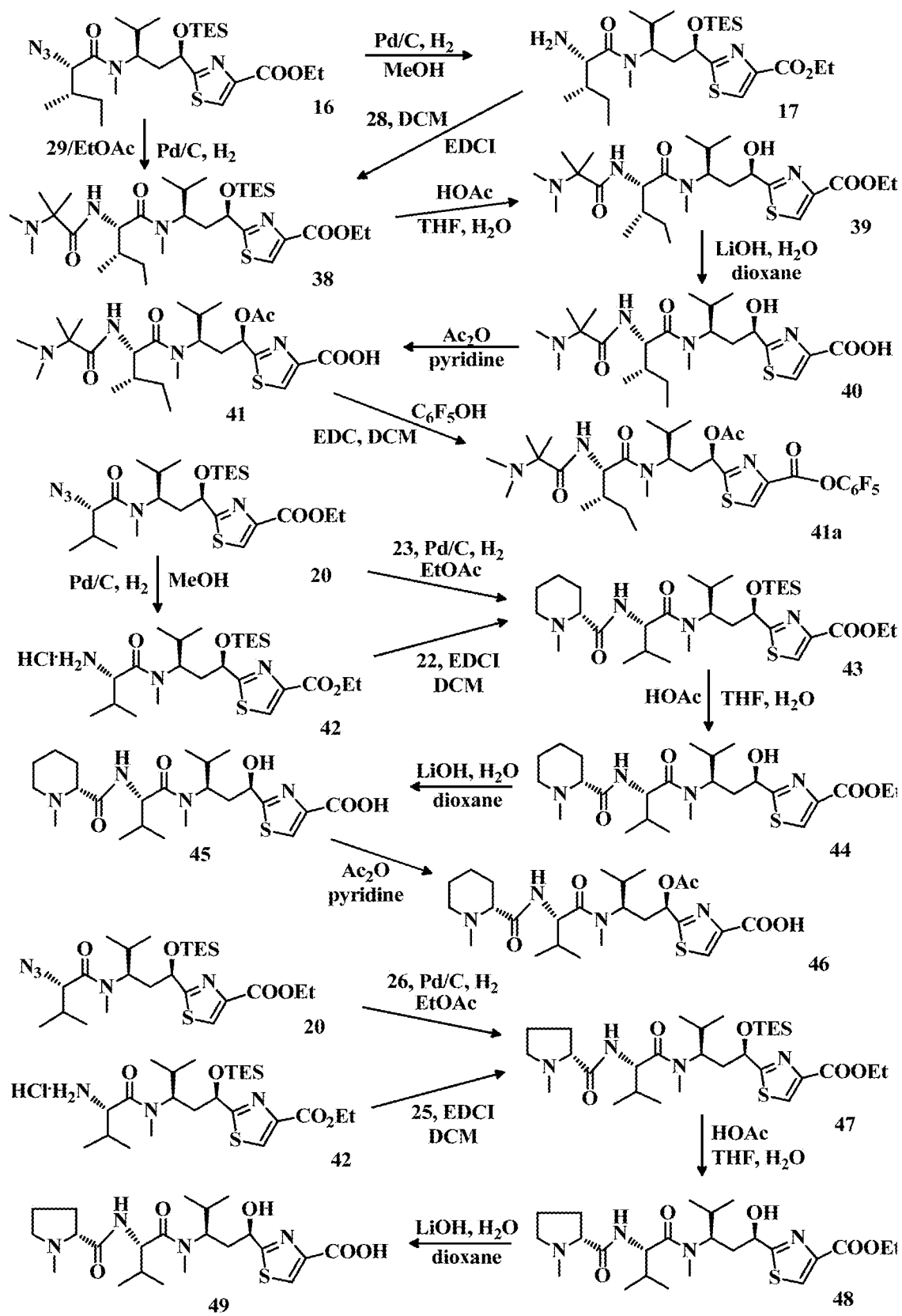
FIG. 3 shows the synthesis of tubulysin components.
Figure 4:
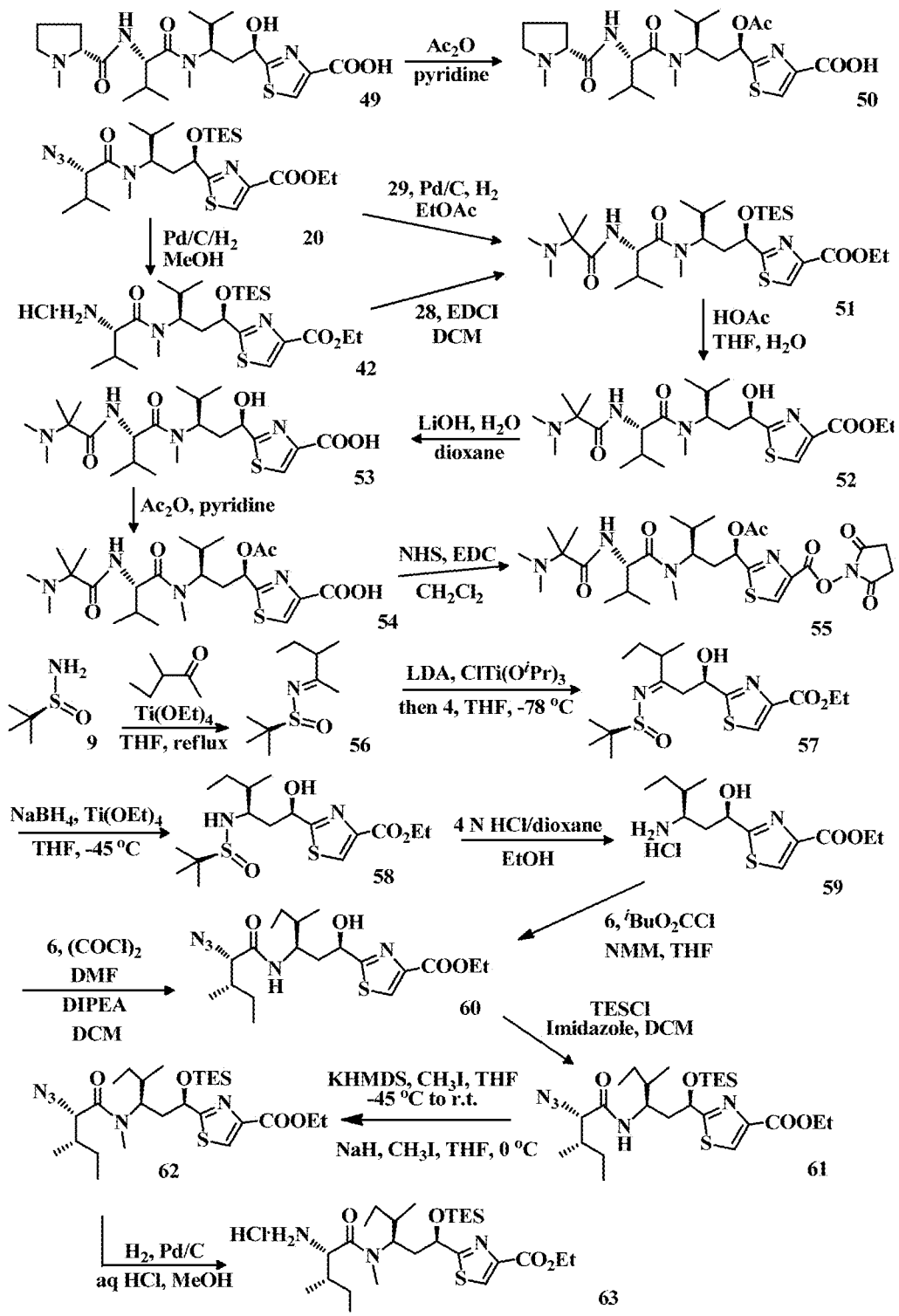
FIG. 4 shows the synthesis of components of tubulysin analogs.
Figure 5:
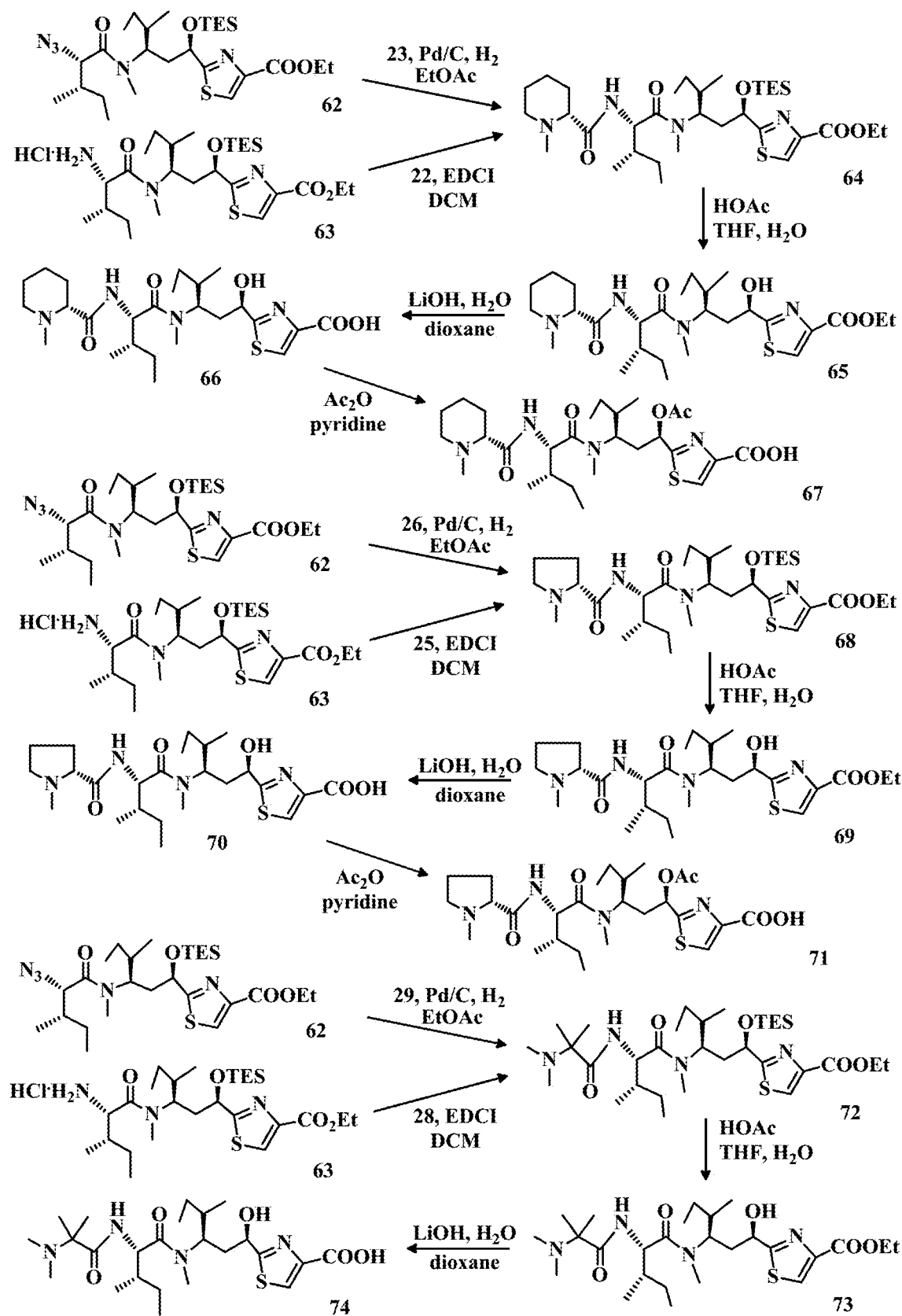
FIG. 5 shows the synthesis of components of tubulysin analogs.
Figure 6:
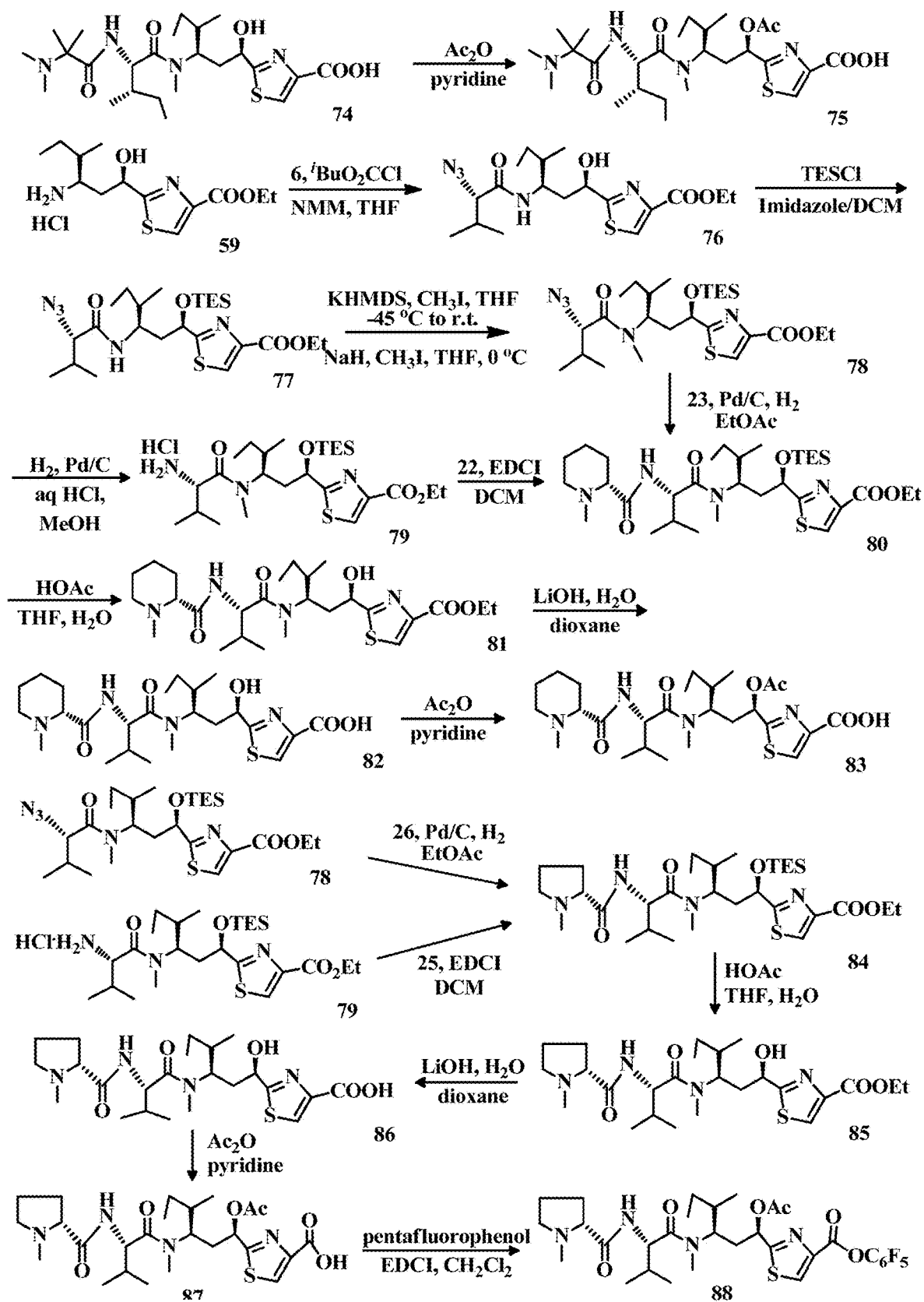
FIG. 6 shows the synthesis of components of tubulysin analogs.
Figure 7:
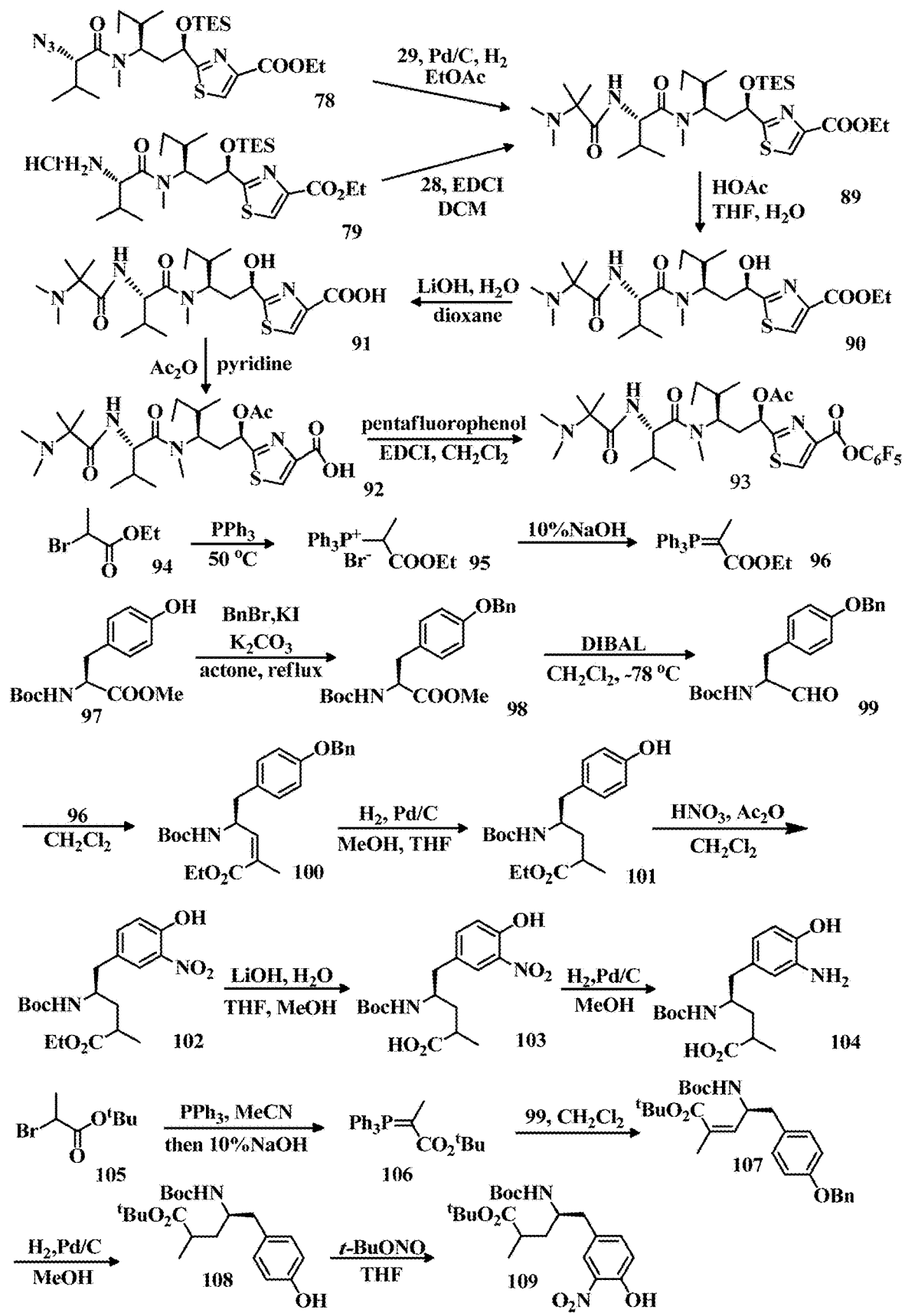
FIG. 7 shows the synthesis of components of tubulysin analogs.
Figure 8:
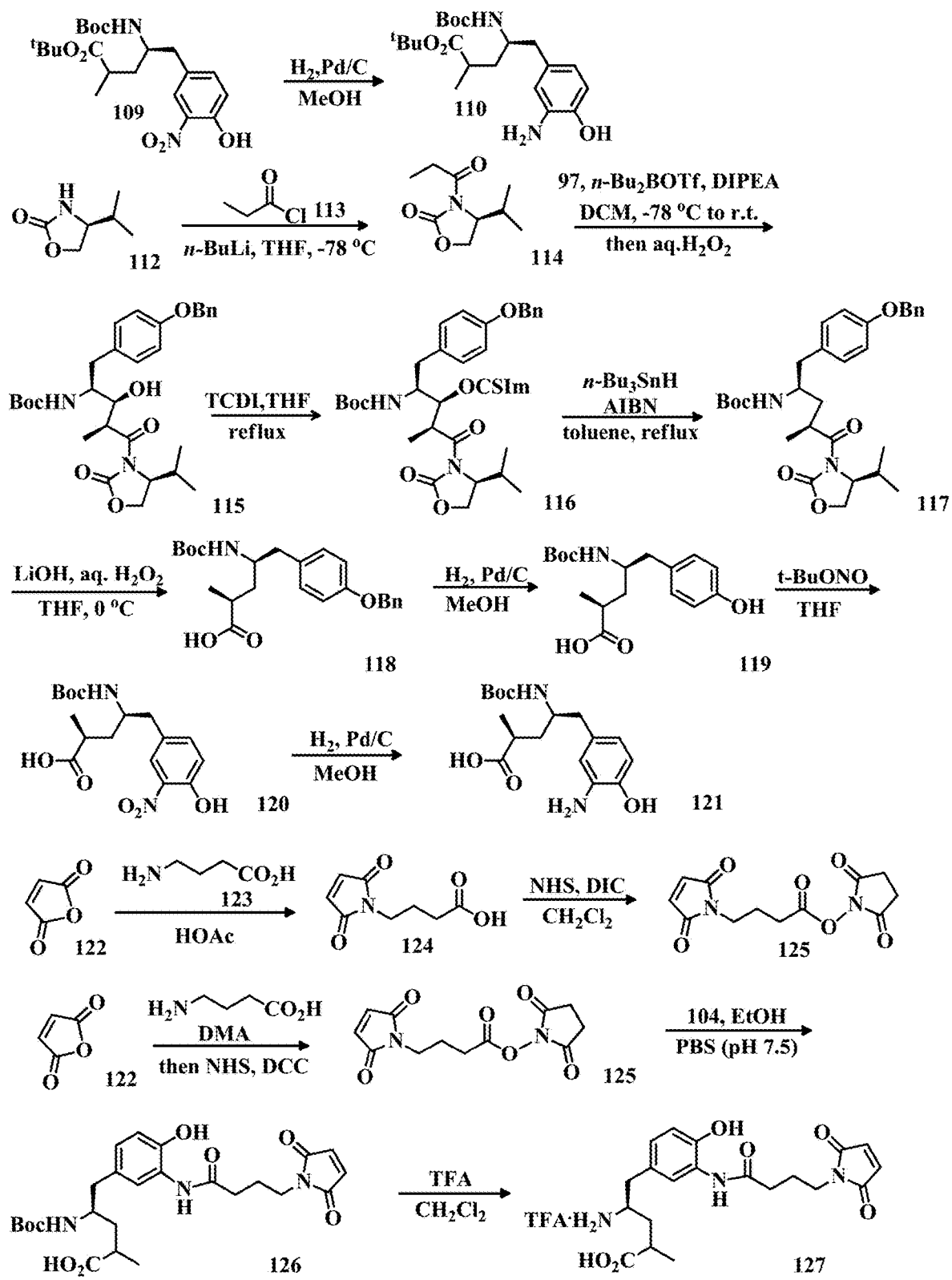
FIG. 8 shows the synthesis of components of tubulysin analogs containing a conjugate linker.
Figure 9:
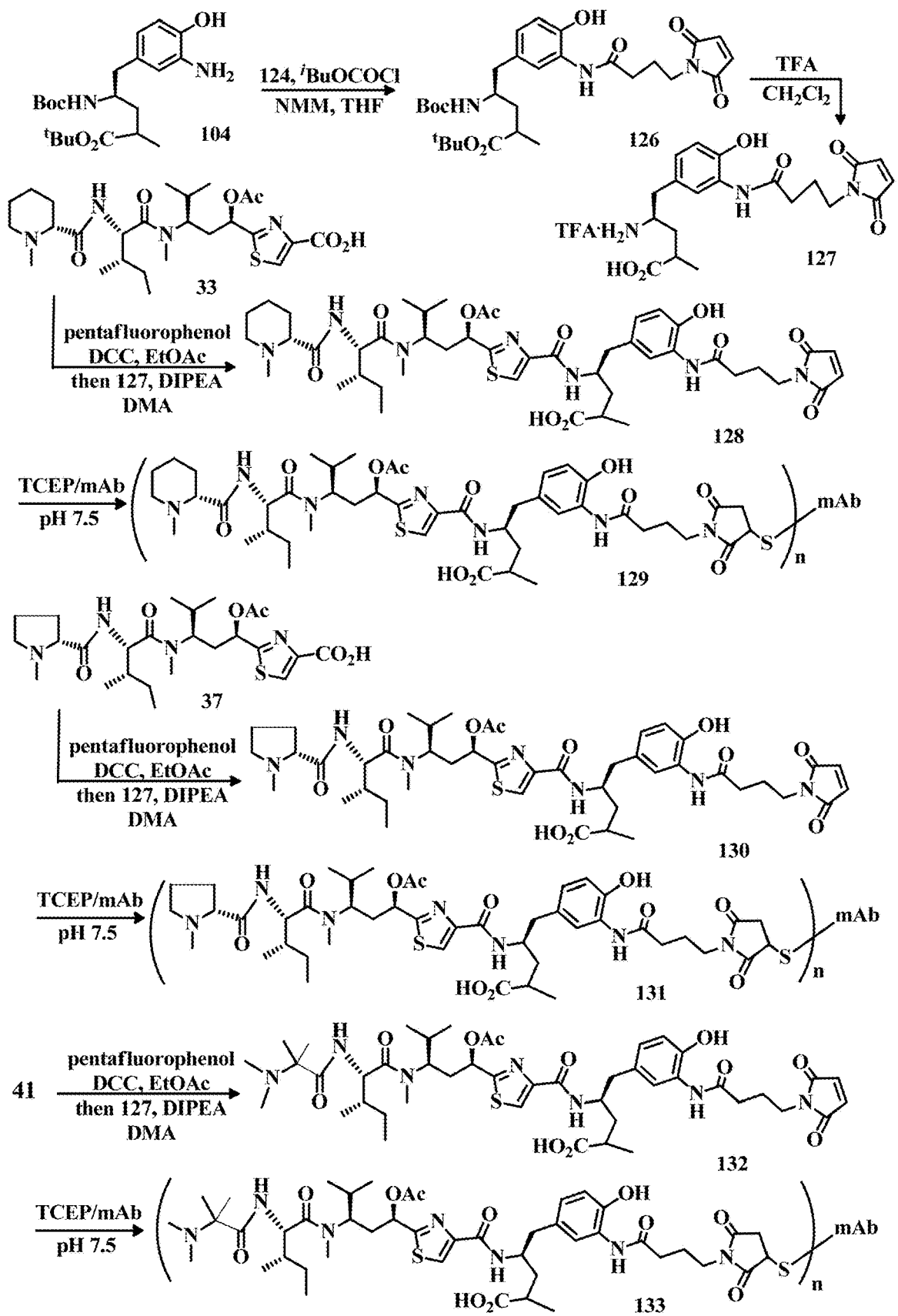
FIG. 9 shows the synthesis of components of tubulysin analogs and their conjugations to an antibody.
Figure 10:
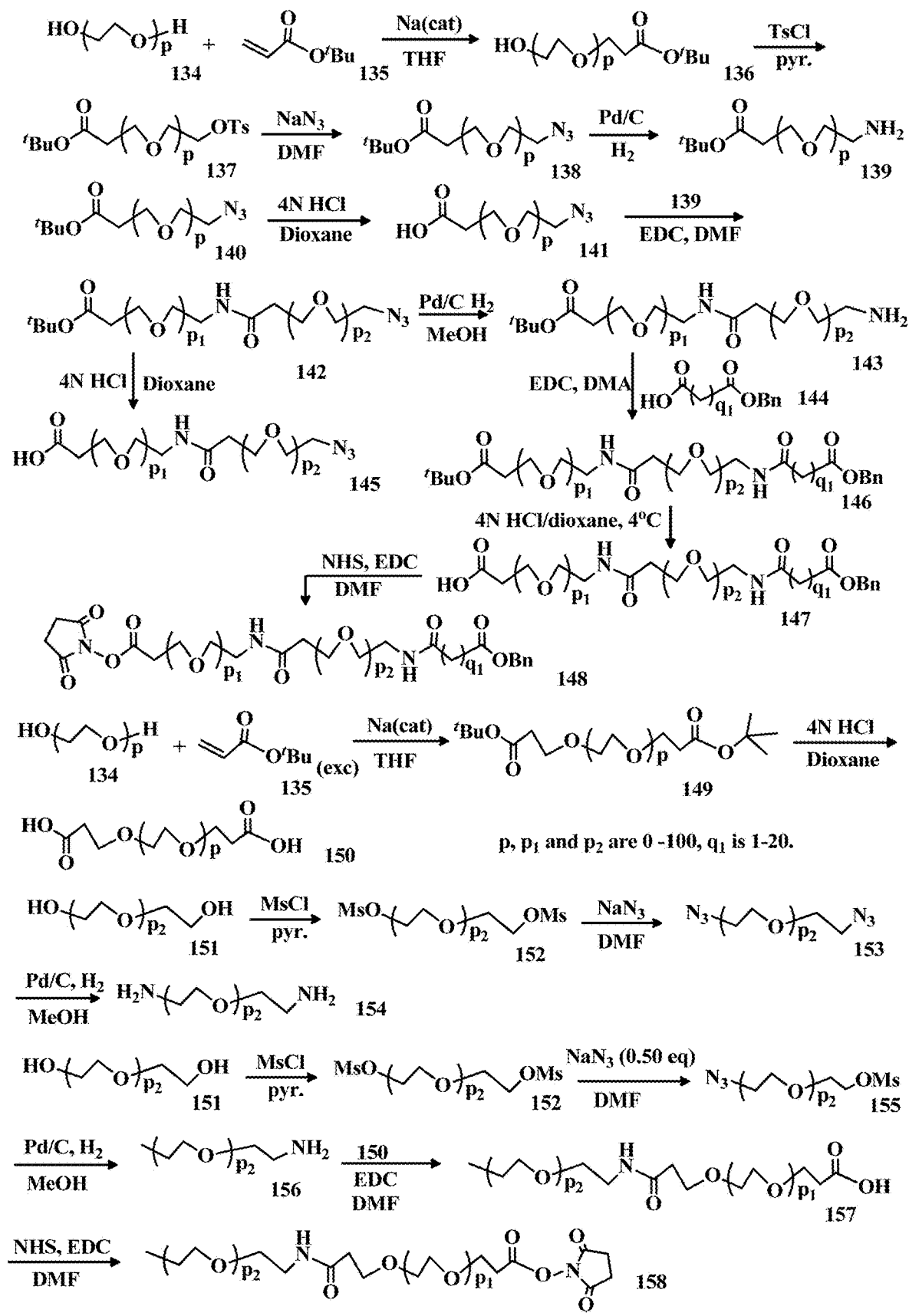
FIG. 10 shows the synthesis of components of a side-chain linker.
Figure 11:
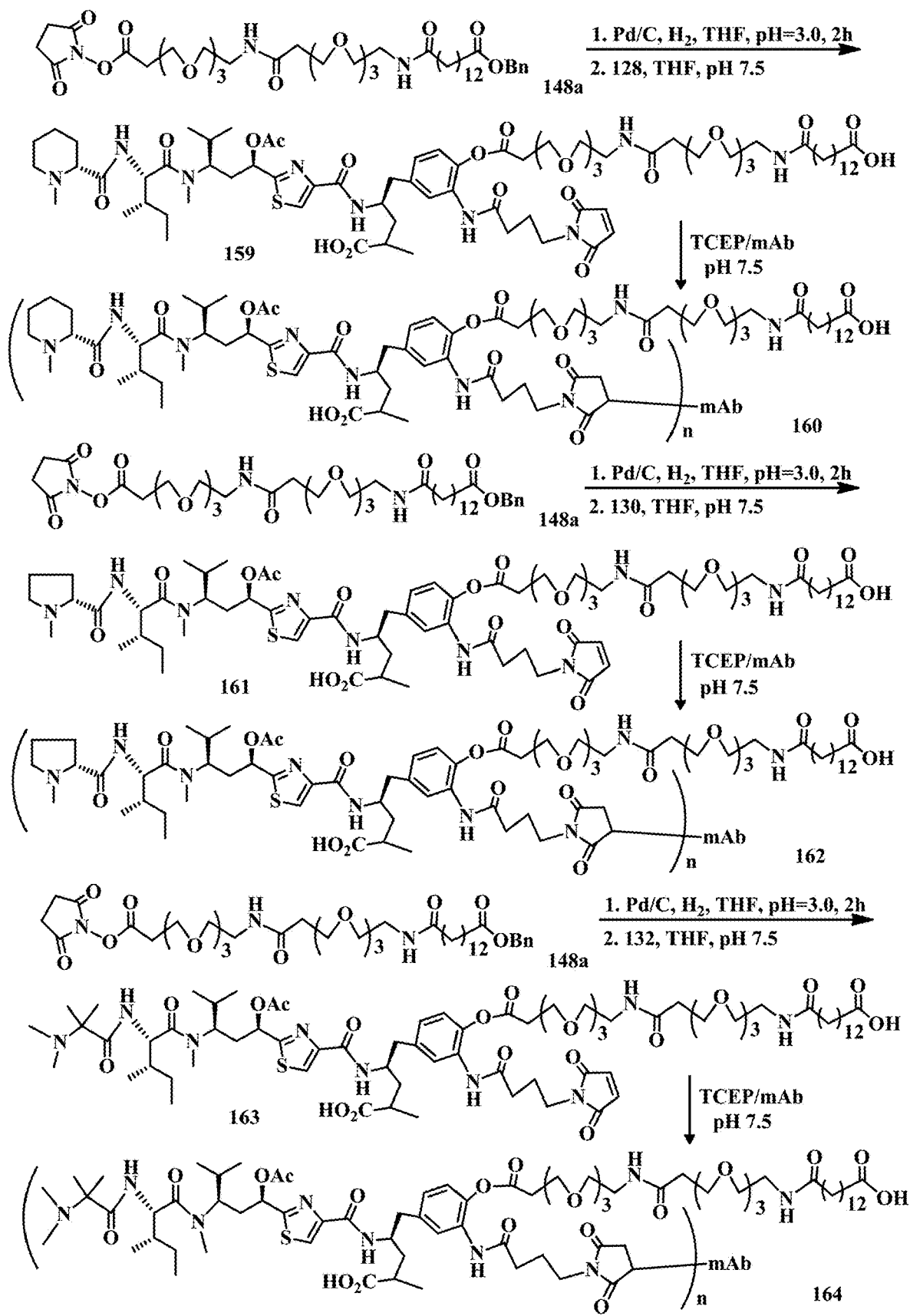
FIG. 11 shows the synthesis of Tubulysin analogs containing a side-chain linker and their conjugations to an antibody.
Figure 12:
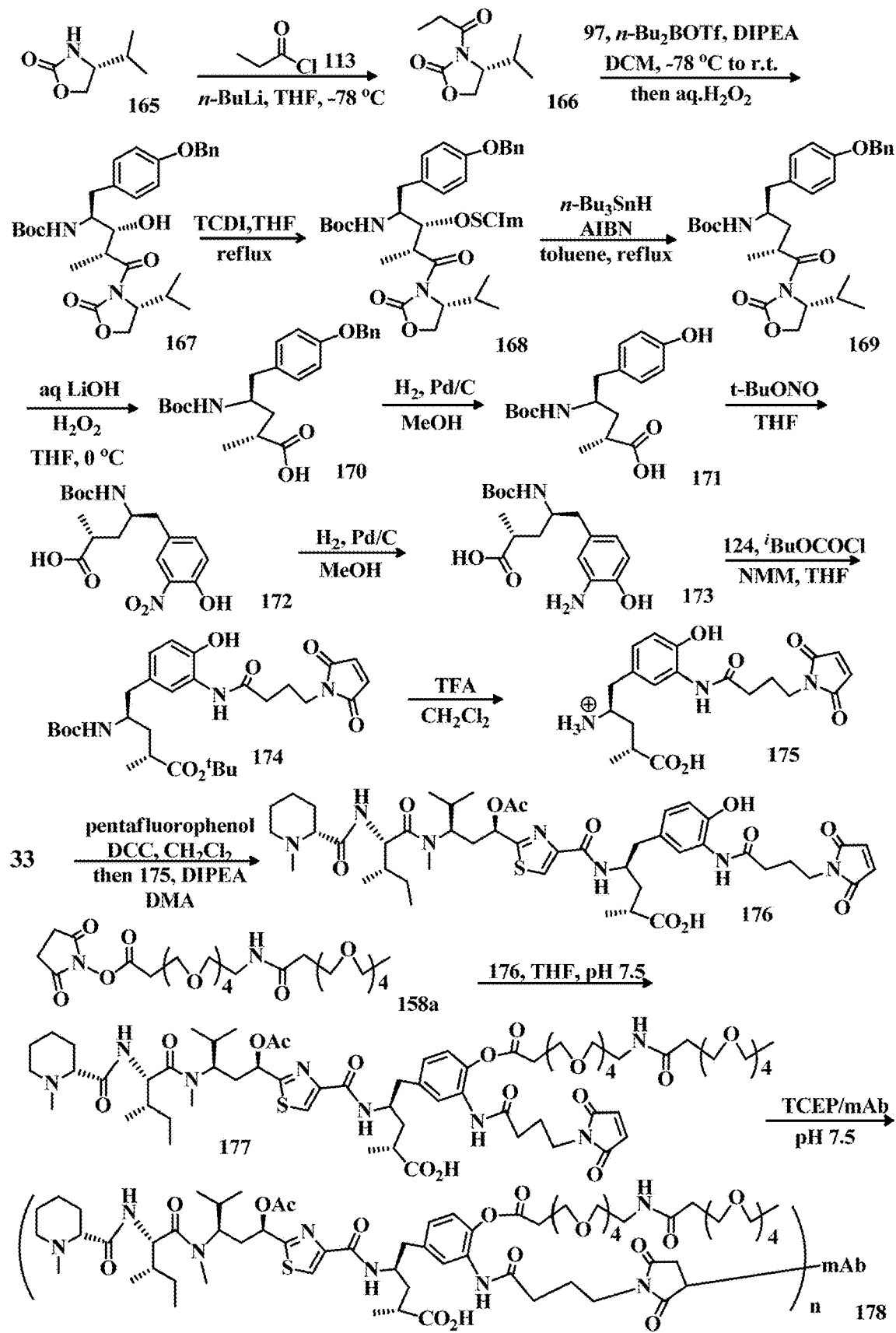
FIG. 12 shows the synthesis of Tubulysin analogs containing a side-chain linker and their conjugations to an antibody.
Figure 13:
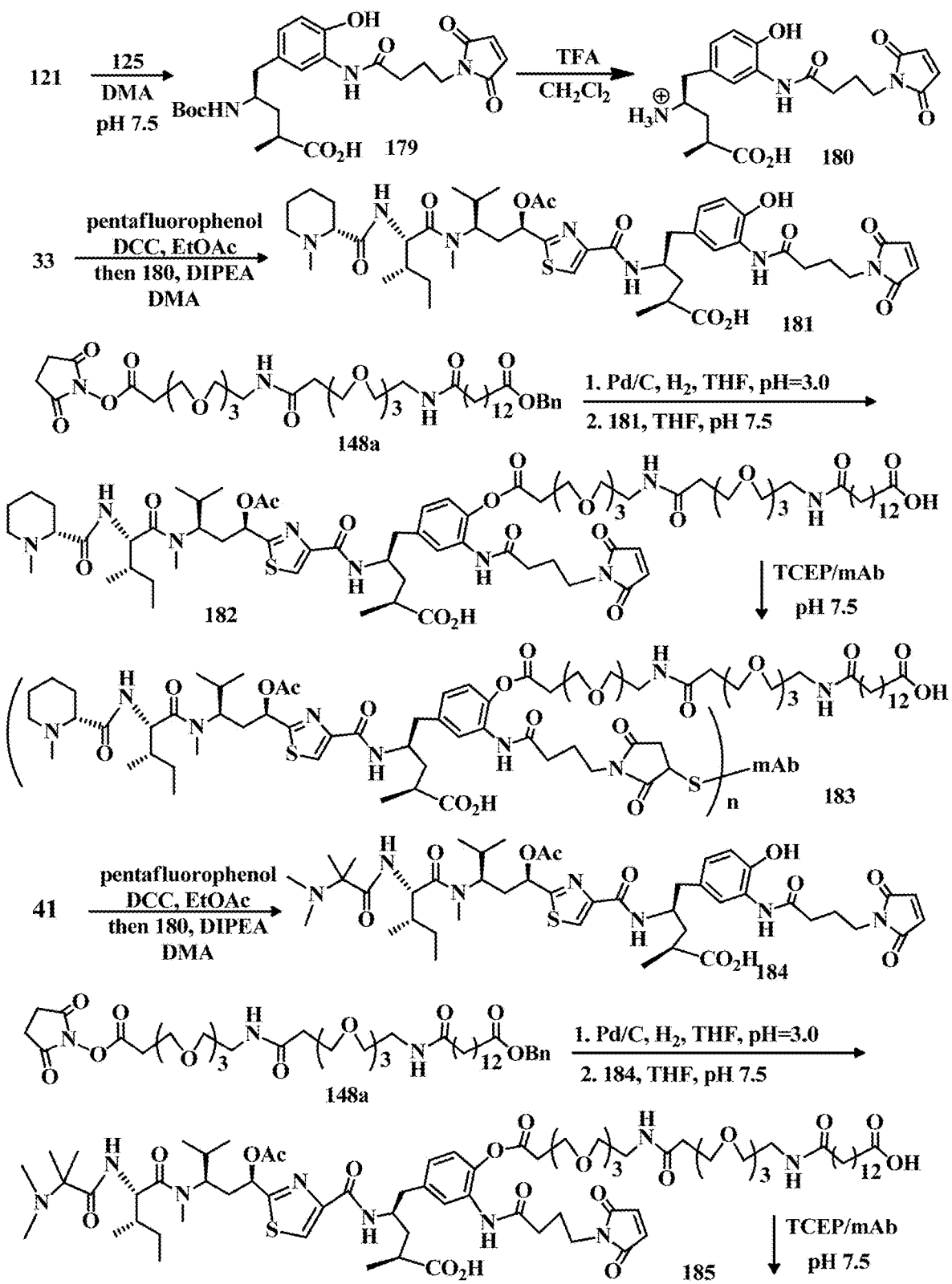
FIG. 13 shows the synthesis of Tubulysin analogs containing a side-chain linker and their conjugations to an antibody.
Figure 14:
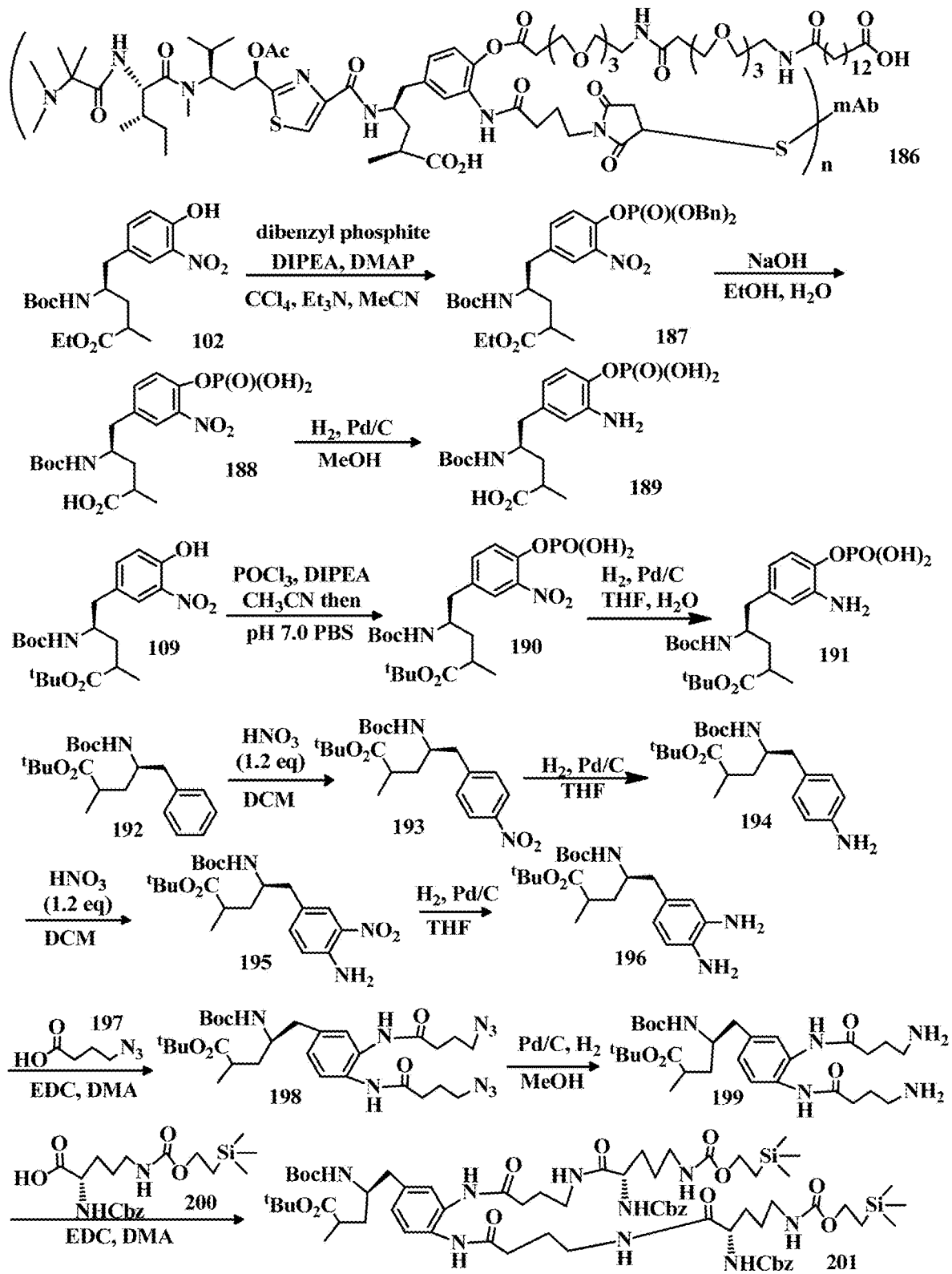
FIG. 14 shows the synthesis of components of tubulysin analogs containing a side-chain linker and their conjugations to an antibody.
Figure 15:
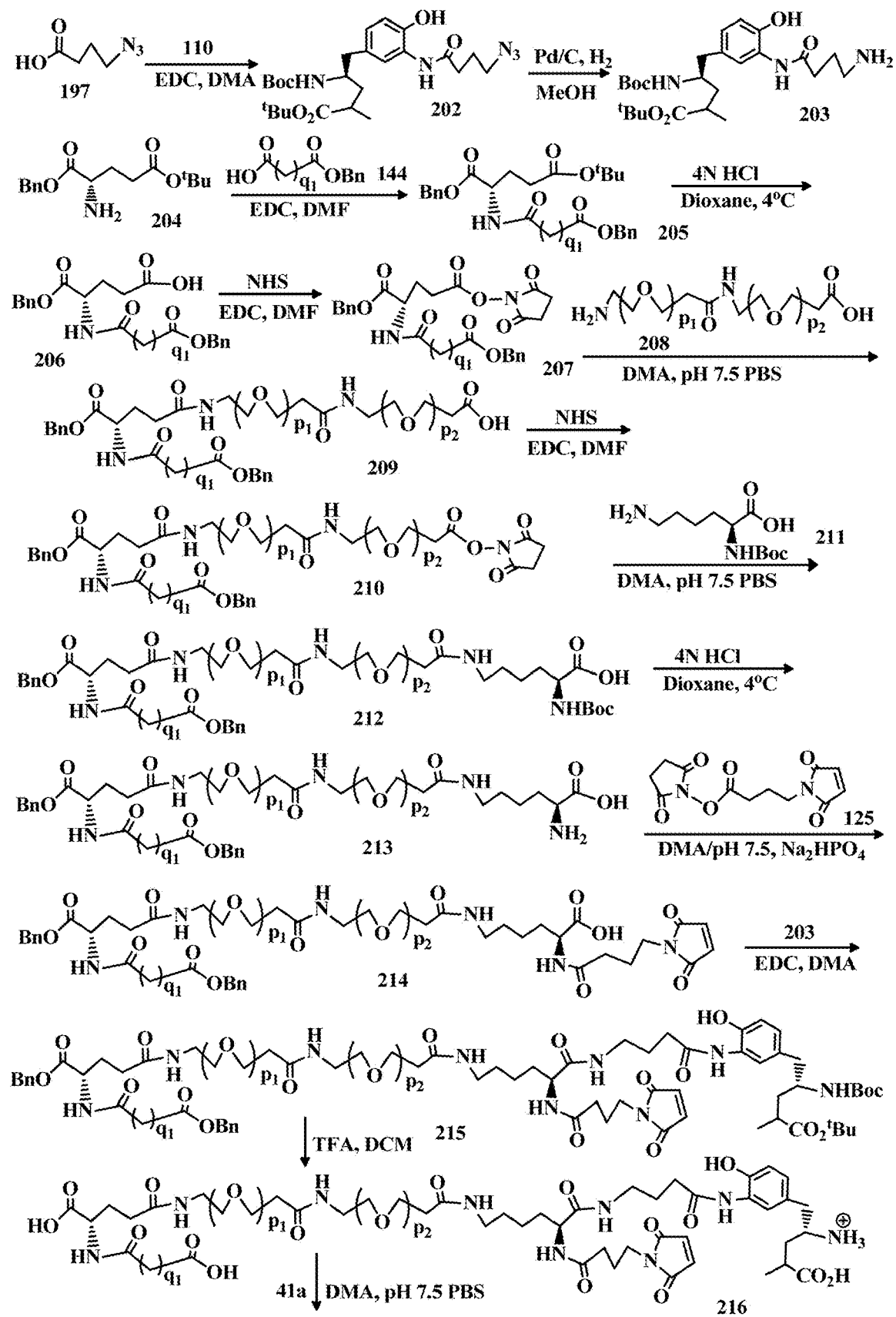
FIG. 15 shows the synthesis of components of a side-chain linker and their linkage to a Tup component.
Figure 16:
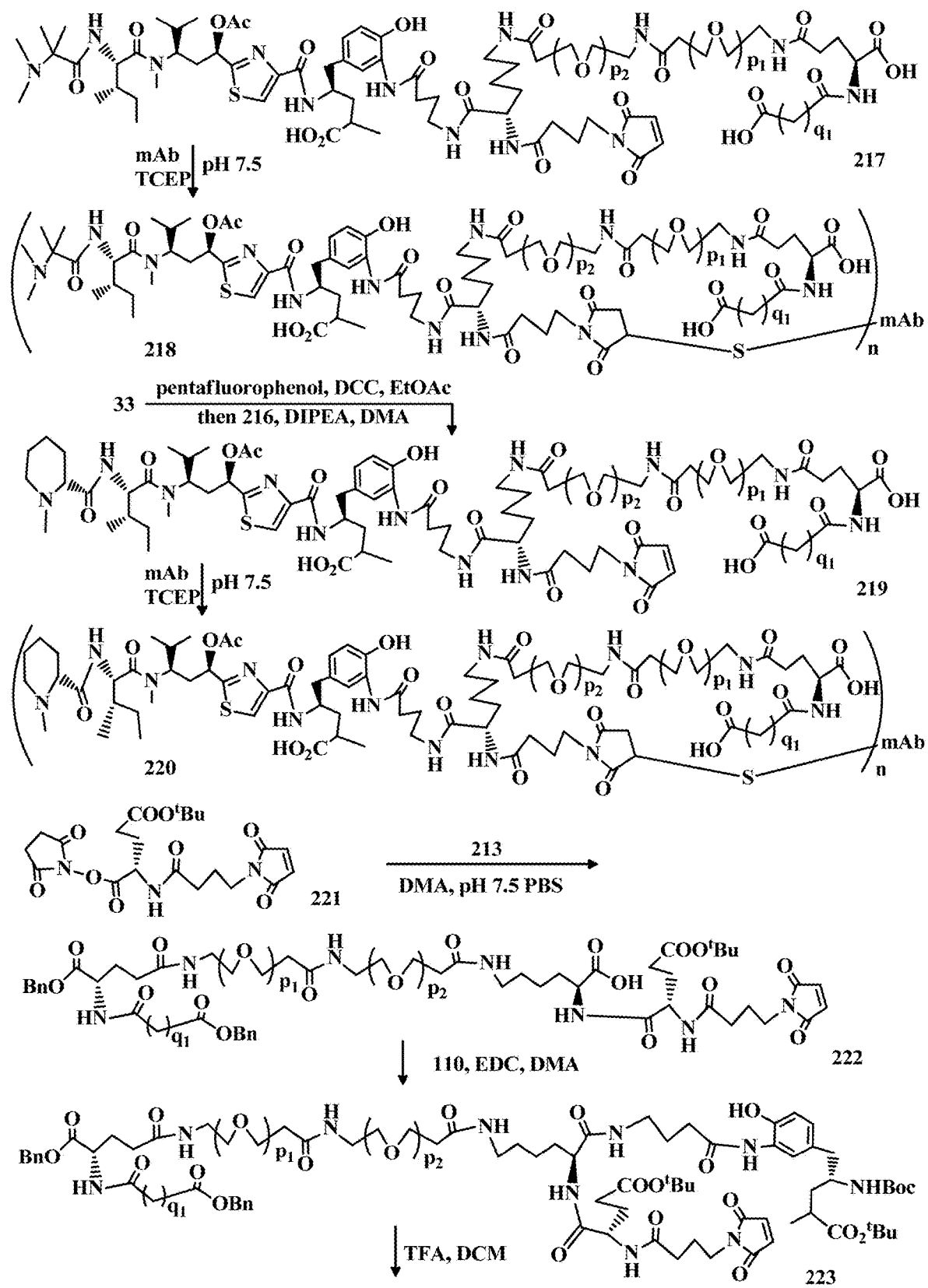
FIG. 16 shows the synthesis of Tubulysin analogs containing a side-chain linker and their conjugations to an antibody.
Figure 17:
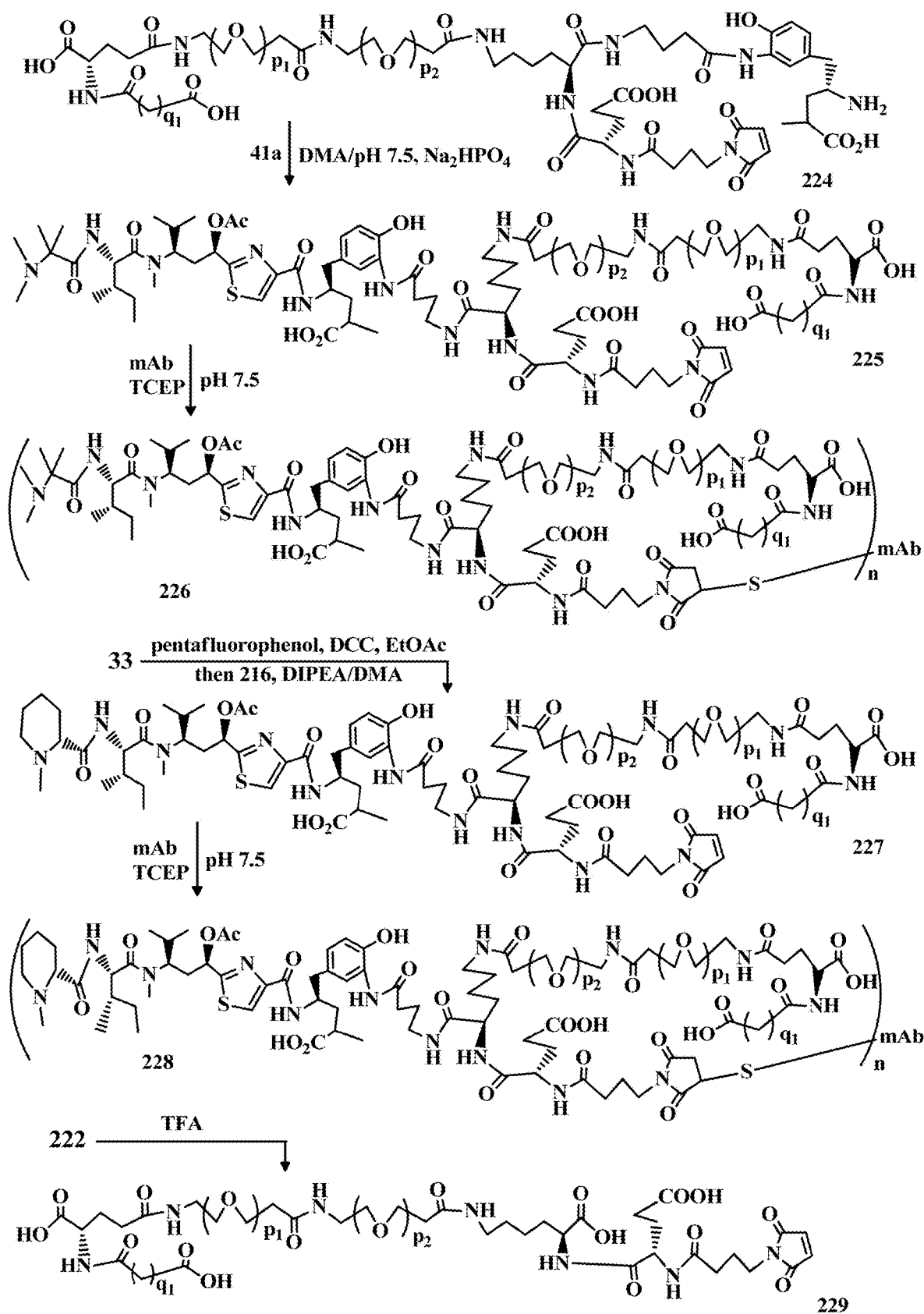
FIG. 17 shows the synthesis of Tubulysin analogs containing a side-chain linker and their conjugations to an antibody.
Figure 18:
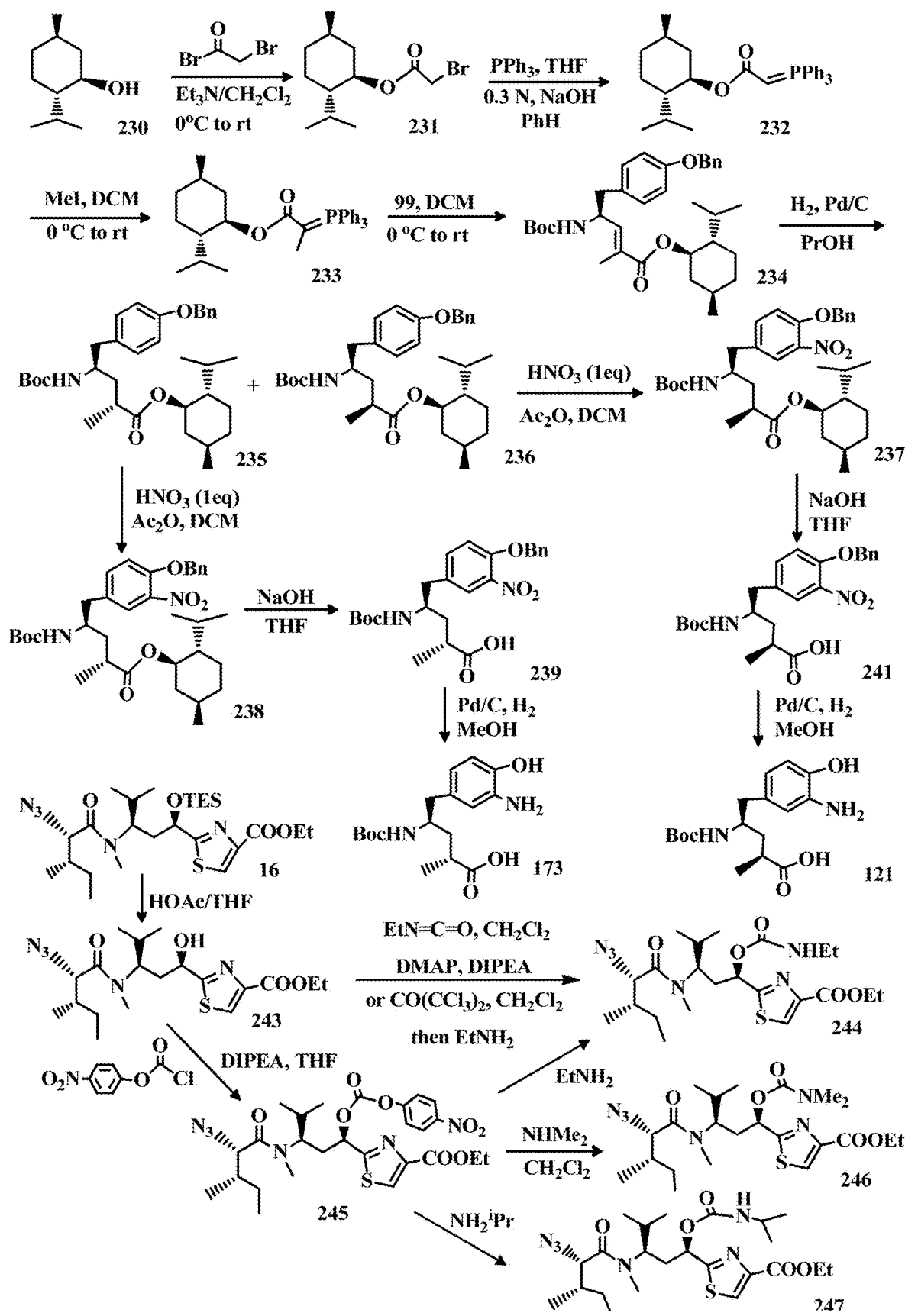
FIG. 18 shows the synthesis of components of tubulysin analogs.
Figure 19:
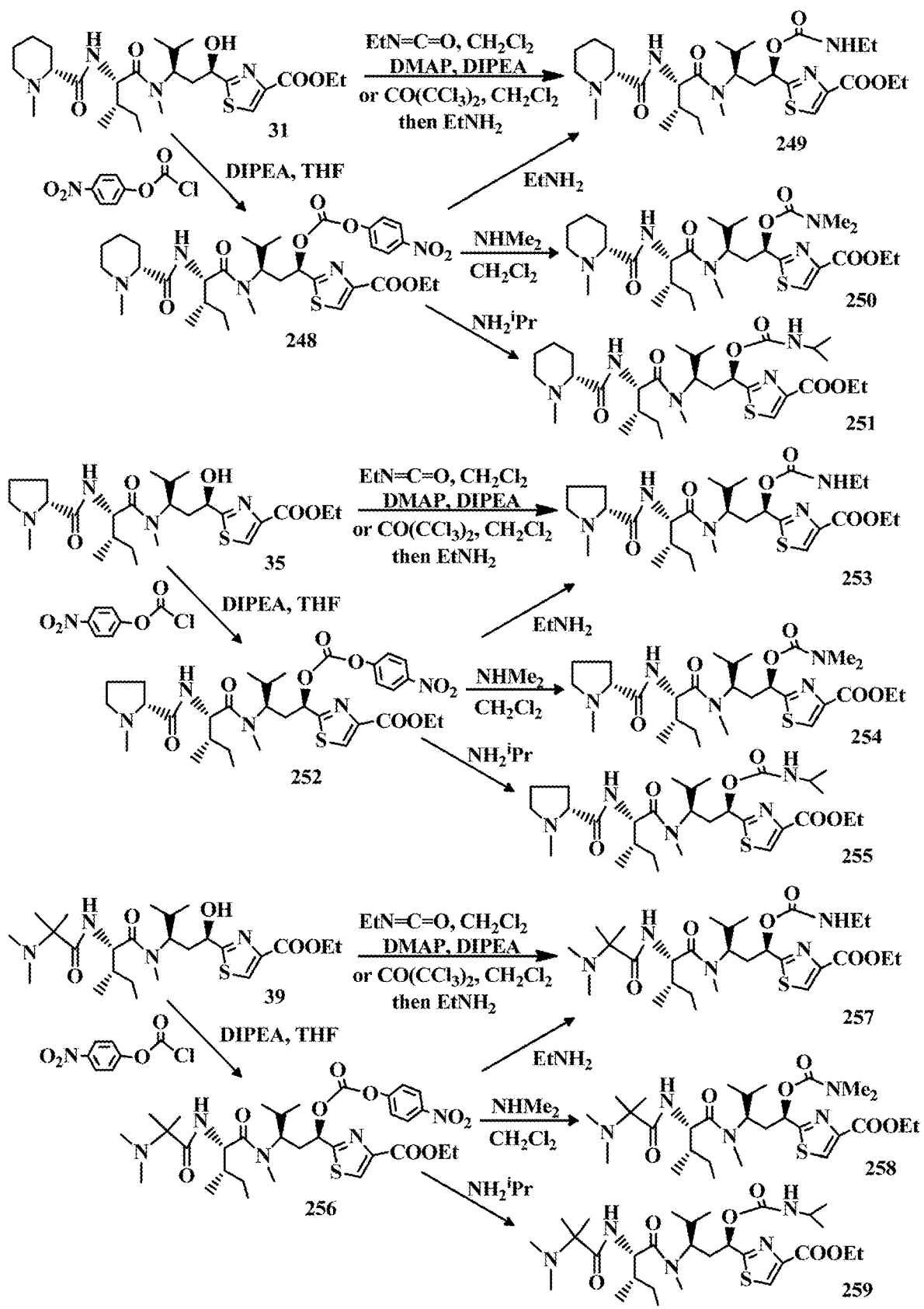
FIG. 19 shows the synthesis of components of tubulysin analogs.
Figure 20:
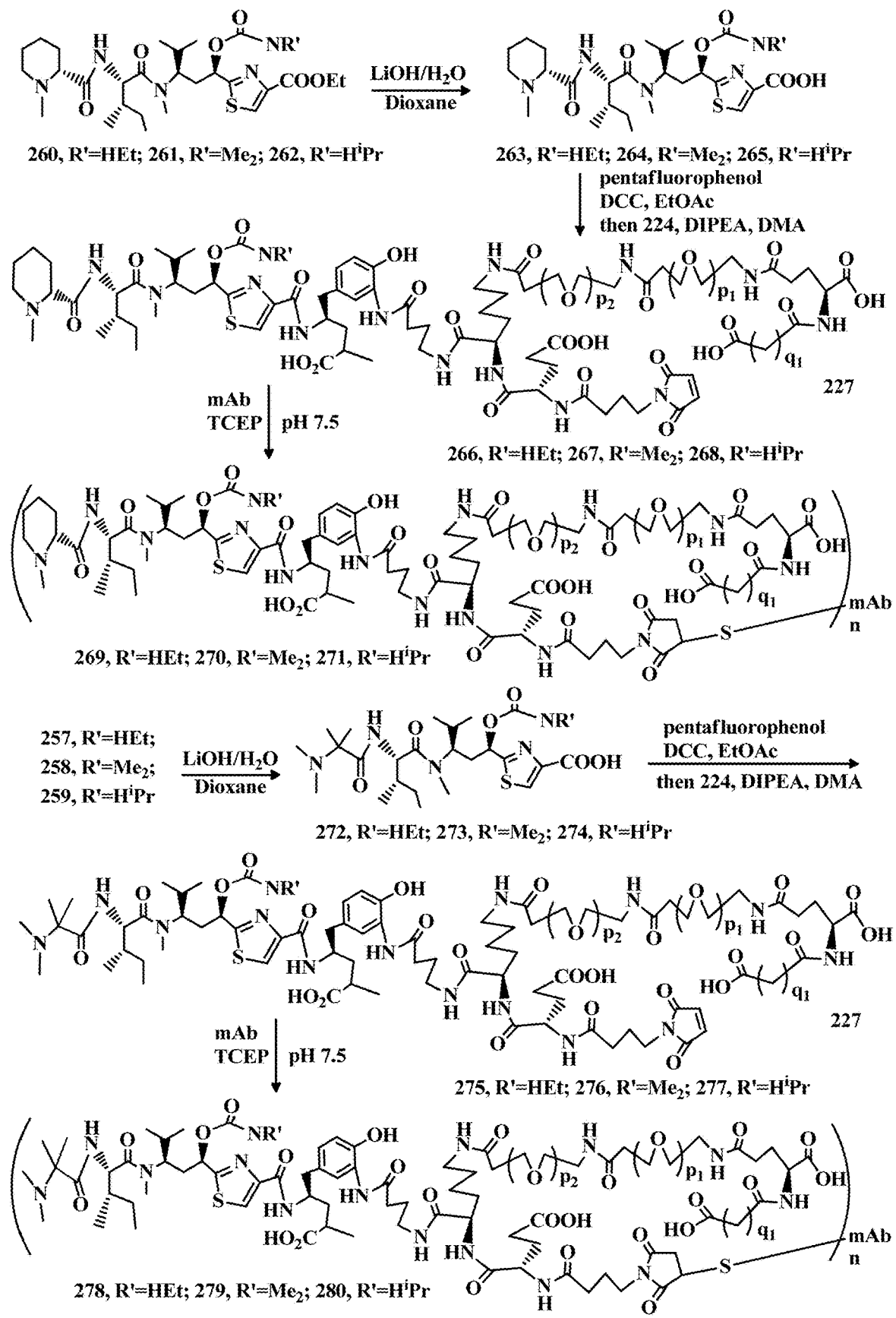
FIG. 20 shows the synthesis of Tubulysin analogs containing a side-chain linker and their conjugations to an antibody.
Figure 21:
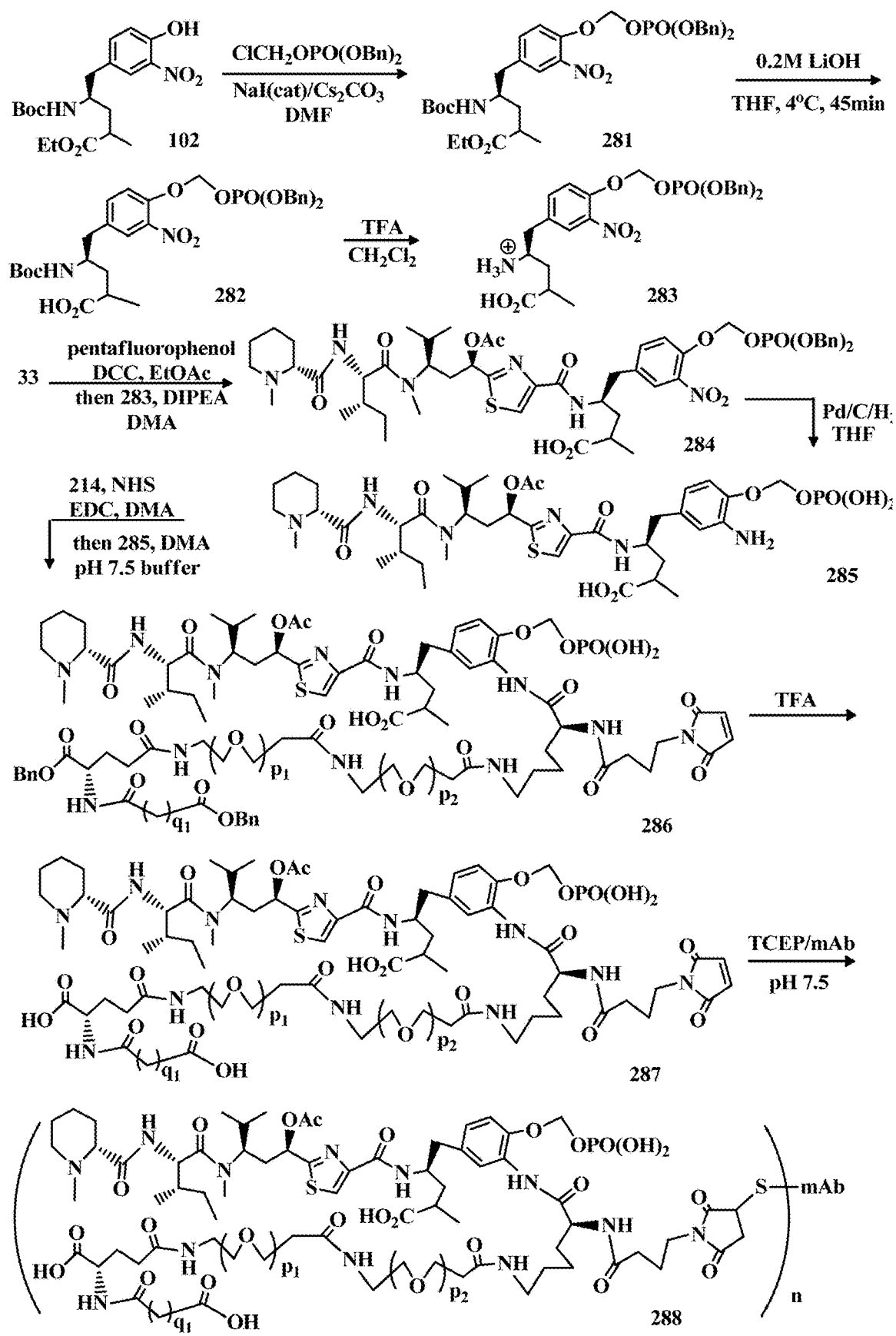
FIG. 21 shows the synthesis of Tubulysin analogs containing a side-chain linker and their conjugations to an antibody.
Figure 22:
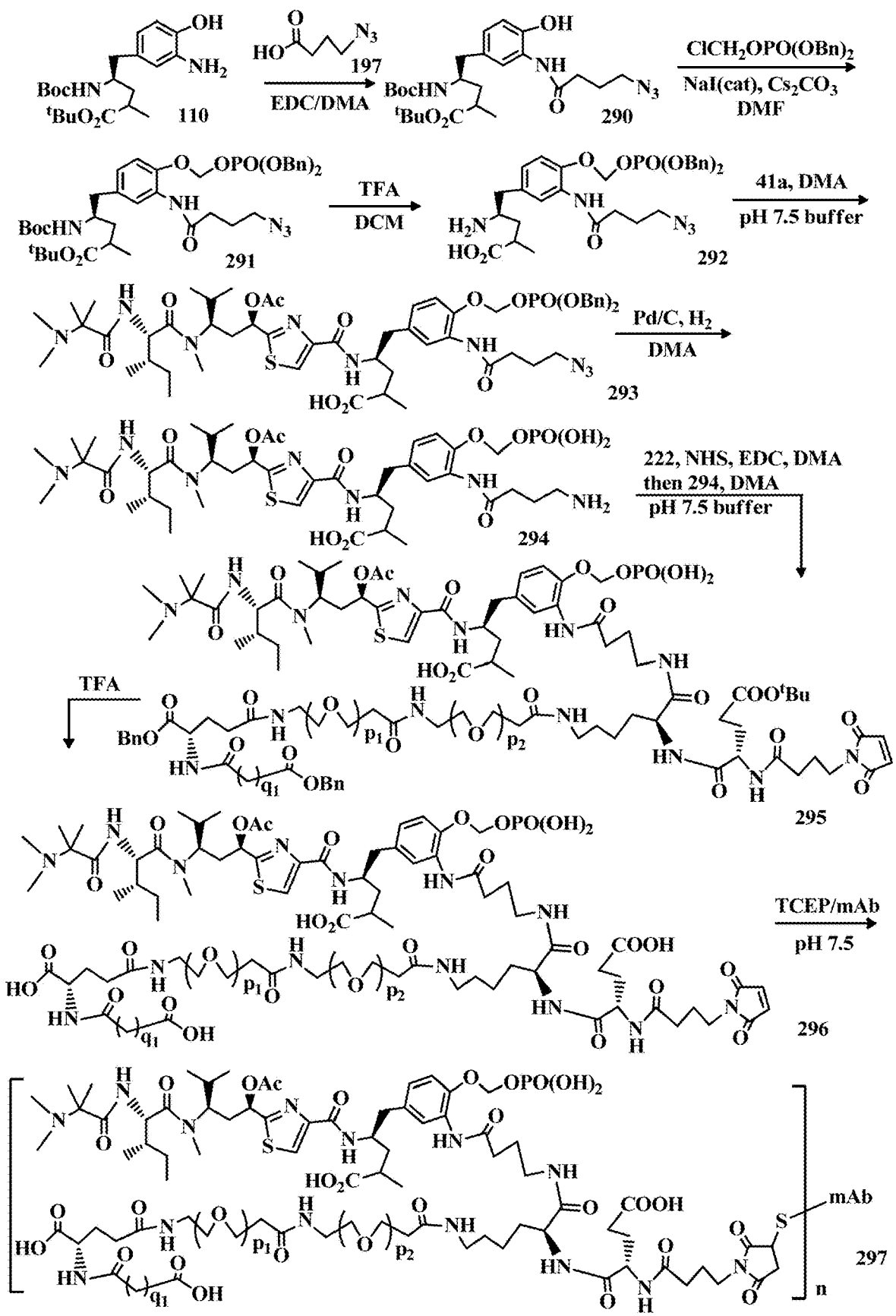
FIG. 22 shows the synthesis of Tubulysin analogs containing a side-chain linker and their conjugations to an antibody.
Figure 23:
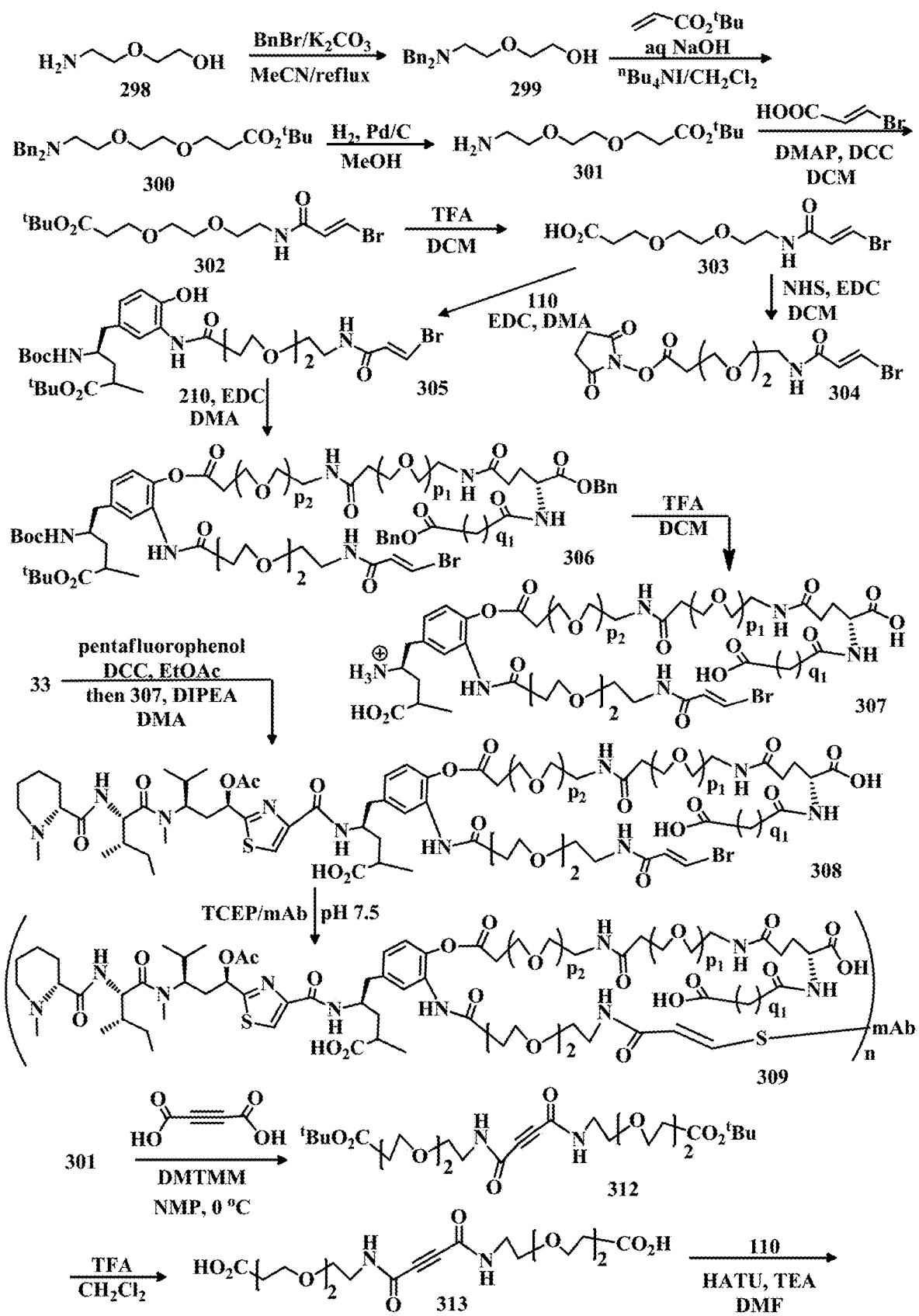
FIG. 23 shows the synthesis of Tubulysin analogs containing a side-chain linker and their conjugations to an antibody.
Figure 24:
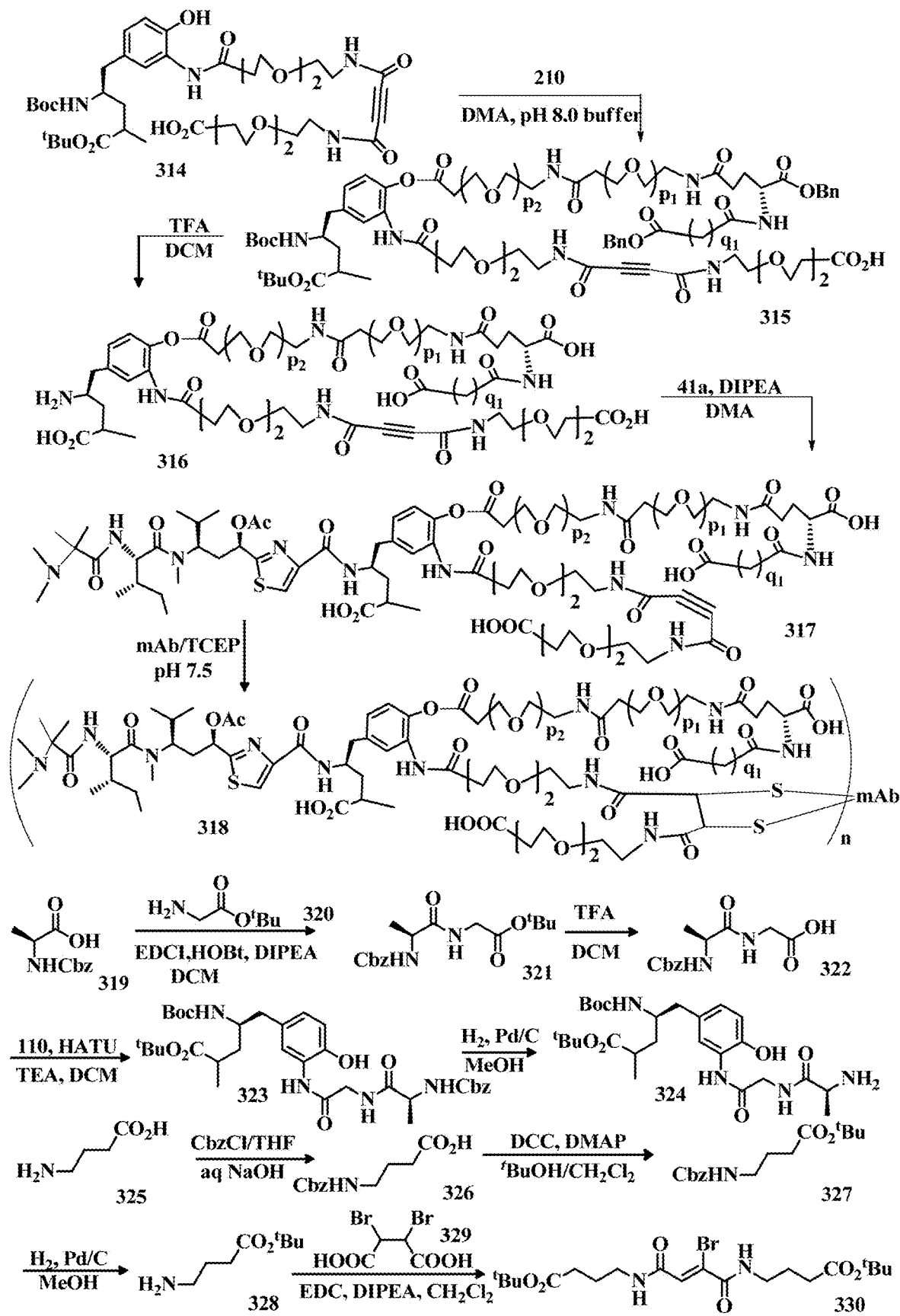
FIG. 24 shows the synthesis of Tubulysin analogs containing a side-chain linker and their conjugations to an antibody.
Figure 25:
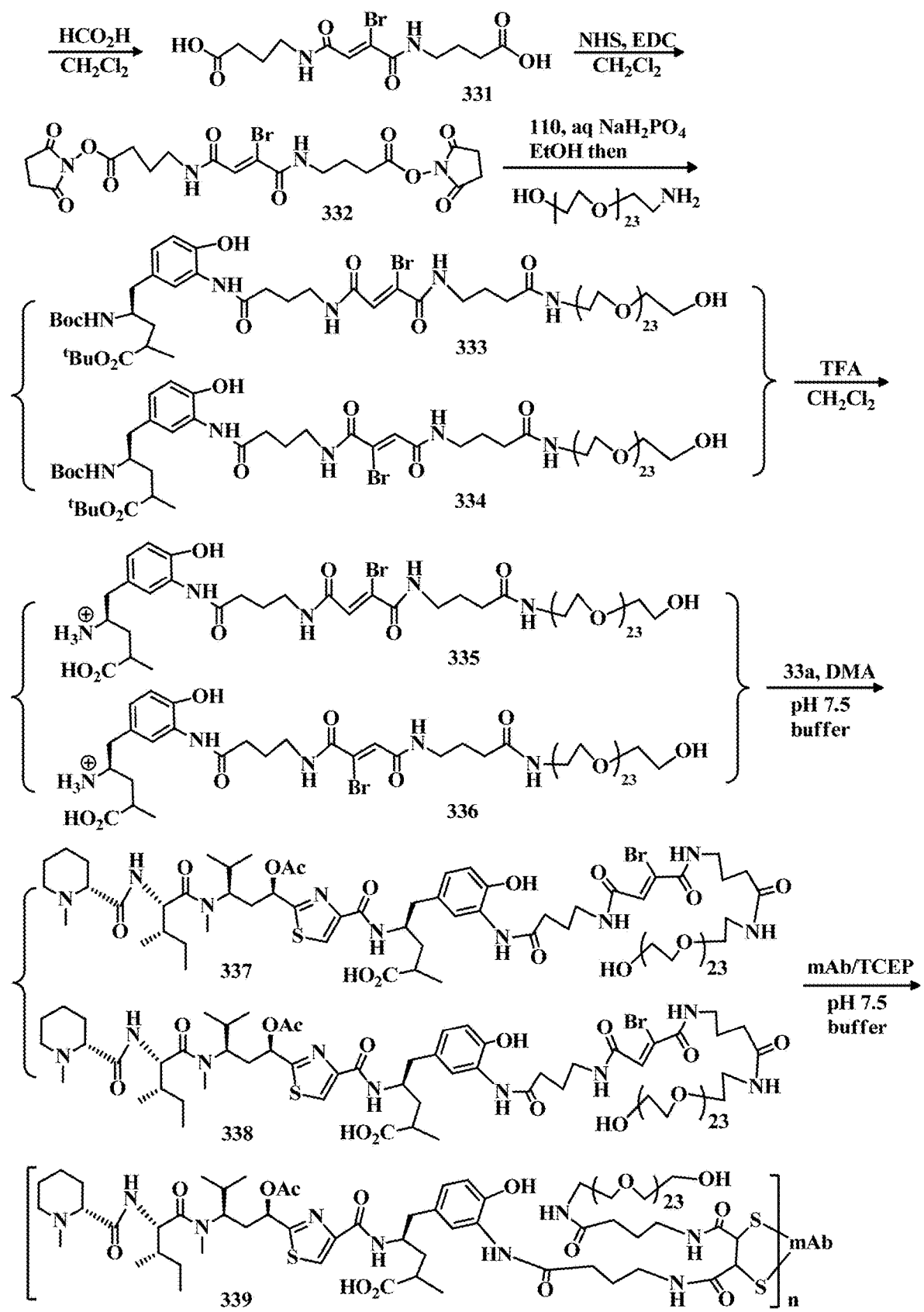
FIG. 25 shows the synthesis of Tubulysin analogs containing a side-chain linker and their conjugations to an antibody.
Figure 26:
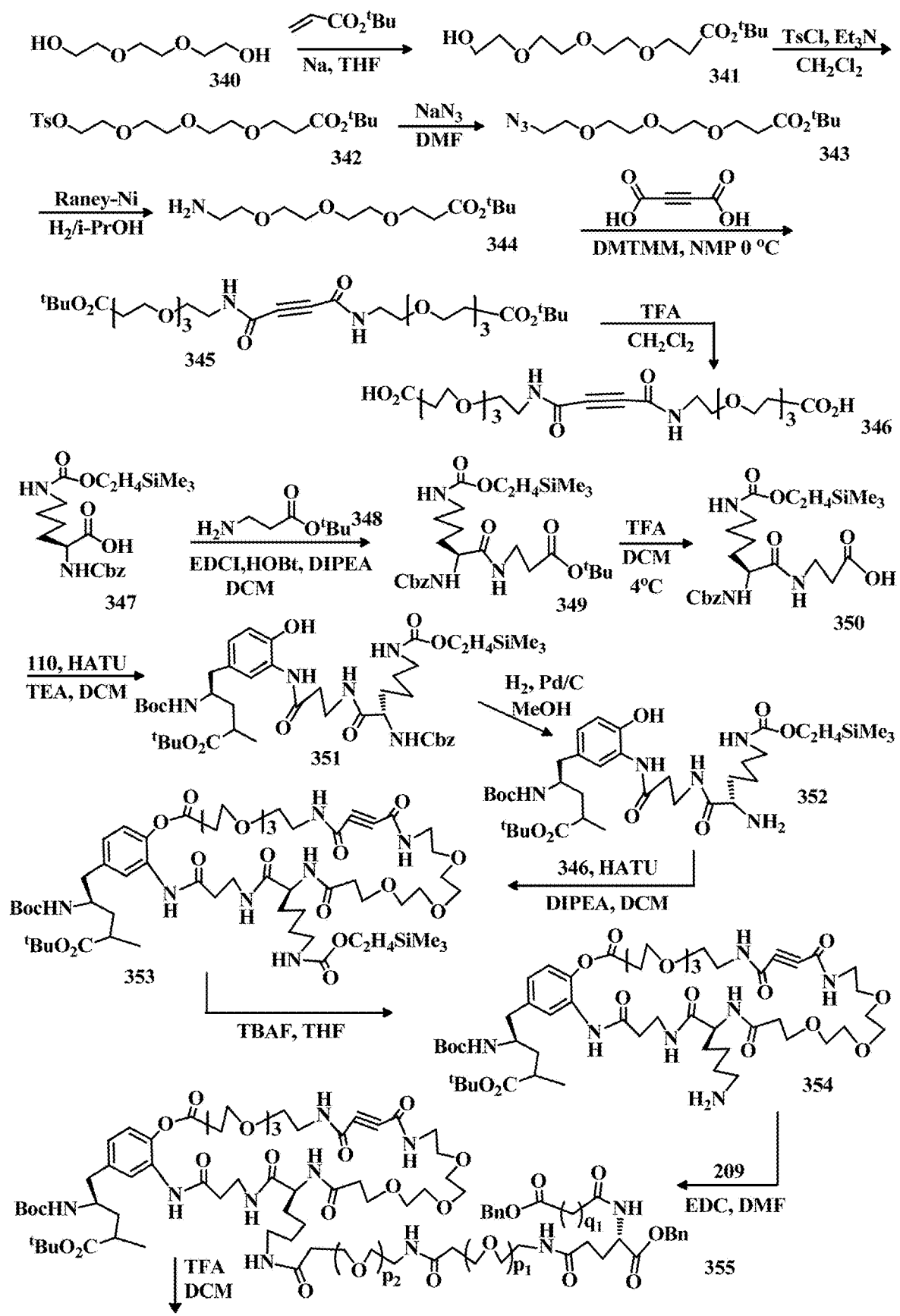
FIG. 26 shows the synthesis of Tubulysin components containing a side-chain linker.
Figure 27:
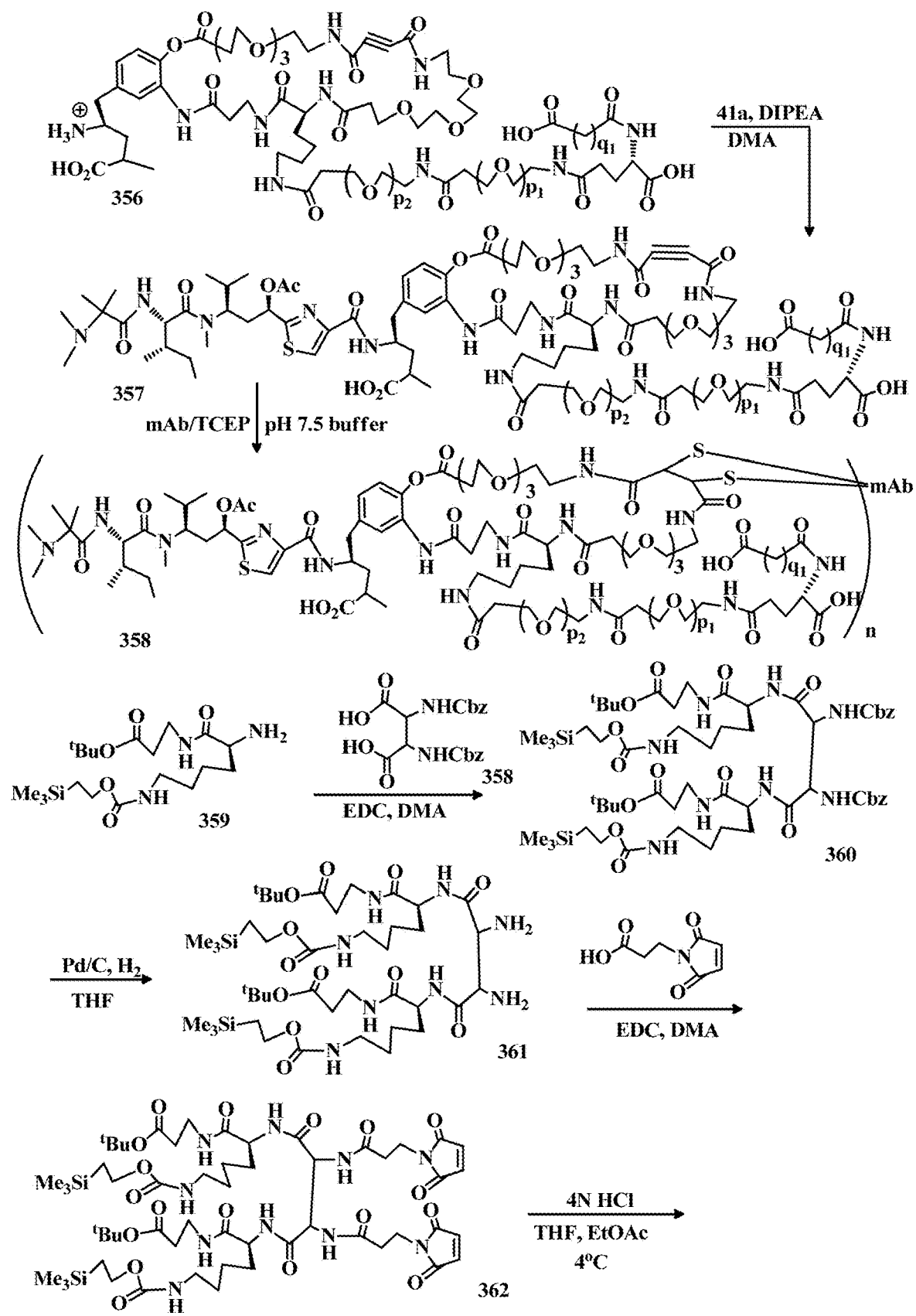
FIG. 27 shows the synthesis of Tubulysin analogs containing a side-chain linker and their conjugations to an antibody via a pair of thiols in the antibody.
Figure 28:
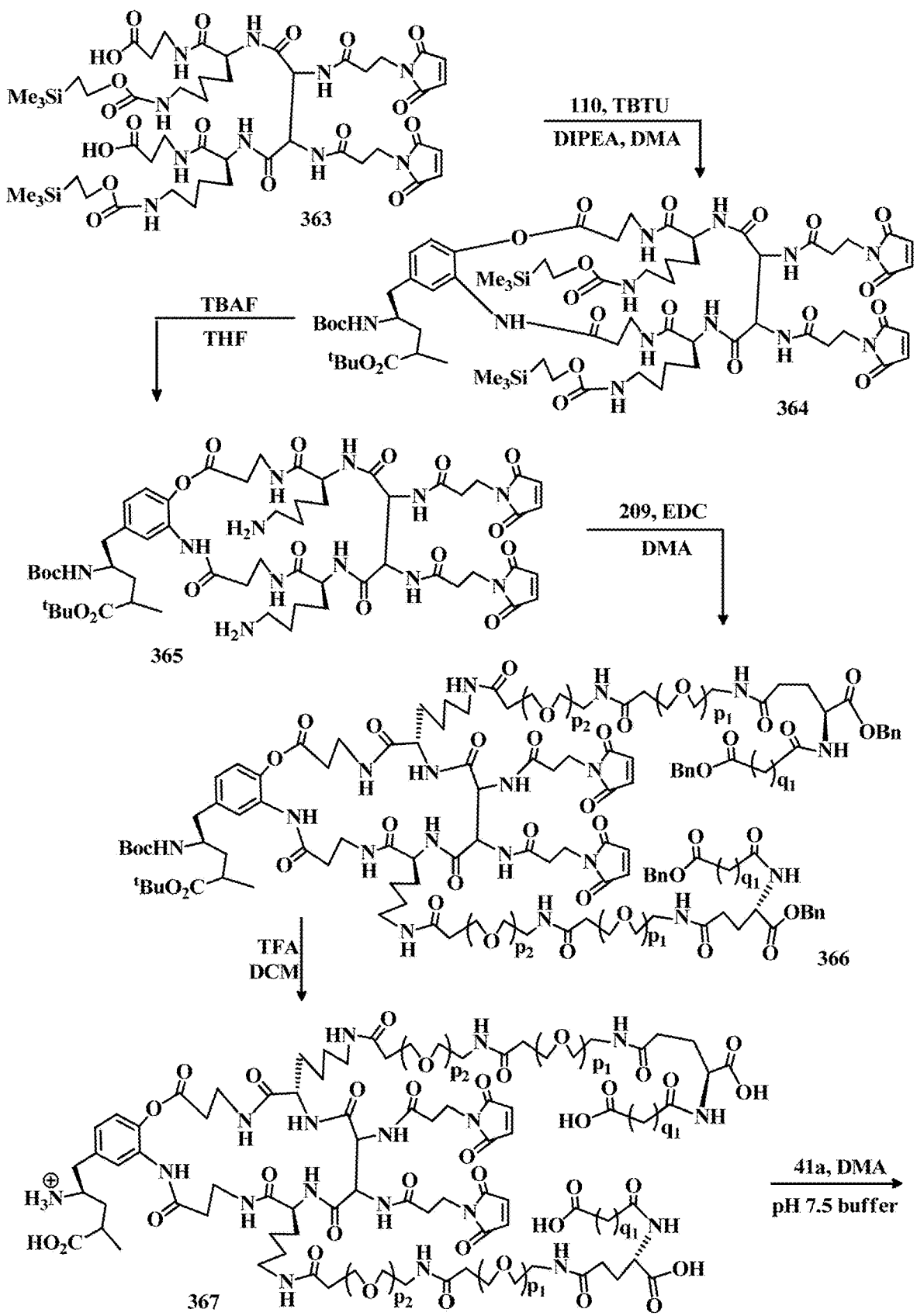
FIG. 28 shows the synthesis of Tubulysin components containing side-chain linkers.
Figure 29:
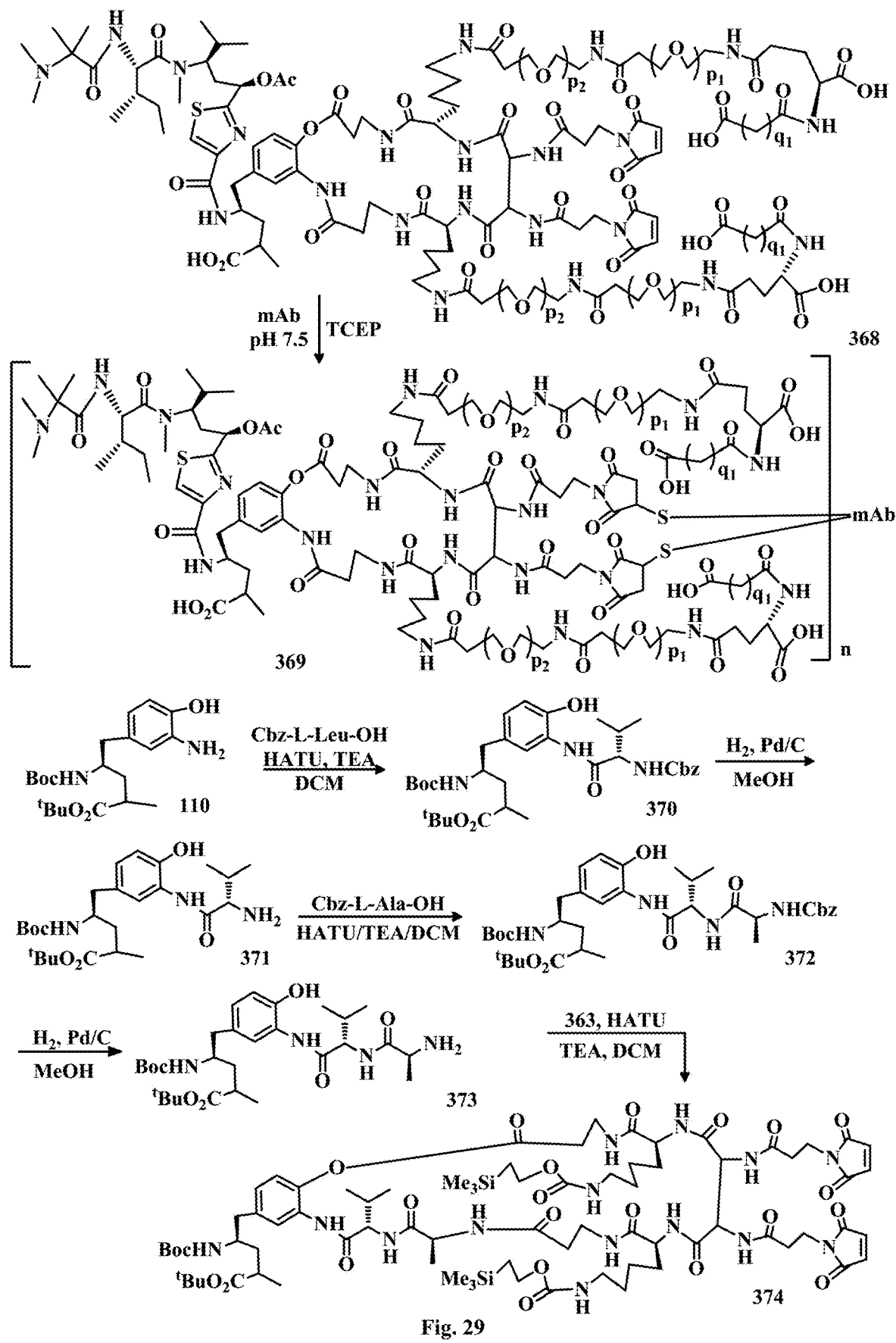
FIG. 29 shows the synthesis of Tubulysin analogs containing a side-chain linker and their conjugations to an antibody via a pair of thiols in the antibody.
Figure 30:
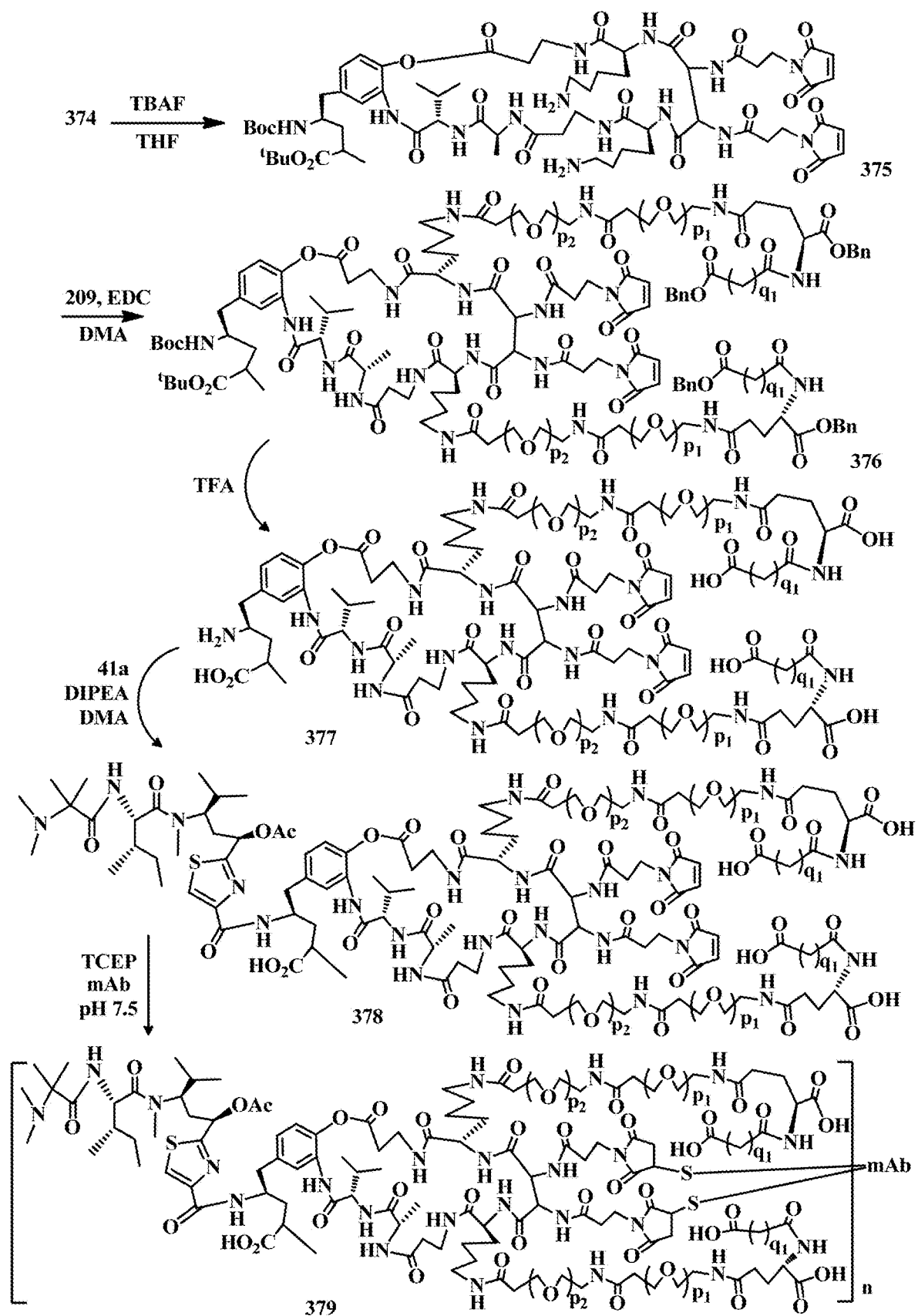
FIG. 30 shows the synthesis of Tubulysin analogs containing side-chain linkers and their conjugations to an antibody via a pair of thiols in the antibody.
Figure 31:
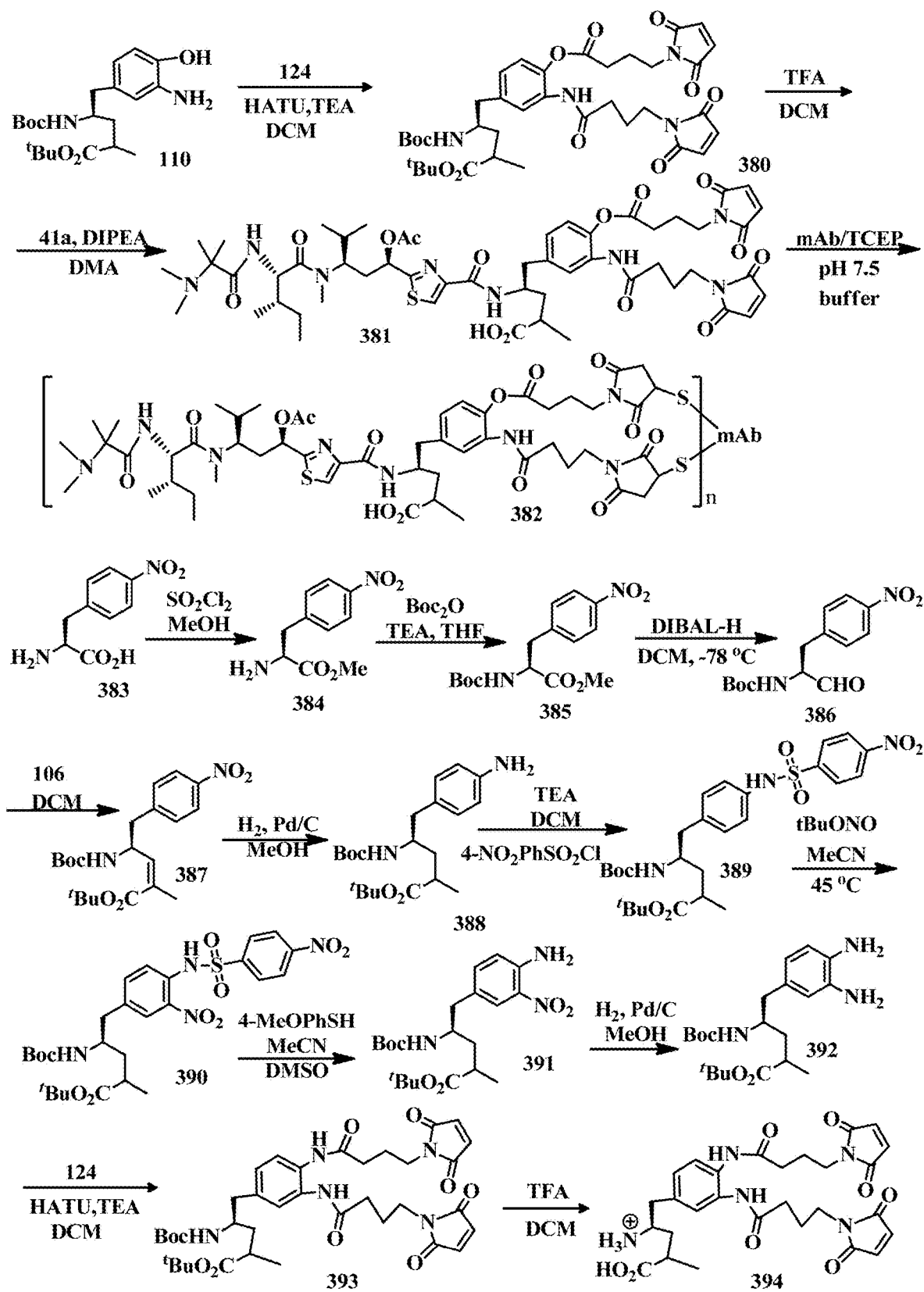
FIG. 31 shows the synthesis of Tubulysin components.
Figure 32:
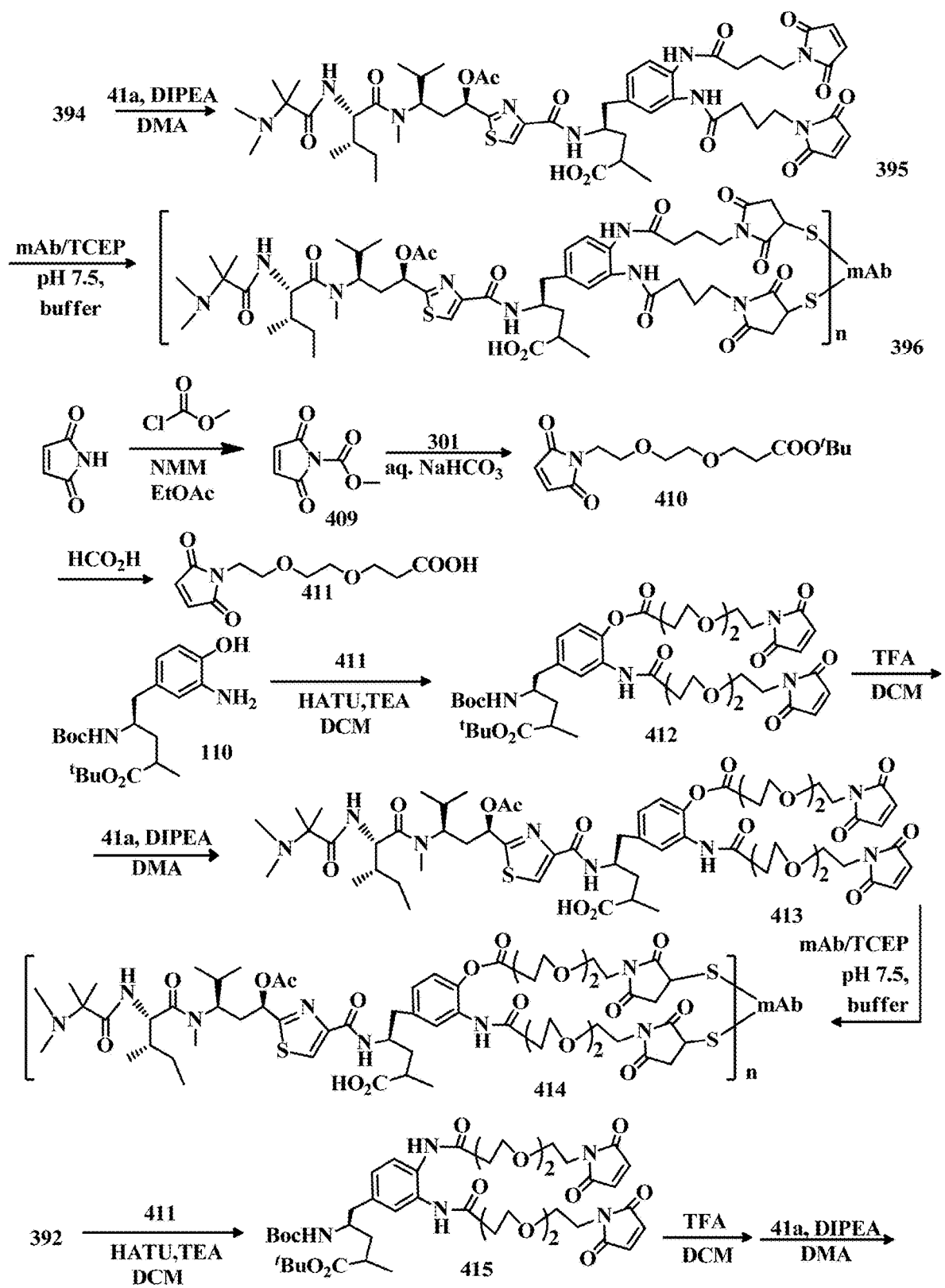
FIG. 32 shows the synthesis of Tubulysin components.
Figure 33:
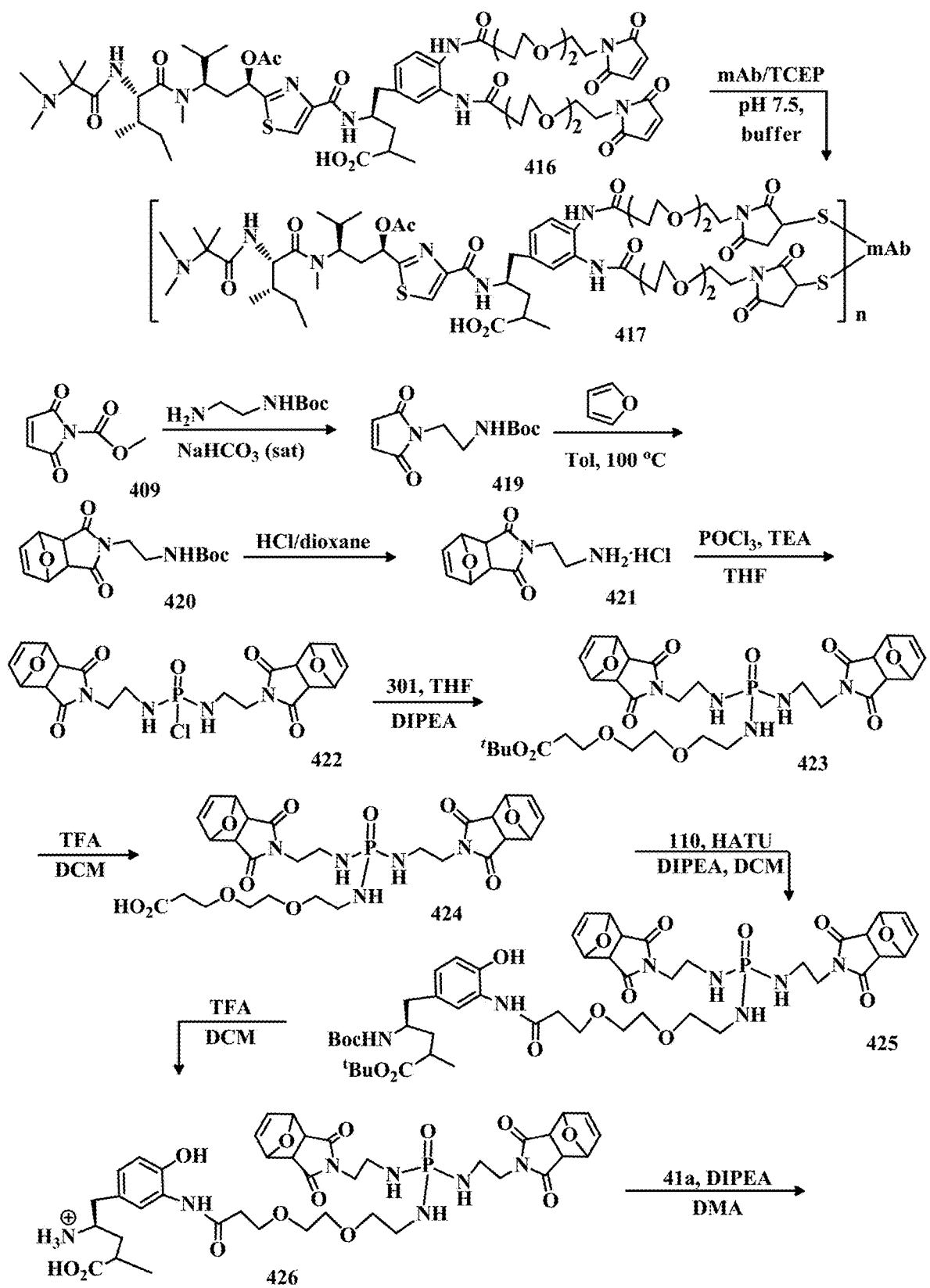
FIG. 33 shows the synthesis of Tubulysin components.
Figure 34:
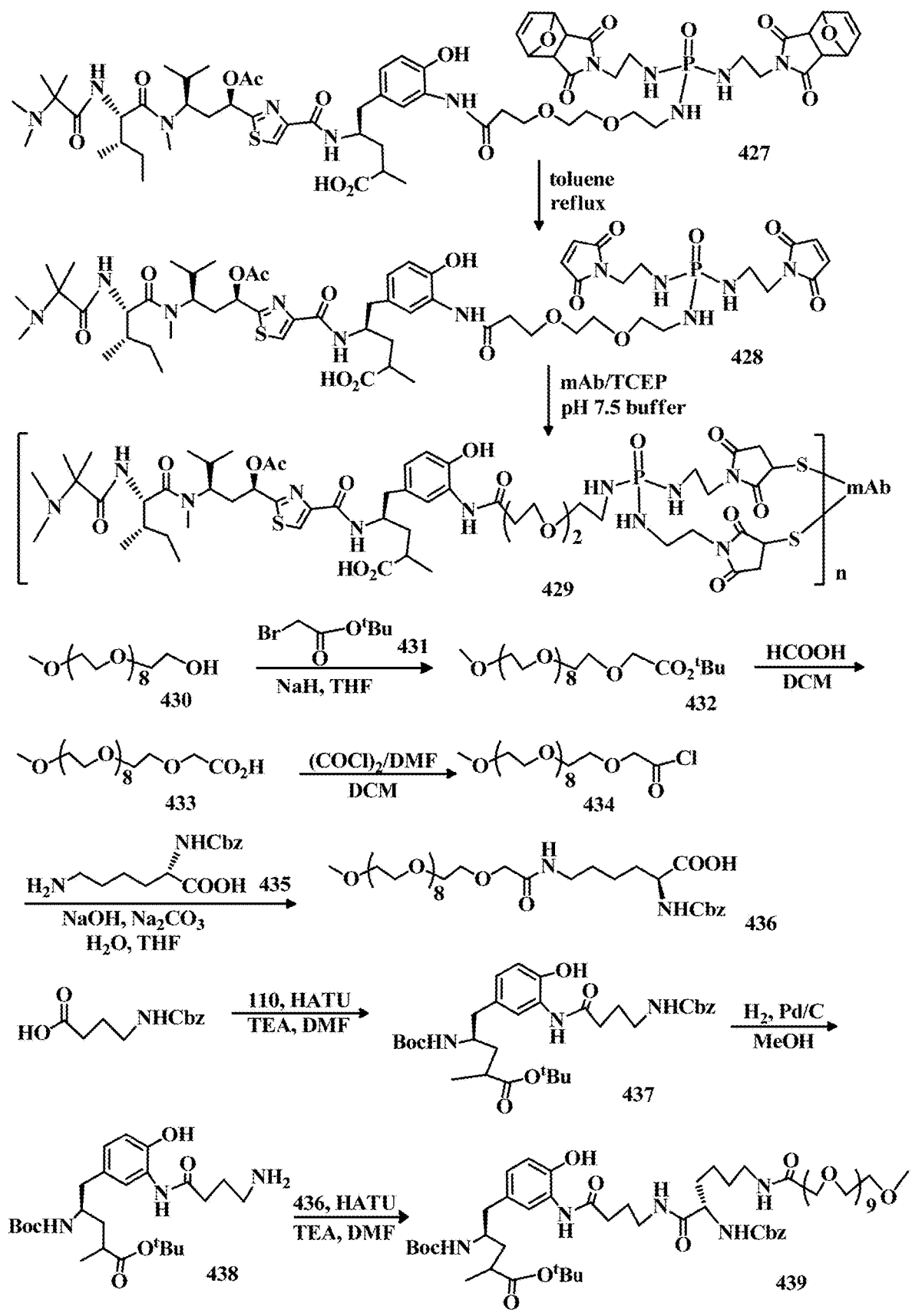
FIG. 34 shows the synthesis of Tubulysin components containing a side-chain linker.
Figure 35:
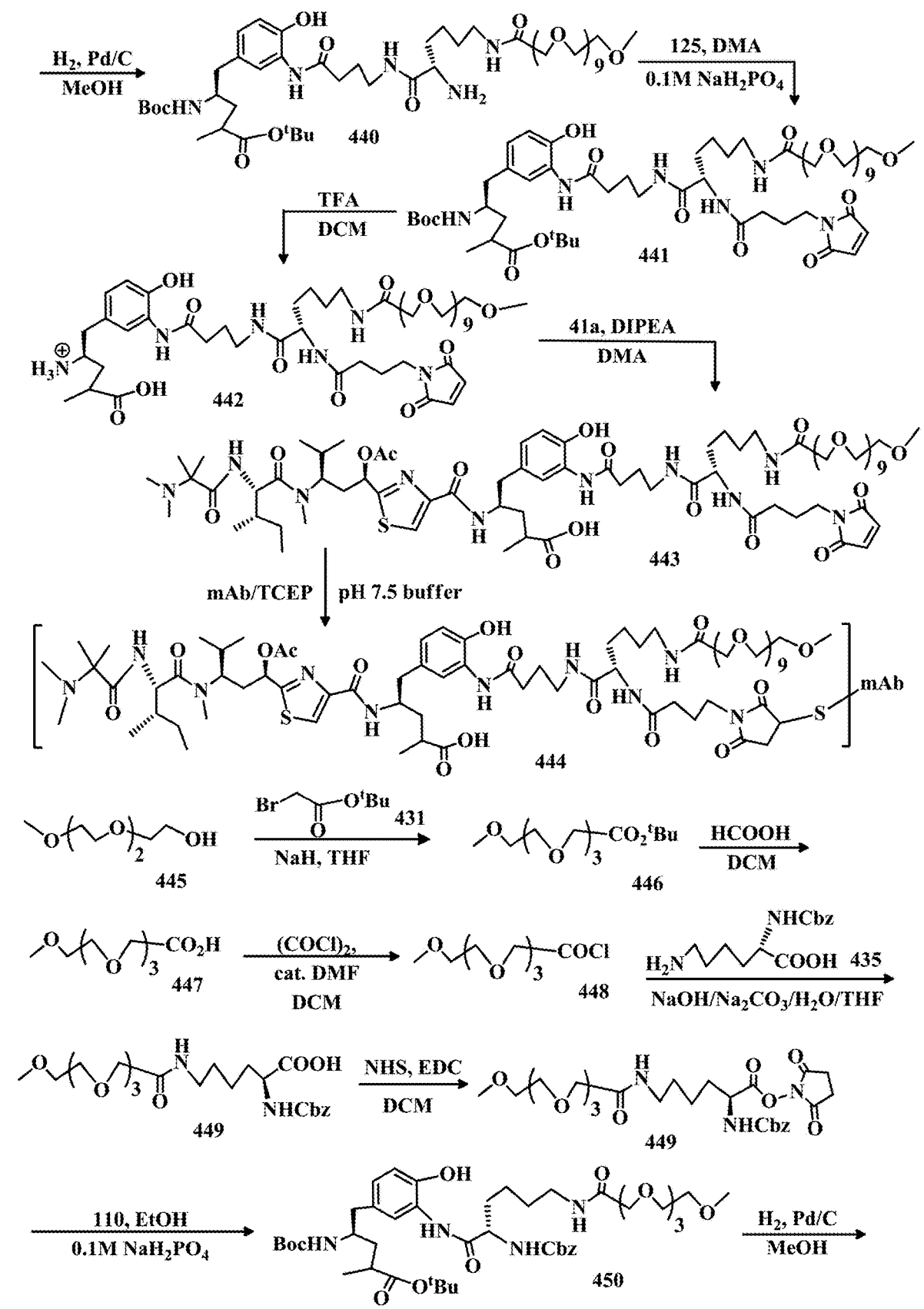
FIG. 35 shows the synthesis of a Tubulysin analog containing a side-chain linker and its conjugation to an antibody.
Figure 36:
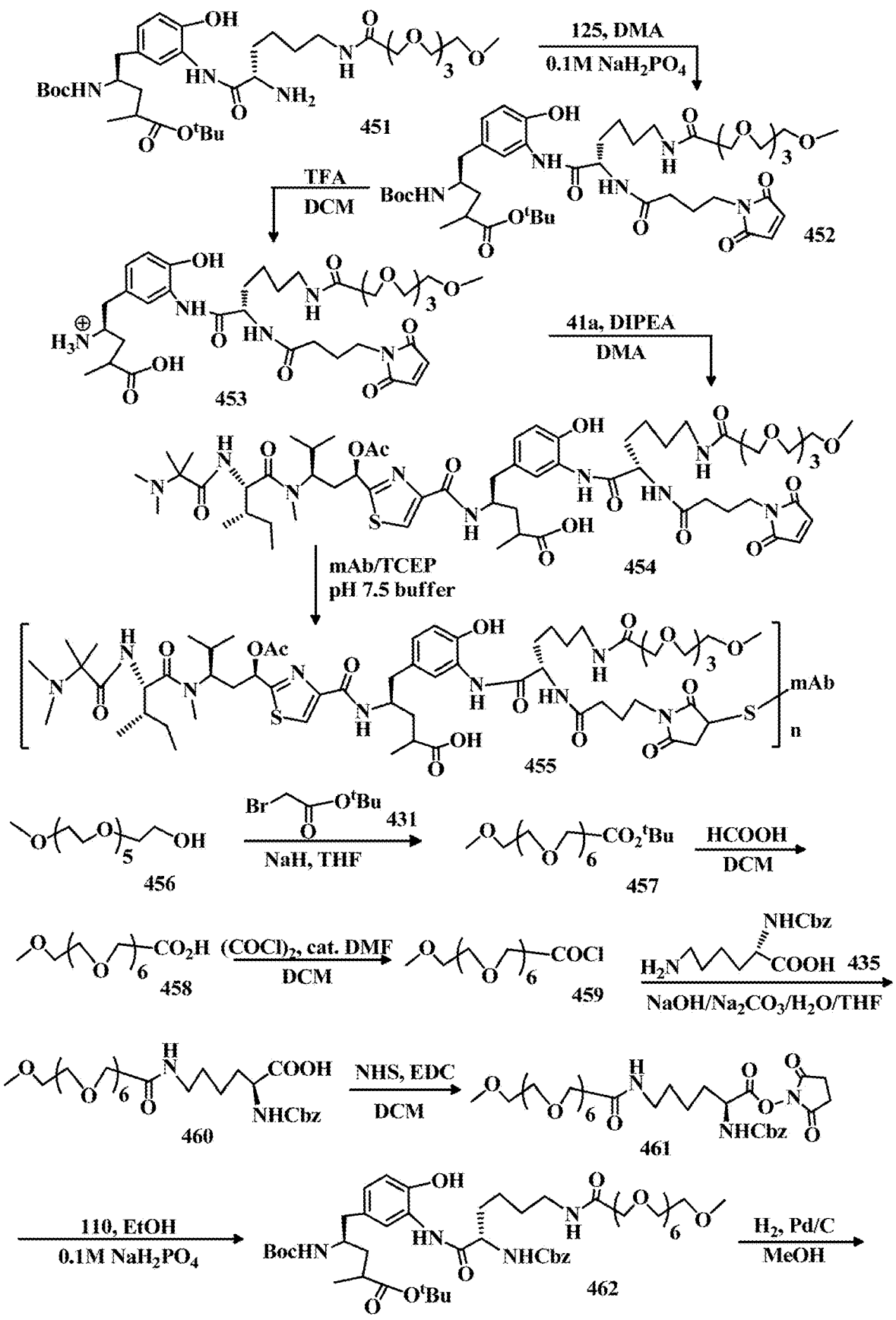
FIG. 36 shows the synthesis of a Tubulysin analog containing a side-chain linker and its conjugation to an antibody.
Figure 37:
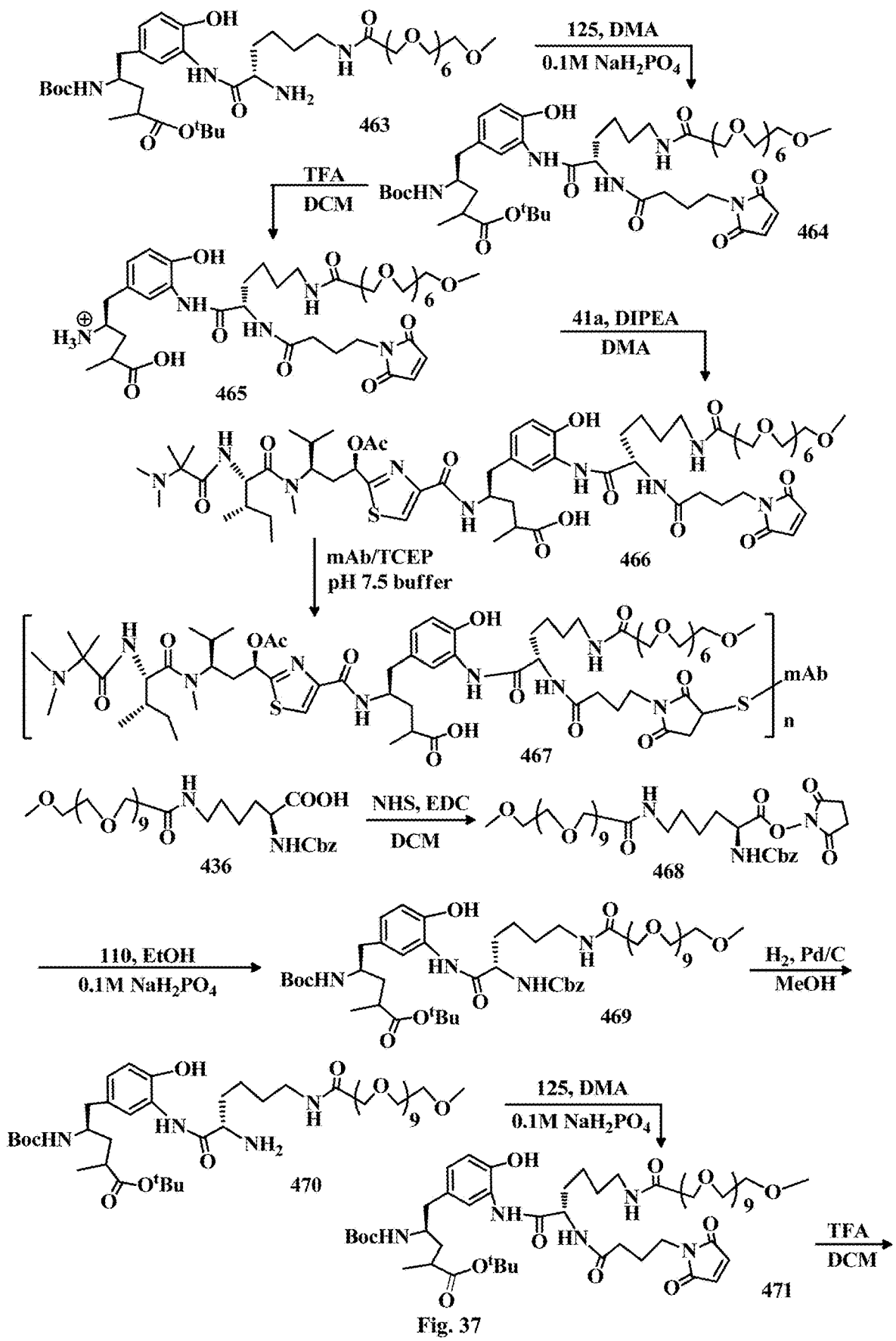
FIG. 37 shows the synthesis of a Tubulysin analog containing a side-chain linker and its conjugation to an antibody.
Figure 38:
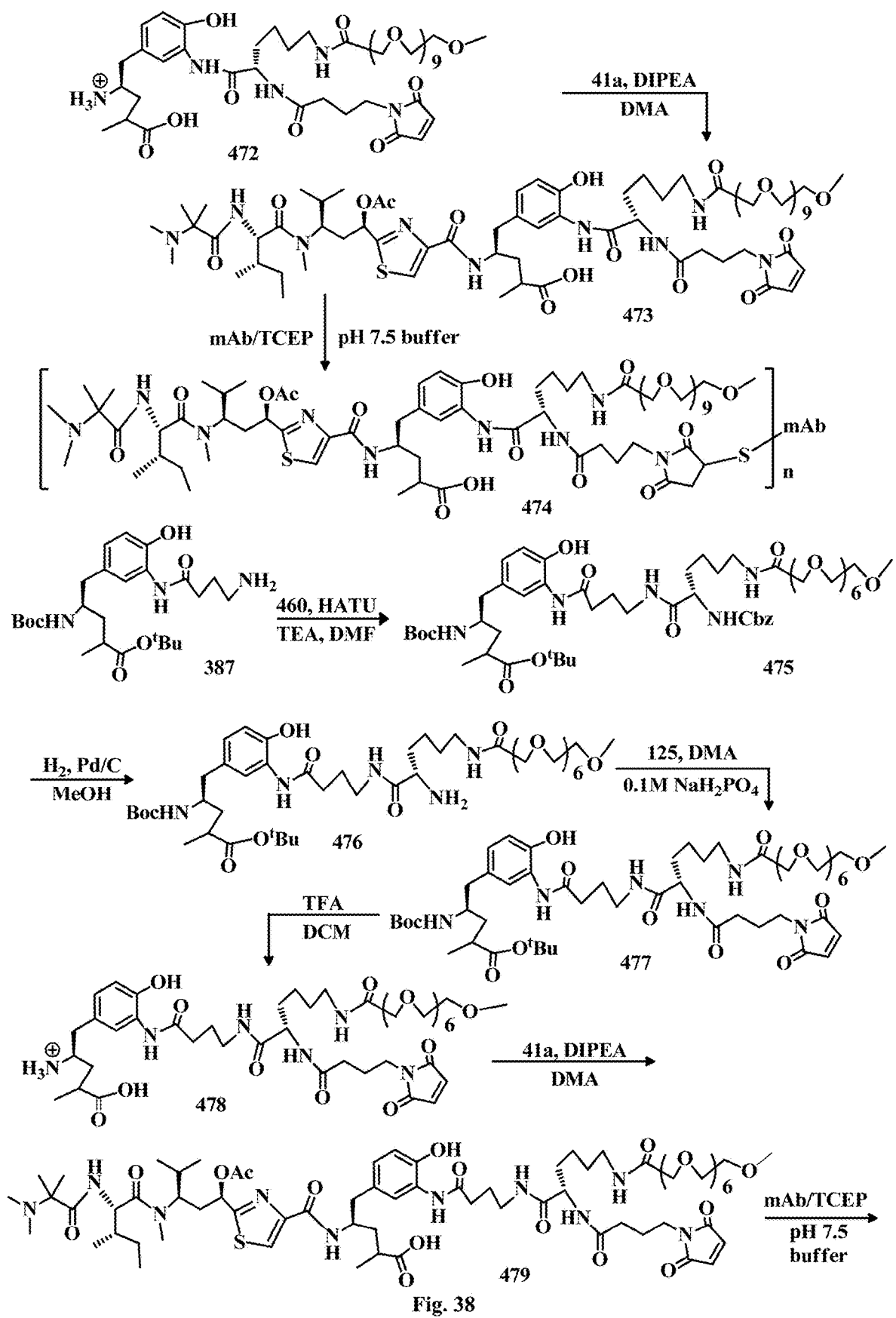
FIG. 38 shows the synthesis of a Tubulysin analog containing a side-chain linker and its conjugation to an antibody.
Figure 39:
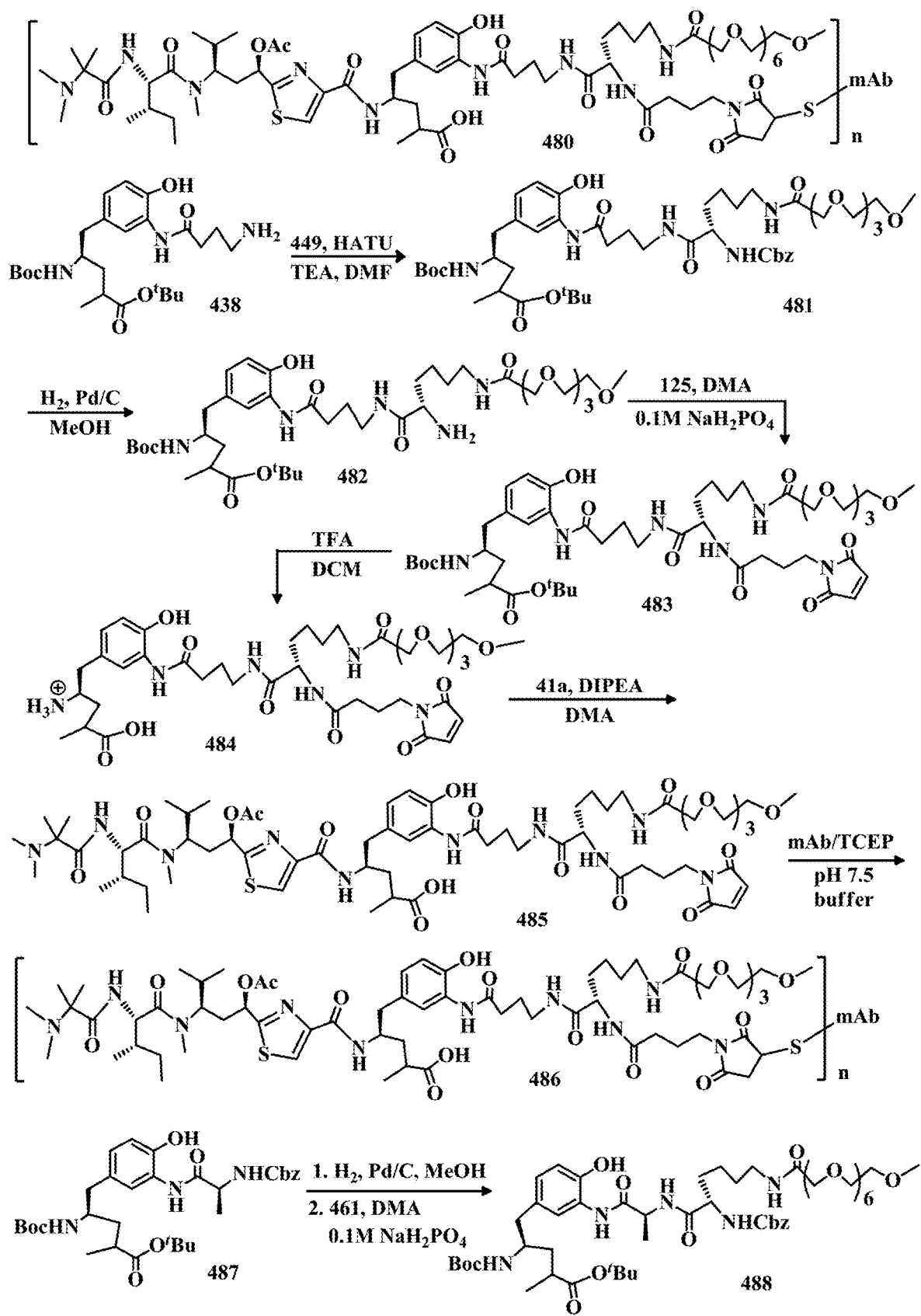
FIG. 39 shows the synthesis of a Tubulysin analog containing a side-chain linker and its conjugation to an antibody.
Figure 40:
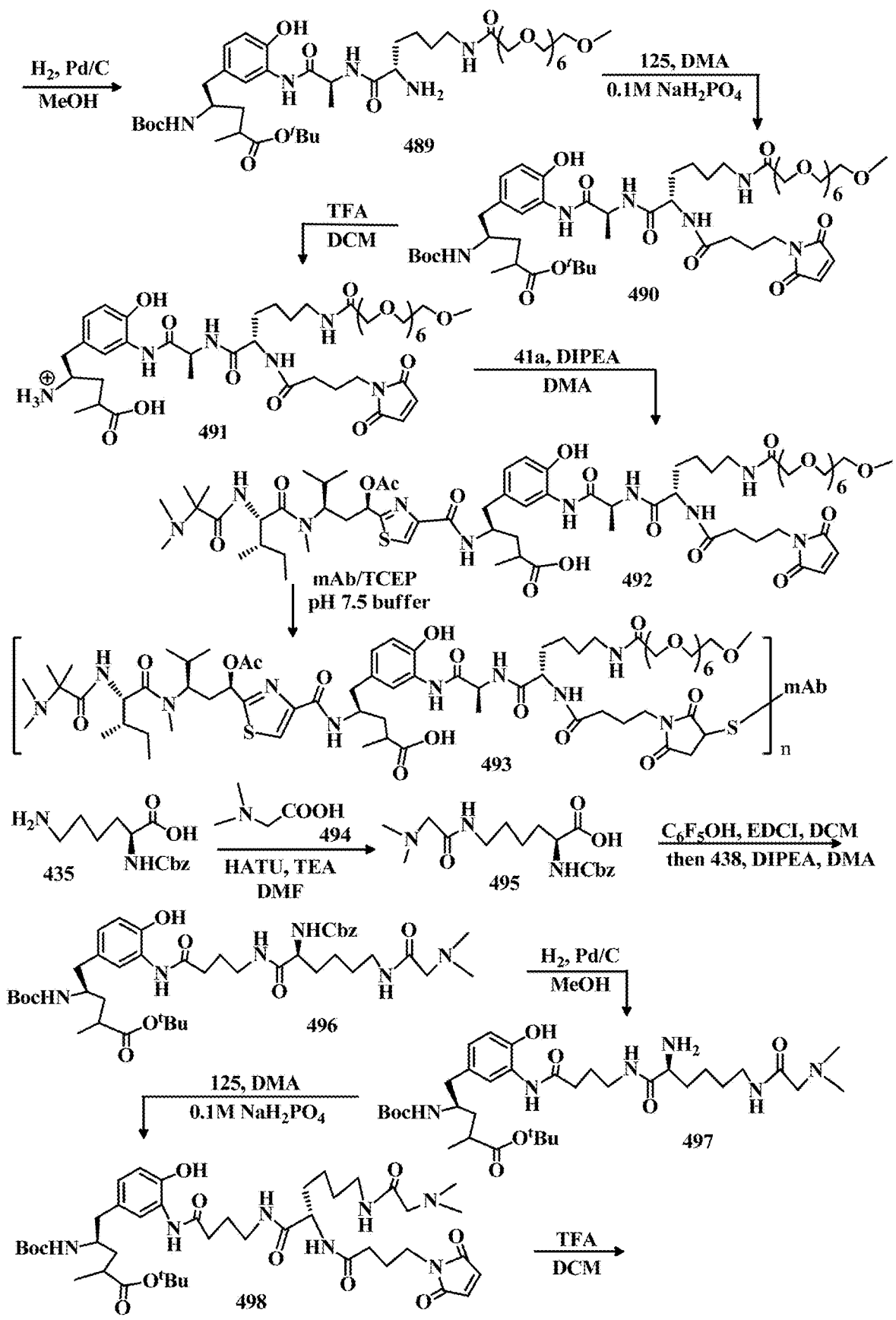
FIG. 40 shows the synthesis of a Tubulysin analog containing a side-chain linker and its conjugation to an antibody.
Figure 41:
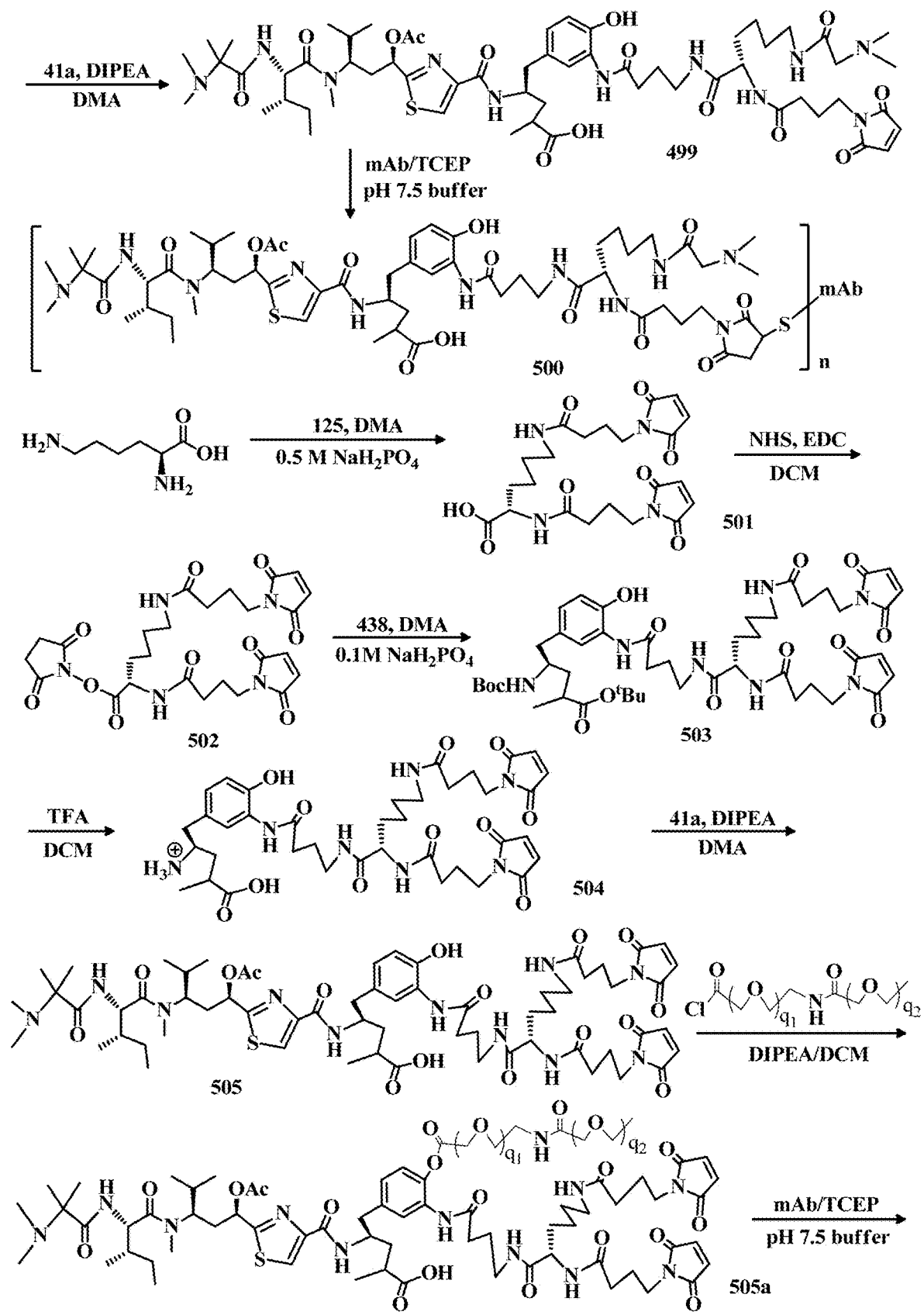
FIG. 41 shows the synthesis of a Tubulysin analog containing a side-chain linker and its conjugation to an antibody.
Figure 42:
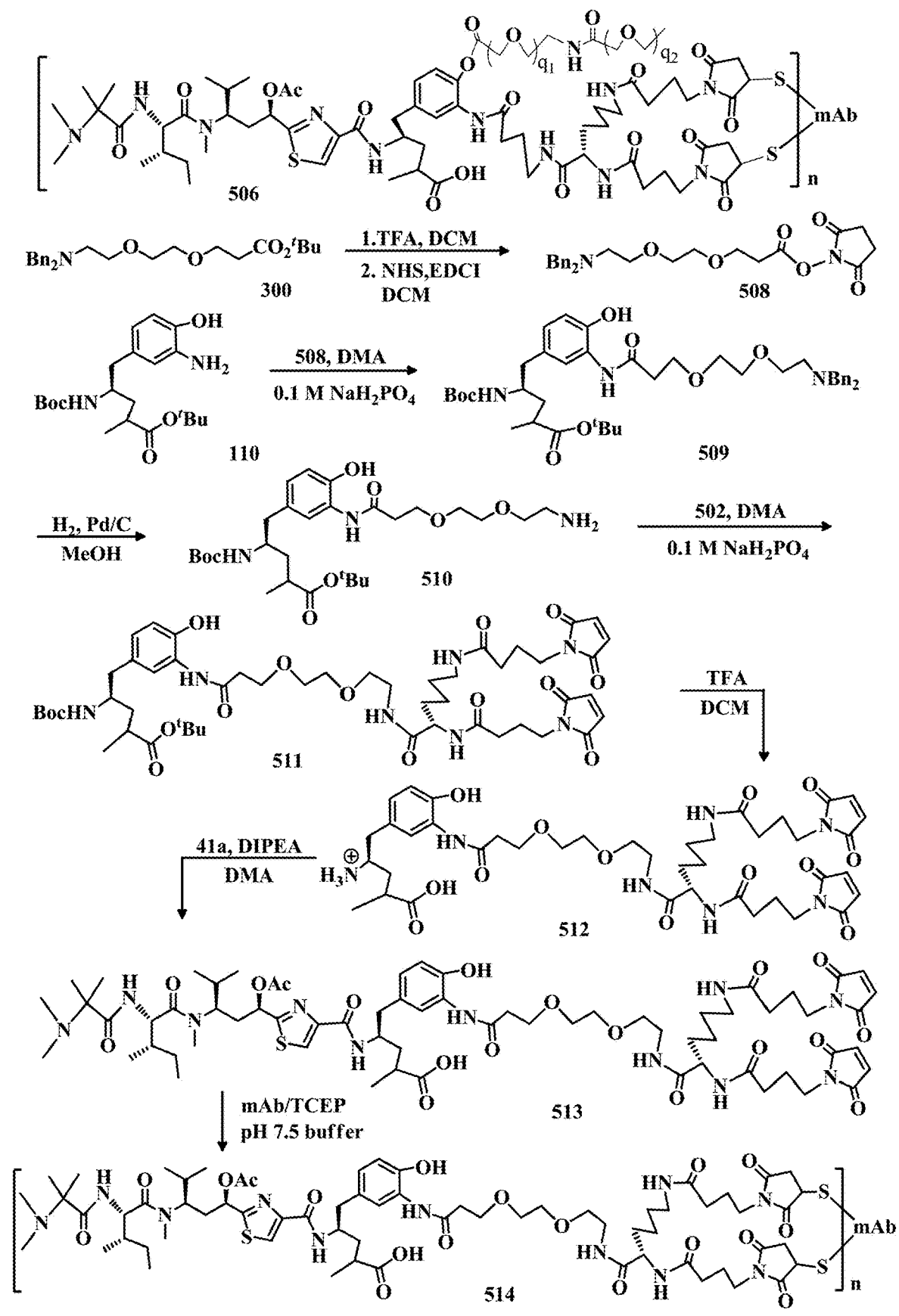
FIG. 42 shows the synthesis of a Tubulysin analog.
Figure 43:
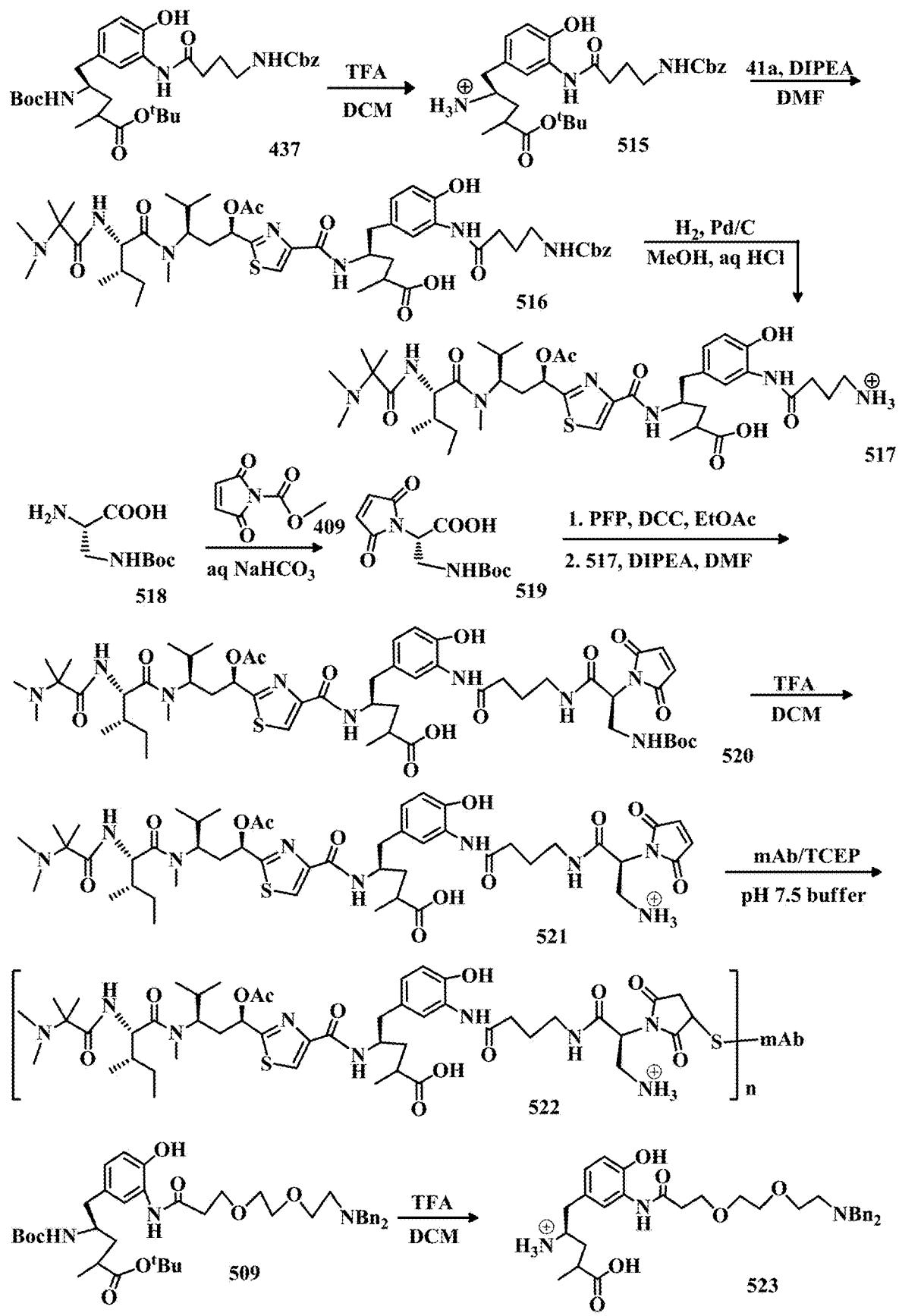
FIG. 43 shows the synthesis of a Tubulysin analog.
Figure 44:
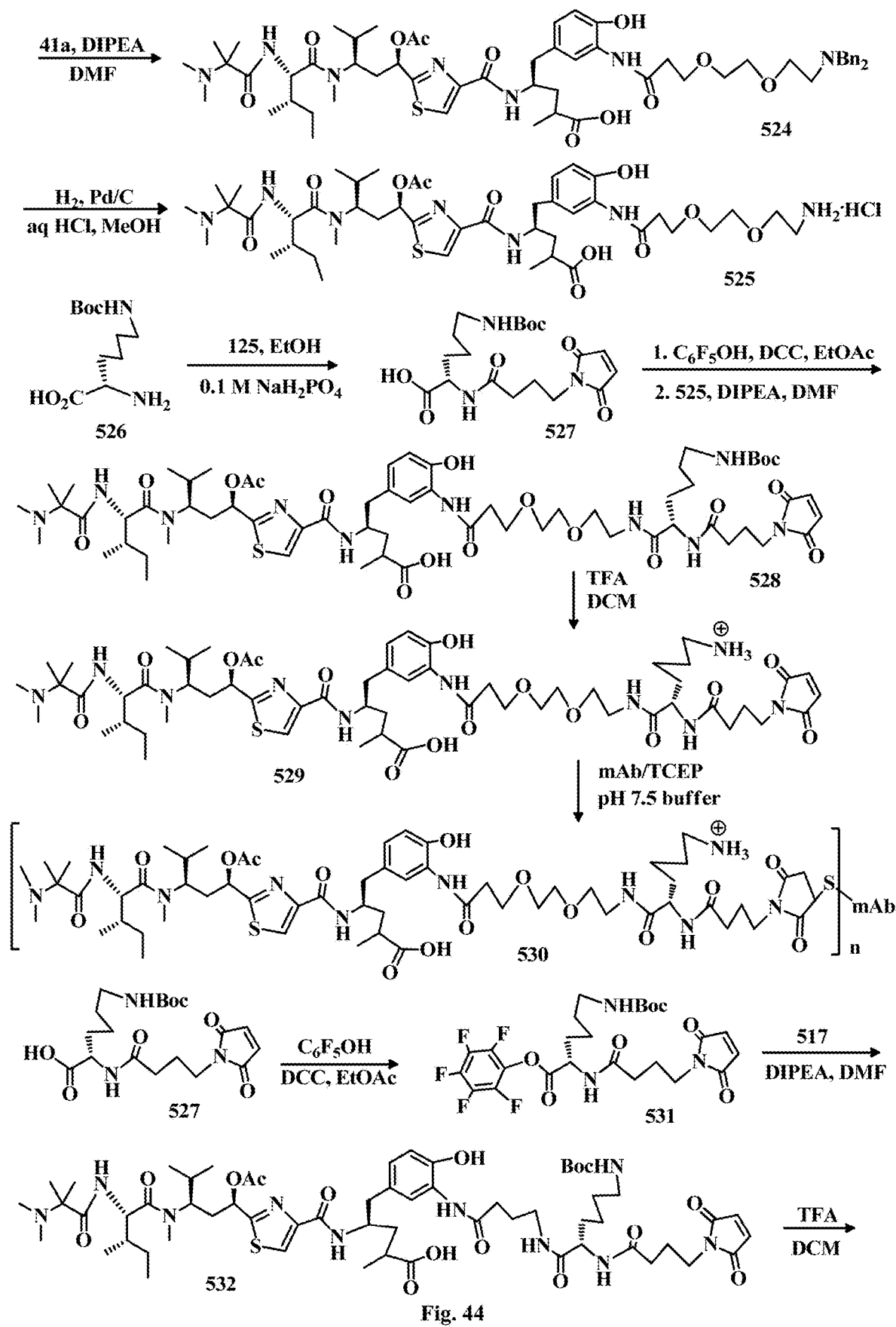
FIG. 44 shows the synthesis of a Tubulysin analog.
Figure 45:
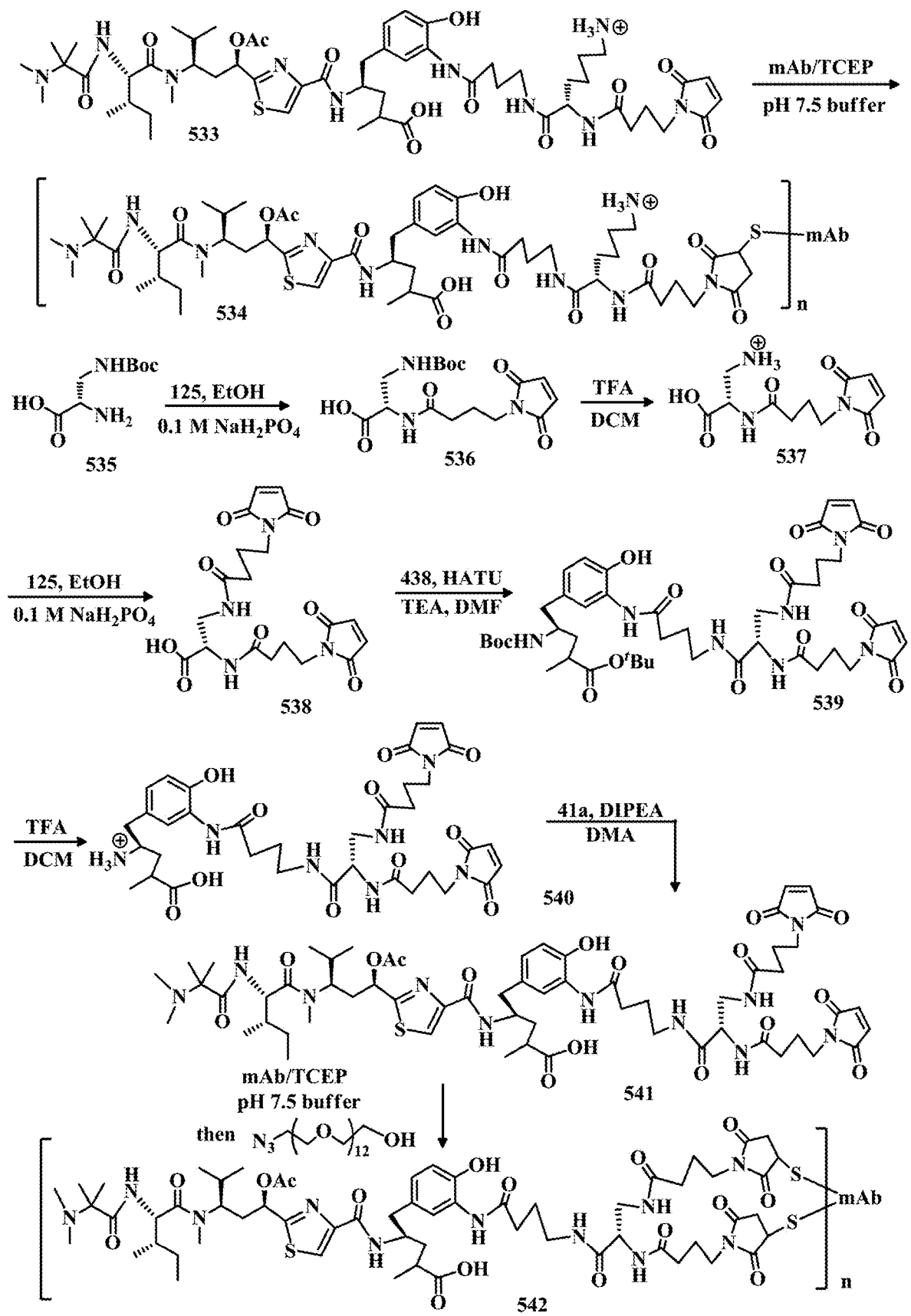
FIG. 45 shows the synthesis of a Tubulysin analog and its conjugation to an antibody.
Figure 46:
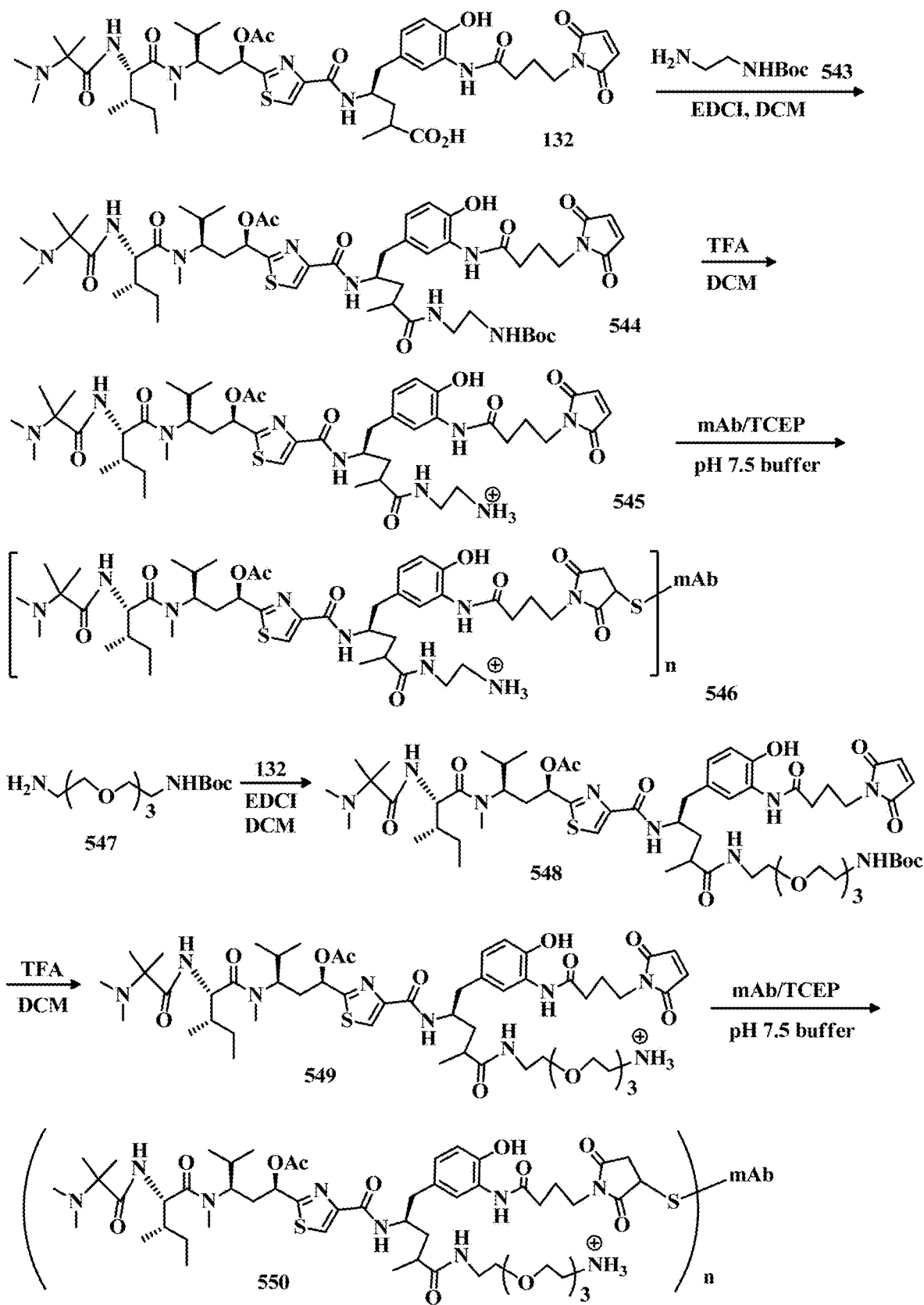
FIG. 46 shows the synthesis of a Tubulysin analog and its conjugation to an antibody.
Figure 47:
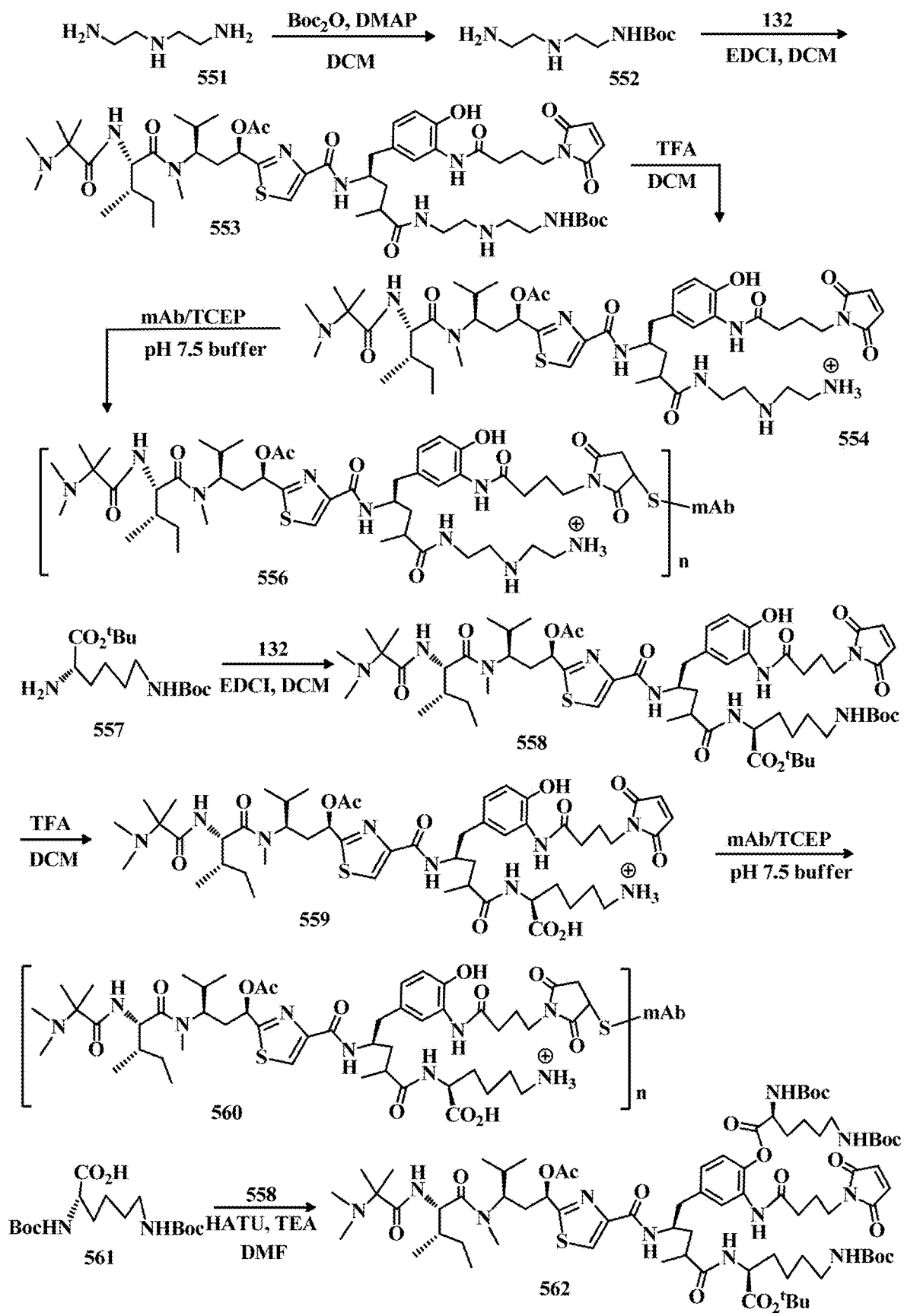
FIG. 47 shows the synthesis of a Tubulysin analog.
Figure 48:
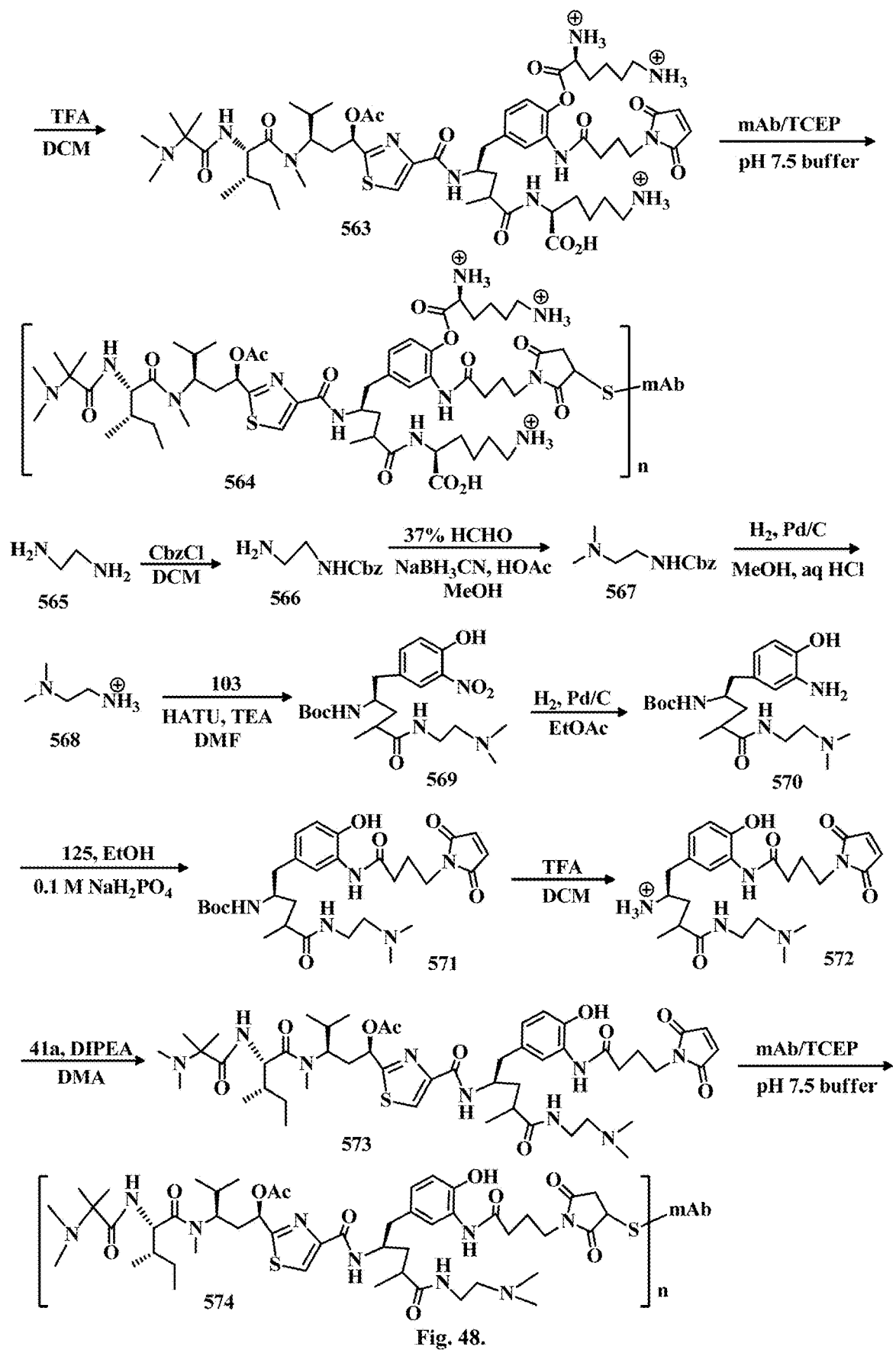
FIG. 48 shows the synthesis of a Tubulysin analog and its conjugation to an antibody.
Figure 49:
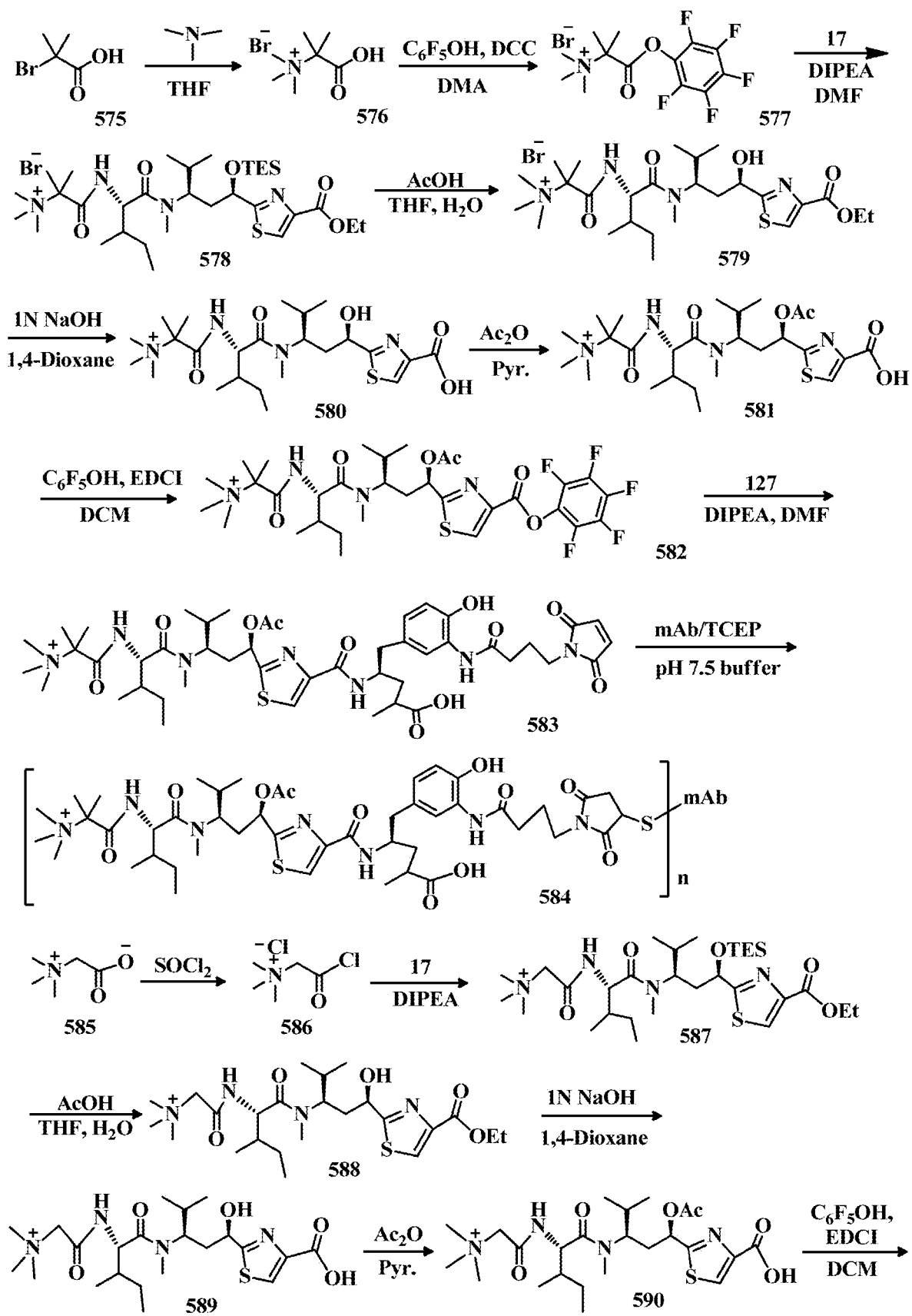
FIG. 49 shows the synthesis of a Tubulysin analog and its conjugation to an antibody.
Figure 50:
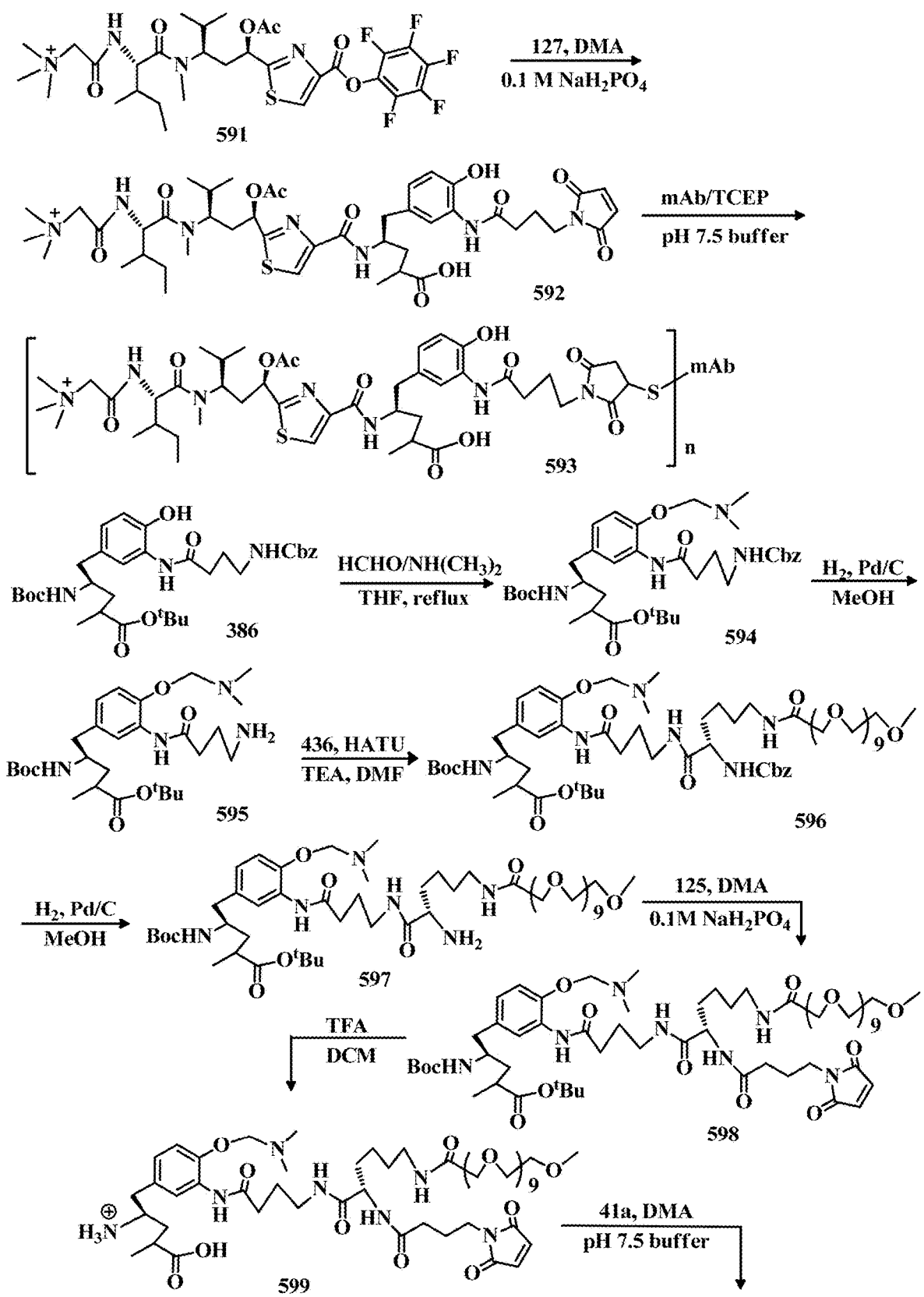
FIG. 50 shows the synthesis of a Tubulysin analog containing a side-chain linker and its conjugation to an antibody.
Figure 51:
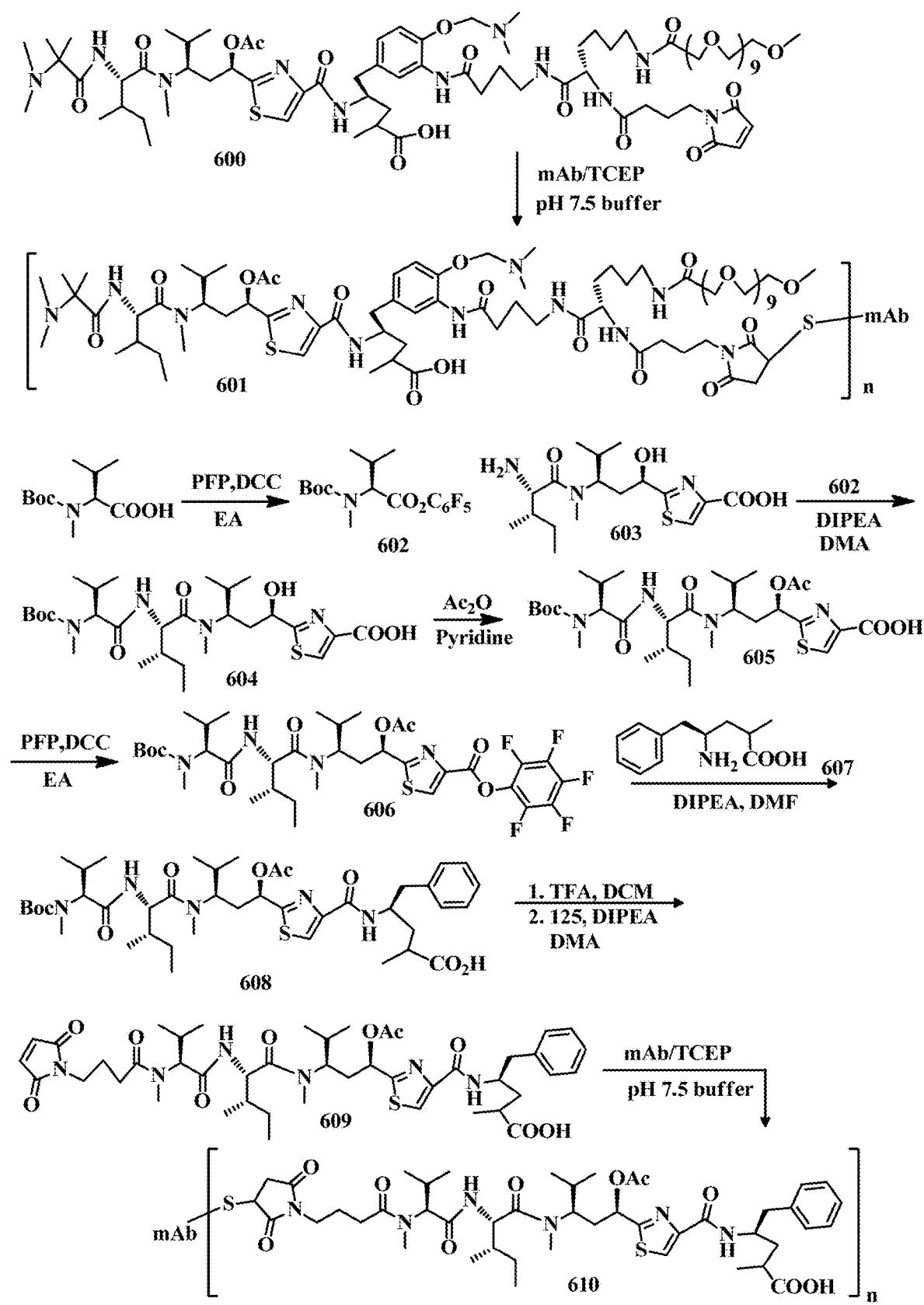
FIG. 51 shows the synthesis of a Tubulysin analog and its conjugation to an antibody.
Figure 52:
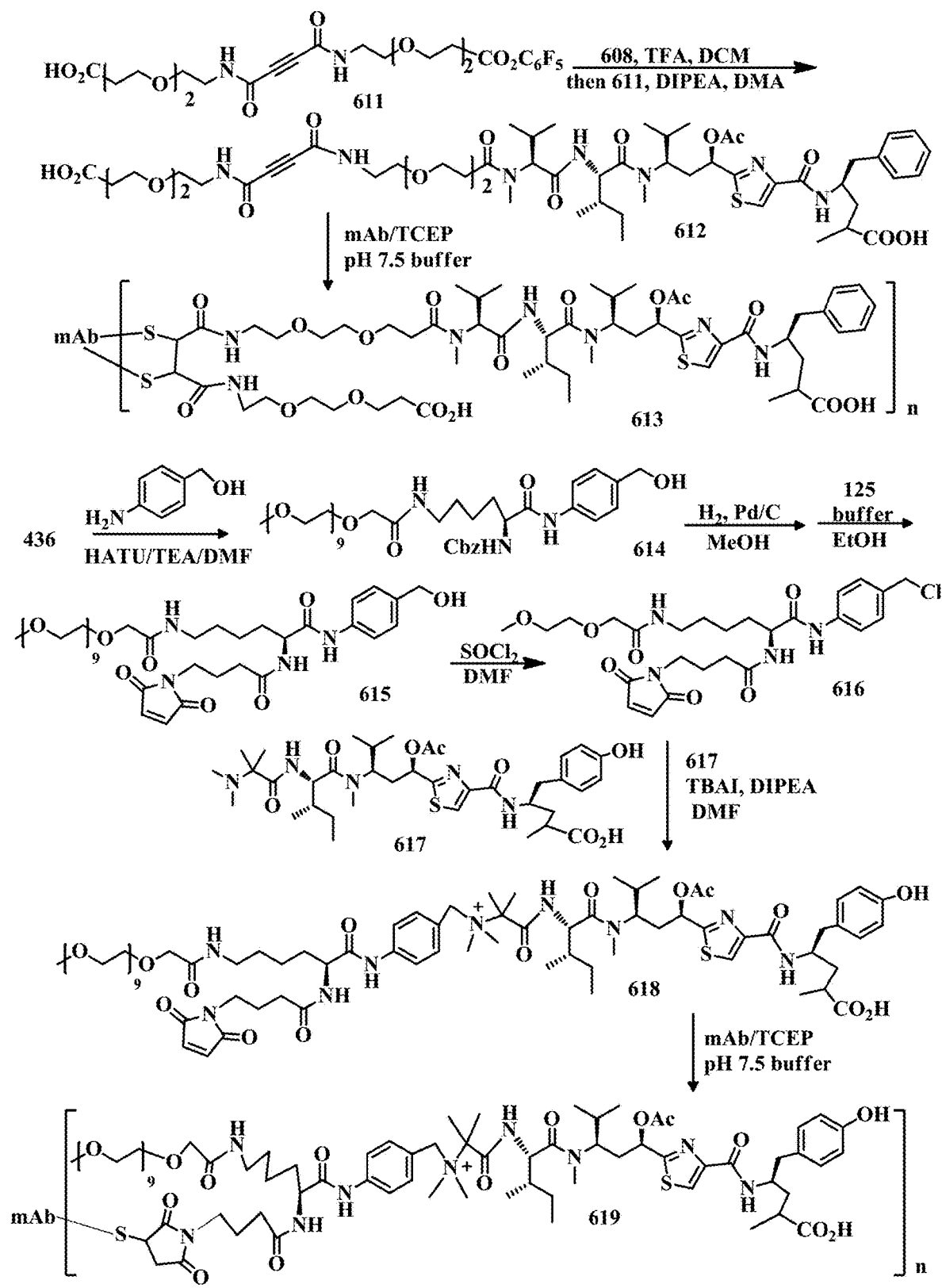
FIG. 52 shows the synthesis of a Tubulysin analog containing a side-chain linker and its conjugation to an antibody.
Figure 53:
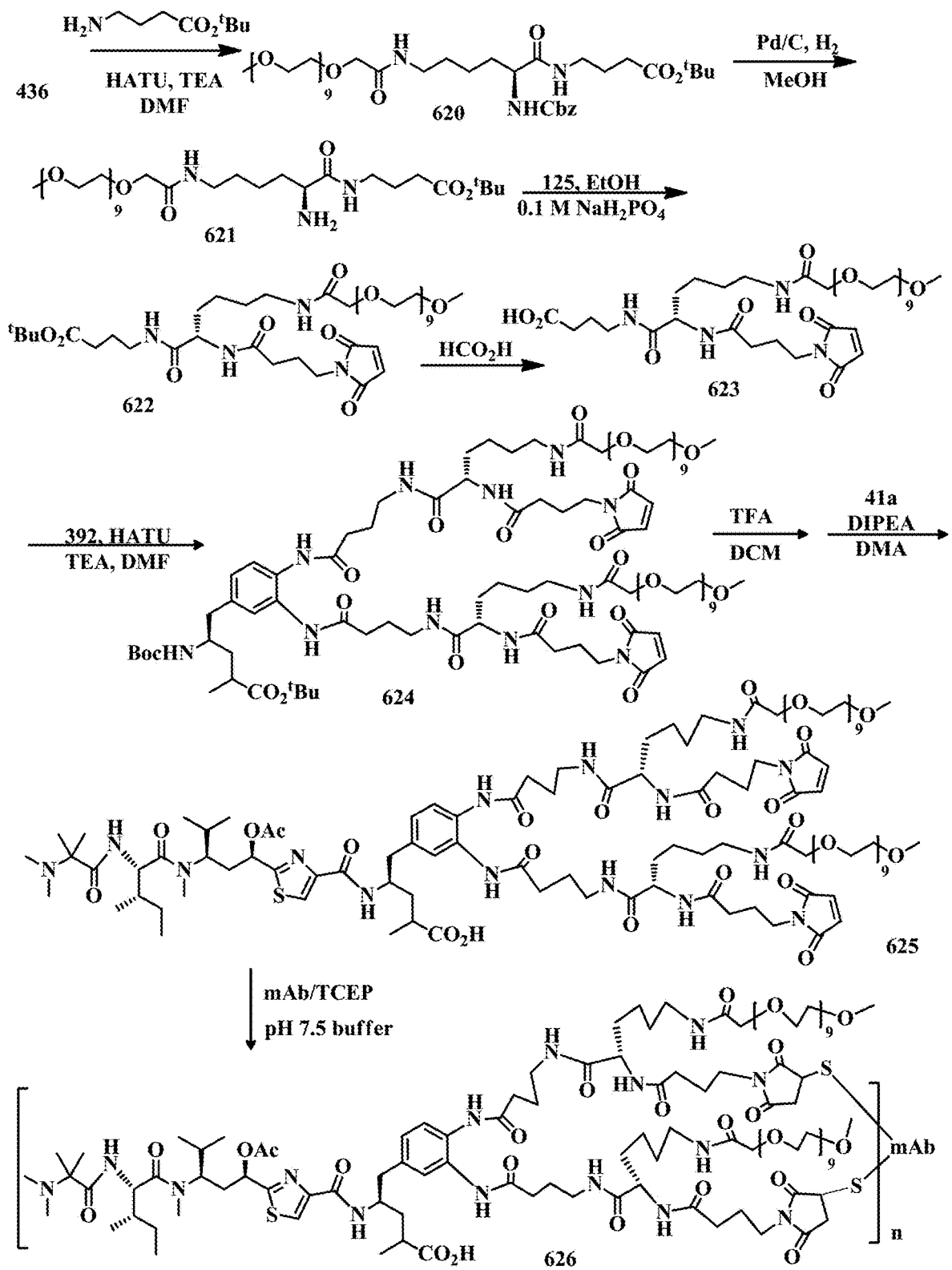
FIG. 53 shows the synthesis of Tubulysin analogs containing side-chain linkers and their conjugations to an antibody via a pair of thiols in the antibody.
Figure 54:
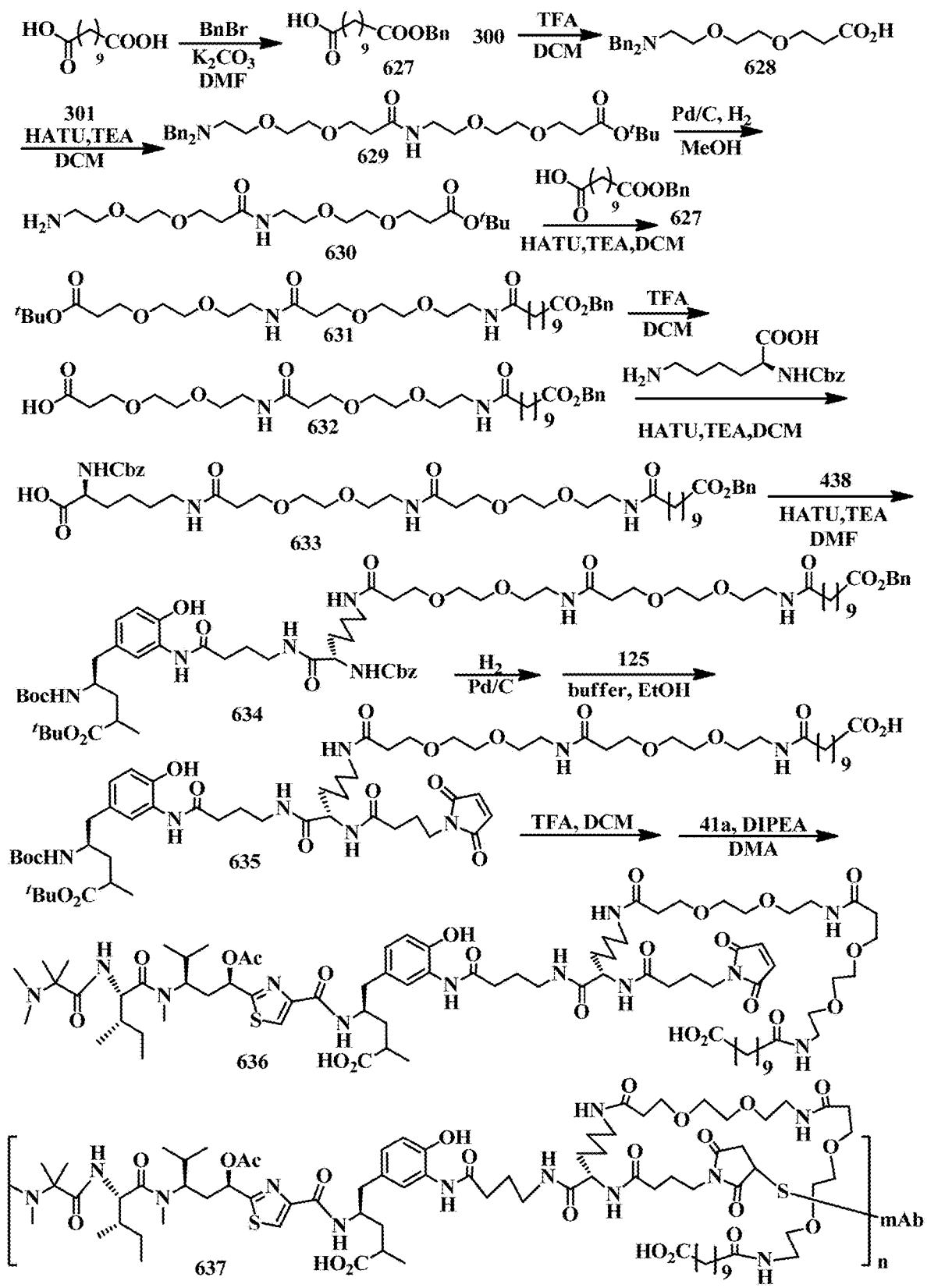
FIG. 54 shows the synthesis of a Tubulysin analog containing a side-chain linker and its conjugations to an antibody.
Figure 55:
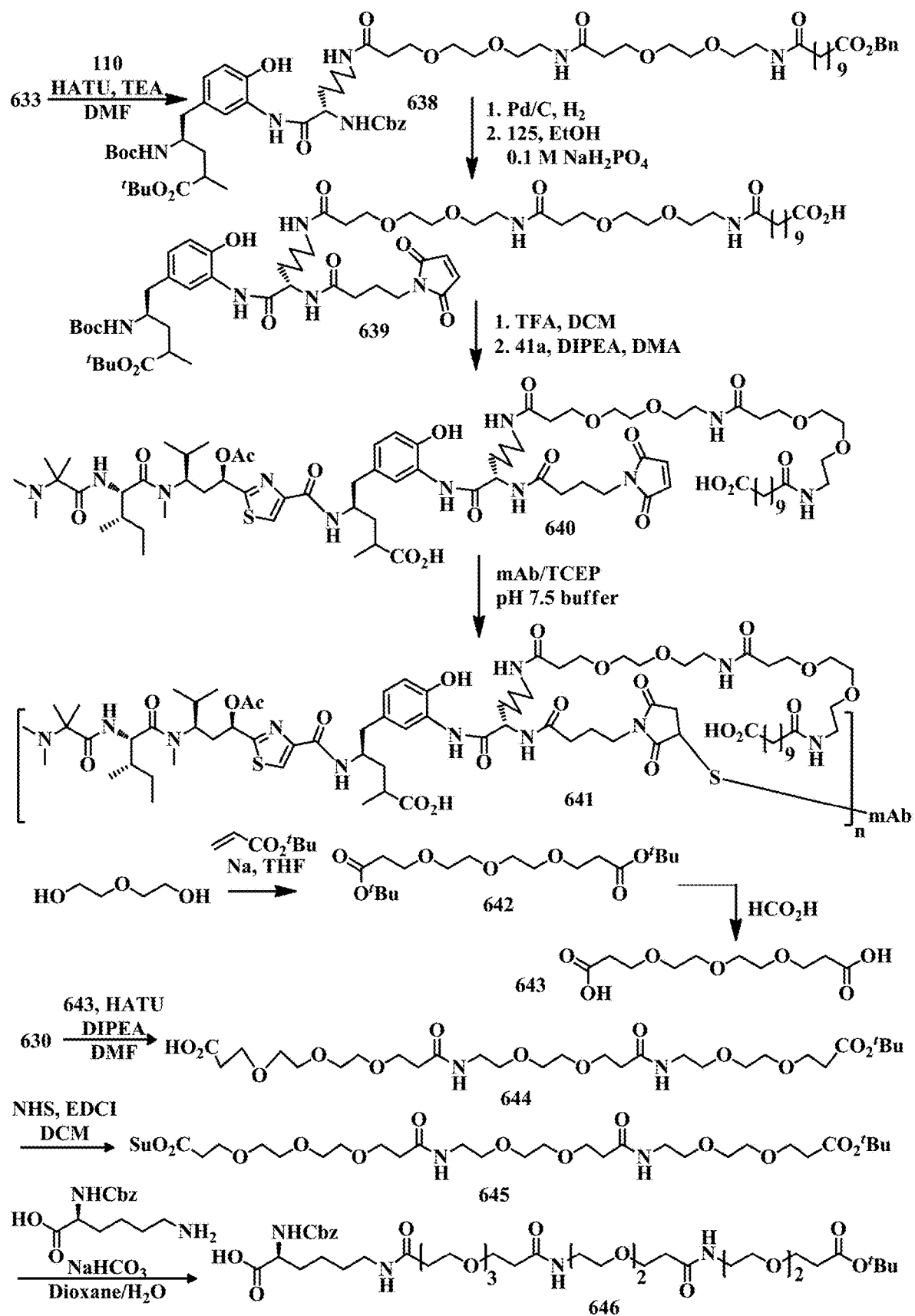
FIG. 55 shows the synthesis of a Tubulysin analog containing a side-chain linker to an antibody.
Figure 56:
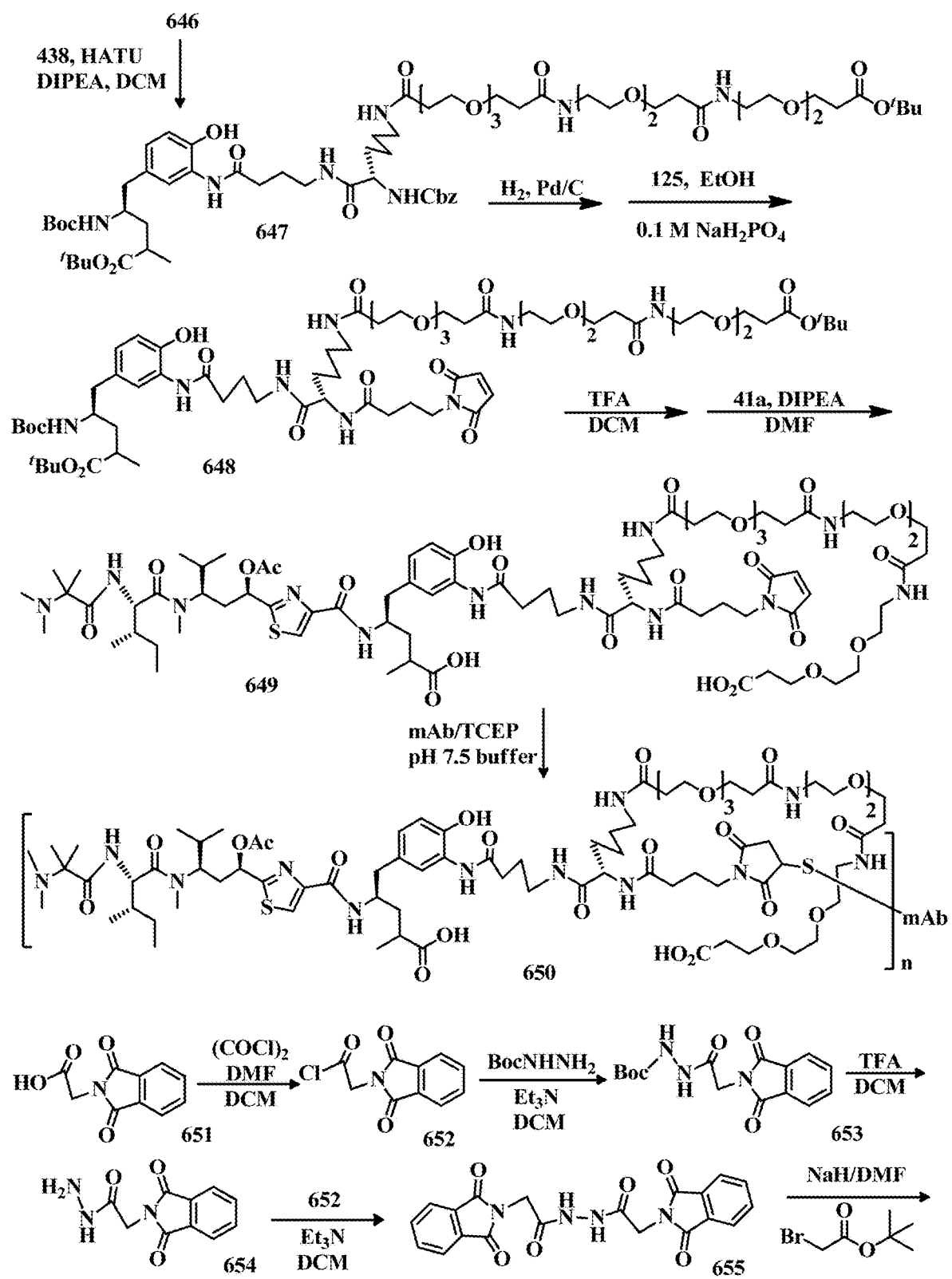
FIG. 56 shows the synthesis of a Tubulysin analog containing a side-chain linker and its conjugation to an antibody.
Figure 57:
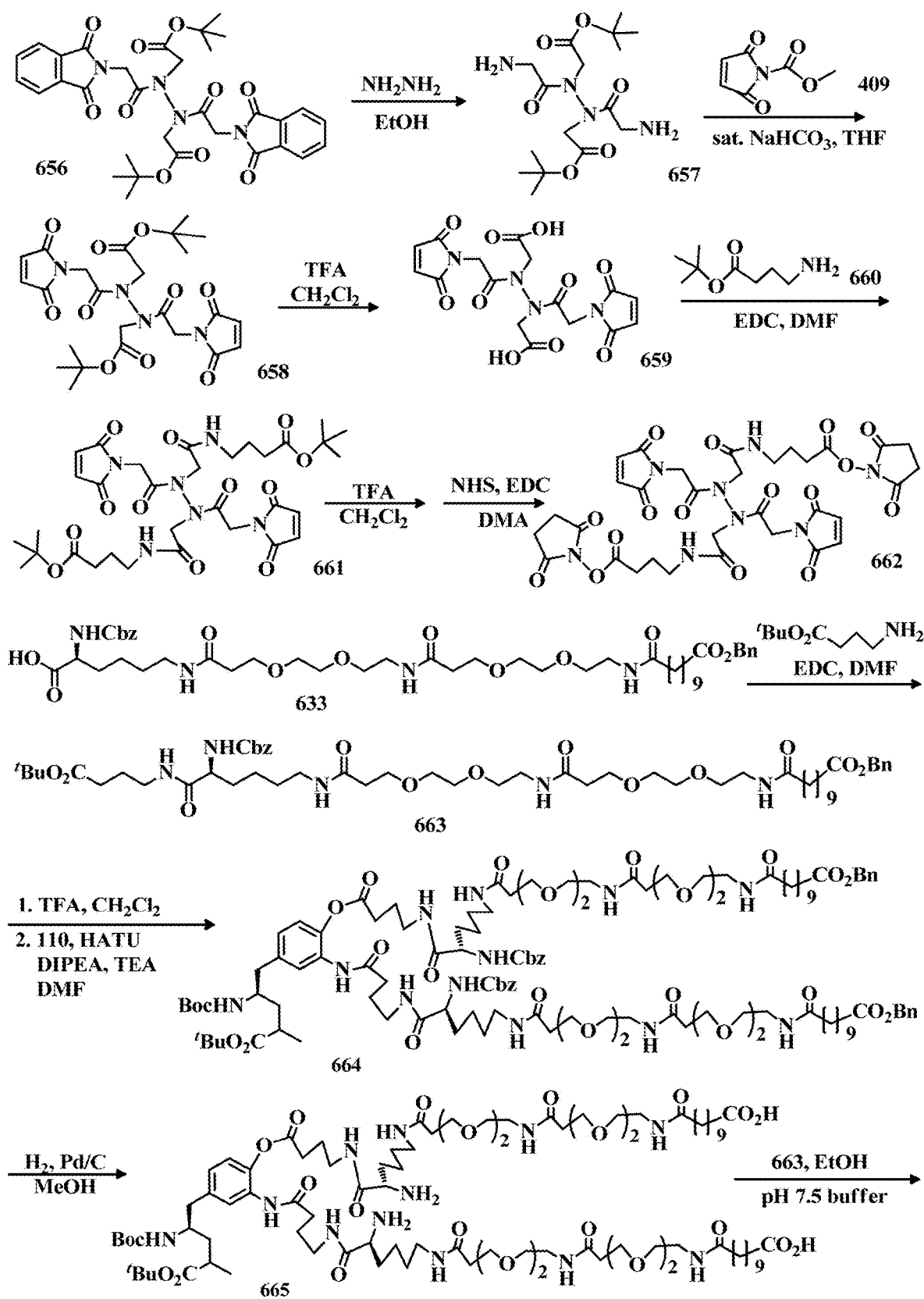
FIG. 57 shows the synthesis of a Tubulysin analog containing a side-chain linker.
Figure 58:
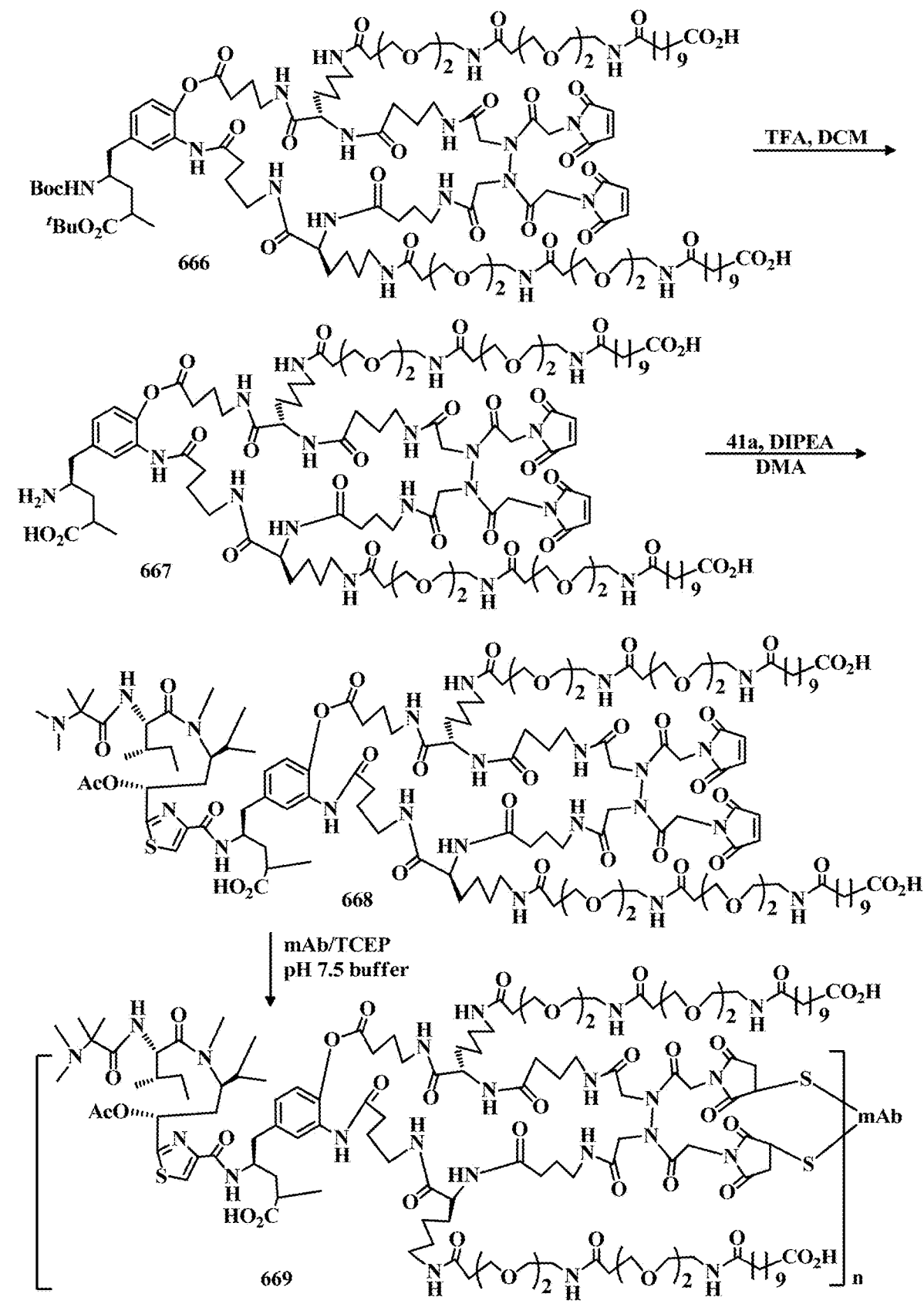
FIG. 58 shows the synthesis of Tubulysin analogs containing side-chain linkers and their conjugations to an antibody via a pair of thiols in the antibody.
Figure 59:
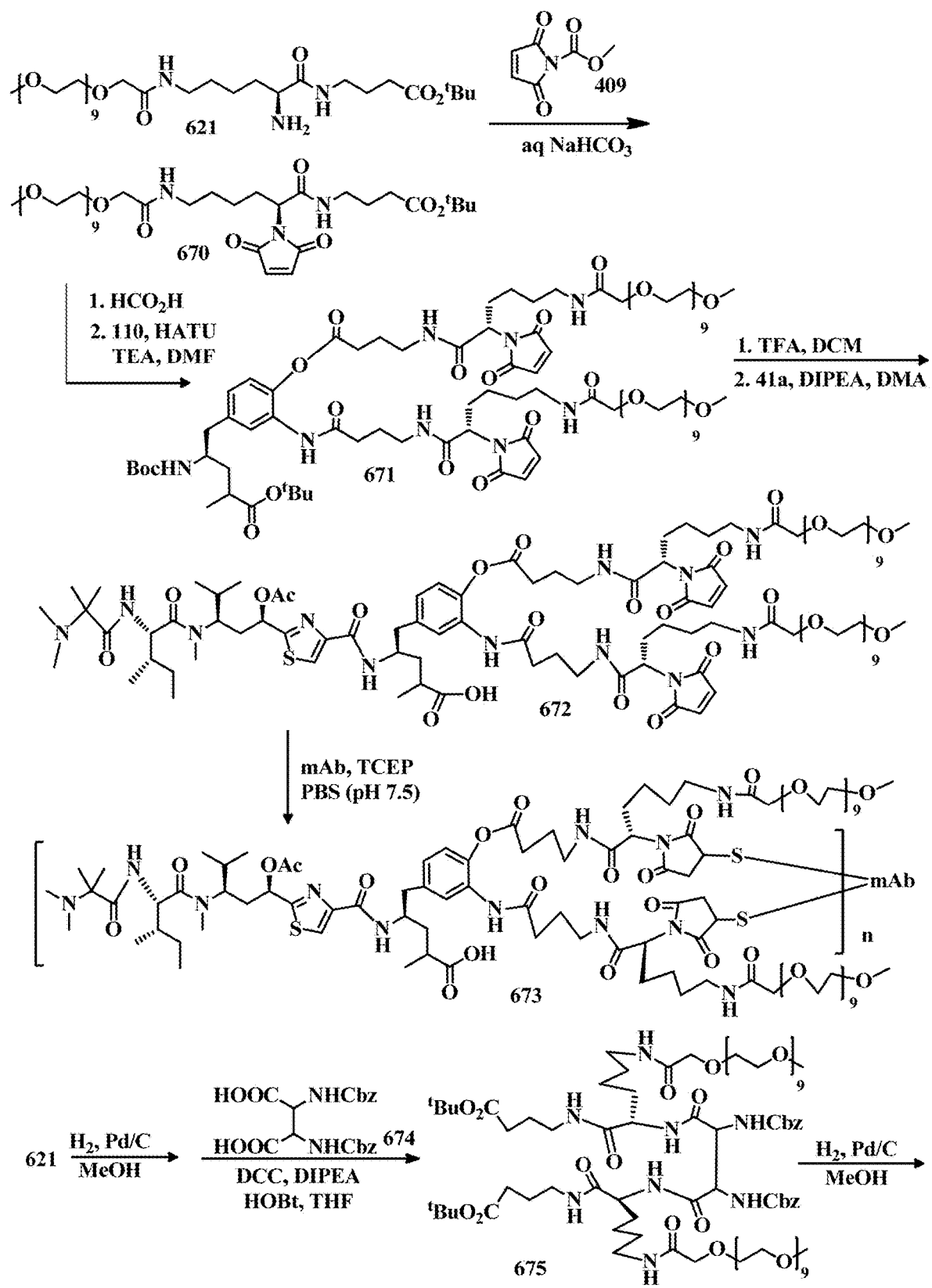
FIG. 59 shows the synthesis of Tubulysin analogs containing side-chain linkers and their conjugations to an antibody via a pair of thiols in the antibody.
Figure 60:
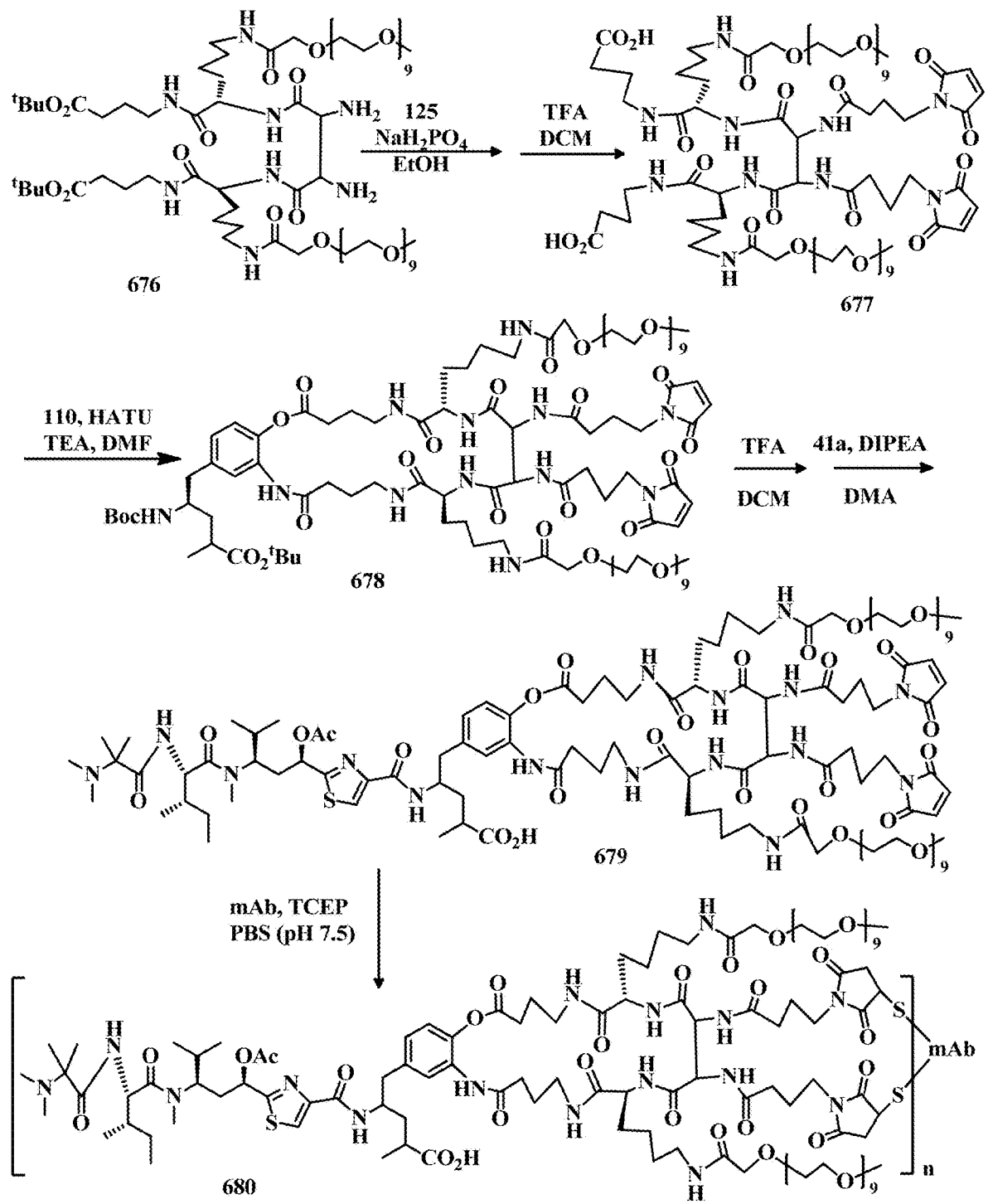
FIG. 60 shows the synthesis of Tubulysin analogs containing side-chain linkers and their conjugations to an antibody via a pair of thiols in the antibody.
Figure 61:
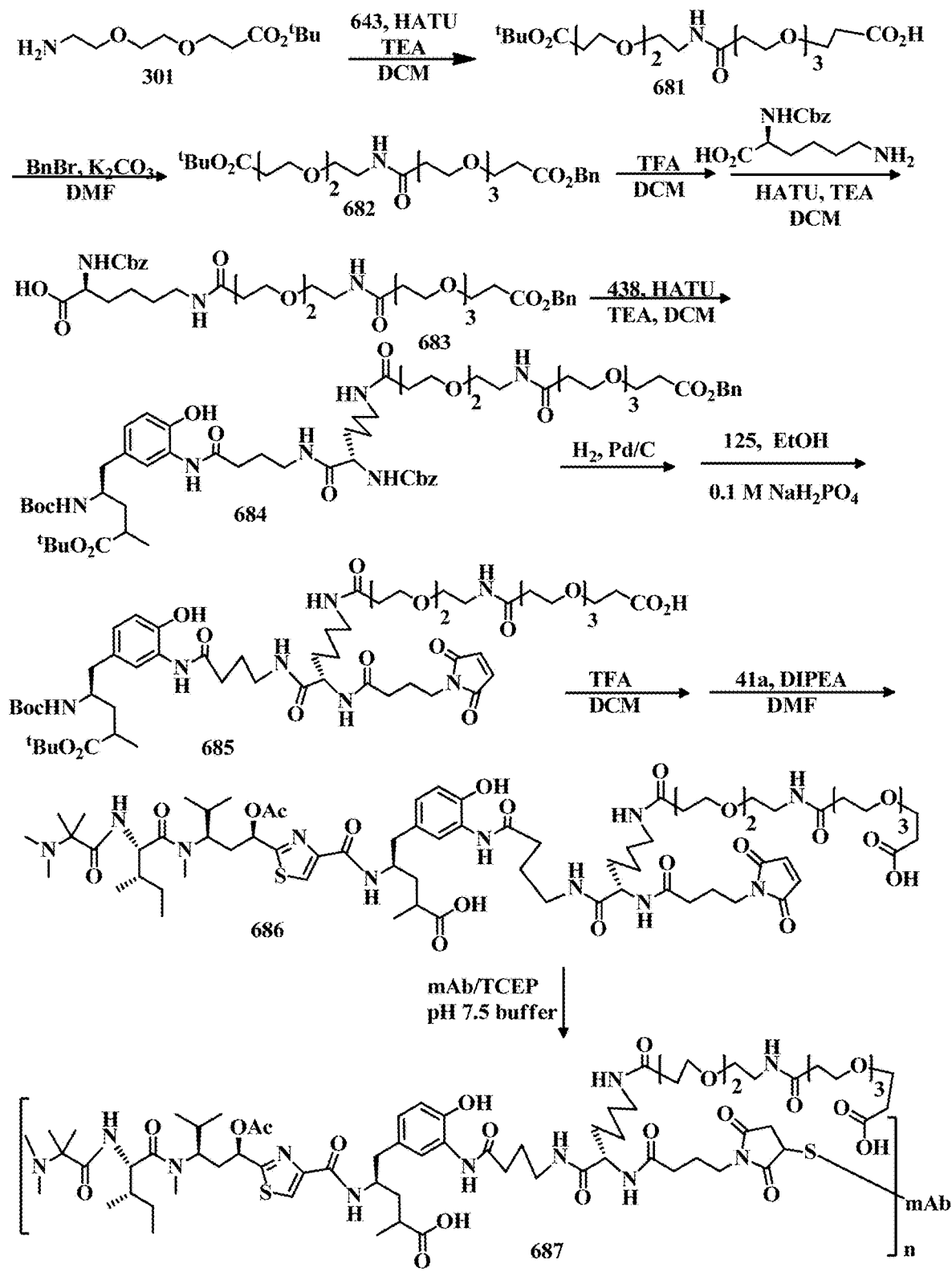
FIG. 61 shows the synthesis of a Tubulysin analog containing a side-chain linker and its conjugation to an antibody.
Figure 62:
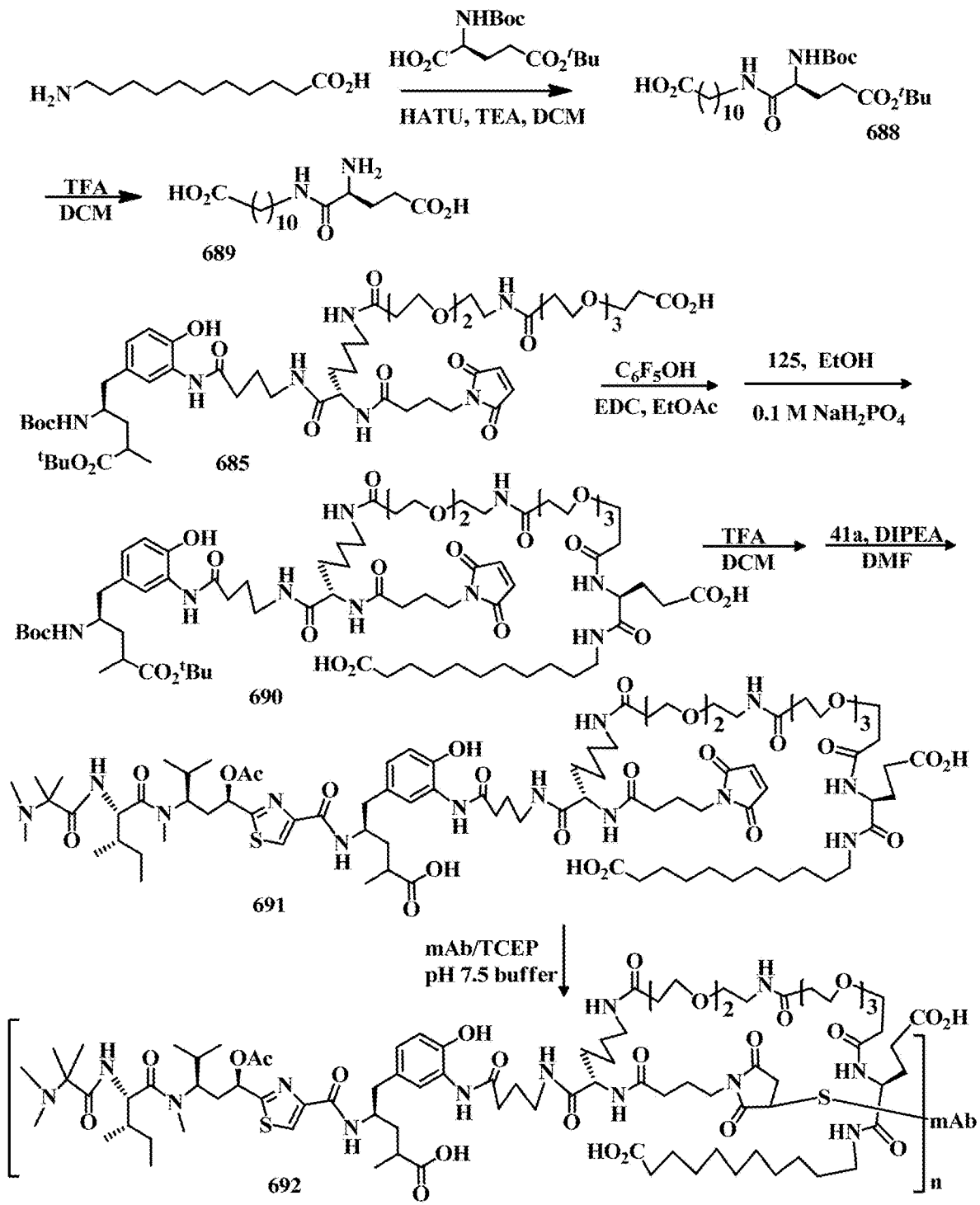
FIG. 62 shows the synthesis of a Tubulysin analog containing a side-chain linker and its conjugation to an antibody.

"Alkyl" refers to an aliphatic hydrocarbon group or univalent groups derived from alkane by removal of one or two hydrogen atoms from carbon atoms. It may be straight or branched having $C_1$-$C_8$ (1 to 8 carbon atoms) in the chain. "Branched" means that one or more lower C numbers of alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl, cyclopentyl, cyclohexyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SR', —S(O)$_2$R', —S(O)R', —OH, -halogen, —N$_3$, —NH$_2$, —NH(R'), —N(R') 2 and —CN; where each R' is independently selected from —$C_1$-$C_8$ alkyl and aryl.

"Halogen" refers to fluorine, chlorine, bromine or iodine atom; preferably fluorine and chlorine atom.

"Heteroalkyl" refers to $C_2$-$C_8$ alkyl in which one to four carbon atoms are independently replaced with a heteroatom from the group consisting of O, S and N.

"Carbocycle" refers to a saturated or unsaturated ring having 3 to 8 carbon atoms as a monocycle or 7 to 13 carbon atoms as a bicycle. Monocyclic carbocycles have 3 to 6 ring atoms, more typically 5 or 6 ring atoms. Bicyclic carbocycles have 7 to 12 ring atoms, arranged as a bicycle [4,5], [5,5], [5,6] or [6,6] system, or 9 or 10 ring atoms arranged as a bicycle [5,6] or [6,6] system. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl.

A "$C_3$-$C_8$ carbocycle" refers to a 3-, 4-, 5-, 6-, 7- or 8-membered saturated or unsaturated nonaromatic carbocyclic ring. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SR', —S(O)R', —S(O)$_2$R', —OH, -halogen, —N$_3$, —NH$_2$, —NH(R'), —N(R') 2 and —CN; where each R' is independently selected from —$C_1$-$C_8$ alkyl and aryl.

"Alkenyl" refers to an aliphatic hydrocarbon group containing a carbon-carbon double bond which may be straight or branched having 2 to 8 carbon atoms in the chain. Exemplary alkenyl groups include ethenyl, propenyl, n-butenyl, i-butenyl, 3-methylbut-2-enyl, n-pentenyl, hexylenyl, heptenyl, octenyl.

"Alkynyl" refers to an aliphatic hydrocarbon group containing a carbon-carbon triple bond which may be straight or branched having 2 to 8 carbon atoms in the chain. Exemplary alkynyl groups include ethynyl, propynyl, n-butynyl, 2-butynyl, 3-methylbutynyl, 5-pentynyl, n-pentynyl, hexylynyl, heptynyl, and octynyl.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—CH$_2$—), 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene, propargyl and 4-pentynyl.

"Aryl" or Ar refers to an aromatic or hetero aromatic group, composed of one or several rings, comprising three to fourteen carbon atoms, preferentially six to ten carbon atoms. The term of "hetero aromatic group" refers one or several carbon on aromatic group, preferentially one, two, three or four carbon atoms are replaced by O, N, Si, Se, P or S, preferentially by O, S, and N. The term aryl or Ar also refers to an aromatic group, wherein one or several H atoms are replaced independently by —R', -halogen, —OR', or —SR', —NR'R", —N=NR', —N=R', —NR'R", —N$_{02}$, —S(O)R', —S(O)$_2$R', —S(O)$_2$OR', —OS(O)$_2$OR', —PR'R", —P(O)R'R", —P(OR')(OR"), —P(O)(OR')(OR") or —OP(O)(OR')(OR") wherein R', R" are independently H, alkyl, alkenyl, alkynyl, heteroalkyl, aryl, arylalkyl, carbonyl, or pharmaceutical salts.

"Heterocycle" refers to a ring system in which one to four of the ring carbon atoms are independently replaced with a heteroatom from the group of O, N, S, Se, B, Si and P. Preferable heteroatoms are O, N and S. Heterocycles are also described in The Handbook of Chemistry and Physics, 78th Edition, CRC Press, Inc., 1997-1998, p. 225 to 226, the disclosure of which is hereby incorporated by reference. Preferred nonaromatic heterocyclic include epoxy, aziridinyl, thiiranyl, pyrrolidinyl, pyrazolidinyl, imidazolidinyl, oxiranyl, tetrahydrofuranyl, dioxolanyl, tetrahydropyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrimidinyl, dihydrothiopyranyl, azepanyl, as well as the fused systems resulting from the condensation with a phenyl group.

The term "heteroaryl" or aromatic heterocycles refers to a 3 to 14, preferably 5 to 10 membered aromatic hetero, mono-, bi-, or multi-cyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazolyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "alkenyl", "alkynyl", "aryl", "heteroaryl", "heterocyclic" and the like refer also to the corresponding "alkylene", "cycloalkylene", "alkenylene", "alkynylene", "arylene", "heteroarylene", "heterocyclene" and the likes which are formed by the removal of two hydrogen atoms.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

"Heteroarylalkyl" refers to an acyclic alkyl radical in which one of the hydrogen atoms bonded to a carbon atom, typically a terminal or sp$^3$ carbon atom, is replaced with a heteroaryl radical. Examples of heteroarylalkyl groups are 2-benzimidazolylmethyl, 2-furylethyl.

Examples of a "hydroxyl protecting group" includes, methoxymethyl ether, 2-methoxyethoxymethyl ether, tetrahydropyranyl ether, benzyl ether, p-methoxybenzyl ether, trimethylsilyl ether, triethylsilyl ether, triisopropylsilyl ether, t-butyldimethylsilyl ether, triphenylmethylsilyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, a halide (e.g., chloride, bromide, and iodide), methanesulfonyl (mesyl), p-toluenesulfonyl (tosyl), trifluoromethylsulfonyl (triflate), and trifluoromethylsulfonate. A preferred leaving group is selected from nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions or for Mitsunobu reactions.

The following abbreviations may be used herein and have the indicated definitions: Boc, tert-butoxy carbonyl; BroP, bromotrispyrrolidinophosphonium hexafluorophosphate; CDI, 1,1'-carbonyldiimidazole; DCC, dicyclohexylcarbodiimide; DCE, dichloroethane; DCM, dichloromethane; DEAD is diethylazodicarboxylate, DIAD, diisopropylazodicarboxylate; DIBAL-H, diisobutyl-aluminium hydride; DIPEA or DEA, diisopropylethylamine; DEPC, diethyl phosphorocyanidate; DMA, N,N-dimethyl acetamide; DMAP, 4-(N, N-dimethylamino)pyridine; DMF, N,N-dimethylformamide; DMSO, dimethylsulfoxide; DTPA is diethylenetriaminepentaacetic acid; DTT, dithiothreitol; EDC, 1-(3-dimethylaminopropyl)-3-ethylcarbodiimide hydrochloride; ESI-MS, electrospray mass spectrometry; EtOAc is ethyl acetate; Fmoc is N-(9-fluorenylmethoxycarbonyl); HATU, O-(7-azabenzotriazol-1-yl)-N, N, N', N'-tetramethyluronium hexafluorophosphate; HOBt, 1-hydroxybenzotriazole; HPLC, high pressure liquid chromatography; NHS, N-Hydroxysuccinimide; MeCN is acetonitrile; MeOH is methanol; MMP, 4-methylmorpholine; PAB, p-aminobenzyl; PBS, phosphate-buffered saline (pH 7.0-7.5); Ph is phenyl; phe is L-phenylalanine; PyBrop is bromo-tris-pyrrolidino-phosphonium hexafluorophosphate; PEG, polyethylene glycol; SEC, size-exclusion chromatography; TCEP, tris(2-carboxyethyl)phosphine; TFA, trifluoroacetic acid; THF, tetrahydrofuran; Val, valine; TLC is thin layer chromatography; UV is ultraviolet.

The "amino acid(s)" can be natural and/or unnatural amino acids, preferably alpha-amino acids. Natural amino acids are those encoded by the genetic code, which are alanine, arginine, asparagine, aspartic acid, cysteine, glutamic acid, glutamine, glycine, histidine, isoleucine, leucine, lysine, methionine, phenylalanine, proline, serine, threonine, tyrosine, tryptophan and valine. The unnatural amino acids are derived forms of proteinogenic amino acids. Examples include hydroxyproline, lanthionine, 2-aminoisobutyric acid, dehydroalanine, gamma-aminobutyric acid (the neurotransmitter), ornithine, citrulline, beta alanine (3-aminopropanoic acid), gamma-carboxyglutamate, selenocysteine (present in many noneukaryotes as well as most eukaryotes, but not coded directly by DNA), pyrrolysine (found only in some archaea and one bacterium), N-formylmethionine (which is often the initial amino acid of proteins in bacteria, mitochondria, and chloroplasts), 5-hydroxytryptophan, L-dihydroxyphenylalanine, triiodothyronine, L-3,4-dihydroxyphenylalanine (DOPA), and O-phosphoserine. The term amino acid also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. Preferably, an amino acid mimetic is a compound that has a structure different from the general chemical structure of an alpha-amino acid but functions in a manner similar to one. The term "unnatural amino acid" is intended to represent the "D" stereochemical form, the natural amino acids being of the "L" form. When 1-8 amino acids are used in this patent application, amino acid sequence is then preferably a cleavage recognition sequence for a protease. Many cleavage recognition sequences are known in the art. See, e.g., Matayoshi et al. Science 247: 954 (1990); Dunn et al. Meth. Enzymol. 241: 254 (1994); Seidah et al. Meth. Enzymol. 244: 175 (1994); Thornberry, Meth. Enzymol. 244: 615 (1994); Weber et al. Meth. Enzymol. 244: 595 (1994); Smith et al. Meth. Enzymol. 244: 412 (1994); and Bouvier et al. Meth. Enzymol. 248: 614 (1995); the disclosures of which are incorporated herein by reference. In particular, the sequence is selected from the group consisting of Val-Cit, Ala-Val, Ala-Ala, Val-Val, Val-Ala-Val, Lys-Lys, Ala-Asn-Val, Val-Leu-Lys, Cit-Cit, Val-Lys, Ala-Ala-Asn, Asp-Lys, Asp-Glu, Glu-Lys, Lys, Cit, Ser, and Glu.

The "glycoside" is a molecule in which a sugar group is bonded through its anomeric carbon to another group via a glycosidic bond. Glycosides can be linked by an O— (an O-glycoside), N— (a glycosylamine), S— (a thioglycoside), or C— (a C-glycoside) glycosidic bond. Its core the empirical formula is $C_m(H_2O)_n$ (where m could be different from n, and m and n are <36), Glycoside herein includes glucose (dextrose), fructose (levulose) allose, altrose, mannose, gulose, iodose, galactose, talose, galactosamine, glucosamine, sialic acid, N-acetylglucosamine, sulfoquinovose (6-deoxy-6-sulfo-D-glucopyranose), ribose, arabinose, xylose, lyxose, sorbitol, mannitol, sucrose, lactose, maltose, trehalose, maltodextrins, raffinose, Glucuronic acid (glucuronide), and stachyose. It can be in D form or L form, 5 atoms cyclic furanose forms, 6 atoms cyclic pyranose forms, or acyclic form, α-isomer (the —OH of the anomeric carbon below the plane of the carbon atoms of Haworth projection), or a β-isomer (the —OH of the anomeric carbon above the plane of Haworth projection). It is used herein as a monosaccharide, disaccharide, polyols, or oligosaccharides containing 3-6 sugar units.

The term "antibody," as used herein, refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g. IgG, IgE, IgM, IgD, IgA and IgY), class (e.g., IgG1, IgG2, IgG3, IgG4, IgA1 and IgA2) or subclass of immunoglobulin molecule. The immunoglobulins can be derived from any species. Preferably, however, the immunoglobulin is of human, murine, or rabbit origin. Antibodies useful in the invention are preferably monoclonal, and include, but are not limited to, polyclonal, monoclonal, bispecific, human, humanized or chimeric antibodies, single chain antibodies, Fv, Fab fragments, F(ab') fragments, F(ab')$_2$ fragments, fragments produced by a Fab expression library, anti-idiotypic (anti-Id) antibodies, CDR's, and epitope-binding fragments of any of the above which immunospecifically bind to cancer cell antigens, viral antigens or microbial antigens.

An "enantiomer", also known as an "optical isomer", is one of two stereoisomers that are mirror images of each other that are non-superposable (not identical), much as one's left and right hands are the same except for being reversed along one axis (the hands cannot be made to appear identical simply by reorientation). A single chiral atom or similar structural feature in a compound causes that compound to have two possible structures which are non-superposable, each a mirror image of the other. The presence of multiple chiral features in a given compound increases the number of geometric forms possible, though there may be some perfect-mirror-image pairs.

Enantiopure compounds refer to samples having, within the limits of detection, molecules of only one chirality. When present in a symmetric environment, enantiomers have identical chemical and physical properties except for their ability to rotate plane-polarized light (+/−) by equal amounts but in opposite directions (although the polarized light can be considered an asymmetric medium). They are sometimes called optical isomers for this reason. A mixture of equal parts of an optically active isomer and its enantiomer is termed racemic and has zero net rotation of plane-polarized light because the positive rotation of each (+) form is exactly counteracted by the negative rotation of a (−) one. Enantiomer members often have different chemical reactions with other enantiomer substances. Since many biological molecules are enantiomers, there is sometimes a marked difference in the effects of two enantiomers on biological organisms. In drugs, for example, often only one of a drug's enantiomers is responsible for the desired physiologic effects, while the other enantiomer is less active, inactive, or sometimes even productive of adverse effects. Owing to this discovery, drugs composed of only one enantiomer ("enantiopure") can be developed to enhance the pharmacological efficacy and sometimes eliminate some side effects.

Isotopes are variants of a particular chemical element which differs in neutron number. All isotopes of a given element have the same number of protons in each atom. Each atomic number identifies a specific element, but not the isotope; an atom of a given element may have a wide range in its number of neutrons. The number of nucleons (both protons and neutrons) in the nucleus is the atom's mass number, and each isotope of a given element has a different mass number. For example, carbon-12, carbon-13 and carbon-14 are three isotopes of the element carbon with mass numbers 12, 13 and 14 respectively. The atomic number of carbon is 6, which means that every carbon atom has 6 protons, so that the neutron numbers of these isotopes are 6, 7 and 8 respectively. Hydrogen atom has three isotopes of protium ($^1H$), deuterium ($^2H$), and tritium ($^3H$), which deuterium has twice the mass of protium and tritium has three times the mass of protium. Isotopic substitution can be used to determine the mechanism of a chemical reaction and via the kinetic isotope effect. Isotopic substitution can be used to study how the body affects a specific xenobiotic/chemical after administration through the mechanisms of absorption and distribution, as well as the metabolic changes of the substance in the body (e.g. by metabolic enzymes such as cytochrome P450 or glucuronosyltransferase enzymes), and the effects and routes of excretion of the metabolites of the drug. This study is called pharmacokinetics (PK). Isotopic substitution can be used to study of the biochemical and physiologic effects of drugs. The effects can include those manifested within animals (including humans), microorganisms, or combinations of organisms (for example, infection). This study is called pharmacodynamics (PD). The effects can include those manifested within animals (including humans), microorganisms, or combinations of organisms (for example, infection). Both together influence dosing, benefit, and adverse effects of the drug. isotopes can contain a stable (non-radioactive) or an unstable element. Isotopic substitution of a drug may have a different thrapeutical efficacy of the original drug.

"Pharmaceutically" or "pharmaceutically acceptable" refer to molecular entities and compositions that do not produce an adverse, allergic or other untoward reaction when administered to an animal, or a human, as appropriate.

"Pharmaceutically acceptable solvate" or "solvate" refer to an association of one or more solvent molecules and a disclosed compound. Examples of solvents that form pharmaceutically acceptable solvates include, but are not limited to, water, isopropanol, ethanol, methanol, DMSO, ethyl acetate, acetic acid and ethanolamine.

"Pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions as suitable therapeutic combinations.

As used herein, "pharmaceutical salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucuronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutical salts of the present invention can be synthesized from the parent compound which contains a basic or acidic moiety by conventional chemical methods. Generally, such salts can be prepared via reaction the free acidic or basic forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, PA, 1985, p. 1418, the disclosure of which is hereby incorporated by reference.

"Administering" or "administration" refers to any mode of transferring, delivering, introducing or transporting a pharmaceutical drug or other agent to a subject. Such modes include oral administration, topical contact, intravenous, intraperitoneal, intramuscular, intralesional, intranasal, subcutaneous or intrathecal administration. Also contemplated by the present invention is utilization of a device or instrument in administering an agent. Such device may utilize active or passive transport and may be slow-release or fast-release delivery device.

In the context of cancer, the term "treating" includes any or all of: preventing growth of tumor cells or cancer cells, preventing replication of tumor cells or cancer cells, lessening of overall tumor burden and ameliorating one or more symptoms associated with the disease.

In the context of an autoimmune disease, the term "treating" includes any or all of: preventing replication of cells associated with an autoimmune disease state including, but not limited to, cells capable of producing an autoimmune antibody, lessening the autoimmune-antibody burden and ameliorating one or more symptoms of an autoimmune disease.

In the context of an infectious disease, the term "treating" includes any or all of: preventing the growth, multiplication or replication of the pathogen that causes the infectious disease and ameliorating one or more symptoms of an infectious disease.

Examples of a "mammal" or "animal" include, but are not limited to, a human, rat, mouse, guinea pig, monkey, pig, goat, cow, horse, dog, cat, bird and fowl.

The novel conjugates disclosed herein use the bridge linkers. Examples of some suitable linkers and their synthesis are shown in FIGS. 1 to 34.

A Conjugate of a Cell-Binding Agent-A Cytotoxic Molecule Via the Side Chain-Linkage In one aspect of the present invention, a conjugate containing a side chain-linkage is represented by Formula (I):

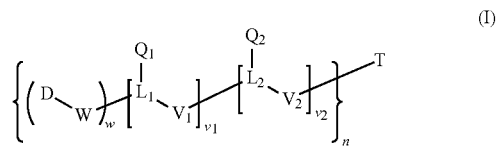

(I)

wherein

"—" represents a single bond; n is 1 to 30;

T is a cell-binding agent/molecule, selected from the group consisting of an antibody, a single chain antibody, an antibody fragment that binds to a target cell, a monoclonal antibody, a single chain monoclonal antibody, a monoclonal antibody fragment that binds to the target cell, a chimeric antibody, a chimeric antibody fragment that binds to the target cell, a domain antibody, a domain antibody fragment that binds to the target cell, an adnectin that mimics antibody, DARPins, a lymphokine, a hormone, a vitamin, a growth factor, a colony stimulating factor, a nutrient-transport molecule (a transferrin), and/or a cell-binding peptide, protein, or small molecule attached on albumin, a polymer, a dendrimer, a liposome, a nanoparticle, a vesicle, or on a (viral) capsid;

$L_1$ and $L_2$ are a chain of atoms selected from C, N, O, S, Si, and P, preferably having 0-500 atoms, which covalently connects to W and $V_1$, and $V_1$ and $V_2$. The atoms used in forming the $L_1$ and $L_2$ may be combined in all chemically relevant ways, such as forming alkylene, alkenylene, and alkynylene, ethers, polyoxyalkylene, esters, amines, imines, polyamines, hydrazines, hydrazones, amides, ureas, semicarbazides, carbazides, alkoxyamines, alkoxylamines, urethanes, amino acids, peptides, acyloxylamines, hydroxamic acids, or combination above thereof.

Preferably $L_1$ and $L_2$ are, the same or different, independently selected from O, NH, N, S, P, NNH, NHNH, N($R_3$), N($R_3$)N($R_{3'}$), CH, CO, C(O)NH, C(O)O, NHC(O)NH, NHC(O)O, polyethyleneoxy unit of formula $(OCH_2CH_2)_pOR_3$, or $(OCH_2CH-(CH_3))_pOR_3$, or $NH(CH_2CH_2O)_pR_3$, or $NH(CH_2CH(CH_3)O)_pR_3$, or $N[(CH_2CH_2O)_pR_3]$—$[(CH_2CH_2O)_pR_{3'}]$, or $(OCH_2CH_2)_pCOOR_3$, or $CH_2CH_2(OCH_2CH_2)_pCOOR_3$, wherein p and p' are independently an integer selected from 0 to about 1000, or combination thereof; $C_1$~$C_8$ of alkyl; $C_2$-$C_8$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or $(Aa)_r$, r=1-12(one to 12 amino acid units), which is composed from natural or unnatural amino acids, or the same or different sequences of dipeptide, tripeptide, tetrapeptide, pentapeptide, hexapeptide, heptapeptide, octapeptide, nonapeptide, decapeptide, undecapeptide or dodecapeptide unit;

W is a stretcher unit having $C_1$-$C_{18}$, normally a self-immolative spacer, a peptidic unit, a hydrazone, a disulfide, a thioether, an ester, or an amide bond; w is 1 or 2 or 3;

$V_1$ and $V_2$ are independently a spacer unit and selected from O, NH, S, $C_1$-$C_8$ alkyl, $C_2$-$C_8$ heteroalkyl, alkenyl, or alkynyl, $C_3$-$C_8$ aryl, heterocyclic, carbocyclic, cycloalkyl, alkylcycloalkyl, heterocycloalkyl, heteroaralkyl, heteroalkylcycloalkyl, or alkylcarbonyl, or $(Aa)_r$, r=1-12(one to 12 amino acid units), which is composed from a natural or unnatural amino acid, or the same or different sequences of dipeptide, tripeptide, tetrapeptide, pentapeptide, hexapeptide, heptapeptide, octapeptide, nonapeptide, decapeptide, undecapeptide or dodecapeptide unit; or $(CH_2CH_2O)_p$, p is 0-1000; and $v_1$ and $v_2$ are independently 0, 1 or 2, but $v_1$ and $v_2$ are 0 at the same time; when $v_1$ or $v_2$ is 0, it means one of the side chain $Q_1$ or $Q_2$ fragment is absent.

$Q_1$ and $Q_2$ are independently represented by Formula (I-q1):

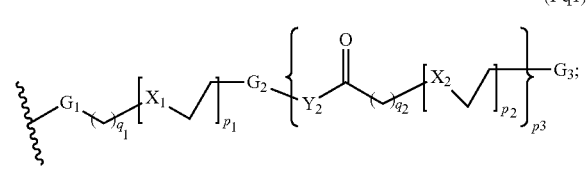

(I-q1)

wherein ～ is the site linked to $L_1$ or $L_2$; Gi and $G_2$ are independently OC(O), NHC(O), C(O), $CH_2$, NH, OC(O)NH, NHC(O)NH, O, S, B, P(O)(OH), NHP(O)(OH), NHP(O)(OH)NH, $CH_2P(O)(OH)NH$, OP(O)(OH)O, $CH_2P(O)(OH)O$, $NHS(O)_2$, $NHS(O)_2NH$, $CH_2S(O)_2NH$, $OS(O)_2O$, $CH_2S(O)_2O$, Ar, $ArCH_2$, ArO, ArNH, ArS, $ArNR_1$, or $(Aa)_{q1}$; $G_3$ is OH, SH, $OR_1$, $SR_1$, $OC(O)R_1$, $NHC(O)R_1$, $C(O)R_1$, $CH_3$, $NH_2$, $NR_1$, $^+NH(R_1)$, $^+N(R_1)(R_2)$, C(O)OH, $C(O)NH_2$, $NHC(O)NH_2$, $BH_2$, $BR_1R_2$, $P(O)(OH)_2$, $NHP(O)(OH)_2$, $NHP(O)(NH_2)_2$, $S(O)_2(OH)$, $(CH_2)_{q1}C(O)OH$, $(CH_2)_{q1}P(O)(OH)_2$, $C(O)(CH_2)_{q1}C(O)OH$, $OC(O)(CH_2)_{q1}C(O)OH$, $NHC(O)(CH_2)_{q1}C(O)OH$, $CO(CH_2)_{q1}P(O)(OH)_2$, $NHC(O)O(CH_2)_{q1}C(O)OH$, $OC(O)NH(CH_2)_{q1}C(O)OH$, $NHCO(CH_2)_{q1}P(O)(OH)_2$, $NHC(O)(NH)(CH_2)_{q1}C(O)OH$, $CONH(CH_2)_{q1}P(O)(OH)_2$, $NHS(O)_2(CH_2)_{q1}C(O)OH$, $CO(CH_2)_{q1}S(O)_2(OH)$, $NHS(O)_2NH(CH_2)_{q1}C(O)OH$, $OS(O)_2NH(CH_2)_{q1}C(O)OH$, $NHCO(CH_2)_{q1}S(O)_2(OH)$, $NHP(O)(OH)(NH)(CH_2)_{q1}C(O)OH$, $CONH(CH_2)_{q1}S(O)(OH)$, $OP(O)(OH)_2$, $(CH_2)_{q1}P(O)(NH_2)_2$, $NHS(O)_2(OH)$, $NHS(O)_2NH_2$, $CH_2S(O)_2NH_2$, $OS(O)_2OH$, $OS(O)_2OR_1$, $CH_2S(O)_2OR_1$, Ar, $ArR_1$, ArOH, $ArNH_2$, ArSH, $ArNHR_1$, or $(Aa)_{q1}$; $(Aa)_{q1}$ is a peptide containing the same or different sequence of natural or unnatural amino acids; $X_1$ and $X_2$ are independently O, $CH_2$, S, S(O), NHNH, NH, N($R_1$), $^+NH(R_1)$, $^+N(R_1)(R_2)$, C(O), OC(O), OC(O)O, OC(O)NH, NHC(O)NH; $Y_2$ is O. NH, $NR_1$, $CH_2$. S, NHNH, Ar; $p_1$, $p_2$ and $p_3$ are independently 0-100 but are not 0 at the same time; $q_1$ and $q_2$ are independently 0-24; $R_1$, $R_2$, $R_3$ and $R_{3'}$ are independently H, $C_1$~$C_8$ alkyl; $C_2$~$C_8$ heteroalkyl, or heterocyclic; $C_3$~$C_8$ aryl, Ar-alkyl, cycloalkyl, alkylcycloalkyl, heterocycloalkyl, heteroalkylcycloalkyl, carbocyclic, or alkylcarbonyl;

Preferably $Q_1$ and $Q_2$ are independently a $C_2$-$C_{100}$ polycarboxylacid, a $C_2$-$C_{90}$ polyalkylamine, a $C_6$-$C_{90}$ oligosaccharide or polysaccharide, a $C_6$-$C_{100}$ zwitterionic betaines or zwitterionic poly(sulfobetaine)) (PSB)s that consist of a quaternary ammonium cation and a sulfonate anion, a $C_6$-$C_{100}$ biodegradable polymer, such as composed of poly (lactic/glycolic acid) (PLGA), poly(acrylates), chitosan, copolymer of N-(2-hydroxypropyl)methacrylamide, poly[2-(methacryloyloxy)ethyl phosphorylcholine] (PMPC), poly-L-glutamic acid, poly(lactide-co-glycolide) (PLG), poly (lactide-co-glycolide), Poly(ethylene glycol)(PEG), poly (propylene glycol)(PPG), poly(lactide-co-glycolide), poly (ethylene glycol)-modified peptides, poly(ethylene glycol)-containing an aminoacid or peptides, poly(ethylene glycol)-modified lipids, poly(ethylene glycol)-modified alkylcarboxic acid, poly(ethylene glycol)-modified alkylamine, poly(lactide-co-glycolide, hyaluronic acid (HA) (glycosaminoglycan), heparin/heparan sulfate (HSGAGs), chondroitin sulfate/dermatan sulfate (CSGAGs), poly(ethylene glycol)-modified alkylsulfate, poly(ethylene glycol)-modified alkylphosphate, or poly(ethylene glycol)-modified alkyl quaternary ammonium;

Example structures of $Q_1$ and $Q_2$ are shown below:

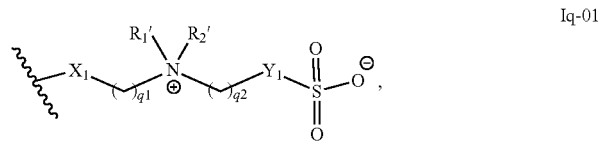

Iq-01

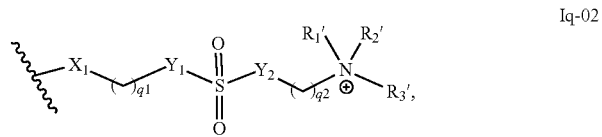

Iq-02

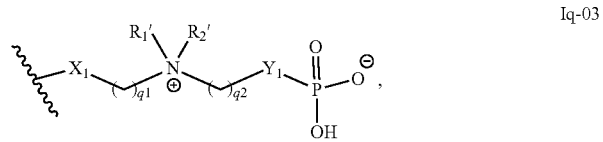

Iq-03

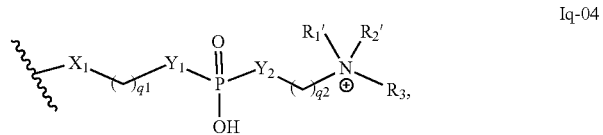

Iq-04

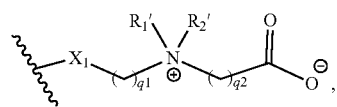
Iq-05
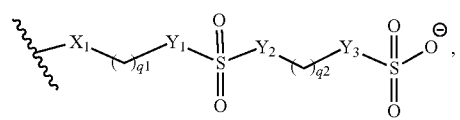
Iq-06
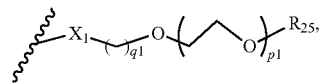
Iq-07
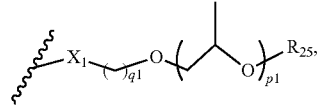
Iq-08
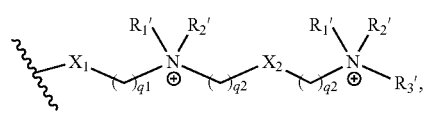
Iq-09
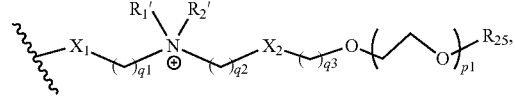
Iq-10
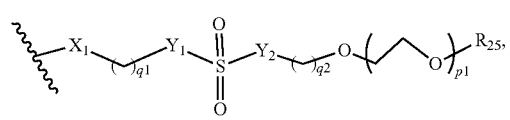
Iq-11
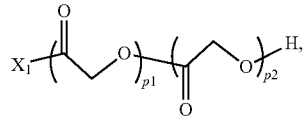
Iq-12
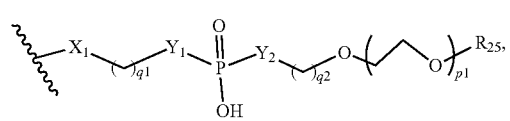
Iq-13
Iq-14
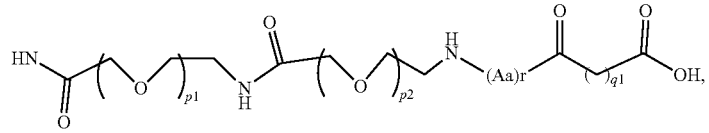
Iq-15
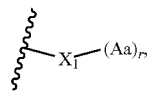
Iq-16
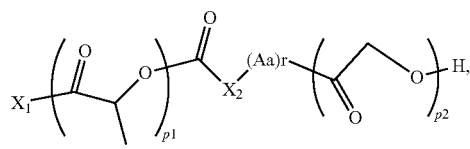
Iq-17
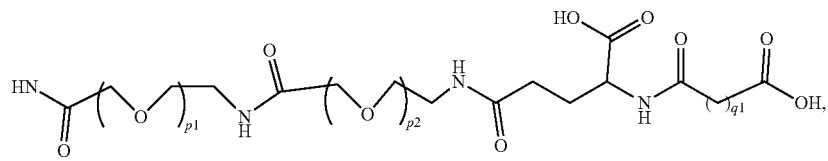
Iq-18
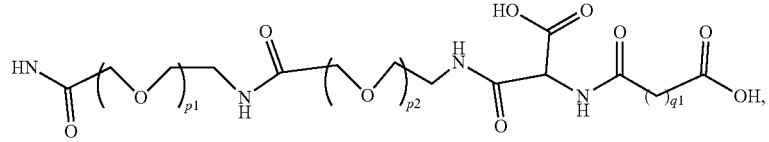
Iq-19
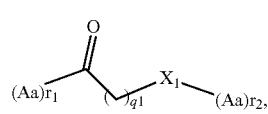
Iq-20
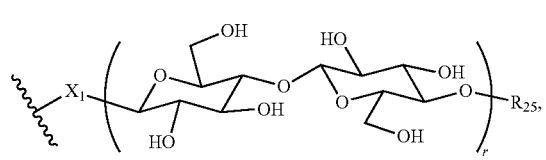
Iq-21
Iq-22

-continued

Iq-23
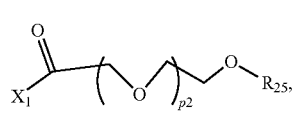

Iq-24
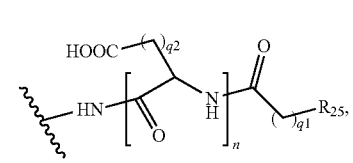

Iq-25
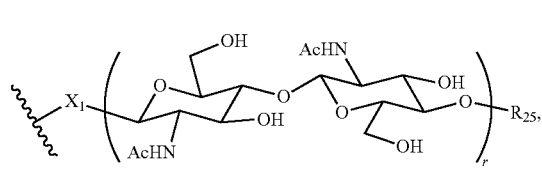

Iq-26
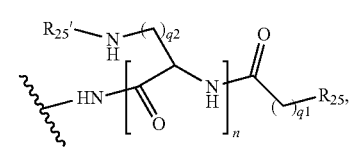

Iq-27
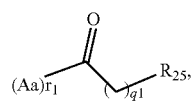

Iq-28
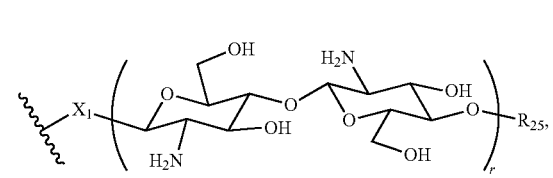

Iq-29
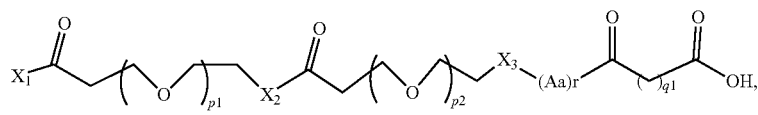

Iq-30
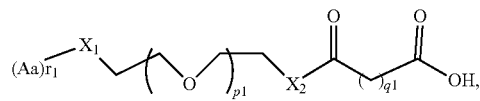

Iq-31
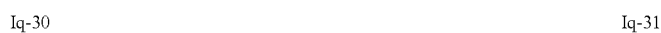

Iq-32
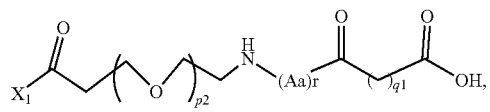

Iq-33
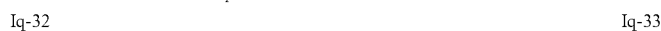

Iq-34
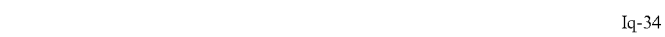

Iq-35
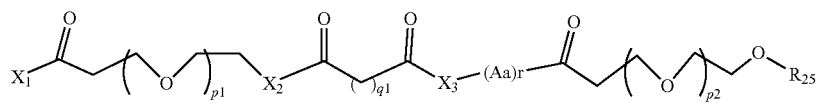

wherein $R_{25}$ and $R_{25'}$ are independently selected from H; HC(O), $CH_3C(O)$, $CH_3C(NH)$, $C_1$-$C_{18}$ alkyl, $C_1$-$C_{18}$ alkyl-$Y_1$—$SO_3H$, $C_1$-$C_{18}$ alkyl-$Y_1$—$PO_3H_2$, $C_1$-$C_{18}$ alkyl-$Y_1$—$CO_2H$, $C_1$-$C_{18}$ alkyl-$Y_1$—$N^+R_1'R_2'R_3'R_4'$, $C_1$-$C_{18}$ alkyl-$Y_1$—$CONH_2$, $C_2$-$C_{18}$ alkylene, $C_2$-$C_{18}$ ester, $C_2$-$C_{18}$ ether, $C_2$-$C_{18}$ amine, $C_2$-$C_{18}$ alkyl carboxylamide, $C_3$-$C_{18}$ Aryl, $C_3$-$C_{18}$ cyclic alkyl, $C_3$-$C_{18}$ heterocyclic, 1-24 amino acids; $C_2$-$C_{18}$ lipid, a $C_2$-$C_{18}$ fatty acid or a $C_2$-$C_{18}$ fatty ammonium lipid; $X_1$ and $X_2$ are independently selected from NH, N(R1'), O, $CH_2$, S, C(O), S(O), S($O_2$), P(O)(OH), NHNH, CH=CH, Ar or (Aa)$q_1$, $q_1$=0-24 (0-24 amino acids, $q_1$=0 means absent); $X_1$, $X_2$, $X_3$, $X_4$, $Y_1$, $Y_2$ and $Y_3$ are independently selected from NH, N($R_1'$), O, C(O), $CH_2$, S, S(O), NHNH, C(O), OC(O), OC(O)O, OC(O)NH, NHC(O) NH, Ar or Ar or (Aa)$q_1$, $X_1$, $X_2$, $X_3$, $X_4$, $Y_1$, $Y_2$ and $Y_3$ can be independently absent; $p_1$, $p_2$ and $p_3$ are independently 0-100 but are not 0 at the same time; $q_1$, $q_2$ and $q_3$ are independently 0-24; $R_1'$, $R_2'$, $R_3'$ and $R_4'$ are independently selected from H and $C_1$-$C_6$ alkyl; Aa is natural or unnatural amino acid; Ar or (Aa)$q_1$, is the same or different sequence of peptides; $q_1$=0 means (Aa)$q_1$ absent;

D is tubulysin analog having the following formula (II):

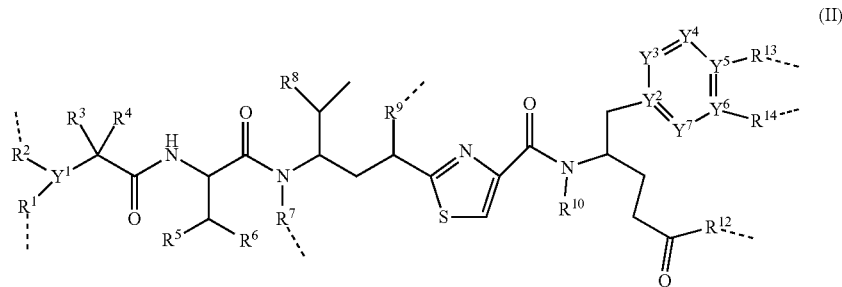

or a pharmaceutically acceptable salt, hydrates, or hydrated salt; or a polymorphic crystalline structure; or an optical isomer, racemate, diastereomer or enantiomer thereof, wherein - - - - - is a linkage site that links to W independently;

wherein $R^1$, $R^2$, $R^3$, and $R^4$ are independently H, $C_1$-$C_8$ alkyl; $C_2$-$C_8$ heteroalkyl, or heterocyclic; $C_3$~$C_8$ aryl, Ar-alkyl, cycloalkyl, alkylcycloalkyl, heterocycloalkyl, heteroalkylcycloalkyl, carbocyclic, or alkylcarbonyl; or $R^1R^2$, $R^1R^3$, $R^2R^3$, $R^3R^4$, $R^5R^6$, $R^{11}R^{12}$ or $R^{13}R^{14}$ form a 3-7 membered carbocyclic, cycloalkyl, heterocyclic, heterocycloalkyl, aromatic or heteroaromatic ring system; $R^1$ and $R^2$ can be independently absent when they link to W independently or simultaneously, $Y^1$ is N or CH;

wherein $R^5$, $R^6$, $R^8$, $R^{10}$ and $R^{11}$ are independently H, or $C_1$~$C_4$ alkyl or heteroalkyl;

wherein $R^7$ is independently H, $R^{14}$, —$R^{14}$C(=O)$X^1R^{15}$; or —$R^{14}X^1R^{15}$; $X^1$ is O, S, S—S, NH, $CH_2$ or $NR^{14}$;

wherein $R^9$ is selected from H, OH, —O—, =O, —$OR^{14}$, —OC(=O)$R^{14}$, —OC(=O)NH$R^{14}$—, —OC(=O)$R_{14}SSR^{15}$—, OP(=O)(O$R^{14}$)—, —OC(=O)N$R^{14}R^{15}$, OP(=O)(O$R_{14}$), or O$R_{14}$OP(=O)(O$R_{15}$);

wherein $R^{11}$ is independently H, $R^{14}$, —$R^{14}$C(=O)$R^{16}$, —$R^{14}X^2R^{16}$, —$R^{14}$C(=O)$X^2$, wherein $X^2$ is —O—, —S—, —NH—, —N($R^{14}$)—, —O—$R^{14}$—, —S—$R^{14}$—, —S(=O)—$R^{14}$—, or —NH$R^{14}$;

wherein $R^{12}$ is $R^{15}$, —OH, —SH, —$NH_2$, NH, $NHNH_2$, —NH($R^{15}$), —$OR^{15}$, —$R^{15}COR^{16}$, $R^{15}COOR^{16}$, —$R^{15}$C(O)$NH_2$, —$R^{15}$C(O)NH$R^{17}$, —S$R^{16}$, $R^{15}$S(=O)$R^{16}$, —$R^{15}$P(=O)(O$R^{17}$)$_2$, -$R^{15}$OP(=O)(O$R^{17}$)$_2$, —$CH_2$OP(=O)(O$R^{17}$)$_2$, —$R^{15}SO_2R^{17}$, —$R^{15}X^2R^{16}$, —$R^{15}$C(=O)$X^2$, where $X^2$ is —O—, OH, SH, —S—, $NH_2$, —NH—, —N($R^{15}$)—, —O—$R^{15}$—, —S—$R^{15}$—, —S(=O)—$R^{15}$—, $CH_2$ or —NH$R^{15}$—;

$R^{13}$ and $R^{14}$ are independently H, O, S, NH, N($R^{15}$), NHNH, —OH, —SH, —$NH_2$, NH, $NHNH_2$, —NH($R^{15}$), —$OR^{15}$, CO, —$COX^2$, —$COX^2R^{16}$, $R^{17}$, F, Cl, Br, I, $SR^{16}$, $NR^{16}R^{17}$, N=$NR^{16}$, N=$R^{16}$, $NO_2$, $SOR^{16}R^{17}$, $SO_2R^{16}$, $SO_3R^{16}$, $OSO_3R^{16}$, $PR^{16}R^{17}$, $POR^{16}R^{17}$, $PO_2R^{16}R^{17}$, OP(O)(O$R^{17}$)$_2$, $OCH_2$OP(O)(O$R^{17}$)$_2$, OC(O)$R^{17}$, OC(O)OP(O)(O$R^{17}$)$_2$, PO(O$R^{16}$)(O$R^{17}$), OP(O)(O$R^{17}$)OP(O)(O$R^{17}$)$_2$, OC(O)NH$R^{17}$; —O—($C_4$-$C_{12}$ glycoside), —N—($C_4$-$C_{12}$ glycoside); $C_1$-$C_8$ alkyl, heteroalkyl; $C_2$-$C_8$ of alkenyl, alkynyl, heteroalkyl, heterocycloalkyl; $C_3$-$C_8$ of aryl, Ar-alkyl, carbocyclic, cycloalkyl, heteroalkylcycloalkyl, alkylcarbonyl, heteroaryl, or 2-8 carbon atoms of esters, ether, or amide; or peptides containing 1-8 amino acids (NH(Aa)l-s or CO(Aa)l-s (N-terminal or C-terminal 1-8 the same or different amino acids), or polyethyleneoxy unit of formula $(OCH_2CH_2)_p$ or $(OCH_2CH(CH_3))_p$, wherein p is an integer from 0 to about 1000, or combination of above groups thereof; $X^2$ is O, S, S—S, NH, $CH_2$, OH, SH, $NH_2$, $CHR^{14}$ or $NR^{14}$;

$R^{15}$, $R^{16}$ and $R^{17}$ is independently H, $C_1$-$C_8$ alkyl, heteroalkyl; $C_2$-$C_8$ of alkenyl, alkynyl, heteroalkyl, heterocycloalkyl; $C_3$-$C_5$ of aryl, Ar-alkyl, carbocyclic, cycloalkyl, heteroalkylcycloalkyl, alkylcarbonyl, heteroaryl, alkylcarbonyl, or $Na^+$, $K^+$, $Cs^+$, $Li^+$, $Ca^{2+}$, $Mg^+$, $Zn^{2+}$, $N^+(R^1)(R^2)(R^3)(R^4)$, $HN^+(C_2H_5OH)_3$ salt;

$Y^1$ and $Y^2$ are independently N or CH; q is 0 or 1; when q=0, $Y^3$ does not exist, $Y^4$, $Y^5$, $Y^6$ and $Y^7$ are independently CH, N, NH, O, S, or N ($R_1$), thus $Y^2$, $Y^4$, $Y^5$ $Y^6$ and $Y^7$ form a heteroaromatic ring of furan, pyrrole thiophene, thiazole, oxazole and imidazole, pyrazole, triazole, tetrazole, thiadiazole; when q=1, $Y^3$, $Y^4$, $Y^5$, $Y^6$ and $Y^7$ are independently CH or N, thus $Y^2$, $Y^3$, $Y^4$, $Y^5$, $Y^6$ and $Y^7$ form aromatic ring of benzene, pyridine, pyridazine, pyrimidine, pyrazine, triazine, tetrazine, pentazine;

Examples of the tubulysin structures are shown below:

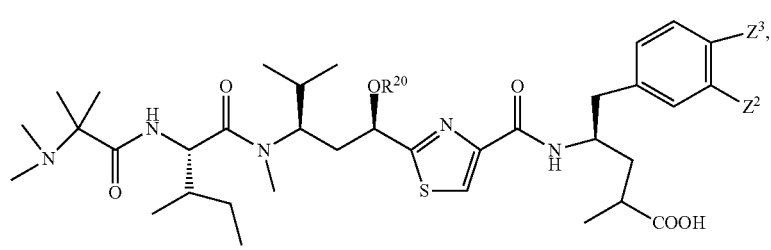

I-01

-continued
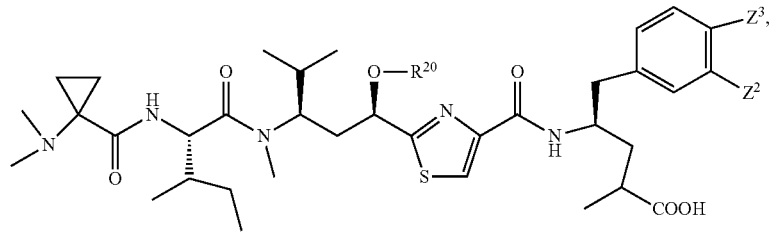
I-02
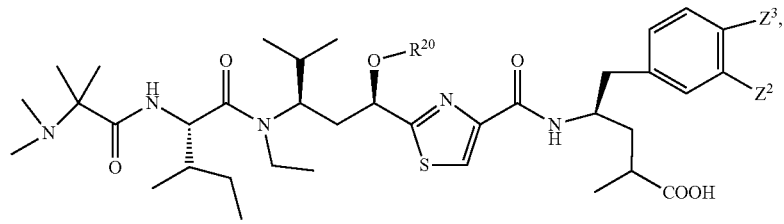
I-03
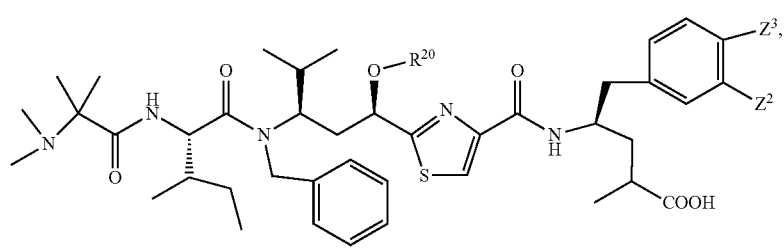
I-04
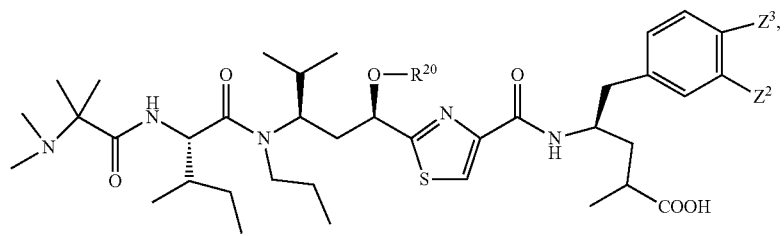
I-05
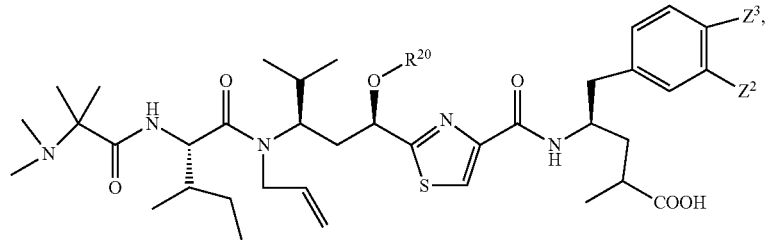
I-06
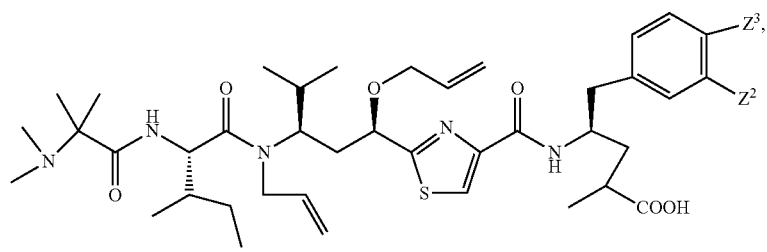
I-07

-continued
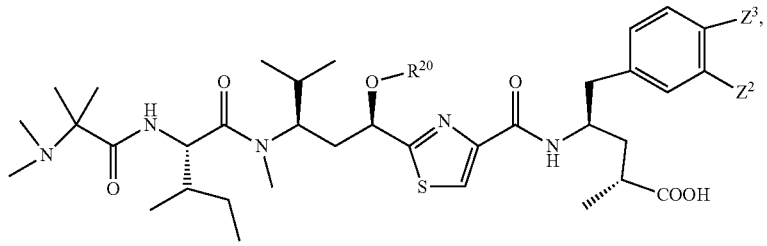
I-08
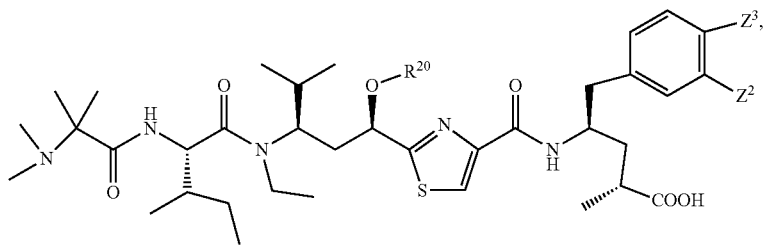
I-09
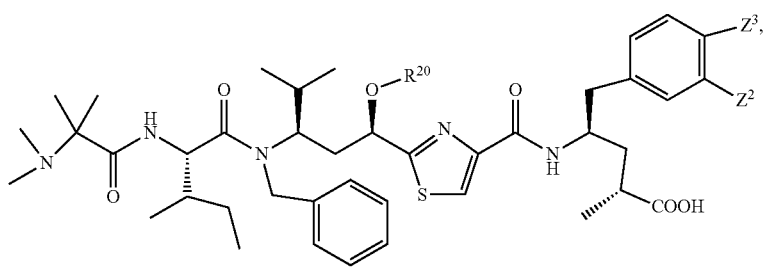
I-10
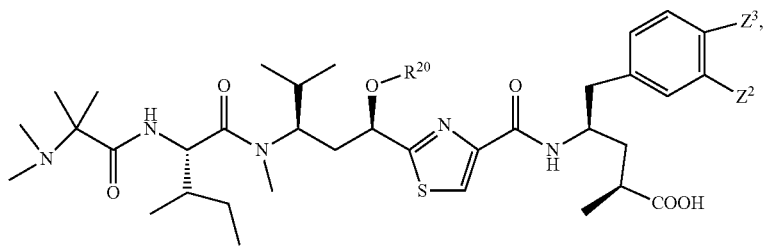
I-11
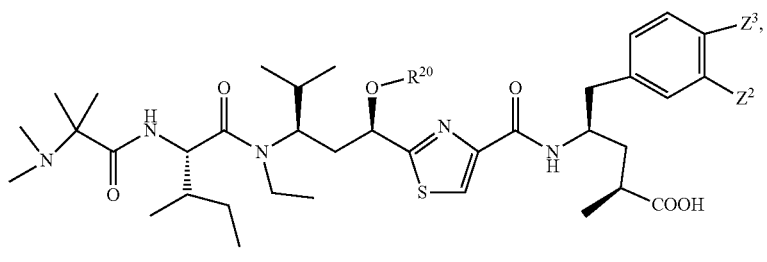
I-12
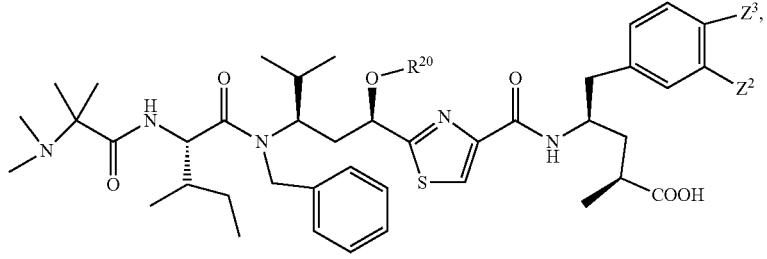
I-13

-continued
I-14
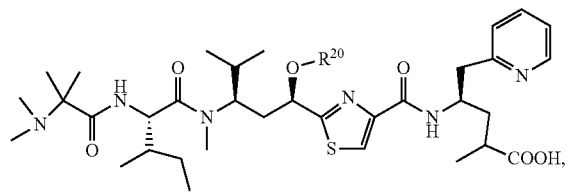
I-15
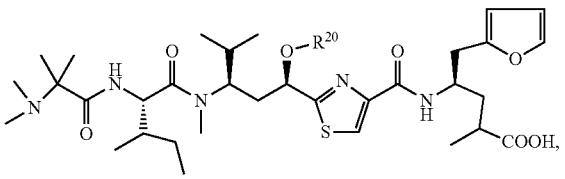
I-16
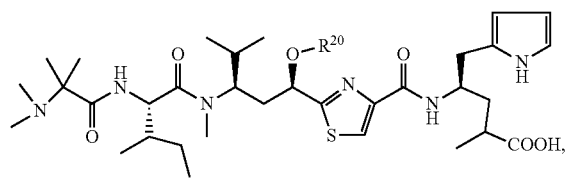
I-17
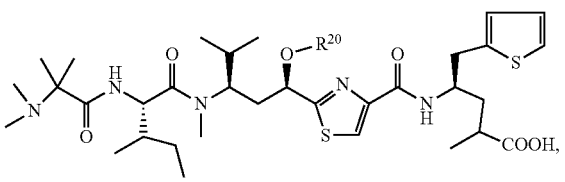
I-18
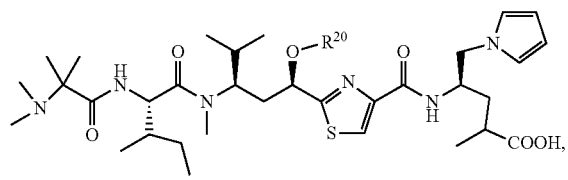
I-19
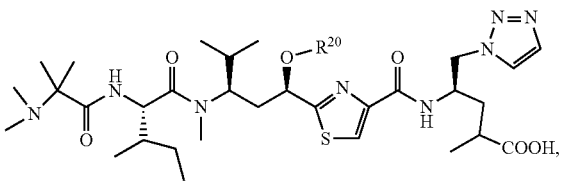
I-20
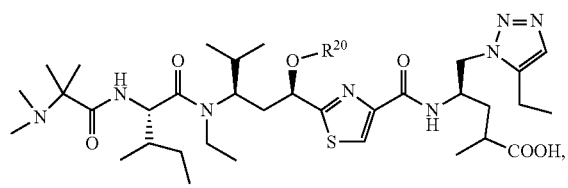
I-21
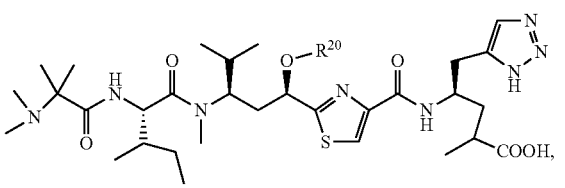
I-22
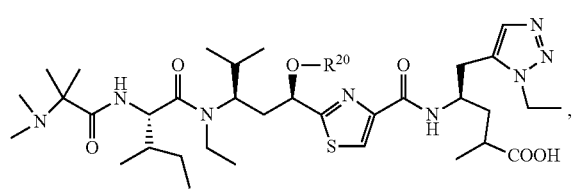
I-23
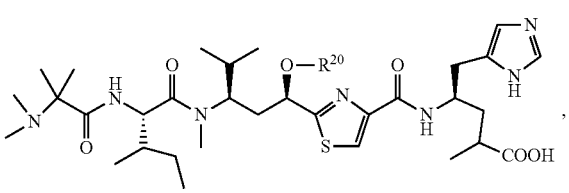
I-24
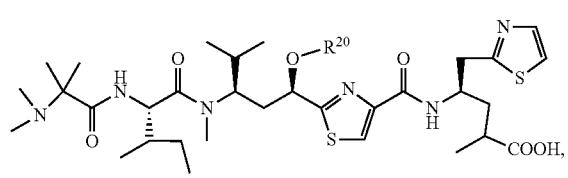
I-25
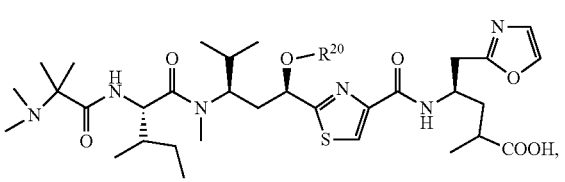
I-26
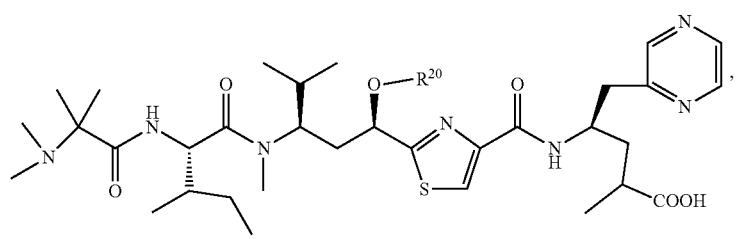

-continued
I-27
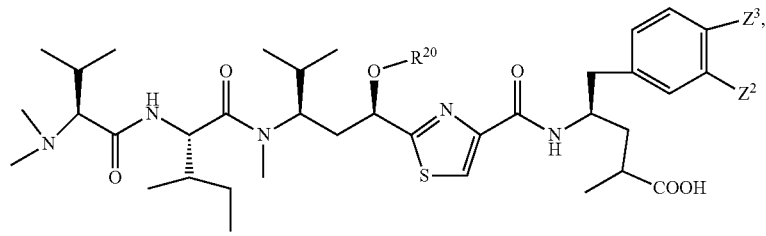
I-28
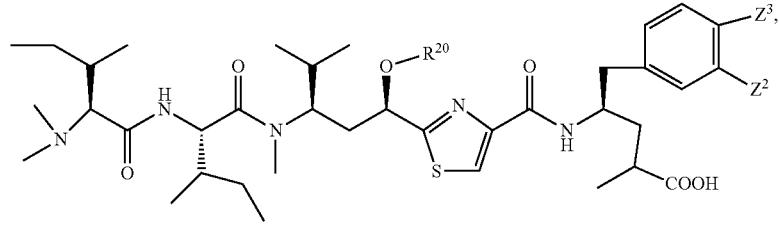
I-29
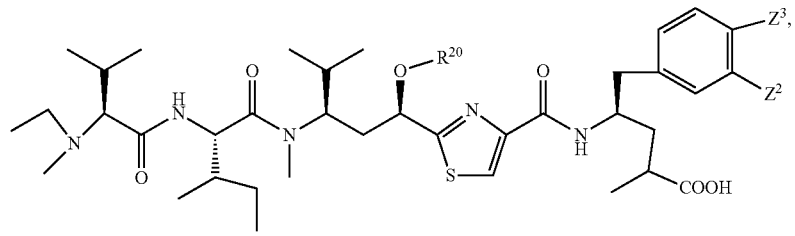
I-30
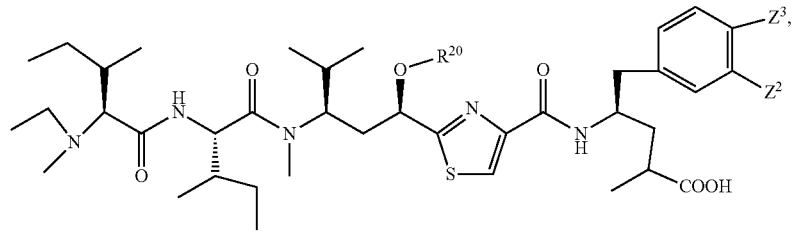
I-31
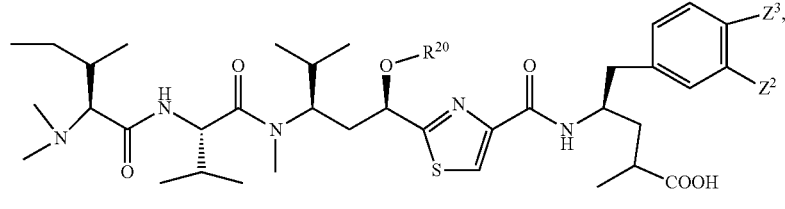
I-32
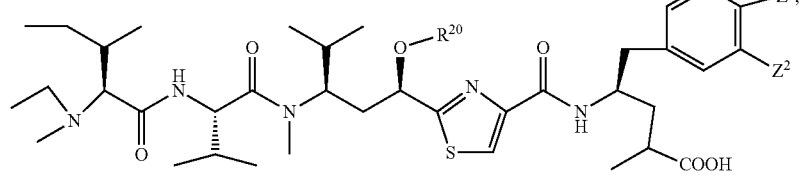
I-33
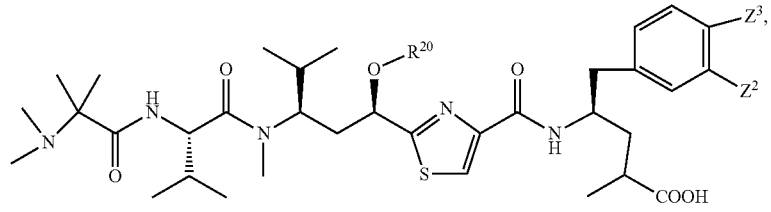

-continued
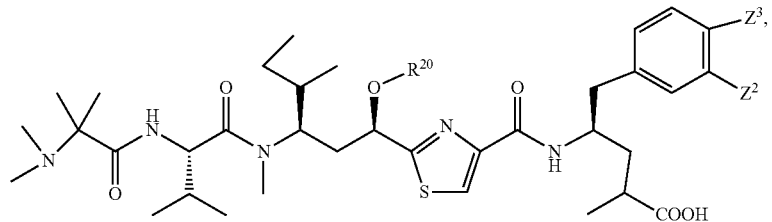
I-34
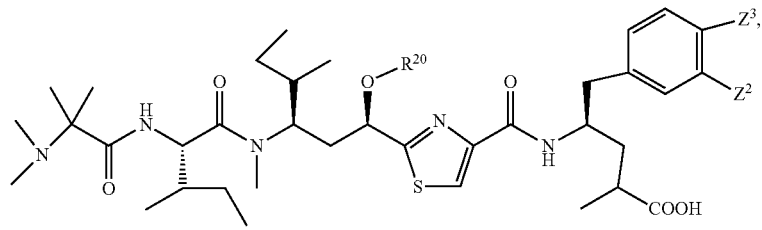
I-35
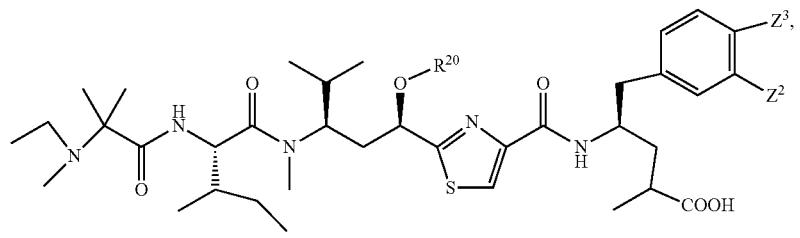
I-36
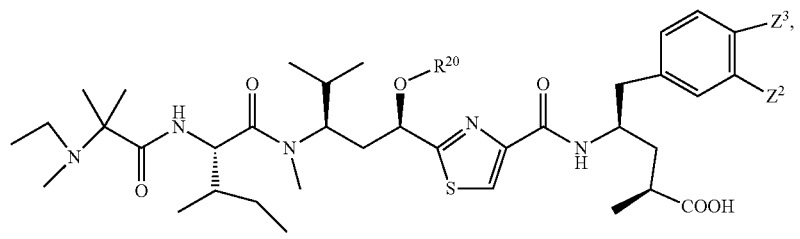
I-37
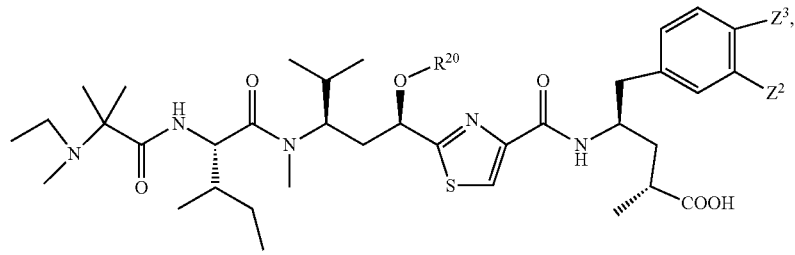
I-38
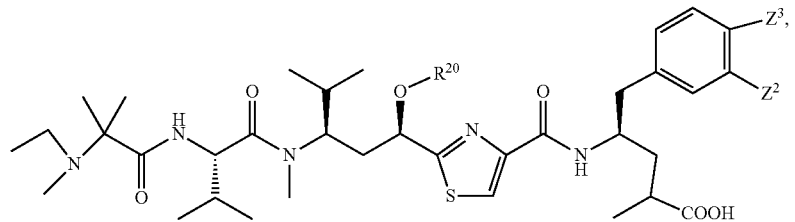
I-39

-continued
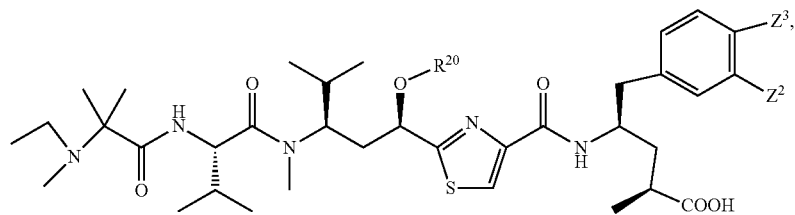
I-40
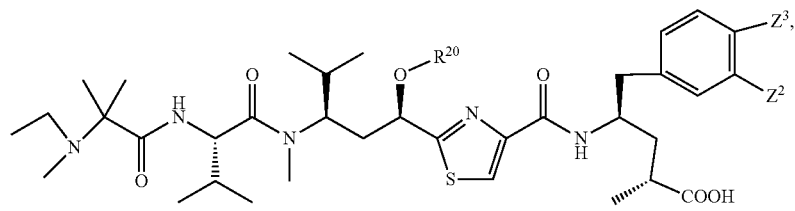
I-41
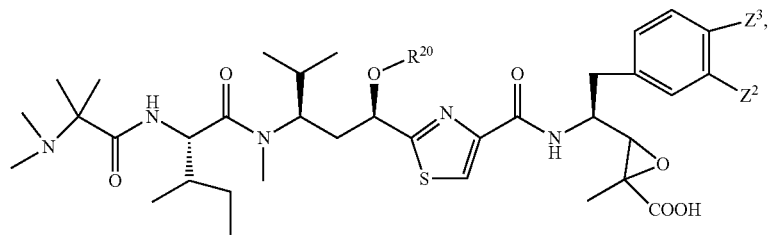
I-42
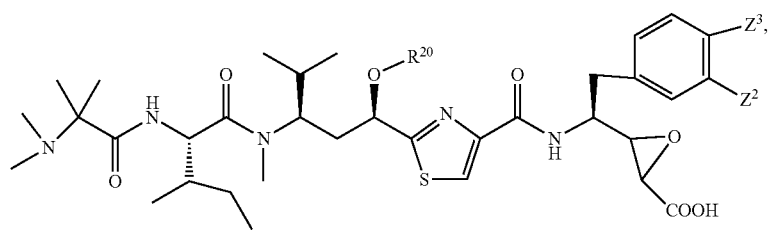
I-43
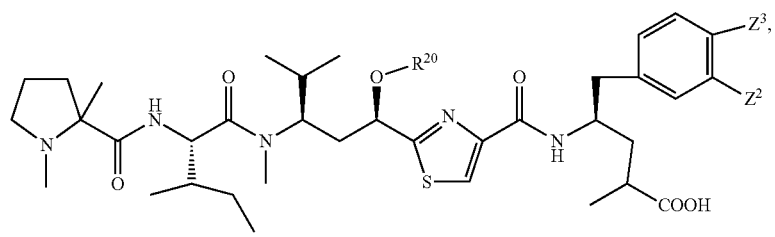
I-44
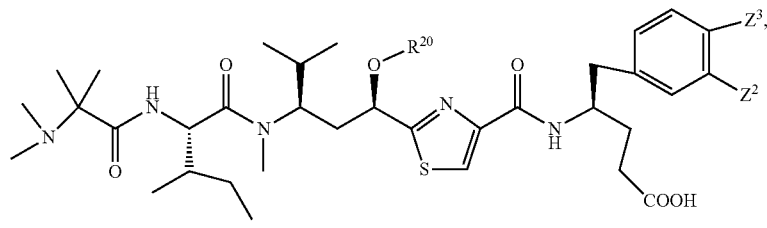
I-45
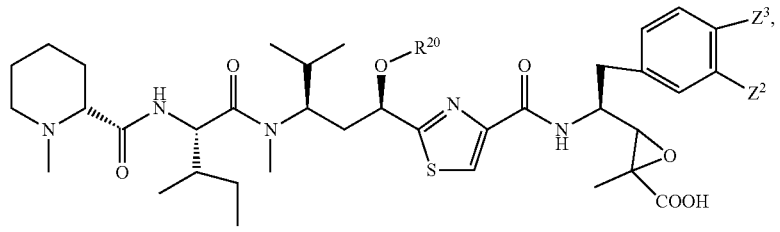
I-46

-continued
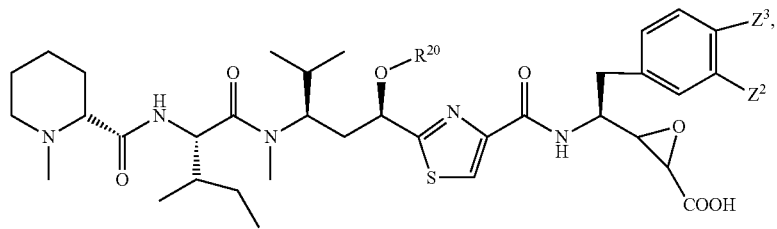
I-47
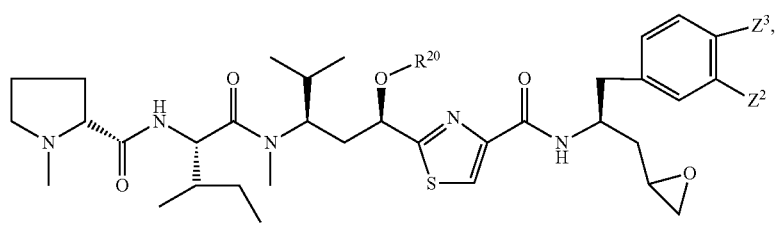
I-48
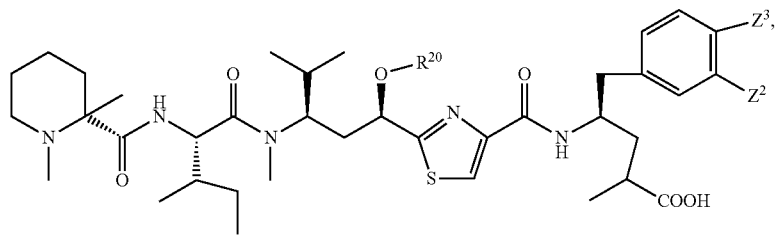
I-49
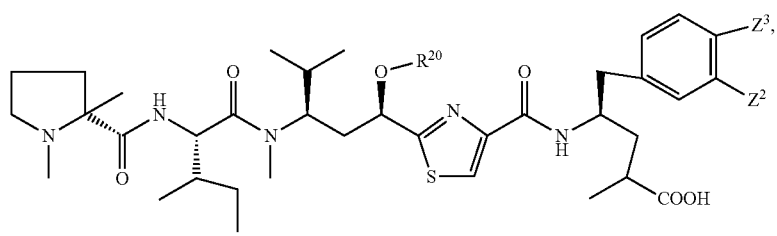
I-50
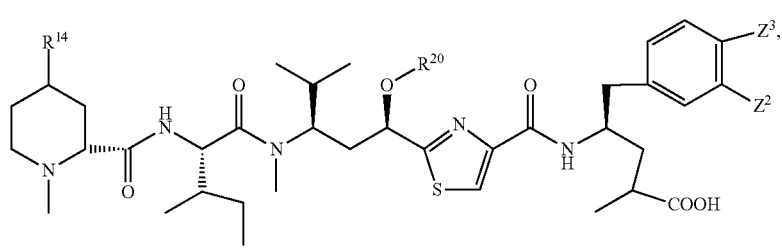
I-51
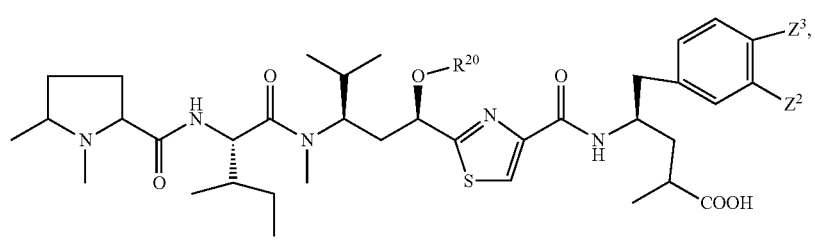
I-52

-continued
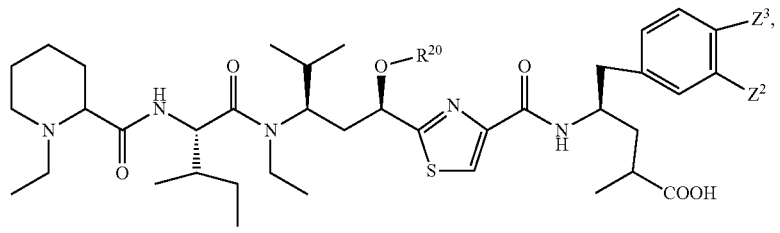
I-53
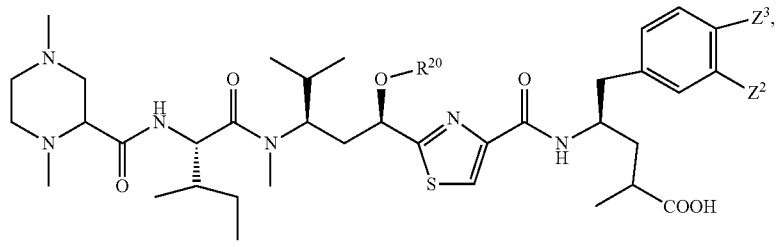
I-54
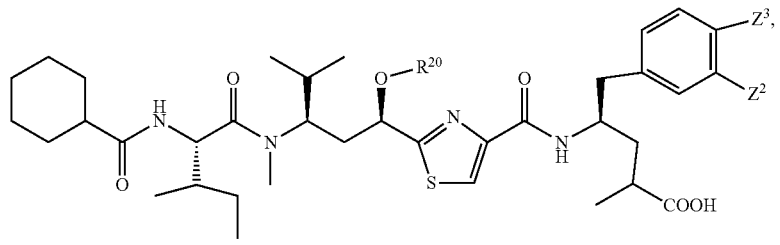
I-55
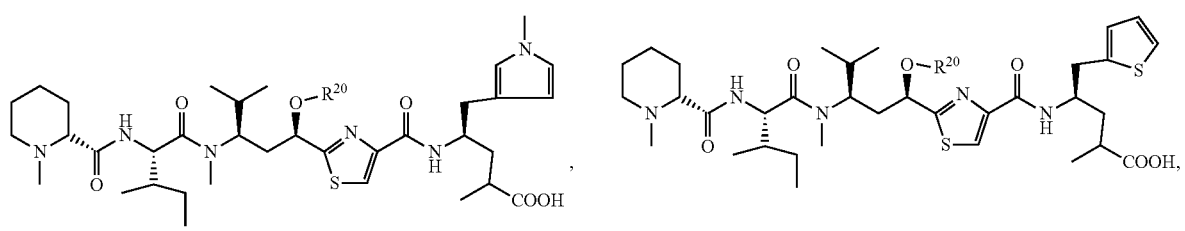
I-56 I-57
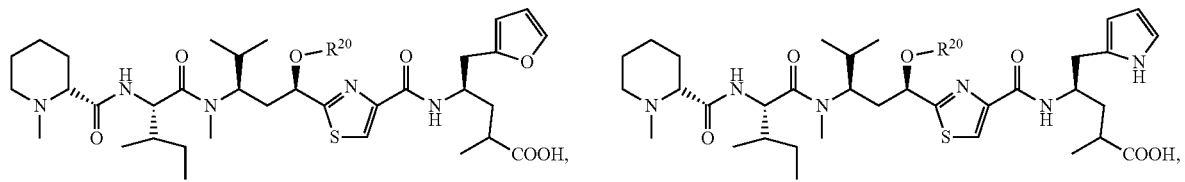
I-58 I-59
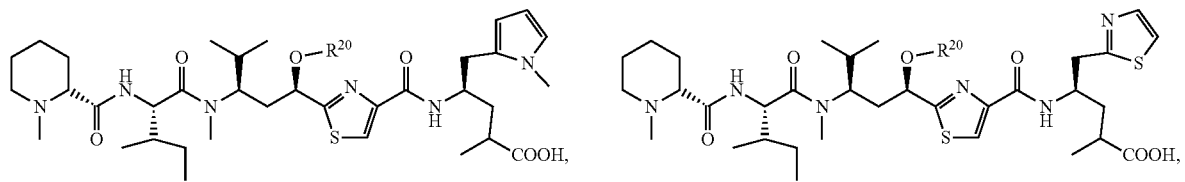
I-60 I-61
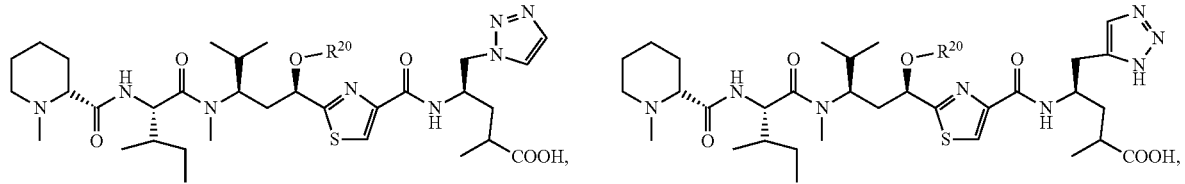
I-62 I-63

-continued
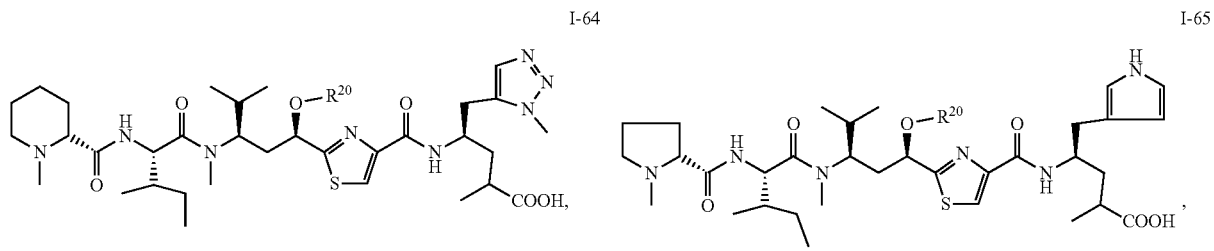
I-64
I-65
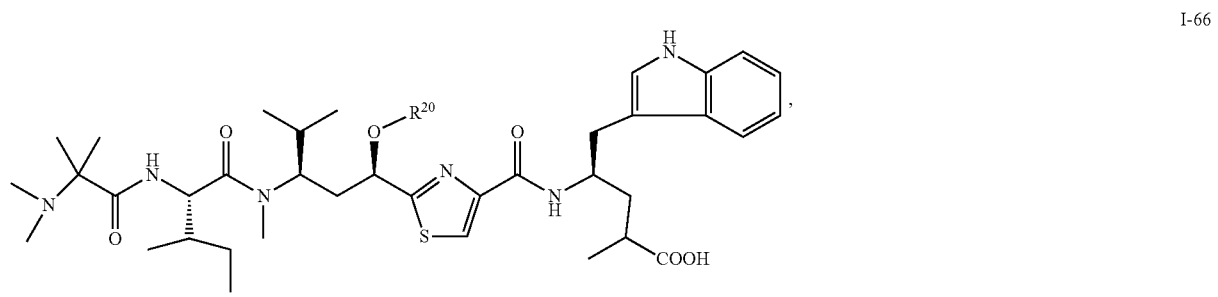
I-66
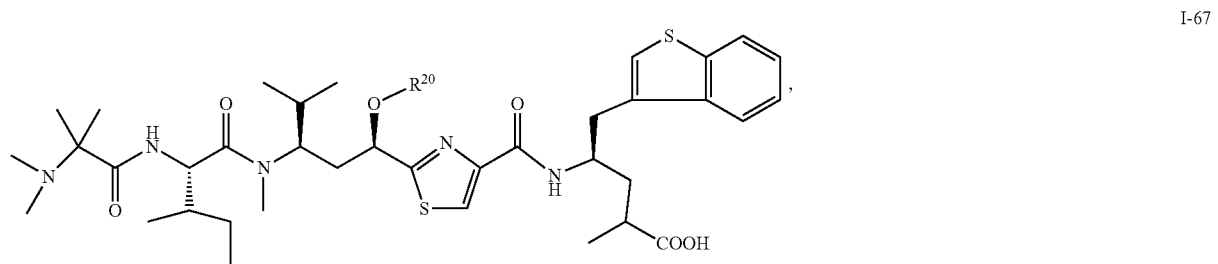
I-67
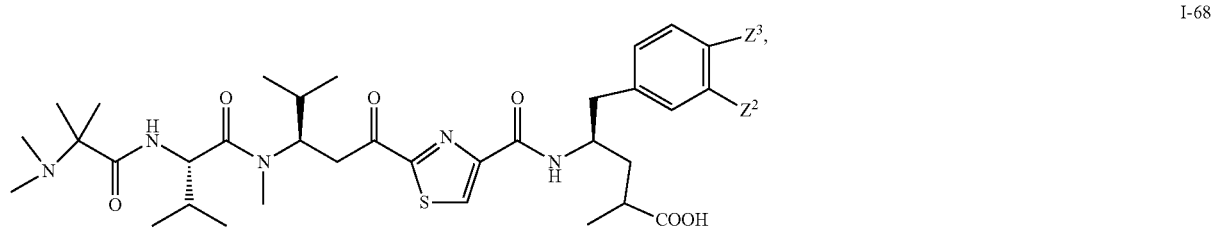
I-68
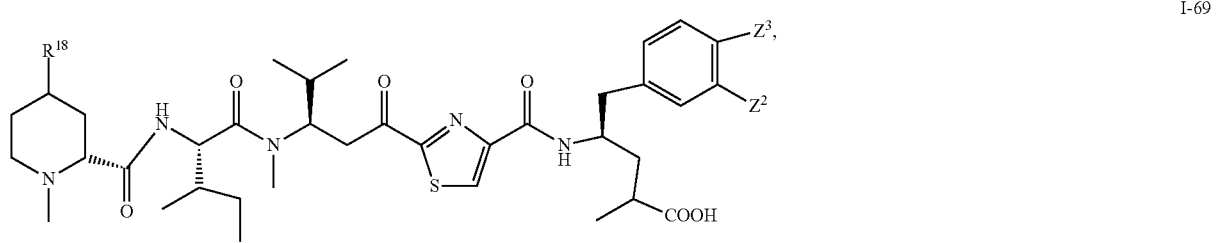
I-69
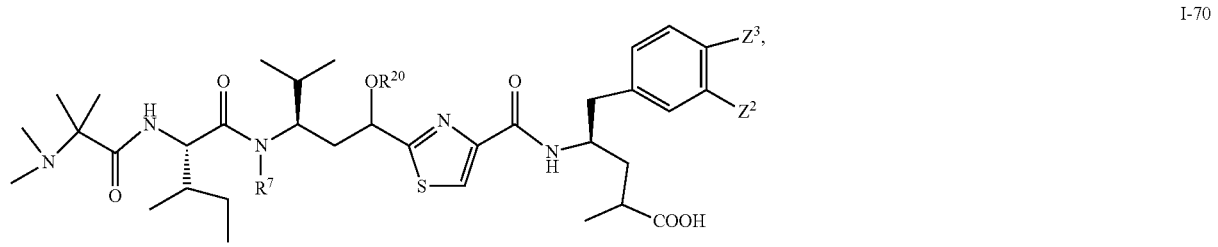
I-70

-continued

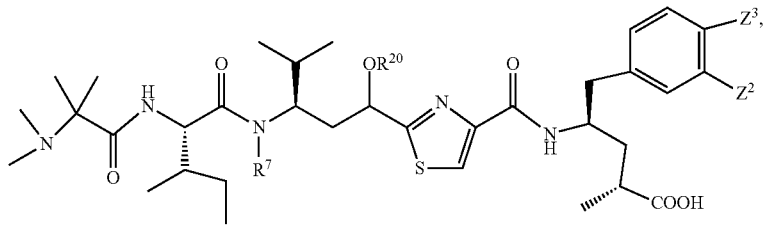

I-71

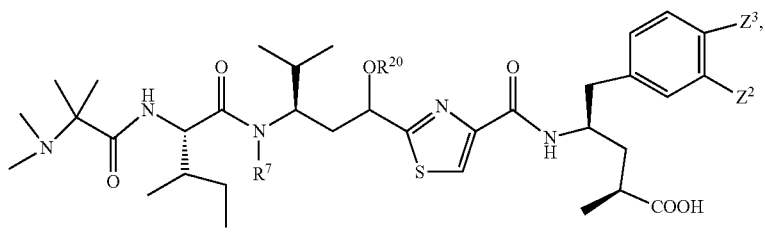

I-72

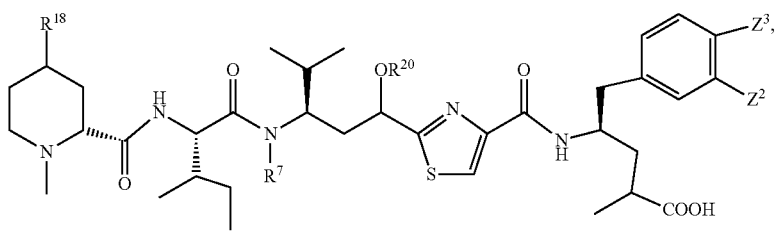

I-73

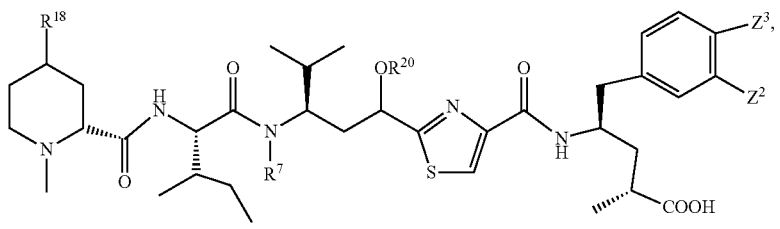

I-74

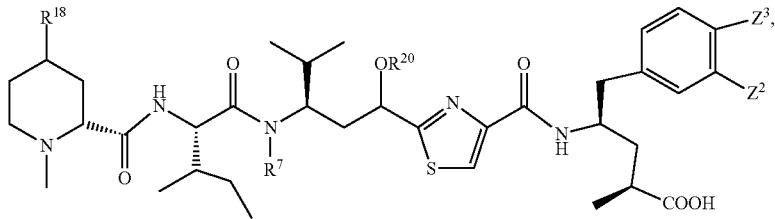

I-75 wherein $R^{20}$ is H; $C_1$-$C_8$ of linear or branched alkyl or heteroalkyl; $C_2$-$C_8$ of linear or branched alkenyl, alkynyl, alkylcycloalkyl, heterocycloalkyl; $C_3$-$C_8$ linear or branched of aryl, Ar-alkyl, heterocyclic, carbocyclic, cycloalkyl, heteroalkylcycloalkyl, alkylcarbonyl, heteroaryl; carbonate (—C(O)OR$^{17}$), carbamate (—C( )NR$^{17}$R$^{18}$); r 1-8 carbon atoms of carboxylate, esters, ether, or amide; or 1-8 amino acids; or polyethyleneoxy unit of formula (OCH$_2$CH$_2$)$_p$ or (OCH$_2$CH(CH$_3$))$_p$, wherein p is an integer from 0 to about 1000; or $R^{20}$ is absent and the oxygen forms a ketone, or combination above thereof; $Z^3$ and $Z^3$ are independently H, OH, NH$_2$, O, NH, COOH, COO, C(O), C(O), C(O)NH, C(O)NH$_2$, R$^{18}$, OCH$_2$OP(O)(OR$^{18}$)$_2$, OC(O)OP(O)(OR$^{18}$)$_2$, OPO(OR$^{18}$)$_2$, NHPO(OR$^{18}$)$_2$, OP(O)(OR$^{18}$)OP(O)(OR$^{18}$)$_2$, OC(O)R$^1$, OC(O)NHR$^{18}$, OSO$_2$(OR$^8$), O—(C$_4$-C$_{12}$-glycoside), of linear or branched alkyl or heteroalkyl; $C_2$-$C_8$ of linear or branched alkenyl, alkynyl, alkylcycloalkyl, heterocycloalkyl; $C_3$-$C_5$ linear or branched of aryl, Ar-alkyl, heterocyclic, carbocyclic, cycloalkyl, heteroalkylcycloalkyl, alkylcarbonyl, heteroaryl; carbonate (—C(O)OR$^{17}$), carbamate (—C(O)NR$^{17}$R$^{18}$); R$^{17}$ and R$^{18}$ are independently H, linear or branched alkyl or heteroalkyl; $C_2$-$C_8$ of linear or branched alkenyl, alkynyl, alkylcycloalkyl, heterocycloalkyl; $C_3$-$C_8$ linear or branched of aryl, Ar-alkyl, heterocyclic, carbocyclic, cycloalkyl, heteroalkylcycloalkyl, alkylcarbonyl, heteroaryl; carbonate (—C(O)OR$^{17}$), carbamate (—C(O)NR$^{17}$R$_{18}$); R$^{19}$ is H, OH, NH$_2$, OSO$_2$(OR$^{18}$), XCH$_2$OP (O)(OR$^{18}$)$_2$, XPO(OR$^{18}$)$_2$, XC(O)OP(O)(OR$^{18}$)$_2$, XC(O)R$^{18}$, XC(O)NHR$^{18}$, $C_1$-$C_8$ alkyl or carboxylate; $C_2$-$C_8$ alkenyl, alkynyl, alkylcycloalkyl, heterocycloalkyl; $C_3$-$C_8$ aryl or alkylcarbonyl; or pharmaceutical salts; X is O, S, NH, NHNH, or CH$_2$; R$^7$ is defined the same above.

Additionally W, $L_1$, $L_2$, $V_1$, and $V_2$, may independently be composed of one or more linker components of 6-maleimidocaproyl ("MC"), maleimidopropanoyl ("MP"), valine-citrulline ("val-cit" or "vc"), alanine-phenylalanine ("ala-phe" or "af"), p-aminobenzyloxy-carbonyl ("PAB"), 4-thiopentanoate ("SPP"), 4-(N-maleimidomethyl)cyclohexane-1 carboxylate ("MCC"), (4-acetyl)amino-benzoate ("SIAB"), 4-thio-butyrate (SPDB), 4-thio-2-hydroxysulfonyl-butyrate (2-Sulfo-SPDB), as the structures shown below or natural or unnatural peptides having 1-12 natural or unnatural amino acid unites. The natural aminoacid is preferably selected from aspartic acid, glutamic acid, arginine, histidine, lysine, serine, threonine, asparagine, glutamine, cysteine, selenocysteine, tyrosine, phenylalanine, glycine, proline, tryptophan, alanine;

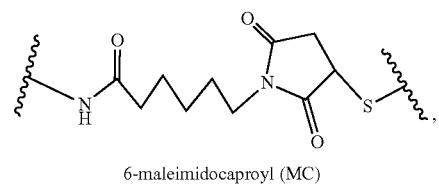

6-maleimidocaproyl (MC)

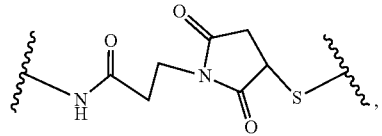

maleimido propanoyl (MP)

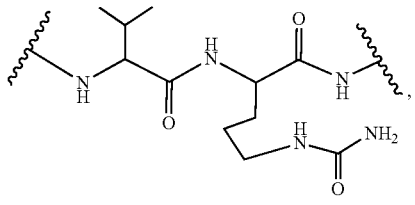

valine-citrulline (val-cit)

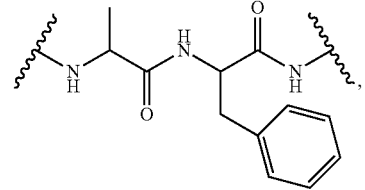

alanine-phenylalanine (ala-phe)

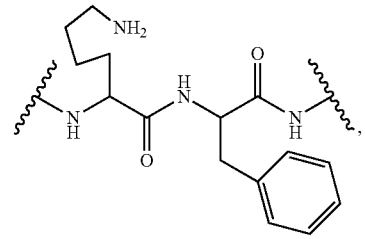

lysine-phenylalanine (lys-phe)

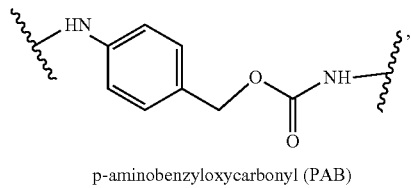

p-aminobenzyloxycarbonyl (PAB)

-continued

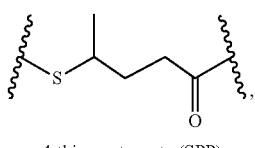

4-thio-pentanoate (SPP)

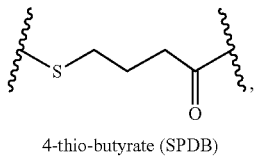

4-thio-butyrate (SPDB)

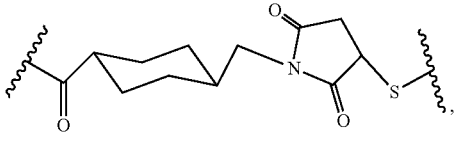

4-(N-maleimidomethyl)cyclo-hexane-1-carboxylate (MCC)

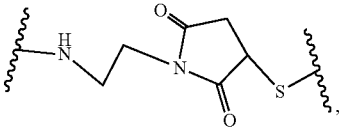

maleimidoethyl (ME)

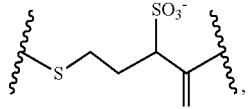

4-thio-2-hydroxysulfonyl-butyrate (2-Sulfo-SPDB)

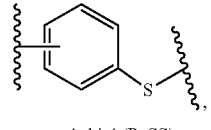

aryl-thiol (PySS)

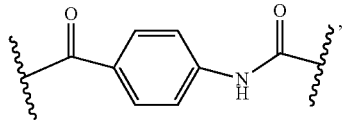

(4-acetyl)aminobenzoate (SIAB)

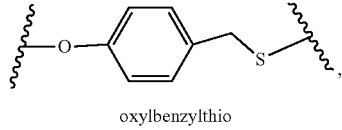

oxylbenzylthio

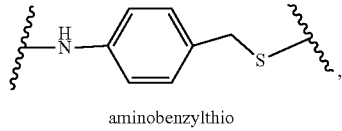

aminobenzylthio

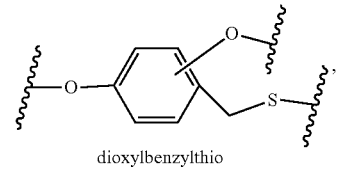

dioxylbenzylthio

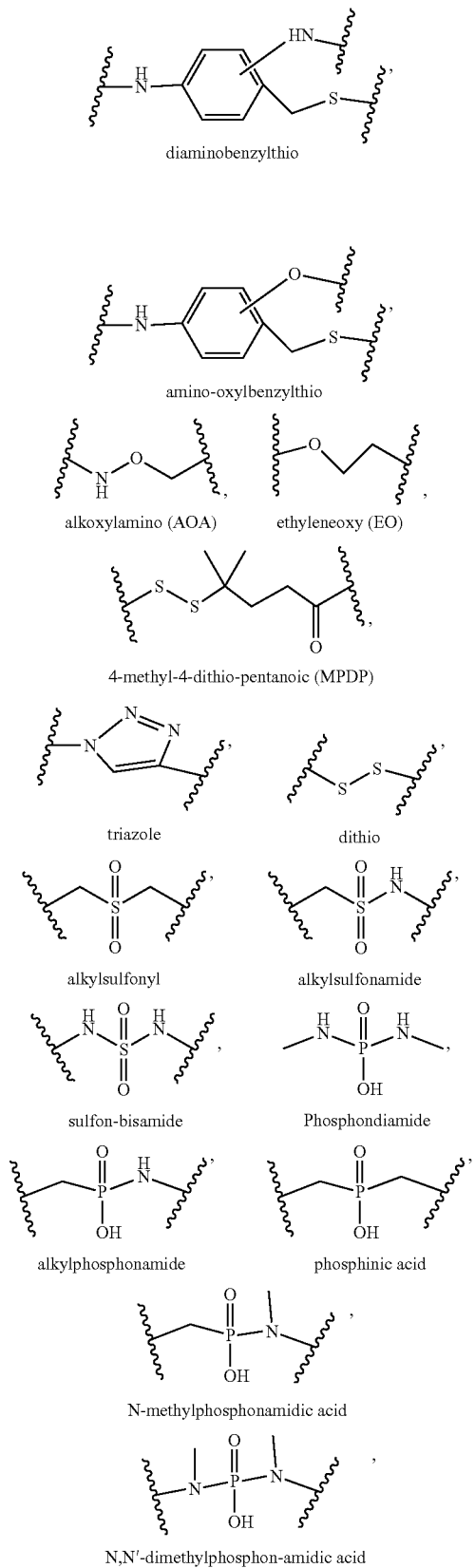
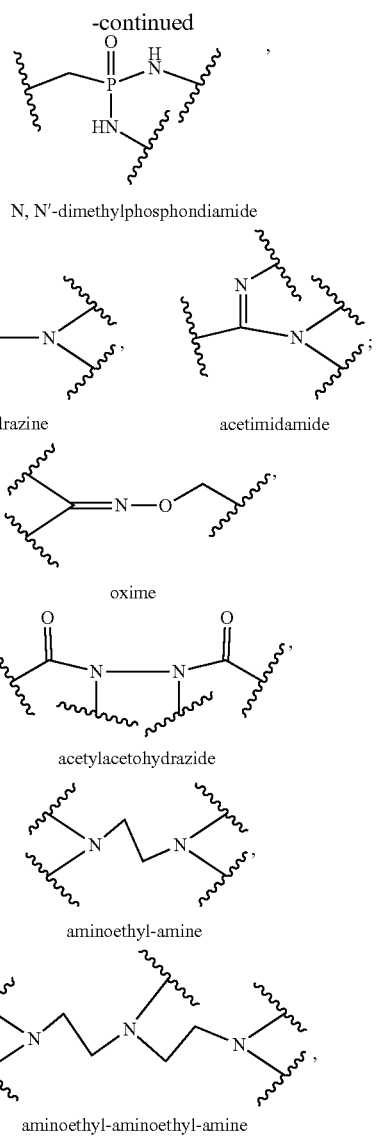

and L- or D-, natural or unnatural peptides containing 1-20 amino acids; W, $L_1$, $L_2$ $V_1$, and $V_2$ may also independently contain a self-immolative or a non-self-immolative component, peptidic units, a hydrazone bond, a disulfide, an ester, an oxime, an amide, or a thioether bond. The self-immolative unit includes, but is not limited to, aromatic compounds that are electronically similar to the para-aminobenzylcarbamoyl (PAB) groups such as 2-aminoimidazol-5-methanol derivatives, heterocyclic PAB analogs, beta-glucuronide, and ortho or para-aminobenzylacetals;

Preferably, the self-immolative linker component has one of the following structures:

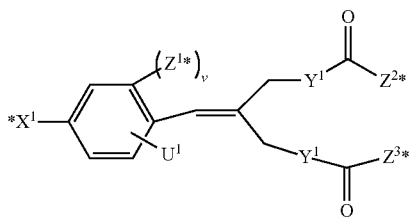

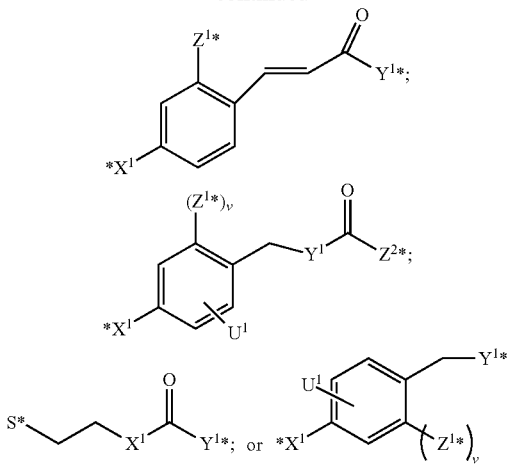

wherein the (*) atom is the point of attachment of additional spacer or releasable linker units, or the cytotoxic agent, and/or the binding molecule (CBA); $X^1$, $Y^1$, $Z^2$ and $Z^3$ are independently NH, O, or S; $Z^1$ is independently H, $NHR_1$, $OR_1$, $SR_1$, $COX_1R_1$, wherein $X_1$ and $R_1$ are defined above; v is 0 or 1; $U^1$ is independently H, OH, $C_1$-$C_6$ alkyl, $(OCH_2CH_2)_n$, F, Cl, Br, I, $OR_5$, $SR_5$, $NR_5R_5'$, $N{=}NR_5$, $N{=}R_5$, $NR_5R_5'$, $NO_2$, $SOR_5R_5'$, $SO_2R_5$, $SO_3R_5$, $OSO_3R_5$, $PR_5R_5'$, $POR_5R_5'$, $PO_2R_5R_5'$, $OPO(OR_5)(OR_5')$, or $OCH_2PO(OR_5)(OR_5')$, wherein $R_5$ and $R_5'$ are independently selected from H, $C_1$~$C_8$ of alkyl; $C_2$~$C_8$ of alkenyl, alkynyl, heteroalkyl, or amino acid; $C_3$~$C_8$ of aryl, heterocyclic, carbocyclic, cycloalkyl, heterocycloalkyl, heteroaralkyl, alkylcarbonyl, or glycoside; or pharmaceutical cation salts;

W, $L_1$, $L_2$ $V_1$, and $V_2$ may also independently contain non-self-immolative linker component having one of the following structures:

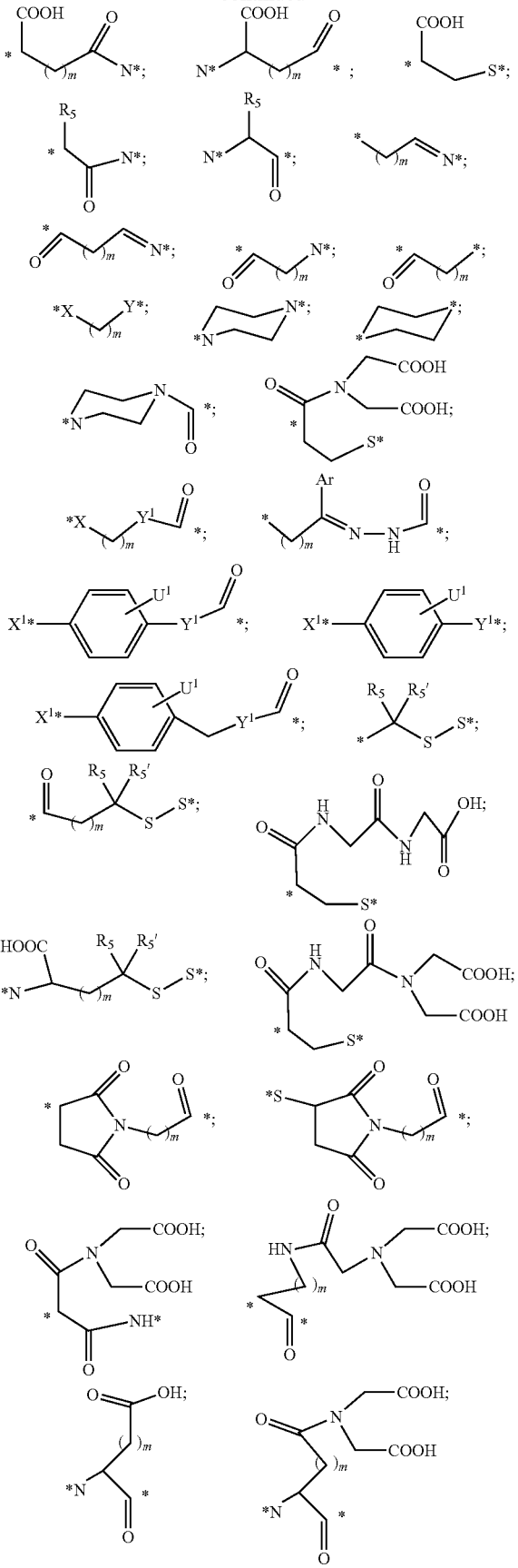

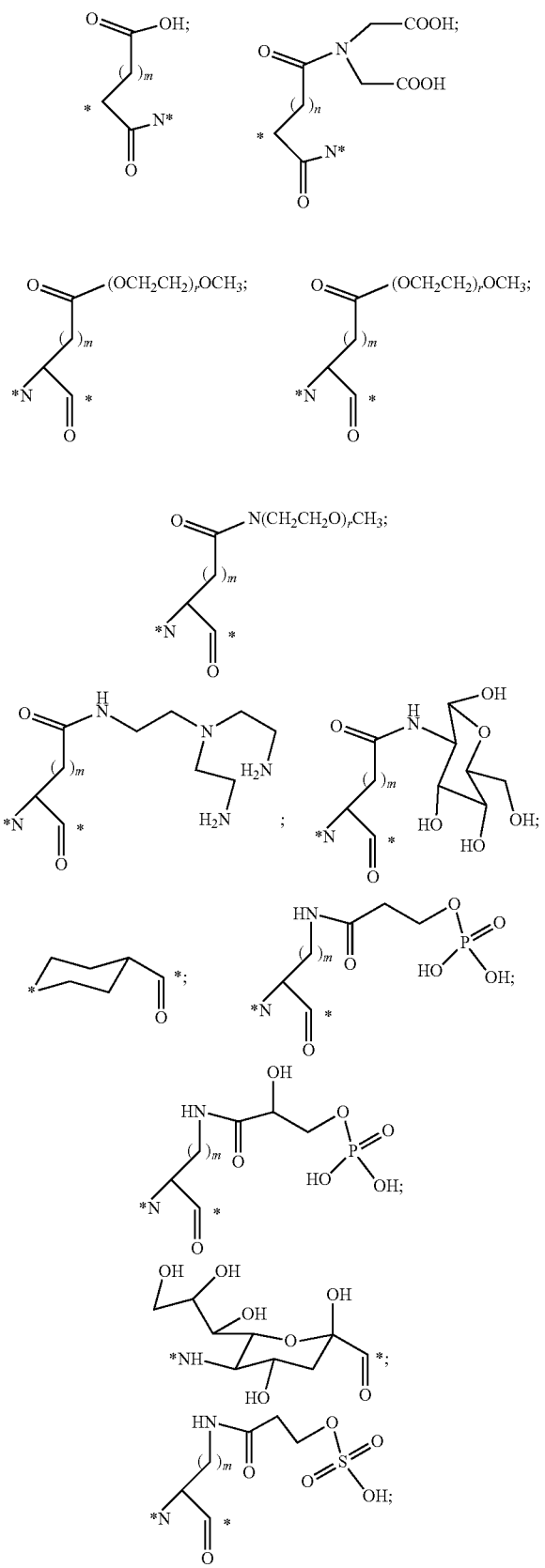
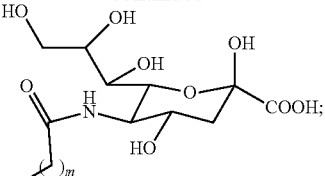

wherein the (*) atom is the point of attachment of additional spacer or releasable linkers, the cytotoxic agents, and/or the binding molecules; $X^1, Y^1, U^1, R_5, R_5'$ are defined as above; r is 0-100; m and n are 0-6 independently;

Further preferably, W, $L_1$, $L_2$ $V_1$, and $V_2$ may independently be a releasable linker component. The term releasable refers to a linker that includes at least one bond that can be broken under physiological conditions, such as a pH-labile, acid-labile, base-labile, oxidatively labile, metabolically labile, biochemically labile or enzyme-labile bond. It is appreciated that such physiological conditions resulting in bond breaking do not necessarily include a biological or metabolic process, and instead may include a standard chemical reaction, such as a hydrolysis or substitution reaction, for example, an endosome having a lower pH than cytosolic pH, and/or disulfide bond exchange reaction with a intracellular thiol, such as a millimolar range of abundant of glutathione inside the malignant cells; Examples of the releasable components of W, $L_1$, $L_2$ $V_1$, and $V_2$ independently include, but not limited:

—$(CR_5R_6)_m(Aa)_r(CR_7R_8)_n(OCH_2CH_2)_r$—, —$(CR_5R_6)_m(CR_7R_8)_n(Aa)_r(OCH_2CH_2)_r$—, -$(Aa)_r$-$(CR_5R_6)_m(CR_7R_8)_n(OCH_2CH_2)_r$—, —$(CR_5R_6)_m(CR_7R_8)_n(OCH_2CH_2)_r(Aa)_r$-, —$(CR_5R_6)_m$—$(CR_7$=$CR_8)(CR_9R_{10})_n(Aa)_t(OCH_2CH_2)_r$—, —$(CR_5R_6)_m(NR_{11}CO)(Aa)_t(CR_9R_{10})_n$—$(OCH_2CH_2)_r$—, —$(CR_5R_6)_m(Aa)_t(NR_{11}CO)(CR_9R_{10})_n(OHC_2CH_2)_r$—, —$(CR_5R_6)_m(OCO)(Aa)_t(CR_9R_{10})_n$—$(OCH_2CH_2)_r$—,

—$(CR_5R_6)_m(OCNR_7)(Aa)_t(CR_9R_{10})_n(OCH_2CH_2)_r$—,
—$(CR_5R_6)_m(CO)(Aa)_t$-$(CR_9R_{10})_n(OCH_2CH_2)_r$—,
—$(CR_5R_6)_m(NR_{11}CO)(Aa)_t(CR_9R_{10})_n(OCH_2CH_2)_r$—,
—$(CR_5R_6)_m$—$(OCO)(Aa)_t(CR_9R_{10})_n$—$(OCH_2CH_2)_r$—,
—$(CR_5R_6)_m(OCNR_7)(Aa)_t(CR_9R_{10})_n(OCH_2CH_2)_r$—,
—$(CR_5R_6)_m(CO)(Aa)_t(CR_9R_{10})_n$—$(OCH_2CH_2)_r$—,
—$(CR_5R_6)_m$-phenyl-$CO(Aa)_t(CR_7R_8)_n$—, —$(CR_5R_6)_m$-furyl-$CO(Aa)_t(CR_7R_8)_n$—, —$(CR_5R_6)_m$-oxazolyl-$CO(Aa)_t(CR_7R_8)_n$—, —$(CR_5R_6)_m$-thiazolyl-$CO(Aa)_t(CCR_7R_8)_n$—, —$(CR_7R_8)_n$—, —$(CR_5R_6)_t$-thienyl-$CO(CR_7R_8)_n$—, —$(CR_5R_6)_t$-imidazolyl-CO—$(CR_7R_8)_n$—, —$(CR_5R_6)_t$-morpholino-$CO(Aa)_t$-$(CR_7R_8)_n$—, —$(CR_5R_6)_t$piperazino-$CO(Aa)_t$-$(CR_7R_8)_n$—, —$(CR_5R_6)_t$—N-methylpiperazin-$CO(Aa)_t$-$(CR_7R_8)_n$—, —$(CR_5R)_m$-$(Aa)_t$phenyl-, —$(CR_5R_6)_m$-$(Aa)_t$furyl-, —$(CR_5R_6)_m$-oxazolyl$(Aa)_t$-, —$(CR_5R_6)_m$-thiazolyl$(Aa)_t$-, —$(CR_5R_6)_m$-thienyl-$(Aa)_t$-, —$(CR_5R_6)_m$-imidazolyl$(Aa)_t$-, —$(CR_5R_6)_m$-morpho-lino-$(Aa)_t$-, —$(CR_5R_6)_m$-piperazino-$(Aa)_t$-, —$(CR_5R_6)_m$—N-methylpiperazino-$(Aa)_t$-, —$K(CR_5R_6)_m$-$(Aa)r(CR_7R_8)_n(OCH_2CH_2)_t$—, —$K(CR_5R_6)_m(CR_7R_8)_n(Aa)_t(OCH_2CH_2)_t$—, —$K(Aa)_r$-$(CR_5R_6)_m(CR_7R_8)_n(OCH_2CH_2)_t$—, —$K(CR_5R_6)_m(CR_7R_8)_n(OCH_2CH_2)_r(Aa)_t$-, —$K(CR_5R_6)_m$—$(CR_7=CR_8)$—$(CR_9R_{10})_n(Aa)_t(OCH_2CH_2)_r$—, —$K(CR_5R_6)_m(NR_{11}CO)(Aa)_t(CR_9R_{10})_n(OCH_2CH_2)_r$—, —$K(CR_5R_6)_m(Aa)_t(NR_{11}CO)(CR_9R_{10})_n(OCH_2CH_2)_r$—, —$K(CR_5R_6)_m(OCO)(Aa)_t(CR_9R_{10})_n$—$(OCH_2CH_2)_r$—, —$K(CR_5R_6)_m(OCNR_7)(Aa)_t(CR_9R_{10})_n(OCH_2CH_2)_r$—, —$K(CR_5R_6)_m(CO)(Aa)_t$-$(CR_9R_{10})_n(OCH_2CH_2)_r$—, —$K(CR_5R_6)_m(NR_{11}CO)(Aa)_t(CR_9R_{10})_n(OCH_2CH_2)_r$—, —$K(CR_5R_6)_m$—$(OCO)(Aa)_t(CR_9R_{10})_n(OCH_2CH_2)_r$—, —$K(CR_5R_6)_m(OCNR_7)(Aa)_t(CR_9R_{10})_n(OCH_2CH_2)_r$—, —K—$(CR_5R_6)_m(CO)(Aa)_t(CR_9R_{10})_n(OCH_2CH_2)_r$—, —$K(CR_5R_6)_m$-phenyl-$CO(Aa)_t(CR_7R_8)_n$—, —K—$(CR_5R_6)_m$-furyl-$CO(Aa)_t$-$(CR_7R_8)_n$—, —$K(CR_5R_6)_m$-oxazolyl-$CO(Aa)_t(CR_7R_8)_n$—, —$K(CR_5R_6)_m$-thiazolyl-$CO(Aa)_t$-$(CR_7R_8)_n$—, —$K(CR_5R_6)_t$-thienyl-$CO(CR_5R_6)_n$—, —$K(CR_5R_6)_t$imidazolyl-CO—$(CR_7R_8)_n$—, —$K(CR_5R_6)_t$morpholino-$CO(Aa)_t(CR_7R_8)_n$—, —$K(CR_5R_6)_t$piperazino-$CO(Aa)_t$-$(CR_7R_8)_n$—, —$K(CR_5R_6)_t$—N-methylpiperazin$CO(Aa)_t(CR_7TR)_n$—, —$K(CR_5R)_m(Aa)_t$phenyl, —K—$(CR_5R_6)_m$-$(Aa)_t$furyl-, —$K(CR_5R_6)_m$-oxazolyl$(Aa)_t$-, —$K(CR_5R_6)_m$-thiazolyl$(Aa)_t$-, —$K(CR_5R_6)_m$-thienyl-$(Aa)_t$-, —$K(CR_5R_6)_m$-imidazolyl$(Aa)_t$-, —$K(CR_5R_6)_m$-morpholino$(Aa)_t$-, —$K(CR_5R_6)_m$-piperazino-$(Aa)_tG$, —$K(CR_5R_6)_m$N-methylpiperazino$(Aa)_t$-; wherein m, Aa, m, n, $R_3$, $R_4$, and $R_5$ are described above; t and r here are 0-100 independently; $R_6$, $R_7$, $R_8$, $R_9$, and $R_{10}$ are independently chosen from H; halide; $C_1$~$C_8$ of alkyl, aryl, alkenyl, alkynyl, ether, ester, amine or amide, which optionally substituted by one or more halide, CN, $NR_1R_2$, $CF_3$, $OR_1$, Aryl, heterocycle, $S(O)R_1$, $SO_2R_1$, —$CO_2H$—, —$SO_3H$, —$OR_1$, —$CO_2R_1$, —$CONR_1$, —$PO_2R_1R_2$, —$PO_3H$ or $P(O)R_1R_2R_3$; K is $NR_1$, —SS—, —C(=O)—, —C(=O)NH—, —C(=O)O—, —C=NH—O—, —C=N—NH—, —C(=O)NH—NH—, O, S, Se, B, Het (heterocyclic or heteroaromatic ring having $C_3$-$C_8$), or peptides containing 1-20 amino acids;

Additionally components of W, $L_1$, $L_2$ $V_1$, and $V_2$ may independently contain one of the following hydrophilic structures:

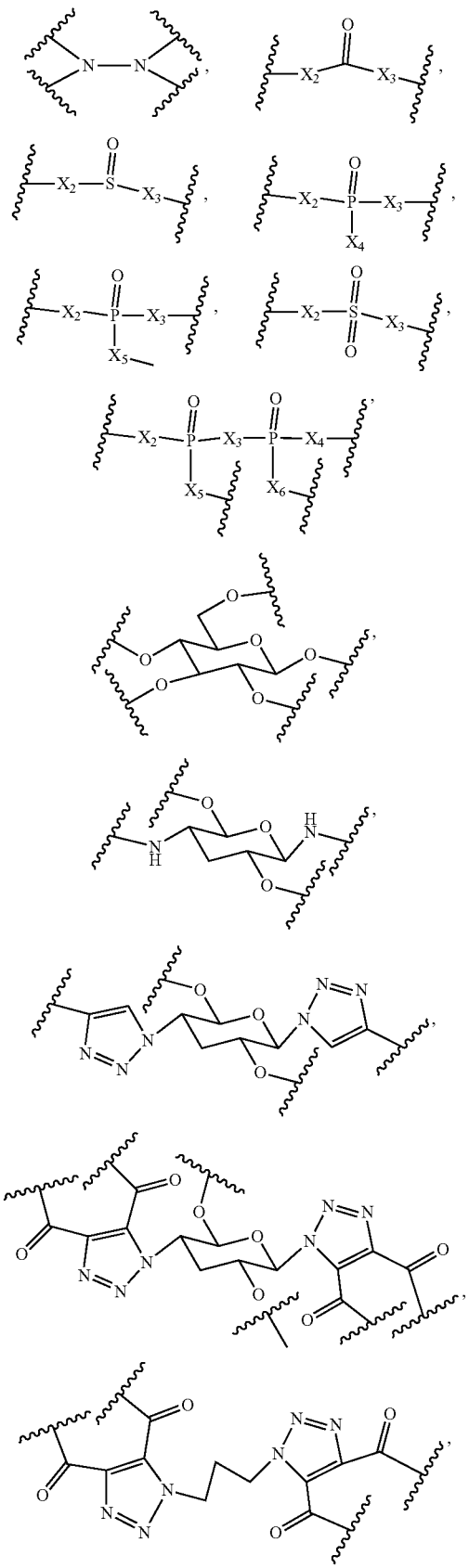

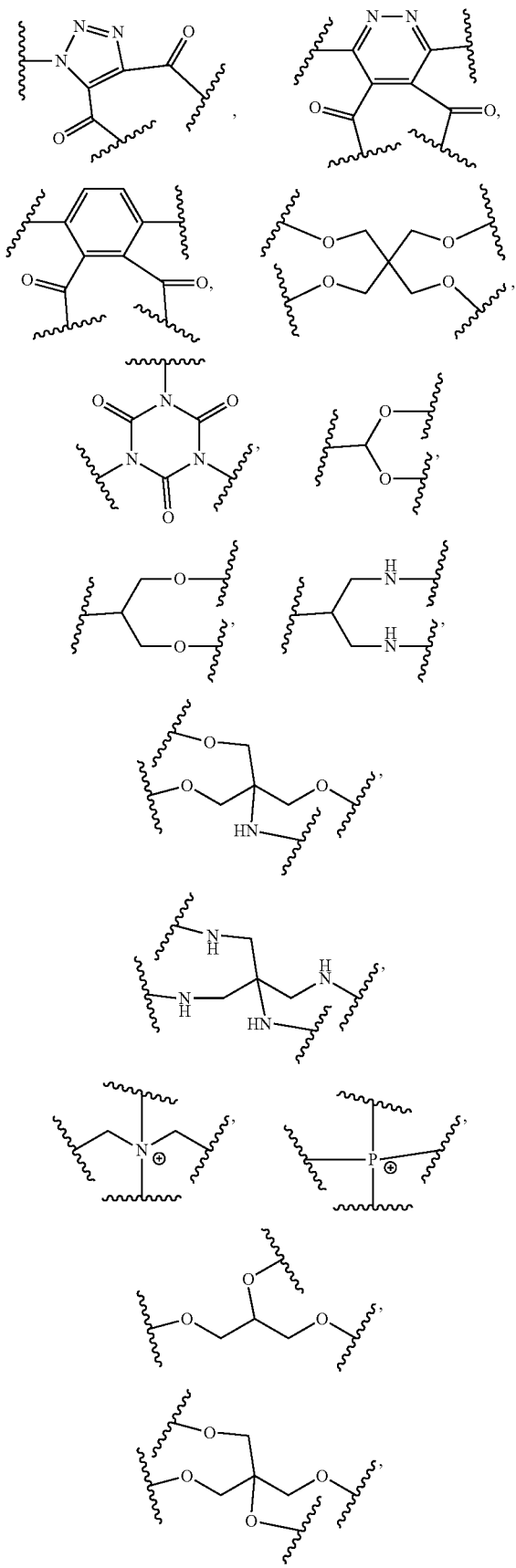

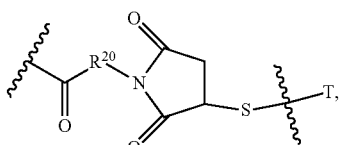

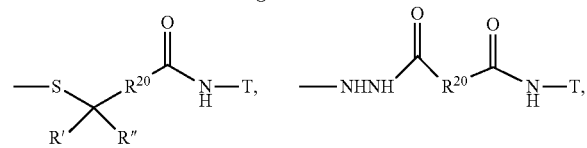

wherein $\xi$ is the site of linkage; $X_2$, $X_3$, $X_4$, $X_5$, or $X_6$, are independently selected from NH; NHNH; $N(R_3)$; $N(R_3)N(R_{3'})$; O; S; $C_1$-$C_6$ of alkyl; $C_2$-$C_6$ of heteroalkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 amino acids; Wherein $R_3$ and $R_{3'}$ are independently H; $C_1$-$C_8$ of alkyl; $C_2$-$C_8$ of hetero-alkyl, alkylcycloalkyl, heterocycloalkyl; $C_3$-$C_8$ of aryl, Ar-alkyl, heterocyclic, carbocyclic, cycloalkyl, heteroalkylcycloalkyl, alkylcarbonyl, heteroaryl; or 1-8 carbon atoms of esters, ether, or amide; or polyethyleneoxy unit of formula $(OCH_2CH_2)_p$ or $(OCH_2CH(CH_3))_p$, wherein p is an integer from 0 to about 1000, or combination above thereof;

More preferably, components of W, $L_1$, $L_2$ $V_1$, and $V_2$ are independently linear alkyl having from 1-6 carbon atoms, or polyethyleneoxy unit of formula $(OCH_2CH_2)_p$, p=1-5000, or a peptide containing 1~4 units of aminoacids (L or D form), or combination above.

Alternatively, any one or more of W, $Q_1$, $Q_2$, $L_1$, $L_2$, $V_1$, or $V_2$, can be independently absent but $Q_1$, and $Q_2$ are not absent at the same time.

Generally stated, in another aspect, when $V_1$ and/or $V_2$ linked to the cell-binding molecule, T, or when $L_1$ and/or $L_2$ directly linked to T (wherein $V_1$, and $V_2$, are absent), it could have one or more of the following structures of the linkage:

-continued
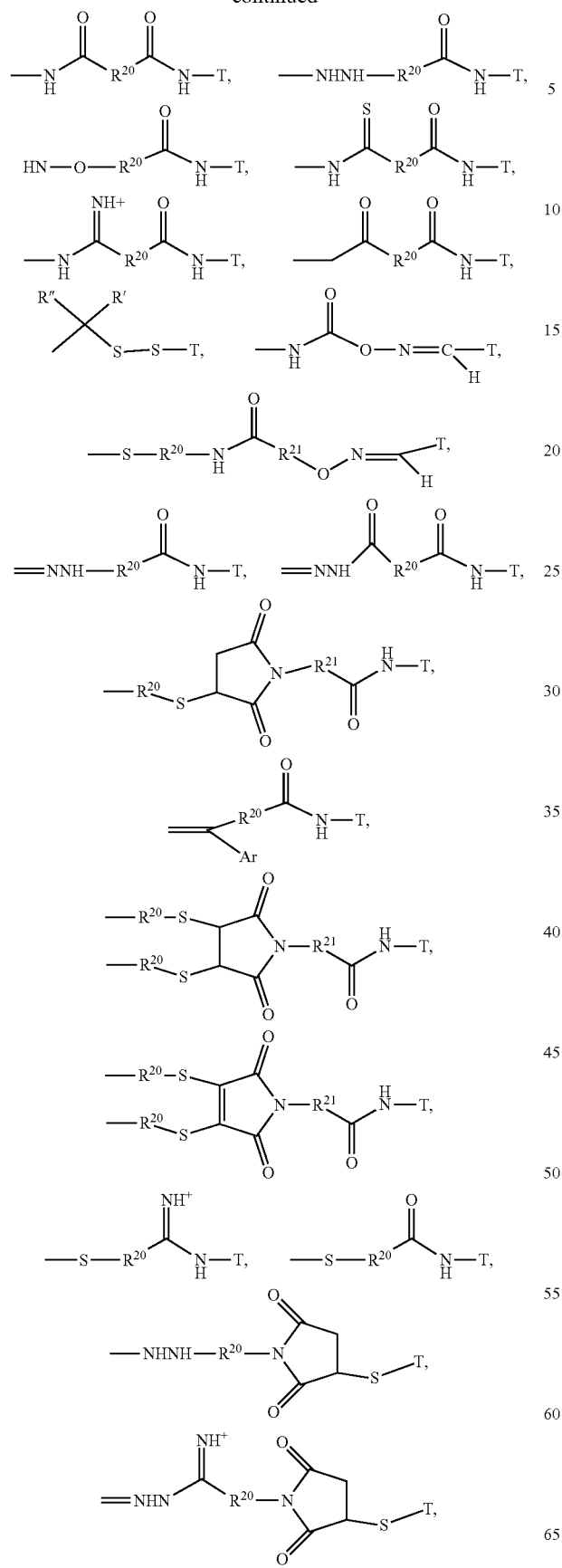
-continued
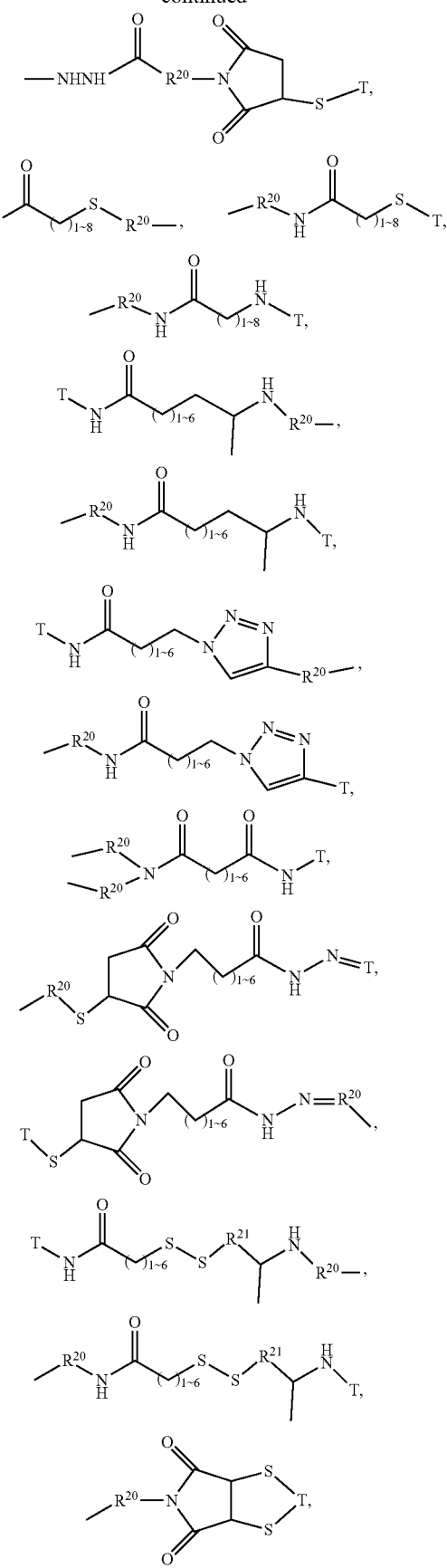

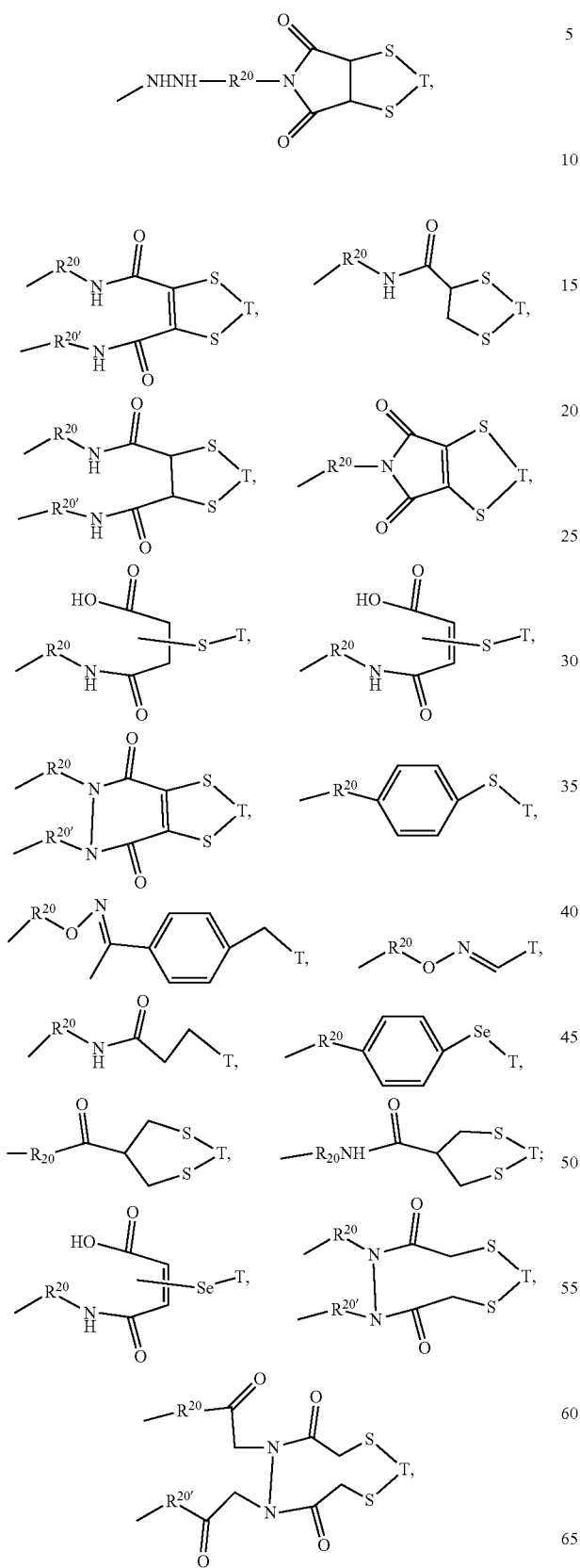
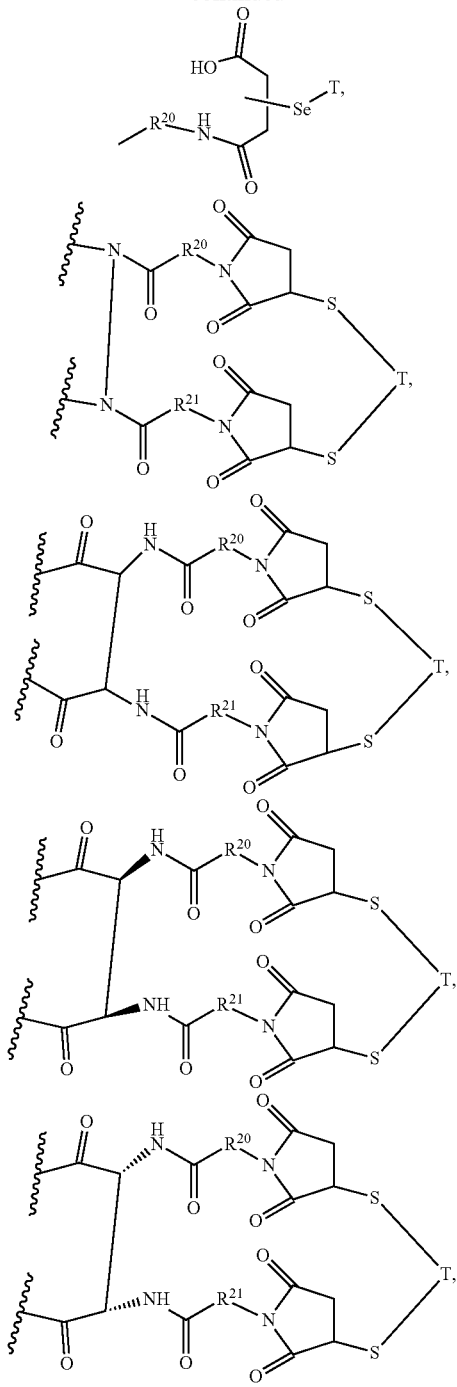

wherein $R^{20}$ and $R^{21}$ are independently $C_1$~$C_8$ alkyl; $C_2$~$C_8$ heteroalkyl, or heterocyclic; $C_3$~$C_8$ aryl, Ar-alkyl, cycloalkyl, alkylcycloalkyl, heterocycloalkyl, heteroalkylcycloalkyl, carbocyclic, or alkylcarbonyl; or $C_2$-$C_{100}$ polyethylene glycol having formula of $(CH_2CH_2O)_p$, p is defined above.

In another further aspect, $Q_1$ and $Q_2$ are preferably selected from a polyalkylene glycol containing a $C_2$-$C_{18}$ lipid, or a $C_2$-$C_{18}$ fatty acid, or a $C_2$-$C_{18}$ fatty ammonium lipid. The polyalkylene glycol chain not only helps the conjugate more hydrophilic during the production, but also prevents the conjugate linker from hydrolysis by a hydrolase, e.g. a proteinase or an esterase. The lipid can help the conjugate to bind to an albumin in mammal bloods and then leads to the conjugate slowly dissociation from this complex during the blood circulation. Thus, the side chain linker of the present patent application makes the conjugate more stable in the circulation. Polyalkylene glycols here include, but are not limited to, poly(ethylene glycols) (PEGs), poly (propylene glycol) and copolymers of ethylene oxide and propylene oxide; particularly preferred are PEGs, and more particularly preferred are monofunctionally activated hydroxyPEGs (e.g., hydroxyl PEGs activated at a single terminus, including reactive esters of hydroxyPEG-monocarboxylic acids, hydroxyPEG-monoaldehydes, hydroxyPEG-monoamines, hydroxyPEG-monohydrazides, hydroxyPEG-monocarbazates, hydroxyl PEG-monoiodoacetamides, hydroxyl PEG-monomaleimides, hydroxyl PEG-monoorthopyridyl disulfides, hydroxyPEG-monooximes, hydroxyPEG-monophenyl carbonates, hydroxyl PEG-monophenyl glyoxals, hydroxyl PEG-monothiazolidine-2-thiones, hydroxyl PEG-monothioesters, hydroxyl PEG-monothiols, hydroxyl PEG-monotriazines and hydroxyl PEG-monovinylsulfones). The polyalkylene glycol has a molecular weight of from about 10 Daltons to about 200 kDa, preferably about 88 Da to about 40 kDa; two branch chains each with a molecular weight of about 88 Da to about 40 kDa; and more preferably two branches, each of about 88 Da to about 20 kDa. In one particular embodiment, the polyalkylene glycol is poly(ethylene) glycol and has a molecular weight of about 10 kDa; about 20 kDa, or about 40 kDa. In specific embodiments, the PEG is a PEG 10 kDa (linear or branched), a PEG 20 kDa (linear or branched), or a PEG 40 kDa (linear or branched). A number of US patents have disclosed the preparation of linear or branched "non-antigenic" PEG polymers and derivatives or conjugates thereof, e.g., U.S. Pat. Nos. 5,428,128; 5,621,039; 5,622, 986; 5,643,575; 5,728,560; 5,730,990; 5,738,846; 5,811, 076; 5,824,701; 5,840,900; 5,880,131; 5,900,402; 5,902, 588; 5,919,455; 5,951,974; 5,965,119; 5,965,566; 5,969, 040; 5,981,709; 6,011,042; 6,042,822; 6,113,906; 6,127, 355; 6,132,713; 6,177,087, and 6,180,095.

Examples of Formula (I) are listed below:

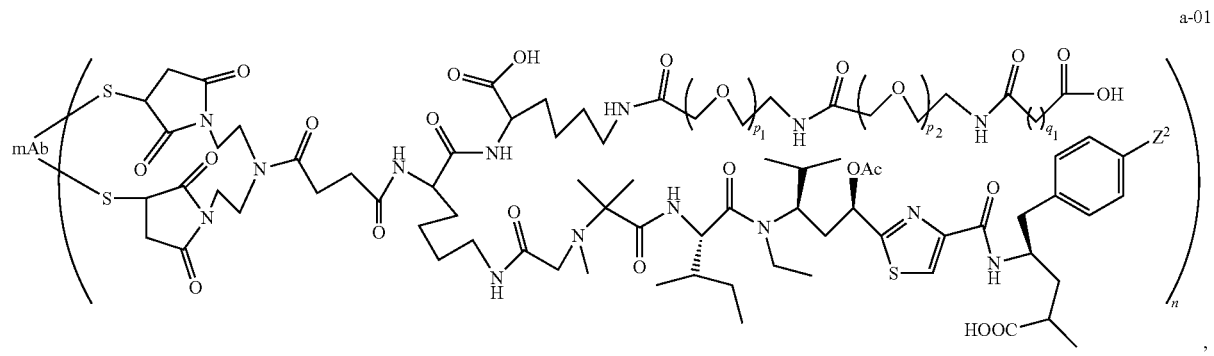

a-01

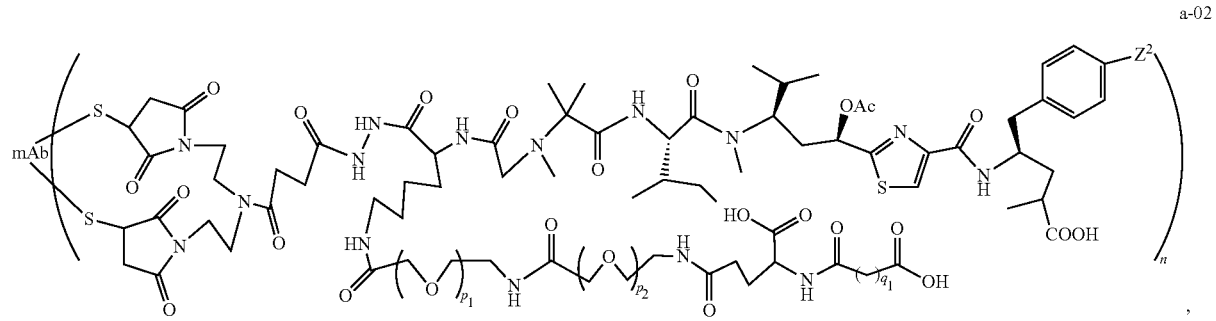

a-02

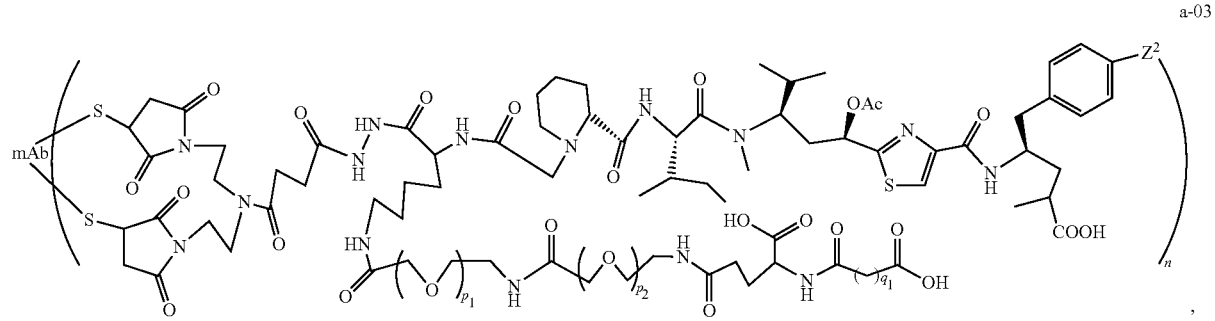

a-03

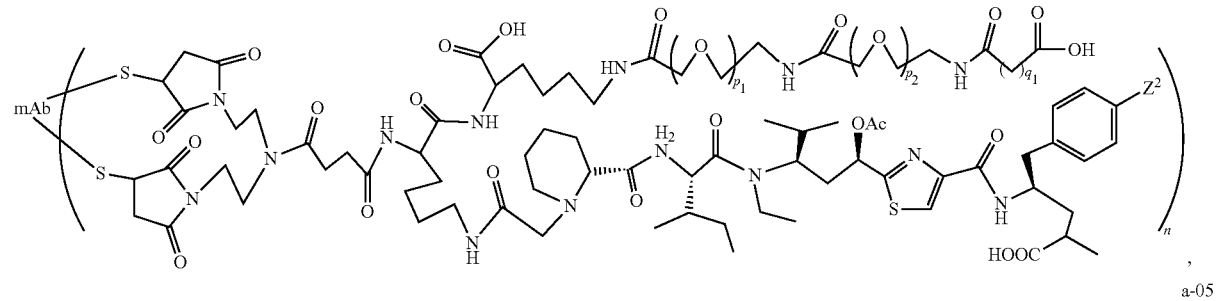
a-04
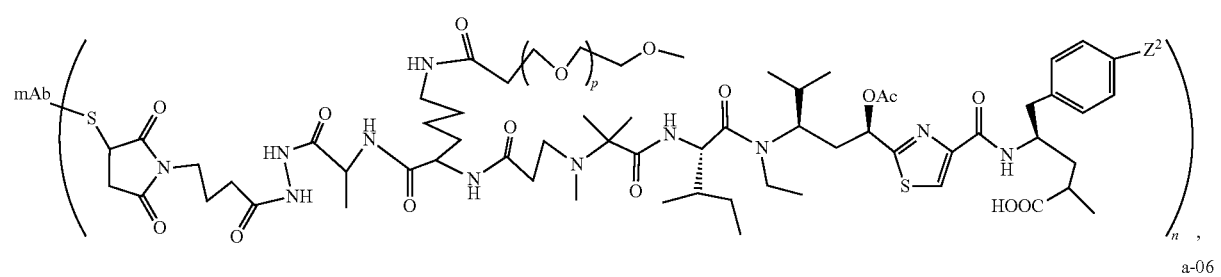
a-05

a-06
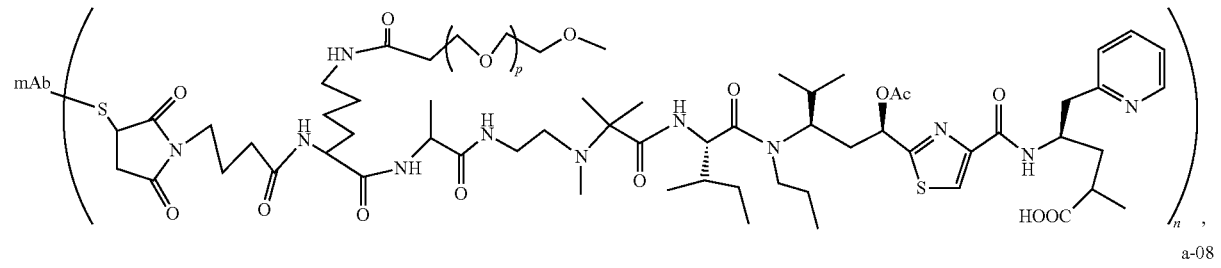
a-07
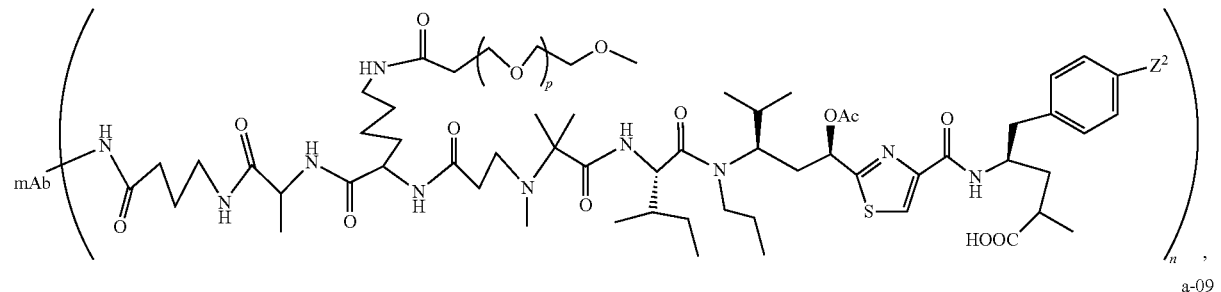
a-08
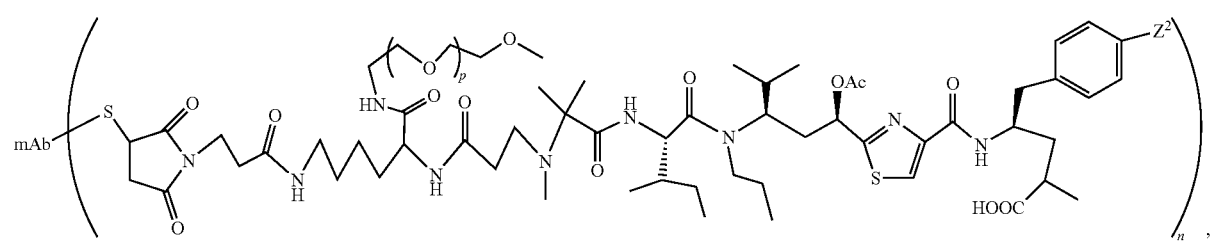
a-09

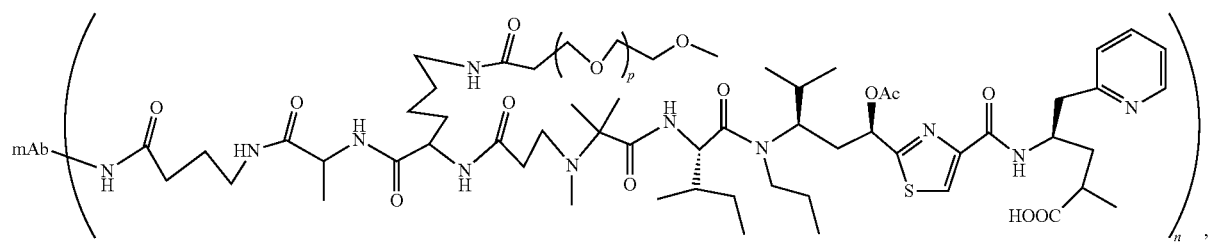
a-10
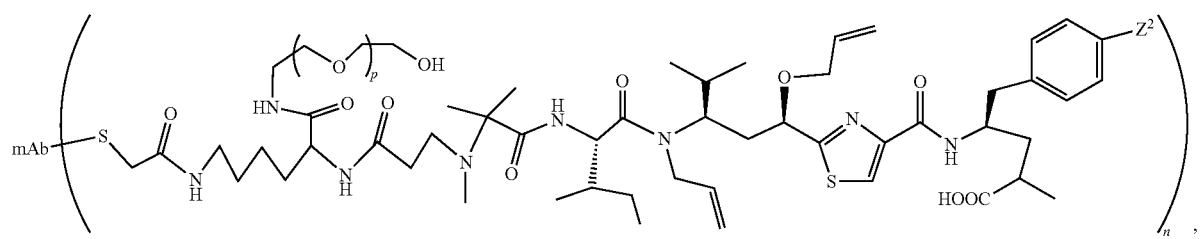
a-11
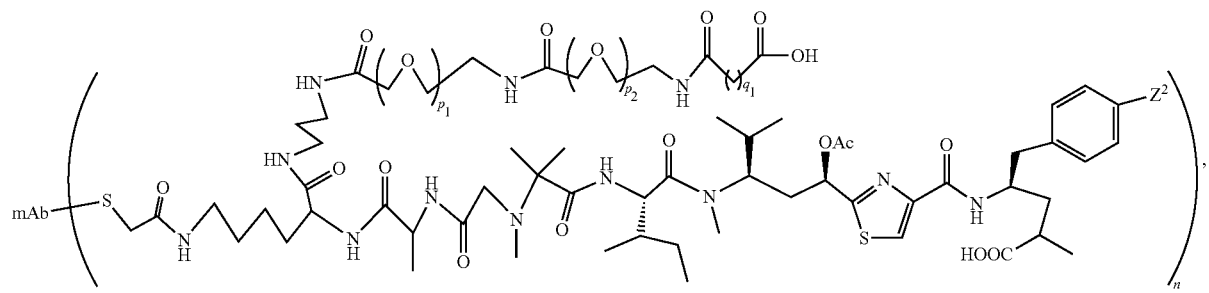
a-12
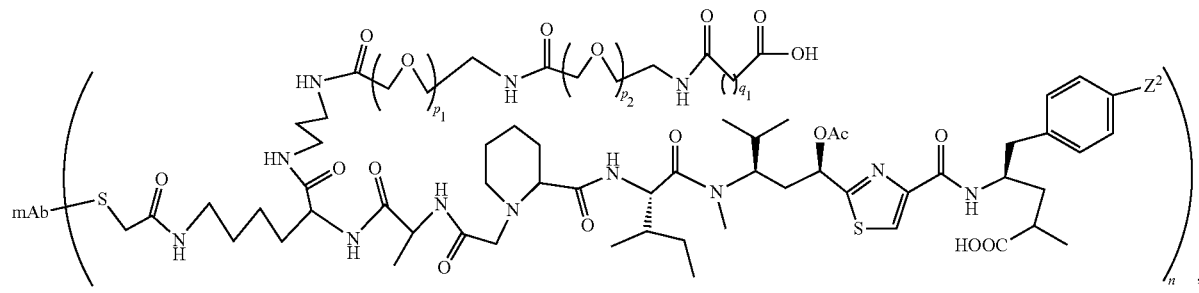
a-13
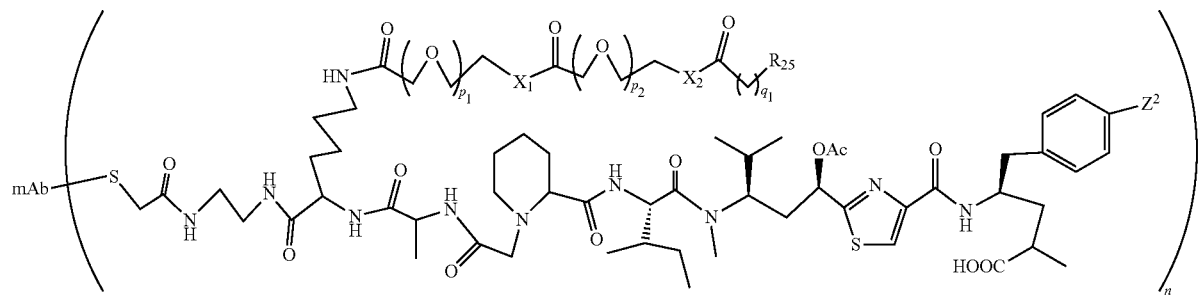
a-14

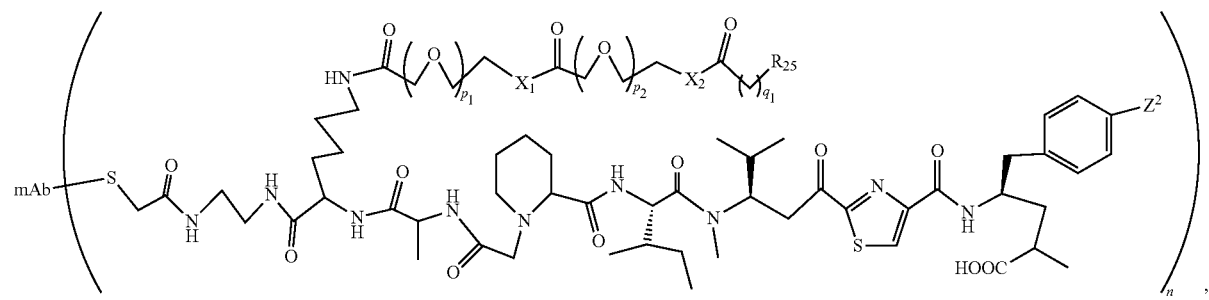
a-15
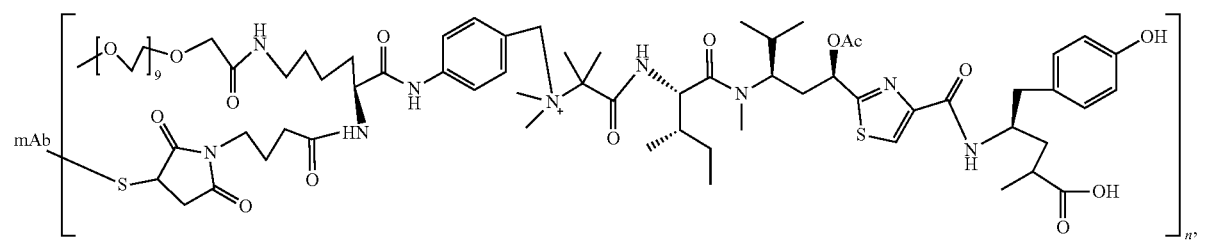
a-16

a-17
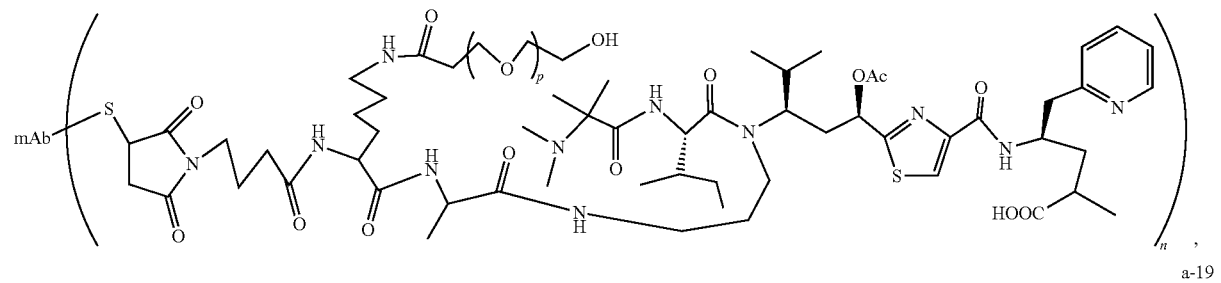
a-18
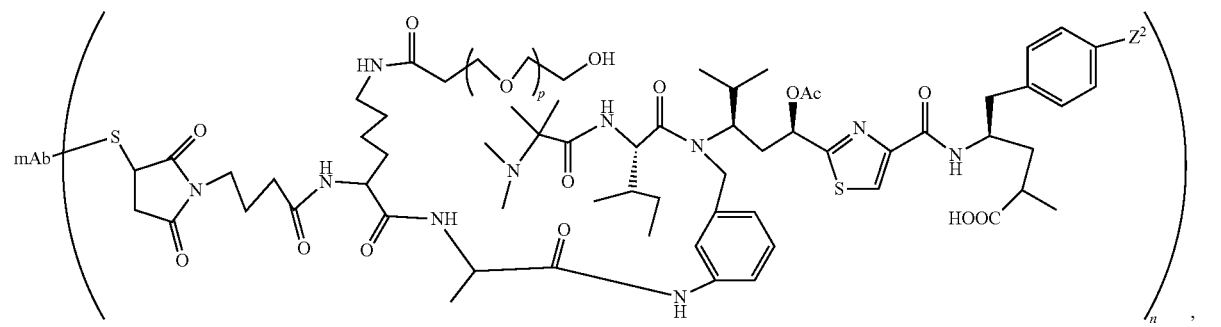
a-19

-continued
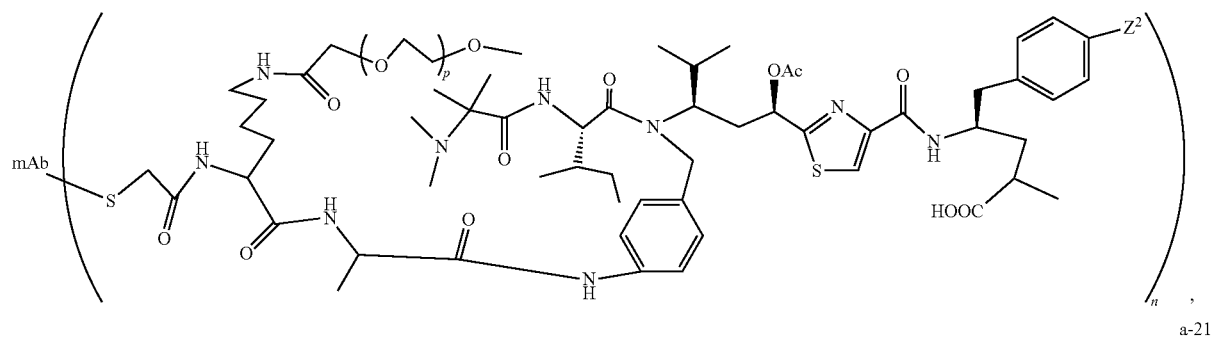
a-20
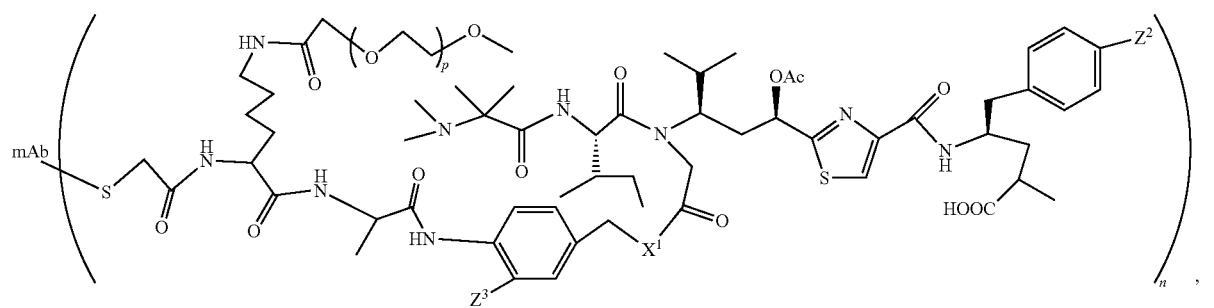
a-21
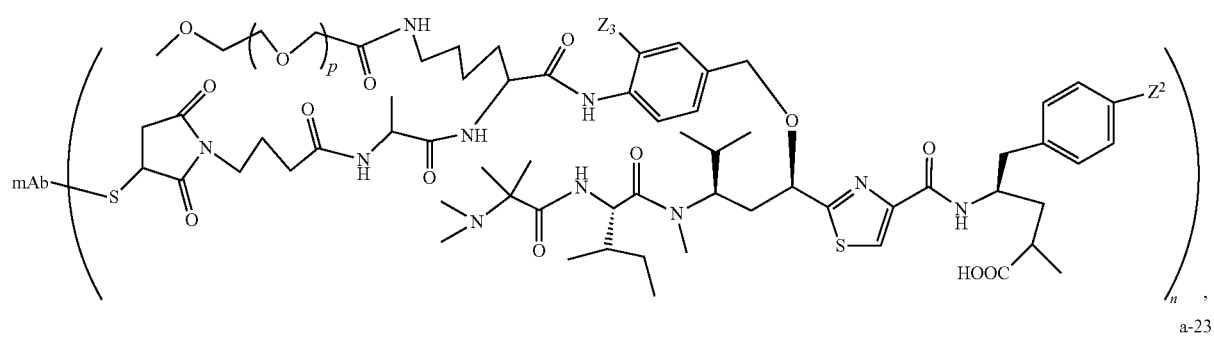
a-22
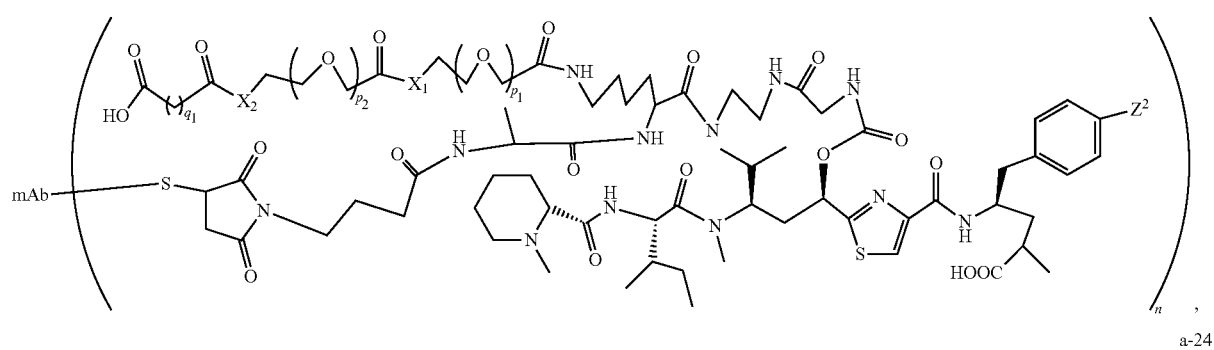
a-23
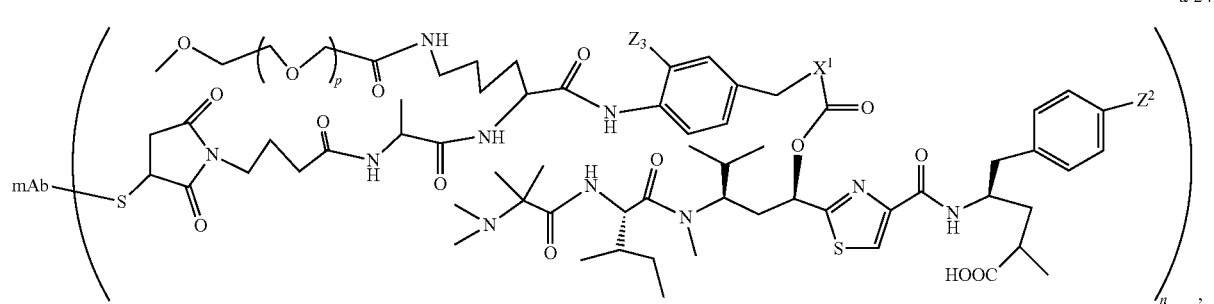
a-24

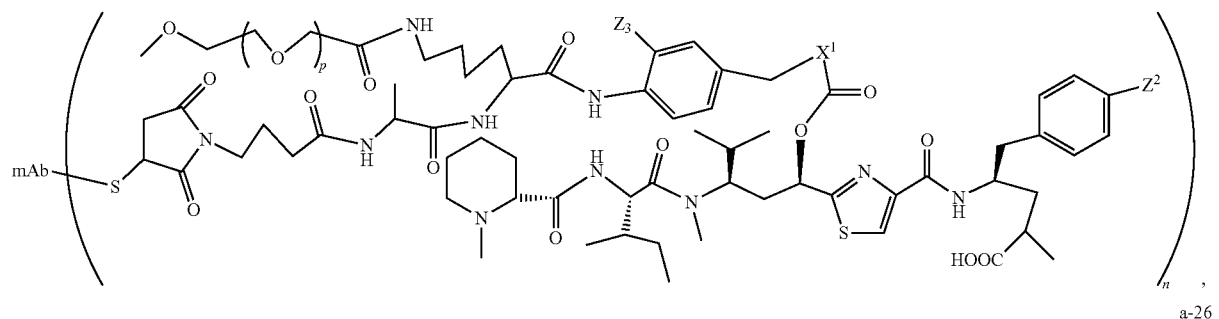
a-25
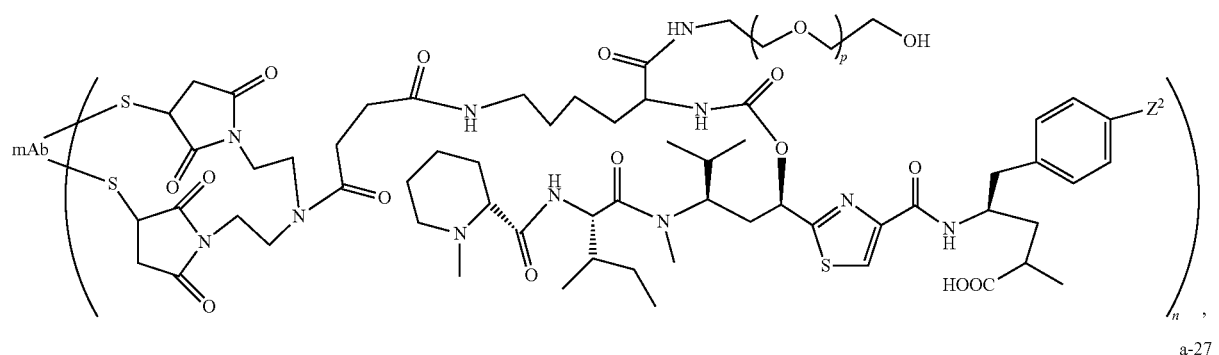
a-26

a-27
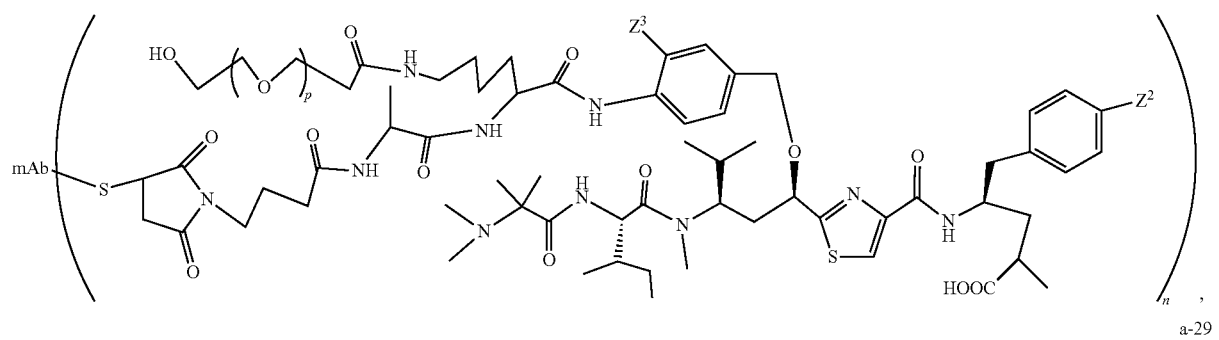
a-28
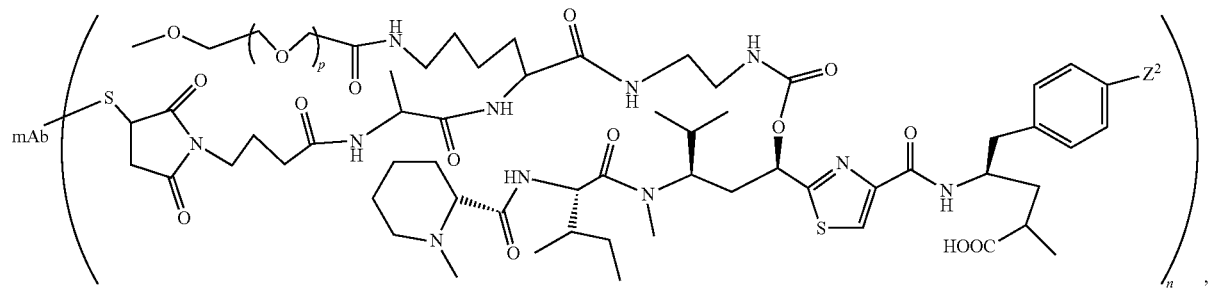
a-29

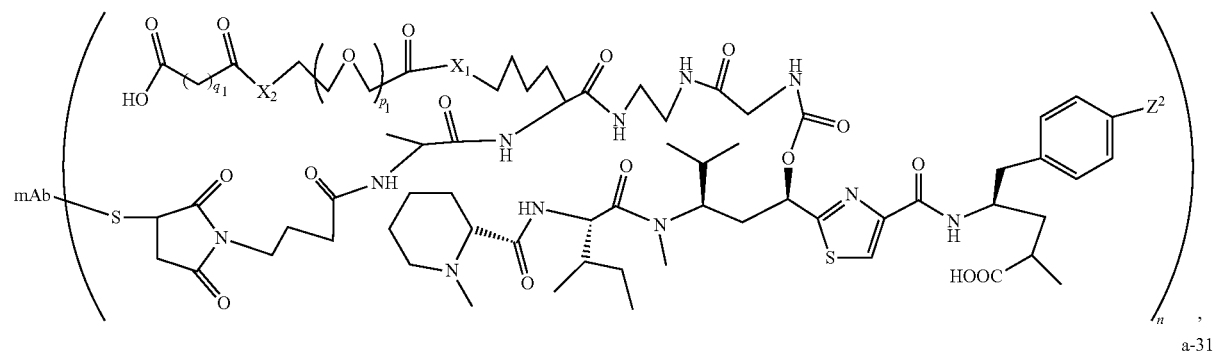
a-30
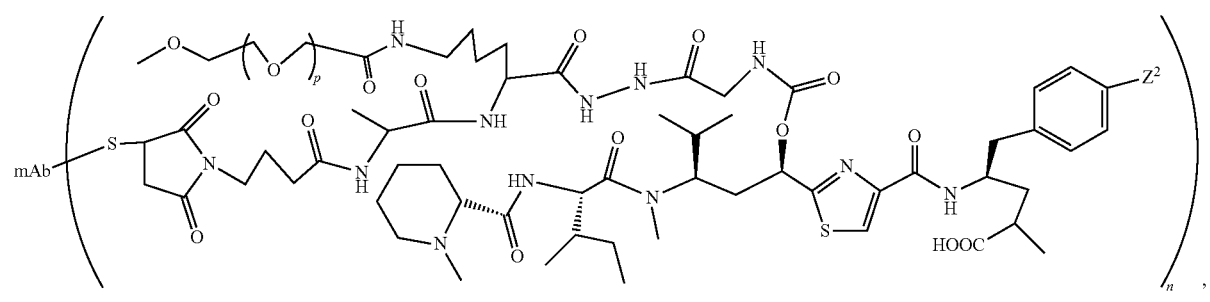
a-31
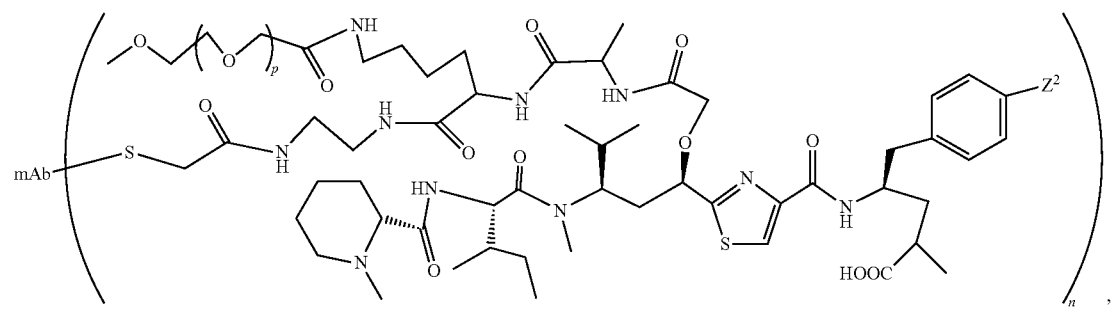
a-32
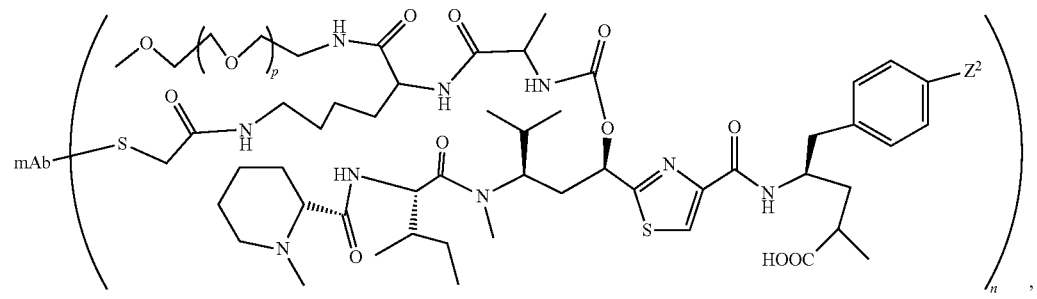
a-33
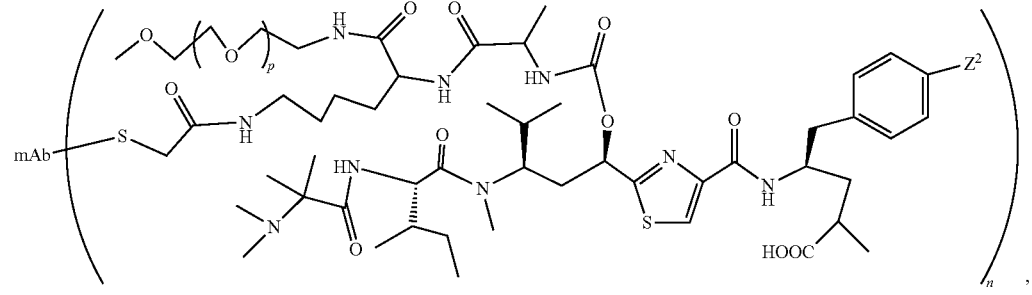
a-34

-continued
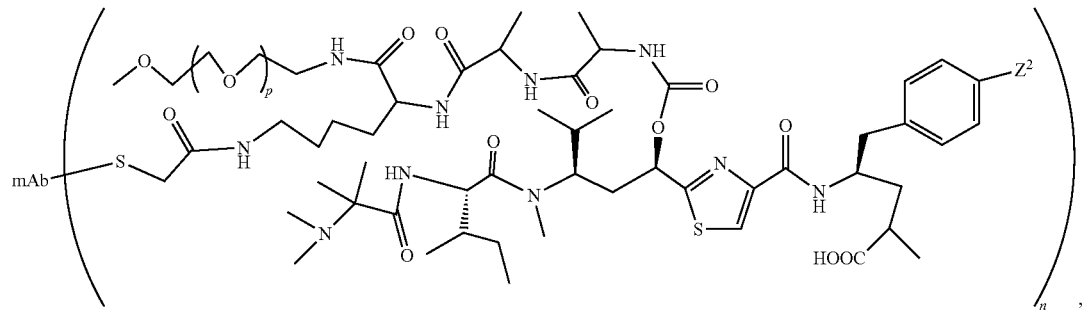
a-35
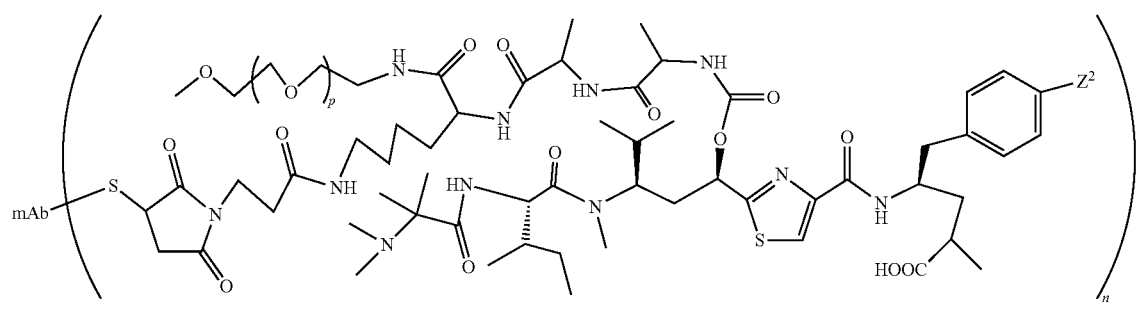
a-36
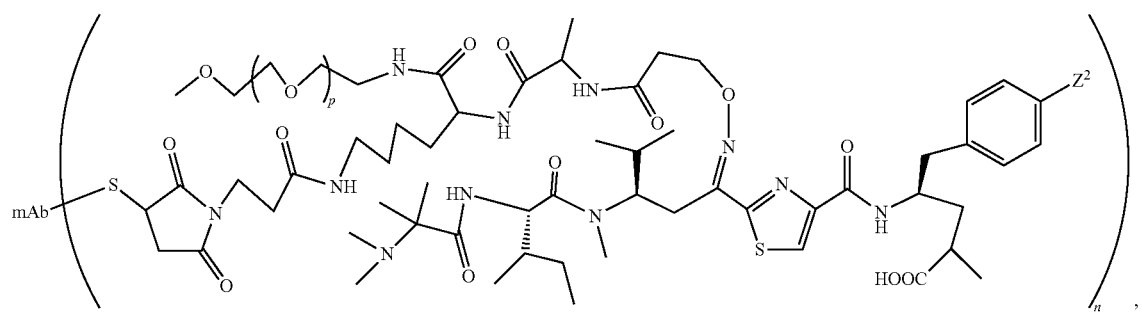
a-37
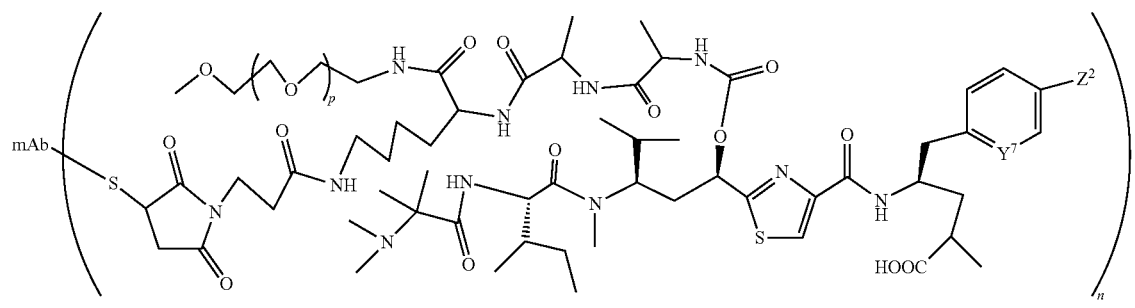
a-38
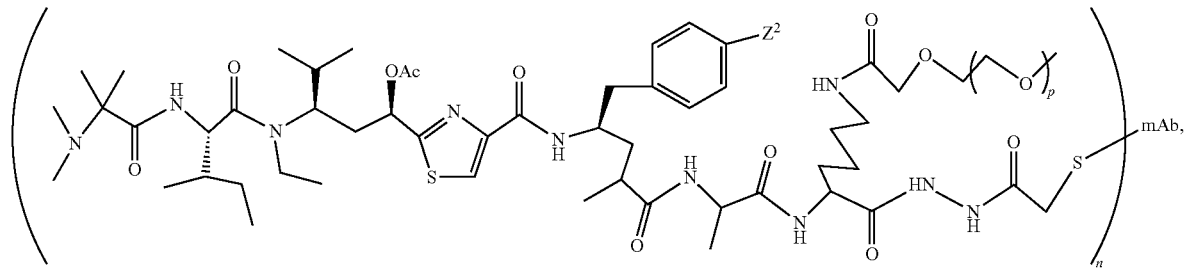
a-39

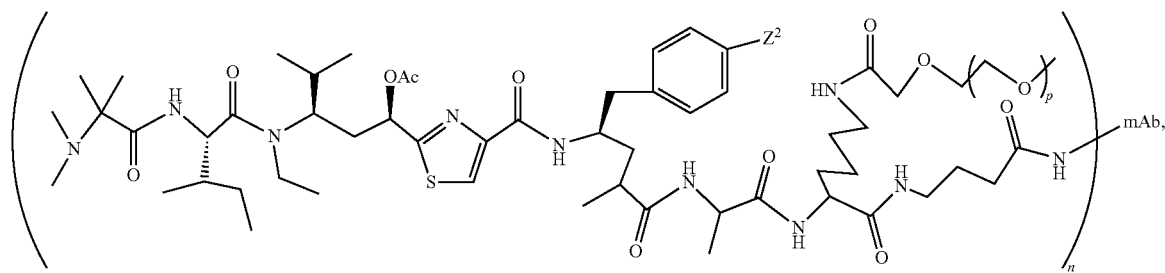
a-40
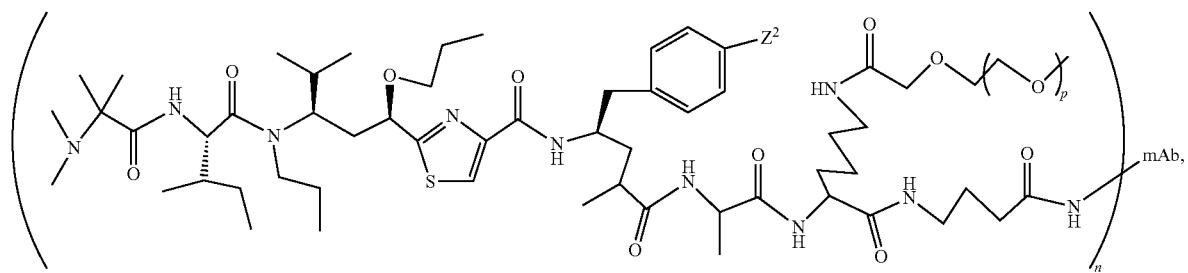
a-41
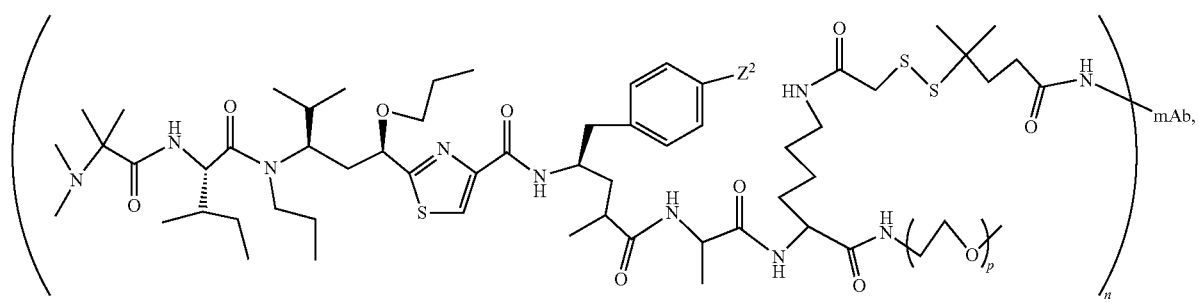
a-42
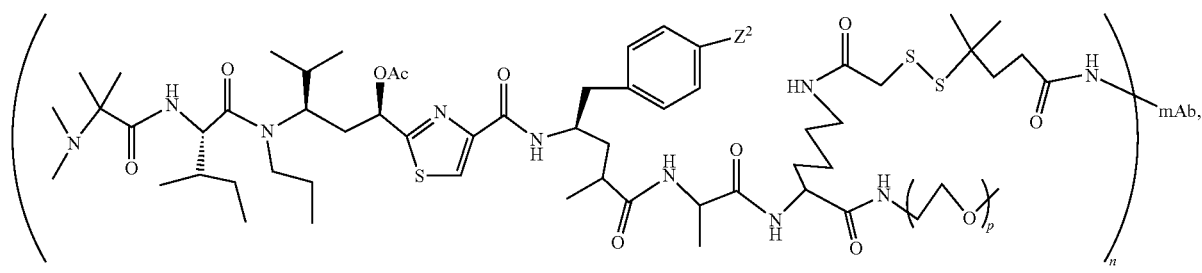
a-43
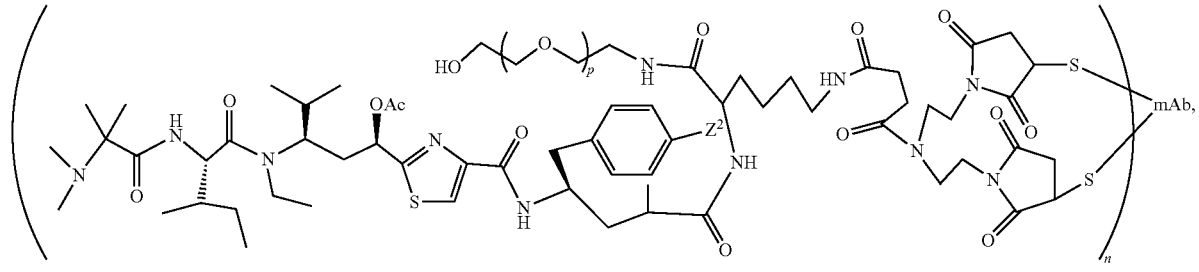
a-44

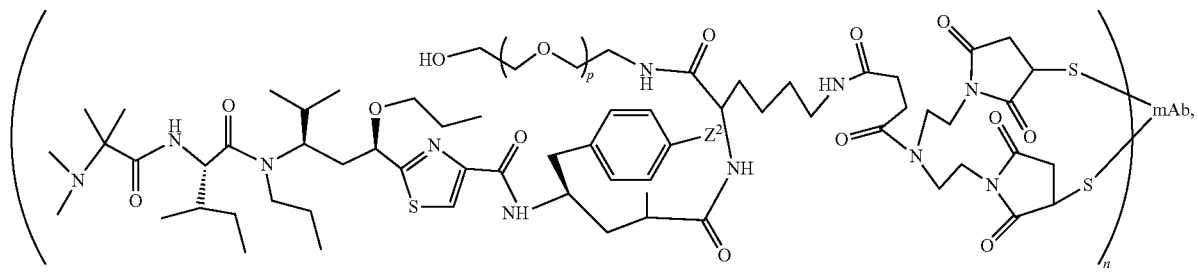
a-45
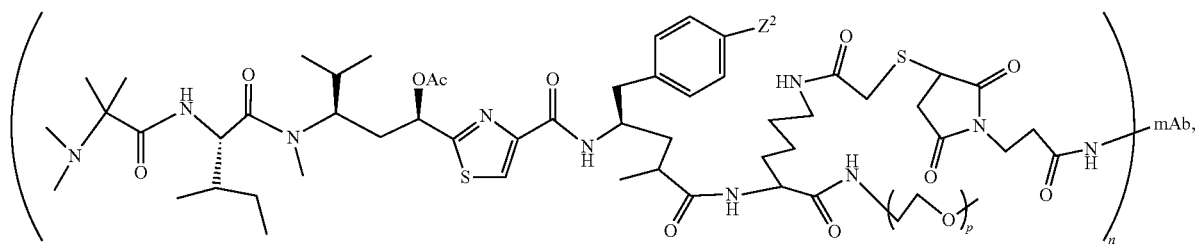
a-46
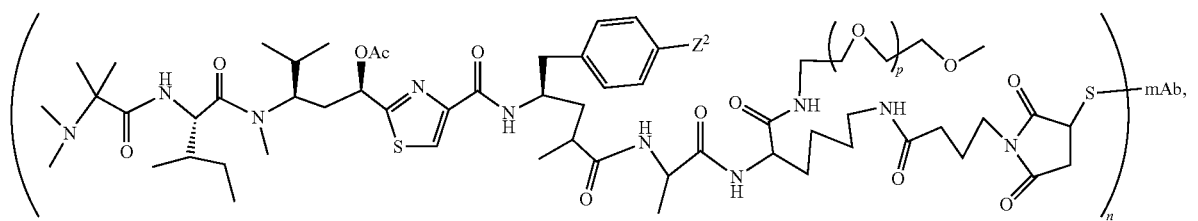
a-47
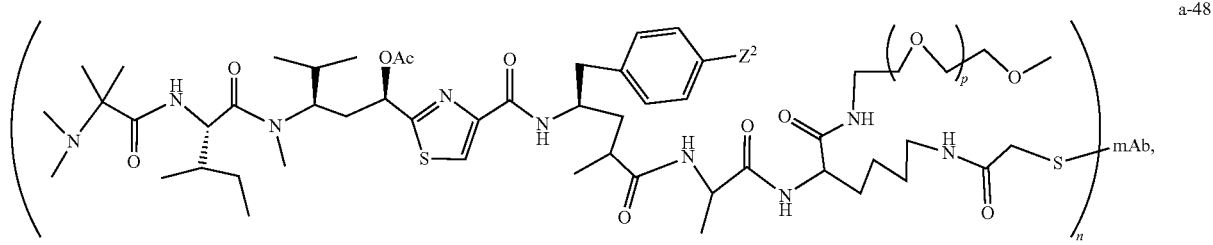
a-48
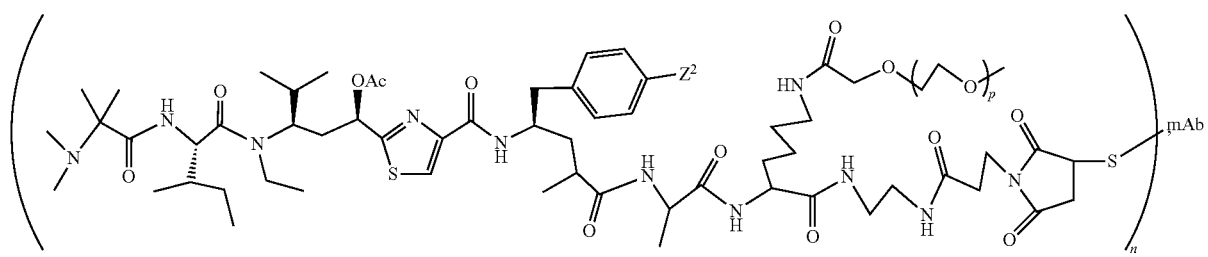
a-49
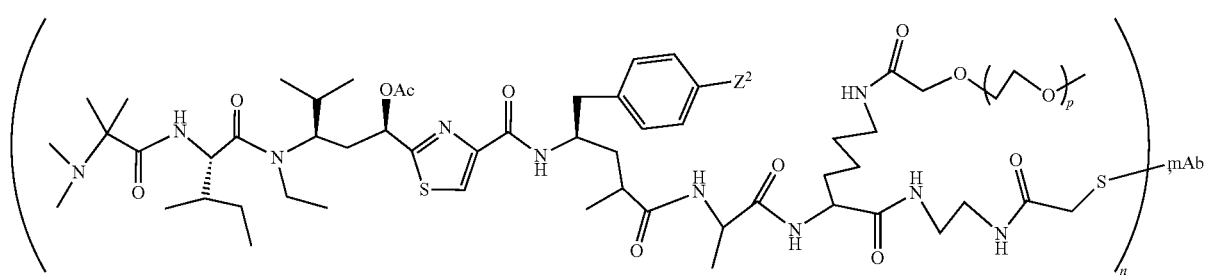
a-50

-continued
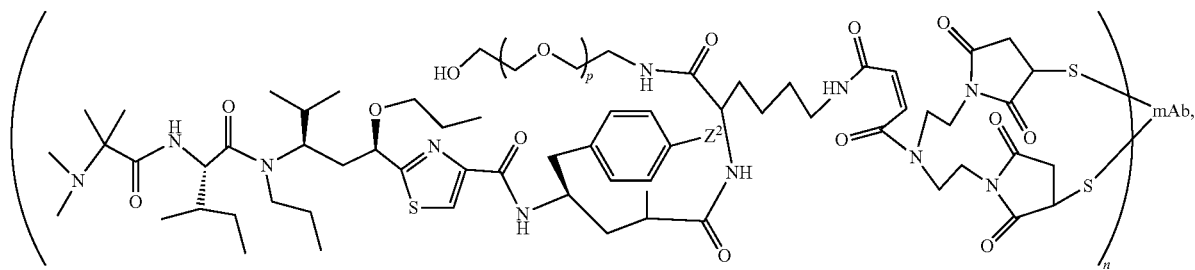
a-51
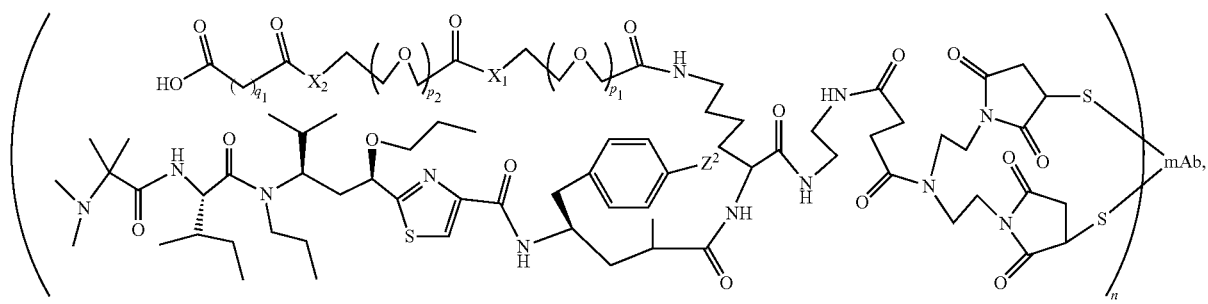
a-52
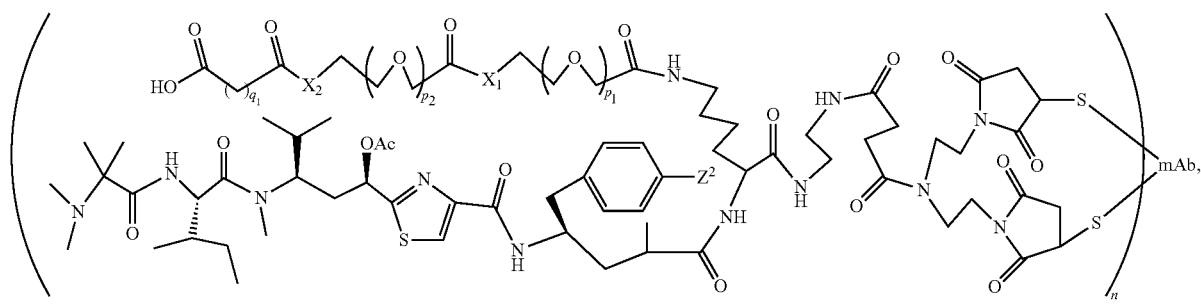
a-53
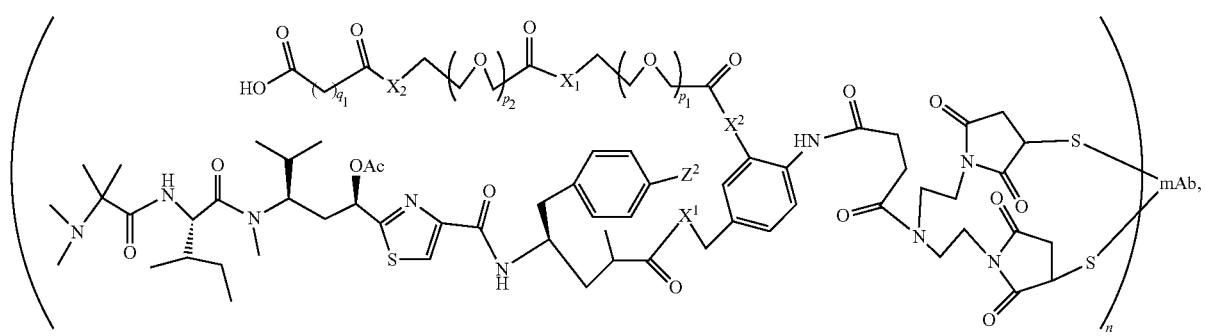
a-54
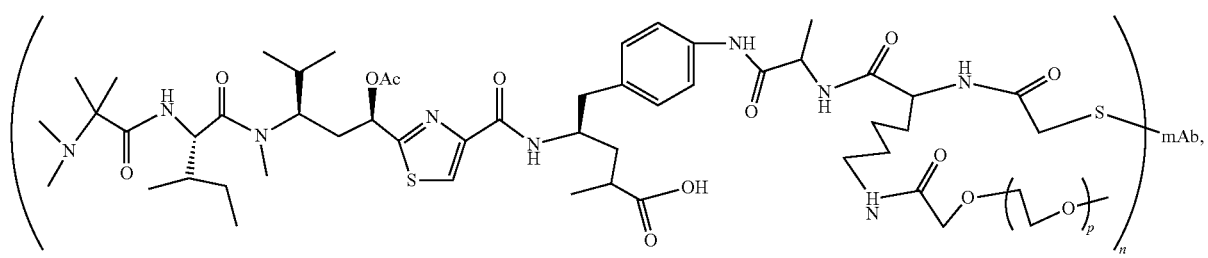
a-55 a-56
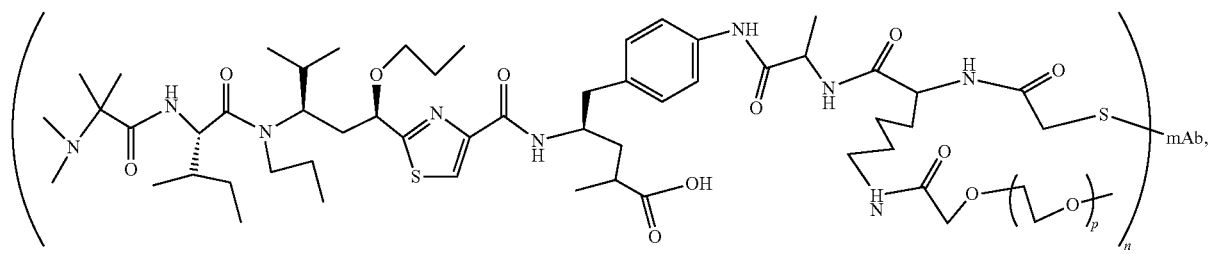
a-57
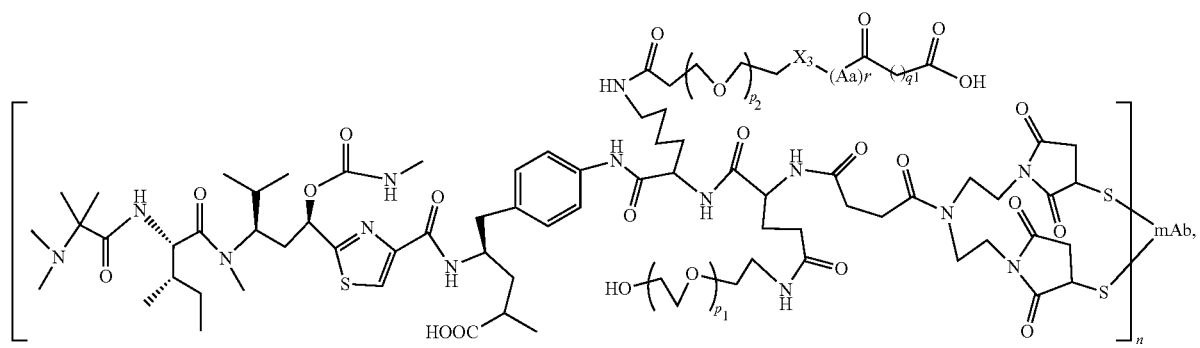
a-58
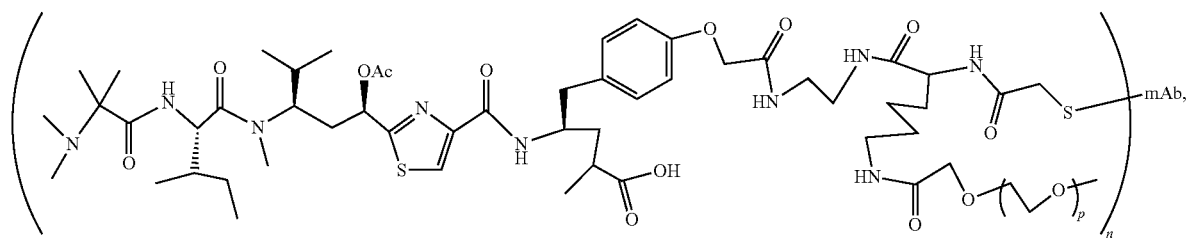
a-59
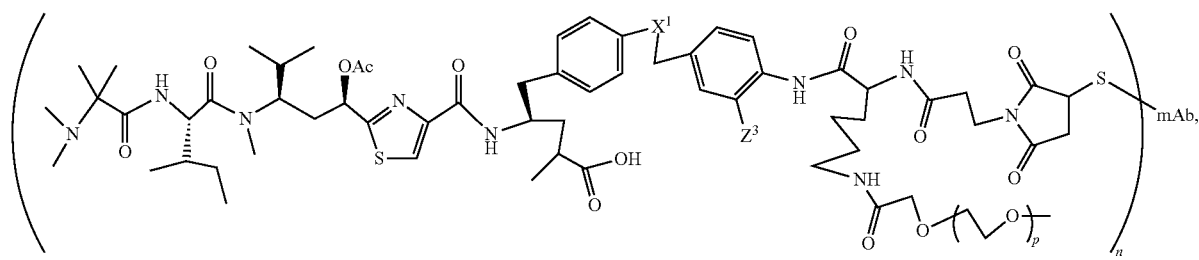
a-60
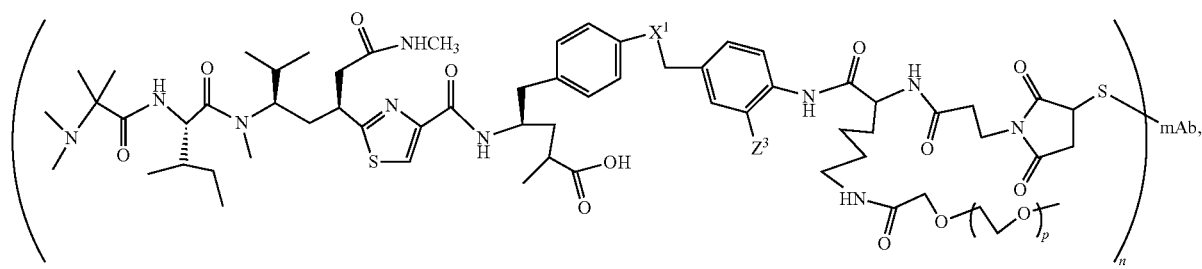

-continued
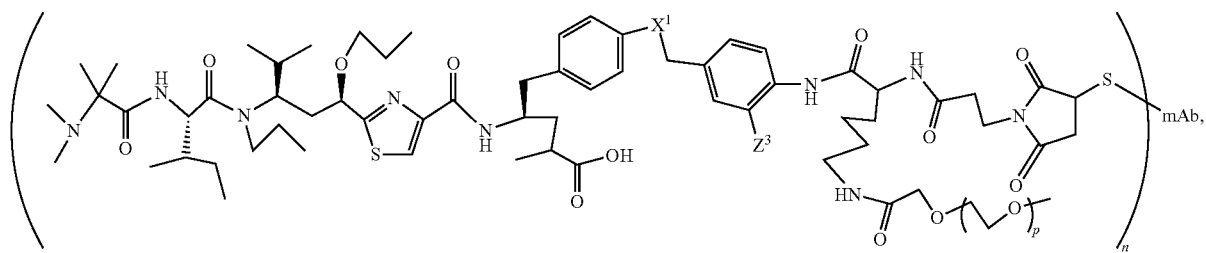
a-61
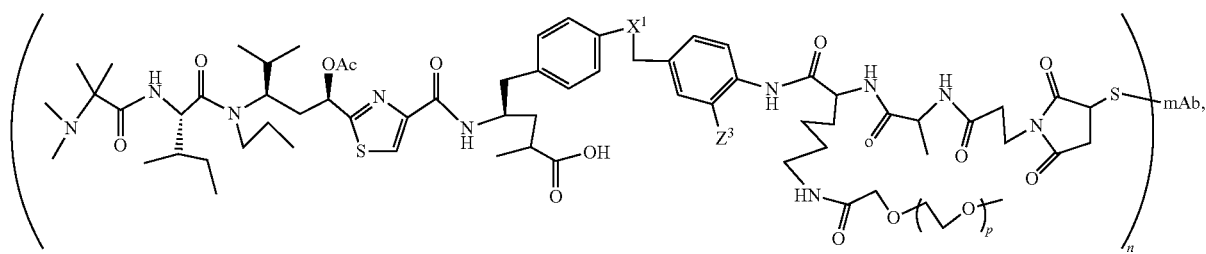
a-62
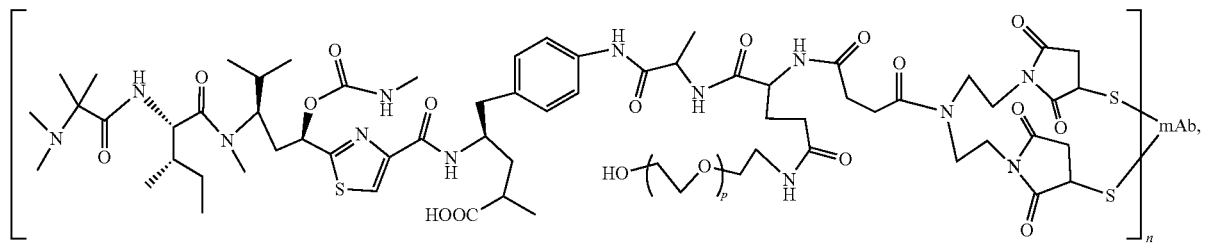
a-63
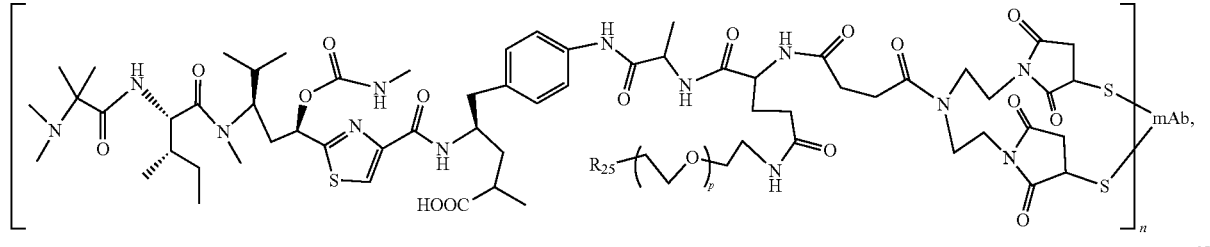
a-64
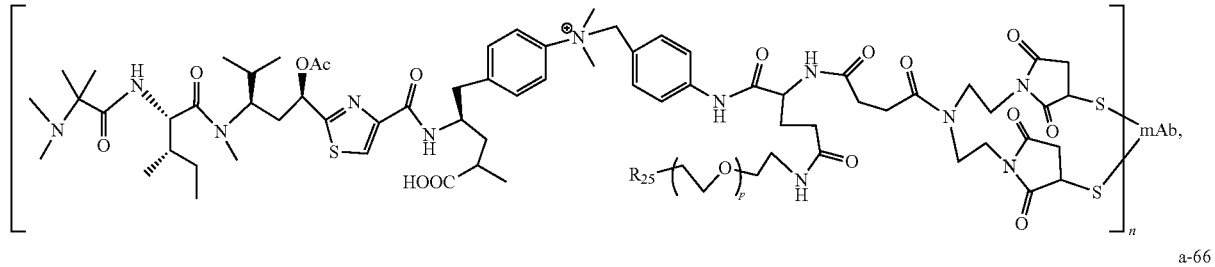
a-65
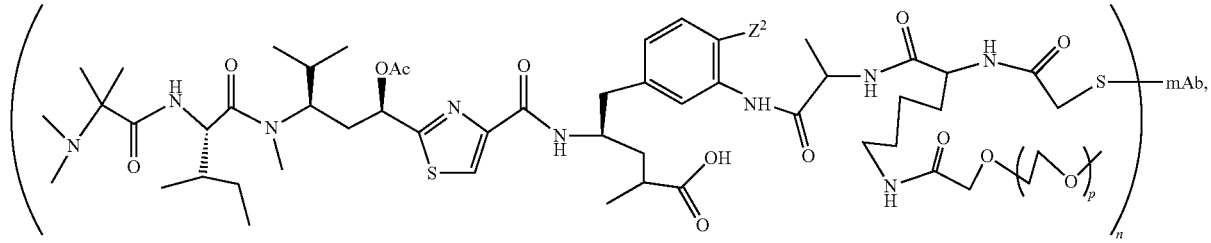
a-66 a-67
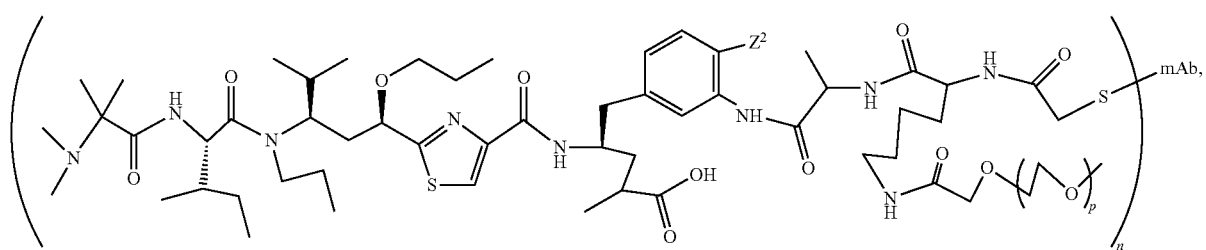
a-68
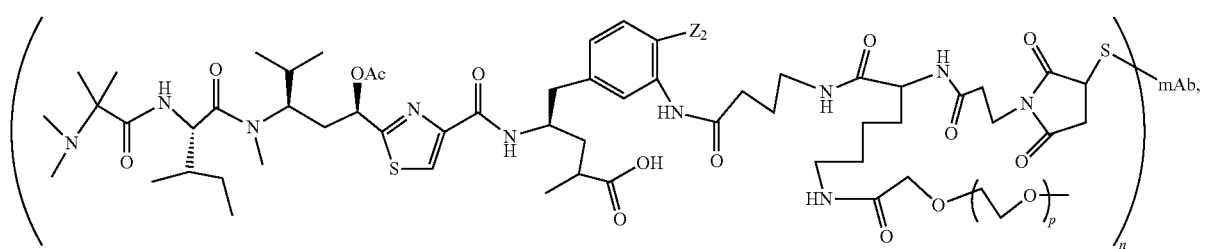
a-69
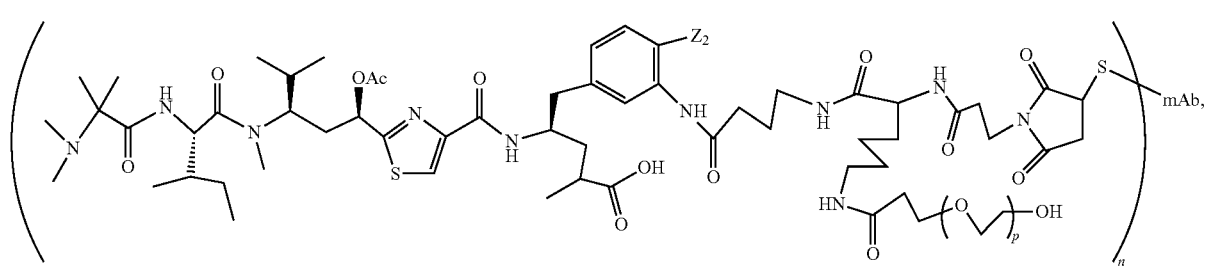
a-70
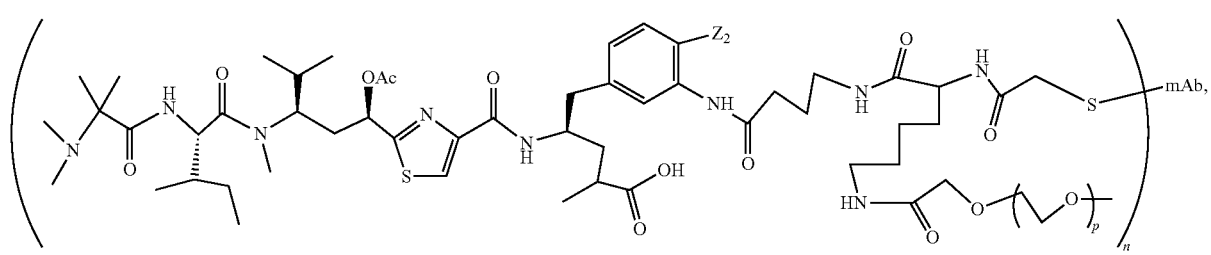
a-71
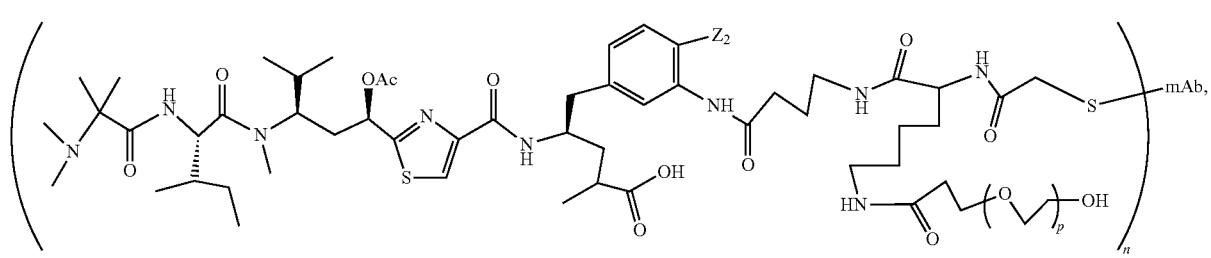
a-72
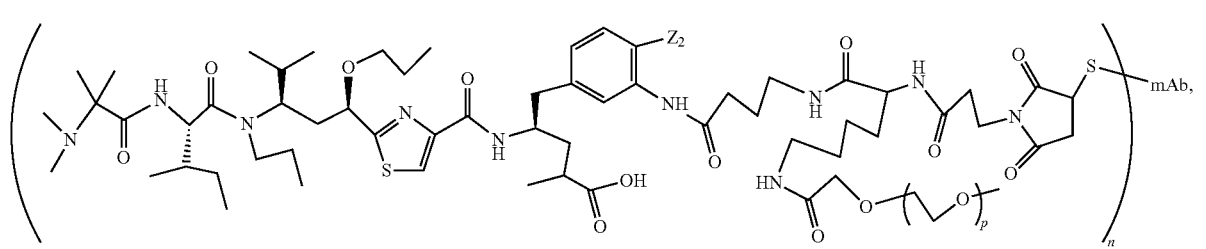

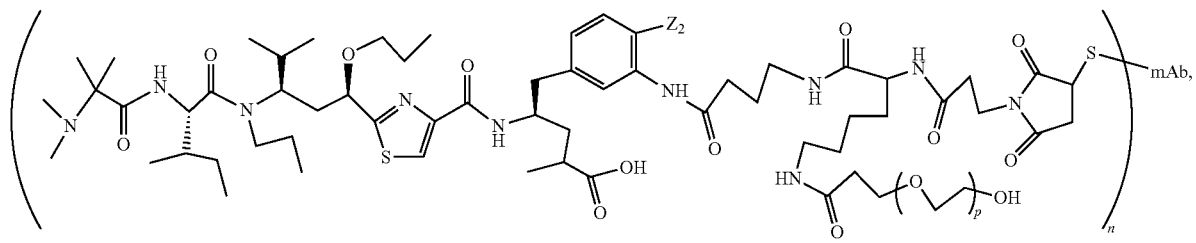
a-73
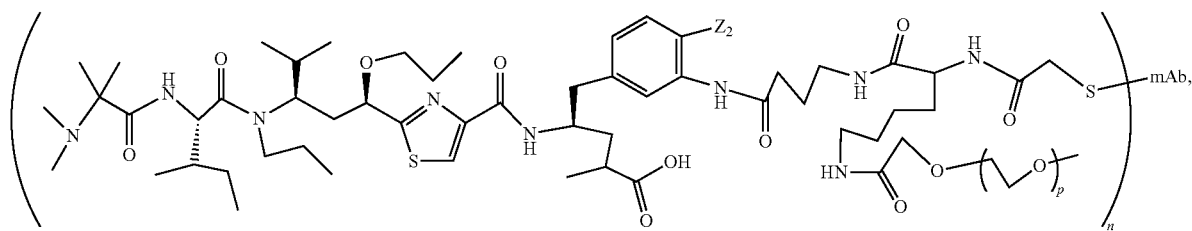
a-74
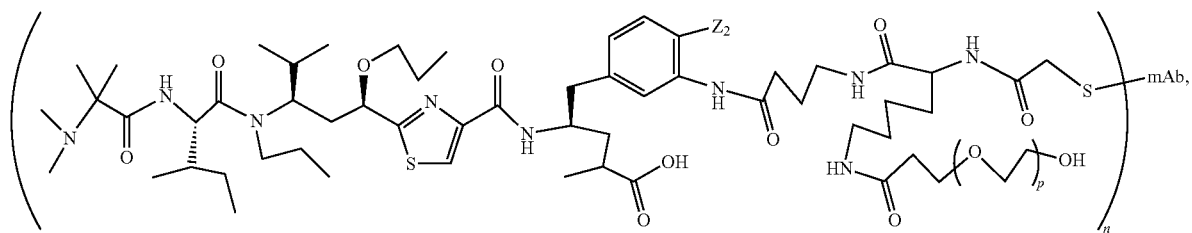
a-75
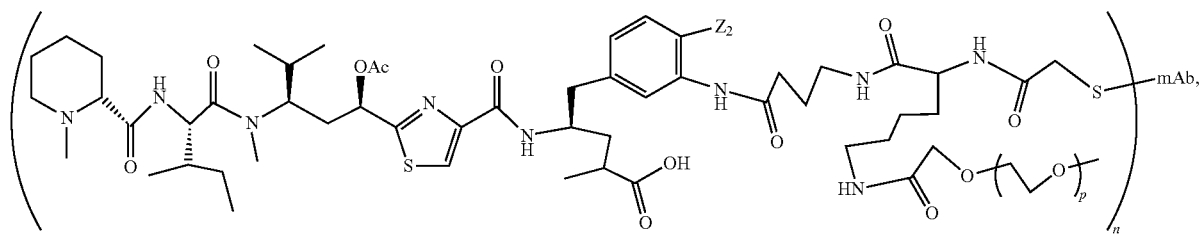
a-76
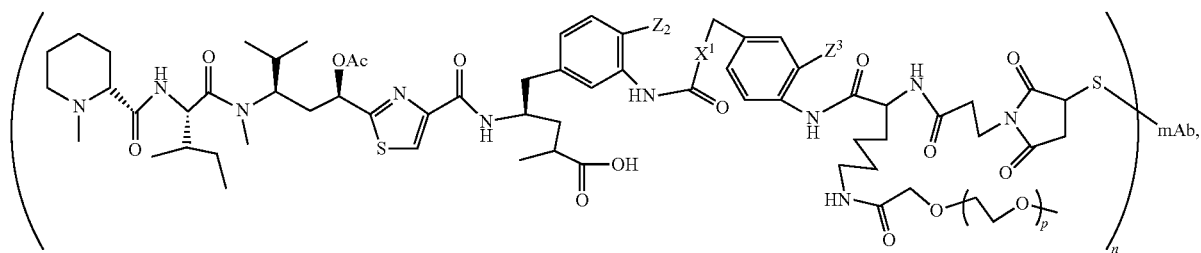
a-77
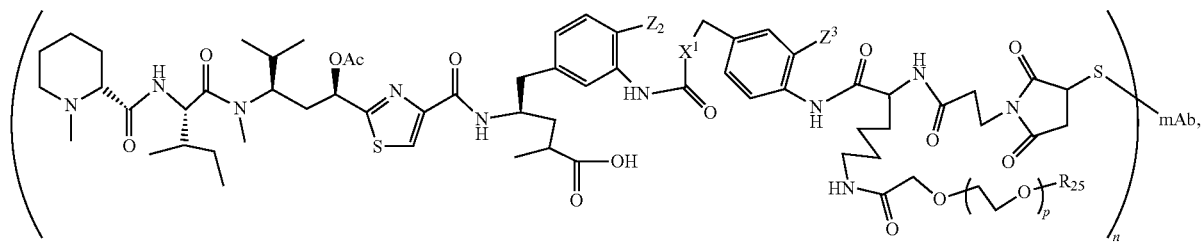
a-78

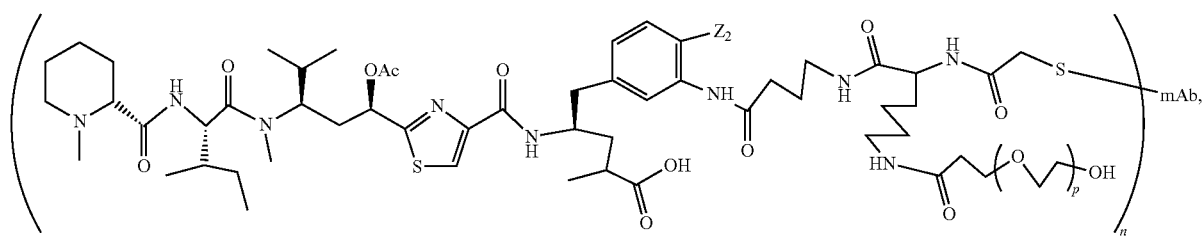
a-79
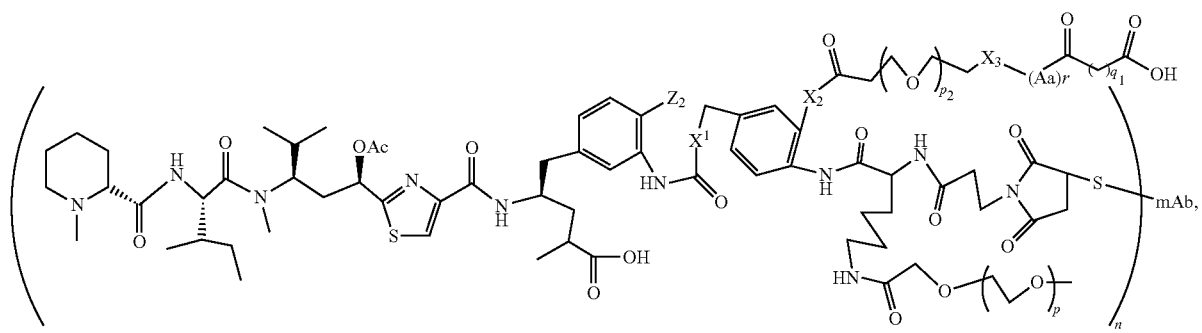
a-80
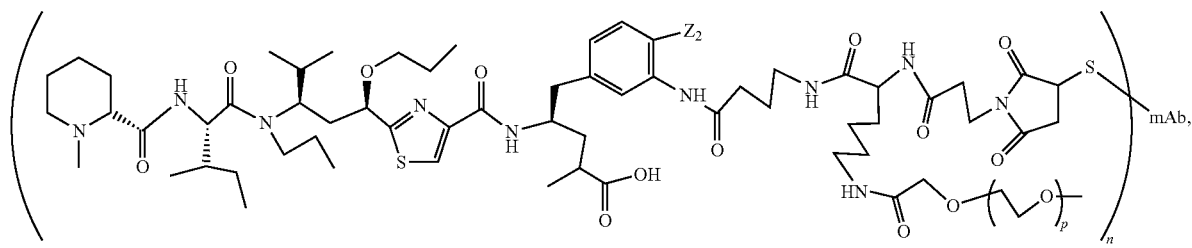
a-81
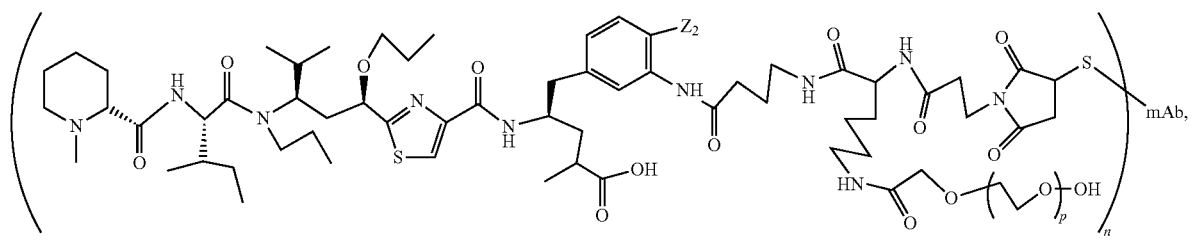
a-82
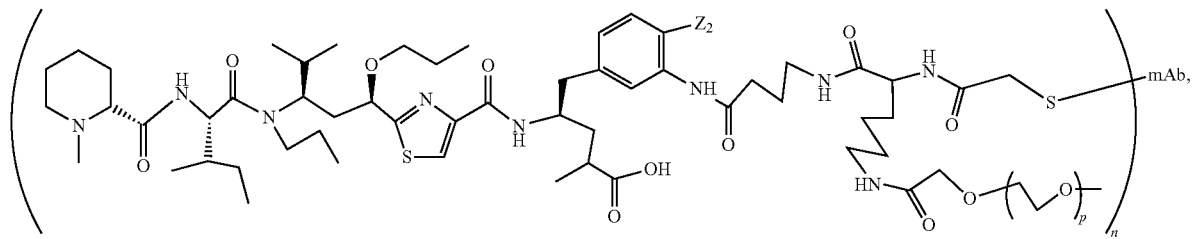
a-83

-continued
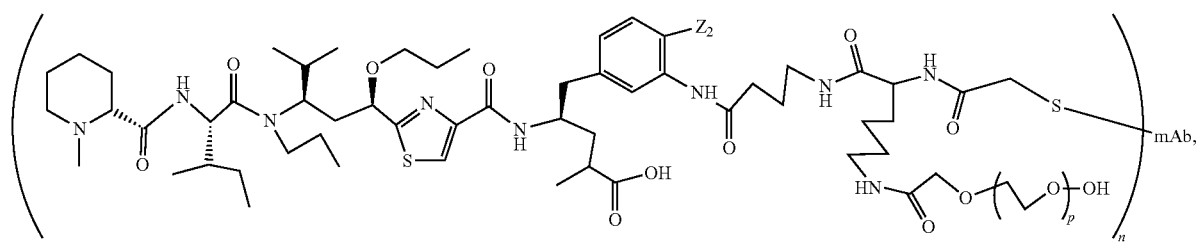
a-84
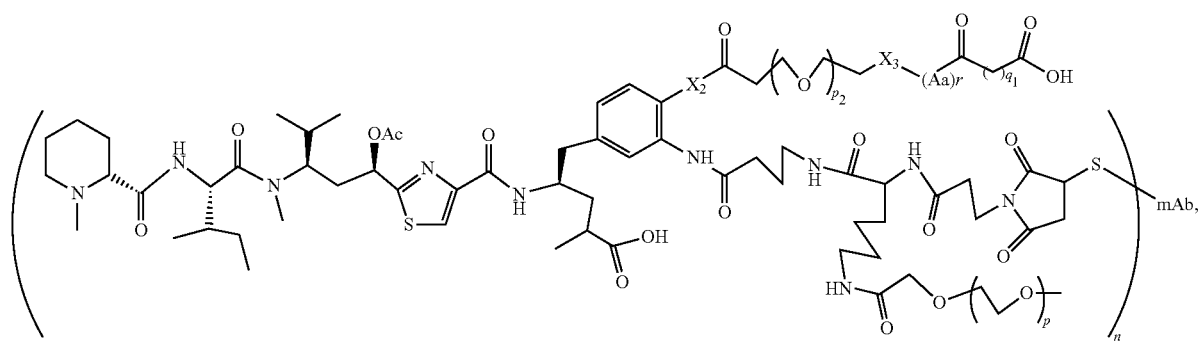
a-85
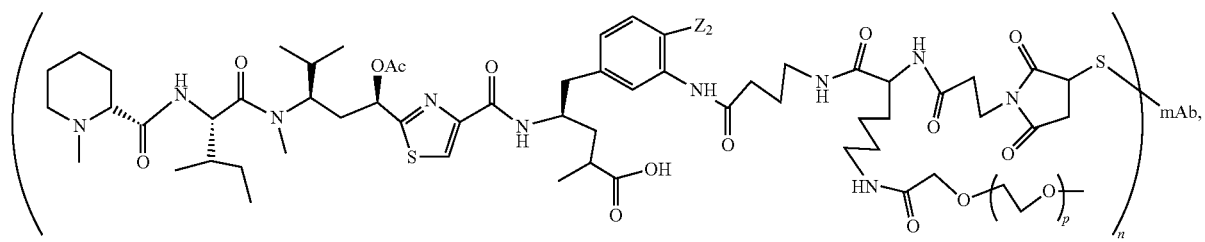
a-86
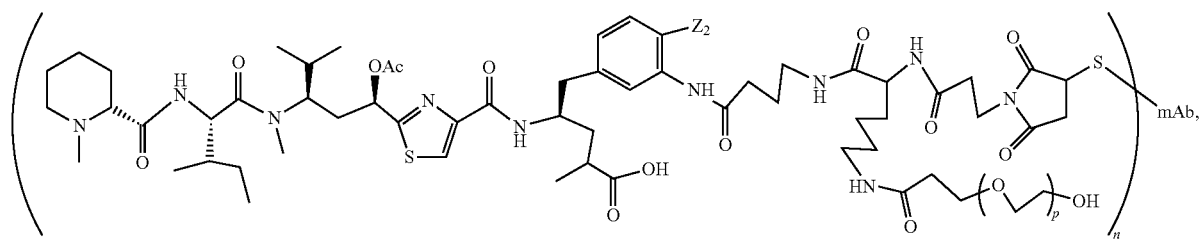
a-87
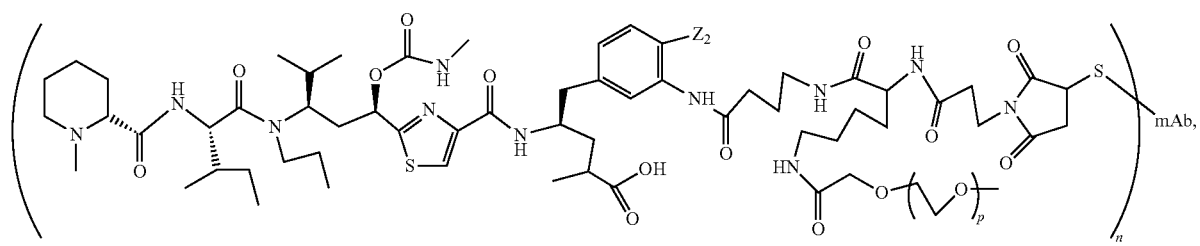
a-88 a-89
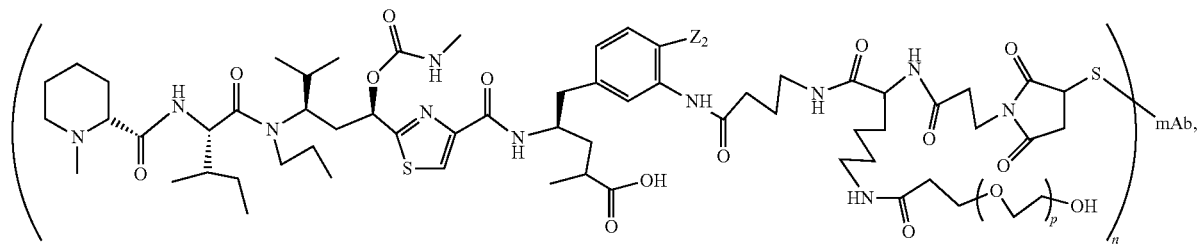
a-90
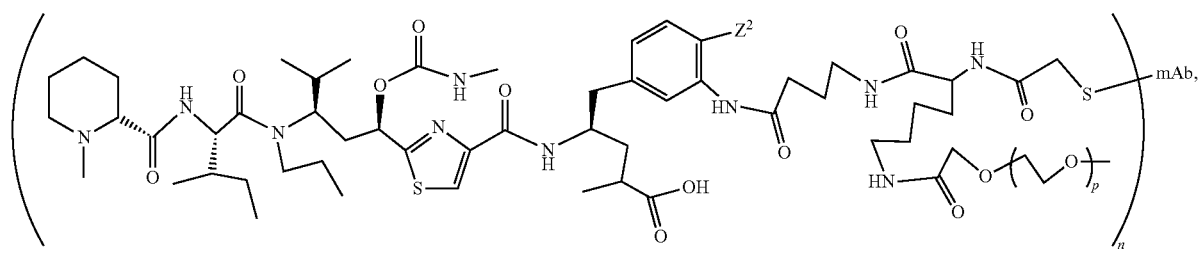
a-91
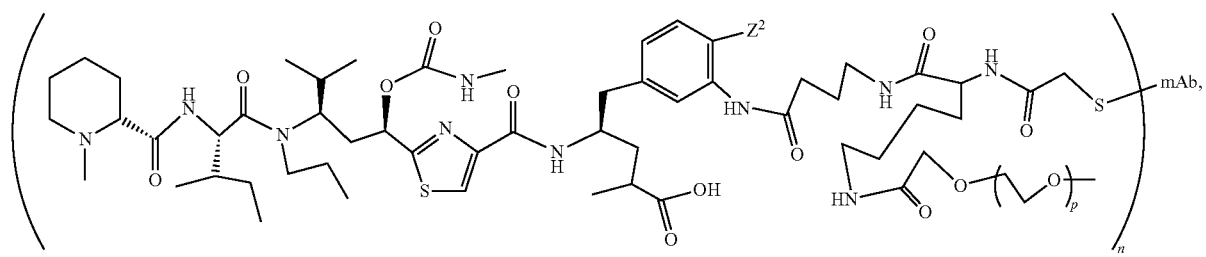
a-92
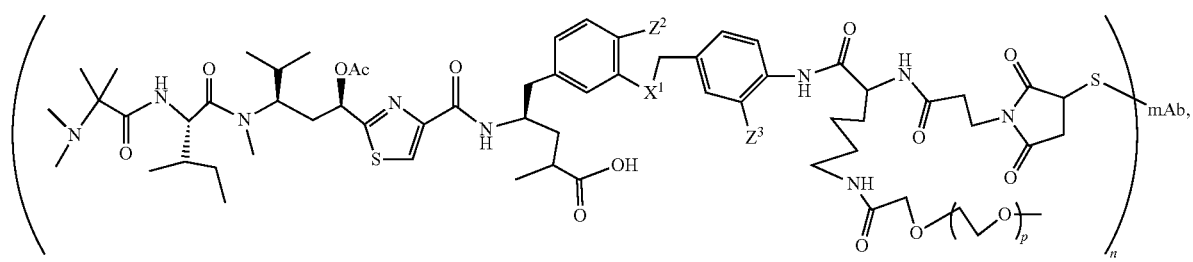
a-93
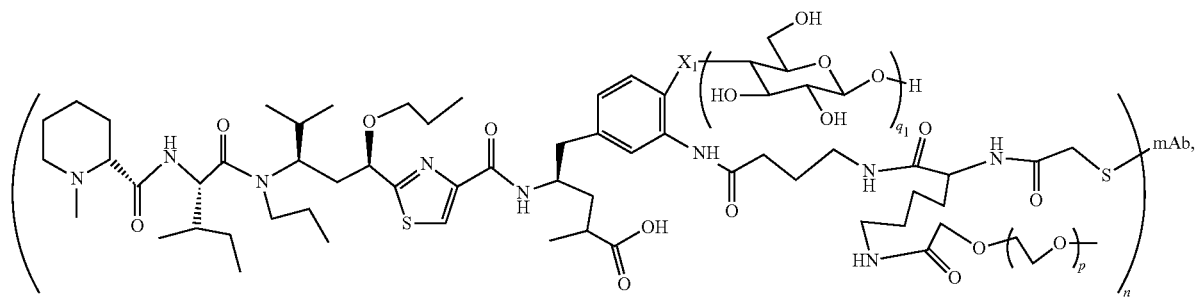

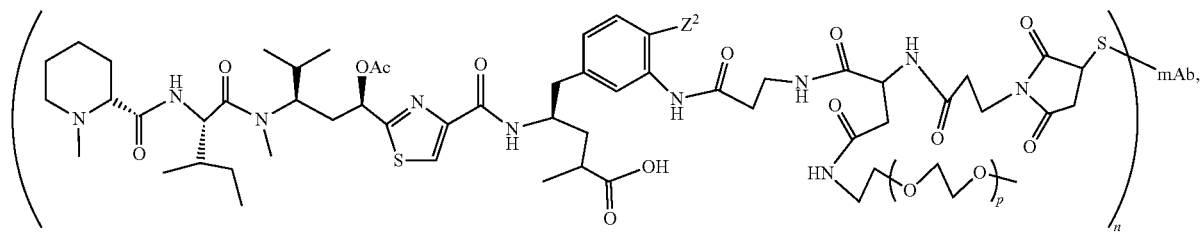
a-94
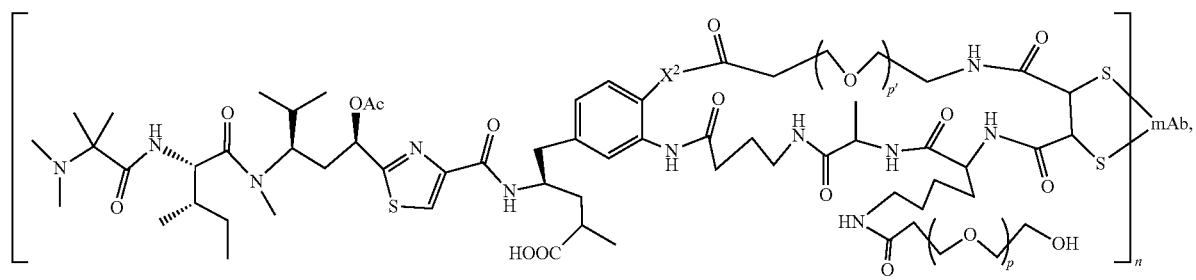
a-95
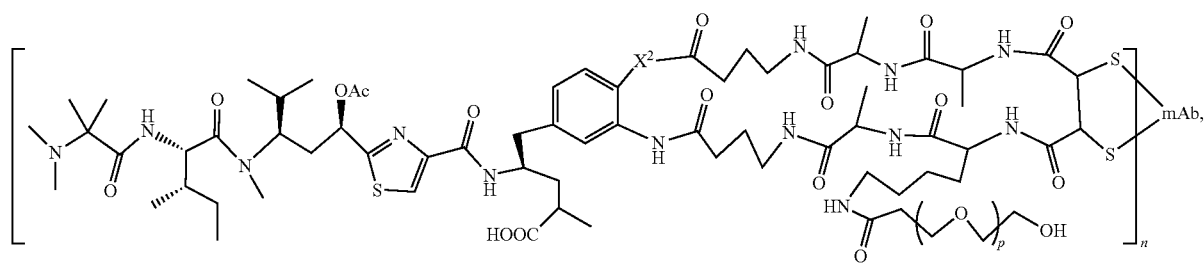
a-96
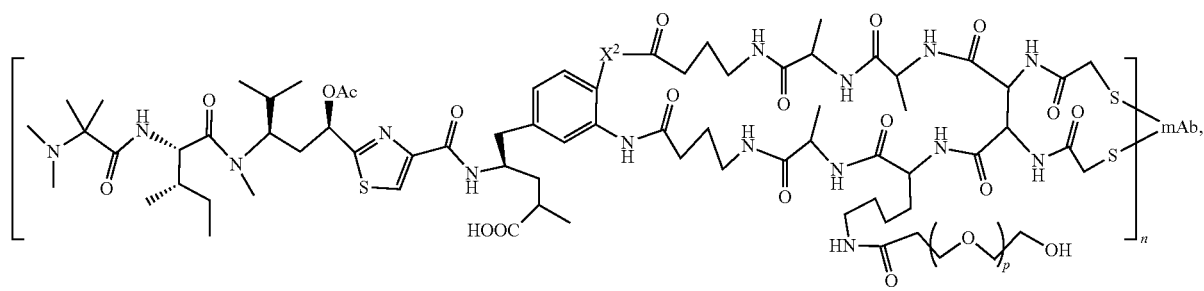
a-97
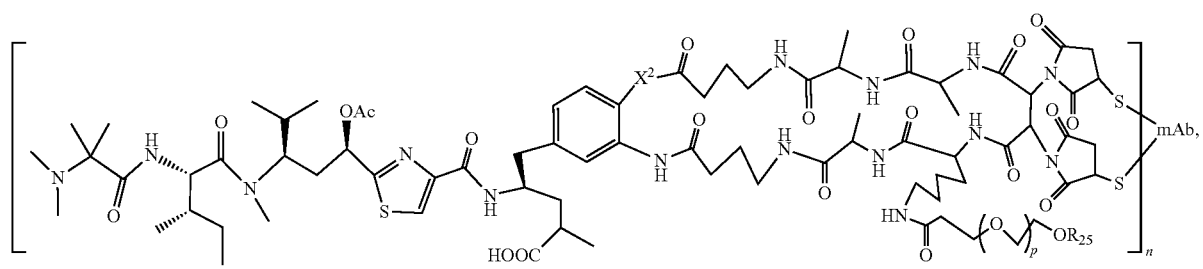
a-98

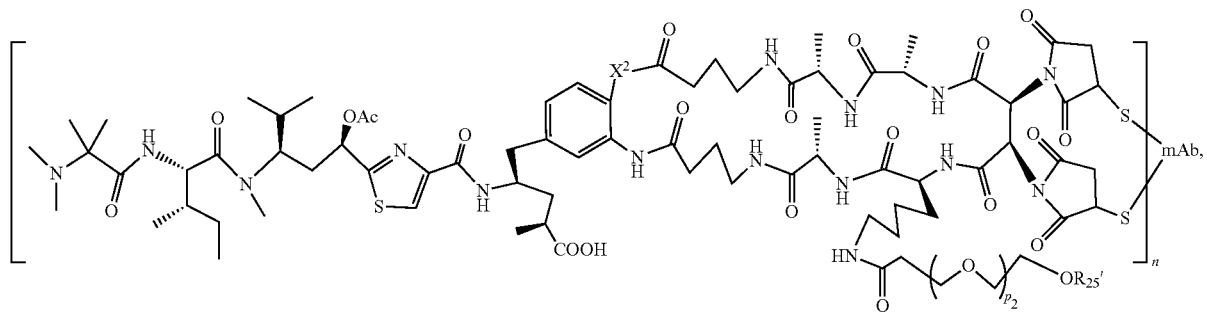

a-99

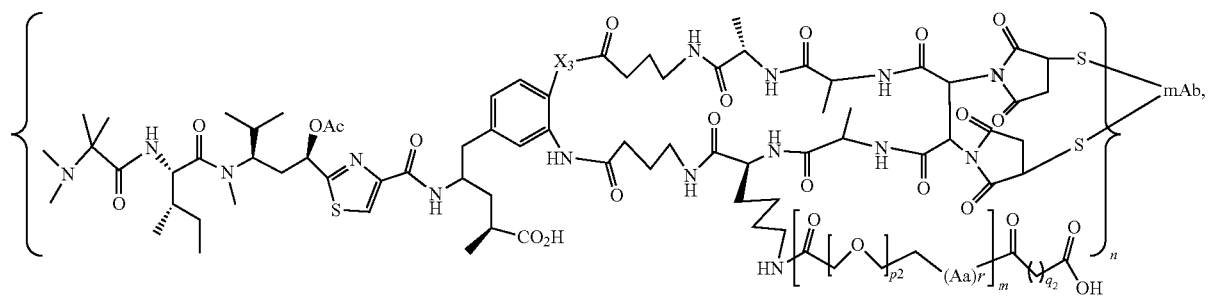

a-100 or their pharmaceutically acceptable salts, hydrates, or hydrated salts; or the polymorphic crystalline structures of these compounds; or their optical isomers, racemates, diastereomers or enantiomers; wherein $Z^3$ and $Z^3$ are independently H, OH, $NH_2$, O, NH, COOH, COO, C(O), C(O), C(O)NH, C(O)$NH_2$, $R^{18}$, $OCH_2OP(O)(OR^{18})_2$, OC(O)OP(O)$(OR^{18})_2$, OPO$(OR^{18})_2$, NHPO$(OR^{18})_2$, OP(O)$(OR^8)$OP(O)$(OR^8)_2$, OC(O)$R^{18}$, OC(O)NH$R^{18}$, OSO$_2(OR^{18})$, O—($C_4$-$C_{12}$glycoside), of linear or branched alkyl or heteroalkyl; $C_2$-$C_8$ of linear or branched alkenyl, alkynyl, alkylcycloalkyl, heterocycloalkyl; $C_3$-$C_8$ linear or branched of aryl, Ar-alkyl, heterocyclic, carbocyclic, cycloalkyl, heteroalkylcycloalkyl, alkylcarbonyl, heteroaryl; carbonate (—C(O)$OR^{17}$), carbamate (—C(O)$NR^{17}R^{18}$); or polyalkylene glycols have a molecular weight of from about 88 Daltons to about 20 kDa; $R^{17}$ and $R^{18}$ are independently H, linear or branched alkyl or heteroalkyl; $C_2$-$C_8$ of linear or branched alkenyl, alkynyl, alkylcycloalkyl, heterocycloalkyl; $C_3$-$C_8$ linear or branched of aryl, Ar-alkyl, heterocyclic, carbocyclic, cycloalkyl, heteroalkylcycloalkyl, alkylcarbonyl, heteroaryl; carbonate (—C(O)$OR^{17}$), carbamate (—C(O)$NR^{17}R^{18}$); $R^{19}$ is H, OH, $NH_2$, OSO$_2(OR^{18})$, XCH$_2$OP(O)$(OR^{18})_2$, XPO$(OR^{18})_2$, XC(O)OP(O)$(OR^8)_2$, XC(O)$R^{18}$, XC(O)NH$R^{18}$, $C_1$~$C_8$ alkyl or carboxylate; $C_2$~$C_8$ alkenyl, alkynyl, alkylcycloalkyl, heterocycloalkyl; $C_3$~$C_8$ aryl or alkylcarbonyl; or pharmaceutical salts; X, $X_1$, $X_2$ and $X_3$ are independently O, S, NH, NHNH, or $CH_2$; $q_1$, $q_2$ and $q_3$ are independently selected from 0-24; p, $p_1$ and $p_2$ are independently 1-100; $R_1'$, $R_2'$, $R_3'$ and $R_4'$ are independently selected from H and $C_1$-$C_6$ alkyl; Aa is natural or unnatural amino acid; r is 0-12; (Aa)r is a peptide containing the same or different sequence of amino acids when r>2; r=0 means (Aa)r absent; m and n are independently 1-30.

In another aspect of the present invention, a conjugate containing a side chain-linkage is represented by Formula (III):

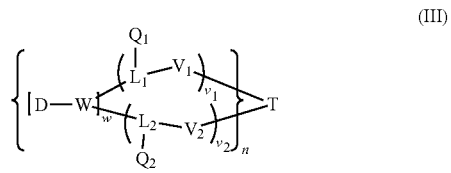

(III)

wherein D, W, w, $L_1$, $L_2$, $Q_1$, $Q_2$, $V_1$, $V_2$, $v_1$, $v_2$, n, T are defined the same as in Formula (I). Examples of formula (III) structures are as following:

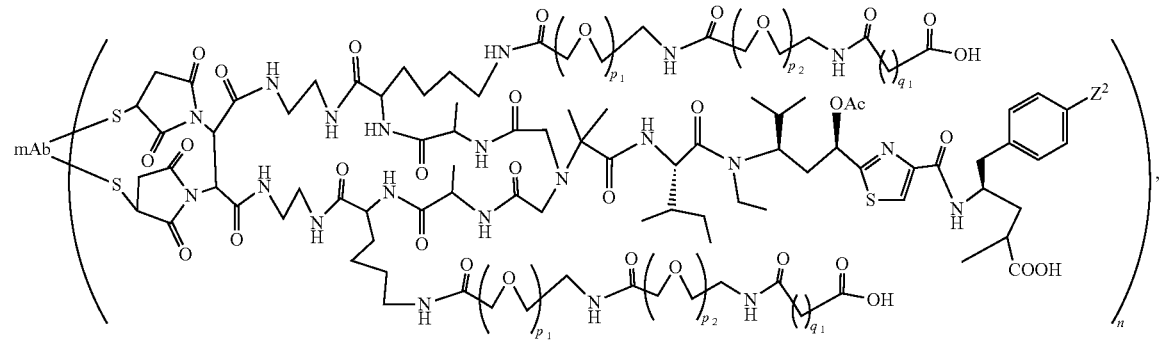
b-01
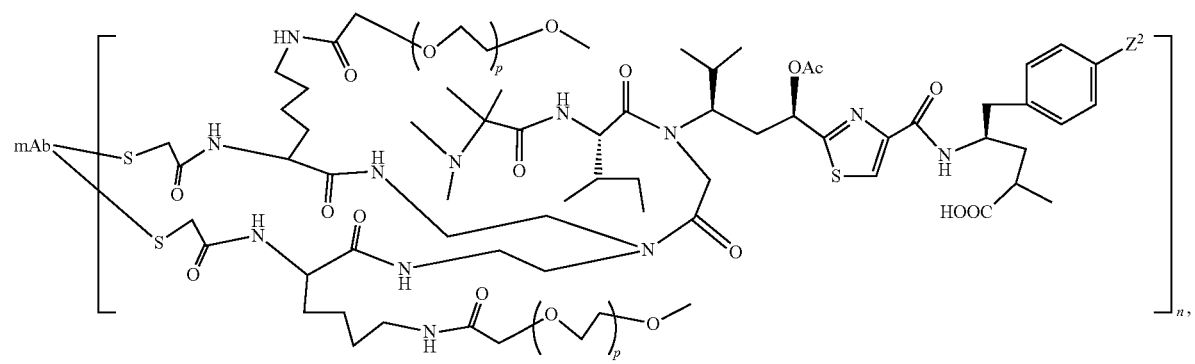
b-02
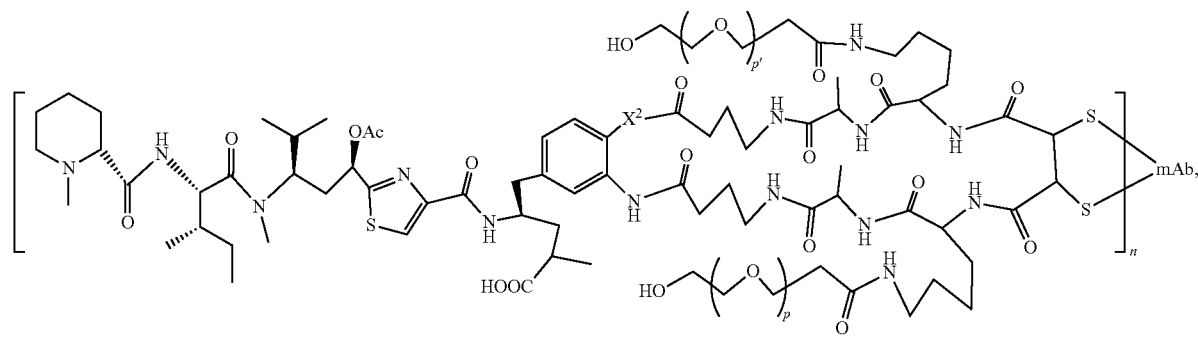
b-03
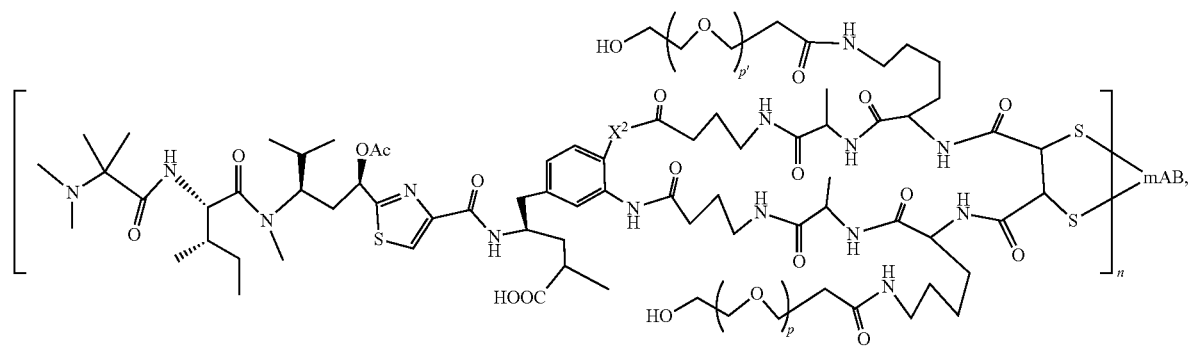
b-04 b-05
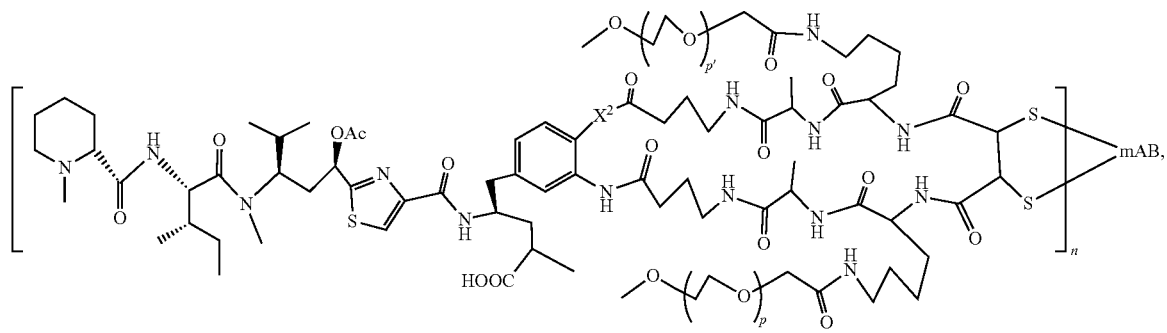
b-06
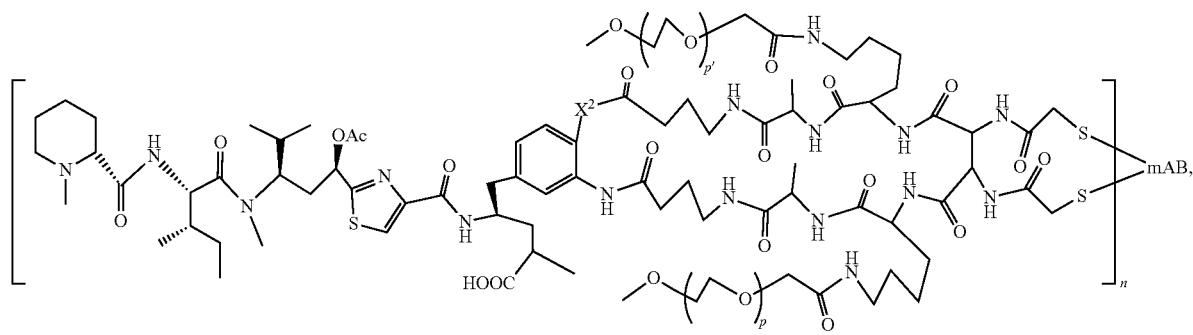
b-07
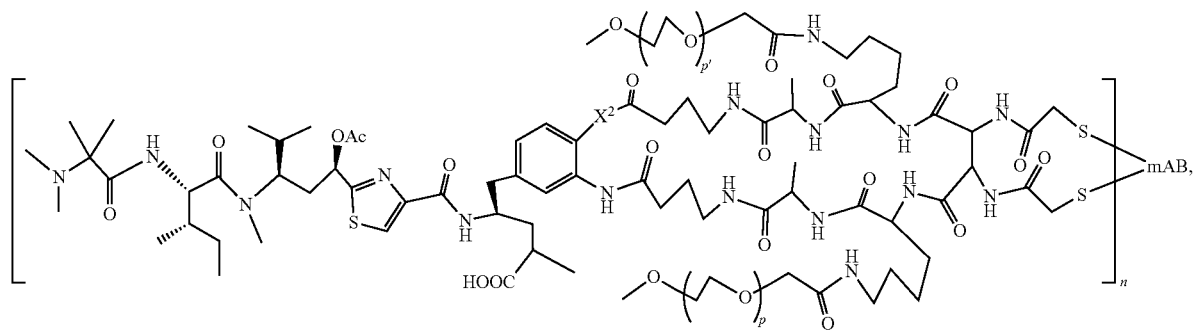
b-08
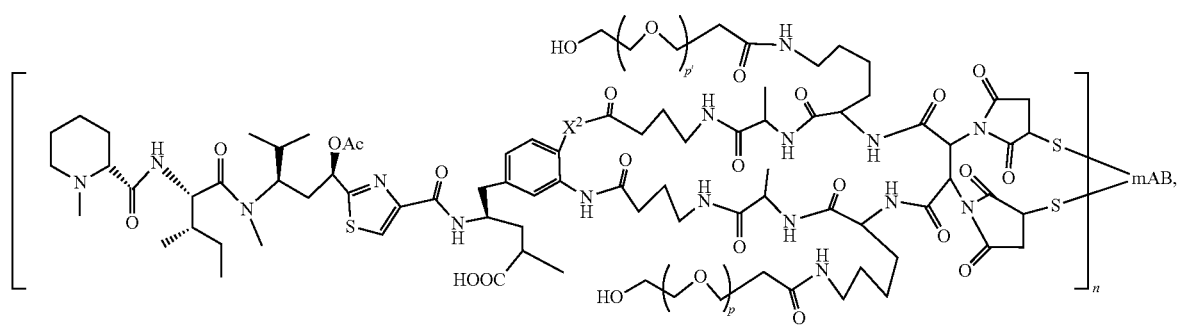

-continued
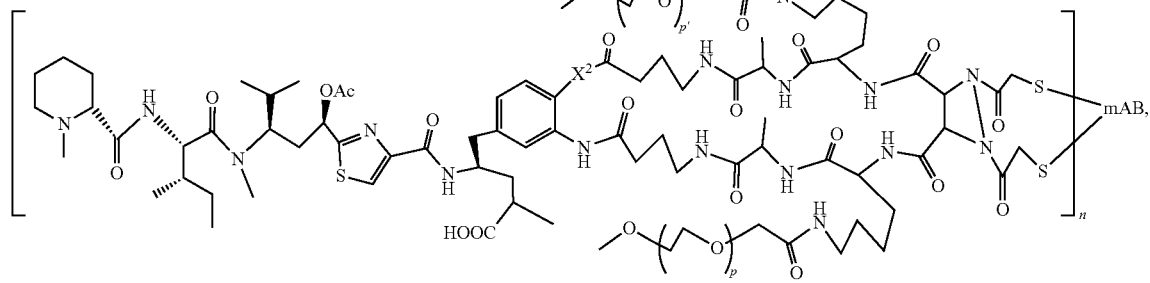
b-09
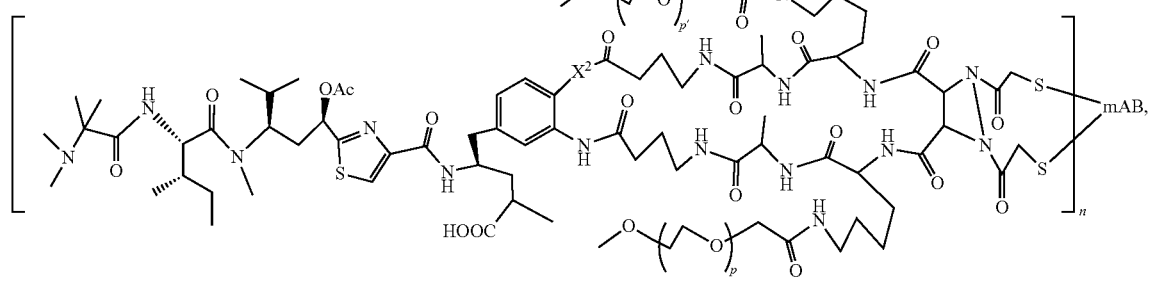
b-10
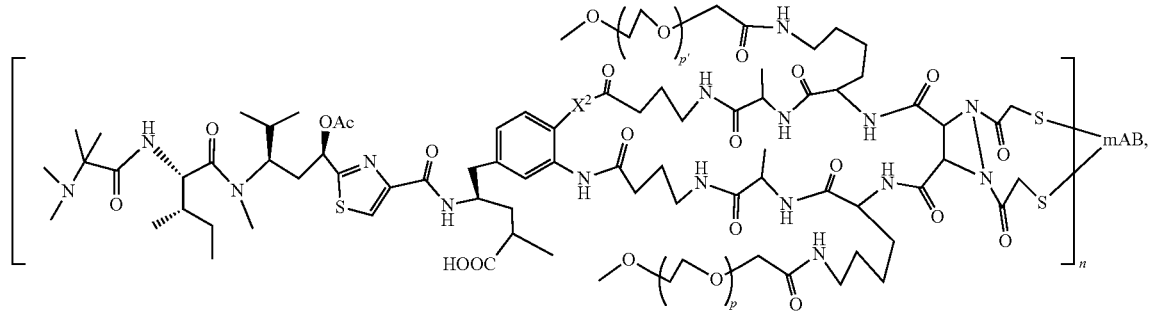
b-11
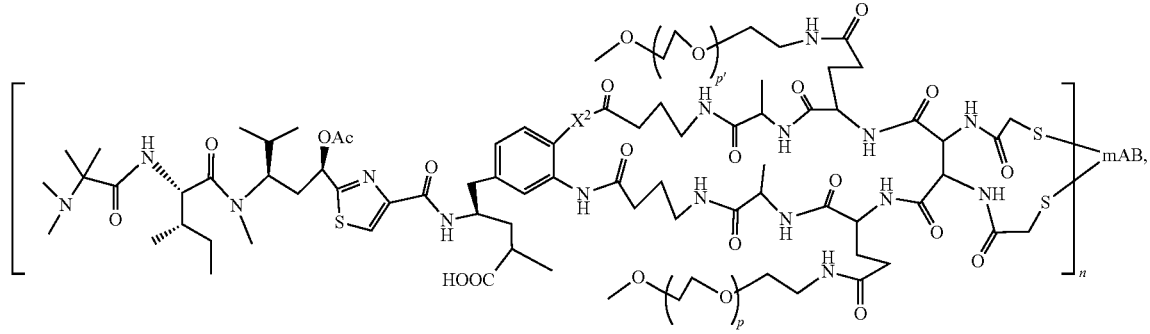
b-12
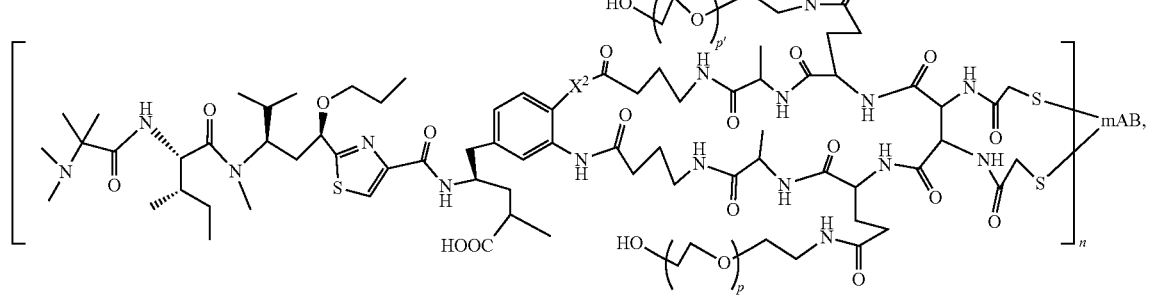
b-13

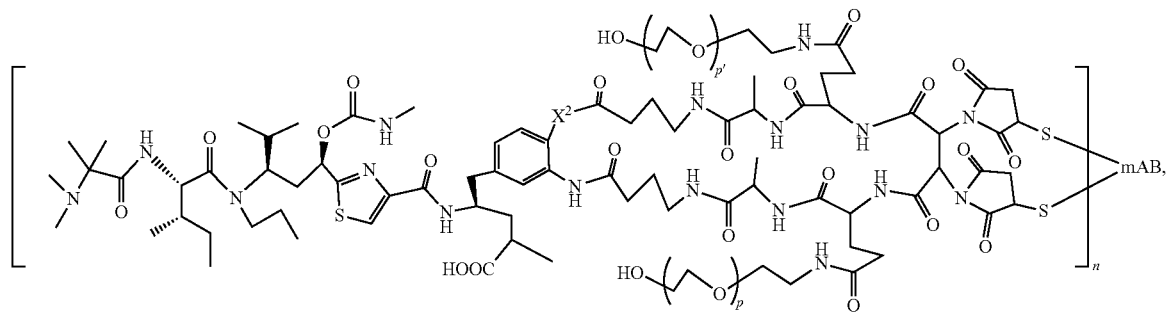
b-14
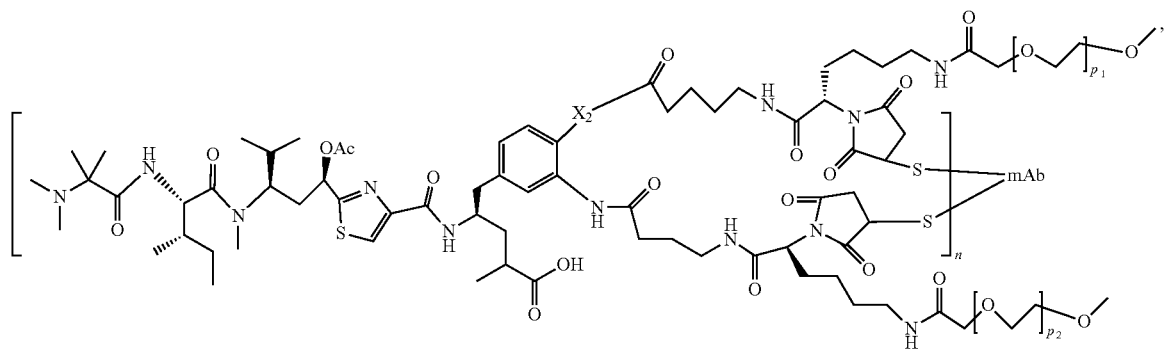
b-15
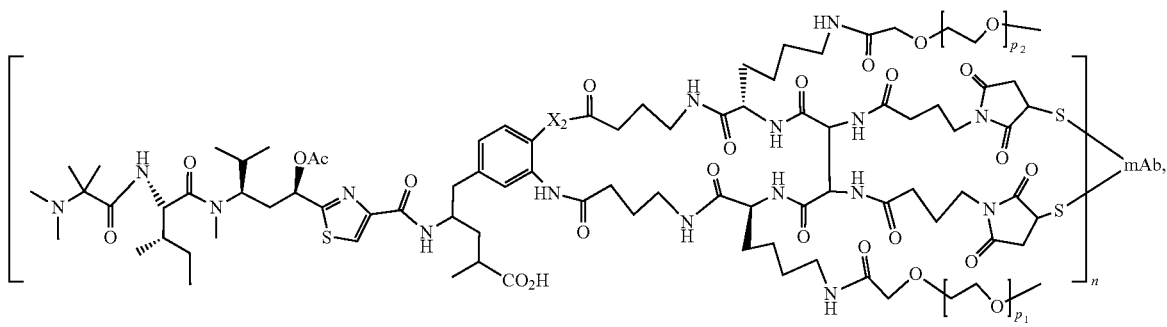
b-16
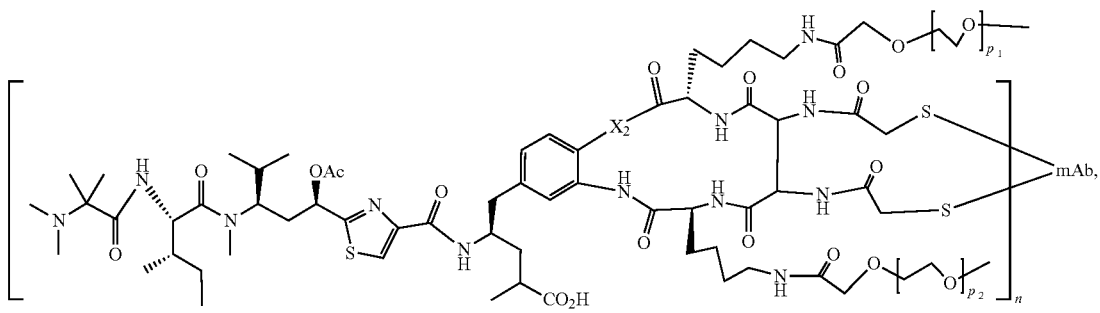
b-17

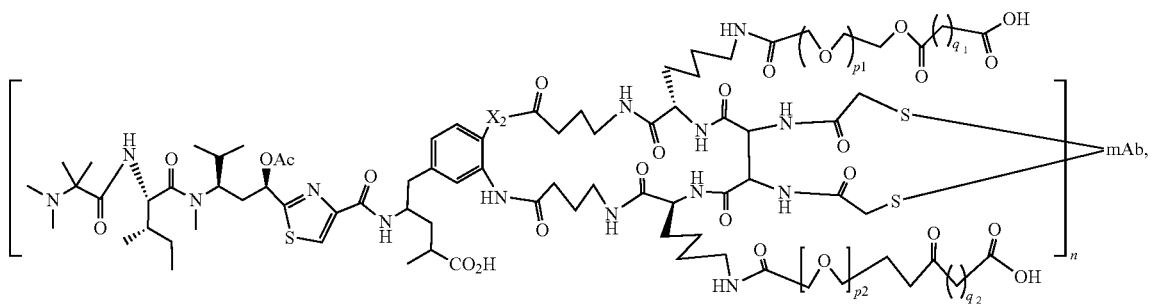
b-18
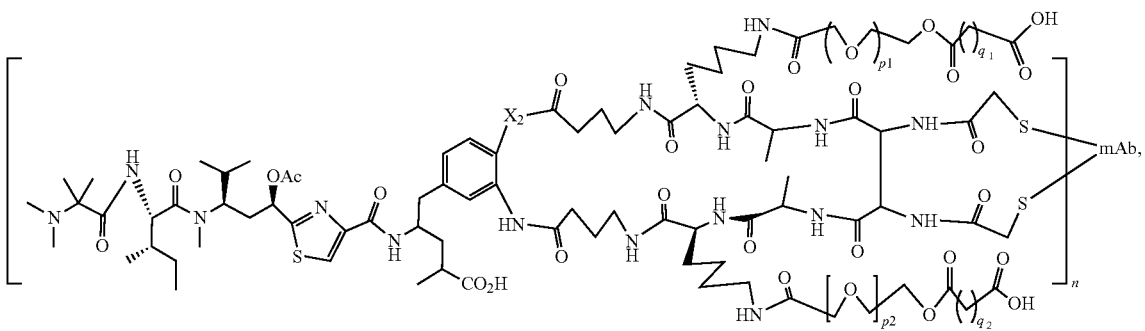
b-19
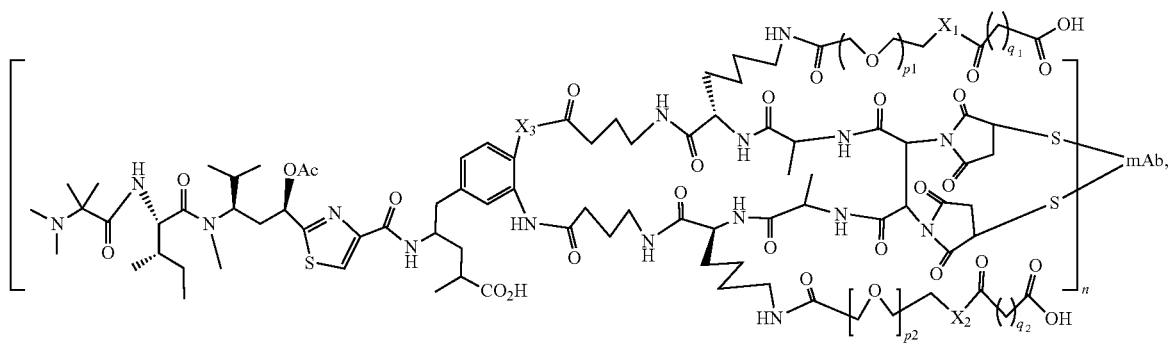
b-20
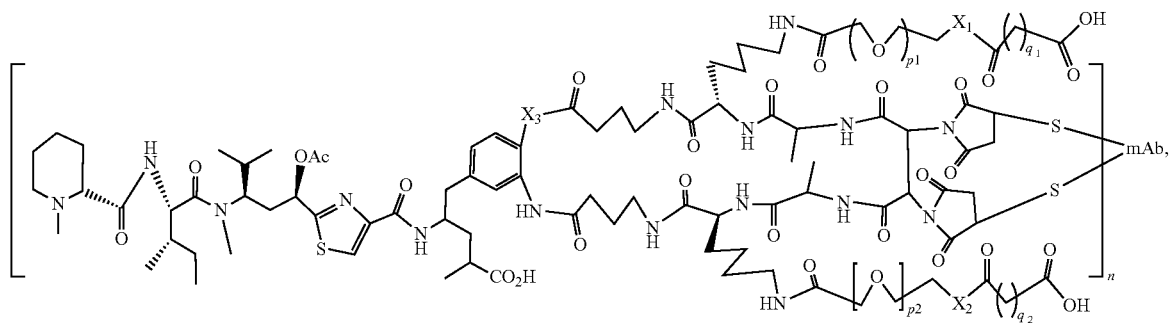
b-21

-continued
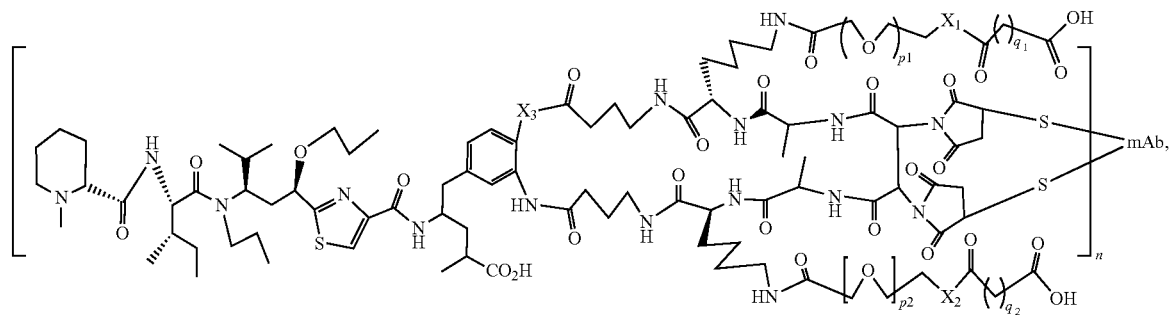
b-22
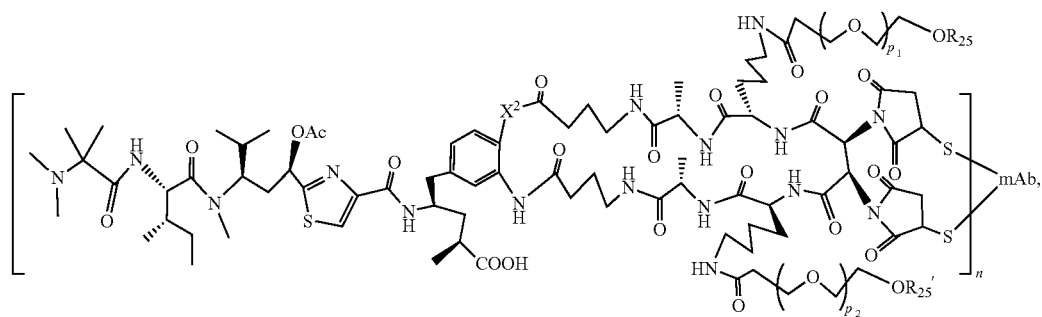
b-23
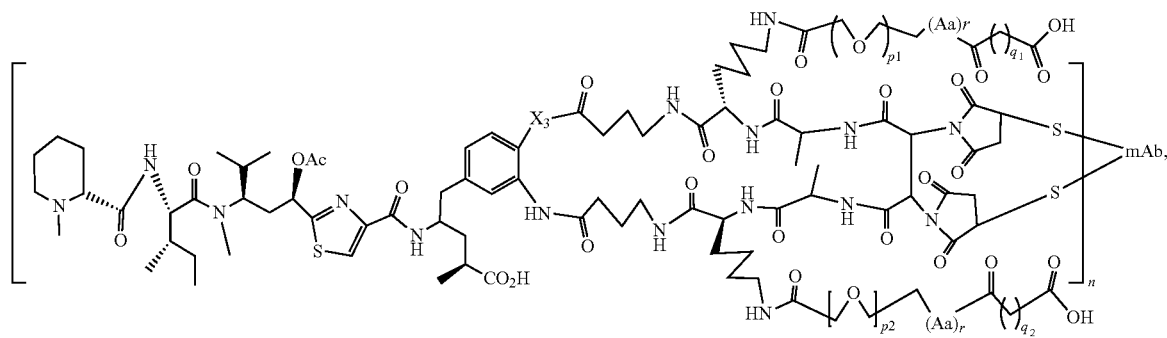
b-24
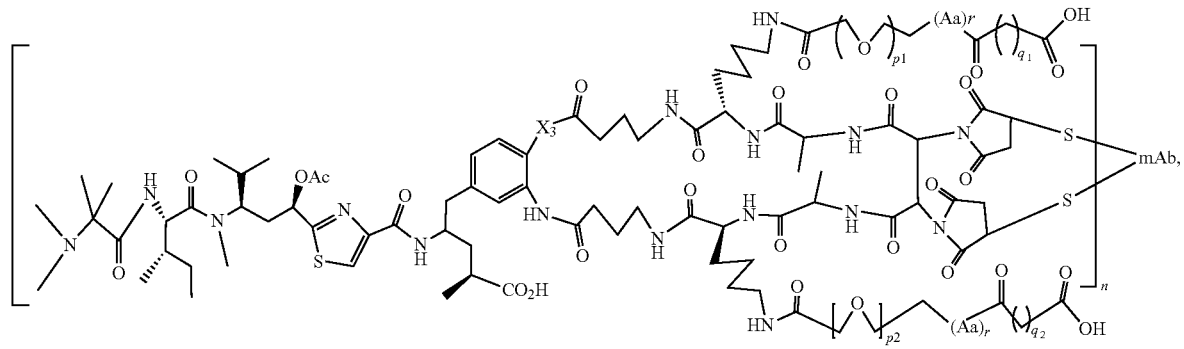
b-25

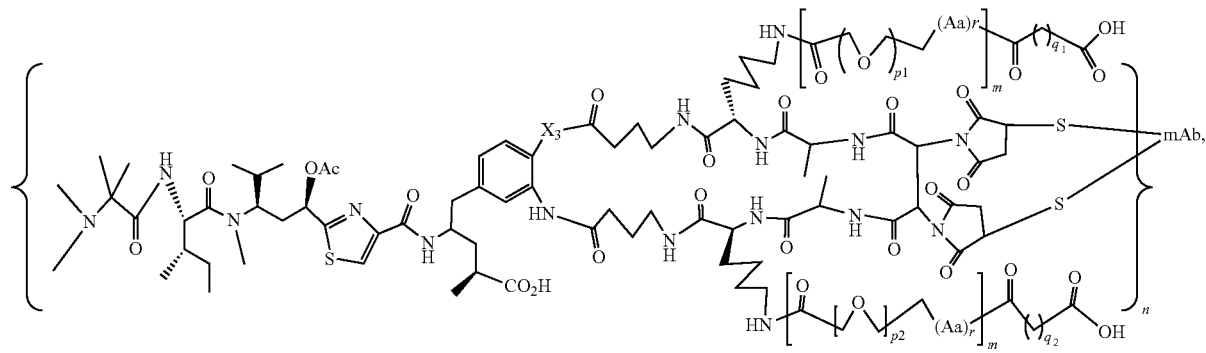
b-26
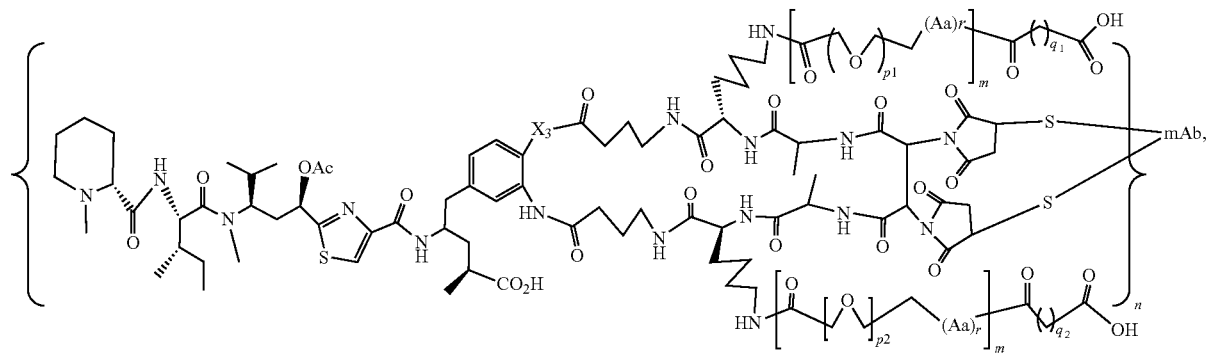
b-27
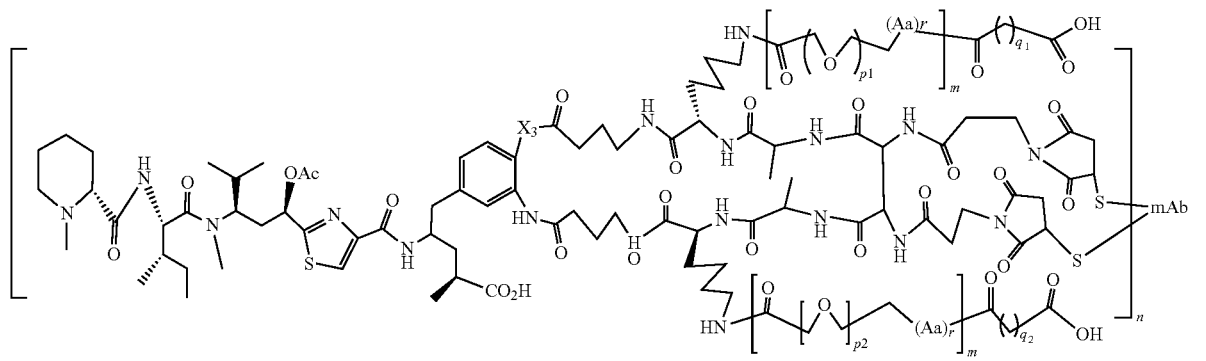
b-28
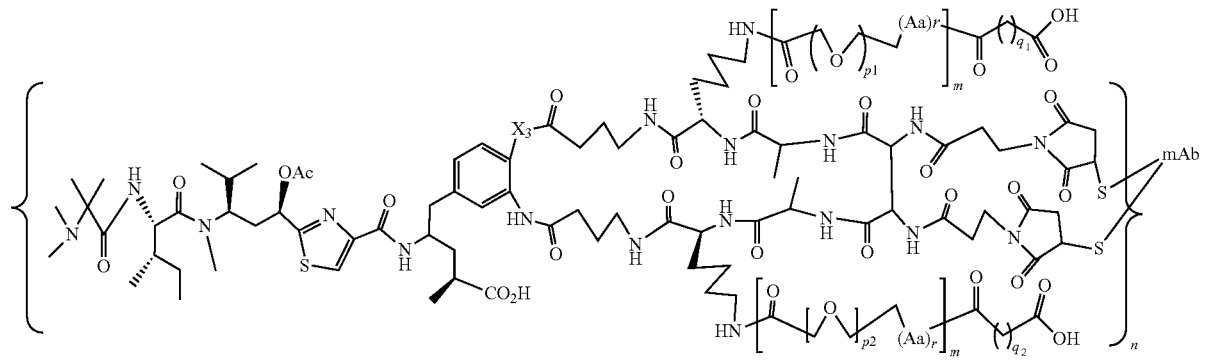
b-29 or their pharmaceutically acceptable salts, hydrates, or hydrated salts; or the polymorphic crystalline structures of these compounds; or their optical isomers, racemates, diastereomers or enantiomers; wherein $X_1$, $X_2$, $X_3$, m, n, $(Aa)_r$, $p_1$, $p_2$, $p_3$, $q_1$, $q_2$ are described above.

In another aspect of the present invention, the side chain-linkage compound is represented by Formula (IV), which can readily react to a cell-binding molecule T, or to a modified cell-binding molecule T to form a conjugate of Formula (I):

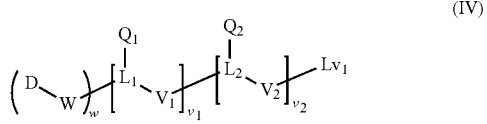

(IV)

wherein D, W, w, $L_1$, $L_2$, $Q_1$, $Q_2$, $V_1$, $V_2$, $v_1$, $v_2$, and n, are defined the same as in Formula (I);

$Lv_1$ is a reacting group that can be reacted with a thiol, amine, carboxylic acid, selenol, phenol or hydroxyl group on a cell-binding molecule. Such reacting groups are, but are not limited to, a halide (e.g., fluoride, chloride, bromide, and iodide), methanesulfonyl (mesyl), toluenesulfonyl (tosyl), trifluoromethyl-sulfonyl (triflate), trifluoromethylsulfonate, nitrophenoxyl, N-succinimidyloxyl (NHS), phenoxyl; dinitrophenoxyl; pentafluorophenoxyl, tetrafluorophenoxyl, trifluorophenoxyl, difluorophenoxyl, monofluorophenoxyl, pentachlorophenoxyl, 1H-imidazole-1-yl, chlorophenoxyl, dichlorophenoxyl, trichlorophenoxyl, tetrachlorophenoxyl, N-(benzotriazol-yl)oxyl, 2-ethyl-5-phenylisoxazolium-3'-sulfonyl, phenyloxadiazole-sulfonyl (-sulfone-ODA), 2-ethyl-5-phenylisoxazolium-yl, phenyloxadiazol-yl (ODA), oxadiazol-yl, unsaturated carbon (a double or a triple bond between carbon-carbon, carbon-nitrogen, carbon-sulfur, carbon-phosphrus, sulfur-nitrogen, phosphrus-nitrogen, oxygen-nitrogen, or carbon-oxygen), or an intermediate molecule generated with a condensation reagent for Mitsunobu reactions. The examples of condensation reagents are: EDC (N-(3-Dimethyl-aminopropyl)-N'-ethyl-carbodiimide), DCC (Dicyclohexyl-carbodiimide), N,N'-Di-isopropyl-carbodiimide (DIC), N-Cyclohexyl-N'-(2-morpholino-ethyl)carbodiimide metho-p-toluenesulfonate (CMC, or CME-CDI), 1,1'-Carbonyldiimi-dazole (CDI), TBTU (O-(Benzotriazol-1-yl)-N,N,N',N'-tetramethyluronium tetrafluoroborate), N,N,N',N'-Tetramethyl-O-(1H-benzotriazol-1-yl)-uronium hexafluorophosphate (HBTU), (Benzotriazol-1-yloxy)tris-(dimethylamino)-phosphonium hexafluorophosphate (BOP), (Benzotriazol-1-yloxy)tripyrroli-dinophosphonium hexafluorophosphate (PyBOP), Diethyl cyanophosphonate (DEPC), Chloro-N,N,N',N'-tetramethylformamidiniumhexafluorophosphate, 1-[Bis(dimethylamino)methylene]-1H-1,2,3-triazolo[4,5-b]pyridinium 3-oxid hexafluorophos-phate (HATU), 1-[(Dimethylami-no)(morpholino)methylene]-1H-[1,2,3]triazolo[4,5-b]pyridine-1-ium 3-oxide hexafluoro-phosphate (HDMA), 2-Chloro-1,3-dimethyl-imidazolidinium hexafluorophosphate (CIP), Chlorotripyrrolidinophosphonium hexafluorophosphate (PyCloP), Fluoro-N,N,N',N'-bis(tetramethylene)formami-dinium hexafluorophosphate (BTFFH), N,N,N',N'-Tetramethyl-S-(1-oxido-2-pyridyl)thiuronium hexafluorophos-phate, O-(2-Oxo-1 (2H)pyridyl)-N,N,N',N'-tetramethyluronium tetrafluoroborate (TPTU), S-(1-Oxido-2-pyridyl)-N,N,N',N'-tetramethylthiuronium tetrafluoroborate, O-[(Ethoxycarbonyl)-cyanomethyl-enamino]-N,N,N',N'-tetramethyluronium hexafluorophosphate (HOTU), (1-Cyano-2-ethoxy-2-oxoethylidenamino-oxy)dimethylamino-morpholino-carbenium hexafluorophosphate (COMU), O-(Benzotriazol-1-yl)-N,N,N',N'-bis(tetramethylene)uronium hexafluorophosphate (HBPyU), N-Benzyl-N'-cyclohexyl-carbodiimide (with, or without polymer-bound), Dipyrrolidino(N-succinimidyl-oxy)carbenium hexafluoro-phosphate (HSPyU), Chlorodipyrrolidinocarbenium hexafluoro-phosphate (PyC1U), 2-Chloro-1,3-dimethylimidazolidinium tetrafluoroborate (CIB), (Benzotriazol-1-yloxy)dipiperidino-carbenium hexafluorophosphate (HBPipU), O-(6-Chlorobenzotriazol-1-yl)-N,N,N',N'-tetramethyluronium tetrafluorob orate (TCTU), Bromotris(dimethylamino)-phosphonium hexafluorophosphate (BroP), Propylphosphonic anhydride (PPACA, T3P®), 2-Morpholinoethyl isocyanide (MEI), N,N,N',N'-Tetramethyl-O—(N-succinimidyl)uronium hexafluorophosphate (HSTU), 2-Bromo-1-ethyl-pyridinium tetrafluoro-borate (BEP), O-[(Ethoxycarbonyl)cyano-methylenamino]-N,N,N',N'-tetra-methyluronium tetrafluorobo-rate (TOTU), 4-(4,6-Dimethoxy-1,3,5-triazin-2-yl)-4-methylmorpholiniumchloride (MM™, DMTMM), N,N,N',N'-Tetramethyl-O—(N-succinimidyl)uronium tetrafluoroborate (TSTU), O-(3,4-Dihydro-4-oxo-1,2,3-benzotriazin-3-yl)-N,N,N',N'-tetramethyluronium tetrafluoro-b orate (TDBTU), 1,1'-(Azodicarbonyl)-dipiperidine (ADD), Di-(4-chlorobenzyl)-azodicarboxylate (DCAD), Di-tert-butyl azodicarboxylate (DBAD), Diisopropyl azodicarboxy-late (DIAD), Diethyl azodicarboxylate (DEAD). In addition, $Lv_1$ and $Lv_2$ can be an anhydride, formed by acid themselves or formed with other $C_1$~$C_8$ acid anhydrides; Preferably $Lv_1$ is selected from, a halide (e.g., fluoride, chloride, bromide, and iodide), methanesulfonyl (mesyl), toluenesulfonyl (tosyl), trifluoromethyl-sulfonyl (triflate), trifluoromethylsulfonate, nitrophenoxyl, N-succinimidyloxyl (NHS), phenoxyl; dinitrophenoxyl; pentafluorophenoxyl, tetrafluorophenoxyl, trifluorophenoxyl, difluorophenoxyl, monofluoro-phenoxyl, pentachlorophenoxyl, 1H-imidazole-1-yl, chlorophenoxyl, dichlorophenoxyl, trichlorophenoxyl, tetrachlorophenoxyl, N-(benzotriazol-yl)oxyl, 2-ethyl-5-phenylisoxazolium-3'-sulfonyl, phenyloxadiazole-sulfonyl (-sulfone-ODA), 2-ethyl-5-phenylisoxazolium-yl, phenyloxadiazol-yl (ODA), oxadiazol-yl, unsaturated carbon (a double or a triple bond between carbon-carbon, carbon-nitrogen, carbon-sulfur, carbon-phosphrus, sulfur-nitrogen, phosphrus-nitrogen, oxygen-nitrogen, or carbon-oxygen), or one of the following structure:

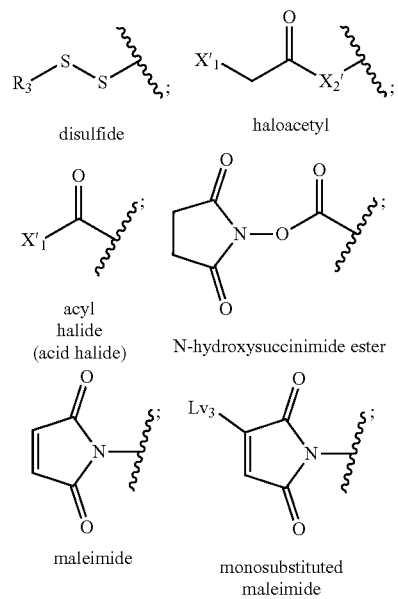

disulfide haloacetyl acyl halide (acid halide)

N-hydroxysuccinimide ester maleimide monosubstituted maleimide

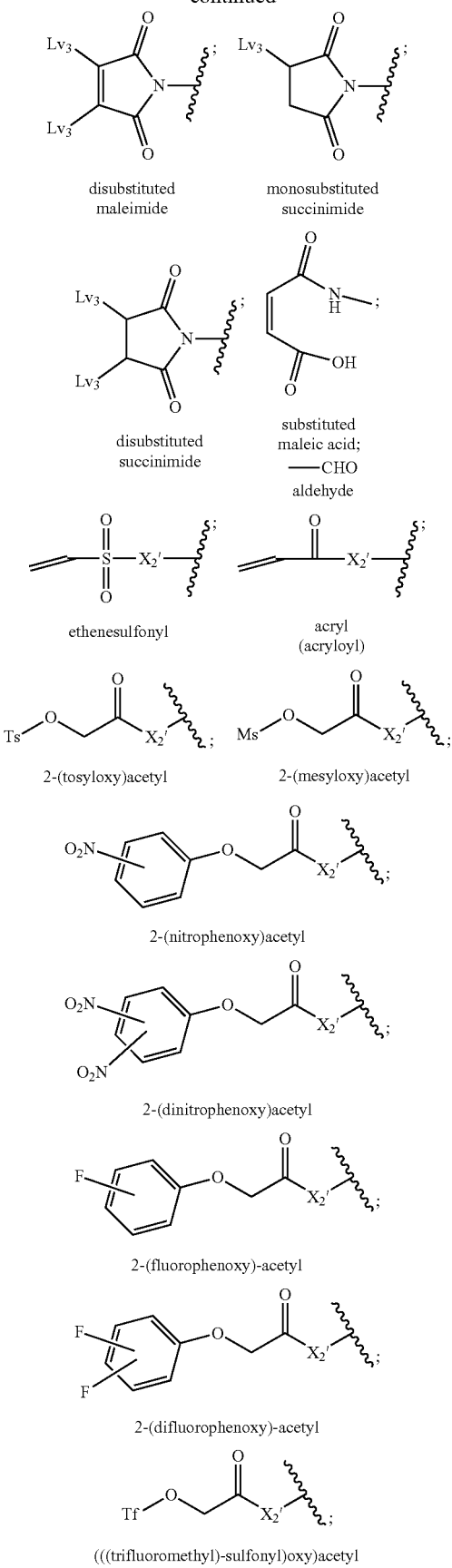
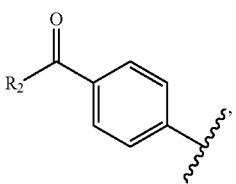

wherein $X_1'$ is F, Cl, Br, I or $Lv_3$; $X_2'$ is O, NH, $N(R_1)$, or $CH_2$; $R_3$ is independently H, aromatic, heteroaromatic, or aromatic group wherein one or several H atoms are replaced independently by —$R_1$, -halogen, —$OR_1$, —$SR_1$, —$NR_1R_2$, —$NO_2$, —$S(O)R_1$, —$S(O)_2R_1$, or —$COOR_1$; $Lv_3$ is a leaving group selected from F, Cl, Br, I, nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxybenzotriazole; tosylate; mesylate; 2-ethyl-5-phenylisoxazolium-3'-sulfonate, anhydrides formed its self, or formed with the other anhydride, e.g. acetyl anhydride, formyl anhydride; or an intermediate molecule generated with a condensation reagent for peptide coupling reactions or for Mitsunobu reactions.

Examples of Formula (IV) are shown below:
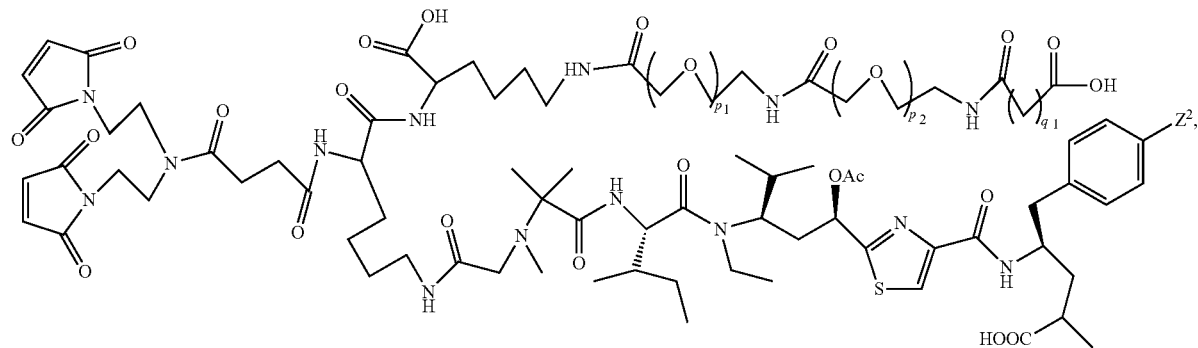
c-01
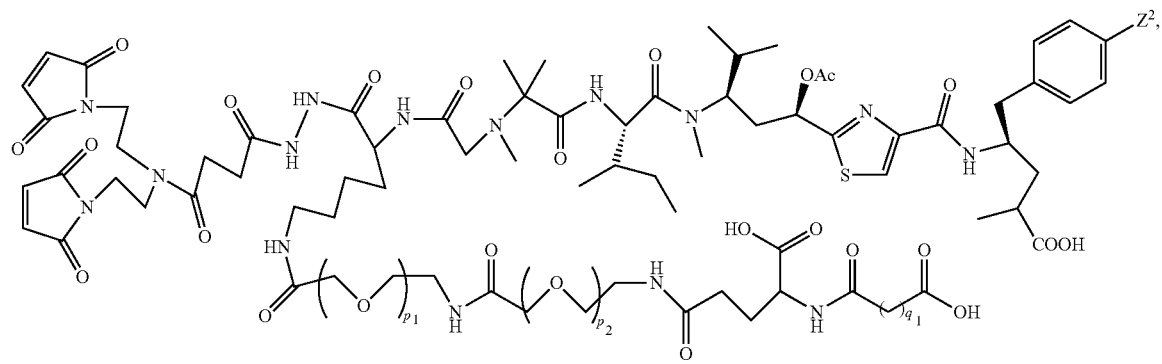
c-02
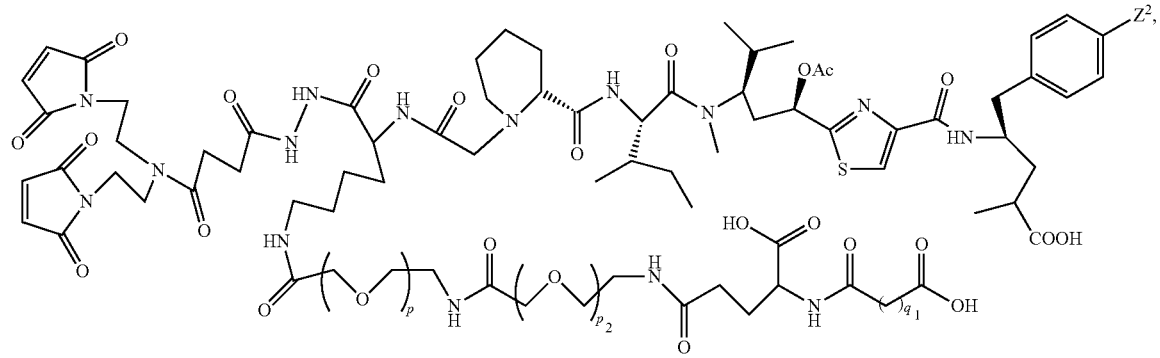
c-03
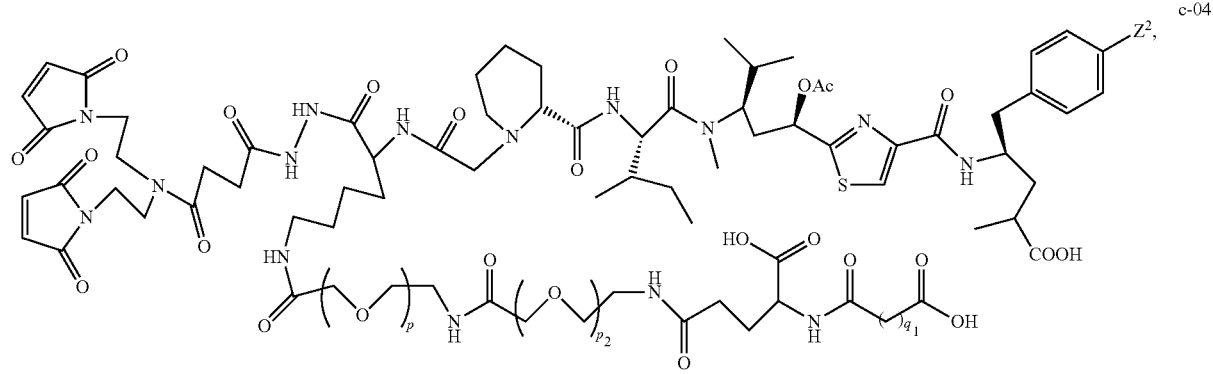
c-04

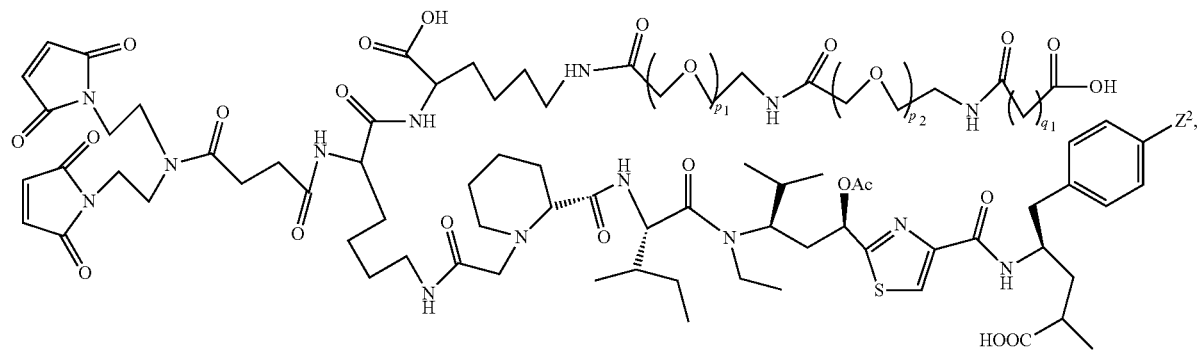
c-05
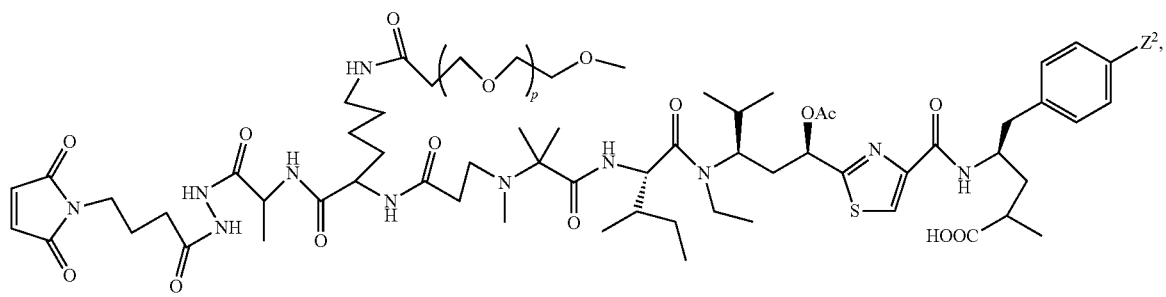
c-06
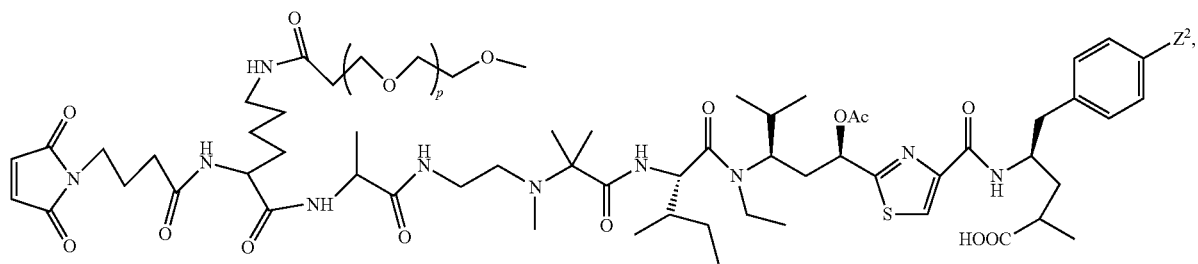
c-07
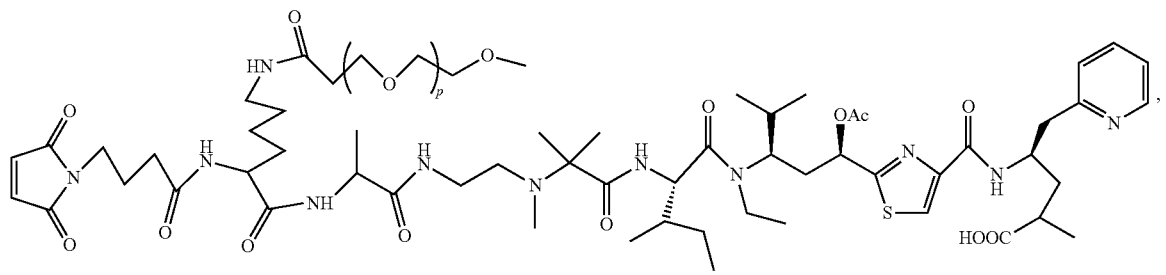
c-08
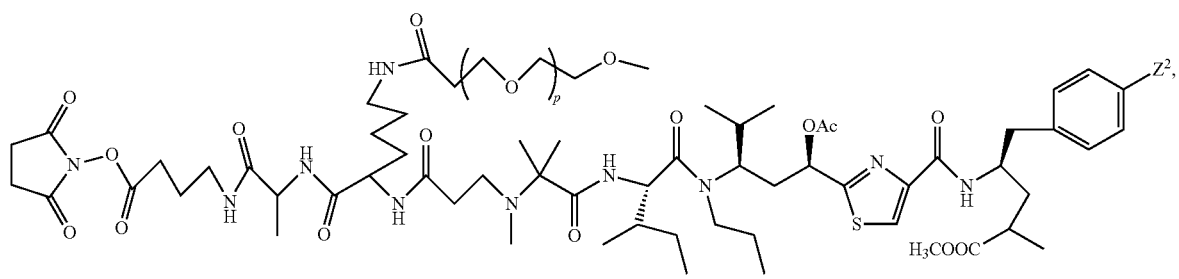
c-09

-continued
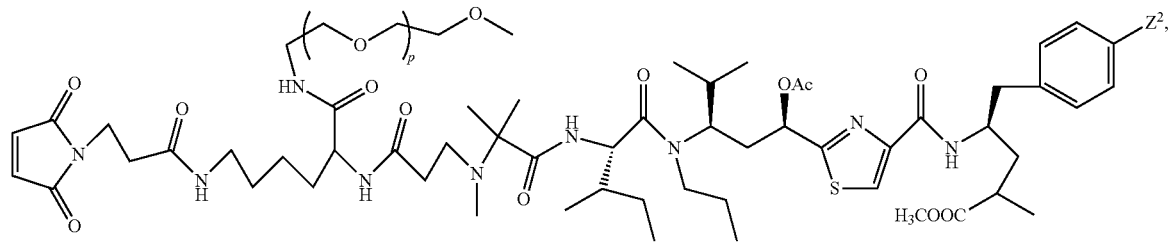
c-10
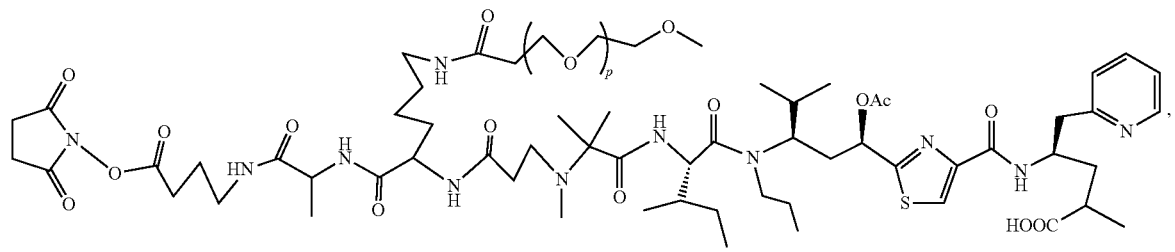
c-11
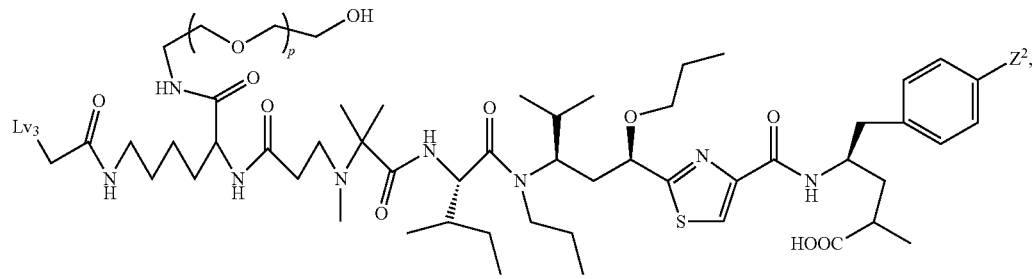
c-12
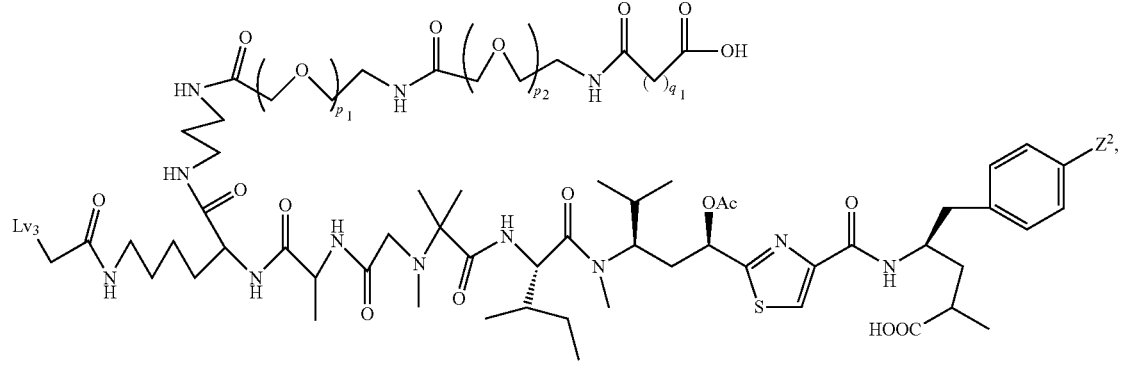
c-13
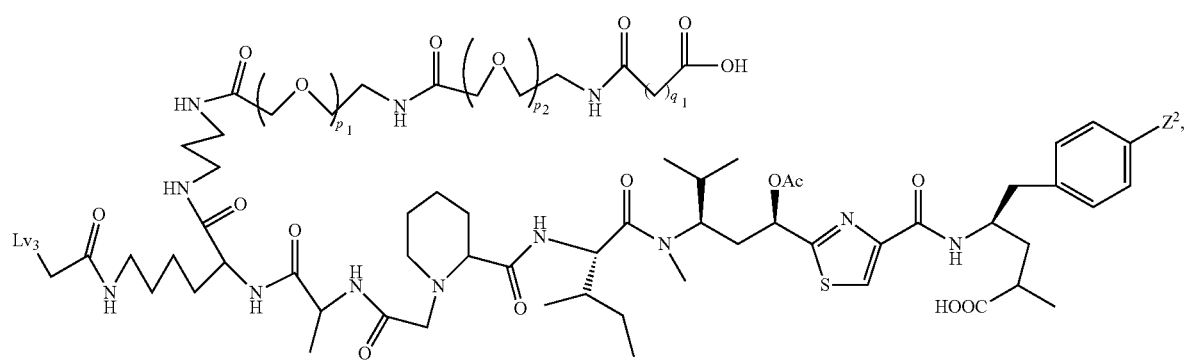
c-14

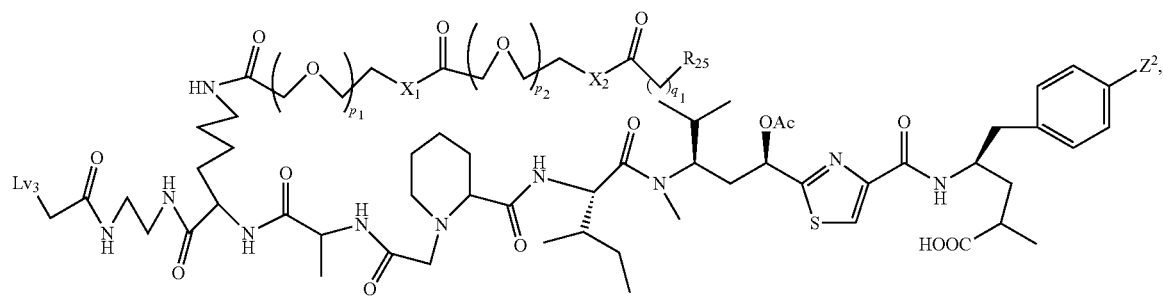
c-15
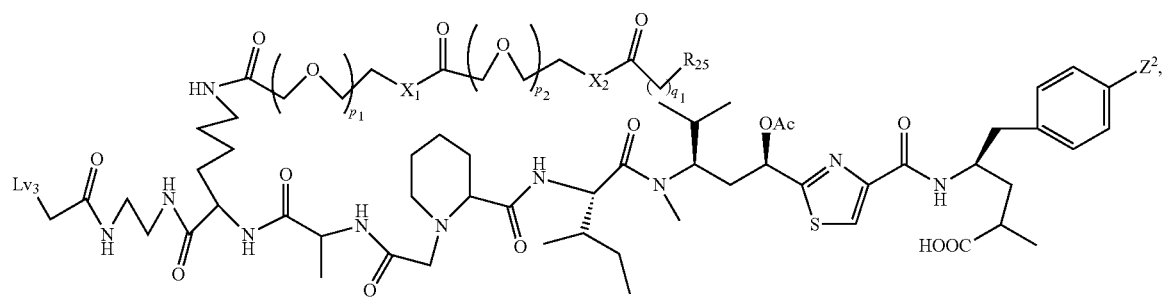
c-16
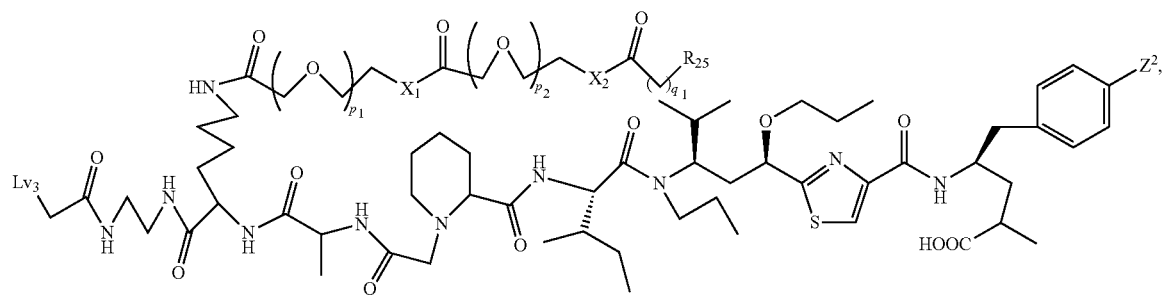
c-17
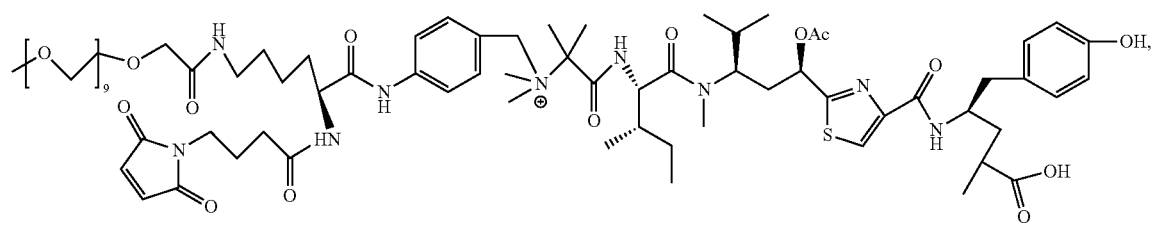
c-18
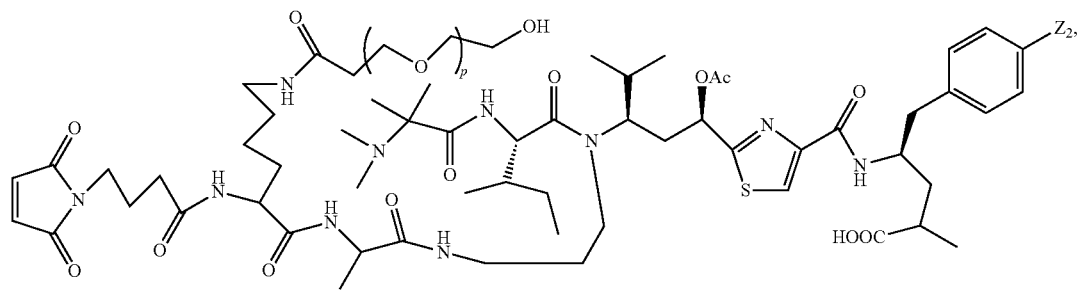
c-19

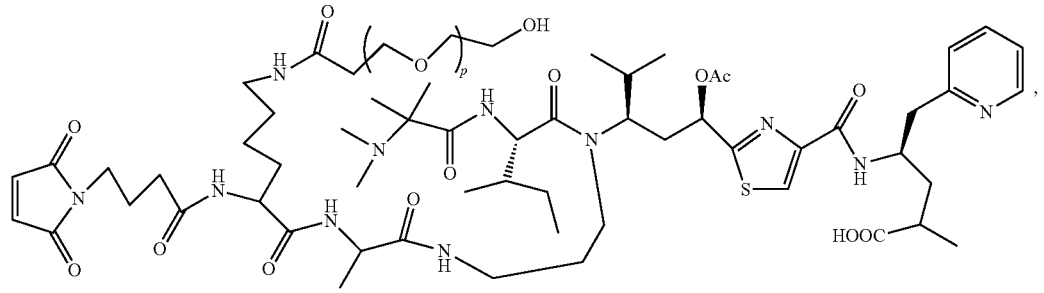
c-20
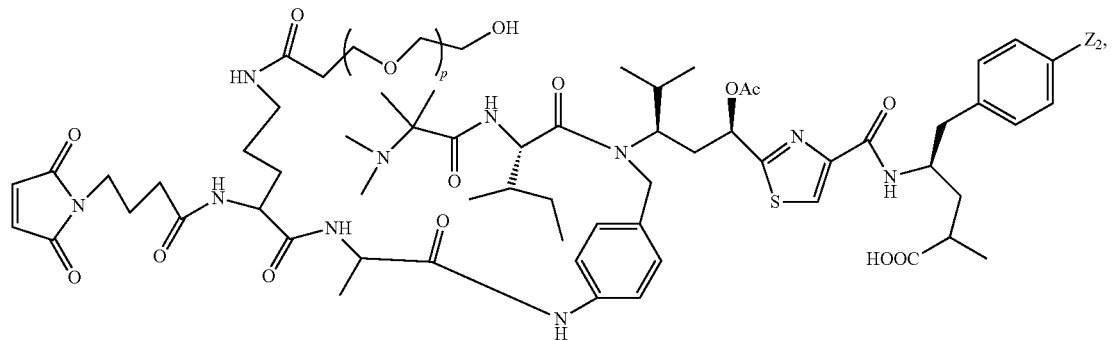
c-21
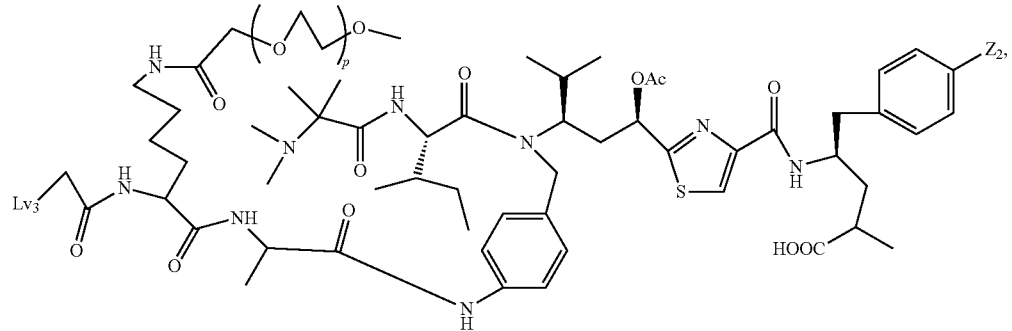
c-22
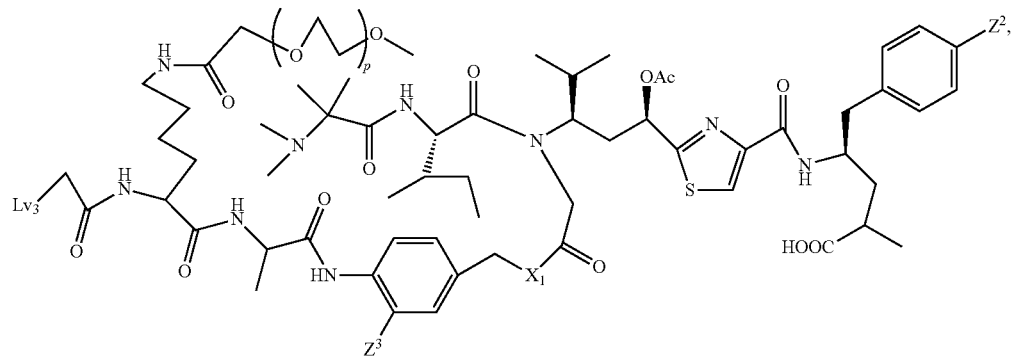
c-23

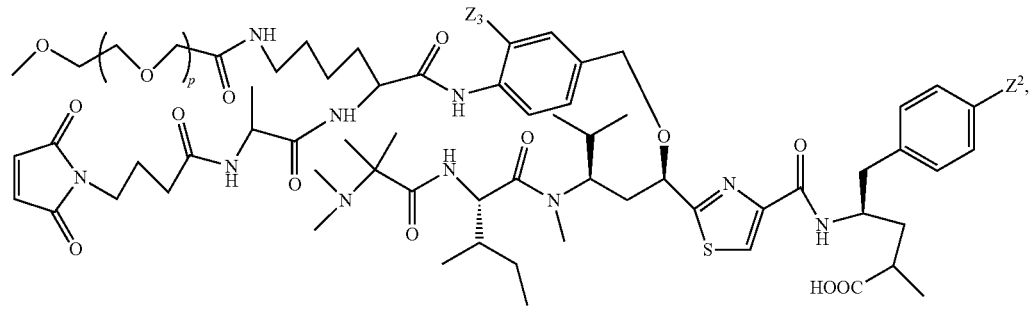
c-24
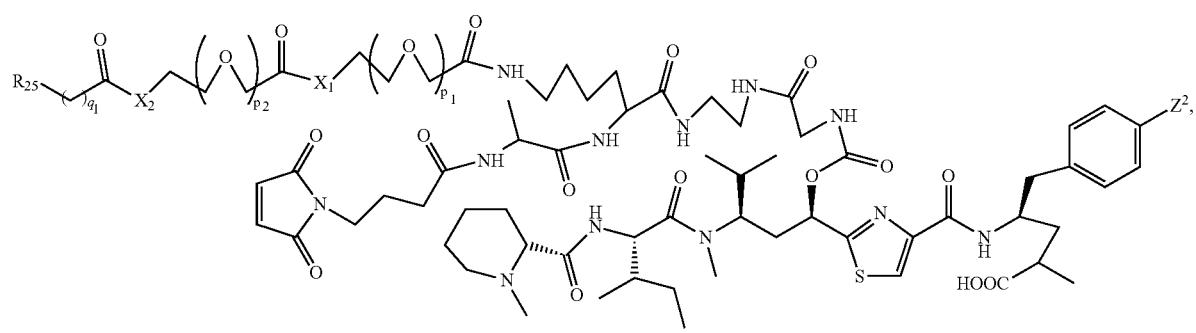
c-25
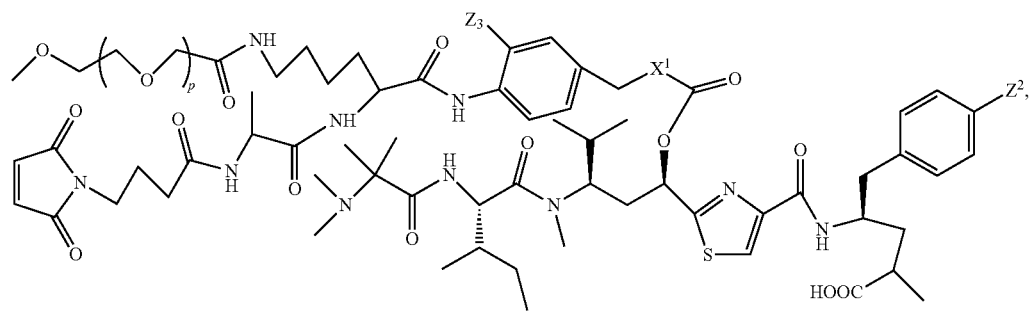
c-26
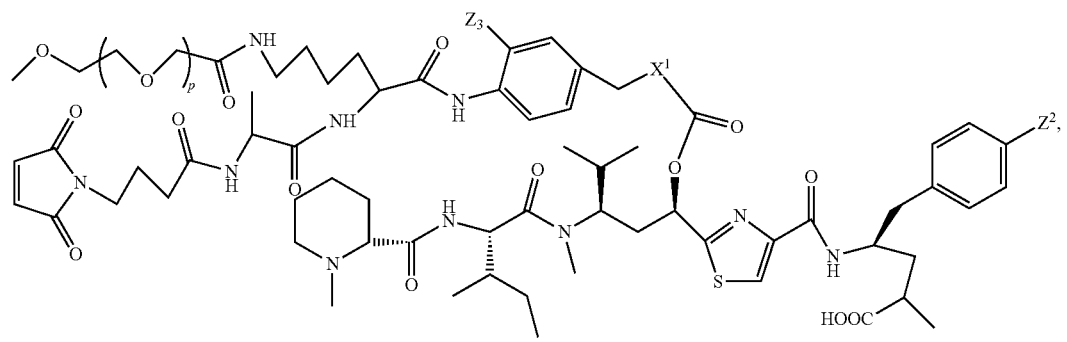
c-27 c-28
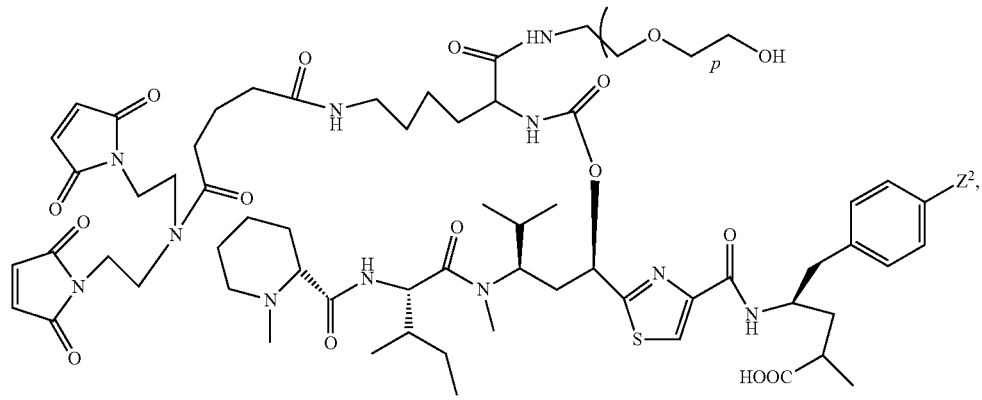
c-29
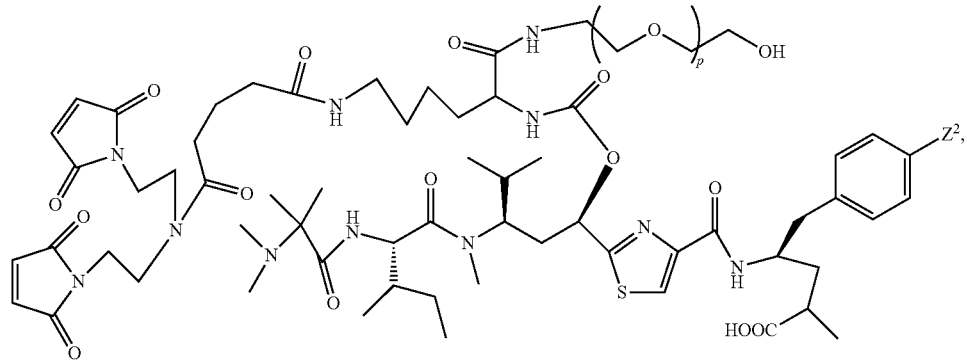
c-30
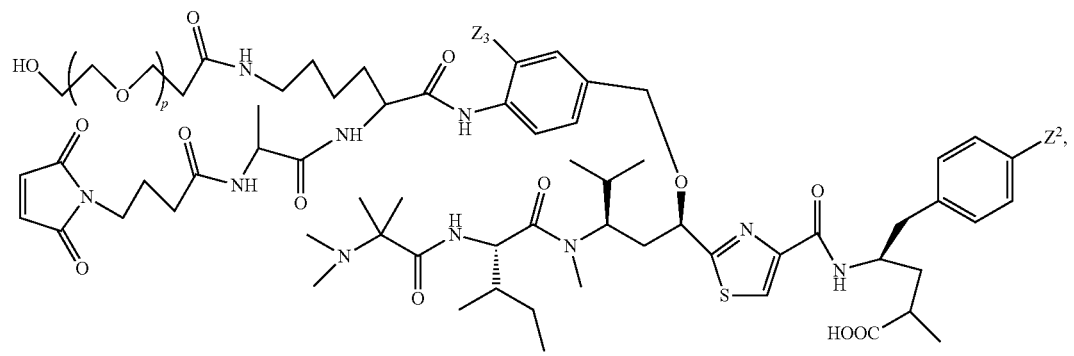
c-31
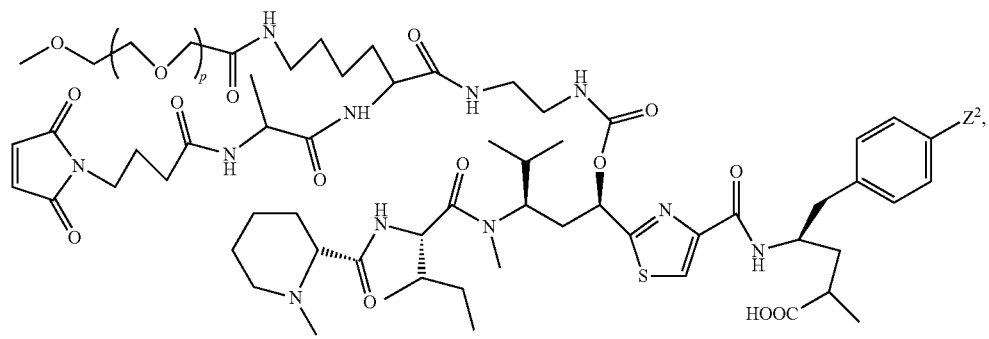

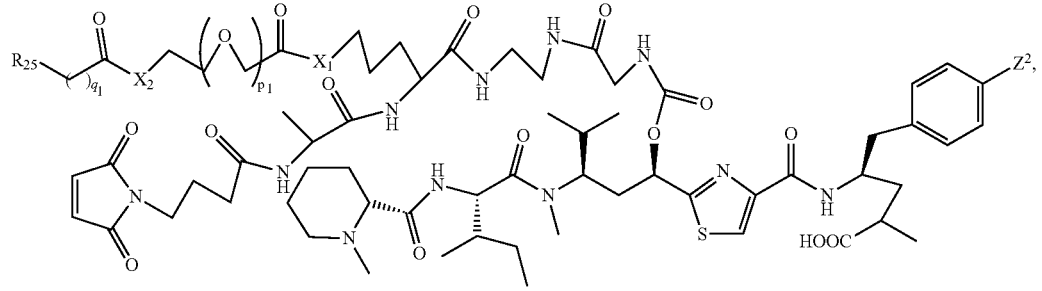
c-32
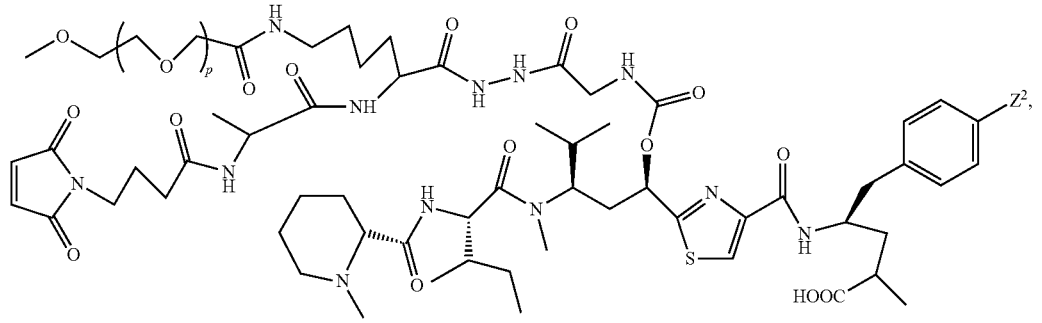
c-33
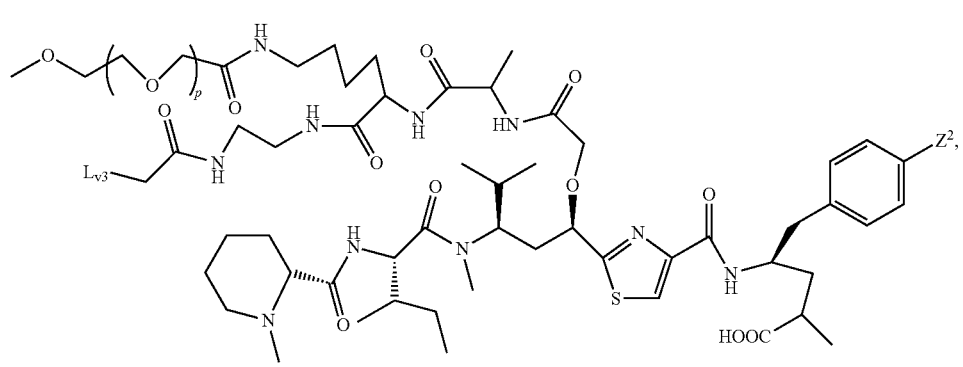
c-34
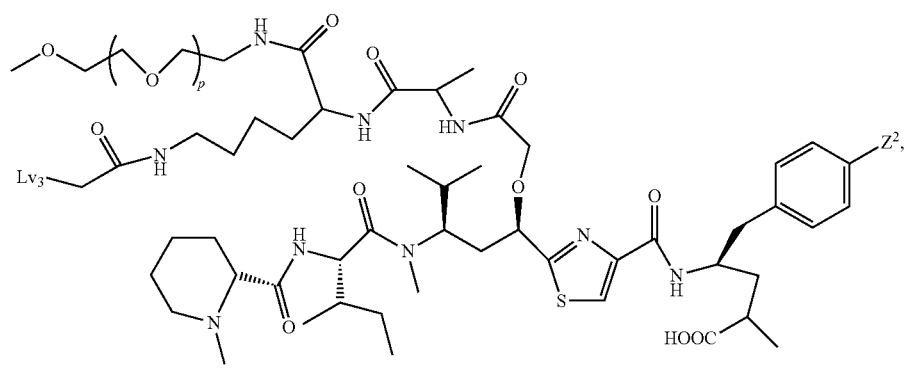
c-35

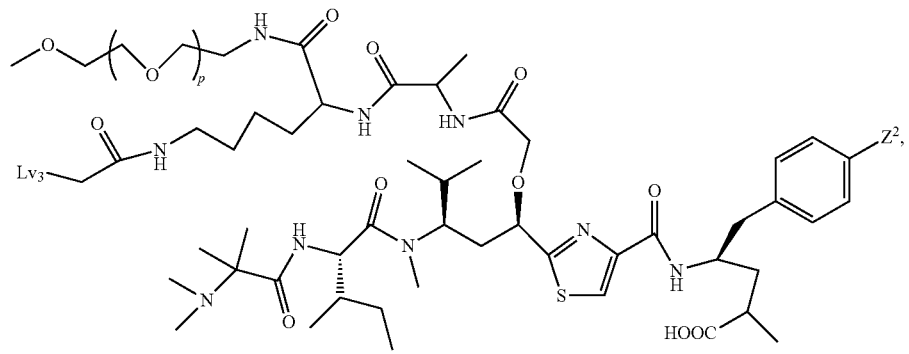
c-36
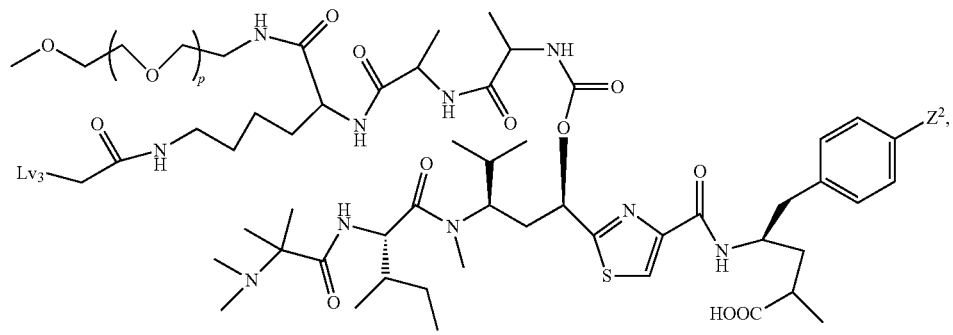
c-37
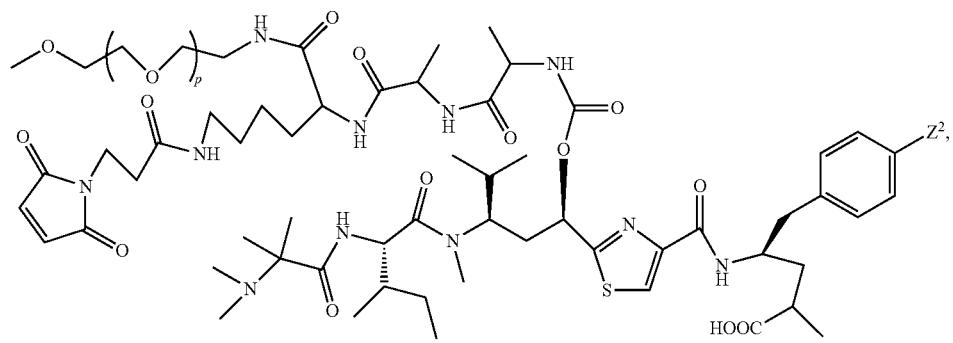
c-38
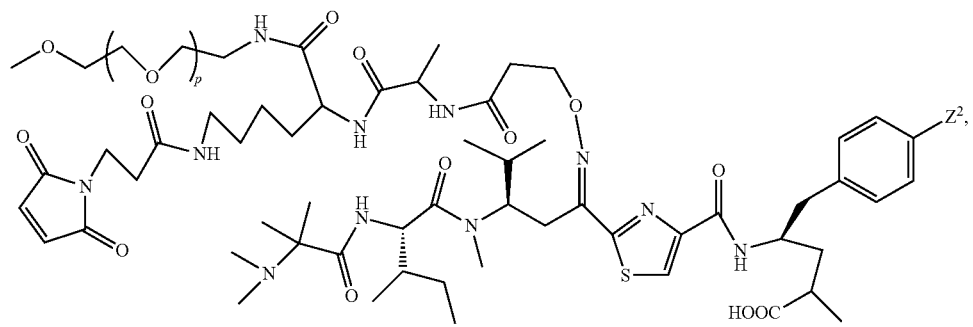
c-39

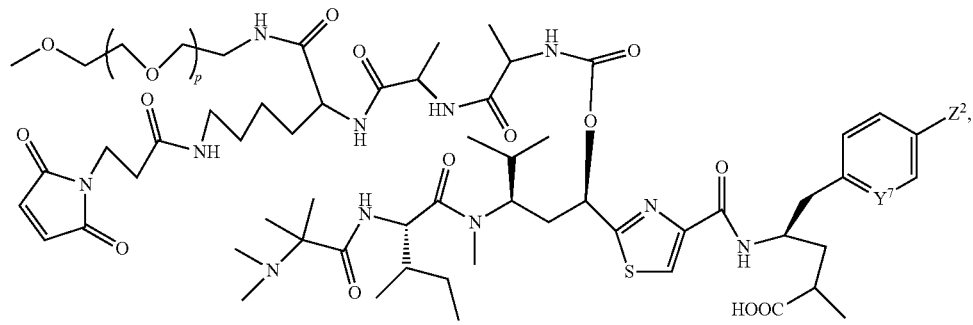
c-40
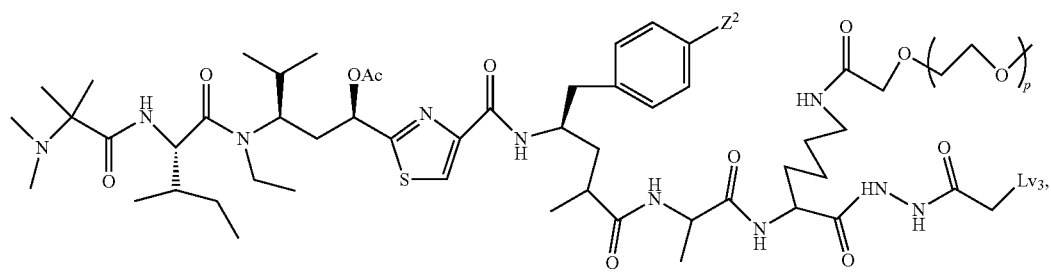
c-41
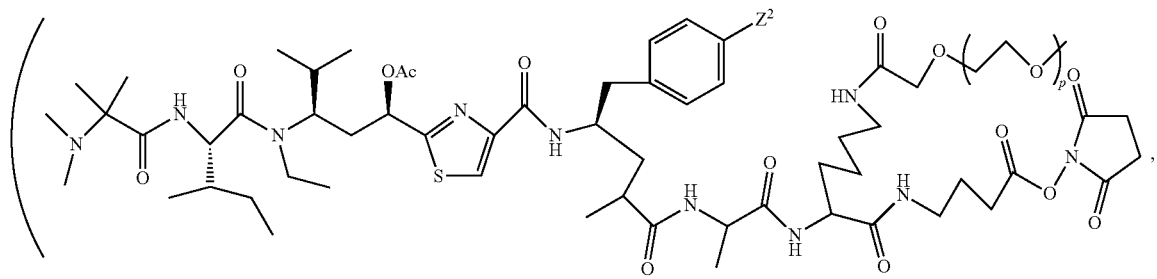
c-42
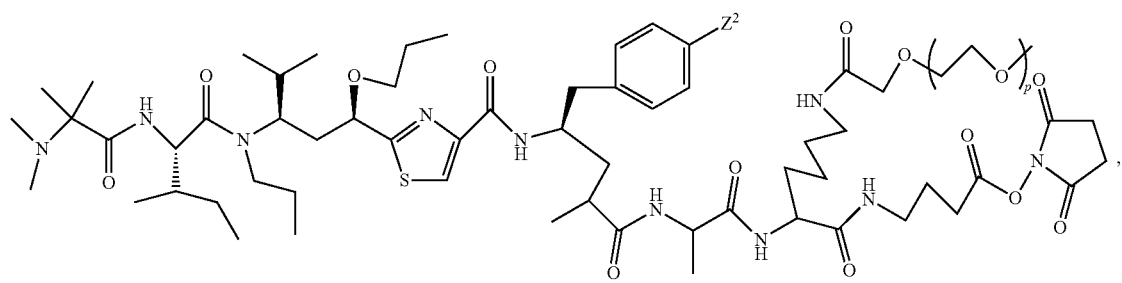
c-43
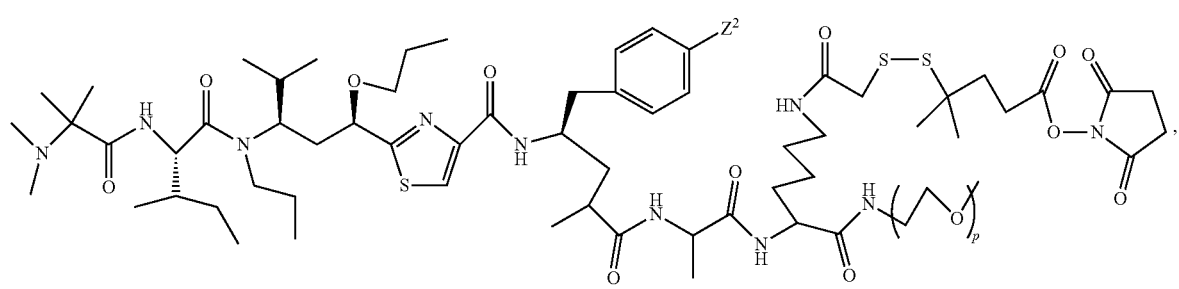
c-44

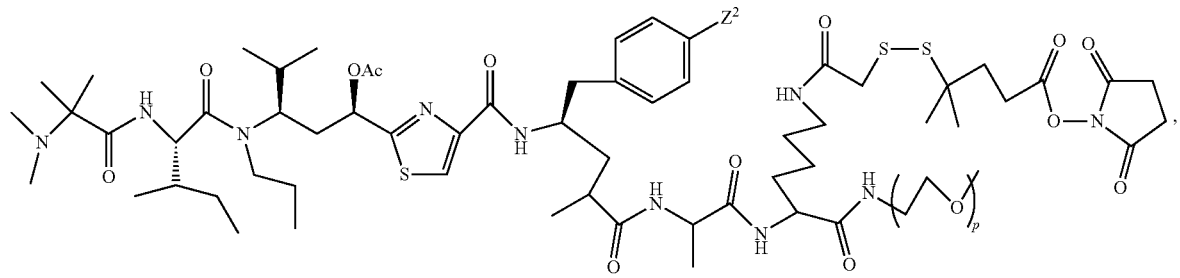
c-45
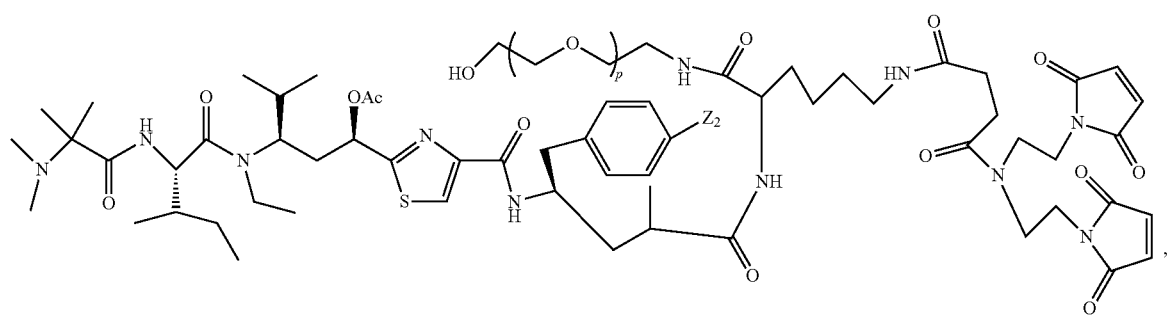
c-46
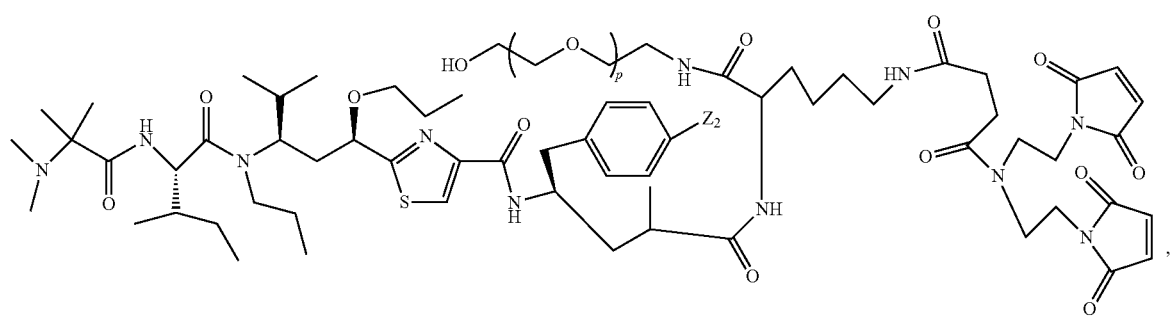
c-47
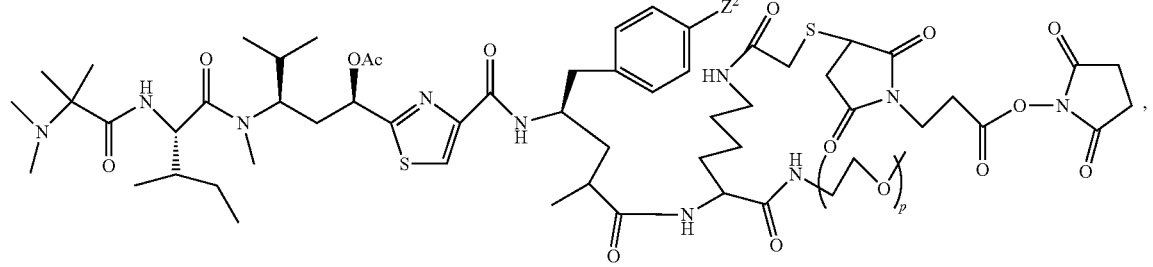
c-48
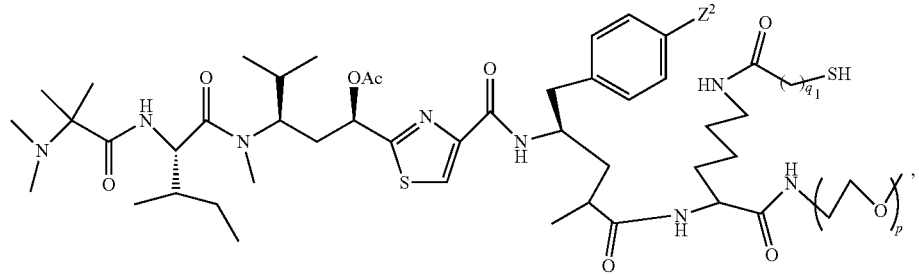
c-49

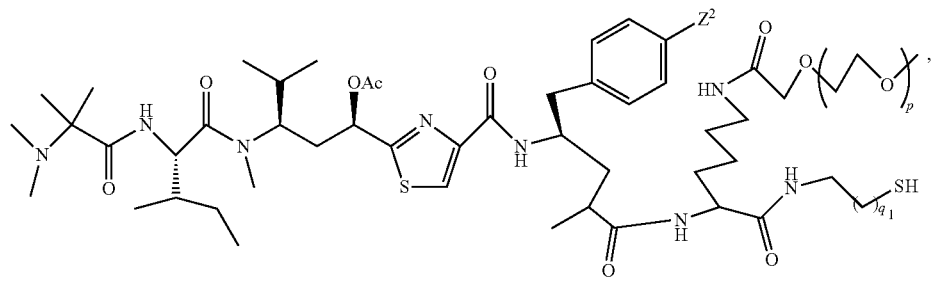
c-50
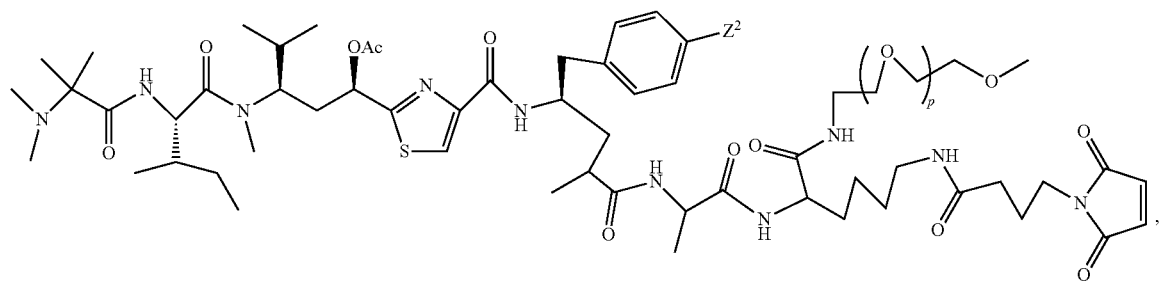
c-51
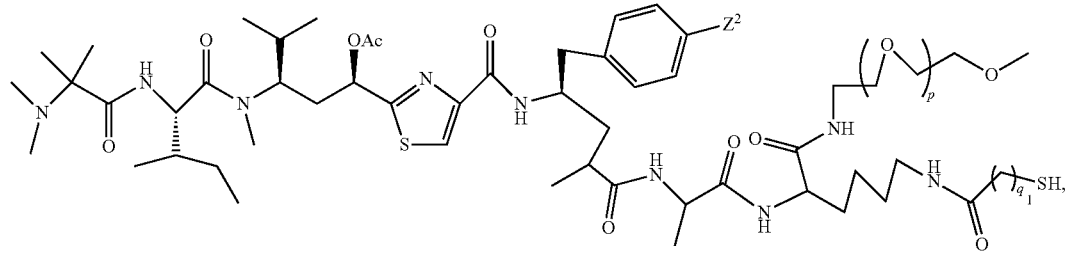
c-52
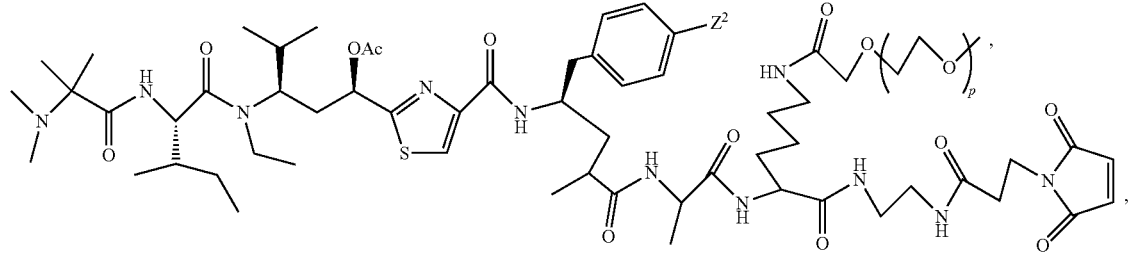
c-53
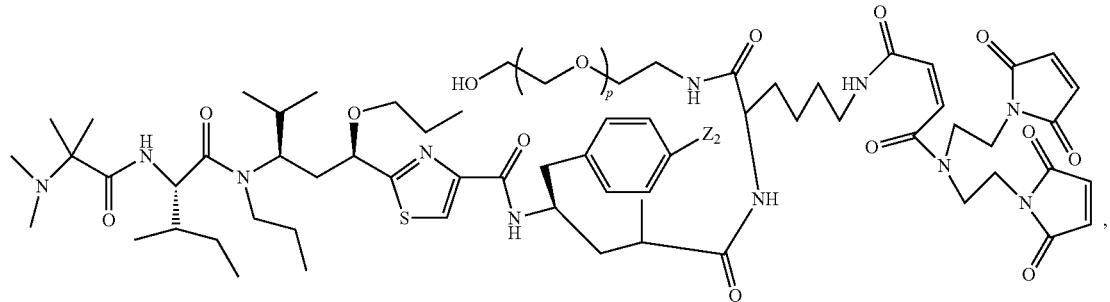
c-54

-continued
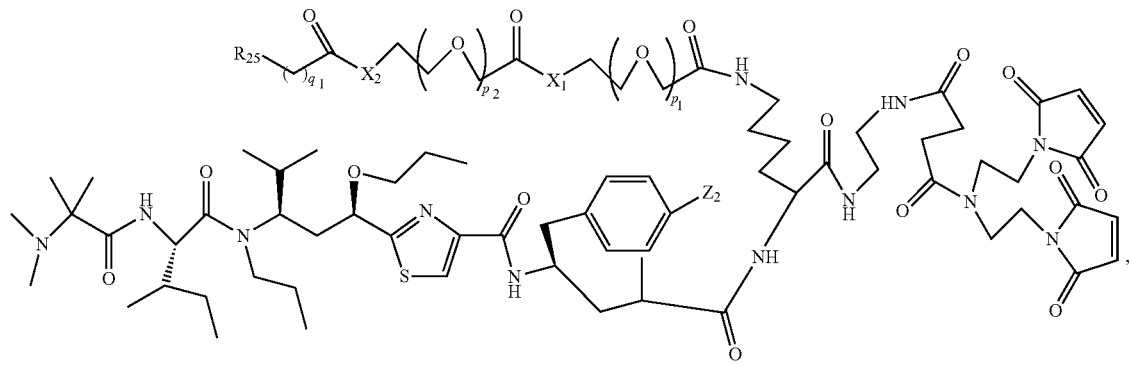
c-55
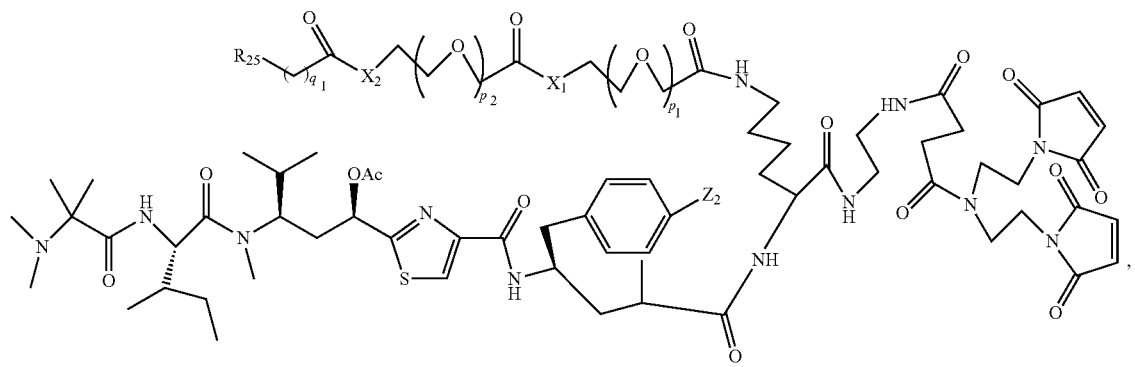
c-56
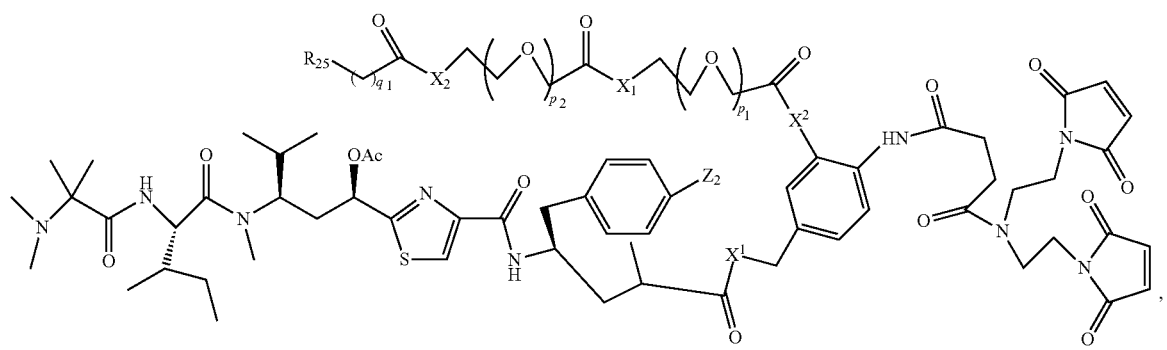
c-57
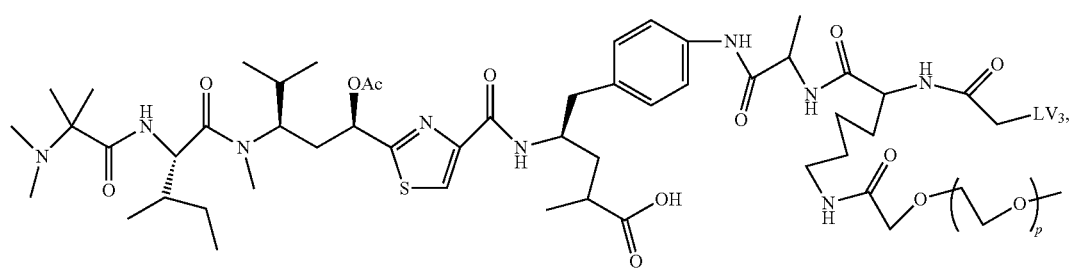
c-58
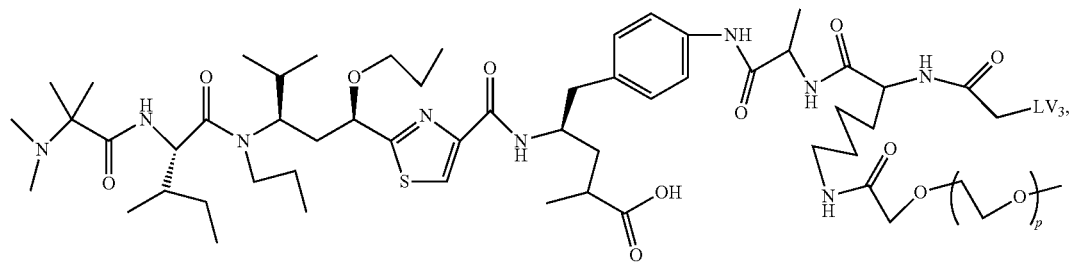
c-59

-continued
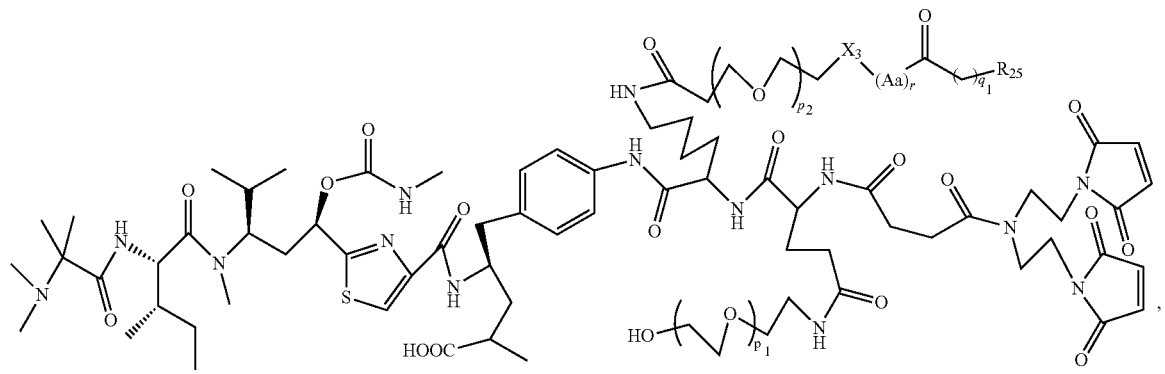
c-60
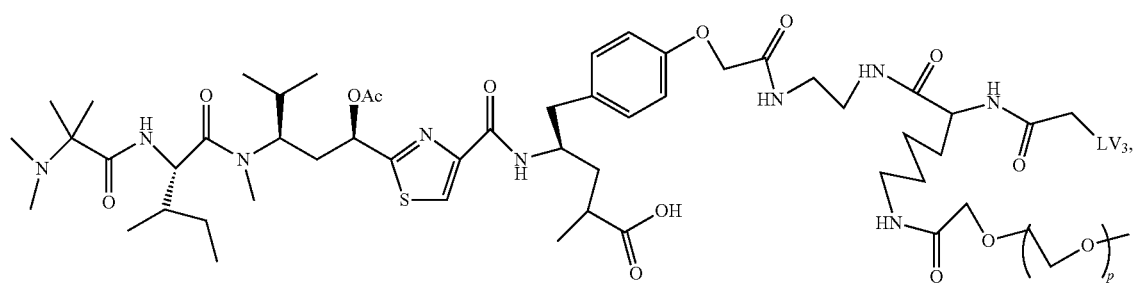
c-61
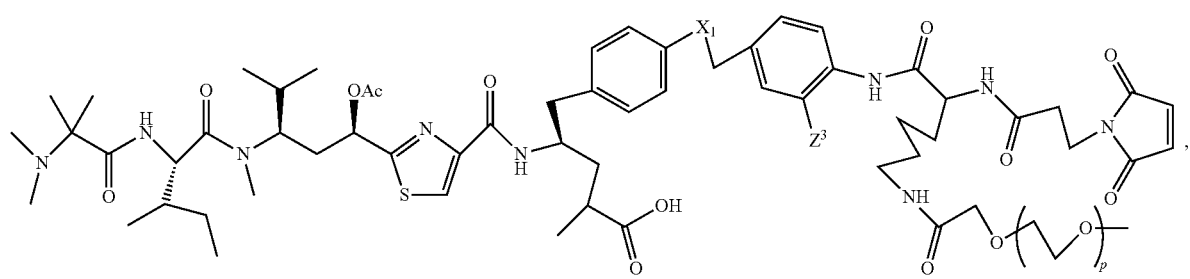
c-62
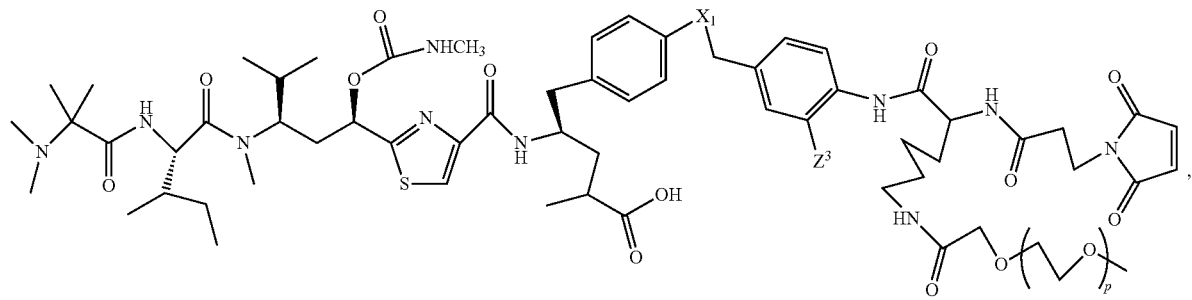
c-63
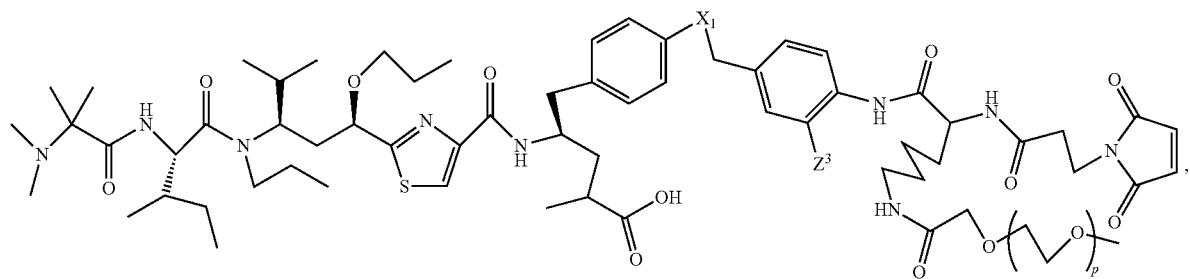
c-64

-continued
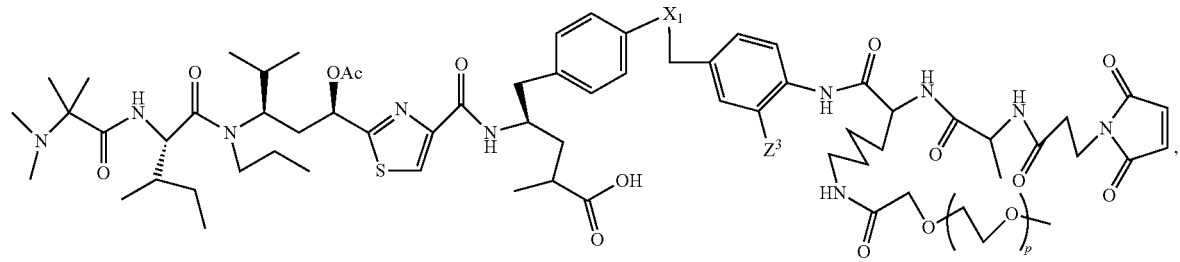
c-65
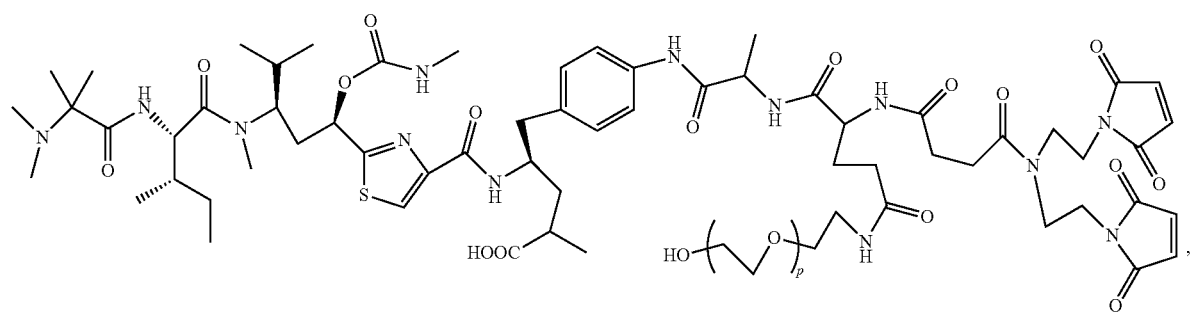
c-66
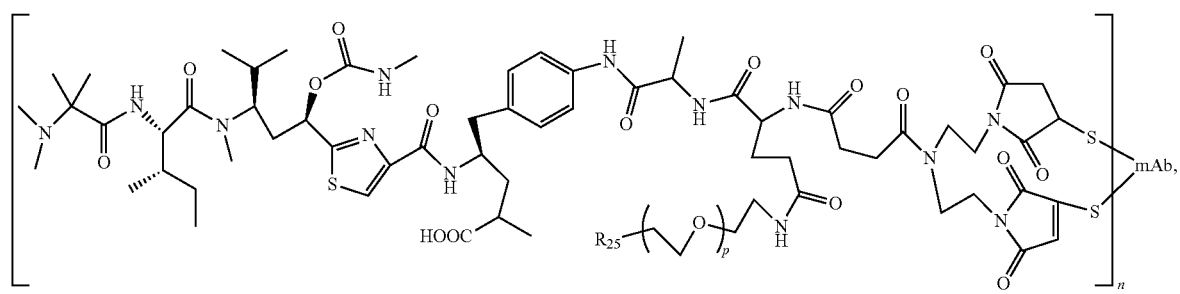
c-67
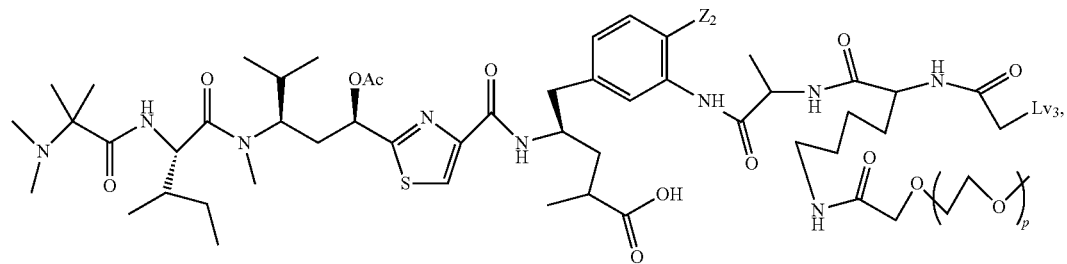
c-68
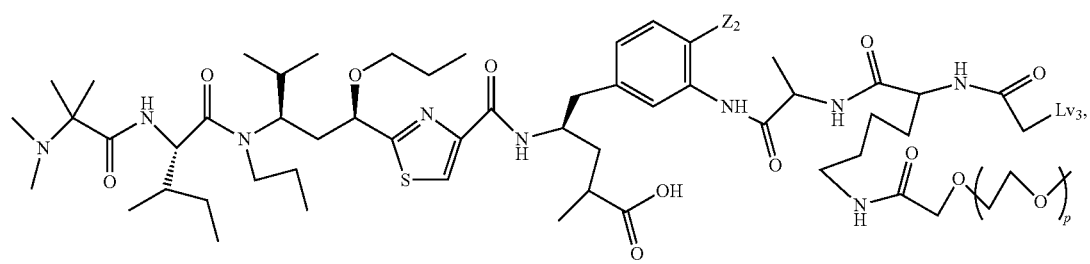
c-69

-continued
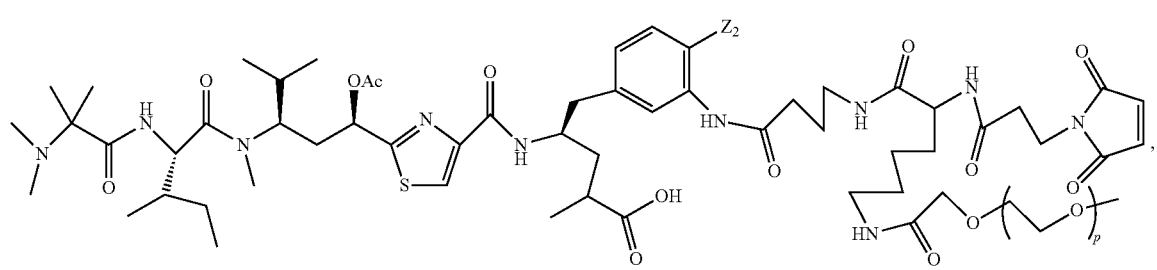
c-70
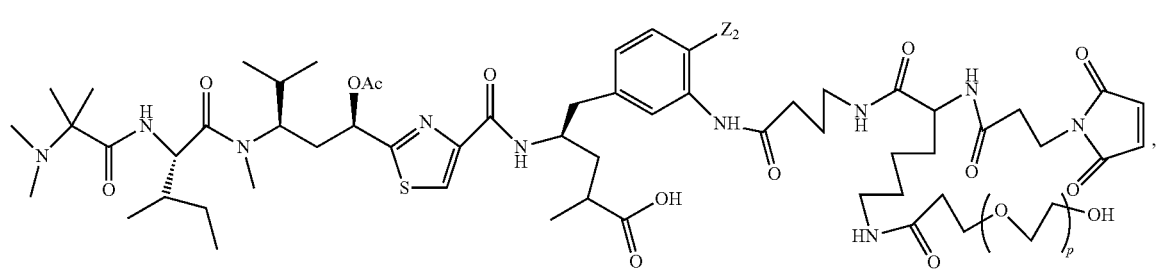
c-71
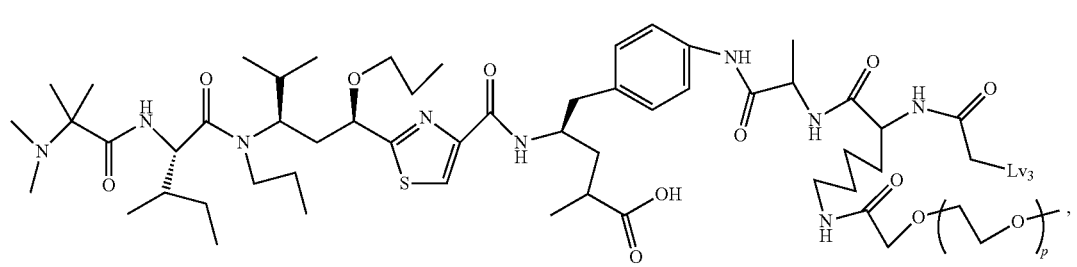
c-72
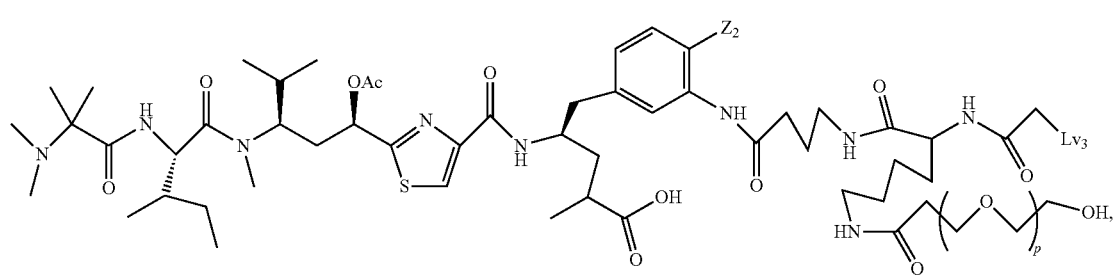
c-73
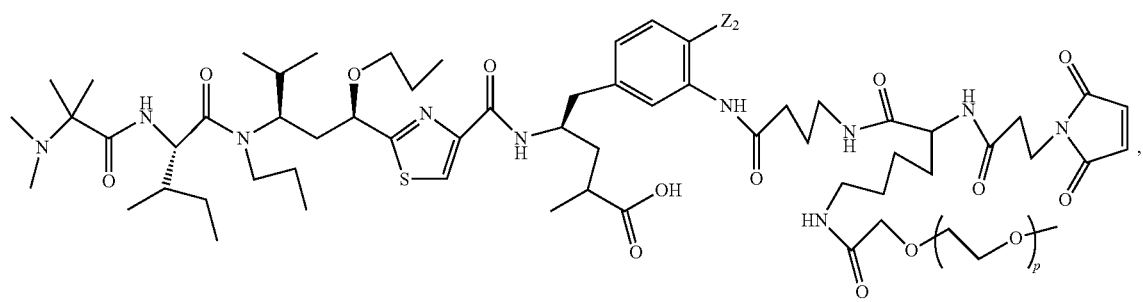
c-74

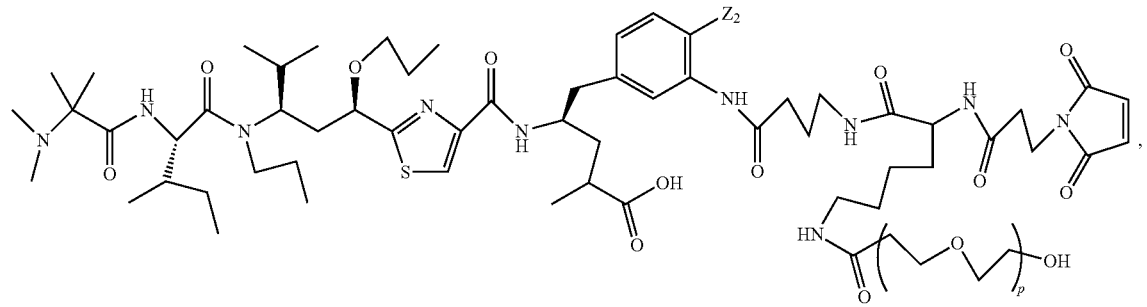
c-75
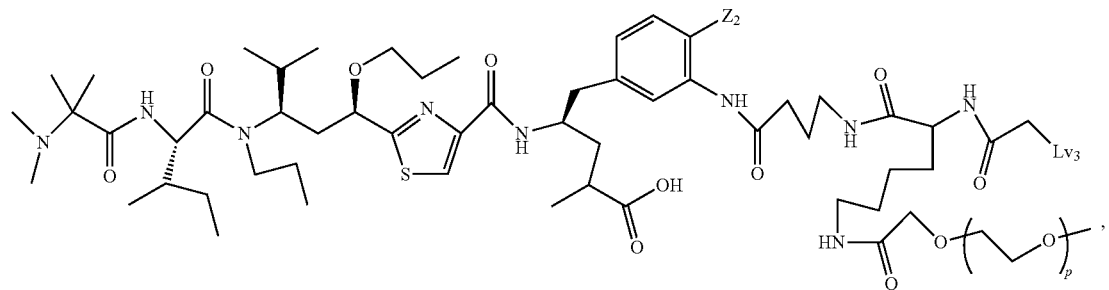
c-76
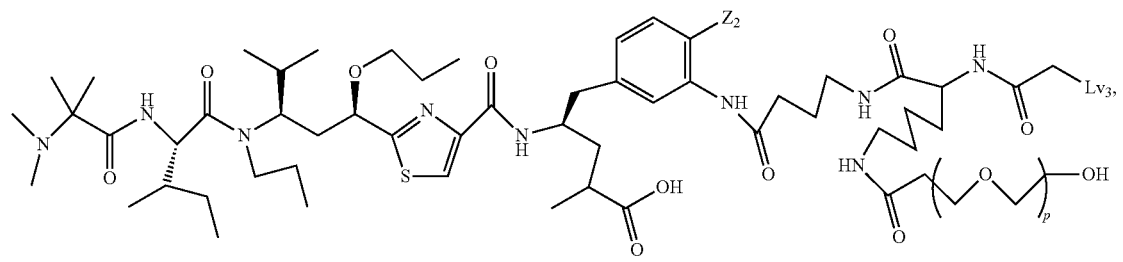
c-77
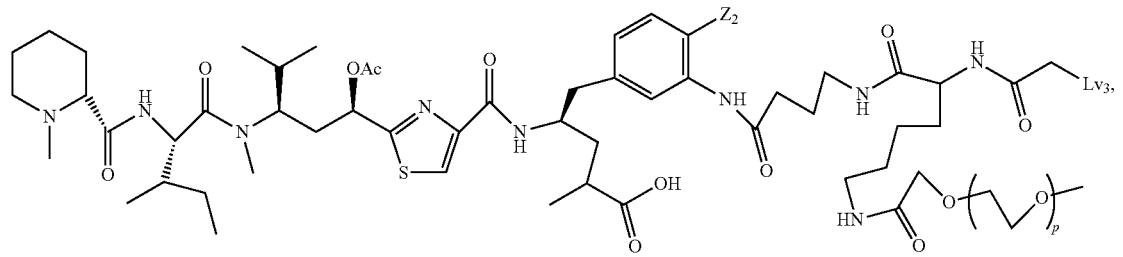
c-78
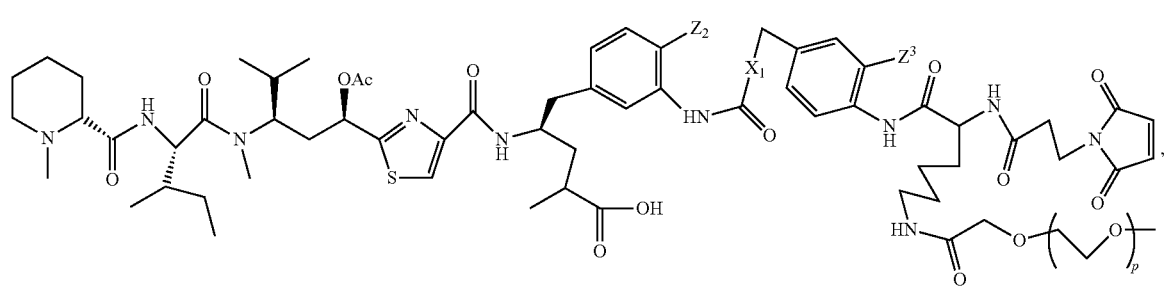
c-79

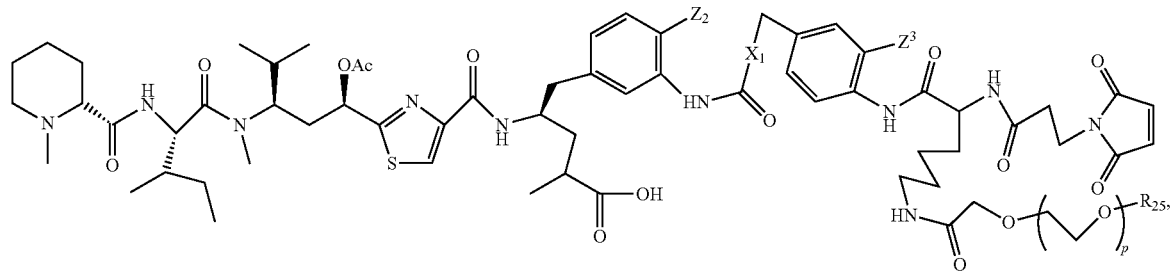
c-80
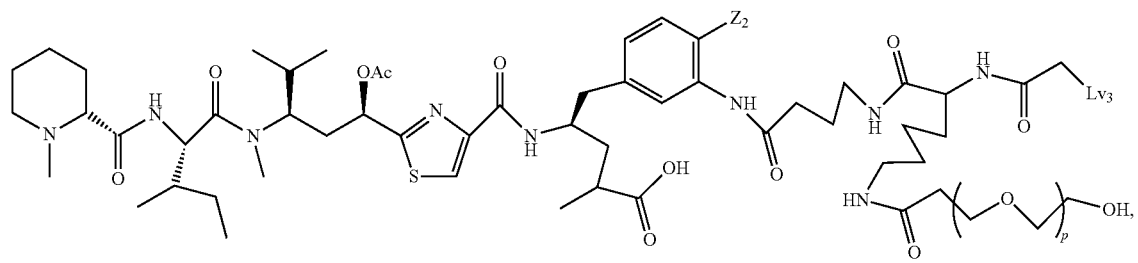
c-81
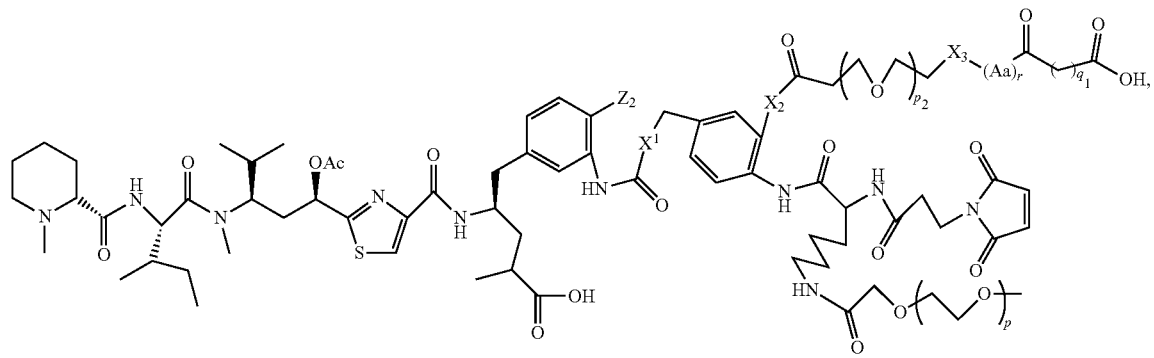
c-82
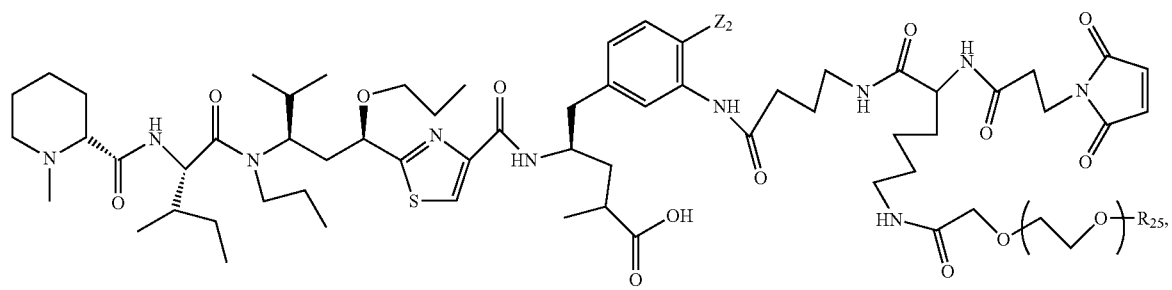
c-83
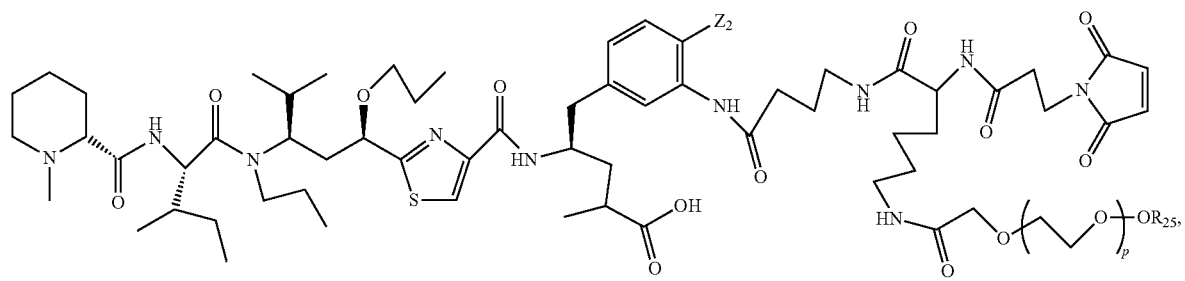
c-84

-continued
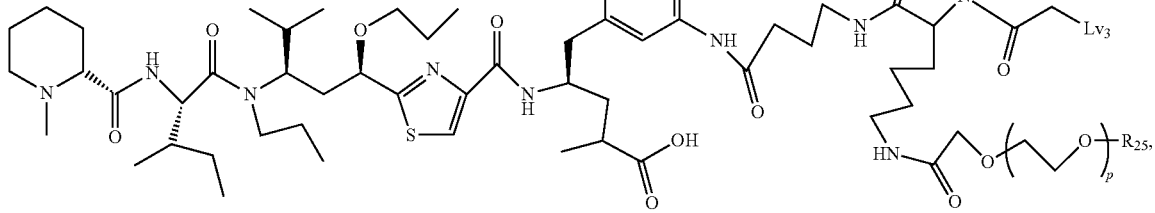
c-85
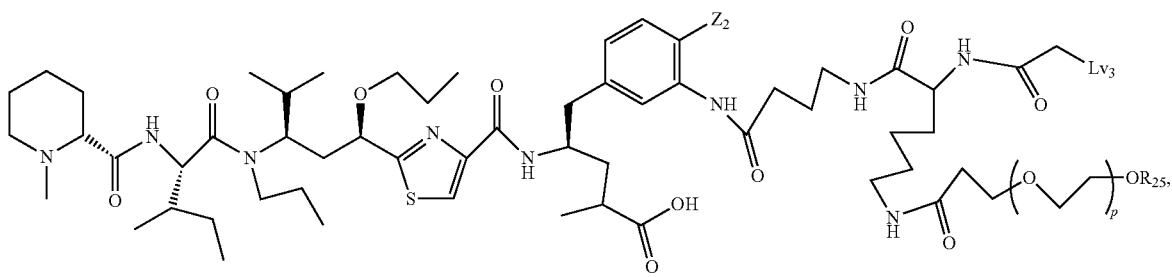
c-86
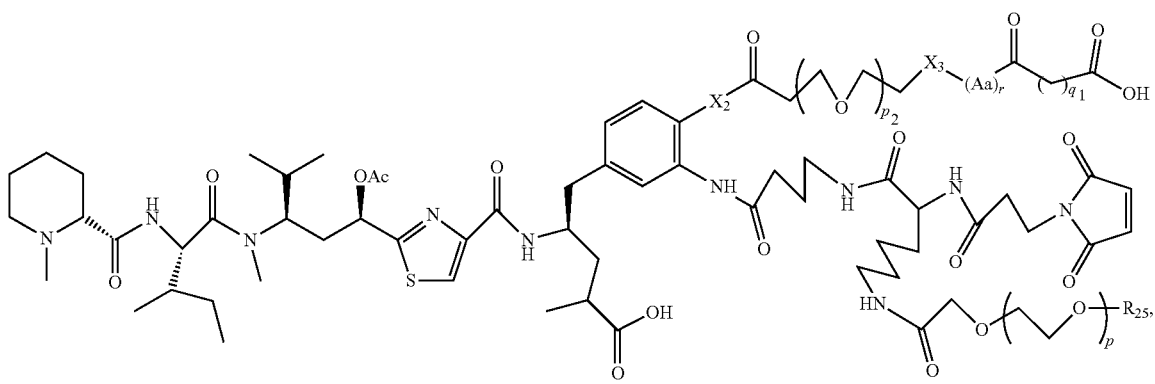
c-87
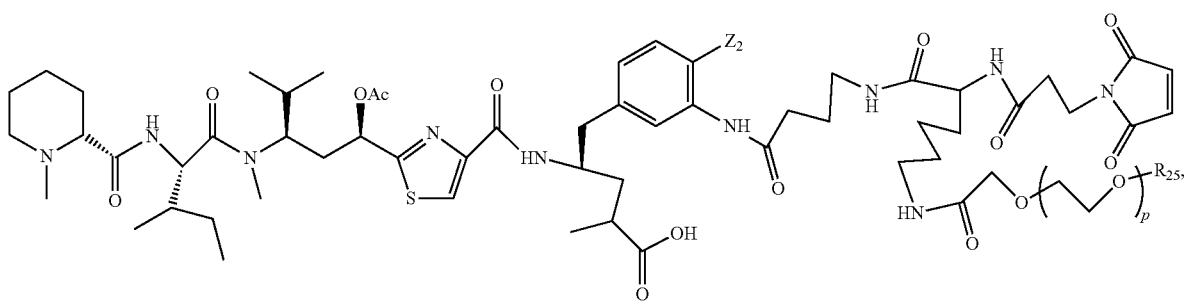
c-88
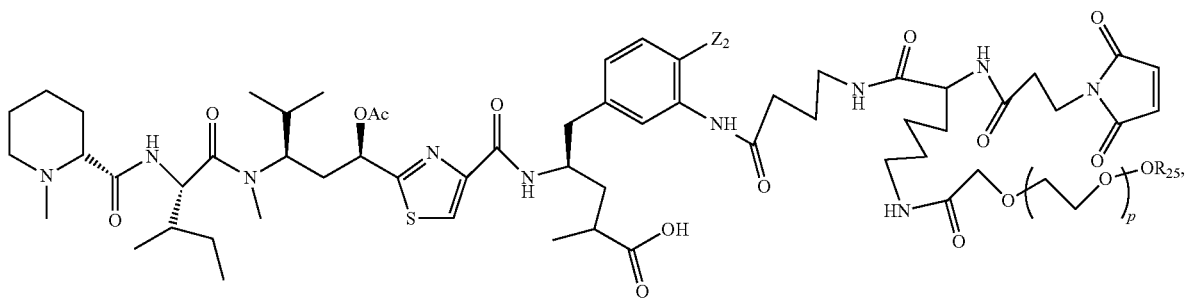
c-89

-continued
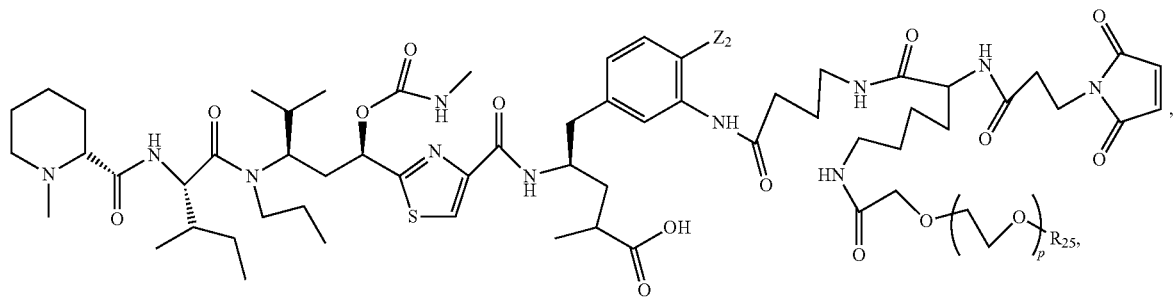
c-90
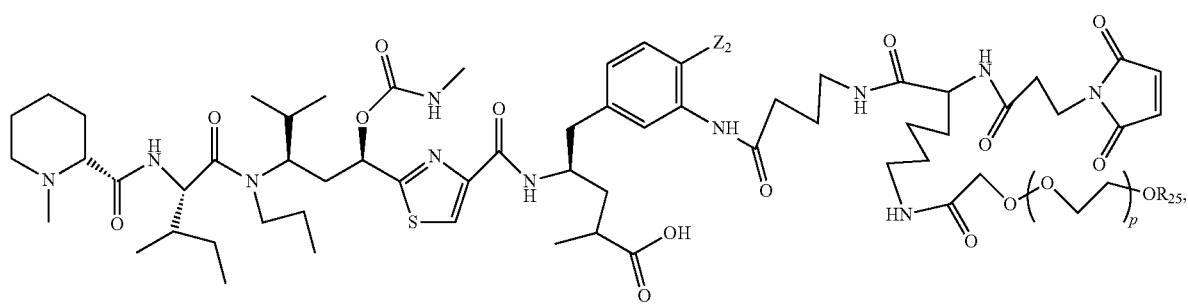
c-91
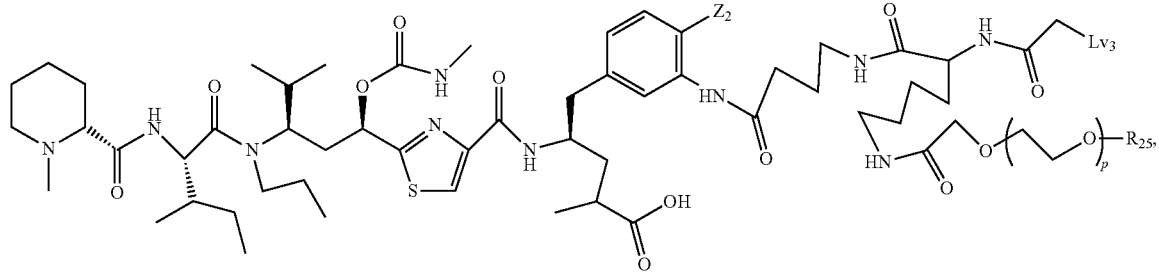
c-92
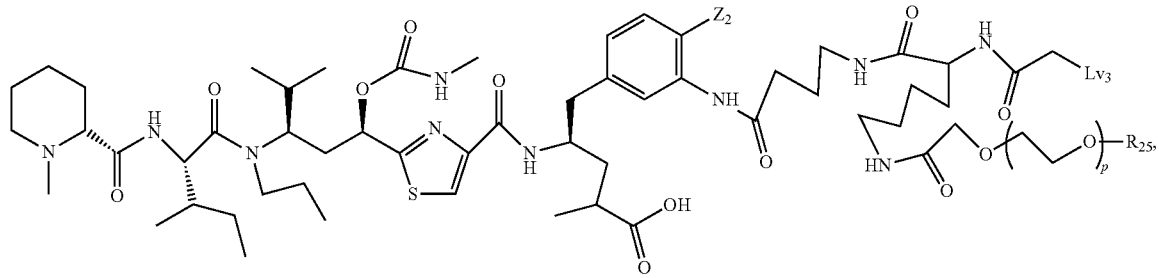
c-93
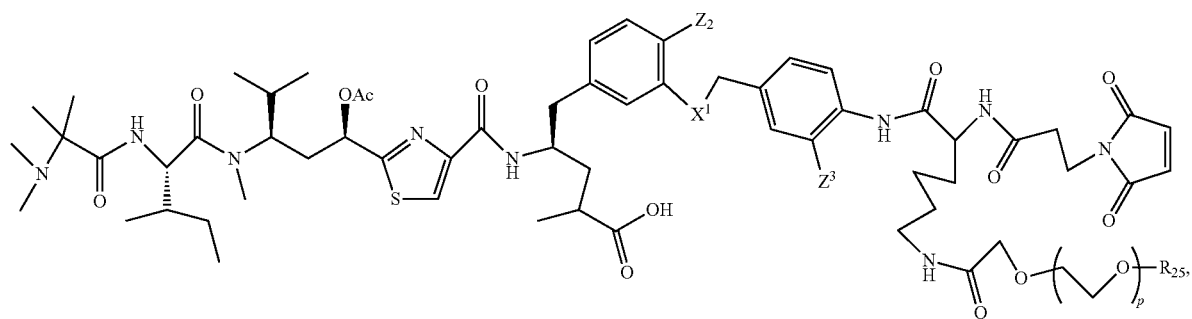
c-94

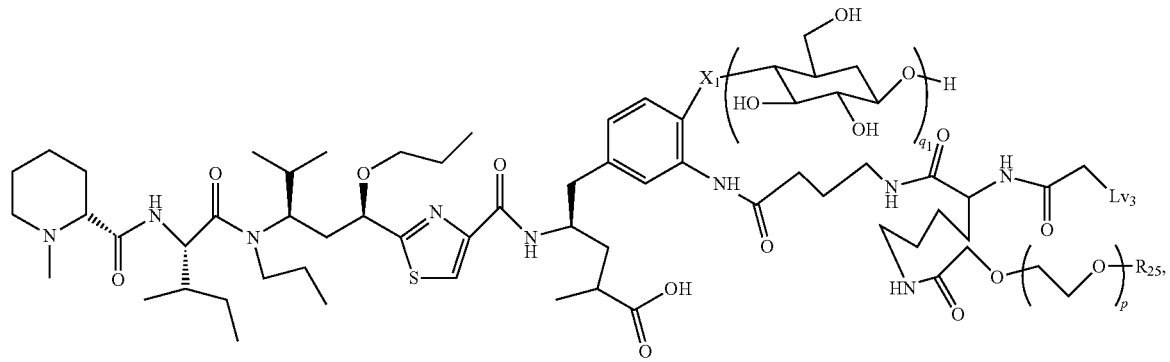
c-95
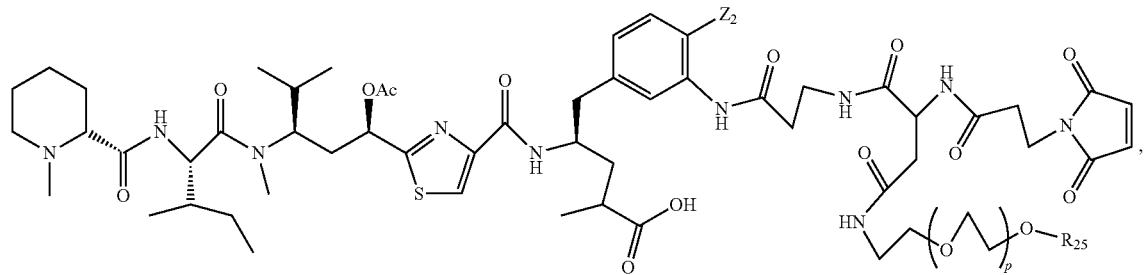
c-96
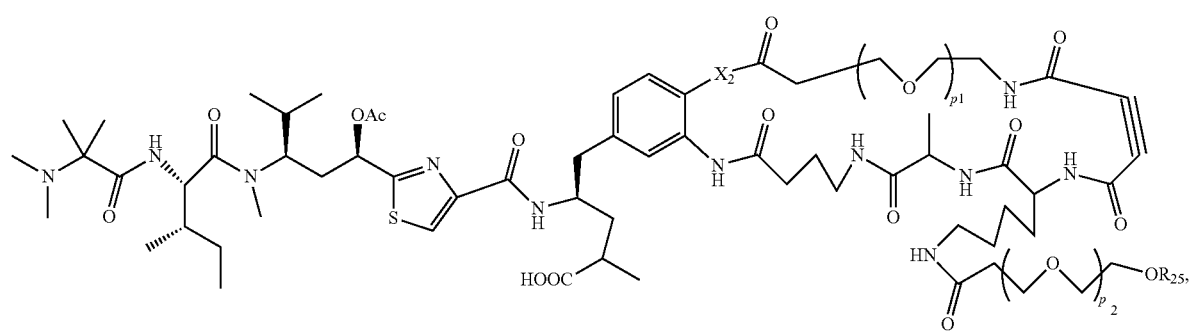
c-97
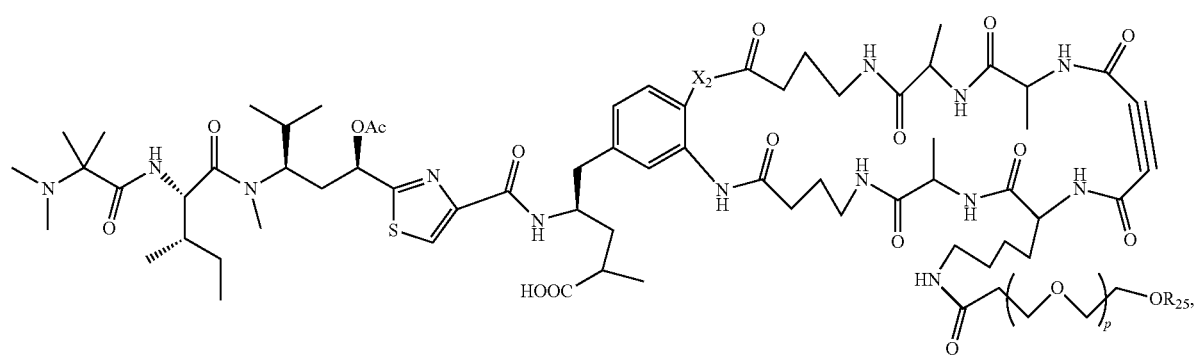
c-98 c-99

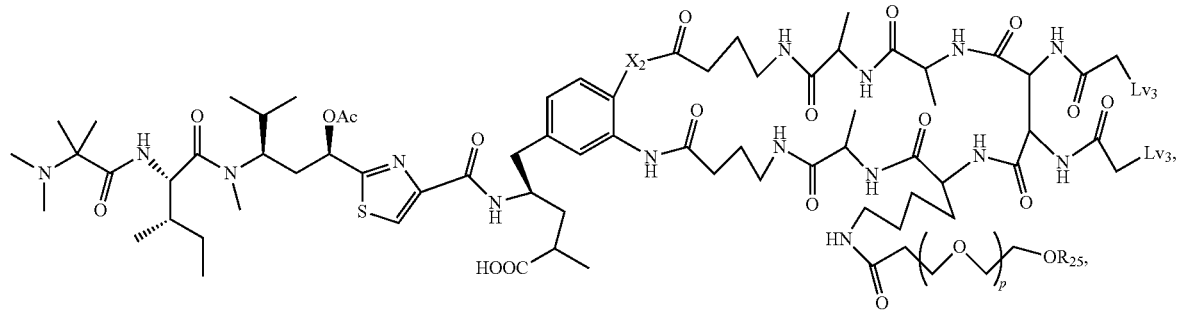

c-100

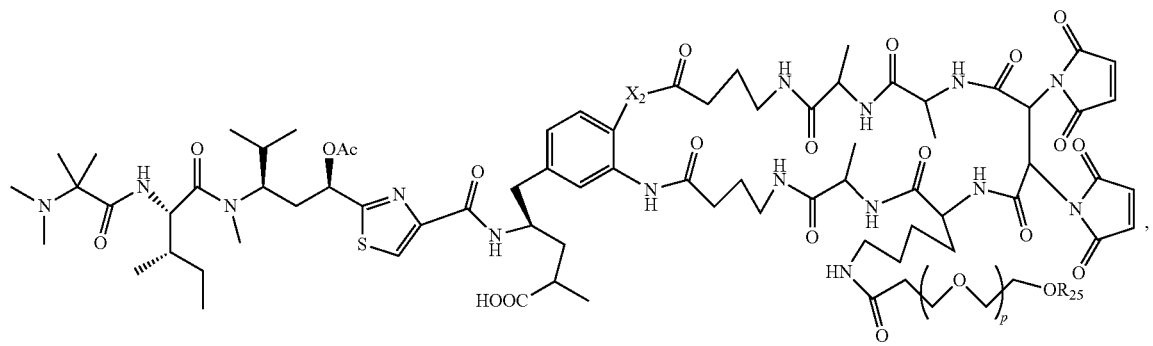

c-101

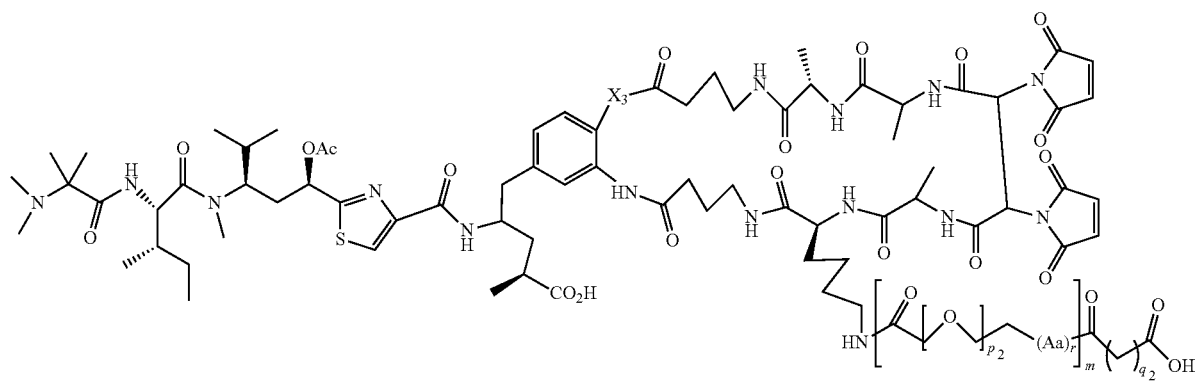

or their pharmaceutically acceptable salts, hydrates, or hydrated salts; or the polymorphic crystalline structures of these compounds; or their optical isomers, racemates, diastereomers or enantiomers; wherein $X_1$, $X_2$, $X_3$, $Z_2$, $Z_3$, p. $p_1$, $p_2$, $p_3$, $q_1$, $q_2$, $Lv_3$, $(Aa)_r$, $R_{25}$, $R_{25'}$, and m are described above.

In another aspect of the present invention, the side chain-linkage compound is represented by Formula (V), which can readily react to a cell-binding molecule T to form a conjugate of Formula (III):

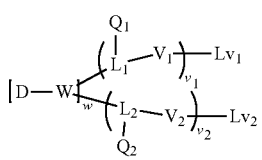

(V)

wherein D, W, w, $L_1$, $L_2$, $Q_1$, $Q_2$, $V_1$, $V_2$, $v_1$, $v_2$, and n, are defined the same as in Formula (I); wherein $Lv_1$ and $Lv_2$ have independently the same definition of $Lv_1$ in formula (IV) and both $Lv_1$ and $Lv_2$ can be the same or different in Formula (V).

Examples of Formula (V) are shown below:
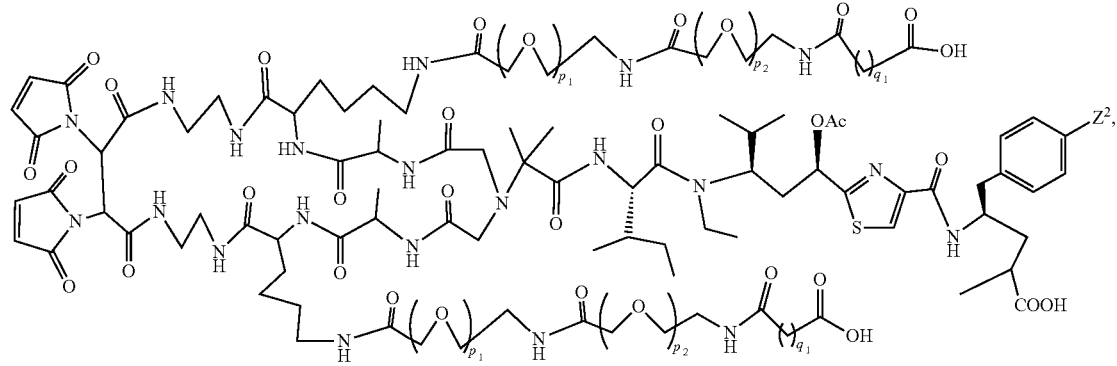
d-01
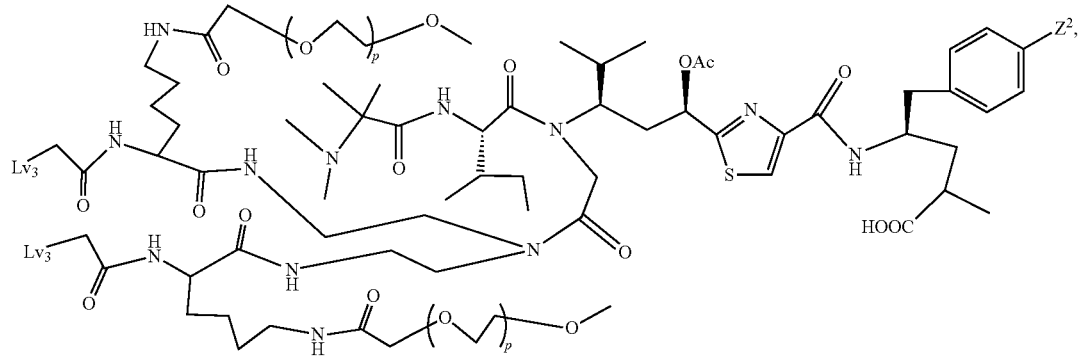
d-02
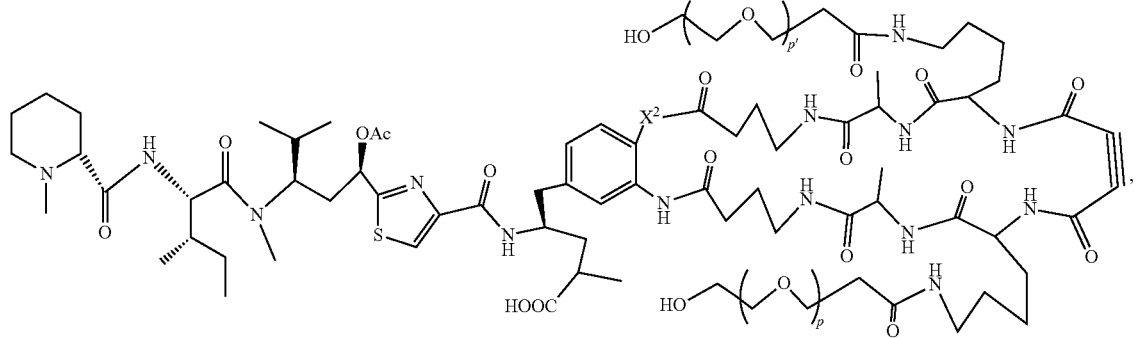
d-03
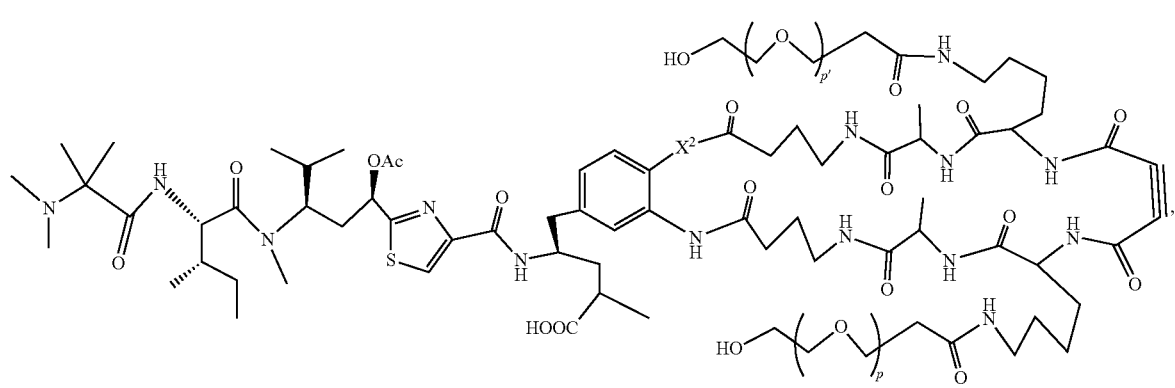
d-04

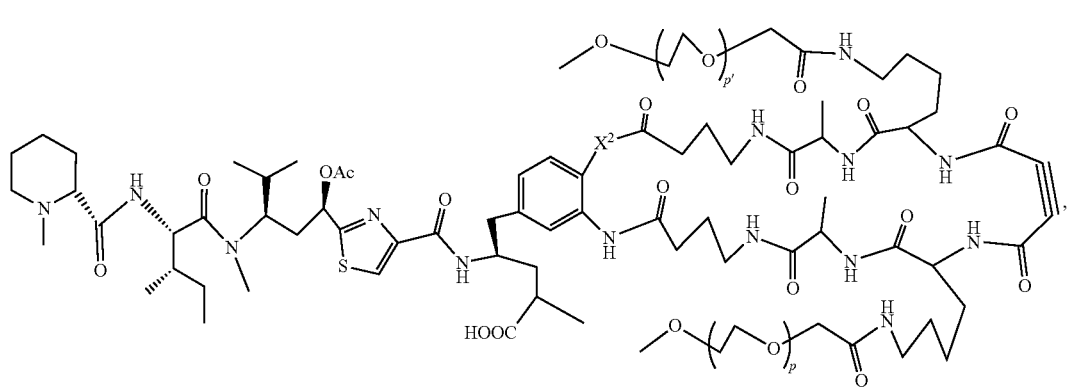
d-05
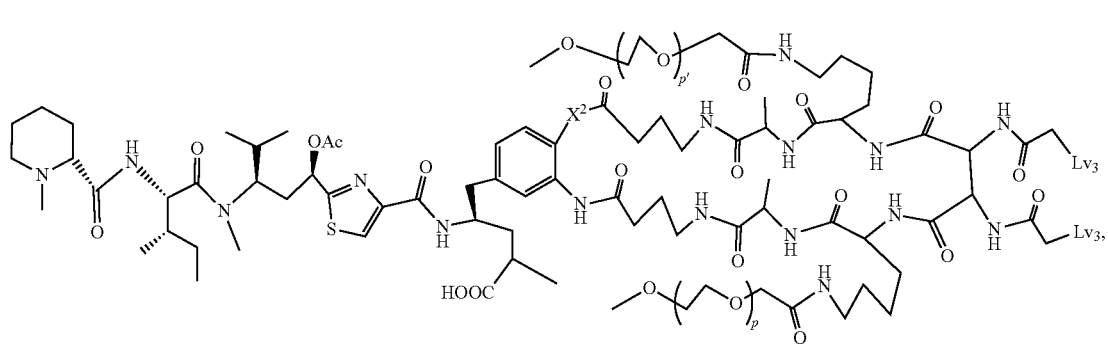
d-05
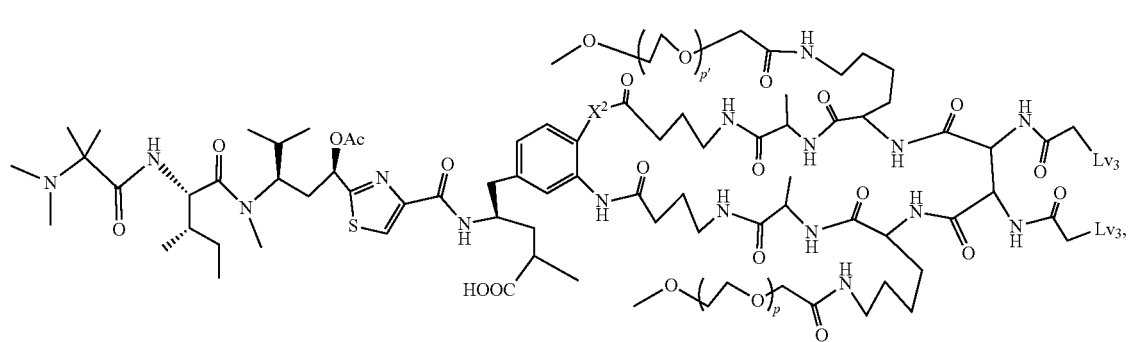
d-06
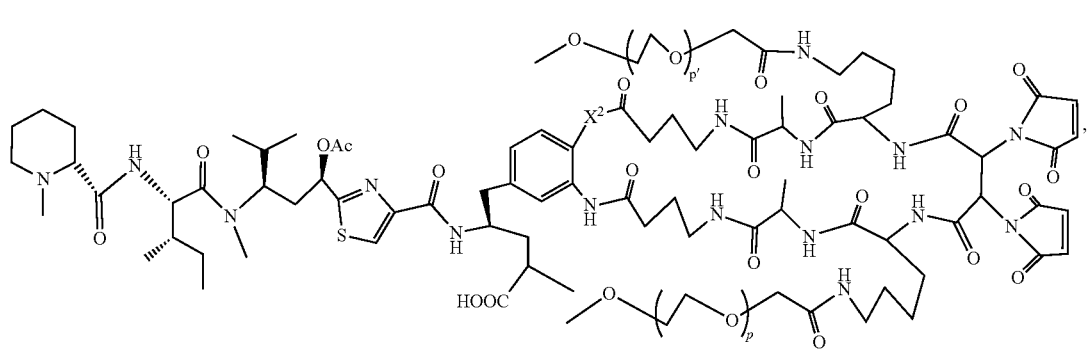
d-07

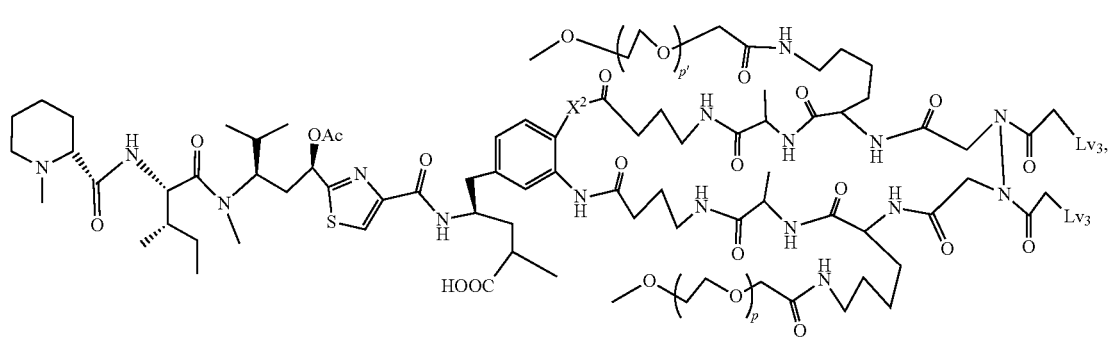
d-08
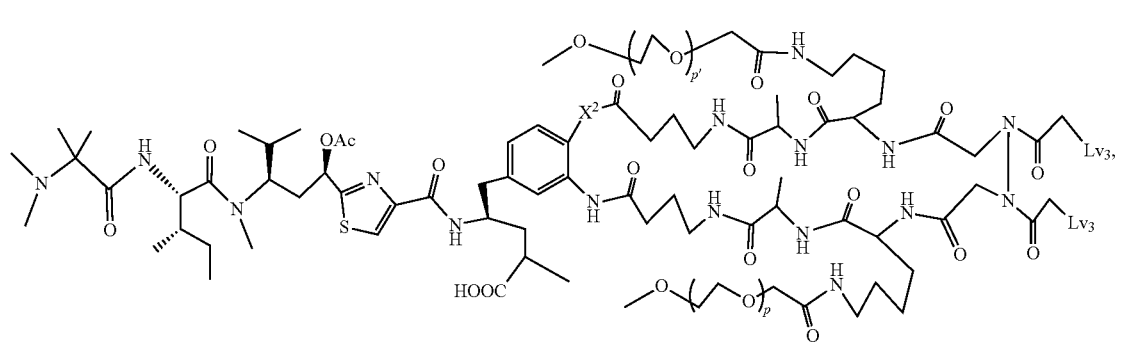
d-09
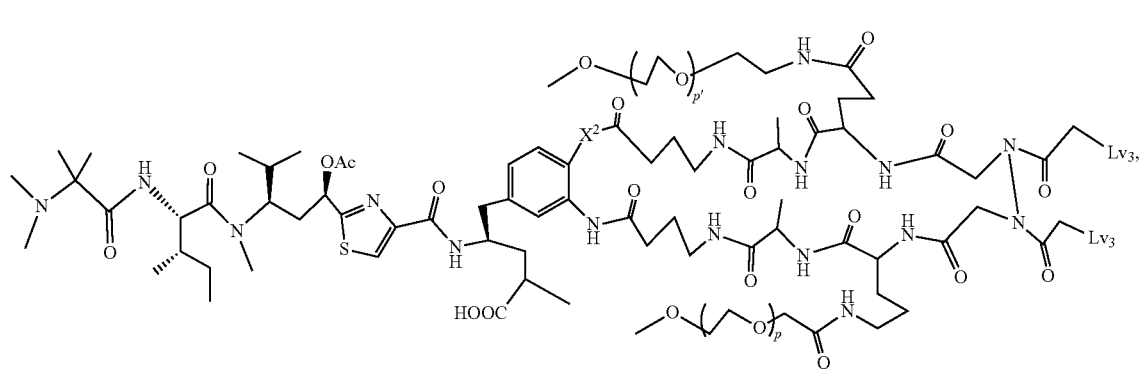
d-10
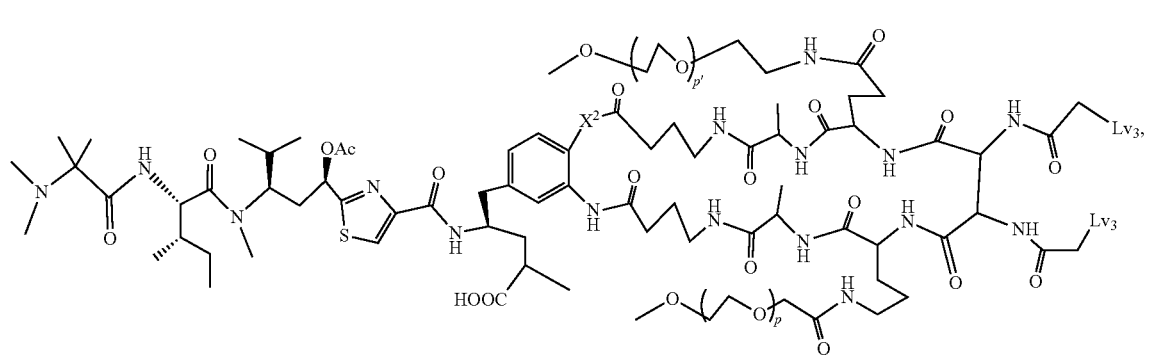
d-11

-continued
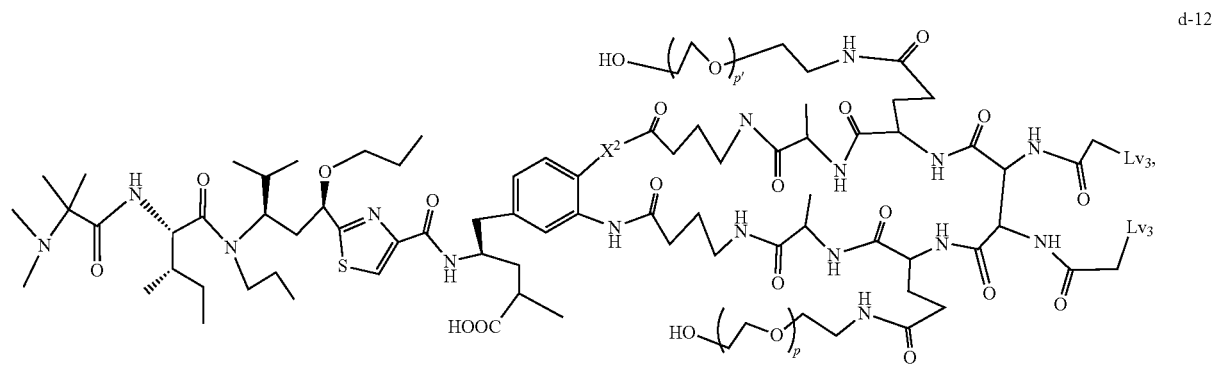
d-12
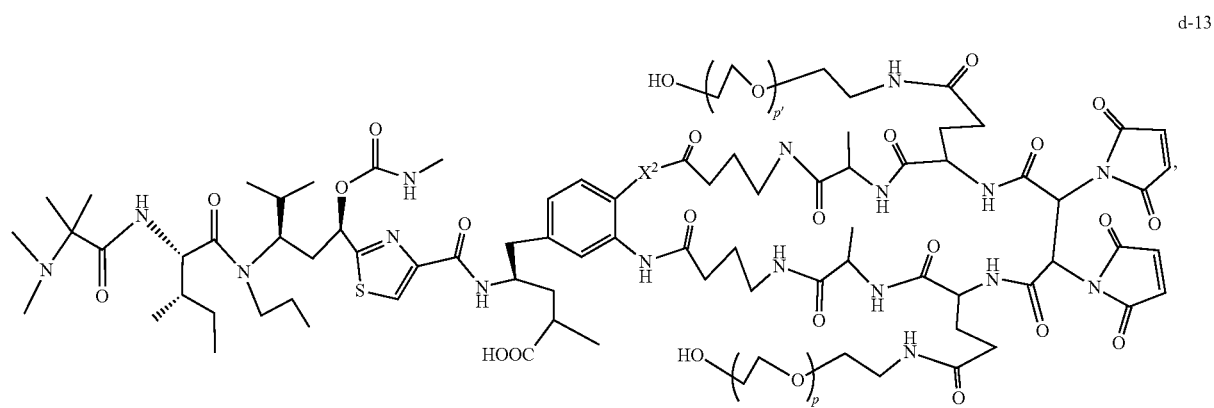
d-13
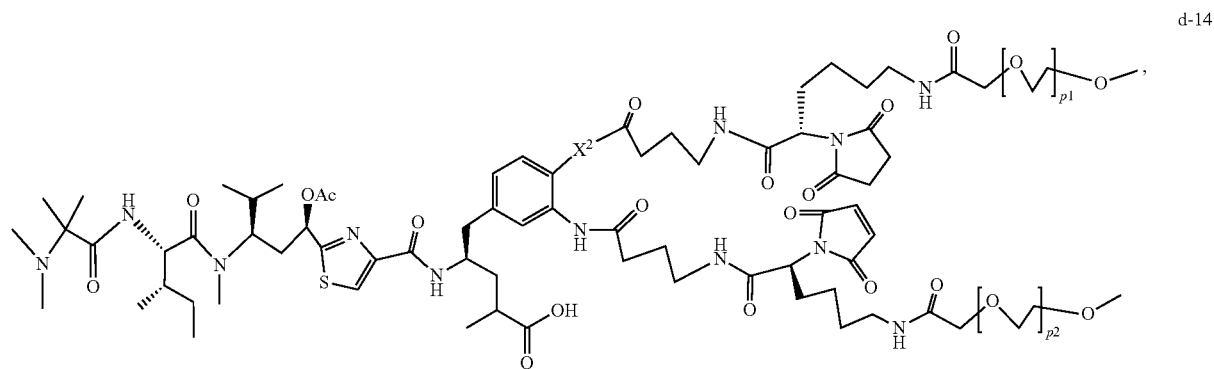
d-14
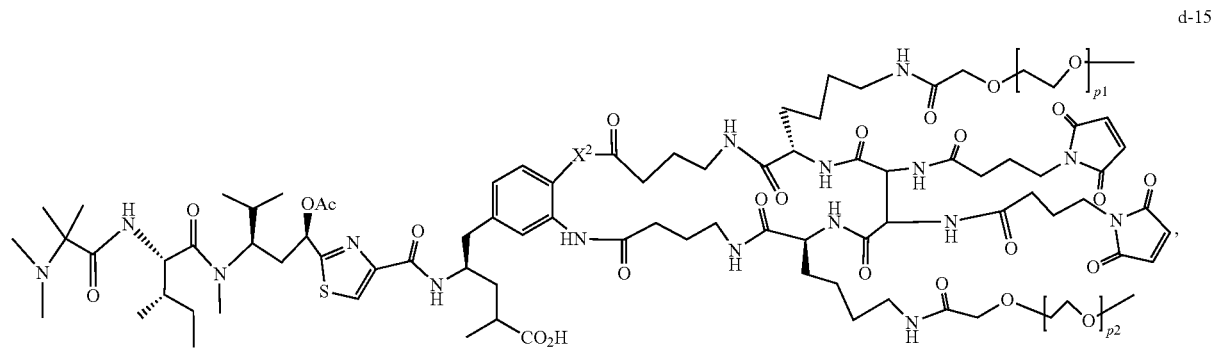
d-15

-continued
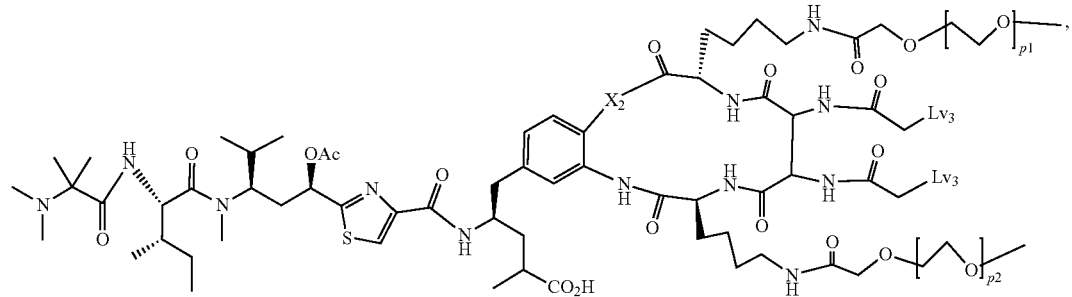
d-16
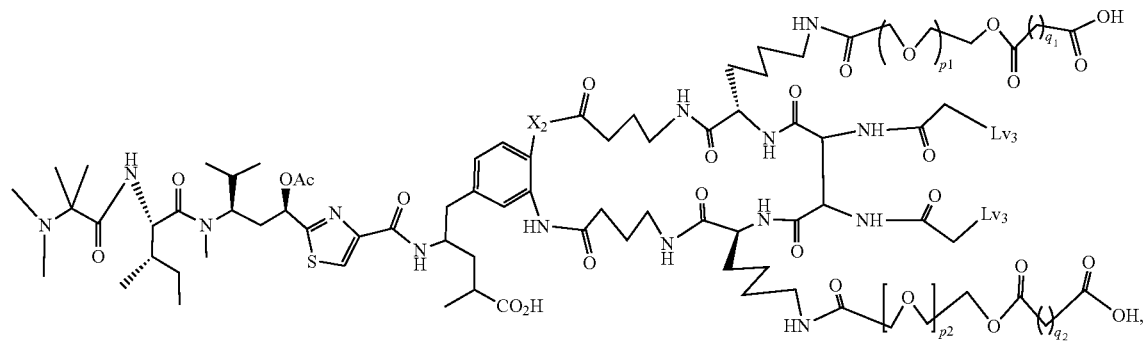
d-17
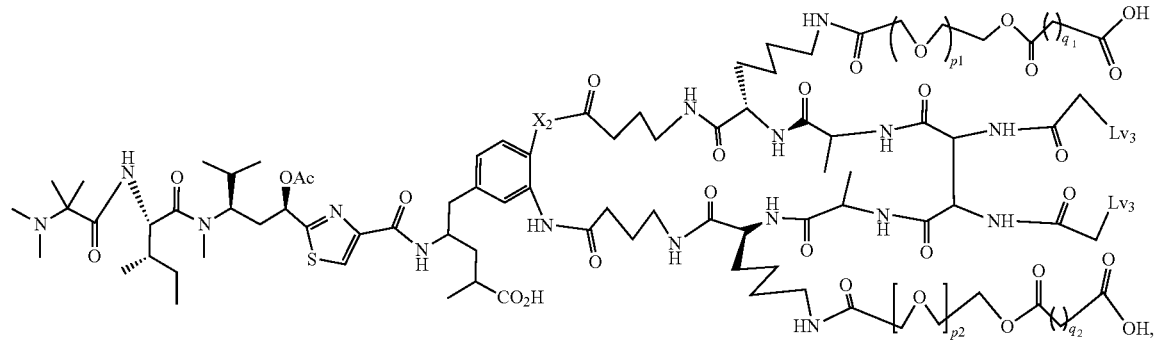
d-18
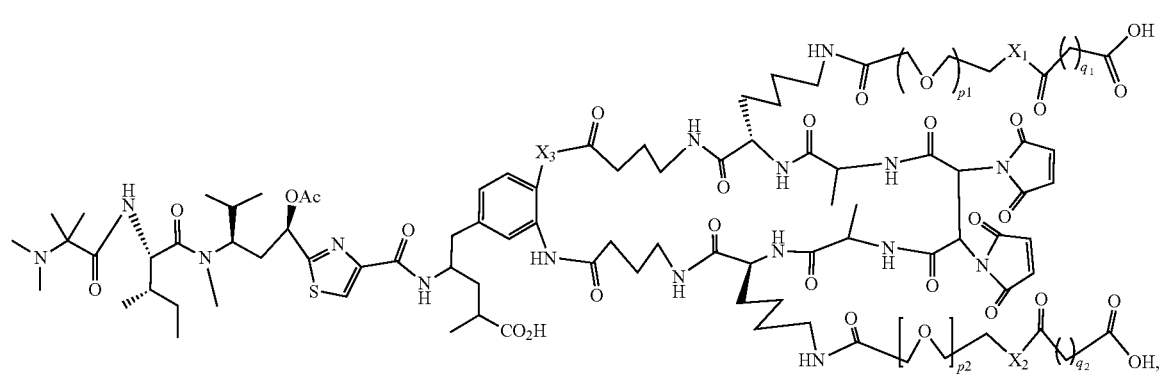
d-19

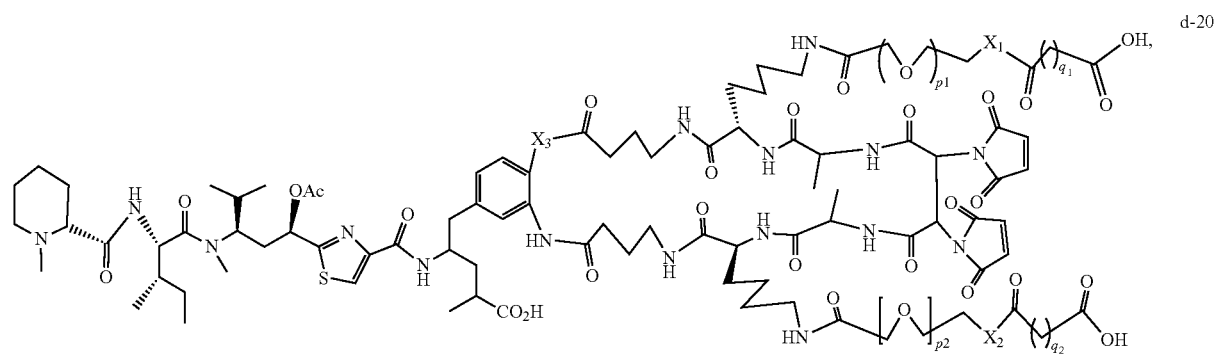
d-20
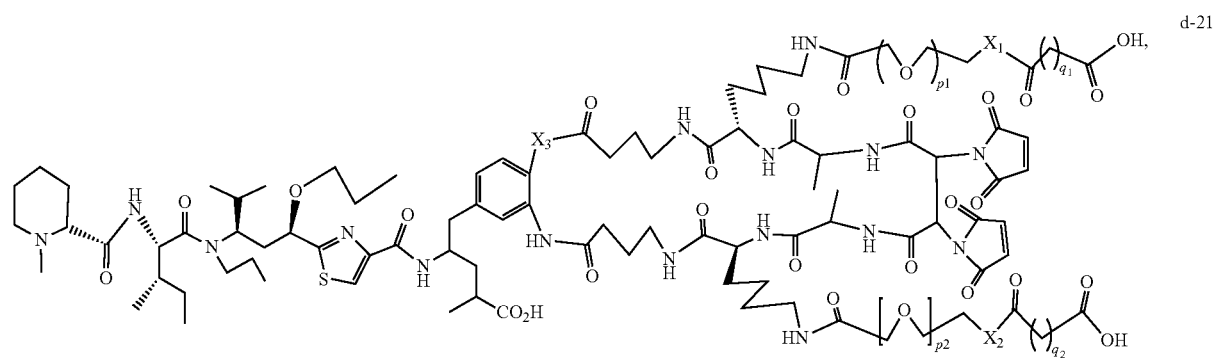
d-21
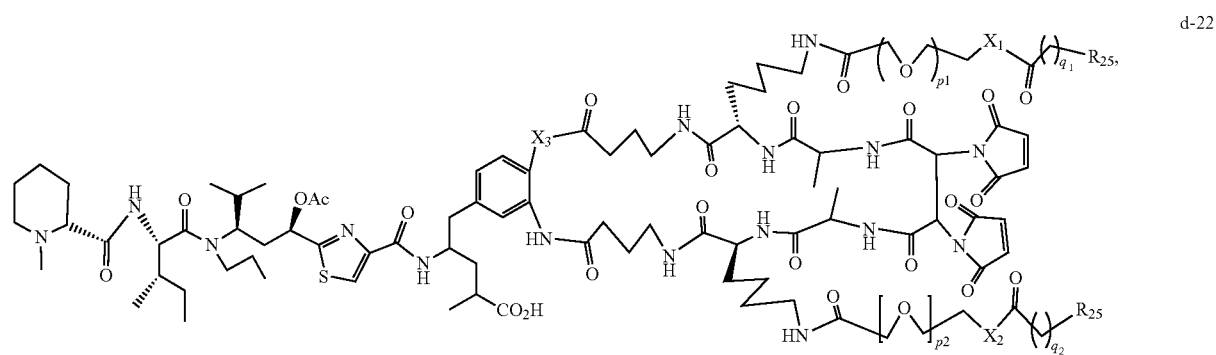
d-22
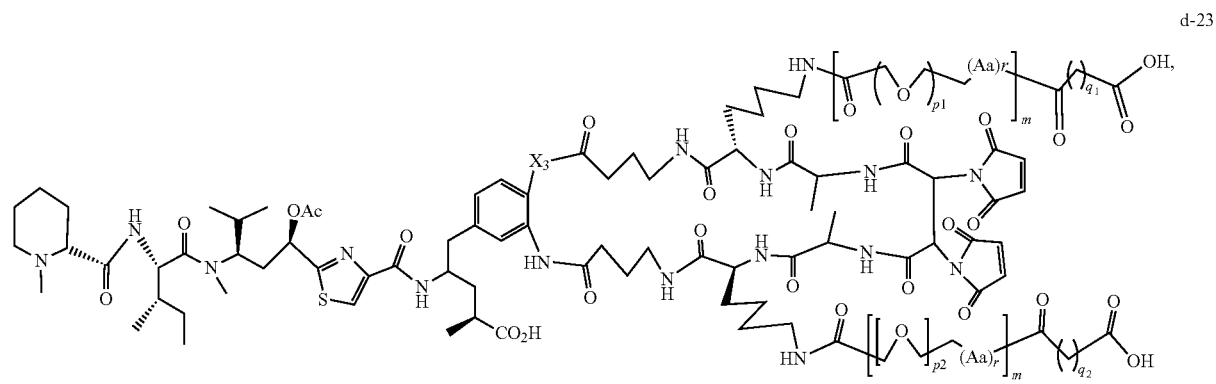
d-23

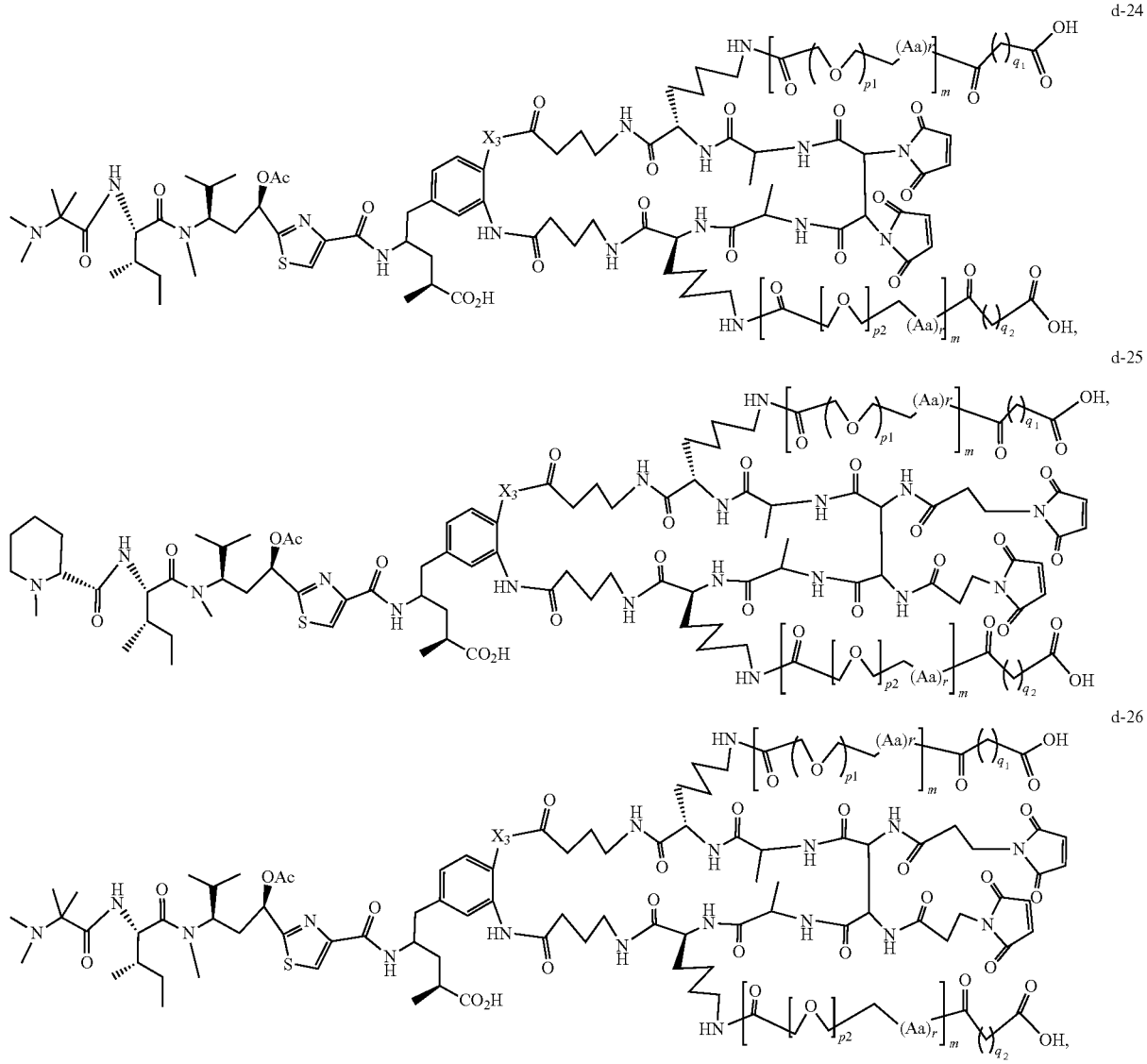

wherein $X_1$, $X_2$, $X_3$, $Z_2$, $Z_3$, p, $p_1$, $p_2$, $p_3$, $q_1$, $q_2$, $Lv_3$, $(Aa)_r$, $R_{25}$, $R_{25'}$, and m are described above.

The present invention further relates to a method of making a cell-binding molecule-tubulysin analog conjugate of Formula (I) and Formula (III) as well the application of the conjugates of Formula (I) and Formula (I).

A cell-binding agent/molecule, T, can be any kind presently known, or that become known, of a molecule that binds to, complexes with, or reacts with a moiety of a cell population sought to be therapeutically or otherwise biologically modified. Preferably the cell-binding agent/molecule is an immunotherapeutic protein, an antibody, a single chain antibody; an antibody fragment that binds to the target cell; a monoclonal antibody; a single chain monoclonal antibody; or a monoclonal antibody fragment that binds the target cell; a chimeric antibody; a chimeric antibody fragment that binds to the target cell; a domain antibody; a domain antibody fragment that binds to the target cell; adnectins that mimic antibodies; DARPins; a lymphokine; a hormone; a vitamin; a growth factor; a colony stimulating factor; or a nutrient-transport molecule (a transferrin); a binding peptides having over four aminoacids, or protein, or antibody, or small cell-binding molecule or ligand attached on albumin, polymers, dendrimers, liposomes, nanoparticles, vesicles, or (viral) capsids;

Preferably $Lv_1$ and $Lv_2$ react to pairs of thiols of a cell-binding agent/molecule. The thiols are preferably pairs of sulfur atoms reduced from the inter chain disulfide bonds of the cell-binding agent by a reducing agent selected from dithiothreitol (DTT), dithioerythritol (DTE), L-glutathione (GSH), tris (2-carboxyethyl) phosphine (TCEP), 2-mercaptoethylamine (13-MEA), or/and beta mercaptoethanol (13-ME, 2-ME);

The Preparation of the Conjugates of a Tubulysin Analog to a Cell Binding Molecules Via a Side Chain-Linkage The preparation of the conjugates of a tubulysin analog to a cell binding molecules of the present invention and the synthetic routes to produce the conjugates via side chain-linkage are shown in FIGS. 1-51.

The conjugates of Formula (I) and (III) can be prepared through the intermediate compounds of Formula (IV) and (V) respectively. In general, tubulysin analogs of Formula (IV) and (V) are synthesized to have the function groups of Lv1 and Lv2 that can be readily reacted to a cell-binding molecule or a modified cell-binding molecule. The synthesis of tubulysin analogs of Formula (IV) and (V) and some preparations of Formula (I) and (III) are structurally shown in the FIGS. 1-51.

To synthesize the conjugate of Formula (I), in general, a function group $Lv_1$ on Formula (IV) reacts one, two or more residues of a cell binding molecule at 0-60° C., pH 5-9 aqueous media with or without addition of 0-30% of water mixable (miscible) organic solvents, such as DMA, DMF, ethanol, methanol, acetone, acetonitrile, THF, isopropanol, dioxane, propylene glycol, or ethylene diol, following by dialysis or chromatographic purification to form a conjugate compound of Formula (I). Some of the residue (reacting group for conjugation) of the cell-binding molecule can be obtained through protein engineering.

The conjugates of the Formula (III) can also be obtained through the reaction of the function group $Lv_1$ and $Lv_2$ of linkers of the Formula (V) to two or more residues of a cell binding molecule, preferably a pair of free thiols generated through reduction of disulfide bonds of the cell-binding molecule at 0-60° C., pH 5-9 aqueous media with or without addition of 0-30% of water mixable (miscible) organic solvents, to form the conjugate molecule. The pairs of thiols are preferred pairs of disulfide bonds reduced from the inter chain disulfide bonds of the cell-binding agent by a reducing agent which can selected from dithiothreitol (DTT), dithioerythritol (DTE), L-glutathione (GSH), tris (2-carboxyethyl) phosphine (TCEP), 2-mercaptoethylamine (β-MEA), or/and beta mercaptoethanol (β-ME, 2-ME) at pH4-9 aqueous media with or without addition of 0-30% of water mixable (miscible) organic solvents.

The reactive groups of $Lv_1$ and $Lv_2$ on Formula (IV) and Formula (V), which can be independently disulfide, thiol, thioester, maleimido, halogen substituted maleimidoes, haloacetyl, azide, 1-yne, ketone, aldehyde, alkoxyamino, triflate, carbonylimidazole, tosylate, mesylate, 2-ethyl-5-phenylisoxazolium-3'-sulfonate, or carboxyl acid esters of nitrophenol, N-hydroxysuccinimide (NHS), phenol; dinitrophenol, pentafluorophenol, tetrafluorophenol, difluorophenol, monofluorophenol, pentachlorophenol, dichlorophenol, tetrachlorophenol, 1-hydroxybenzotriazole, anhydrides, or hydrazide groups, or other acid ester derivatives, can react to one, two or more groups on a cell-binding molecule/agent, simultaneously or sequentially at 0-60° C., pH 4-9.5 aqueous media with or without addition of 0-30% of water mixable (miscible) organic solvents, to yield a conjugate of the Formula (I) and Formula (III), after column purification or dialysis. The reactive groups of $Lv_1$ and $Lv_2$ on Formula (IV) and Formula (V) react to the modified cell-binding molecule in different ways accordingly. For example, a linkage containing disulfide bonds in a cell-binding agent-tubulysin analog conjugate of Formula (I) is achieved by a disulfide exchange between the disulfide bond in the modified cell-binding agent and $Lv_1$ and $Lv_2$ having a free thiol group, or by a disulfide exchange between a free thiol group in the modified cell-binding agent and a disulfide bond on $Lv_1$ and/or $Lv_2$. In order to swift the disulfide exchange reaction, the disulfide group normally are a group of disulfanylpyridine, di sulfanyl-nitropyridine, disulfanyl-nitrobenzene, disulfanyl-nitrobenzoic acid, or disulfanyl-dinitrobenzene, etc. A linkage containing thioether bonds in the conjugates of Formula (I) and Formula (III) is achieved by reaction of the maleimido or haloacetyl or ethylsulfonyl either on a modified cell-binding agent or a tubulysin analog of Formula (IV) and Formula (V) to a free thiol group on a tubulysin analog of Formula (IV) and Formula (V) or on a modified cell-binding agent respectively; A linkage containing a bond of an acid labile hydrazone in the conjugates can be achieved by reaction of a carbonyl group of the drug of Formula (IV) and Formula (V) or of cell-binding molecule with the hydrazide moiety on a modified cell-binding molecule or on the drug of Formula (IV) and Formula (V) accordingly, by methods known in the art (see, for example, P. Hamann et al., Cancer Res. 53, 3336-34, 1993; B. Laguzza et al., J. Med. Chem., 32; 548-55, 1959; P. Trail et al., Cancer Res., 57; 100-5, 1997); A linkage containing a bond of triazole in the conjugates can be achieved by reaction of a 1-yne group of the drug of Formula (IV) and Formula (V) or of cell-binding molecule with the azido moiety on the other counterpart accordingly, through the click chemistry (Huisgen cycloaddition) (Lutz, J-F. et al, 2008, Adv. Drug Del. Rev. 60, 958-70; Sletten, E. M. et a 2011, AccChem. Research 44, 666-76). A linkage containing a bond of oxime in the conjugates linked via oxime is achieved by reaction of a group of a ketone or aldehyde group of the drug of Formula (IV) and Formula (V) or of a cell-binding molecule with a group of oxylamine on the other counterpart respectively. A thiol-containing cell-binding molecule can react with the drug molecule linker of Formula (IV) and Formula (V) bearing a maleimido, or a haloacetyl, or an ethylsulfonyl substituent at pH 5.5~9.0 in aqueous buffer to give a thioether linkage conjugate of Formula (I) and Formula (III). A thiol-containing cell-binding molecule can undergo disulfide exchange with a drug linker of Formula (IV) and Formula (V) bearing a pyridyldithio moiety to give a conjugate having a disulfide bond linkage. A cell-binding molecule bearing a hydroxyl group or a thiol group can be reacted with a drug linker of Formula (IV) and Formula (V) bearing a halogen, particularly the alpha halide of carboxylates, in the presence of a mild base, e.g. pH 8.0~9.5, to give a modified drug bearing an ether or thiol ether linkage. A hydroxyl or an amino group on a cell-binding molecule can be condensed with a cross drug linker of Formula (IV) and Formula (V) bearing a carboxyl group, in the presence of a dehydrating agent, such as EDC or DCC, to give ester linkage. A cell-binding molecule containing an amino group can condensate with a group of carboxyl ester of NHS, imidazole, nitrophenol; N-hydroxysuccinimide (NHS); phenol; dinitrophenol; pentafluorophenol; tetrafluorophenol; difluorophenol; monofluorophenol; pentachlorophenol; triflate; imidazole; dichlorophenol; tetrachlorophenol; 1-hydroxyben-zotriazole; tosylate; mesylate; or 2-ethyl-5-phenylisoxazolium-3'-sulfonate on the drug-linker of Formula (IV) and Formula (V) to give a conjugate via amide bond linkage.

The synthetic conjugate may be purified by standard biochemical means, such as gel filtration on a Sephadex G25 or Sephacryl S300 column, adsorption chromatography, and ion exchange or by dialysis. In some cases, a small molecule as a cell-binding agent (e.g. folic acid, melanocyte stimulating hormone, EGF etc.) conjugated with a small molecular drugs can be purified by chromatography such as by HPLC, medium pressure column chromatography or ion exchange chromatography.

In order to achieve a higher yield of conjugation reaction for the Formula (I) or Formula (III) with a pair of free thiols on the cell-binding molecule, preferably on an antibody, a small percentage of water miscible organic solvents, or phase transfer agents, may be required to add to the reaction mixture. To cross-linking reagent (linker) of Formula (IV) or Formula (V) can be first dissolved in a polar organic solvent that is miscible with water, for example in different alcohols, such as methanol, ethanol, and propanol, acetone, acetonitrile, tetrahydrofuran (THF), 1,4-dioxane, dimethyl formamide (DMF), dimethyl acetamide (DMA), or dimethylsulfoxide (DMSO) at a high concentration, for example 1-500 mM. Meanwhile, the cell-binding molecule, such as antibody dissolved in an aqueous buffer pH 4-9.5, preferably pH 6-8.5, at 1-50 mg/ml concentration was treated with 0.5-20 equivalent of TCEP or DTT for 20 min to 48 hour. After the reduction, DTT can be removed by SEC chromatographic purification. TCEP can be optionally removed by SEC chromatography too, or staying in the reaction mixture for the next step reaction without further purification, but preferably TCEP is neutralized with azide compounds, such as 4-azidobenzoic acid, 4-(azidomethyl)benzoic acid, or azido-polyethylene glycolyl (e. g. 2-(2-(2-(2-azidoethoxy)ethoxy)ethoxy)ethanol). Furthermore, the reduction of antibodies or the other cell-binding agents with TCEP can be performed along with existing a drug-linker molecule of Formula (IV) or Formula (V), for which the cross-linking conjugation of the cell-binding molecules can be achieved simultaneously along with the TCEP reduction.

The aqueous solutions for the modification of cell-binding agents are buffered between pH 4 and 9, preferably between 6.0 and 7.5 and can contain any non-nucleophilic buffer salts useful for these pH ranges. Typical buffers include phosphate, acetate, triethanolamine HCl, HEPES, and MOPS buffers, which can contain additional components, such as cyclodextrins, hydroxypropyl-3-cyclodextrin, polyethylene glycols, sucrose and salts, for examples, NaCl and KCl. After the addition of the drug-linker of Formula (IV) or Formula (V) into the solution containing the reduced cell-binding molecules, the reaction mixture is incubated at a temperature of from 4° C. to 45° C., preferably at 15° C.-ambient temperature. The progress of the reaction can be monitored by measuring the decrease in the absorption at a certain UV wavelength, such as at 252 nm, or increase in the absorption at a certain UV wavelength, such as 280 nm, or the other appropriate wavelength. After the reaction is complete, isolation of the modified cell-binding agent can be performed in a routine way, using for example a gel filtration chromatography, an ion exchange chromatography, an adsorptive chromatography or column chromatography over silica gel or alumina, crystallization, preparatory thin layer chromatography, ion exchange chromatography, or HPLC.

The extent of modification can be assessed by measuring the absorbance of the nitropyridine thione, dinitropyridine dithione, pyridine thione, carboxylamidopyridine dithione and dicarboxyl-amidopyridine dithione group released via UV spectra. For the conjugation without a chromophore group, the modification or conjugation reaction can be monitored by LC-MS, preferably by HPLC-MS/MS, UPLC-QTOF mass spectrometry, or Capilary electrophoresis-mass spectrometry (CE-MS). The side chain cross-linkers described herein have diverse functional groups that can react with any cell-binding molecules, particularly a modified cell-binding molecule that possess a suitable substituent. For examples, the modified cell-binding molecules bearing an amino or hydroxyl substituent can react with drugs bearing an N-hydroxysuccinimide (NHS) ester, the modified cell-binding molecules bearing a thiol substituent can react with drugs bearing a maleimido or haloacetyl group. Additionally, the modified cell-binding molecules bearing a carbonyl (ketone or aldehyde) substituent either through protein engineering, enzymatical reaction or chemical modification can react with drugs bearing a hydrazide or an alkoxyamine. One skilled in the art can readily determine which modified drug-linker to be used based on the known reactivity of the available functional group on the modified cell-binding molecules.

Cell-Binding Agents

The cell-binding molecule, Cb, that comprises the conjugates and the modified cell-binding agents of the present invention may be of any kind presently known, or that become known, molecule that binds to, complexes with, or reacts with a moiety of a cell population sought to be therapeutically or otherwise biologically modified.

The cell binding molecules/agents include, but are not limited to, large molecular weight proteins such as, for example, antibody, an antibody-like protein, full-length antibodies (polyclonal antibodies, monoclonal antibodies, dimers, multimers, multispecific antibodies (e.g., bispecific antibodies); single chain antibodies; fragments of antibodies such as Fab, Fab', F(ab')$_2$, Fv, [Parham, J. Immunol. 131, 2895-902 (1983)], fragments produced by a Fab expression library, anti-idiotypic (anti-Id) antibodies, CDR's, diabody, triabody, tetrabody, miniantibody, small immune proteins (SIP), and epitope-binding fragments of any of the above which immuno-specifically bind to cancer cell antigens, viral antigens, microbial antigens or a protein generated by the immune system that is capable of recognizing, binding to a specific antigen or exhibiting the desired biological activity (Miller et al (2003) J. of Immunology 170: 4854-61); interferons (such as type I, II, III); peptides; lymphokines such as IL-2, IL-3, IL-4, IL-5, IL-6, IL-10, GM-CSF, interferon-gamma (IFN-γ); hormones such as insulin, TRH (thyrotropin releasing hormones), MSH (melanocyte-stimulating hormone), steroid hormones, such as androgens and estrogens, melanocyte-stimulating hormone (MSH); growth factors and colony-stimulating factors such as epidermal growth factors (EGF), granulocyte-macrophage colony-stimulating factor (GM-CSF), transforming growth factors (TGF), such as TGFα, TGFβ, insulin and insulin like growth factors (IGF-I, IGF-II) G-CSF, M-CSF and GM-CSF [Burgess, Immunology Today, 5, 155-8 (1984)]; vaccinia growth factors (VGF); fibroblast growth factors (FGFs); smaller molecular weight proteins, poly-peptide, peptides and peptide hormones, such as bombesin, gastrin, gastrin-releasing peptide; platelet-derived growth factors; interleukin and cytokines, such as interleukin-2 (IL-2), interleukin-6 (IL-6), leukemia inhibitory factors, granulocyte-macrophage colony-stimulating factor (GM-CSF); vitamins, such as folate; apoproteins and glycoproteins, such as transferrin [O'Keefe et al, 260 J. Biol. Chem. 932-7 (1985)]; sugar-binding proteins or lipoproteins, such as lectins; cell nutrient-transport molecules; and small molecular inhibitors, such as prostate-specific membrane antigen (PSMA) inhibitors and small molecular tyrosine kinase inhibitors (TKI), non-peptides or any other cell binding molecule or substance, such as bioactive polymers (Dhar, et al, Proc. Natl. Acad. Sci. 2008, 105, 17356-61); fusion proteins; kinase inhibitors; gene-targeting agents; bioactive dendrimers (Lee, et al, Nat. Biotechnol. 2005, 23, 1517-26; Almutairi, et al; Proc. Natl. Acad. Sci. 2009, 106, 685-90); nanoparticles (Liong, et al, ACS Nano, 2008, 2, 1309-12; Medarova, et al, Nat. Med. 2007, 13, 372-7; Javier, et al, Bioconjugate Chem. 2008, 19, 1309-12); liposomes (Medinai, et al, Curr. Phar. Des. 2004, 10, 2981-9); viral capsides (Flenniken, et al, Viruses Nanotechnol. 2009, 327, 71-93).

In general, a monoclonal antibody is preferred as a cell-surface binding agent if an appropriate one is available. And the antibody may be murine, human, humanized, chimeric, or derived from other species.

Production of antibodies used in the present invention involves in vivo or in vitro procedures or combinations thereof. Methods for producing polyclonal anti-receptor peptide antibodies are well-known in the art, such as in U.S. Pat. No. 4,493,795 (to Nestor et al). A monoclonal antibody is typically made by fusing myeloma cells with the spleen cells from a mouse that has been immunized with the desired antigen (Kohler, G.; Milstein, C. (1975). Nature 256: 495-7). The detailed procedures are described in "Antibodies--A Laboratory Manual", Harlow and Lane, eds., Cold Spring Harbor Laboratory Press, New York (1988), which is incorporated herein by reference. Particularly monoclonal antibodies are produced by immunizing mice, rats, hamsters or any other mammal with the antigen of interest such as the intact target cell, antigens isolated from the target cell, whole virus, attenuated whole virus, and viral proteins. Splenocytes are typically fused with myeloma cells using polyethylene glycol (PEG) 6000. Fused hybrids are selected by their sensitivity to HAT (hypoxanthine-aminopterin-thymine). Hybridomas producing a monoclonal antibody useful in practicing this invention are identified by their ability to immunoreacted specified receptors or inhibit receptor activity on target cells.

A monoclonal antibody used in the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques, such as using protein-A affinity chromatography; anion, cation, hydrophobic, or size exclusive chromatographies (particularly by affinity for the specific antigen after protein A, and sizing column chromatography); centrifugation, differential solubility, or by any other standard technique for the purification of proteins.

Media useful for the preparation of these compositions are both well-known in the art and commercially available and include synthetic culture media. An exemplary synthetic medium is Dulbecco's minimal essential medium (DMEM; Dulbecco et al., Virol. 8, 396 (1959)) supplemented with 4.5 gm/l glucose, 0-20 mM glutamine, 0-20% fetal calf serum, several ppm amount of heavy metals, such as Cu, Mn, Fe, or Zn, etc, or/and the other heavy metals added in their salt forms, and with an anti-foaming agent, such as polyoxyethylene-polyoxypropylene block copolymer.

In addition, antibody-producing cell lines can also be created by techniques other than fusion, such as direct transformation of B lymphocytes with oncogenic DNA, or transfection with an oncovirus, such as Epstein-Barr virus (EBV, also called human herpesvirus 4 (HHV-4)) or Kaposi's sarcoma-associated herpesvirus (KSHV). See, U.S. Pat. Nos. 4,341,761; 4,399,121; 4,427,783; 4,444,887; 4,451,570; 4,466,917; 4,472,500; 4,491,632; 4,493,890. A monoclonal antibody may also be produced via an anti-receptor peptide or peptides containing the carboxyl terminal as described well-known in the art. See Niman et al., Proc. Natl. Acad. Sci. USA, 80: 4949-53 (1983); Geysen et al., Proc. Natl. Acad. Sci. USA, 82: 178-82 (1985); Lei et al. Biochemistry 34(20): 6675-88, (1995). Typically, the anti-receptor peptide or a peptide analog is used either alone or conjugated to an immunogenic carrier, as the immunogen for producing anti-receptor peptide monoclonal antibodies.

There are also a number of other well-known techniques for making monoclonal antibodies as binding molecules in this invention. Particularly useful are methods of making fully human antibodies. One method is phage display technology which can be used to select a range of human antibodies binding specifically to the antigen using methods of affinity enrichment. Phage display has been thoroughly described in the literature and the construction and screening of phage display libraries are well known in the art, see, e.g., Dente et al, Gene. 148(1):7-13 (1994); Little et al, Biotechnol Adv. 12(3): 539-55 (1994); Clackson et al., Nature 352: 264-8 (1991); Huse et al., Science 246: 1275-81 (1989).

Monoclonal antibodies derived by hybridoma technique from another species than human, such as mouse, can be humanized to avoid human anti-mouse antibodies when infused into humans. Among the more common methods of humanization of antibodies are complementarity-determining region grafting and resurfacing. These methods have been extensively described, see e.g. U.S. Pat. Nos. 5,859, 205 and 6,797,492; Liu et al, Immunol Rev. 222: 9-27 (2008); Almagro et al, Front Biosci. 13: 1619-33 (2008); Lazar et al, Mol Immunol. 44(8): 1986-98 (2007); $L_1$ et al, Proc. Natl. Acad. Sci. USA. 103(10): 3557-62 (2006) each incorporated herein by reference. Fully human antibodies can also be prepared by immunizing transgenic mice, rabbits, monkeys, or other mammals, carrying large portions of the human immunoglobulin heavy and light chains, with an immunogen. Examples of such mice are: the Xenomouse. (Abgenix/Amgen), the HuMAb-Mouse (Medarex/BMS), the VelociMouse (Regeneron), see also U.S. Pat. Nos. 6,596, 541, 6,207,418, 6,150,584, 6,111,166, 6,075,181, 5,922,545, 5,661,016, 5,545,806, 5,436,149 and 5,569,825. In human therapy, murine variable regions and human constant regions can also be fused to construct called "chimeric antibodies" that are considerably less immunogenic in man than murine mAbs (Kipriyanov et al, Mol Biotechnol. 26: 39-60 (2004); Houdebine, Curr Opin Biotechnol. 13: 625-9 (2002) each incorporated herein by reference). In addition, site-directed mutagenesis in the variable region of an antibody can result in an antibody with higher affinity and specificity for its antigen (Brannigan et al, Nat Rev Mol Cell Biol. 3: 964-70, (2002)); Adams et al, J Immunol Methods. 231: 249-60 (1999)) and exchanging constant regions of a mAb can improve its ability to mediate effector functions of binding and cytotoxicity.

Antibodies immunospecific for a malignant cell antigen can also be obtained commercially or produced by any method known to one of skill in the art such as, e.g., chemical synthesis or recombinant expression techniques. The nucleotide sequence encoding antibodies immune-specific for a malignant cell antigen can be obtained commercially, e.g., from the GenBank database or a database like it, the literature publications, or by routine cloning and sequencing.

Apart from an antibody, a peptide or protein that bind/block/target or in some other way interact with the epitopes or corresponding receptors on a targeted cell can be used as a binding molecule. These peptides or proteins could be any random peptide or proteins that have an affinity for the epitopes or corresponding receptors and they don't necessarily have to be of the immune-globulin family. These peptides can be isolated by similar techniques as for phage display antibodies (Szardenings, J Recept Signal Transduct Res. 2003, 23(4): 307-49). The use of peptides from such random peptide libraries can be similar to antibodies and antibody fragments. The binding molecules of peptides or proteins may be conjugated on or linked to a large molecules or materials, such as, but is not limited, an albumin, a polymer, a liposome, a nano particle, a dendrimer, as long as such attachment permits the peptide or protein to retain its antigen binding specificity.

Examples of antibodies used for conjugation of drugs via the linkers of this prevention for treating cancer, autoimmune disease, and/or infectious disease include, but are not limited to, 3F8 (anti-GD2), Abagovomab (anti CA-125), Abciximab (anti CD41 (integrin alpha-IIb), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin (CD62 L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (a chain of IL-2 receptor), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL-23) Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedelizumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC1), Conatumumab (anti-TRAIL-R2), CR6261 (anti-Influenza A hemagglutinin), Dacetuzumab (anti-CD40), Daclizumab (Zenapax, anti-CD25 (a chain of IL-2 receptor)), Daratumumab (anti-CD38 (cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-C5), Edobacomab (anti-endotoxin), Edrecolomab (Panorex, MAb17-1A, anti-EpCAM), Efalizumab (Raptiva, anti-LFA-1 (CD11a), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD18)), Ertumaxomab (Rexomun, anti-HER2/neu, CD3), Etaracizumab (Abegrin, anti-integrin av33), Exbivirumab (anti-hepatitis B surface antigen), Fanolesomab (Neutro-Spec, anti-CD15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-α), Intetumumab (anti-CD51), Inolimomab (anti-CD25 (a chain of IL-2 receptor)), Inotuzumab (anti-CD22), Ipilimumab (anti-CD152), Iratumumab (anti-CD30 (TNFRSF8)), Keliximab (anti-CD4), Labetuzumab (CEA-Cide, anti-CEA), Lebrikizumab (anti-IL-13), Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin α$_4$), Nebacumab (anti-endotoxin), Necitumumab (anti-EGFR), Nerelimomab (anti-TNF-α), Nimotuzumab (Theracim, Theraloc, anti-EGFR), Nofetumomab, Ocrelizumab (anti-CD20), Odulimomab (Afolimomab, anti-LFA-1 (CD11a)), Ofatumumab (Arzerra, anti-CD20), Olaratumab (anti-PDGF-R α), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-HER2/neu), Pexelizumab (anti-C5), Pintumomab (anti-adenocarcinoma antigen), Priliximab (anti-CD4), Pritumumab (anti-vimentin), PRO 140 (anti-CCR$_5$), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-α), Rovelizumab (LeukArrest, anti-CD11, CD18), Ruplizumab (Antova, anti-CD154 (CD40L)), Satumomab (anti-TAG-72), Sevirumab (anti-cytomegalovirus), Sibrotuzumab (anti-FAP), Sifalimumab (anti-IFN-α), Siltuximab (anti-IL-6), Siplizumab (anti-CD2), (Smart) MI95 (anti-CD33), Solanezumab (anti-beta amyloid), Sonepcizumab (anti-sphingosine-1-phosphate), Sontuzumab (anti-episialin), Stamulumab (anti-myostatin), Sulesomab (LeukoScan, (anti-NCA-90 (granulocyte antigen), Tacatuzumab (anti-alpha-fetoprotein), Tadocizumab (anti-integrin IIbm33), Talizumab (anti-IgE), Tanezumab (anti-NGF), Taplitumomab (anti-CD19), Tefibazumab (Aurexis, (anti-clumping factor A), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4), Tigatuzumab (anti-TRAIL-R2), TNX-650 (anti-IL-13), Tocilizumab (Atlizumab, Actemra, RoActemra, (anti-IL-6 receptor), Toralizumab (anti-CD154 (CD40L)), Tositumomab (anti-CD20), Trastuzumab (Herceptin, (anti-HER2/neu), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab, (anti-integrin α$_4$β$_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin α$_5$β$_1$), Votumumab (HumaSPECT, anti-tumor antigen CTAA16.88), Zalutumumab (HuMax-EGFr, (anti-EGFR), Zanolimumab (HuMax-CD4, anti-CD4), Ziralimumab (anti-CD147 (basigin)), Zolimomab (anti-CD5), Etanercept (Enbrel®), Alefacept (Amevive®), Abatacept (Orencia®), Rilonacept (Arcalyst), 14F7 [anti-IRP-2 (Iron Regulatory Protein 2)], $14G_2a$ (anti-GD2 ganglioside, from Nat. Cancer Inst. for melanoma and solid tumors), J591 (anti-PSMA, Weill Cornell Medical School for prostate cancers), 225.28S [anti-HMW-MAA (High molecular weight-melanoma-associated antigen), Sorin Radiofarmaci S.R.L. (Milan, Italy) for melanoma], COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F [anti-TNF (tumor necrosis factor; TNFA, TNF-alpha; TNFSF2), from Abbott/Knoll for Sepsis toxic shock], MEDI-500 [T10B9, anti-CD3, TRaP3 (T cell receptor alpha/beta), complex, from MedImmune Inc for Graft-versus-host disease], RING SCAN [anti-TAG 72 (tumour associated glycoprotein 72), from Neoprobe Corp. for Breast, Colon and Rectal cancers], Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA; KS1/4 antigen; M4S; tumor antigen 17-1A; CD326, from NeoRx Corp. for Colon, Ovarian, Prostate cancers and NHL]; LymphoCide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone, NJ) and Cetuximab (ImClone, NJ).

Other antibodies as cell binding molecules/ligands include, but are not limited to, are antibodies against the following antigens: Aminopeptidase N (CD13), Annexin A1, $B7-H_3$ (CD276, various cancers), CA125 (ovarian), CA15-3 (carcinomas), CA19-9 (carcinomas), $L_6$ (carcinomas), Lewis Y (carcinomas), Lewis X (carcinomas), alpha fetoprotein (carcinomas), CA242 (colorectal), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T cell lymphoma, lung, breast, gastric, ovarian cancers, autoimmune diseases, malignant ascites), CD19 (B cell malignancies), CD20 (non-Hodgkin's lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (Metastatic melanoma, sarcoma), CD52 (leukemia), CD56 (small cell lung cancers, ovarian cancer, Merkel cell carcinoma, and the liquid tumor, multiple myeloma), CD66e (cancers), CD70 (metastatic renal cell carcinoma and non-Hodgkin lymphoma), CD74 (multiple myeloma), CD80 (lymphoma), CD98 (cancers), mucin (carcinomas), CD221 (solid tumors), CD227 (breast, ovarian cancers), CD262 (NSCLC and other cancers), CD309 (ovarian cancers), CD326 (solid tumors), CEACAM3 (colorectal, gastric cancers), CEACAM5 (carcinoembryonic antigen; CEA, CD66e) (breast, colorectal and lung cancers), DLL3 (delta-like-3), DLL4 (delta-like-4), EGFR (Epidermal Growth Factor Receptor, various cancers), CTLA4 (melanoma), CXCR4 (CD184, Heme-oncology, solid tumors), Endoglin (CD105, solid tumors), EPCAM (epithelial cell adhesion molecule, bladder, head, neck, colon, NHL prostate, and ovarian cancers), ERBB2 (Epidermal Growth Factor Receptor 2; lung, breast, prostate cancers), FCGR1 (autoimmune diseases), FOLR (folate receptor, ovarian cancers), GD2 ganglioside (cancers), G-28 (a cell surface antigen glyvolipid, melanoma), GD3 idiotype (cancers), Heat shock proteins (cancers), HER1 (lung, stomach cancers), HER2 (breast, lung and ovarian cancers), HLA-DR10 (NHL), HLA-DRB (NHL, B cell leukemia), human chorionic gonadotropin (carcinoma), IGF1R (insulin-like growth factor 1 receptor, solid tumors, blood cancers), IL-2 receptor (interleukin 2 receptor, T-cell leukemia and lymphomas), IL-6R (interleukin 6 receptor, multiple myeloma, RA, Castleman's disease, IL6 dependent tumors), Integrins (αvβ3, α5β1, α6β4, αIIβ3, α5β5, αvβ5, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 or MUC1-KLH (breast, ovarian, cervix, bronchus and gastrointestinal cancer), MUC16 (CA125) (Ovarian cancers), CEA (colorectal), gp100 (melanoma), MART1 (melanoma), MPG (melanoma), MS4A1 (membrane-spanning 4-domains subfamily A, small cell lung cancers, NHL), Nucleolin, Neu oncogene product (carcinomas), P21 (carcinomas), Paratope of anti-(N-glycolylneuraminic acid, Breast, Melanoma cancers), PLAP-like testicular alkaline phosphatase (ovarian, testicular cancers), PSMA (prostate tumors), PSA (prostate), ROBO4, TAG 72 (tumour associated glycoprotein 72, AML, gastric, colorectal, ovarian cancers), T cell transmembrane protein (cancers), Tie (CD202b), TNFRSF10B (tumor necrosis factor receptor superfamily member 10B, cancers), TNFRSF13B (tumor necrosis factor receptor superfamily member 13B, multiple myeloma, NHL, other cancers, RA and SLE), TPBG (trophoblast glycoprotein, Renal cell carcinoma), TRAIL-R1 (Tumor necrosis apoprosis Inducing ligand Receptor 1, lymphoma, NHL, colorectal, lung cancers), VCAM-1 (CD106, Melanoma), VEGF, VEGF-A, VEGF-2 (CD309) (various cancers). Some other tumor associated antigens recognized by antibodies have been reviewed (Gerber, et al, mAbs 1:3, 247-53 (2009); Novellino et al, Cancer Immunol Immunother. 54(3), 187-207 (2005). Franke, et al, Cancer Biother Radiopharm. 2000, 15, 459-76).

The cell-binding agents, more preferred antibodies, can be any agents that are able to against tumor cells, virus infected cells, microorganism infected cells, parasite infected cells, autoimmune cells, activated cells, myeloid cells, activated T-cells, B cells, or melanocytes. More specifically the cell binding agents can be any agent/molecule that is able to against any one of the following antigens or receptors: CD1, CD1a, CD1b, CD1c, CD1d, CD1e, CD2, CD3, CD3d, CD3e, CD3g, CD4, CD5, CD6, CD7, CD8, CD8a, CD8b, CD9, CD10, CD11a, CD11b, CD11c, CD11d, CD12w, CD14, CD15, CD16, CD16a, CD16b, CDw17, CD18, CD19, CD20, CD21, CD22, CD23, CD24, CD25, CD26, CD27, CD28, CD29, CD30, CD31, CD32, CD32a, CD32b, CD33, CD34, CD35, CD36, CD37, CD38, CD39, CD40, CD41, CD42, CD42a, CD42b, CD42c, CD42d, CD43, CD44, CD45, CD46, CD47, CD48, CD49b, CD49c, CD49c, CD49d, CD49f, CD50, CD51, CD52, CD53, CD54, CD55, CD56, CD57, CD58, CD59, CD60, CD60a, CD60b, CD60c, CD61, CD62E, CD62L, CD62P, CD63, CD64, CD65, CD65s, CD66, CD66a, CD66b, CD66c, CD66d, CD66e, CD66f, CD67, CD68, CD69, CD70, CD71, CD72, CD73, CD74, CD75, CD75s, CD76, CD77, CD78, CD79, CD79a, CD79b, CD80, CD81, CD82, CD83, CD84, CD85, CD85a, CD85b, CD85c, CD85d, CD85e, CD85f, CD85g, CD85g, CD85i, CD85j, CD85k, CD85m, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109 CD110, CD111, CD112, CD113, CD114, CD115, CD116, CD117, CD118, CD119, CD120, CD120a, CD120b, CD121, CD121a, CD121b, CD122, CD123, CD123a, CD124, CD125, CD126, CD127, CD128, CD129, CD130, CD131, CD132, CD133, CD134, CD135, CD136, CD137, CD138, CD139, CD140, CD140a, CD140b, CD141, CD142, CD143, CD144, CD145, CDw145, CD146, CD147, CD148, CD149, CD150, CD151, CD152, CD153, CD154, CD155, CD156, CD156a, CD156b, CD156c, CD156d, CD157, CD158, CD158a, CD158b1, CD158b2, CD158c, CD158d, CD158e1, CD158e2, CD158f2, CD158g, CD158h, CD158i, CD158j, CD158k, CD159, CD159a, CD159b, CD159c, CD160, CD161, CD162, CD163, CD164, CD165, CD166, CD167, CD167a, CD167b, CD168, CD169, CD170, CD171, CD172, CD172a, CD172b, CD172g, CD173, CD174, CD175, CD175s, CD176, CD177, CD178, CD179, CD179a, CD179b, CD180, CD181, CD182, CD183, CD184, CD185, CD186, CDw186, CD187, CD188, CD189, CD190, CD191, CD192, CD193, CD194, CD195, CD196, CD197, CD198, CD199, CDw198, CDw199, CD200, CD201, CD202, CD202 (a, b), CD203, CD203c, CD204, CD205, CD206, CD207, CD208, CD209, CD210, CDw210a, CDw210b, CD211, CD212, CD213, CD213a1, CD213a2, CD214, CD215, CD216, CD217, CD218, CD218a, CD218, CD21b9, CD220, CD221, CD222, CD223, CD224, CD225, CD226, CD227, CD228, CD229, CD230, CD231, CD232, CD233, CD234, CD235, CD235a, CD235b, CD236, CD237, CD238, CD239, CD240, CD240ce, CD240d, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD281, CD282, CD283, CD284, CD285, CD286, CD287, CD288, CD289, CD290, CD291, CD292, CD293, CD294, CD295, CD296, CD297, CD298, CD299, CD300, CD300a, CD300b, CD300c, CD301, CD302, CD303, CD304, CD305, CD306, CD307, CD307a, CD307b, CD307c, CD307d, CD307e, CD307f, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD341, CD342, CD343, CD344, CD345, CD346, CD347, CD348, CD349, CD350, CD351, CD352, CD353, CD354, CD355, CD356, CD357, CD358, CD359, CD360, CD361, CD362, CD363, CD364, CD365, CD366, CD367, CD368, CD369, CD370, CD371, CD372, CD373, CD374, CD375, CD376, CD377, CD378, CD379, CD381, CD382, CD383, CD384, CD385, CD386, CD387, CD388, CD389, CRIPTO, CR, CR1, CRGF, CRIPTO, CXCR5, LY64, TDGF1, 4-1BB, APO2, ASLG659, BMPR1B, 4-1BB, 5AC, 5T4 (Trophoblast glycoprotein, TPBG, 5T4, Wnt-Activated Inhibitory Factor 1 or WAIF1), Adenocarcinomaantigen, AGS-5, AGS-22M6, Activin receptor-like kinase 1, AFP, AKAP-4, ALK, Alpha intergrin, Alpha v beta6, Amino-peptidase N, Amyloid beta, Androgen receptor, Angiopoietin 2, Angiopoietin 3, Annexin A1, Anthrax toxin-protective antigen, Anti-transferrin receptor, AOC3 (VAP-1), B7-H3, *Bacillus* anthracisanthrax, BAFF (B-cell activating factor), B-lymphoma cell, bcr-abl, Bombesin, BORIS, $C_5$, $C_{242}$ antigen, CA125 (carbohydrate antigen 125, MUC16), CA-IX (or CAIX, carbonic anhydrase 9), CALLA, CanAg, *Canis lupus* familiaris IL31, Carbonic anhydrase IX, Cardiac myosin, CCL11 (C—C motif chemokine 11), $CCR_4$ (C—C chemokine receptor type 4, CD194), CCR5, CD3E (epsilon), CEA (Carcinoembryonic antigen), CEACAM3, CEACAM5 (carcinoembryonic antigen), CFD (Factor D), Ch4D5, Cholecystokinin 2 (CCK2R), CLDN18 (Claudin-18), Clumping factor A, CRIPTO, FCSF1R (Colony stimulating factor 1 receptor, CD115), CSF2 (colony stimulating factor 2, Granulocyte-macrophage colony-stimulating factor (GM-CSF)), CTLA4 (cytotoxic T-lymphocyte associated protein 4), CTAA16.88 tumor antigen, CXCR4 (CD184), C—X—C chemokine receptor type 4, cyclic ADP ribose hydrolase, Cyclin B1, CYP1B1, Cytomegalovirus, Cytomegalovirus glycoprotein B, Dabigatran, DLL3 (delta-like-ligand 3), DLL4 (delta-like-ligand 4), DPP4 (Dipeptidyl-peptidase 4), DR5 (Death receptor 5), *E. coli* shiga toxintype-1, *E. coli* shiga toxintype-2, ED-B, EGFL7 (EGF-like domain-containing protein 7), EGFR, EGFRII, EGFRvIII, Endoglin (CD105), Endothelin B receptor, Endotoxin, EpCAM (epithelial cell adhesion molecule), EphA2, Episialin, ERBB2 (Epidermal Growth Factor Receptor 2), ERBB3, ERG (TM-PRSS2 ETS fusion gene), *Escherichia coli*, ETV6-AML, FAP (Fibroblast activation protein alpha), FCGR1, alpha-Fetoprotein, Fibrin II, beta chain, Fibronectin extra domain-B, FOLR (folate receptor), Folate receptor alpha, Folate hydrolase, Fos-related antigen 1, F protein of respiratory syncytial virus, Frizzled receptor, Fucosyl GM1, GD2 ganglioside, G-28 (a cell surface antigen glyvolipid), GD3 idiotype, GloboH, Glypican 3, N-glycolylneuraminic acid, GM3, GMCSF receptor α-chain, Growth differentiation factor 8, GP100, GPNMB (Transmembrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influeza hemagglutinin, IgE, Fc region, IGHE, IL-1, IL-2 receptor (interleukin 2 receptor), IL-4, IL-5, IL-6, IL-6R (interleukin 6 receptor), IL-9, IL-10, IL-12, IL-13, IL-17, IL-17A, IL-20, IL-22, IL-23, IL31RA, ILGF2 (Insulin-like growth factor 2), Integrins (α4, $α_{IIb}β_3$, αvβ3, $α_4β_7$, α5β1, α6β4, α7β7, αIIβ3, α5β5, αvβ5), Interferon gamma-induced protein, ITGA2, ITGB2, KIR2D, LCK, Le, Legumain, Lewis-Y antigen, LFA-1(Lymphocyte function-associated antigen 1, CD11a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MART1, MCP-1, MIF (Macrophage migration inhibitory factor, or glycosylation-inhibiting factor (GIF)), MS4A1 (membrane-spanning 4-domains subfamily A member 1), MSLN (mesothelin), MUC1(Mucin 1, cell surface associated (MUC1) or polymorphic epithelial mucin (PEM)), MUC1-KLH, MUC16 (CA125), MCP1(monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY—BR-1, NY-ESO-1, OX-40, OxLDL (Oxidized low-density lipoprotein), OY-TES1, P21, p53 nonmutant, P97, Page4, PAP, Paratope of anti-(N-glycolylneuraminic acid), PAX3, PAX5, PCSK9, PDCD1 (PD-1, Programmed cell death protein 1, CD279), PDGF-Ra (Alpha-type platelet-derived growth factor receptor), PDGFR-β, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidylserine), Prostatic carcinoma cells, *Pseudomonas aeruginosa*, PSMA, PSA, PSCA, Rabies virus glycoprotein, RHD (Rh polypeptide 1 (RhPI), CD240), Rhesus factor, RANKL, RhoC, Ras mutant, RGS5, ROBO4, Respiratory syncytial virus, RON, Sarcoma translocation breakpoints, SART3, Sclerostin, SLAMF7 (SLAM family member 7), Selectin P, SDC1 (Syndecan 1), sLe(a), Somatomedin C, SIP (Sphingosine-1-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF13B (tumor necrosis factor receptor superfamily member 13B), TPBG (trophoblast glycoprotein), TRAIL-$R_1$ (Tumor necrosis aproprosis Inducing ligand Receptor 1), TRAILR2 (Death receptor 5 (DR5)), tumor-associated calcium signal transducer 2, tumor specific glycosylation ofMUC1, TWEAK receptor, TYRP1 (glycoprotein 75), TROP-2, TRP-2, Tyrosinase, VCAM-1 (CD106), VEGF, VEGF-A, VEGF-2 (CD309), VEGFR-1, VEGFR2, or vimentin, WT1, XAGE 1, or cells expressing any insulin growth factor receptors, or any epidermal growth factor receptors.

In another specific embodiment, the cell-binding molecule can be a ligand or a receptor agonist selected from: folate derivatives (binding to the folate receptor, a protein over-expressed in ovarian cancer and in other malignancies) (Low, P. S. et al 2008, Acc. Chem. Res. 41, 120-9); glutamic acid urea derivatives (binding to the prostate specific membrane antigen, a surface marker of prostate cancer cells) (Hillier, S. M. et al, 2009, Cancer Res. 69, 6932-40); Somatostatin (also known as growth hormone-inhibiting hormone (GHIH) or somnatotropin release-inhibiting factor (SRIF)) or somatotropin release-inhibiting hormone) and its analogues such as octreotide (Sandostatin) and lanreotide (Somatuline) (particularly for neuroendocrine tumors, GH-producing pituitary adenoma, paraganglioma, nonfunctioning pituitary adenoma, pheochromocytomas) (Ginj, M., et al, 2006, Proc. Natl. Acad. Sci. U.S.A. 103, 16436-41); Somatostatin receptor subtypes (sst1, sst2, sst3, sst4, and sst5) in GH-secreting pituitaryadenomas (Reubi J. C., Landolt, A. M. 1984 J. Clin. Endocrinol Metab 59: 1148-51; Reubi J. C., Landolt A. M. 1987 J Clin Endocrinol Metab 65: 65-73; Moyse E, et al, J Clin Endocrinol Metab 61: 98-103), gastroenteropancreatic tumors (Reubi J. C., et al, 1987 J Clin Endocrinol Metab 65: 1127-34; Reubi, J. C, et al, 1990 Cancer Res 50: 5969-77), pheochromocytomas (Epel-baum J, et al 1995 J Clin Endocrinol Metab 80:1837-44; Reubi J. C., et al, 1992 J Clin Endocrinol Metab 74: 1082-9), neuroblastomas (Prevost G, 1996 Neuroendocrinology 63:188-197; Moertel, C. L, et al 1994 Am J Clin Path 102:752-756), medullary thyroid cancers (Reubi, J. C, et al 1991 Lab Invest 64:567-573) small cell lung cancers (Sagman U, et al, 1990 Cancer 66:2129-2133), meningiomas, medulloblastomas, or gliomas (Reubi J. C., et al 1986 J Clin Endocrinol Metab 63: 433-8; Reubi J. C., et al 1987 Cancer Res 47: 5758-64; Fruhwald, M. C, et al 1999 Pediatr Res 45: 697-708), breast carcinomas (Reubi J. C., et al 1990 Int J Cancer 46: 416-20; Srkalovic G, et al 1990 J Clin Endocrinol Metab 70: 661-669), lymphomas (Reubi J. C., et al 1992, Int J Cancer50: 895-900), renal cell cancers (Reubi J. C., et al 1992, Cancer Res 52: 6074-6078), mesenchymal tumors (Reubi J. C., et al 1996 Cancer Res 56: 1922-31), prostatic (Reubi J. C., et al 1995, J. Clin. Endocrinol Metab 80: 2806-14; et al 1989, Prostate 14:191-208; Halmos G, et al J. Clin. Endo-crinol Metab 85: 2564-71), ovarian (Halmos, G, et al, 2000 J Clin Endocrinol Metab 85: 3509-12; Reubi J. C., et al 1991 Am J Pathol 138:1267-72), gastric (Reubi J. C., et al 1999, Int J Cancer 81: 376-86; Miller, G. V, 1992 Br J Cancer 66: 391-95), hepatocellular (Kouroumalis E, et al 1998 Gut 42: 442-7; Reubi J. C., et al 1999 Gut 45: 66-774) and nasopharyngeal carcinomas (Loh K. S, et al, 2002 Virchows Arch 441: 444-8); Aromatic sulfonamides (specific to carbonic anhydrase IX) (a marker of hypoxia and of renal cell carcinoma) (Neri, D., et al, Nat. Rev. Drug Discov. 2011, 10, 767-7); Pituitary adenylate cyclase activating peptides (PACAP) (PAC1) for pheochromocytomas and paragangliomas; Vasoactive intestinal peptides (VIP) and their receptor subtypes (VPAC1, VPAC2); α-Melanocyte-stimulating hormone (α-MSH) receptors; Cholecystokinin (CCK)/gastrin receptors and their receptor subtypes (CCK1 (formerly CCK-A) and CCK2; Bombesin(Pyr-Gln-Arg-Leu-Gly-Asn-Gln-Trp-Ala-Val-Gly-His-Leu-Met-$NH_2$)/gastrin-releasing peptide (GRP) and their receptor subtypes (BB1, GRP receptor subtype (BB2), the BB3 and BB4) (Ohlisson, B., et al, 1999, Scand. J. Gastroenterology 34(12): 1224-9; Weber, H. C., 2009, Cur. Opin. Endocri. Diab. Obesity 16(1): 66-71, Gonzalez N, et al, 2008, Cur. Opin. Endocri. Diab. Obesity 15(1), 58-64); Neurotensin receptors and its receptor subtypes(NTR1, NTR2, NTR3); Substance P receptors and their receptor subtypes(such as NK1 receptor for Glial tumors, Hennig I. M., et al 1995 Int. J. Cancer 61, 786-792); Neuropeptide Y (NPY) receptors and its receptor subtypes ($Y_1$-$Y_6$); Homing Peptides include RGD (Arg-Gly-Asp), NGR (Asn-Gly-Arg), the dimeric and multimeric cyclic RGD peptides (e.g. cRGDfV) (Laakkonen P, Vuorinen K. 2010, Integr Biol (Camb). 2(7-8): 326-337; Chen K, Chen X. 2011, Theranostics. 1:189-200; Garanger E, et al, Anti-Cancer Agents Med Chem. 7 (5): 552-558; Kerr, J. S. et al, Anticancer Research, 19(2A), 959-968; Thumshim, G, et al, 2003 Chem. Eur. J. 9, 2717-2725), and TAASGVRSMH or LTLRWVGLMS (chondroitin sulfate proteoglycan NG2 receptor) and F3 peptides (31 amino acid peptide that binds to cell surface-expressed nucleolin receptor) (Zitzmann, S., 2002 Cancer Res., 62, 18, pp. 5139-5143, Temminga, K., 2005, Drug Resistance Updates, 8, 381-402; P. Laakkonen and K. Vuorinen, 2010 Integrative Biol, 2(7-8), 326-337; M. A. Burg, 1999 Cancer Res., 59(12), 2869-2874; K. Porkka, et al 2002, Proc. Nat. Acad. Sci. USA 99(11), 7444-9); Cell Penetrating Peptides (CPPs) (Nakase I, et al, 2012, J. Control Release. 159(2), 181-188); Peptide Hormones, such as luteinizing hormone-releasing hormone (LHRH) agonists and antagonists, and gonadotropin-releasing hormone (GnRIH) agonist, acts by targeting follicle stimulating hormone (FSH) and luteinising hormone (LH), as well as testosterone production, e.g. buserelin (Pyr-His-Trp-Ser-Tyr-D-Ser(OtBu)-Leu-Arg-Pro-NHEt), Gonadorelin (Pyr-His-Trp-Ser-Tyr-Gly-Leu-Arg-Pro-Gly-$NH_2$), Goserelin (Pyr-His-Trp-Ser-Tyr-D-Ser(OtBu)-Leu-Arg-Pro-AzGly-$NH_2$), Histrelin (Pyr-His-Trp-Ser-Tyr-D-His(N-benzyl)-Leu-Arg-Pro-NHEt), leuprolide (Pyr-His-Trp-Ser- Tyr-D-Leu-Leu-Arg-Pro-NHEt), Nafarelin (Pyr-His-Trp-Ser-Tyr-2Nal-Leu-Arg-Pro-Gly-NH$_2$), Triptorelin (Pyr-His-Trp-Ser-Tyr-D-Trp-Leu-Arg-Pro-Gly-NH$_2$), Nafarelin, Deslorelin, Abarelix (Ac-D-2Nal-D-4-chloroPhe-D-3-(3-pyridyl)Ala-Ser-(N-Me)Tyr-D-Asn-Leu-isopropylLys-Pro-DAla-NH$_2$), Cetrorelix (Ac-D-2Nal-D-4-chloro-Phe-D-3-(3-pyridyl)Ala-Ser-Tyr-D-Cit-Leu-Arg-Pro-D-Ala-NH$_2$), Degarelix (Ac-D-2Nal-D-4-chloroPhe-D-3-(3-pyridyl)Ala-Ser-4-aminoPhe(L-hydroorotyl)-D-4-aminoPhe(carbamoyl)-Leu-isopropylLys-Pro-D-Ala-NH$_2$), and Ganirelix (Ac-D-2Nal-D-4-chloroPhe-D-3-(3-pyridyl)Ala-Ser-Tyr-D-(N9, N10-diethyl)-homoArg-Leu-(N9, N10-diethyl)-homoArg-Pro-D-Ala-NH$_2$) (Thundimadathil, J., J. Amino Acids, 2012, 967347, doi:10.1155/2012/967347; Boccon-Gibod, L.; et al, 2011, Therapeutic Advances in Urology 3(3): 127-140; Debruyne, F., 2006, Future Oncology, 2(6), 677-696; Schally A. V; Nagy, A. 1999 Eur J Endocrinol 141:1-14; Koppan M, et al 1999 Prostate 38:151-158); and Pattern Recognition Receptors (PRRs), such as Toll-like receptors (TLRs), C-type lectins and Nodlike Receptors (NLRs) (Fukata, M., et al, 2009, Semin. Immunol. 21, 242-253; Maisonneuve, C., et al, 2014, Proc. Natl. Acad. Sci. U.S.A 111, 1-6; Botos, I., et al, 2011, Structure 19, 447-459; Means, T. K., et al, 2000, Life Sci. 68, 241-258) that range in size from small molecules (imiquimod, guanisine and adenosine analogs) tolarge and complex biomacromolecules such as lipopolysaccharide (LPS), nucleic acids (CpG DNA, polyI:C) and lipopeptides (Pam3CSK4) (Kasturi, S. P., et al, 2011, Nature 470, 543-547; Lane, T., 2001, J. R. Soc. Med. 94, 316; Hotz, C., and Bourquin, C., 2012, Oncoimmunology 1, 227-228; Dudek, A. Z., et al, 2007, Clin. Cancer Res. 13, 7119-25); Calcitonin receptors which is a 32-amino-acid neuropeptide involved in the regulation of calcium levels largely through its effects on osteoclasts and on the kidney (Zaidi M, et al, 1990 Crit Rev Clin Lab Sci 28, 109-174; Gorn, A. H., et al 1995 J Clin Invest 95:2680-91); And integrin receptors and their receptor subtypes (such as $\alpha v\beta_1$, $\alpha v\beta_3$, $\alpha v\beta_5$, $\alpha v\beta_6$, $\alpha_6\beta_4$, $\alpha_7\beta_1$, $\alpha_L\beta_2$, $\alpha_{IIb}\beta_3$, etc.) which generally play important roles in angiogenesis are expressed on the surfaces of a variety of cells, in particular, of osteoclasts, endothelial cells and tumor cells (Ruoslahti, E. et al, 1994 Cell 77, 477-8; Albelda, S. M. et al, 1990 Cancer Res., 50, 6757-64). Short peptides, GRGD-SPK and Cyclic RGD pentapeptides, such as cyclo(RGDfV) (L$_1$) and its derives [cyclo(-N(Me)R-GDfV), cyclo(R-Sar-DfV), cyclo-(RG-N(Me)D-fV), cyclo(RGD-N(Me)f-V), cyclo(RGDf-N(Me)V-)(Cilengitide)] have shown high binding affinities of the intergrin receptors (Dechantsreiter, M. A. et al, 1999 J. Med. Chem. 42, 3033-40, Goodman, S. L., et al, 2002 J. Med. Chem. 45, 1045-51).

The cell-binding molecule/ligands or cell receptor agonists can be Ig-based and non-Ig-based protein scaffold molecules. The Ig-Based scaffolds can be selected, but not limited, from Nanobody (a derivative of VHH (camelid Ig)) (Muyldermans S., 2013 Annu Rev Biochem. 82, 775-97); Domain antibodies (dAb, a derivative of VH or VL domain) (Holt, L. J, et al, 2003, Trends Biotechnol. 21, 484-90); Bispecific T cell Engager (BiTE, a bispecific diabody) (Baeuerle, P. A, et al, 2009, Curr. Opin. Mol. Ther. 11, 22-30); Dual Affinity ReTargeting (DART, a bispecific diabody) (Moore P. A. P, et al. 2011, Blood 117(17), 4542-51); Tetravalent tandem antibodies (TandAb, a dimerized bispecific diabody) (Cochlovius, B, et al. 2000, Cancer Res. 60(16):4336-4341). The Non-Ig scaffolds can be selected, but not limited, from Anticalin (a derivative of Lipocalins) (Skerra A. 2008, FEBS J., 275(11): 2677-83; Beste G, et al, 1999 Proc. Nat. Acad. USA. 96(5):1898-903; Skerra, A. 2000 Biochim Biophys Acta, 1482(1-2): 337-50; Skerra, A. 2007, Curr Opin Biotechnol. 18(4): 295-304; Skerra, A. 2008, FEBS J. 275(11):2677-83); Adnectins (10th FN3 (Fibronectin)) (Koide, A, et al, 1998 J. Mol. Biol., 284(4): 1141-51; Batori V, 2002, Protein Eng. 15(12): 1015-20; Tolcher, A. W, 2011, Clin. Cancer Res. 17(2): 363-71; Hackel, B. J, 2010, Protein Eng. Des. Sel. 23(4): 211-19); Designed Ankyrin Repeat Proteins (DARPins) (a derivative of ankrin repeat (AR) proteins) (Boersma, Y. L, et al, 2011 Curr Opin Biotechnol. 22(6): 849-57), e.g. DARPin C9, DARPin Ec4 and DARPin E69_LZ3_E01 (Winkler J, et al, 2009 Mol Cancer Ther. 8(9), 2674-83; Patricia M-K. M., et al, Clin Cancer Res. 2011; 17(1):100-10; Boersma Y. L, et al, 2011 J. Biol. Chem. 286(48), 41273-85); Avimers (a domain A/low-density lipoprotein (LDL) receptor) (Boersma Y. L, 2011 J. Biol. Chem. 286(48): 41273-41285; Silverman J, et al, 2005 Nat. Biotechnol., 23(12):1556-61).

Examples of the small molecule structures of the cell-binding molecules/ligands or cell receptor agonists of the patent application are the following: LB01 (Folate), LB02 (PMSA ligand), LB03 (PMSA ligand), LB04 (PMSA ligand), LB05 (Somatostatin), LB06 (Somatostatin), LB07 (Octreotide, a Somatostatin analog), LB08 (Lanreotide, a Somatostatin analog), LB09 (Vapreotide (Sanvar), a Somatostatin analog), LB10 (CAIX ligand), LB11 (CAIX ligand), LB12 (Gastrin releasing peptide receptor (GRPr), MBA), LB13 (luteinizing hormone-releasing hormone (LH-RH) ligand and GnRH), LB14 (luteinizing hormone-releasing hormone (LH-RH) and GnRH ligand), LB15 (GnRH antagonist, Abarelix), LB16 (cobalamin, vitamin B12 analog), LB17 (cobalamin, vitamin B12 analog), LB18 (for av33 integrin receptor, cyclic RGD pentapeptide), LB19 (hetero-bivalent peptide ligand for VEGF receptor), LB20 (Neuromedin B), LB21 (bombesin for a G-protein coupled receptor), LB22 (TLR2 for a Toll-like receptor,), LB23 (for an androgen receptor), LB24 (Cilengitide/cyclo(-RGDfV-) for an av intergrin receptor, LB23 (Fludrocortisone), LB25 (Rifabutin analog), LB26 (Rifabutin analog), LB27 (Rifabutin analog), LB28 (Fludrocortisone), LB29 (Dexamethasone), LB30 (fluticasone propionate), LB31 (Beclometasone dipropionate), LB32 (Triamcinolone acetonide), LB33 (Prednisone), LB34 (Prednisolone), LB35 (Methylprednisolone), LB36 (Betamethasone), LB37 (Irinotecan analog), LB38 (Crizotinib analog), LB39 (Bortezomib analog), LB40 (Carfilzomib analog), LB41 (Carfilzomib analog), LB42 (Leuprolide analog), LB43 (Triptorelin analog), LB44 (Clindamycin), LB45 (Liraglutide analog), LB46 (Semaglutide analog), LB47 (Retapamulin analog), LB48 (Indibulin analog), LB49 (Vinblastine analog), LB50 (Lixisenatide analog), LB51 (Osimertinib analog), LB52 (a neucleoside analog), LB53 (Erlotinib analog) and LB54 (Lapatinib analog) which are shown in the following structures:

LB01
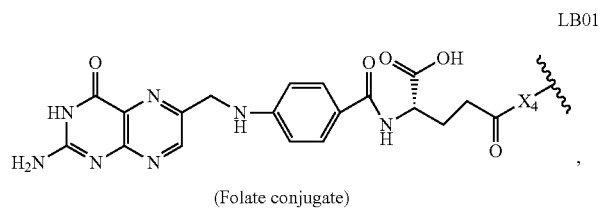
(Folate conjugate)
LB02
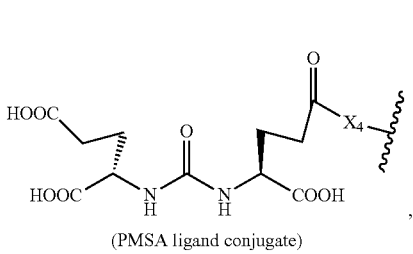
(PMSA ligand conjugate)
LB03
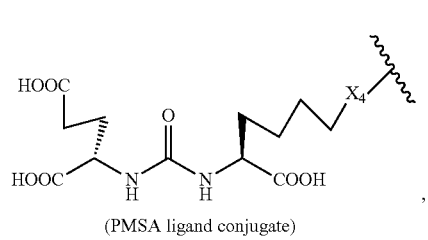
(PMSA ligand conjugate)
LB04
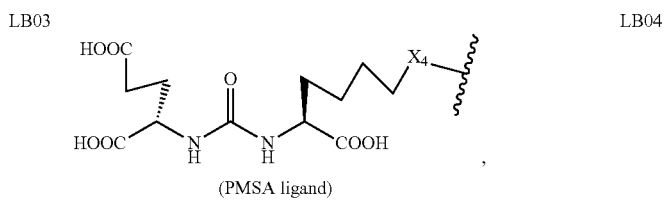
(PMSA ligand)
LB05
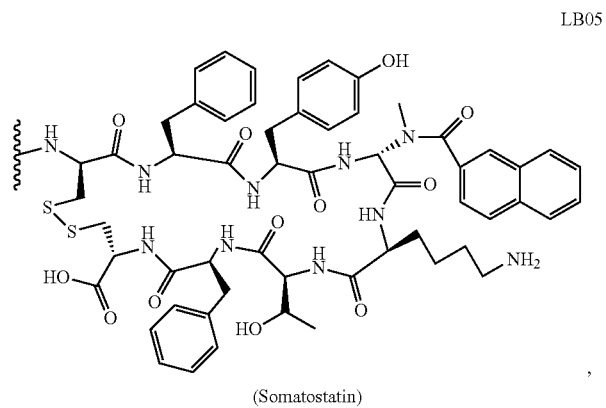
(Somatostatin)
LB06
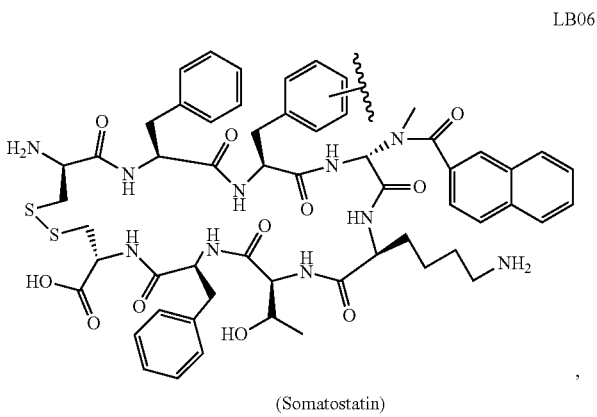
(Somatostatin)
LB07
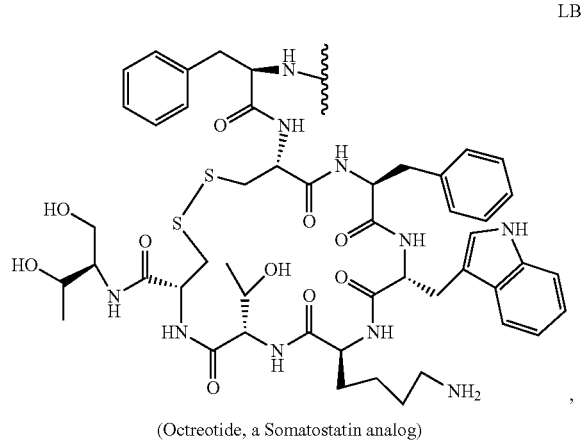
(Octreotide, a Somatostatin analog)
LB08
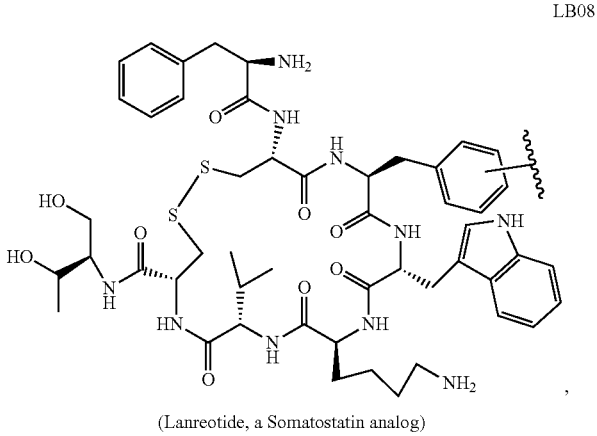
(Lanreotide, a Somatostatin analog)

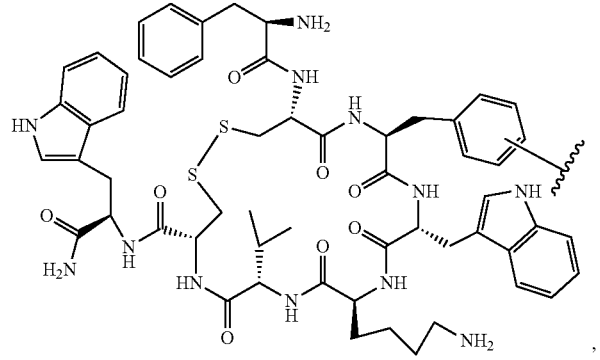
(Vapreotide (Sanvar), a Somatostatin analog)
LB09
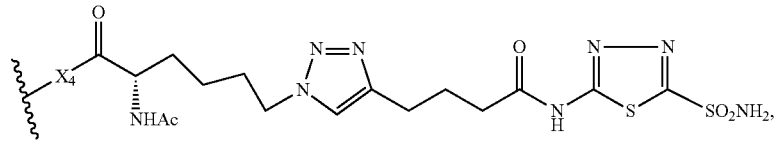
(CAIX ligand)
LB10
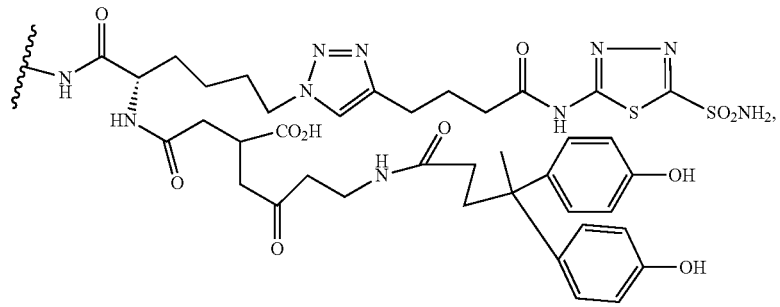
(CAIX ligand)
LB11
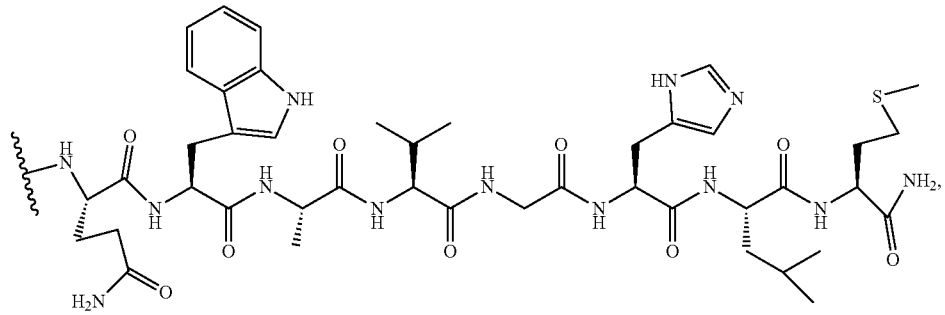
(Gastrin releasing peptide receptor (GRPr), MBA)
LB12

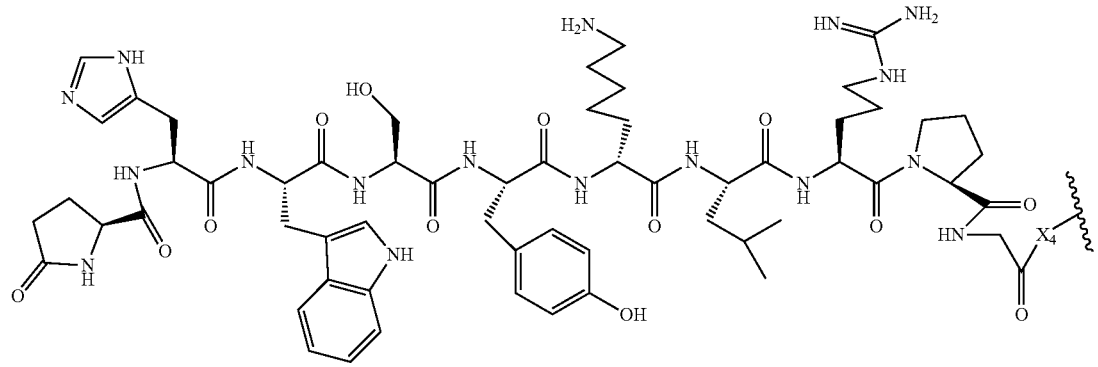
(luteinizing hormone-releasing hormone (LH-RH) ligand and GnRH)
LB13
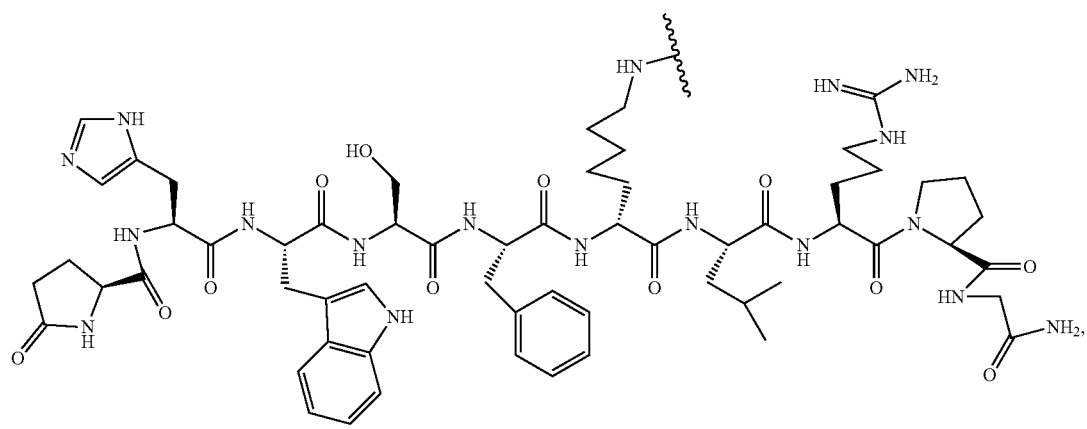
(luteinizing hormone-releasing hormone (LH-RH) and GnRH ligand)
LB14
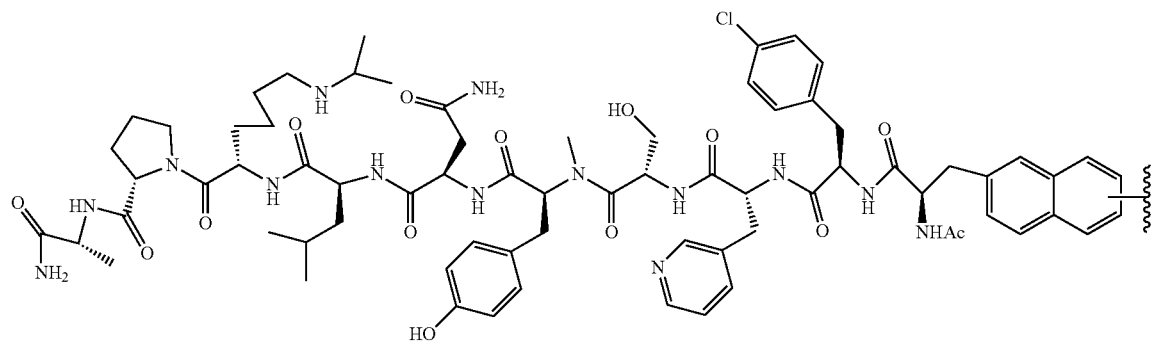
(GnRH antagonist, Abarelix)
LB15

-continued
LB16
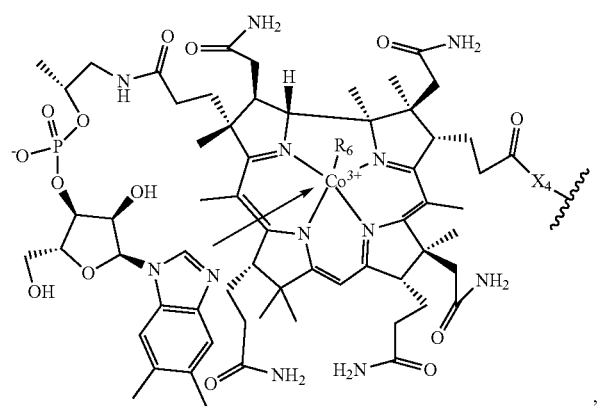
(cobalamin, vitamin B12 analog)
LB17
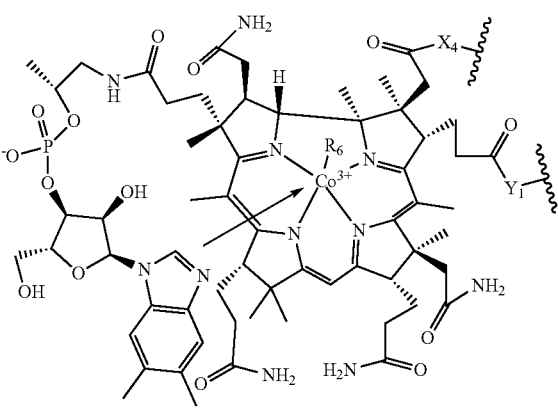
(cobalamin, vitamin B12 analog)
LB18
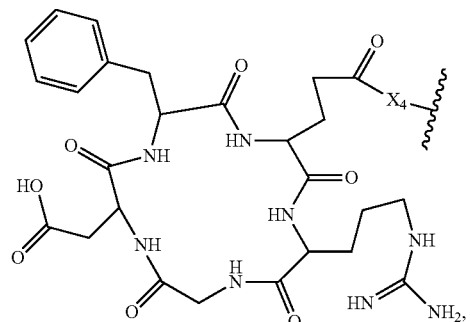
(for α$_v$β$_3$ integrin receptor, cyclic RGD pentapeptide)
LB19
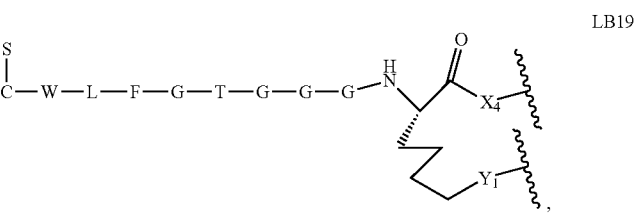
(hetero-bivalent peptide ligand conjugate for VEGF receptor)
LB20
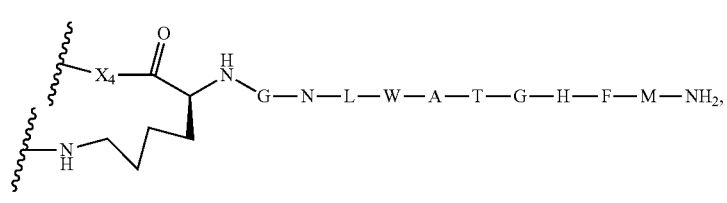
(Neuromedin B)
LB21
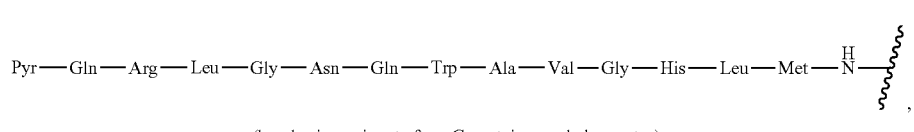
(bombesin conjugate for a G-protein coupled receptor)
LB22
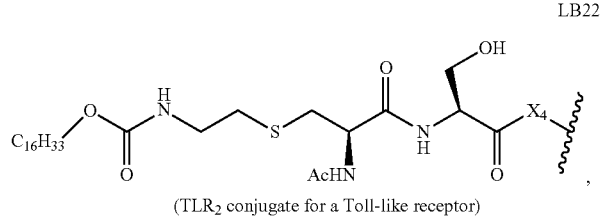
(TLR$_2$ conjugate for a Toll-like receptor)
LB23
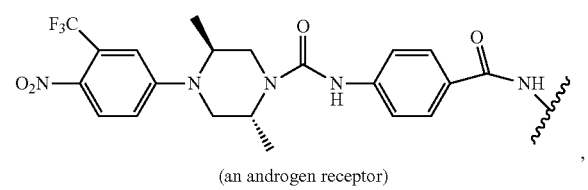
(an androgen receptor)

-continued
LB24
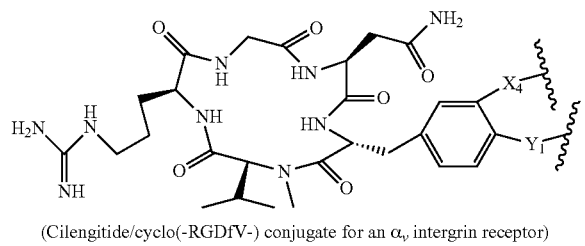
(Cilengitide/cyclo(-RGDfV-) conjugate for an α$_v$ intergrin receptor)
LB25
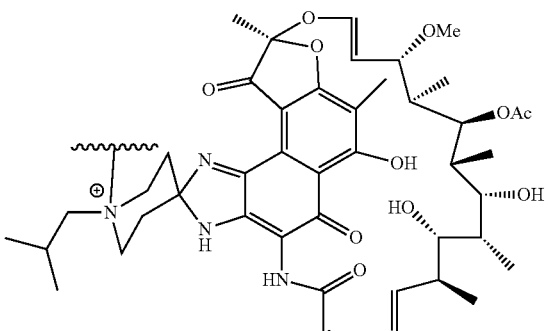
(Rifabutin analog)
LB26
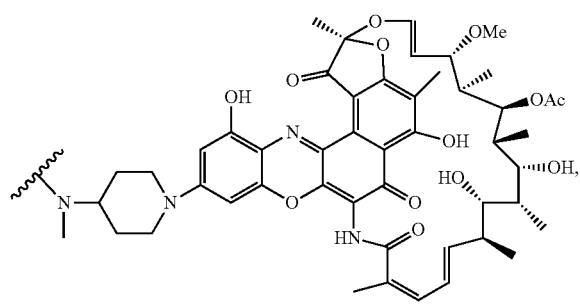
(Rifabutin analog)
LB27
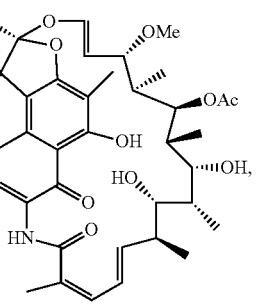
(Rifabutin analog)
LB28
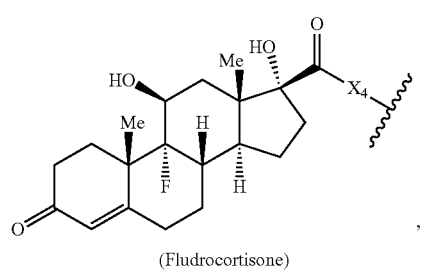
(Fludrocortisone)
LB29
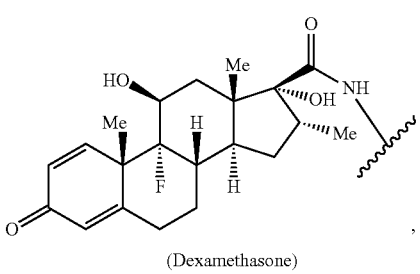
(Dexamethasone)
LB30
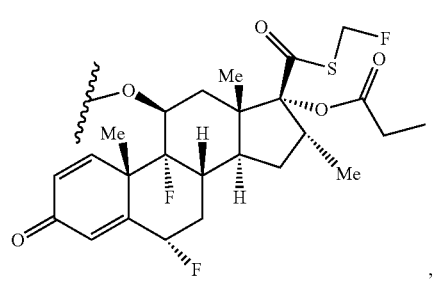
(fluticasone propionate)
LB31
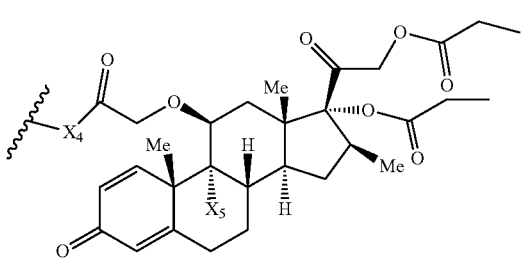
(Beclometasone dipropionate)
LB32
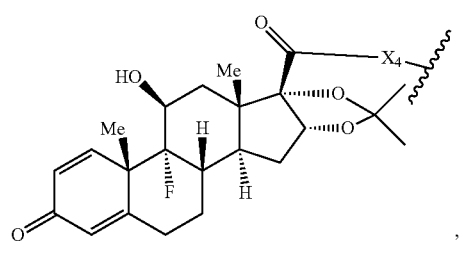
(Triamcinolone acetonide)
LB33
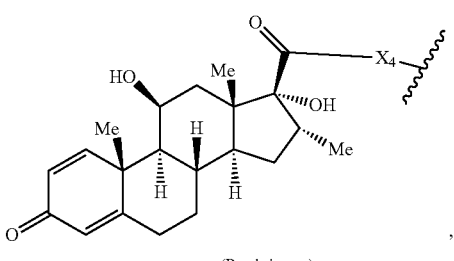
(Prednisone)

-continued
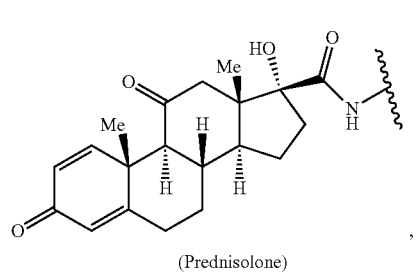
(Prednisolone)
LB34
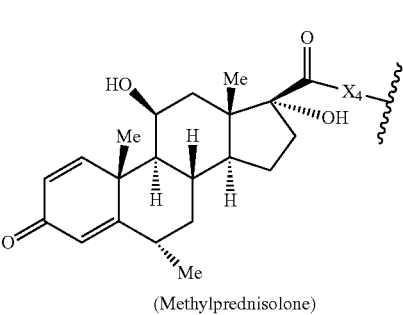
(Methylprednisolone)
LB35
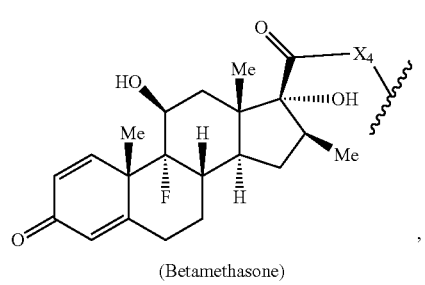
(Betamethasone)
LB36
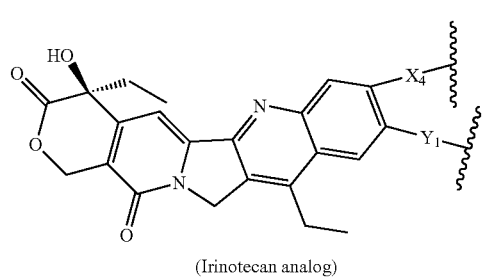
(Irinotecan analog)
LB37
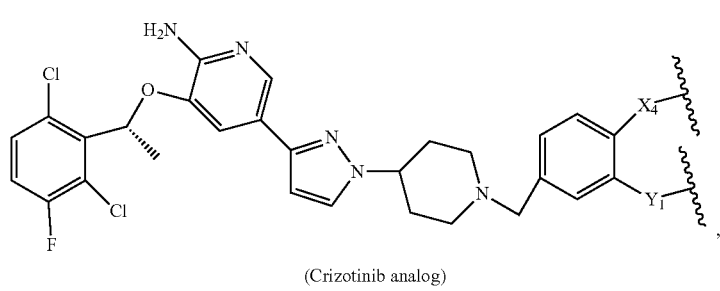
(Crizotinib analog)
LB38
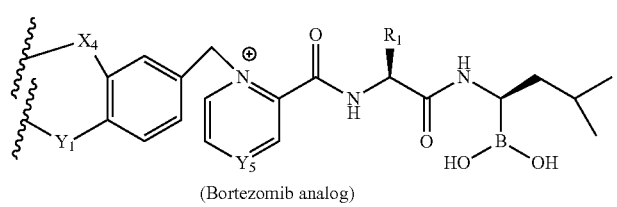
(Bortezomib analog)
LB39
, wherein $Y_5$, is N, CH, C(Cl), C(CH$_3$), or C(COOR$_1$); R$_1$ is H, C$_1$-C$_6$ Alkyl, C$_3$-C$_8$ Ar;
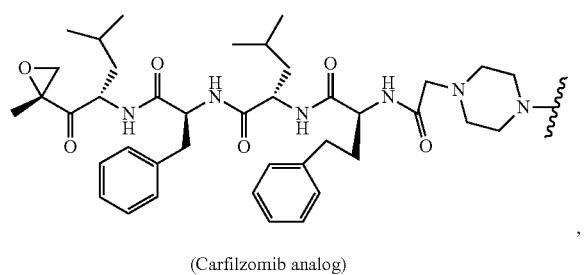
(Carfilzomib analog)
LB40
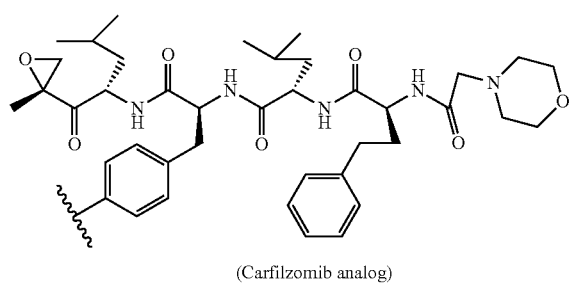
(Carfilzomib analog)
LB41

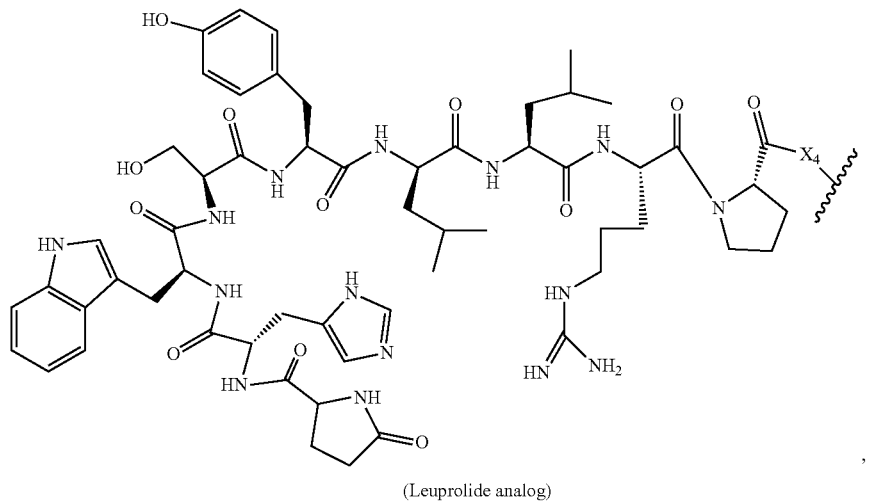
(Leuprolide analog) LB42
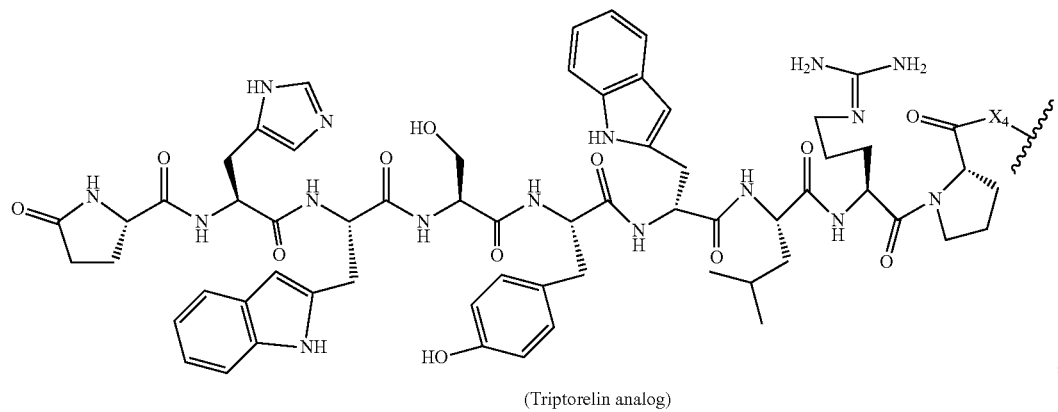
(Triptorelin analog) LB43
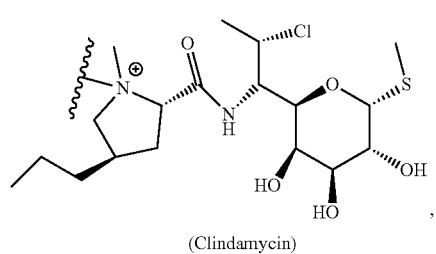
(Clindamycin) LB44
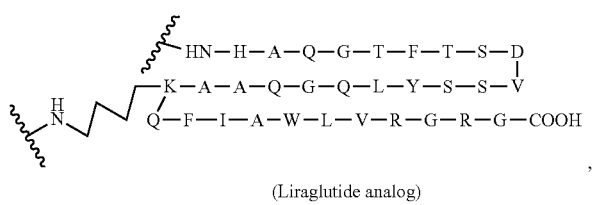
(Liraglutide analog) LB45
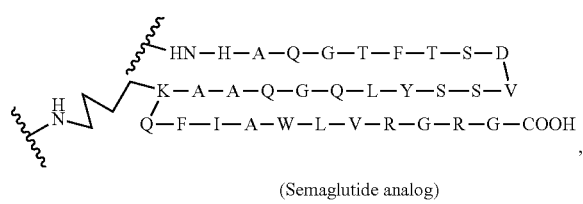
(Semaglutide analog) LB46
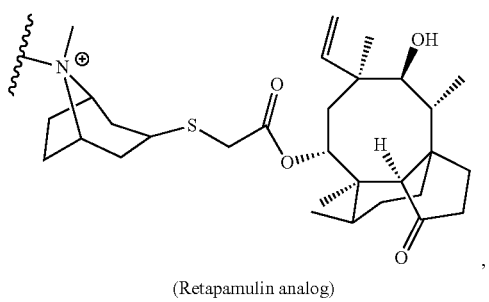
(Retapamulin analog) LB47

-continued

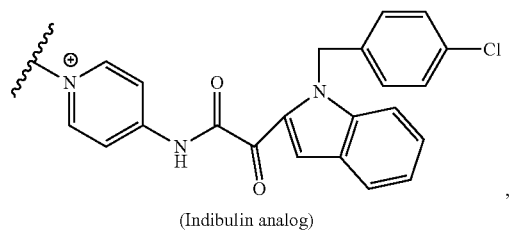
(Indibulin analog) LB48

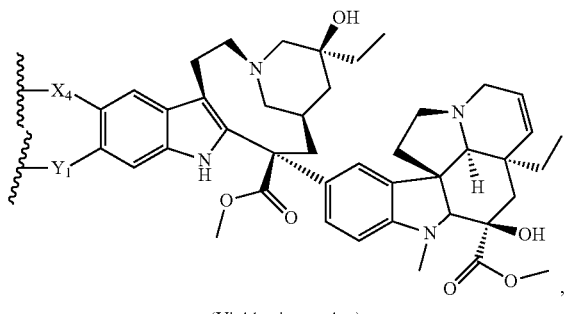
(Vinblastine analog) LB49

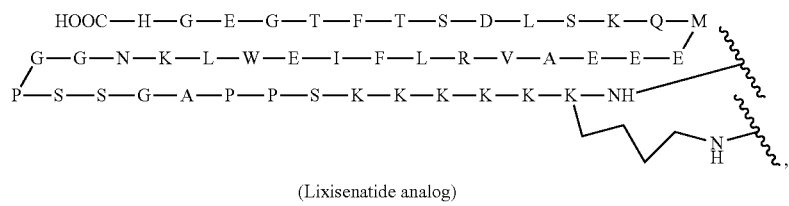
(Lixisenatide analog) LB50

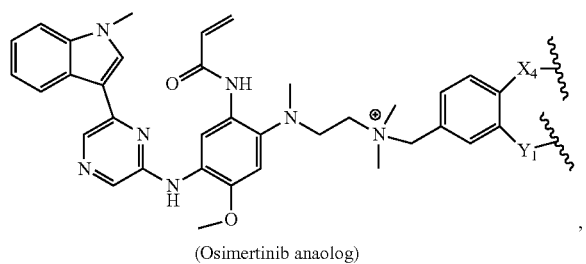
(Osimertinib anaolog) LB51

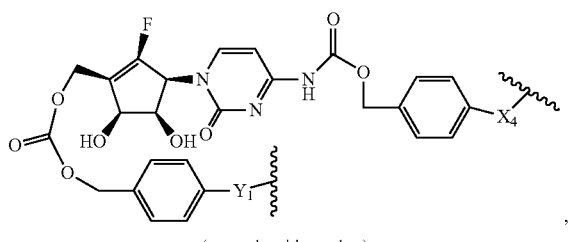
(a neucleoside analog) LB52

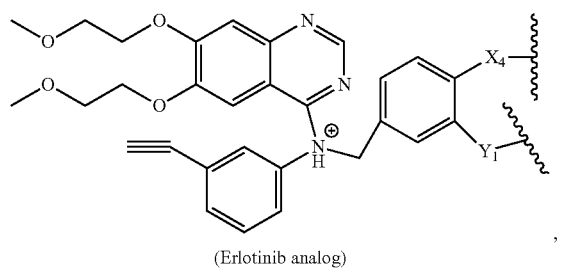
(Erlotinib analog) LB53

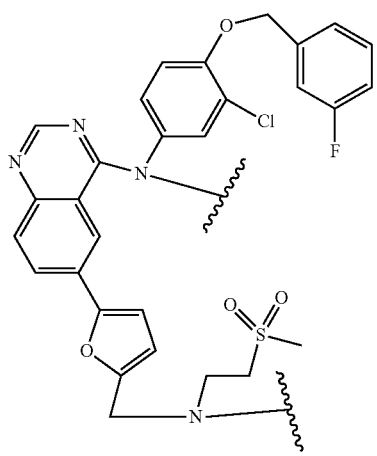
(Lapatinib analog) LB54 wherein " ~~~ " is the site to link the side chain linker of the present patent; $X_4$, and $Y_1$ are independently O, NH, NHNH, $NR_1$, S, C(O)O, C(O)NH, OC(O)NH, OC(O)O, NHC(O)NH, NHC(O)S, OC(O)N($R_1$), N($R_1$)C(O)N($R_1$), $CH_2$, C(O)NHNHC(O) and C(O)$NR_1$; $X_1$ is H, $CH_2$, OH, O, C(O), C(O)NH, C(O)N($R_1$), $R_1$, $NHR_1$, $NR_1$, C(O)$R_1$ or C(O)O; $X_5$ is H, $CH_3$, F, or $C_1$; $M_1$ and $M_2$ are independently H, Na, K, Ca, Mg, $NH_4$, N($R_1R_2R_3R_4$); $R_1$, $R_2$, $R_3$ and $R_4$ are defined in Formula (I);

Application of the Conjugate

In a specific embodiment, the cell-binding ligand-drug conjugates via the side chain linkers of this invention are used for the targeted treatment of cancers. The targeted cancers include, but are not limited, Adrenocortical Carcinoma, Anal Cancer, Bladder Cancer, Brain Tumor (Adult, Brain Stem Glioma, Childhood, Cerebellar Astrocytoma, Cerebral Astrocytoma, Ependymoma, Medulloblastoma, Supratentorial Primitive Neuroectodermal and Pineal Tumors, Visual Pathway and Hypothalamic Glioma), Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Eye Cancer, Intraocular Melanoma, Gallbladder Cancer, Gastric Cancer (Stomach), Germ Cell Tumor, Extragonadal, Gestational Trophoblastic Tumor, Head and Neck Cancer, Hypopharyngeal Cancer, Islet Cell Carcinoma, Kidney Cancer (renal cell cancer), Laryngeal Cancer, Leukemia (Acute Lymphoblastic, Acute Myeloid, Chronic Lymphocytic, Chronic Myelogenous, Hairy Cell), Lip and Oral Cavity Cancer, Liver Cancer, Lung Cancer (Non-Small Cell, Small Cell, Lymphoma (AIDS-Related, Central Nervous System, Cutaneous T-Cell, Hodgkin's Disease, Non-Hodgkin's Disease, Malignant Mesothelioma, Melanoma, Merkel Cell Carcinoma, Metasatic Squamous Neck Cancer with Occult Primary, Multiple Myeloma, and Other Plasma Cell Neoplasms, Mycosis Fungoides, Myelodysplastic Syndrome, Myeloproliferative Disorders, Nasopharyngeal Cancer, Neuroblastoma, Oral Cancer, Oropharyngeal Cancer, Osteosarcoma, Ovarian Cancer (Epithelial, Germ Cell Tumor, Low Malignant Potential Tumor), Pancreatic Cancer (Exocrine, Islet Cell Carcinoma), Paranasal Sinus and Nasal Cavity Cancer, Parathyroid Cancer, Penile Cancer, Pheochromocytoma Cancer, Pituitary Cancer, Plasma Cell Neoplasm, Prostate Cancer Rhabdomyosarcoma, Rectal Cancer, Renal Cell Cancer (kidney cancer), Renal Pelvis and Ureter (Transitional Cell), Salivary Gland Cancer, Sezary Syndrome, Skin Cancer, Skin Cancer (Cutaneous T-Cell Lymphoma, Kaposi's Sarcoma, Melanoma), Small Intestine Cancer, Soft Tissue Sarcoma, Stomach Cancer, Testicular Cancer, Thymoma (Malignant), Thyroid Cancer, Urethral Cancer, Uterine Cancer (Sarcoma), Unusual Cancer of Childhood, Vaginal Cancer, Vulvar Cancer, Wilms' Tumor.

In another specific embodiment, the cell-binding-drug conjugates of this invention are used in accordance with the compositions and methods for the treatment or prevention of an autoimmune disease. The autoimmune diseases include, but are not limited, Achlorhydra Autoimmune Active Chronic Hepatitis, Acute Disseminated Encephalomyelitis, Acute hemorrhagic leukoencephalitis, Addison's Disease, Agammaglobulinemia, Alopecia areata, Amyotrophic Lateral Sclerosis, Ankylosing Spondylitis, Anti-GBM/TBM Nephritis, Antiphospholipid syndrome, Antisynthetase syndrome, Arthritis, Atopic allergy, Atopic Dermatitis, Autoimmune Aplastic Anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome Types I, II, & III, Autoimmune progesterone dermatitis, Autoimmune thrombocytopenic purpura, Autoimmune uveitis, Balo disease/Balo concentric sclerosis, Bechets Syndrome, Berger's disease, Bickerstaffs encephalitis, Blau syndrome, Bullous Pemphigoid, Castleman's disease, Chagas disease, Chronic Fatigue Immune Dysfunction Syndrome, Chronic inflammatory demyelinating polyneuropathy, Chronic recurrent multifocal ostomyelitis, Chronic lyme disease, Chronic obstructive pulmonary disease, Churg-Strauss syndrome, Cicatricial Pemphigoid, Coeliac Disease, Cogan syndrome, Cold agglutinin disease, Complement component 2 deficiency, Cranial arteritis, CREST syndrome, Crohns Disease (a type of idiopathic inflammatory bowel diseases), Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Dressler's syndrome, Discoid lupus erythematosus, Eczema, Endometriosis, Enthesitis-related arthritis, Eosinophilic fasciitis, Epidermolysis bullosa acquisita, Erythema nodosum, Essential mixed cryoglobulinemia, Evan's syndrome, Fibrodysplasia ossificans progressiva, Fibromyalgia, Fibromyositis, Fibrosing aveolitis, Gastritis, Gastrointestinal pemphigoid, Giant cell arteritis, Glomerulonephritis, Goodpasture's syndrome, Graves' disease, Guillain-Barre syndrome, Hashimoto's encephalitis, Hashimoto's thyroiditis, Haemolytic anaemia, Henoch-Schonlein purpura, Herpes gestationis, Hidradenitis suppurativa, Hughes syndrome (See Antiphospholipid syndrome), Hypogamma-globulinemia, Idiopathic Inflammatory Demyelinating Diseases, Idiopathic pulmonary fibrosis, Idiopathic thrombocytopenic purpura (See Autoimmune thrombocytopenic purpura), IgA nephropathy (Also Berger's disease), Inclusion body myositis, Inflammatory demyelinating polyneuopathy, Interstitial cystitis, Irritable Bowel Syndrome, Juvenile idiopathic arthritis, Juvenile rheumatoid arthritis, Kawasaki's Disease, Lambert-Eaton myasthenic syndrome, Leukocytoclastic vasculitis, Lichen planus, Lichen sclerosus, Linear IgA disease (LAD), Lou Gehrig's Disease (Also Amyotrophic lateral sclerosis), Lupoid hepatitis, Lupus erythematosus, Majeed syndrome, Meniere's disease, Microscopic polyangiitis, Miller-Fisher syndrome, Mixed Connective Tissue Disease, Morphea, Mucha-Habermann disease, Muckle-Wells syndrome, Multiple Myeloma, Multiple Sclerosis, Myasthenia gravis, Myositis, Narcolepsy, Neuromyelitis optica (Devic's Disease), Neuromyotonia, Occular cicatricial pemphigoid, Opsoclonus myoclonus syndrome, Ord thyroiditis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria, Parry Romberg syndrome, Parsonnage-Turner syndrome, Pars planitis, Pemphigus, Pemphigus vulgaris, Pernicious anaemia, Perivenous encephalomyelitis, POEMS syndrome, Polyarteritis *nodosa*, Polymyalgia rheumatica, Polymyositis, Primary biliary cirrhosis, Primary sclerosing cholangitis, Progressive inflammatory neuropathy, Psoriasis, Psoriatic Arthritis, Pyoderma gangrenosum, Pure red cell aplasia, Rasmussen's encephalitis, Raynaud phenomenon, Relapsing polychondritis, Reiter's syndrome, Restless leg syndrome, Retroperitoneal fibrosis, Rheumatoid arthritis, Rheumatoid fever, Sarcoidosis, Schizophrenia, Schmidt syndrome, Schnitzler syndrome, Scleritis, Scleroderma, Sjögren's syndrome, Spondyloarthropathy, Sticky blood syndrome, Still's Disease, Stiff person syndrome, Subacute bacterial endocarditis, Susac's syndrome, Sweet syndrome, Sydenham Chorea, Sympathetic ophthalmia, Takayasu's arteritis, Temporal arteritis (giant cell arteritis), Tolosa-Hunt syndrome, Transverse Myelitis, Ulcerative Colitis (a type of idiopathic inflammatory bowel diseases), Undifferentiated connective tissue disease, Undifferentiated spondyloarthropathy, Vasculitis, Vitiligo, Wegener's granulomatosis, Wilson's syndrome, Wiskott-Aldrich syndrome In another specific embodiment, a binding molecule used for the conjugate via the side chain-linkers of this invention for the treatment or prevention of an autoimmune disease can be, but are not limited to, anti-elastin antibody; Abys against epithelial cells antibody; Anti-Basement Membrane Collagen Type IV Protein antibody; Anti-Nuclear Antibody; Anti ds DNA; Anti ss DNA, Anti Cardiolipin Antibody IgM, IgG; anti-celiac antibody; Anti Phospholipid Antibody IgK, IgG; Anti SM Antibody; Anti Mitochondrial Antibody; Thyroid Antibody; Microsomal Antibody, T-cells antibody; Thyroglobulin Antibody, Anti SCL-70; Anti-Jo; Anti-U.sub.1RNP; Anti-La/SSB; Anti SSA; Anti SSB; Anti Perital Cells Antibody; Anti Histones; Anti RNP; C-ANCA; P-ANCA; Anti centromere; Anti-Fibrillarin, and Anti GBM Antibody, Anti-ganglioside antibody; Anti-Desmogein 3 antibody; Anti-$p_{62}$ antibody; Anti-sp100 antibody; Anti-Mitochondrial(M2) antibody; Rheumatoid factor antibody; Anti-MCV antibody; Anti-topoisomerase antibody; Anti-neutrophil cytoplasmic(cANCA) antibody.

In certain preferred embodiments, the binding molecule for the conjugate in the present invention, can bind to both a receptor and a receptor complex expressed on an activated lymphocyte which is associated with an autoimmune disease. The receptor or receptor complex can comprise an immunoglobulin gene superfamily member (e.g. CD2, CD3, CD4, CD8, CD19, CD20, CD22, CD28, CD30, CD33, CD37, CD38, CD56, CD70, CD79, CD79b, CD90, CD125, CD137, CD138, CD147, CD152/CTLA-4, PD-1, or ICOS), a TNF receptor superfamily member (e.g. CD27, CD40, CD95/Fas, CD134/OX40, CD137/4-1BB, INF—R1, TNFR-2, RANK, TACI, BCMA, osteoprotegerin, Apo2/TRAIL-R1, TRAIL-R2, TRAIL-R3, TRAIL-R4, and APO-3), an integrin, a cytokine receptor, a chemokine receptor, a major histocompatibility protein, a lectin (C-type, S-type, or I-type), or a complement control protein.

In another specific embodiment, useful cell binding ligands that are immunospecific for a viral or a microbial antigen are humanized or human monoclonal antibodies. As used herein, the term "viral antigen" includes, but is not limited to, any viral peptide, polypeptide protein (e.g. HIV gpl20, HIV nef, RSV F glycoprotein, influenza virus neuraminidase, influenza virus hemagglutinin, HTLV tax, herpes simplex virus glycoprotein (e.g. gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacteria, fungi, pathogenic protozoa, or yeast polypeptides including, e.g., LPS and capsular polysaccharide 5/8) that is capable of eliciting an immune response. Examples of antibodies available 1 for the viral or microbial infection include, but are not limited to, Palivizumab which is a humanized anti-respiratory syncytial virus monoclonal antibody for the treatment of RSV infection; PR0542 which is a CD4 fusion antibody for the treatment of HIV infection; Ostavir which is a human antibody for the treatment of hepatitis B virus; PROTVIR which is a humanized IgG.sub. 1 antibody for the treatment of cytomegalovirus; and anti-LPS antibodies.

The cell binding molecules-drug conjugates via the side chain-linkers of this invention can be used in the treatment of infectious diseases. These infectious diseases include, but are not limited to, Acinetobacter infections, Actinomycosis, African sleeping sickness (African trypanosomiasis), AIDS (Acquired immune deficiency syndrome), Amebiasis, Anaplasmosis, Anthrax, Arcano-bacterium haemolyticum infection, Argentine hemorrhagic fever, Ascariasis, Aspergillosis, Astrovirus infection, Babesiosis, *Bacillus cereus* infection, Bacterial pneumonia, Bacterial vaginosis, Bacteroides infection, Balantidiasis, Baylisascaris infection, BK virus infection, Black piedra, *Blastocystis hominis* infection, Blastomycosis, Bolivian hemorrhagic fever, Borrelia infection, Botulism (and Infant botulism), Brazilian hemorrhagic fever, Brucellosis, Burkholderia infection, Buruli ulcer, Calicivirus infection (Norovirus and Sapovirus), Campylobacteriosis, Candidiasis (Moniliasis; Thrush), Cat-scratch disease, Cellulitis, Chagas Disease (American trypanosomiasis), Chancroid, Chickenpox, Chlamydia, *Chlamydophila pneumoniae* infection, Cholera, Chromoblastomycosis, Clonorchiasis, *Clostridium difficile* infection, Coccidioido-mycosis, Colorado tick fever, Common cold (Acute viral rhinopharyngitis; Acute coryza), Creutzfeldt-Jakob disease, Crimean-Congo hemorrhagic fever, Cryptococcosis, Cryptosporidiosis, Cutaneous larva migrans, Cyclosporiasis, Cysticercosis, Cytomegalovirus infection, Dengue fever, Dientamoebiasis, Diphtheria, Diphyllobothriasis, Dracunculiasis, Ebola hemorrhagic fever, Echinococcosis, Ehrlichiosis, Enterobiasis (Pinworm infection), Enterococcus infection, Enterovirus infection, Epidemic typhus, Erythema infectiosum (Fifth disease), Exanthem subitum, Fasciolopsiasis, Fasciolosis, Fatal familial insomnia, Filariasis, Food poisoning by *Clostridium perfringens*, Free-living amebic infection, Fusobacterium infection, Gas gangrene (Clostridial myonecrosis), Geotrichosis, Gerstmann-Straussler-Scheinker syndrome, Giardiasis, Glanders, Gnathosto-miasis, Gonorrhea, Granuloma inguinale (Donovanosis), Group A streptococcal infection, Group B streptococcal infection, *Haemophilus influenzae* infection, Hand, foot and mouth disease (HFMD), Hantavirus Pulmonary Syndrome, *Helicobacter pylori* infection, Hemolytic-uremic syndrome, Hemorrhagic fever with renal syndrome, Hepatitis A, Hepatitis B, Hepatitis C, Hepatitis D, Hepatitis E, Herpes simplex, Histoplasmosis, Hookworm infection, *Human bocavirus* infection, Human ewingii ehrlichiosis, Human granulocytic anaplasmosis, *Human metapneumovirus* infection, Human monocytic ehrlichiosis, Human papillomavirus infection, Human parainfluenza virus infection, Hymenolepiasis, Epstein-Barr Virus Infectious Mononucleosis (Mono), Influenza, Isosporiasis, Kawasaki disease, Keratitis, *Kingella kingae* infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever, Measles, Melioidosis (Whitmore's disease), Meningitis, Meningococcal disease, Metagonimiasis, Microsporidiosis, Molluscum contagiosum, Mumps, Murine typhus (Endemic typhus), Mycoplasma pneumonia, Mycetoma, Myiasis, Neonatal conjunctivitis (Ophthalmia neonatorum), (New) Variant Creutzfeldt-Jakob disease (vCJD, nvCJD), Nocardiosis, Onchocerciasis (River blindness), Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease, Pertussis (Whooping cough), Plague, Pneumococcal infection, *Pneumocystis pneumonia*, Pneumonia, Poliomyelitis, Prevotella infection, Primary amoebic meningoencephalitis, Progressive multifocal leukoencephalopathy, Psittacosis, Q fever, Rabies, Rat-bite fever, Respiratory syncytial virus infection, Rhinosporidiosis, Rhinovirus infection, Rickettsial infection, Rickettsial-pox, Rift Valley fever, Rocky mountain spotted fever, Rotavirus infection, Rubella, Salmonellosis, SARS (Severe Acute Respiratory Syndrome), Scabies, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea versicolor (Pityriasis versicolor), Toxocariasis (Ocular Larva Migrans), Toxocariasis (Visceral Larva Migrans), Toxoplasmosis, Trichinellosis, Trichomoniasis, Trichuriasis (Whipworm infection), Tuberculosis, Tularemia, *Ureaplasma urealyticum* infection, Venezuelan equine encephalitis, Venezuelan hemorrhagic fever, Viral pneumonia, West Nile Fever, White piedra (Tinea blanca), Yersinia pseudotuber-culosis infection, Yersiniosis, Yellow fever, Zygomycosis.

The cell binding molecule, which is more preferred to be an antibody described in this patent that are against pathogenic strains include, but are not limit, *Acinetobacter baumannii, Actinomyces israelii, Actinomyces gerencseriae* and *Propionibacterium propionicus, Trypanosoma brucei*, HIV (Human immunodeficiency virus), Entamoeba histolytica, *Anaplasma* genus, *Bacillus anthracis, Arcanobacterium haemolyticum*, Junin virus, Ascaris lumbricoides, *Aspergillus* genus, Astroviridae family, *Babesia* genus, *Bacillus cereus*, multiple bacteria, *Bacteroides* genus, *Balantidium coli, Baylisascaris* genus, BK virus, Piedraia hortae, *Blastocystis hominis, Blastomyces* dermatitides, Machupo virus, *Borrelia* genus, *Clostridium botulinum*, Sabia, *Brucella* genus, usually *Burkholderia cepacia* and other *Burkholderia* species, *Mycobacterium ulcerans*, Caliciviridae family, *Campylobacter* genus, usually *Candida albicans* and other *Candida* species, *Bartonella henselae*, Group A *Streptococcus* and *Staphylococcus, Trypanosoma cruzi, Haemophilus ducreyi*, Varicella zoster virus (VZV), *Chlamydia trachomatis, Chlamydophila pneumoniae, Vibrio cholerae, Fonsecaea pedrosoi, Clonorchis sinensis, Clostridium difficile, Coccidioides immitis* and *Coccidioides posadasii*, Colorado tick fever virus, rhinoviruses, coronaviruses, CJD prion, Crimean-Congo hemorrhagic fever virus, *Cryptococcus neoformans, Cryptosporidium* genus, *Ancylostoma braziliense*; multiple parasites, *Cyclospora cayetanensis, Taenia solium*, Cytomegalovirus, Dengue viruses (DEN-1, DEN-2, DEN-3 and DEN-4) -Flaviviruses, *Dientamoeba fragilis, Corynebacterium diphtheriae, Diphyllobothrium, Dracunculus medinensis*, Ebolavirus, *Echinococcus* genus, *Ehrlichia* genus, *Enterobius vermicularis, Enterococcus* genus, Enterovirus genus, *Rickettsia prowazekii*, Parvovirus B19, Human herpesvirus 6 and Human herpesvirus 7, *Fasciolopsis buski, Fasciola hepatica* and *Fasciola gigantica*, FFI prion, Filarioidea superfamily, *Clostridium perfringens, Fusobacterium* genus, *Clostridium perfringens*; other *Clostridium* species, *Geotrichum candidum*, GSS prion, Giardia intestinalis, *Burkholderia mallei, Gnathostoma spinigerum* and *Gnathostoma hispidum, Neisseria gonorrhoeae, Klebsiella granulomatis, Streptococcus pyogenes, Streptococcus agalactiae, Haemophilus influenzae*, Enteroviruses, mainly Coxsackie A virus and Enterovirus 71, Sin Nombre virus, *Helicobacter pylori, Escherichia coli* O157:H7, Bunyaviridae family, Hepatitis A Virus, Hepatitis B Virus, Hepatitis C Virus, Hepatitis D Virus, Hepatitis E Virus, Herpes simplex virus 1, Herpes simplex virus 2, *Histoplasma capsulatum, Ancylostoma duodenale* and *Necator americanus, Hemophilus influenzae, Human bocavirus, Ehrlichia ewingii, Anaplasma phagocytophilum, Human metapneumovirus, Ehrlichia chaffeensis*, Human papillomavirus, Human parainfluenza viruses, Hymenolepis nana and *Hymenolepis diminuta*, Epstein-Barr Virus, Orthomy-xoviridae family, Isospora belli, *Kingella kingae*, Klebsiella pneumoniae, Klebsiella ozaenas, Klebsiella rhinoscleromotis, Kuru prion, Lassa virus, *Legionella pneumophila, Legionella pneumophila, Leishmania* genus, *Mycobacterium leprae* and *Mycobacterium* lepromatosis, Leptospira genus, Listeria monocytogenes, *Borrelia burgdorferi* and other *Borrelia* species, *Wuchereria bancrofti* and *Brugia malayi*, Lymphocytic choriomeningitis virus (LCMV), *Plasmodium* genus, Marburg virus, Measles virus, *Burkholderia pseudomallei*, Neisseria meningitides, Metagonimus yokagawai, Microsporidia phylum, Molluscum contagiosum virus (MCV), Mumps virus, *Rickettsia typhi, Mycoplasma pneumoniae*, numerous species of bacteria (Actinomycetoma) and fungi (Eumycetoma), parasitic dipterous fly larvae, *Chlamydia trachomatis* and *Neisseria gonorrhoeae*, vCJD prion, *Nocardia asteroides* and other *Nocardia* species, *Onchocerca volvulus, Paracoccidioides brasiliensis, Paragonimus westermani* and other *Paragonimus* species, *Pasteurella* genus, *Pediculus humanus* capitis, *Pediculus humanus* corporis, Phthirus pubis, *Bordetella pertussis, Yersinia pestis, Streptococcus pneumoniae, Pneumocystis jirovecii*, Poliovirus, *Prevotella* genus, *Naegleria fowleri*, JC virus, *Chlamydophila psittaci, Coxiella burnetii*, Rabies virus, *Streptobacillus moniliformis* and Spirillum minus, Respiratory syncytial virus, *Rhinosporidium seeberi*, Rhinovirus, *Rickettsia* genus, *Rickettsia akari*, Rift Valley fever virus, *Rickettsia rickettsii*, Rotavirus, Rubella virus, *Salmonella* genus, SARS coronavirus, *Sarcoptes scabiei, Schistosoma* genus, *Shigella* genus, Varicella zoster virus, Variola major or Variola minor, *Sporothrix schenckii, Staphylococcus* genus, *Staphylococcus* genus, *Staphylococcus aureus, Streptococcus pyogenes, Strongyloides stercoralis, Treponema pallidum, Taenia* genus, *Clostridium tetani, Trichophyton* genus, *Trichophyton tonsurans, Trichophyton* genus, *Epidermophyton floccosum, Trichophyton rubrum*, and *Trichophyton mentagrophytes, Trichophyton rubrum, Hortaea werneckii, Trichophyton* genus, *Malassezia* genus, *Toxocara canis* or *Toxocara cati, Toxoplasma gondii, Trichinella spiralis, Trichomonas vaginalis, Trichuris trichiura, Mycobacterium tuberculosis, Francisella tularensis, Ureaplasma urealyticum*, Venezuelan equine encephalitis virus, *Vibrio* colerae, Guanarito virus, West Nile virus, *Trichosporon beigelii, Yersinia pseudotuberculosis, Yersinia enterocolitica*, Yellow fever virus, Mucorales order (Mucormycosis) and Entomophthorales order (*Entomophthoramycosis*), *Pseudomonas aeruginosa, Campylobacter* (*Vibrio*) *fetus, Aeromonas hydrophila, Edwardsiella tarda, Yersinia pestis, Shigella dysenteriae, Shigella flexneri, Shigella sonnei, Salmonella typhimurium, Treponema pertenue, Treponema carateneum, Borrelia vincentii, Borrelia burgdorferi, Leptospira icterohemorrhagiae, Pneumocystis carinii, Brucella abortus, Brucella suis, Brucella melitensis, Mycoplasma* spp., *Rickettsia* prowazeki, *Rickettsia* tsutsugumushi, Clamydia spp.; pathogenic fungi (*Aspergillus fumigatus, Candida albicans, Histoplasma capsulatum*); protozoa (Entomoeba *histolytica, Trichomonas tenas, Trichomonas hominis, Tryoanosoma gambiense, Trypanosoma rhodesiense, Leishmania donovani, Leishmania tropica, Leishmania braziliensis, Pneumocystis pneumonia, Plasmodium vivax, Plasmodium falciparum, Plasmodium malaria*); or Helminiths (*Schistosoma japonicum, Schistosoma mansoni, Schistosoma haematobium*, and hookworms).

Other conjugates in this invention for treatment of viral disease include, but are not limited to, antibodies against antigens of pathogenic viruses, including as examples and not by limitation: Poxyiridae, Herpesviridae, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Non-A/Non-B Hepatitis virus, Rhinoviridae, Coronaviridae, Rotoviridae, Oncovirus [such as, HBV (Hepatocellular carcinoma), HPV (Cervical cancer, Anal cancer), Kaposi's sarcoma-associated herpesvirus (Kaposi's sarcoma), Epstein-Barr virus (Nasopharyngeal carcinoma, Burkitt's lymphoma, Primary central nervous system lymphoma), MCPyV (Merkel cell cancer), SV40 (Simian virus 40), HCV (Hepatocellular carcinoma), HTLV-I (Adult T-cell leukemia/lymphoma)], Immune disorders caused virus: [such as Human Immunodeficiency Virus (AIDS)]; Central nervous system virus: [such as, JCV (Progressive multifocal leukoencephalopathy), MeV (Subacute sclerosing panencephalitis), LCV (Lymphocytic choriomeningitis), Arbovirus encephalitis, Orthomyxoviridae (probable) (Encephalitis lethargica), RV (Rabies), Chandipura virus, Herpesviral meningitis, Ramsay Hunt syndrome type II; Poliovirus (Poliomyelitis, Post-polio syndrome), HTLV-I (Tropical spastic paraparesis)]; Cytomegalovirus (Cytomegalovirus retinitis, HSV (Herpetic keratitis)); Cardiovascular virus [such as CBV (Pericarditis, Myocarditis)]; Respiratory system/acute viral nasopharyngitis/viral pneumonia: [Epstein-Barr virus (EBV infection/Infectious mononucleosis), Cytomegalovirus; SARS coronavirus (Severe acute respiratory syndrome) Orthomyxoviridae: Influenzavirus A/B/C (Influenza/Avian influenza), Paramyxovirus: Human parainfluenza viruses (Parainfluenza), RSV (Human respiratory syncytialvirus), hMPV]; Digestive system virus [MuV (Mumps), Cytomegalovirus (Cytomegalovirus esophagitis); Adenovirus (Adenovirus infection); Rotavirus, Norovirus, Astrovirus, Coronavirus; HBV (Hepatitis B virus), CBV, HAV (Hepatitis A virus), HCV (Hepatitis C virus), HDV (Hepatitis D virus), HEV (Hepatitis E virus), HGV (Hepatitis G virus)]; Urogenital virus [such as, BK virus, MuV (Mumps)].

According to a further object, the present invention also concerns pharmaceutical compositions comprising the conjugate of the invention together with a pharmaceutically acceptable carrier, diluent, or excipient for treatment of cancers, infections or autoimmune disorders. The method for treatment of cancers, infections and autoimmune disorders can be practiced in vitro, in vivo, or ex vivo. Examples of in vitro uses include treatments of cell cultures in order to kill all cells except for desired variants that do not express the target antigen; or to kill variants that express undesired antigen. Examples of ex vivo uses include treatments of hematopoietic stem cells (HSC) prior to the performance of the transplantation (HSCT) into the same patient in order to kill diseased or malignant cells. For instance, clinical ex vivo treatment to remove tumour cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent graft-versus-host disease, can be carried out as follows. Bone marrow is harvested from the patient or other individual and then incubated in medium containing serum to which is added the conjugate of the invention, concentrations range from about 1 pM to 0.1 mM, for about 30 minutes to about 48 hours at about 37° C. The exact conditions of concentration and time of incubation (=dose) are readily determined by the skilled clinicians. After incubation, the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

Chemoteropeutic Drugs/Cytotoxic Agents for Synergy

Chemoteropeutic drugs that can be used along with the present invention for synergy are small molecule drugs including cytotoxic agents. A "small molecule drug" is broadly used herein to refer to an organic, inorganic, or organometallic compound that may have a molecular weight of, for example, 100 to 2500, more suitably from 200 to 2000. Small molecule drugs are well characterized in the art, such as in WO05058367A2, and in U.S. Pat. No. 4,956,303, among others and are incorporated in their entirety by reference. The drugs include known drugs and those that may become known drugs.

Drugs that are known include, but not limited to,

1). Chemotherapeutic agents: a). Alkylating agents: such as Nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 (including its adozelesin, carzelesin and bizelesin synthetic analogues); Duocarmycin (including the synthetic analogues, KW-2189 and CBI-TMI); Benzodiazepine dimers (e.g., dimmers of pyrrolobenzodiazepine (PBD) or tomaymycin, indolinobenzodiazepines, imidazobenzothiadiazepines, or oxazolidinobenzodiazepines); Nitrosoureas: (carmustine, lomustine, chlorozotocin, fotemustine, nimustine, ranimustine); Alkylsulphonates: (busulfan, treosulfan, improsulfan and piposulfan); Triazenes: (dacarbazine); Platinum containing compounds: (carboplatin, cisplatin, oxaliplatin); aziridines, such as benzodopa, carboquone, meturedopa, and uredopa; ethylenimines and methylamelamines including altretamine, triethylenemel-amine, trietylenephosphoramide, triethylenethio-phosphaoramide and trimethylolomel-amine]; b). Plant Alkaloids: such as *Vinca* alkaloids: (vincristine, vinblastine, vindesine, vinorelbine, navelbin); Taxoids: (paclitaxel, docetaxol) and their analogs, Maytansinoids (DM1, DM2, DM3, DM4, maytansine and ansamitocins) and their analogs, cryptophycins (particularly cryptophycin 1 and cryptophycin 8); epothilones, eleutherobin, discodermolide, bryostatins, dolostatins, auristatins, tubulysins, cephalostatins; pancratistatin; a sarcodictyin; spongistatin; c). DNA Topoisomerase Inhibitors: such as [Epipodophyllins: (9-aminocamptothecin, camptothecin, crisnatol, daunomycin, etoposide, etoposide phosphate, irinotecan, mitoxantrone, novantrone, retinoic acids (retinols), teniposide, topotecan, 9-nitrocamptothecin (RFS 2000)); mitomycins: (mitomycin C)]; d). Anti-metabolites: such as {[Anti-folate: DHFR inhibitors: (methotrexate, trimetrexate, denopterin, pteropterin, aminopterin (4-aminopteroic acid) or the other folic acid analogues); IMP dehydrogenase Inhibitors: (mycophenolic acid, tiazofurin, ribavirin, EICAR); Ribonucleotide reductase Inhibitors: (hydroxyurea, deferoxamine)]; [Pyrimidine analogs: Uracil analogs: (ancitabine, azacitidine, 6-azauridine, capecitabine (Xeloda), carmofur, cytarabine, dideoxyuridine, doxifluridine, enocitabine, 5-Fluorouracil, floxuridine, ratitrexed (Tomudex)); Cytosine analogs: (cytarabine, cytosine arabinoside, fludarabine); Purine analogs: (azathioprine, fludarabine, mercaptopurine, thiamiprine, thioguanine)]; folic acid replenisher, such as frolinic acid}; e). Hormonal therapies: such as {Receptor antagonists: [Anti-estrogen: (megestrol, raloxifene, tamoxifen); LHRH agonists: (goscrclin, leuprolide acetate); Anti-androgens: (bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (CB 1093, EB 1089 KH 1060, cholecalciferol, ergocalciferol); Photodynamic therapies: (verteporfin, phthalocyanine, photosensitizer Pc4, demethoxy-hypocrellin A); Cytokines: (Interferon-alpha, Interferon-gamma, tumor necrosis factor (TNFs), human proteins containing a TNF domain)]}; f). Kinase inhibitors, such as BIBW 2992 (anti-EGFR/Erb2), imatinib, gefitinib, pegaptanib, sorafenib, dasatinib, sunitinib, erlotinib, nilotinib, lapatinib, axitinib, pazopanib. vandetanib, E7080 (anti-VEGFR2), mubritinib, ponatinib (AP24534), bafetinib (INNO-406), bosutinib (SKI-606), cabozantinib, vismodegib, iniparib, ruxolitinib, CYT387, axitinib, tivozanib, sorafenib, bevacizumab, cetuximab, Trastuzumab, Ranibizumab, Panitumumab, ispinesib; g). A poly (ADP-ribose) polymerase (PARP) inhibitors, such as olaparib, niraparib, iniparib, talazoparib, veliparib, veliparib, CEP 9722 (Cephalon's), E7016 (Eisai's), BGB-290 (BeiGene's), 3-aminobenzamide.

h). antibiotics, such as the enediyne antibiotics (e.g. calicheamicins, especially calicheamicin γ1, δ1, α1 and β1, see, e.g., J. Med. Chem., 39 (11), 2103-2117 (1996), Angew Chem Intl. Ed. Engl. 33:183-186 (1994); dynemicin, including dynemicin A and deoxydynemicin; esperamicin, kedarcidin, C-1027, maduropeptin, as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; i). Others: such as Polyketides (acetogenins), especially bullatacin and bullatacinone; gemcitabine, epoxomicins (e. g. carfilzomib), bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors (such as Lovastatin), Dopaminergic neurotoxins (such as 1-methyl-4-phenylpyridinium ion), Cell cycle inhibitors (such as staurosporine), Actinomycins (such as Actinomycin D, dactinomycin), Bleomycins (such as bleomycin A2, bleomycin B2, peplomycin), Anthracyclines (such as daunorubicin, doxorubicin (adriamycin), idarubicin, epirubicin, pirarubicin, zorubicin, mtoxantrone, MDR inhibitors (such as verapamil), $Ca^{2+}$ ATPase inhibitors (such as thapsigargin), Histone deacetylase inhibitors (Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A.; Anti-adrenals, such as aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine (DFMO), elfomithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (especially T-2 toxin, verrucarin A, roridin A and anguidine); urethane, siRNA, antisense drugs, and a nucleolytic enzyme.

2). An anti-autoimmune disease agent includes, but is not limited to, cyclosporine, cyclosporine A, aminocaproic acid, azathioprine, bromocriptine, chlorambucil, chloroquine, cyclophosphamide, corticosteroids (e.g. amcinoride, betamethasone, budesonide, hydrocortisone, flunisolide, fluticasone propionate, fluocortolone danazol, dexamethasone, Triamcinolone acetonide, beclometasone dipropionate), DHEA, enanercept, hydroxychloroquine, infliximab, meloxicam, methotrexate, mofetil, mycophenylate, prednisone, sirolimus, tacrolimus.

3). An anti-infectious disease agent includes, but is not limited to, a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin; b). Amphenicols:azidamfenicol, chloramphenicol, florfenicol, thiamphenicol; c). Ansamycins: geldanamycin, herbimycin; d). Carbapenems: biapenem, doripenem, ertapenem, imipenem/cilastatin, meropenem, panipenem; e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (cefoxitin, cefotetan, cefmetazole), oxacephem (flomoxef, latamoxef); f). Glycopeptides: bleomycin, vancomycin (oritavancin, telavancin), teicoplanin (dalbavancin), ramoplanin; g). Glycylcyclines: e. g. tigecycline; g). 13-Lactamase inhibitors: penam (sulbactam, tazobactam), clavam (clavulanic acid); i). Lincosamides: clindamycin, lincomycin; j). Lipopeptides: daptomycin, A54145, calcium-dependent antibiotics (CDA); k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin; l). Monobactams: aztreonam, tigemonam; m). Oxazolidinones: linezolid; n). Penicillins: amoxicillin, ampicillin (pivampicillin, hetacillin, bacampicillin, metampicillin, talampicillin), azidocillin, azlocillin, benzylpenicillin, benzathine benzylpenicillin, benzathine phenoxymethyl-penicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin; o). Polypeptides: bacitracin, colistin, polymyxin B; p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin; q). Streptogramins: pristinamycin, quinupristin/dalfopristin); r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole); s). Steroid antibacterials: e.g. fusidic acid; t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (e.g. tigecycline; u). Other types of antibiotics: annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (e. g. fosfomycin), nitrofurantoin, paclitaxel, platensimycin, pyrazinamide, quinupristin/dalfopristin, rifampicin (rifampin), tazobactam tinidazole, uvaricin;

4). Anti-viral drugs: a). Entry/fusion inhibitors: aplaviroc, maraviroc, vicriviroc, gp41 (enfuvirtide), PRO 140, CD4 (ibalizumab); b). Integrase inhibitors: raltegravir, elvitegravir, globoidnan A; c). Maturation inhibitors: bevirimat, vivecon; d). Neuraminidase inhibitors: oseltamivir, zanamivir, peramivir; e). Nucleosides &nucleotides: abacavir, aciclovir, adefovir, amdoxovir, apricitabine, brivudine, cidofovir, clevudine, dexelvucitabine, didanosine (ddl), elvucitabine, emtricitabine (FTC), entecavir, famciclovir, fluorouracil (5-FU), 3'-fluoro-substituted 2', 3'-dideoxynucleoside analogues (e.g. 3'-fluoro-2',3'-dideoxythymidine (FLT) and 3'-fluoro-2',3'-dideoxyguanosine (FLG), fomivirsen, ganciclovir, idoxuridine, lamivudine (3TC), 1-nucleosides (e.g., β-1-thymidine and, β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT); f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine; g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir; h). Other types of anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib.

5). The radioisotopes for radiotherapy. Examples of radioisotopes (radionuclides) are $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$n, $^{123}$I, $^{124}$I, $^{125}$I, $^{131}$I, $^{133}$Xe, $^{177}$Lu, $^{211}$At, or $^{213}$Bi. Radioisotope labeled antibodies are useful in receptor targeted imaging experiments or can be for targeted treatment such as with the antibody-radioisotope conjugates (Wu et al (2005) Nature Biotechnology 23(9): 1137-46). The cell binding molecules, e.g. an antibody can be labeled with ligand reagents that bind, chelate or otherwise complex a radioisotope metal, using the techniques described in Current Protocols in Immunology, Volumes 1 and 2, Coligen et al, Ed. Wiley-Interscience, New York, Pubs. (1991). Chelating ligands which may complex a metal ion include DOTA, DOTP, DOTMA, DTPA and TETA (Macrocyclics, Dallas, Tex. USA).

6). Another cell-binding molecule-drug conjugate as a synergy therapy. The preferred synergic conjugate can be a conjugate having a cytotoxic agent of tubulysin analog, maytansinoid analog, taxanoid (taxane) analog, CC-1065 analog, daunorubicin and doxorubicin compound, amatoxin analog, benzodiazepine dimer (e.g., dimers of pyrrolobenzodiazepine (PBD), tomaymycin, anthramycin, indolinobenzodiazepines, imidazobenzothiadiazepines, or oxazolidinobenzodiazepines), calicheamicins and the enediyne antibiotic compound, actinomycin, azaserine, bleomycins, epirubicin, tamoxifen, idarubicin, dolastatins, auristatins (e.g. monomethyl auristatin E, MMAE, MMAF, auristatin PYE, auristatin TP, Auristatins 2-AQ, 6-AQ, EB (AEB), and EFP (AEFP)), duocarmycins, geldanamycins, methotrexates, thiotepa, vindesines, vincristines, hemiasterlins, nazumamides, microginins, radiosumins, alterobactins, microsclerodermins, theonellamides, esperamicins, PNU-159682, and their analogues and derivatives above thereof.

7). The pharmaceutically acceptable salts, acids or derivatives of any of the above drugs.

In yet another embodiment, an immunotoxin can be conjugated to a cell-binding molecule as a synergic drug. An immunotoxin herein is a macromolecular drug which is usually a cytotoxic protein derived from a bacterial or plant protein, such as Diphtheria toxin (DT), Cholera toxin (CT), Trichosanthin (TCS), Dianthin, Pseudomonas exotoxin A (ETA'), Erythrogenic toxins, Diphtheria toxin, AB toxins, Type III exotoxins, etc. It also can be a highly toxic bacterial pore-forming protoxin that requires proteolytic processing for activation. An example of this protoxin is proaerolysin and its genetically modified form, topsalysin. Topsalysin is a modified recombinant protein that has been engineered to be selectively activated by an enzyme in the prostate, leading to localized cell death and tissue disruption without damaging neighboring tissue and nerves.

In another synergistic immunotherapy, an antibody of a checkpoint inhibitor, TCR (T cell receptors) T cells, or CARs (chimeric antigen receptors) T cells, or of B cell receptor (BCR), Natural killer (NK) cells, or the cytotoxic cells, or an antibody of anti-CD3, CD4, CD8, CD16 (FcγRIII), CD27, CD40, CD40L, CD45RA, CD45RO, CD56, CD57, CD57$^{bright}$, TNFP3, Fas ligand, MHC class I molecules (HLA-A, B, C), or NKR—P1 is preferred to use along with the conjugates of the present patent for synergistic therapy.

Formulation and Application

The conjugates of the patent application are formulated to liquid, or suitable to be lyophilized and subsequently be reconstituted to a liquid formulation. The conjugate in a liquid formula or in the formulated lyophilized powder may take up 0.01%-99% by weight as major gradient in the formulation. In general, a liquid formulation comprising 0.1 g/L~300 g/L of concentration of the conjugate active ingredient for delivery to a patient without high levels of antibody aggregation may include one or more polyols (e.g. sugars), a buffering agent with pH 4.5 to 7.5, a surfactant (e.g. polysorbate 20 or 80), an antioxidant (e.g. ascorbic acid and/or methionine), a tonicity agent (e.g. mannitol, sorbitol or NaCl), chelating agents such as EDTA; metal complexes (e.g. Zn-protein complexes); biodegradable polymers such as polyesters; a preservative (e.g. benzyl alcohol) and/or a free amino acid.

Suitable buffering agents for use in the formulations include, but are not limited to, organic acid salts such as sodium, potassium, ammonium, or trihydroxyethylamino salts of citric acid, ascorbic acid, gluconic acid, carbonic acid, tartaric acid, succinic acid, acetic acid or phthalic acid; Tris, tromethamine hydrochloride, sulfate or phosphate buffer. In addition, amino acid cationic components can also be used as buffering agent. Such amino acid component includes without limitation arginine, glycine, glycylglycine, and histidine. The arginine buffers include arginine acetate, arginine chloride, arginine phosphate, arginine sulfate, arginine succinate, etc. In one embodiment, the arginine buffer is arginine acetate. Examples of histidine buffers include histidine chloride-arginine chloride, histidine acetate-arginine acetate, histidine phosphate-arginine phosphate, histidine sulfate-arginine sulfate, histidine succinate-argine succinate, etc. The formulations of the buffers have a pH of 4.5 to pH 7.5, preferably from about 4.5 to about 6.5, more preferably from about 5.0 to about 6.2. In some embodiments, the concentration of the organic acid salts in the buffer is from about 10 mM to about 500 mM.

A "polyol" that may optionally be included in the formulation is a substance with multiple hydroxyl groups. Polyols can be used as stabilizing excipients and/or isotonicity agents in both liquid and lyophilized formulations. Polyols can protect biopharmaceuticals from both physical and chemical degradation pathways. Preferentially excluded co-solvents increase the effective surface tension of solvent at the protein interface whereby the most energetically favorable structural conformations are those with the smallest surface areas. Polyols include sugars (reducing and nonreducing sugars), sugar alcohols and sugar acids. A "reducing sugar" is one which contains a hemiacetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Sugar alcohols are selected from mannitol, xylitol, erythritol, maltitol, lactitol, erythritol, threitol, sorbitol and glycerol. Sugar acids include L-gluconate and metallic salts thereof. The polyol in the liquid formula or in the formulated lyophilized solid can be 0.0%-20% by weight. Preferably, a nonreducing sugar, sucrose or trehalose at a concentration of about from 0.1% to 15% is chosen in the formulation, wherein trehalose being preferred over sucrose, because of the solution stability of trehalose.

A surfactant optionally in the formulations is selected from polysorbate (polysorbate 20, polysorbate 40, polysorbate 65, polysorbate 80, polysorbate 81, polysorbate 85 and the like); poloxamer (e.g. poloxamer 188, poly(ethylene oxide)-poly(propylene oxide), poloxamer 407 or polyethylene-polypropylene glycol and the like); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamido-propyl-betaine (e.g. lauroamidopropyl); myristamidopropyl-, palmidopropyl-, or isostearamido-propyl-dimethylamine; sodium methyl cocoyl-, or disodium methyl oleyl-taurate; dodecyl betaine, dodecyl dimethylamine oxide, cocamidopropyl betaine and coco ampho glycinate; and the MONAQUAT™ series (e.g. isostearyl ethylimidonium ethosulfate); polyethyl glycol, polypropyl glycol, and copolymers of ethylene and propylene glycol (e.g. Pluronics, PF68 etc); etc. Preferred surfactants are polyoxyethylene sorbitan fatty acid esters e.g. polysorbate 20, 40, 60 or 80 (Tween 20, 40, 60 or 80). The concentration of a surfactant in the formulation is range from 0.0% to about 2.0% by weight. In certain embodiments, the surfactant concentration is from about 0.01% to about 0.2%. In one embodiment, the surfactant concentration is about 0.02%.

A "preservative" optionally in the formulations is a compound that essentially reduces bacterial action therein. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The preservative in the liquid formula or in the formulated lyophilized powder can be 0.0%-5.0% by weight. In one embodiment, the preservative herein is benzyl alcohol.

Suitable free amino acids as a bulky material, or tonicity agent, or osmotic pressure adjustment in the formulation, is selected from, but are not limited to, one or more of arginine, cystine, glycine, lysine, histidine, ornithine, isoleucine, leucine, alanine, glycine glutamic acid or aspartic acid. The inclusion of a basic amino acid is preferred i.e. arginine, lysine and/or histidine.

If a composition includes histidine then this may act both as a buffering agent and a free amino acid, but when a histidine buffer is used it is typical to include a non-histidine free amino acid e.g. to include histidine buffer and lysine. An amino acid may be present in its D- and/or L-form, but the L-form is typical. The amino acid may be present as any suitable salt e.g. a hydrochloride salt, such as arginine-HCl. The amino acid in the liquid formula or in the formulated lyophilized powder can be 0.0%-30% by weight.

The formulations can optionally comprise methionine, glutathione, cysteine, cystine or ascorbic acid as an antioxidant at a concentration of about up to 5 mg/ml in the liquid formula or 0.0%-5.0% by weight in the formulated lyophilized powder; The formulations can optionally comprise metal chelating agent, e.g., EDTA, EGTA, etc., at a concentration of about up to 2 mM in the liquid formula or 0.0%-0.3% by weight in the formulated lyophilized powder.

The final formulation can be adjusted to the preferred pH with a buffer adjusting agent (e.g. an acid, such as HCl, $H_2SO_4$, acetic acid, $H_3PO_4$, citric acid, etc, or a base, such as NaOH, KOH, $NH_4OH$, ethanolamine, diethanolamine or triethanol amine, sodium phosphate, potassium phosphate, trisodium citrate, tromethamine, etc) and the formulation should be controlled "isotonic" which is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example. The isotonic agent is selected from mannitol, sorbitol, sodium acetate, potassium chloride, sodium phosphate, potassium phosphate, trisodium citrate, or NaCl. In general, both the buffer salts and the isotonic agent may take up to 30% by weight in the formulation.

Other excipients which may be useful in either a liquid or lyophilized formulation of the patent application include, for example, fucose, cellobiose, maltotriose, melibiose, octulose, ribose, xylitol, arginine, histidine, glycine, alanine, methionine, glutamic acid, lysine, imidazole, glycylglycine, mannosylglycerate, Triton X-100, Pluoronic F-127, cellulose, cyclodextrin, (2-Hydroxypropyl)-P3-cyclodextrin, dextran (10, 40 and/or 70 kD), polydextrose, maltodextrin, ficoll, gelatin, hydroxypropylmeth, sodium phosphate, potassium phosphate, ZnC12, zinc, zinc oxide, sodium citrate, trisodium citrate, tromethamine, copper, fibronectin, heparin, human serum albumin, protamine, glycerin, glycerol, EDTA, metacresol, benzyl alcohol, phenol, polyhydric alcohols, or polyalcohols, hydrogenated forms of carbohydrate having a carbonyl group reduced to a primary or secondary hydroxyl group.

Other contemplated excipients, which may be utilized in the aqueous pharmaceutical compositions of the patent application include, for example, flavoring agents, antimicrobial agents, sweeteners, antioxidants, antistatic agents, lipids such as phospholipids or fatty acids, steroids such as cholesterol, protein excipients such as serum albumin (human serum albumin), recombinant human albumin, gelatin, casein, salt-forming counterions such sodium and the like. These and additional known pharmaceutical excipients and/or additives suitable for use in the formulations of the invention are known in the art, e.g., as listed in "The Handbook of Pharmaceutical Excipients, 4$^{th}$ edition, Rowe et al., Eds., American Pharmaceuticals Association (2003); and Remington: the Science and Practice of Pharmacy, 21$^{th}$ edition, Gennaro, Ed., Lippincott Williams & Wilkins (2005).

A pharmaceutical container or vessel is used to hold the pharmaceutical formulation of any of conjugates of the patent application. The vessel is a vial, bottle, pre-filled syringe, pre-filled or auto-injector syringe. The liquid formula can be freeze-dried or drum-dried to a form of cake or powder in a borosilicate vial or soda lime glass vial. The solid powder can also be prepared by efficient spray drying, and then packed to a vial or a pharmaceutical container for storage and distribution.

In a further embodiment, the invention provides a method for preparing a formulation comprising the steps of: (a) lyophilizing the formulation comprising the conjugates, excipients, and a buffer system; and (b) reconstituting the lyophilized mixture of step (a) in a reconstitution medium such that the reconstituted formulation is stable. The formulation of step (a) may further comprise a stabilizer and one or more excipients selected from a group comprising bulking agent, salt, surfactant and preservative as hereinabove described. As reconstitution media, several diluted organic acids or water, i.e. sterile water, bacteriostatic water for injection (BWFI) or may be used. The reconstitution medium may be selected from water, i.e. sterile water, bacteriostatic water for injection (BWFI) or the group consisting of acetic acid, propionic acid, succinic acid, sodium chloride, magnesium chloride, acidic solution of sodium chloride, acidic solution of magnesium chloride and acidic solution of arginine, in an amount from about 10 to about 250 mM.

A liquid pharmaceutical formulation of the conjugates of the patent application should exhibit a variety of pre-defined characteristics. One of the major concerns in liquid drug products is stability, as proteins/antibodies tend to form soluble and insoluble aggregates during manufacturing and storage. In addition, various chemical reactions can occur in solution (deamination, oxidation, clipping, isomerization etc.) leading to an increase in degradation product levels and/or loss of bioactivity. Preferably, a conjugate in either liquid or lyophilization formulation should exhibit a shelf life of more than 6 months at 25° C. More preferred a conjugate in either liquid or lyophilization formulation should exhibit a shelf life of more than 12 months at 25° C. Most preferred liquid formulation should exhibit a shelf life of about 24 to 36 months at 2-8° C. and the lyophilization formulation should exhibit a shelf life of about preferably up to 60 months at 2-8° C. Both liquid and lyophilization formulations should exhibit a shelf life for at least two years at −20° C., or −70° C.

In certain embodiments, the formulation is stable following freezing (e. g., −20° C., or −70° C.) and thawing of the formulation, for example following 1, 2 or 3 cycles of freezing and thawing. Stability can be evaluated qualitatively and/or quantitatively in a variety of different ways, including evaluation of drug/antibody(protein) ratio and aggregate formation (for example using UV, size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis, or matrix-assisted laser desorption ionization/time-of-flight mass spectrometry (MALDI/TOF MS), or HPLC-MS/MS; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamination (e.g. Asn deamination), oxidation (e.g. Met oxidation), isomerization (e.g. Asp isomerization), clipping/hydrolysis/fragmentation (e.g. hinge region fragmentation), succinimide formation, unpaired cysteine(s), N-terminal extension, C-terminal processing, glycosylation differences, etc.

A stable conjugate should also "retains its biological activity" in a pharmaceutical formulation, if the biological activity of the conjugate at a given time, e. g. 12 month, within about 20%, preferably about 10% (within the errors of the assay) of the biological activity exhibited at the time the pharmaceutical formulation was prepared as determined in an antigen binding assay, and/or in vitro, cytotoxic assay, for example.

For clinical in vivo use, the conjugate via the bis-linkage of the invention will be supplied as solutions or as a lyophilized solid that can be redissolved in sterile water for injection. Examples of suitable protocols of conjugate administration are as follows. Conjugates are given daily, weekly, biweekly, triweekly, once every four weeks or monthly for 8-54 weeks as an i.v. bolus. Bolus doses are given in 50 to 1000 ml of normal saline to which human serum albumin (e.g. 0.5 to 1 mL of a concentrated solution of human serum albumin, 100 mg/mL) can optionally be added. Dosages will be about 50 μg to 20 mg/kg of body weight per week, i.v. (range of 10 μg to 200 mg/kg per injection). 4-54 weeks after treatment, the patient may receive a second course of treatment. Specific clinical protocols with regard to route of administration, excipients, diluents, dosages, times, etc., can be determined by the skilled clinicians.

Examples of medical conditions that can be treated according to the in vivo or ex vivo methods of killing selected cell populations include malignancy of any types of cancer, autoimmune diseases, graft rejections, and infections (viral, bacterial or parasite).

The amount of a conjugate which is required to achieve the desired biological effect, will vary depending upon a number of factors, including the chemical characteristics, the potency, and the bioavailability of the conjugates, the type of disease, the species to which the patient belongs, the diseased state of the patient, the route of administration, all factors which dictate the required dose amounts, delivery and regimen to be administered.

In general terms, the conjugates via the bis-linkers of this invention may be provided in an aqueous physiological buffer solution containing 0.1 to 10% w/v conjugates for parenteral administration. Typical dose ranges are from 1 μg/kg to 0.1 g/kg of body weight daily; weekly, biweekly, triweekly, or monthly, a preferred dose range is from 0.01 mg/kg to 20 mg/kg of body weight weekly, biweekly, triweekly, or monthly, an equivalent dose in a human. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the conjugates by the chosen delivery route, and the speed (bolus or continuous infusion) and schedule of administrations (number of repetitions in a given period of time).

The conjugates via the linkers of the present invention are also capable of being administered in unit dose forms, wherein the term "unit dose" means a single dose which is capable of being administered to a patient, and which can be readily handled and packaged, remaining as a physically and chemically stable unit dose comprising either the active conjugate itself, or as a pharmaceutically acceptable composition, as described hereinafter. As such, typical total daily/weekly/biweekly/monthly dose ranges are from 0.01 to 100 mg/kg of body weight. By way of general guidance, unit doses for humans range from 1 mg to 3000 mg per day, or per week, per two weeks (biweekly), triweekly, or per month. Preferably, the unit dose range is from 1 to 500 mg administered one to four times a month and even more preferably from 1 mg to 100 mg, once a week, biweekly, or triweekly. Conjugates provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasal, particularly in the form of powders, nasal drops, or aerosols; or dermally, for example, topically in ointments, creams, lotions, gels or sprays, or via transdermal patches.

In yet another embodiment, a pharmaceutical composition comprising a therapeutically effective amount of the conjugate of Formula (I) or Formula (III) or any conjugates described through the present patent can be administered concurrently with the other therapeutic agents such as the chemotherapeutic agent, the radiation therapy, immunotherapy agents, autoimmune disorder agents, anti-infectious agents or the other conjugates for synergistically effective treatment or prevention of a cancer, or an autoimmune disease, or an infectious disease. The synergistic agents are preferably selected from one or several of the following drugs: Abatacept, abemaciclib, Abiraterone acetate, Abraxane, Acetaminophen/hydrocodone, Acalabrutinib, aducanumab, Adalimumab, ADXS31-142, ADXS-HER2, afatinib dimaleate, aldesleukin, alectinib, alemtuzumab, Alitretinoin, ado-trastuzumab emtansine, Amphetamine/dextroamphetamine, anastrozole, Aripiprazole, anthracyclines, Aripiprazole, Atazanavir, Atezolizumab, Atorvastatin, Avelumab, Axicabtagene ciloleucel, axitinib, belinostat, BCG Live, Bevacizumab, bexarotene, blinatumomab, Bortezomib, bosutinib, brentuximab vedotin, brigatinib, Budesonide, Budesonide/formoterol, Buprenorphine, Cabazitaxel, Cabozantinib, capmatinib, Capecitabine, carfilzomib, chimeric antigen receptor-engineered T (CAR-T) cells, Celecoxib, ceritinib, Cetuximab, Chidamide, Ciclosporin, Cinacalcet, crizotinib, Cobimetinib, Cosentyx, crizotinib, CTL019, Dabigatran, dabrafenib, dacarbazine, daclizumab, dacomotinib, daptomycin, Daratumumab, Darbepoetin alfa, Darunavir, dasatinib, denileukin diftitox, Denosumab, Depakote, Dexlansoprazole, Dexmethylphenidate, Dexamethasone, DigniCap Cooling System, Dinutuximab, Doxycycline, Duloxetine, Duvelisib, durvalumab, elotuzumab, Emtricibine/Rilpivirine/Tenofovir, disoproxil fumarate, Emtricitbine/tenofovir/efavirenz, Enoxaparin, ensartinib, Enzalutamide, Epoetin alfa, erlotinib, Esomeprazole, Eszopiclone, Etanercept, Everolimus, exemestane, everolimus, exenatide ER, Ezetimibe, Ezetimibe/simvastatin, Fenofibrate, Filgrastim, fingolimod, Fluticasone propionate, Fluticasone/salmeterol, fulvestrant, gazyva, gefitinib, Glatiramer, Goserelin acetate, Icotinib, Imatinib, Ibritumomab tiuxetan, ibrutinib, idelalisib, ifosfamide, Infliximab, imiquimod, ImmuCyst, Immuno BCG, iniparib, Insulin aspart, Insulin detemir, Insulin glargine, Insulin lispro, Interferon alfa, Interferon alfa-1b, Interferon alfa-2a, Interferon alfa-2b, Interferon beta, Interferon beta 1a, Interferon beta 1b, Interferon gamma-1a, lapatinib, Ipilimumab, Ipratropium bromide/salbutamol, Ixazomib, Kanuma, Lanreotide acetate, lenalidomide, lenaliomide, lenvatinib mesylate, letrozole, Levothyroxine, Levothyroxine, Lidocaine, Linezolid, Liraglutide, Lisdexamfetamine, LN-144, lorlatinib, Memantine, Methylphenidate, Metoprolol, Mekinist, mericitabine/Rilpivirine/Tenofovir, Modafinil, Mometasone, Mycidac-C, Necitumumab, neratinib, Nilotinib, niraparib, Nivolumab, ofatumumab, obinutuzumab, olaparib, Olmesartan, Olmesartan/hydrochlorothiazide, Omalizumab, Omega-3 fatty acid ethyl esters, Oncorine, Oseltamivir, Osimertinib, Oxycodone, palbociclib, Palivizumab, panitumumab, panobinostat, pazopanib, pembrolizumab, PD-1 antibody, PD-L1 antibody, Pemetrexed, pertuzumab, Pneumococcal conjugate vaccine, pomalidomide, Pregabalin, ProscaVax, Propranolol, Quetiapine, Rabeprazole, radium 223 chloride, Raloxifene, Raltegravir, ramucirumab, Ranibizumab, regorafenib, ribociclib, Rituximab, Rivaroxaban, romidepsin, Rosuvastatin, ruxolitinib phosphate, Salbutamol, savolitinib, semaglutide, Sevelamer, Sildenafil, siltuximab, Sipuleucel-T, Sitagliptin, Sitagliptin/metformin, Solifenacin, solanezumab, Sonidegib, Sorafenib, Sunitinib, tacrolimus, tacrimus, Tadalafil, tamoxifen, Tafinlar, Talimogene laherparepvec, talazoparib, Telaprevir, talazoparib, Temozolomide, temsirolimus, Tenofovir/emtricitabine, tenofovir disoproxil fumarate, Testosterone gel, Thalidomide, TICE BCG, Tiotropium bromide, Tisagenlecleucel, toremifene, trametinib, Trastuzumab, Trabectedin (ecteinascidin 743), trametinib, tremelimumab, Trifluridine/tipiracil, Tretinoin, Uro-BCG, Ustekinumab, Valsartan, veliparib, vandetanib, vemurafenib, venetoclax, vorinostat, ziv-aflibercept, Zostavax, and their analogs, derivatives, pharmaceutically acceptable salts, carriers, diluents, or excipients thereof, or a combination above thereof.

The drugs/cytotoxic agents used for conjugation via a branched linker of the present patent can be any analogues and/or derivatives of tubulysin described in the present patent. One skilled in the art of drugs/cytotoxic agents will readily understand that each of the tubulysin described herein can be modified in such a manner that the resulting compound still retains the specificity and/or activity of the starting compound. The skilled artisan will also understand that many of these analog or derivative compounds can be used in place of the tubulysin analogs described herein.

Thus, the tubulysin analogs of the present invention include many analogues and derivatives of the tubulysin compounds that may not be described in detail thereof.

All references cited herein and in the examples that follow are expressly incorporated by reference in their entireties.

EXAMPLES

The invention is further described in the following examples, which are not intended to limit the scope of the invention. Cell lines described in the following examples were maintained in culture according to the conditions specified by the American Type Culture Collection (ATCC) or Deutsche Sammlung von Mikroorganismen und Zellkulturen GmbH, Braunschweig, Germany (DMSZ), or The Shanghai Cell Culture Institute of Chinese Acadmy of Science, unless otherwise specified. Cell culture reagents were obtained from Invitrogen Corp., unless otherwise specified. All anhydrous solvents were commercially obtained and stored in Sure-seal bottles under nitrogen. All other reagents and solvents were purchased as the highest grade available and used without further purification. The preparative HPLC separations were performed with Varain PreStar HPLC. NMR spectra were recorded on Bruker 500 MHz Instrument. Chemical shifts (delta) are reported in parts per million (ppm) referenced to tetramethylsilane at 0.00 and coupling constants (J) are reported in Hz. The mass spectral data were acquired on a Waters Xevo QTOF mass spectrum equipped with Waters Acquity UPLC separations module and Acquity TUV detector.

Example 1. Synthesis of Di-Tert-Butyl 1,2-Bis(2-(Tert-Butoxy)-2-Oxoethyl)Hydrazine-1,2-Dicarboxylate

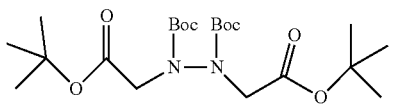 [SMILES: CC(C)(C)OC(=O)CN(C(=O)OC(C)(C)C)N(CC(=O)OC(C)(C)C)C(=O)OC(C)(C)C]

To di-tert-butyl hydrazine-1,2-dicarboxylate (8.01 g, 34.4 mmol) in DMF (150 ml) was added NaH (60% in oil, 2.76 g, 68.8 mmol). After stirred at RT for 30 min, tert-butyl 2-bromoacetate (14.01 g, 72.1 mmol) was added. The mixture was stirred overnight, quenched with addition of methanol (3 ml), concentrated, diluted with EtOAc (100 ml) and water (100 ml), separated, and the aqueous layer was extracted with EtOAc (2×50 ml). The organic layers were combined, dried over MgSO₄, filtered, evaporated, and purified by SiO₂ column chromatography (EtOAc/Hexane1:5 to 1:3) to afforded the title compound (12.98 g, 82% yield) as a colorless oil. MS ESI m/z calcd for $C_{22}H_{41}N_2O_8$ [M+H]+ 461.28, found 461.40.

Example 2. Synthesis of 2,2'-(hydrazine-1,2-diyl)diacetic Acid

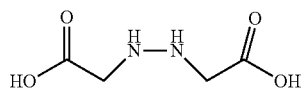

Di-tert-butyl 1,2-bis(2-(tert-butoxy)-2-oxoethyl)hydrazine-1,2-dicarboxylate (6.51 g, 14.14 mmol) in 1,4-dioxane (40 ml) was added HCl (12 M, 10 ml). The mixture was stirred for 30 min, diluted with dioxane (20 ml) and toluene (40 ml), evaporated and co-evaporated with dioxane (20 ml) and toluene (40 ml) to dryness to afford the crude title product for the next step without further production (2.15 g, 103% yield, ~93% pure). MS ESI m/z calcd for $C_4H_9N_2O_4$ [M+H]+149.05, found 149.40.

Example 3. Synthesis of 2,2-2-bis((E)-3-bromoacryloyl)hydrazine-1,2-diyl)diacetic Acid

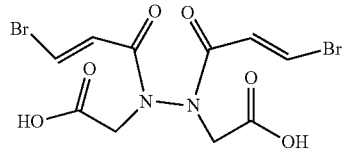 [SMILES: O=C(O)CN(C(=O)/C=C/Br)N(CC(=O)O)C(=O)/C=C/Br]

To a solution of 2,2'-(hydrazine-1,2-diyl)diacetic acid (1.10 g, 7.43 mmol) in the mixture of THF (50 ml) and NaH₂PO₄ (0.1 M, 80 ml, pH 6.0) was added(E)-3-bromoacryloyl bromide (5.01 g, 23.60 mmol). The mixture was stirred for 6 h, concentrated and purified on SiO₂ column eluted with H₂O/CH₃CN (1:9) containing 3% formic acid to afford the title compound (2.35 g, 77% yield, ~93% pure). MS ESI m/z calcd for $C_{10}H_{11}Br_2N_2O_6$ [M+H]+ 412.89, found 413.50.

Example 4. Synthesis of 2,2'-(1,2-Bis((E)-3-Bromoacryloyl)Hydrazine-1,2-Diyl)Diacetyl Chloride

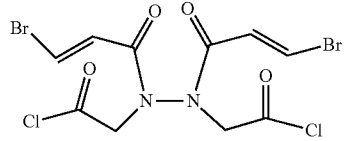 [SMILES: O=C(Cl)CN(C(=O)/C=C/Br)N(CC(=O)Cl)C(=O)/C=C/Br]

2,2'-(1,2-Bis((E)-3-bromoacryloyl)hydrazine-1,2-diyl)diacetic acid (210 mg, 0.509 mmol) in dichloroethane (15 ml) was added (COCl)₂ (505 mg, 4.01 mmol), followed by addition of 0.040 ml of DMF. After stirred at RT for 2 h, the mixture was concentrated and co-evaporated with dichloroethane (2×20 ml) and toluene (2×15 ml) to dryness to afforded the title crude product (which is not stable) for the next step without further purification (245 mg, 107% yield). MS ESI m/z calcd for $C_{10}H_9Br_2Cl_2N_2O_4$ [M+H]+ 448.82, 450.82, 452.82, 454.82, found 448.60, 450.60, 452.60, 454.60.

Example 5. Synthesis of tert-butyl 2,8-dioxo-1,5-oxazocane-5-carboxylate

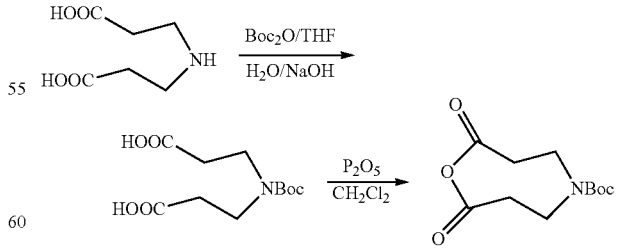

To a solution of 3,3'-azanediyldipropanoic acid(10.00 g, 62.08 mmol) in 1.0 M NaOH (300 ml) at 4° C. was added di-tert-butyl dicarbonate (22.10 g, 101.3 mmol) in 200 ml THF in 1 h. After addition, the mixture was kept to stirring for 2 h at 4° C. The mixture was carefully acidified to pH~4 with 0.2 M H$_3$PO$_4$, concentrated in vacuo, extracted with CH$_2$Cl$_2$, dried over Na2SO4, evaporated and purified with flash SiO$_2$ chromatography eluted with AcOH/MeOH/CH$_2$Cl$_2$ (0.01:1:5) to afford 3,3'-((tert-butoxycarbonyl)azanediyl)dipropanoic acid(13.62 g, 84% yield). ESI MS m/z C$_{11}$H$_{19}$NO$_6$ [M+H]+, cacld. 262.27, found 262.40.

To a solution of 3,3'-((tert-butoxycarbonyl)azanediyl) dipropanoic acid (8.0 g, 30.6 mmol) in CH$_2$Cl$_2$ (500 ml) at 0° C. was added phosphorus pentoxide (8.70 g, 61.30 mmol). The mixture was stirred at 0° C. for 2 h and then r.t. for 1 h, filtered through short SiO$_2$ column, and rinsed the column with EtOAc/CH$_2$Cl$_2$ (1:6). The filtrate was concentrated and triturated with EtOAc/hexane to afford the title compound(5.64 g, 74% yield). ESI MS m/z C$_{11}$H$_{17}$NO$_5$ [M+H]$^+$, cacld. 244.11, found 244.30.

Example 6 Synthesis of 2,5-dioxopyrrolidin-1-yl Propiolate

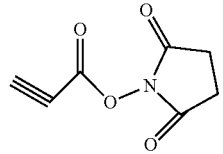

Propiolic acid(5.00 g, 71.4 mmol), NHS (9.01g, 78.3 mmol) and EDC (20.0 g, 104.1 mmol) in CH$_2$Cl$_2$ (150 ml) and DIPEA (5 ml, 28.7 mmol) was stirred for overnight, evaporated and purified by SiO$_2$ column chromatography (EtOAc/Hexane1:4) to afforded the title compound (9.30 g, 79% yield) as a colorless oil. $^1$H NMR (500 MHz, CDCl$_3$) δ 2.68 (s, 1H), 2.61 (s, 4H). MS ESI m/z calcd for C$_7$H$_5$NaNO$_4$ [M+Na]$^+$190.02, found 190.20.

Example 7. Synthesis of tert-butyl 2-propioloylhydrazinecarboxylate

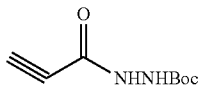

Propiolic acid(5.00 g, 71.4 mmol), tert-butyl hydrazinecarboxylate (9.45g, 71.5 mmol) and EDC (20.0 g, 104.1 mmol) in CH$_2$Cl$_2$ (150 ml) and DIPEA (5 ml, 28.7 mmol) was stirred for overnight, evaporated and purified by SiO$_2$ column chromatography (EtOAc/Hexane1:5) to afforded the title compound (7.92 g, 84% yield) as a colorless oil. $^1$H NMR (500 MHz, CDCl$_3$) δ 8.76 (m, 2H), 2.68 (s, 1H), 1.39 (s, 9H). MS ESI m/z calcd for C$_5$H$_{12}$NaN$_2$O$_2$[M+Na]$^+$ 155.09, found 155.26.

Example 8. Synthesis of Propiolohydrazide, HCl Salt

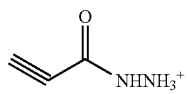

tert-butyl 2-propioloylhydrazinecarboxylate(4.01 g, 30.35 mmol) dissolved in 1,4-dioxane (12 mL) was treated with 4 ml of HCl (conc.) at 4° C. The mixture was stirred for 30 min, diluted with Dioxane (30 ml) and toluene (30 ml) and concentrated under vacuum. The crude mixture was purified on silica gel using a mixture of methanol (from 5% to 10%) and 1% formic acid in methylene chloride as the eluant to give title compound (2.11 g, 83% yield), ESI MS m/z C$_3$H$_5$N$_2$O [M+H]$^+$, cacld. 85.03, found 85.30.

Example 9 Synthesis of Compound 2

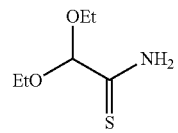

In a 10-L reactor 2,2-diethoxyacetonitrile (1.00 kg, 7.74 mol, 1.0 eq.) was mixed with (NH$_4$)$_2$S (48% aqueous solution, 1.41 kg, 9.29 mol, 1.2 eq.) in methanol (6.0 L) at room temperature. The internal temperature increased to 33° C. and then dropped back to r.t. After stirring overnight, the reaction mixture was concentrated under vacuum and the residue was taken up in ethyl acetate (5 L) and washed with saturated NaHCO$_3$ solution (4×1.0 L). The aqueous layer was back-extracted with ethyl acetate (5×1.0 L). The organic phases were combined and washed with brine (3 L), dried over anhydrous Na$_2$SO$_4$ and concentrated. The resulting solid was collected by vacuum filtration and washed with petroleum ether. The filtrate was concentrated and triturated with petroleum ether to yield a few crops of white or light yellow solid. All crops were combined to give 1.1 kg of desired product (87% yield). $^1$H NMR (500 MHz, CDCl$_3$) δ 7.81 (d, J=71.1 Hz, 2H), 5.03 (s, 1H), 3.73 (dq, J=9.4, 7.1 Hz, 2H), 3.64 (dq, J=9.4, 7.0 Hz, 2H), 1.25 (t, J=7.1 Hz, 6H).

Example 10. Synthesis of Compound 3

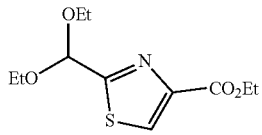

In a 5-L 3-neck round bottle flask, equipped with a reflux condenser and an additional funnel, ethyl bromopyruvate (80% purity, 404 mL, 2.57 mol, 1.2 eq.) was added over 30 min. to a mixture of molecular sieves (3A, 500 g) and thioamide(350 g, 2.14 mol, 1.0 eq.) in 3 L EtOH. During addition, the internal temperature increased slightly. The reaction mixture was then heated to reflux and stirred for 30 min. After cooling to r.t. the reaction mixture was filter over Celite and the filter cake washed with ethyl acetate. The filtrate was concentrated under vacuum. Two batches of the crude product were combined and mixed with silica gel (1.5 kg) and loaded on a silica gel (10 kg packed) column and eluted with ethyl acetate/petroleum ether (10-20%) to give thiazole carboxylate as a brown oil (509 g, 92% yield).

Example 11. Synthesis of Compound 4

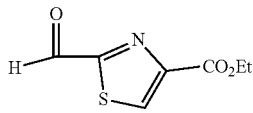

A solution of acetal(300 g, 1.16 mol) in acetone (3.0 L) was heated to reflux and 4N HCl (250 mL) was added over 1.0 h to the refluxing solution. TLC analysis indicated complete consumption of the starting material. The reaction mixture was concentrated under reduced pressure and phases were separated. The organic phase was diluted with ethyl acetate (1.5 L) and washed with saturated NaHCO$_3$ solution (1.0 L), water (1.0 L) and brine (1.0 L), and then dried over anhydrous Na$_2$SO$_4$. All of the aqueous phases were combined and extracted with ethyl acetate. The extracts were combined and dried over anhydrous Na$_2$SO$_4$. The organic solutions were filtered and concentrated under reduced pressure. The crude product was triturated with petroleum ether and diethyl ether (5:1) and the resulting solid was collected by vacuum filtration and washed with petroleum ether and ethyl acetate (10:1). The filtrate was concentrated and chromatographed using 0-15% ethyl acetate/petroleum ether to give another crop of desired product. All white to light yellow solids were combined and weighed 40 g (43% yield). H NMR (500 MHz, CDCl$_3$) δ 10.08-10.06 (m, 1H), 8.53-8.50 (m, 1H), 4.49 (q, J=7.1 Hz, 2H), 1.44 (t, J=7.1 Hz, 3H). MS ESI m/z calcd for C$_7$H$_8$NO$_3$S [M+H]$^+$ 186.01; found 186.01.

Example 12. Synthesis of Compound 6

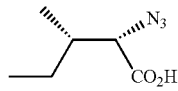

NaN$_3$ (740 g, 11.4 mol) was dissolved in water (2.0 L) and dichloromethane (2.0 L) was added and cooled at 0° C., to which Tf$_2$O (700 mL, 4.10 mol, 1.8 eq.) was added over 1.5 h. After addition was completed, the reaction was stirred at 0° C. for 3 h. The organic phase was separated and the aqueous phase was extracted with dichloromethane (2×500 mL). The combined organic phases were washed with saturated NaHCO$_3$ solution (3×1.0 L). This dichloromethane solution of triflyl azide was added to a mixture of (L)-isoleucine (300 g, 2.28 mol, 1.0 eq.), K$_2$CO$_3$ (472 g, 3.42 mol, 1.5 eq.), CuSO$_4$.5H$_2$O (5.7 g, 22.8 mmol, 0.01 eq.) in water (3.0 L) and methanol (3.0 L) at r.t. During addition, the internal temperature increased slightly. And the mixture was then stirred at r.t. for 16 h. The organic solvents were removed under reduced pressure and the aqueous phase was acidified to pH 6-6.5 with concentrated HCl (about 280 mL added) and then diluted with phosphate buffer (0.25 M, pH 6.2, 6.0 L), washed with EtOAc (6×2.0 L) to remove the sulfonamide by-product. The solution was acidified to pH 3 with concentrated HCl (about 400 mL added), extracted with EtOAc (4×2.0 L). The combined organic layers were washed with brine (2.0 L) and dried over anhydrous Na$_2$SO$_4$, filtered and concentrated to give product 6 (320 g, 89% yield) as a light yellow oil. $^1$H NMR (500 MHz, CDCl$_3$) δ 12.01 (s, 1H), 3.82 (d, J=5.9 Hz, 1H), 2.00 (ddd, J=10.6, 8.6, 5.5 Hz, 1H), 1.54 (dqd, J=14.8, 7.5, 4.4 Hz, 1H), 1.36-1.24 (m, 1H), 1.08-0.99 (m, 3H), 0.97-0.87 (m, 3H).

Example 13. Synthesis of Compound 10

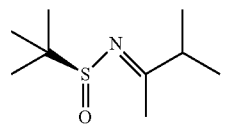

To a solution of (S)-2-methylpropane-2-sulfinamide (100 g, 0.825 mol, 1.0 eq.) in 1 L THF was added Ti(OEt)$_4$ (345 mL, 1.82 mol, 2.2 eq.) and 3-methyl-2-butanone (81 mL, 0.825 mol, 1.0 eq.) under N$_2$ at r.t. The reaction mixture was refluxed for 16 h, then cooled to r.t. and poured onto iced water (1 L). The mixture was filtered and the filter cake was washed with EtOAc. The organic layer was separated, dried over anhydrous Na$_2$SO$_4$ and concentrated to give a residue which was purified by vacuum distillation (15-20 torr, 95° C.) to afforded product 10 (141 g, 90% yield) as a yellow oil. 1H NMR (500 MHz, CDCl$_3$) δ 2.54-2.44 (m, 1H), 2.25 (s, 3H), 1.17 (s, 9H), 1.06 (dd, J=6.9, 5.1 Hz, 6H). MS ESI m/z calcd for C$_9$H$_{19}$NaNOS [M+Na]$^+$212.12; found 212.11.

Example 14. Synthesis of Compound 11

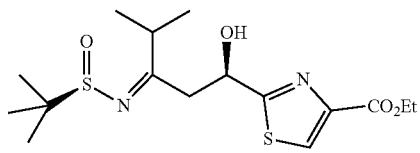

To a solution of diisopropylamine (264 mL, 1.87 mol, 1.65 eq.) in dry THF (1 L) was added n-butyllithium (2.5 M, 681 mL, 1.70 mol, 1.5 eq.) at −78° C. under N$_2$. The reaction mixture was warmed to 0° C. over 30 min and then cooled back to −78°. Compound 10 (258 g, 1.36 mol, 1.2 eq.) was added, and rinsed with THF (50 mL). The reaction mixture was stirred for 1 h before ClTi(O$^i$Pr)$_3$ (834 g, 3.17 mol, 2.8 eq.) in THF (1.05 L) was added dropwise. After stirring for 1 h, compound 4 (210 g, 1.13 mol, 1.0 eq.) dissolved in THF (500 mL) was added dropwise in about 1 hours and the resulting reaction mixture was stirred for 3 h. The completion of the reaction was indicated by TLC analysis. The reaction was quenched by a mixture of acetic acid and THF (v/v 1:1, 300 mL), then poured onto brine (2 L), extracted with EtOAc (8×1 L). The organic phase was washed with water and brine, dried over anhydrous Na$_2$SO$_4$, filtered and concentrated. The residue was purified by column chromatography (DCM/EtOAc/PE 2:1:2) to afforded the compound 11 (298 g, 74% yield) as a colorless oil. $^1$H NMR (500 MHz, CDCl$_3$) δ 8.13 (s, 1H), 6.63 (d, J=8.2 Hz, 1H), 5.20-5.11 (m, 1H), 4.43 (q, J=7.0 Hz, 2H), 3.42-3.28 (m, 2H), 2.89 (dt, J=13.1, 6.5 Hz, 1H), 1.42 (t, J=7.1 Hz, 3H), 1.33 (s, 9H), 1.25-1.22 (m, 6H). MS ESI m/z calcd for C$_{16}$H$_{26}$NaN$_2$O$_4$S$_2$ [M+Na]$^+$397.13, found 397.11.

Example 15. Synthesis of Compound 12

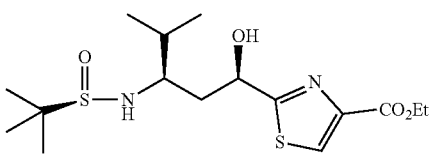

12

A solution of compound 11 (509 g, 1.35 mol, 1.0 eq.) dissolved in THF (200 mL) was cooled to −78° C. Ti(OEt)$_4$ (570 mL, 2.72 mol, 2.0 eq.) was added slowly. After completion of the addition, the mixture was stirred for 1 h, before NaBH$_4$ (51.3 g, 1.36 mol, 1.0 eq.) was added in portions over 90 min. The reaction mixture was stirred at −78° C. for 3 h. TLC analysis showed starting material still remained. EtOH (50 mL) was added slowly, and the reaction was stirred for 1.5 h and then poured onto brine (2 L, with 250 mL HOAc) and warmed to r.t. After filtration over Celite, the organic phase was separated and washed with water and brine, dried over anhydrous Na$_2$SO$_4$, filtered, and concentrated. The residue was purified by column chromatography (EtOAc/PE 1:1) to deliver product 12 (364 g, 71% yield) as a white solid. $^1$H NMR (500 MHz, CDCl$_3$) δ 8.10 (s, 1H), 5.51 (d, J=5.8 Hz, 1H), 5.23-5.15 (m, 1H), 4.41 (q, J=7.0 Hz, 2H), 3.48-3.40 (m, 1H), 3.37 (d, J=8.3 Hz, 1H), 2.29 (t, J=13.0 Hz, 1H), 1.95-1.87 (m, 1H), 1.73-1.67 (m, 1H), 1.40 (t, J=7.1 Hz, 3H), 1.29 (s, 9H), 0.93 (d, J=7.3 Hz, 3H), 0.90 (d, J=7.2 Hz, 3H). MS ESI m/z calcd for C$_{16}$H$_{28}$NaN$_2$O$_4$S$_2$ [M+Na]$^+$ 399.15, found 399.14.

Example 16. Synthesis of Compound 13

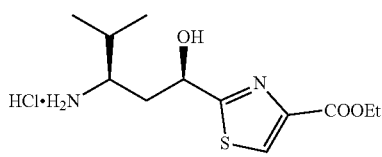

13

To a solution of compound 12 (600 g, 1.60 mol, 1.0 eq.) in ethanol (590 mL) was added 4 N HCl in dioxane (590 mL) slowly at 0° C. The reaction was allowed to warm to r.t. and stirred for 2.5 h. A white precipitate crushed out and was collected by filtration and washed with EtOAc. The filtrate was concentrated and triturated with EtOAc. Two crops of white solid were combined and weighed 446 g (90% yield).

Example 17. Synthesis of Compound 14

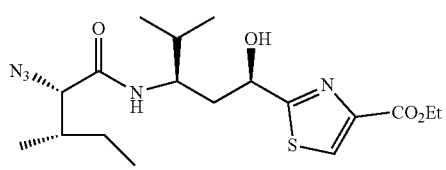

14

Compound 10: Azido-Ile-OH (6, 153 g, 0.97 mol, 2.0 eq.) was dissolved in THF (1.5 L) and cooled to 0° C., to which NMM (214 mL, 1.94 mol, 4.0 eq.) and isobutylchloroformate (95 mL, 0.73 mol, 2.0 eq.) were added in sequence. The reaction was stirred at 0° C. for 1.0 h. Compound 13 (150 g, 0.49 mmol, 1.0 eq.) was added in portions. After stirring at 0° C. for 30 min, the reaction was warmed to r.t. and stirred for 2 h. Water was added at 0° C. to quench the reaction and the resulting mixture was extracted with EtOAc for three times. The combined organic layers were washed with 1N HCl, saturated NaHCO$_3$ and brine, dried over anhydrous Na$_2$SO$_4$, filtered and concentrated. The residue was purified by column chromatography (0-30% EtOAc/PE) to give a white solid (140 g, 70% yield). $^1$H NMR (500 MHz, CDCl$_3$) δ 8.14 (s, 1H), 6.57 (d, J=8.9 Hz, 1H), 4.91 (d, J=11.1 Hz, 1H), 4.44 (dd, J=13.2, 6.3 Hz, 2H), 4.08-3.95 (m, 2H), 2.21 (dd, J=24.4, 11.5 Hz, 2H), 1.90-1.79 (m, 3H), 1.42 (t, J=6.6 Hz, 3H), 1.37-1.27 (m, 2H), 1.11 (d, J=6.4 Hz, 3H), 1.01-0.94 (m, 9H). MS ESI m/z calcd for C$_{18}$H$_{30}$N$_5$O$_4$S [M+H]$^+$ 412.19, found 412.19.

Example 18. Synthesis of Compound 15

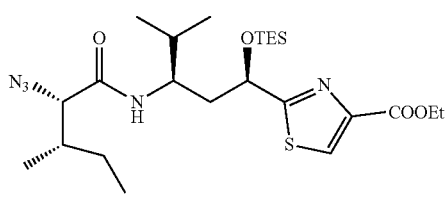

15

Compound 11: To a solution of compound 14 (436 g, 1.05 mol, 1.0 eq.) in CH$_2$Cl$_2$ (50 mL) was added imidazole (94 g, 1.37 mmol, 1.3 eq.), followed by chlorotriethylsilane (222 mL, 1.32 mol, 1.25 eq.) at 0° C. The reaction mixture was allowed to warm to r.t. over 1 hour and stirred for an additional hour. Brine was added to the reaction mixture, the organic layer was separated and the aqueous layer was extracted with EtOAc. The combined organic phases were dried, filtered, concentrated under reduced pressure, and purified by column chromatography with a gradient of 15-35% EtOAc in petroleum ether to afford product 15 (557.4 g, 95% yield) as a colorless oil. $^1$H NMR (500 MHz, CDCl$_3$) δ 8.12 (s, 1H), 6.75 (d, J=8.0 Hz, 1H), 5.20-5.12 (m, 1H), 4.44 (q, J=7.0 Hz, 2H), 4.06-3.97 (m, 1H), 3.87 (d, J=3.8 Hz, 1H), 2.14 (d, J=3.8 Hz, 1H), 2.01-1.91 (m, 3H), 1.42 (t, J=7.1 Hz, 3H), 1.34-1.25 (m, 2H), 1.06 (d, J=6.8 Hz, 3H), 1.00-0.93 (m, 18H), 0.88 (dd, J=19.1, 6.8 Hz, 6H). MS ESI m/z calcd for C$_{24}$H$_{44}$N$_5$O$_4$SSi [M+H]$^+$ 526.28, found 526.28.

Example 19. Synthesis of Compound 16

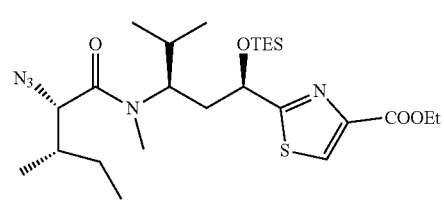

16

To a solution of 15 (408 g, 0.77 mol, 1.0 eq. and methyl iodide (145 mL, 2.32 mol, 3.0 eq.) in THF (4 L) was added sodium hydride (60% dispersion in mineral oil, 62.2 g, 1.55 mol, 2.0 eq.) at 0° C. The resulting mixture was stirred at 0° C. overnight and then poured onto ice-water cooled saturated ammonium chloride (5 L) with vigorous stirring. The mixture was then extracted with EtOAc (3×500 mL) and the organic layers were dried, filtered, concentrated and purified by column chromatography with a gradient of 15-35% EtOAc in petroleum ether to afford product 16 (388 g, 93% yield) as a light yellow oil. $^1$H NMR (500 MHz, CDCl$_3$) δ 8.09 (s, 1H), 4.95 (d, J=6.6 Hz, 1H), 4.41 (q, J=7.1 Hz, 2H), 3.56 (d, J=9.5 Hz, 1H), 2.98 (s, 3H), 2.27-2.06 (m, 4H), 1.83-1.70 (m, 2H), 1.41 (t, J=7.2 Hz, 3H), 1.29 (ddd, J=8.9, 6.8, 1.6 Hz, 3H), 1.01 (d, J=6.6 Hz, 3H), 0.96 (dt, J=8.0, 2.9 Hz, 15H), 0.92 (d, J=6.6 Hz, 3H), 0.90 (d, J=6.7 Hz, 3H). MS ESI m/z calcd for C$_{25}$H$_{46}$N$_5$O$_4$SSi [M+H]$^+$ 540.30, found 540.30.

Example 20. Synthesis of Compound 17

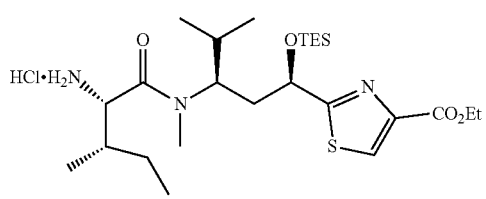

17

To a solution of compound 16 (1.01 g, 1.87 mmol) in methanol (15 mL) was added 0.1N HCl dropwise until a neutral pH was reached. After addition of Pd/C (10 wt %, 583 mg), the mixture was stirred under H$_2$ (1 atm) at room temperature for 16 h. The Pd/C was then removed by filtration, with washing of the filter pad with methanol. The filtrate was concentrated under reduced pressure and the residue was re-dissolved in EtOAc (50 mL), dried over anhydrous Na$_2$SO$_4$, filtered and concentrated to afford compound 17 (900 mg, 94% yield) as a pale yellow oil.

Example 21. Synthesis of Compound 22

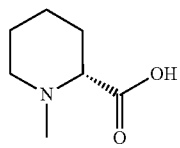

22

To a solution of D-pipecolinic acid (10.0 g, 77.4 mmol, 1.0 eq.) in methanol (100 mL) was added formaldehyde (37% aqueous solution, 30.8 mL, 154.8 mmol, 2.0 eq.), followed by Pd/C (10 wt %, 1.0 g). The reaction mixture was stirred under H$_2$ (1 atm) overnight, and then filtered through Celite, with washing of the filter pad with methanol. The filtrate was concentrated under reduced pressure to afford compound 22 (10.0 g, 90% yield) as a white solid.

Example 22. Synthesis of Compound 23

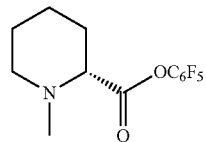

23

To a solution of D-N-methyl pipecolinic acid (2.65 g, 18.5 mmol) in EtOAc (50 mL) were added pentafluorophenol (3.75 g, 20.4 mmol) and DCC (4.21 g, 20.4 mmol). The reaction mixture was stirred at r.t. for 16 h, and then filtered over Celite. The filter pad was washed with 10 mL of EtOAc. The filtrate was used immediately without further purification or concentration.

Example 23. Synthesis of Compound 28

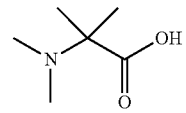

28

A mixture of 2-amino-2-methylpropanoic acid (500 g, 4.85 mol, 1.0 eq.), aqueous formaldehyde (37%, 1.0 L, 12.1 mol, 2.5 eq.) and formic acid (1.0 L) was heated to reflux (80° C.) for 3.0 h. 6 N HCl (850 mL) was then added at r.t. and the reaction mixture was concentrated. The resulting solid was collected by filtration with washing of ethyl acetate for three times (1.0 L). The solid was dissolved in water (1.5 L) and neutralized to pH 7.0 with 4N NaOH (about 1.0 L solution). The solution was concentrated and co-evaporated with ethanol (2.0 L) to remove residual water. MeOH (2.0 L) was added to the residue and the solid (NaCl) was filtered off with washing of ethyl acetate. The filtrate was concentrated under reduced pressure to give a white solid 639.2 g, which contains some NaCl and was used without further treatment.

Example 24. Synthesis of Compound 29

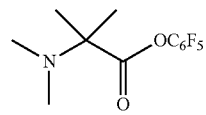

29

To a solution of 2-(dimethylamino)-2-methylpropanoic acid (97 g, 0.74 mol) in EtOAc (1 L) were added pentafluorophenol (163 g, 0.88 mol) and DIC (126 mL, 0.81 mol). The reaction mixture was stirred at r.t. for 24 h, and then filtered over Celite. The filter pad was washed with 10 mL of EtOAc. The filtrate was used immediately without further purification or concentration.

Example 25. Synthesis of Compound 30

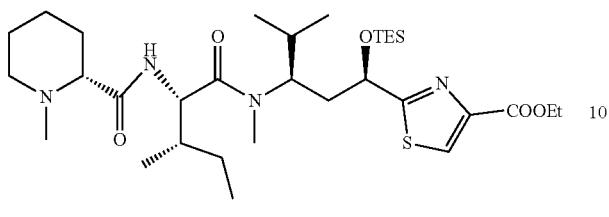
30

Dry Pd/C (10 wt %, 300 mg) and azide compound 16 (3.33 g, 6.61 mmol) were added to pentafluorophenyl ester 23 in EtOAc. The reaction mixture was stirred under hydrogen atmosphere for 27 h, and then filtered through a plug of Celite, with washing of the filter pad with EtOAc. The combined organic portions were concentrated and purified by column chromatography with a gradient of 0-5% methanol in EtOAc to deliver compound 30 (3.90 g, 86% yield). MS ESI m/z calcd for $C_{32}H_{59}N_4O_5SSi$ $[M+H]^+$ 639.39, found 639.39.

Example 26. Synthesis of Compound 31

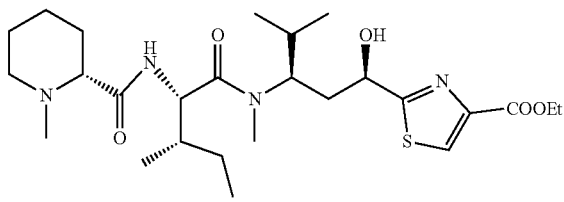
31

The coupled product compound 30 (3.90 g, 6.1 mmol) was dissolved in AcOH/water/THF (v/v/v 3:1:1, 100 mL), and stirred at r.t. for 48 h. The reaction was then concentrated and purified by column chromatography (2:98 to 15:85 MeOH/EtOAc) to afford compound 31 (2.50 g, 72% yield over 2 steps). MS ESI m/z calcd for $C_{26}H_{45}N_4O_5S$ $[M+H]^+$ 525.30, found 525.33.

Example 27. Synthesis of Compound 32

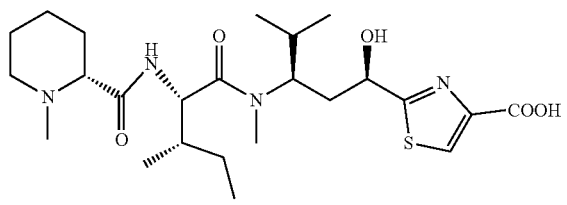
32

An aqueous solution of LiOH (0.4 N, 47.7 mL, 19.1 mmol, 4.0 eq.) was added to a solution of compound 31 (2.50 g, 4.76 mmol, 1.0 eq.) in dioxane (47.7 mL) at 0° C. The reaction mixture was stirred at r.t. for 2 h and then concentrated. Column chromatography (100% $CH_2Cl_2$ to $CH_2Cl_2$/MeOH/$NH_4OH$ 80:20:1) afforded compound 32 (2.36 g, 99% yield) as an amorphous solid. MS ESI m/z calcd for $C_{24}H_{41}N_4O_5S$ $[M+H]^+$ 497.27, found 497.28.

Example 28. Synthesis of Compound 33

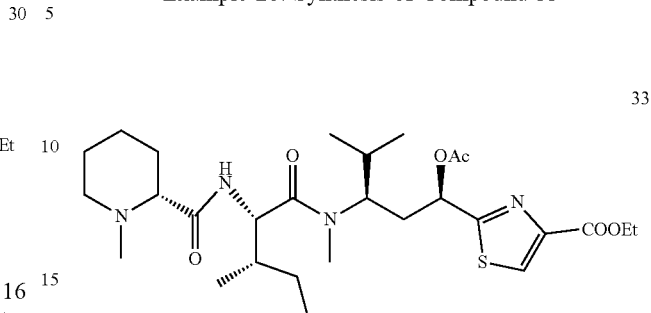
33

To a solution of compound 32 (2.36 g, 4.75 mmol) in pyridine (50 mL) at 0° C., acetic anhydride (2.25 mL, 24 mmol) was added slowly. The reaction mixture was allowed to warm to r.t. over 2 h and stirred at r.t. for 24 h. The reaction was concentrated and then treated with dioxane/water (v/v 1:1, 10 mL) for 1 h to destroy possible anhydride. After concentration the residue was purified by column chromatography (100% $CH_2Cl_2$ to $CH_2Cl_2$/MeOH/$NH_4OH$ 50:50:1) to afford compound 33 (2.25 g, 88% yield) as an amorphous white solid. MS ESI m/z calcd for $C_{26}H_{43}N_4O_6S$ $[M+H]^+$ 539.28, found 539.28.

Example 29. Synthesis of Compound 38

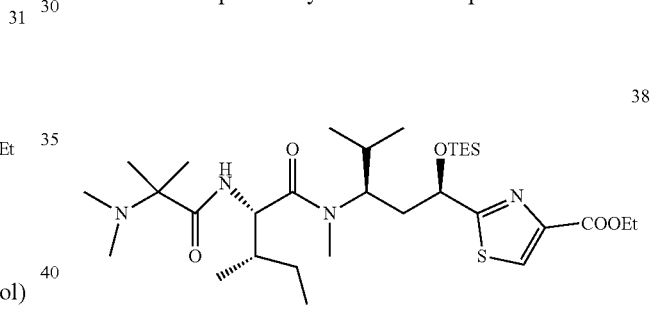
38

To the EtOAc solution of pentafluorophenyl ester 29, compound 16 (200 g, 0.37 mol) and dry Pd/C (10 wt %, 10 g) were added. The reaction mixture was stirred under hydrogen atmosphere (1 atm) for 27 h, and then filtered through a plug of Celite, with washing of the filter pad with EtOAc. The combined organic portions were concentrated and purified by column chromatography with a gradient of 0-5% methanol in EtOAc to deliver compound 38 (184 g, 79% yield). MS ESI m/z calcd for $C_{31}H_{58}N_4O_5SSi$ $[M+H]^+$ 627.39, found 627.39.

Example 30. Synthesis of Compound 39

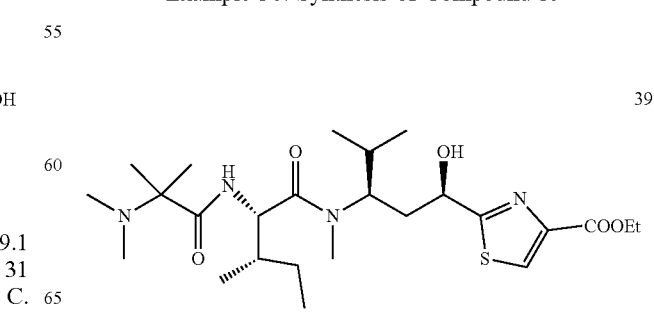
39

Compound 38 (200 g, 0.32 mmol) was dissolved in AcOH/water/THF (v/v/v 3:1:1, 638 mL), and stirred at r.t. for 4 days. After the reaction was concentrated, toluene was added and concentrated again; this step was repeated two times to afford compound 39, which was used directly in the next step. MS ESI m/z calcd for $C_{25}H_{45}N_4O_5S$ [M+H]$^+$ 513.30, found 513.30.

Example 31. Synthesis of Compound 40

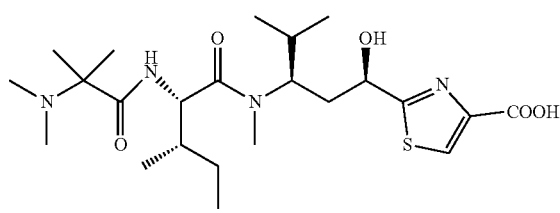

40

An aqueous solution of LiOH (0.4 N, 600 mL, 2.55 mol, 8.0 eq.) was added to a solution of compound 39 (160 g, 0.319 mol, 1.0 eq.) in MeOH (1.2 L) at 0° C. The reaction mixture was stirred at r.t. for 2 h and then concentrated. Column chromatography (pure $CH_2Cl_2$ to 80:20:1 $CH_2Cl_2$/MeOH/NH$_4$OH) afforded compound 40 (140 g, 91% yield for two steps) as an amorphous solid. MS ESI m/z calcd for $C_{23}H_{40}N_4O_5S$ [M+H]$^+$ 485.27, found 485.27.

Example 32. Synthesis of Compound 41

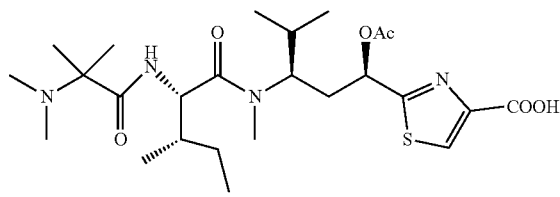

41

A solution of compound 27 (143 g, 0.30 mol, 1.0 eq.) and DMAP (0.36 g, 2.95 mmol, 0.01 eq.) in anhydrous THF (1.4 L) and anhydrous DMF (75 mL) was cooled to 0° C., to which TEA (82.2 mL, 0.59 mmol, 2.0 eq.) and acetic anhydride (56 mL, 0.59 mmol, 2.0 eq.) were added. The reaction mixture was allowed to warm to r.t. and stirred for 24 h, and then concentrated. Column chromatography (5-50% MeOH/DCM) delivered compound 41 (147 g, 95% yield) as an amorphous solid. MS ESI m/z calcd for $C_{25}H_{44}N_4O_6S$ [M+H]$^+$ 527.28, found 527.28.

Example 33. Synthesis of Compound 41a

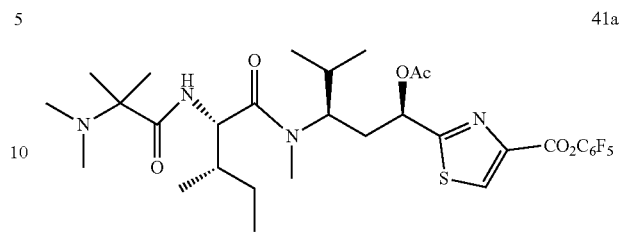

41a

To a solution of compound 41 (5.0 g, 9.5 mmol, 1.0 eq) in anhydrous DCM (100 mL) was added EDC (4.6 g, 23.8 mmol, 2.5 eq) and pentafluorophenol (4.4 g, 23.8 mmol, 2.5 eq) at room temperature under $N_2$. The mixture was stirred at room temperature for 2 h, and then diluted in DCM (100 mL), washed with water (2×200 mL) and brine (200 mL), dried over anhydrous sodium sulfate, filtered, concentrated and purified by $SiO_2$ column chromatography (50% EtOAc/PE) to give compound 41a as a white solid (5.2 g, 79% yield) MS ESI m/z calcd for $C_{31}H_{42}F_5N_4O_6S$ [M+H]$^+$: 693.27, found:693.27.

Example 34. Synthesis of Compound 95

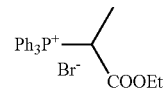

95

In a 500 mL round-bottomed flask equipped with a magnetic stir bar was added triphenylphosphine (100 g, 381 mmol, 1.0 eq.) and ethyl 2-bromopropionate (100 mL, 762 mmol, 2.0 eq.). The mixture was then heated to 50° C. under $N_2$ atmosphere overnight. After the white solid (PPh$_3$) was dissolved, a large amount of white solid was generated. Trituration with petroleum ether/EtOAc and filtration gave compound 95 as a white solid (135 g, 80% yield). MS ESI m/z calcd for $C_{23}H_{24}O_2P$ [M-Br]$^+$363.15, found 363.13.

Example 35. Synthesis of Compound 96

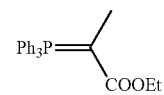

96

A solution of compound 95 (135.42 g, 305.7 mmol) in dichloromethane (500 mL) was added slowly into 10% NaOH solution (450 mL) with vigorous stirring. The organic solution rapidly turned bright yellow. After 30 minutes, TLC analysis showed that the reaction was completed. Layers were separated and the aqueous layer was further extracted with $CH_2Cl_2$ (2×200 mL). Combined organic layers were washed with brine, dried over anhydrous $Na_2SO_4$ and concentrated to give a yellow solid 96 (104 g, 94% yield). MS ESI m/z calcd for $C_{23}H_{24}O_2P$ [M+H]$^+$ 362.14, found 363.13. The crude product was used directly in the next step.

Example 36. Synthesis of Compound 98

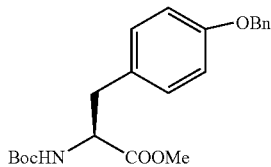

To a mixture of Boc-L-Tyr-OMe (670 g, 2.27 mol, 1.0 eq.), K$_2$CO$_3$ (358 g, 2.5 mol, 1.1 eq.) and KI (38 g, 0.227 mol, 0.1 eq.) in acetone (3 L) was added benzyl bromide (283 mL, 2.38 mol, 1.05 eq.) slowly. The mixture was then refluxed overnight. Water (6 L) was added and the reaction mixture was extracted with EtOAc (5×100 L). The combined organic layers were washed with brine (2 L), dried over anhydrous Na$_2$SO$_4$, filtered, concentrated and purified by SiO$_2$ column chromatography (4:1 hexanes/EtOAc) to give a white solid 98 (795 g, 91% yield). $^1$H NMR (500 MHz, CDCl$_3$) δ 7.43 (d, J=7.0 Hz, 2H), 7.38 (t, J=7.4 Hz, 2H), 7.32 (t, J=7.2 Hz, 1H), 7.04 (d, J=8.5 Hz, 2H), 6.91 (d, J=8.6 Hz, 2H), 5.04 (s, 2H), 4.55 (d, J=6.9 Hz, 1H), 3.71 (s, 3H), 3.03 (qd, J=14.0, 5.8 Hz, 2H), 1.43 (s, 9H). ESI: m/z: calcd for C$_{22}$H$_{28}$NO$_5$ [M+H]$^+$: 386.19, found 386.19.

Example 37. Synthesis of Compound 99

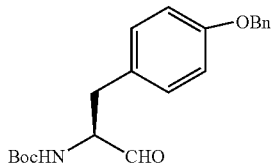

To a solution of ester 98 (380 g, 987 mmol, 1.0 eq.) in anhydrous dichloromethane (1 L) at −78° C. was added DIBAL (1.0 M in hexanes, 2.9 L, 2.9 eq.) over 3 h. After the addition was completed, the mixture was quenched with 3 L of ethanol. 1N HCl was added dropwise until pH 4 was reached. The resulting mixture was allowed to warm to 0° C. Layers were separated and the aqueous layer was further extracted with EtOAc (3×3 L). The combined organic solution was washed with brine, dried over anhydrous Na$_2$SO$_4$, and concentrated. Trituration with PE/EtOAc and filtration gave a white solid 99 (263 g, 75% yield). 1H NMR (500 MHz, CDCl$_3$) δ 9.65 (s, 1H), 7.45 (d, J=7.1 Hz, 2H), 7.41 (t, J=7.4 Hz, 2H), 7.35 (t, J=7.1 Hz, 1H), 7.11 (d, J=8.6 Hz, 2H), 6.95 (d, J=8.6 Hz, 2H), 5.07 (s, 2H), 4.42 (dd, J=12.4, 6.1 Hz, 1H), 3.09 (d, J=6.2 Hz, 2H), 1.46 (s, 9H). ESI: m/z: calcd for C$_{21}$H$_{26}$NO$_4$ [M+H]$^+$: 356.18, found 356.19.

Example 38. Synthesis of Compound 100

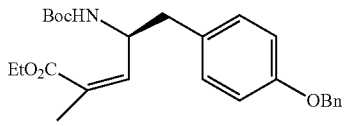

To a solution of aldehyde 99 (81.4 g, 229 mmol, 1.0 eq.) in anhydrous dichloromethane (800 mL) at room temperature was added ylide 96 (2.0 eq.) in anhydrous dichloromethane (800 mL) over 30 min. The mixture was stirred at room temperature overnight then concentrated and purified by SiO$_2$ column chromatography (6:1 petroleum ether/EtOAc) to give a white solid 100 (63.4 g, 63% yield). $^1$H NMR (500 MHz, CDCl$_3$) δ 7.45-7.41 (m, 2H), 7.40-7.35 (m, 2H), 7.33 (d, J=7.2 Hz, 1H), 7.10-7.06 (m, 2H), 6.92-6.88 (m, 2H), 6.50 (dd, J=8.8, 1.3 Hz, 1H), 5.04 (s, 2H), 4.57 (s, 2H), 4.18 (q, J=7.1 Hz, 2H), 2.86 (d, J=8.5 Hz, 1H), 2.72 (dd, J=13.6, 6.8 Hz, 1H), 1.71 (d, J=1.4 Hz, 3H), 1.41 (d, J=2.2 Hz, 9H), 1.28 (td, J=7.5, 5.1 Hz, 4H). MS ESI m/z calcd for C$_{26}$H$_{33}$NaNO$_5$ [M+Na]$^+$462.24, found 462.22.

Example 39. Synthesis of Compound 101

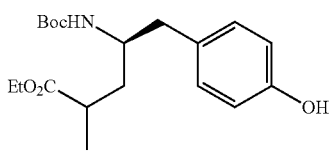

In a hydrogenation bottle, Pd/C (1.83 g, 10 wt %, 50% water) was added to a solution of compound 100 (30.2 g, 68.9 mmol) in THF (100 mL) and methanol (300 mL). The mixture was shaken under 1 atm H$_2$ overnight, filtered through Celite (filter aid), and the filtrate was concentrated to afford compound 101 (25.0 g, theoretical yield) as a colorless oil. $^1$H NMR (500 MHz, CDCl$_3$) δ 6.99 (d, J=7.0 Hz, 2H), 6.72 (d, J=7.6 Hz, 2H), 4.39 (s, 1H), 4.18-4.04 (m, 2H), 3.82 (s, 1H), 2.60 (dd, J=37.2, 20.9 Hz, 4H), 1.95-1.81 (m, 1H), 1.39 (s, 11H), 1.24 (dd, J=9.5, 4.3 Hz, 3H), 1.13 (t, J=8.9 Hz, 3H). MS ESI m/z calcd for C$_{19}$H$_{31}$NO$_5$ [M+H]$^+$ 352.20, found 352.19.

Example 40. Synthesis of Compound 102

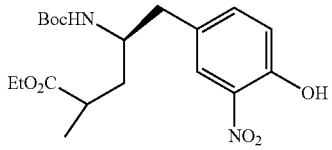

To a solution of compound 101 (5.96 g, 35.9 mmol, 1.0 eq.) in anhydrous dichloromethane (200 mL) was added Ac$_2$O (3.2 mL, 33.9 mmol, 2.0 eq.) and HNO$_3$ (65%-68%, 3.5 mL, 50.79 mmol, 3.0 eq.) at room temperature. The mixture was stirred at room temperature for 30 min, and TLC analysis showed that the reaction was completed. The reaction solution was washed with water (3×200 mL), and the aqueous layer was back-extracted with dichloromethane (3×100 mL). The combined dichloromethane solution was washed with brine, dried over anhydrous Na$_2$SO$_4$, filtered, concentrated and purified by SiO$_2$ column chromatography (5:1 hexanes/EtOAc) to give compound 102 as a yellow solid (4.18 g, 72% yield). H NMR (500 MHz, CDCl$_3$) δ 10.49 (s, 1H), 7.89 (s, 1H), 7.44 (d, J=8.4 Hz, 1H), 7.09 (d, J=8.6 Hz, 1H), 4.32 (d, J=8.3 Hz, 1H), 4.12 (dd, J=14.0, 7.0

Hz, 2H), 3.80 (s, 1H), 2.76 (dd, J=13.0, 6.8 Hz, 2H), 2.59 (s, 1H), 1.88 (s, 1H), 1.37 (t, J=8.7 Hz, 9H), 1.25 (dd, J=13.5, 6.9 Hz, 4H), 1.16 (t, J=8.0 Hz, 3H). MS ESI m/z calcd for $C_{19}H_{28}NaN_2O_7$ [M+Na]$^+$ 419.19, found 419.17.

Example 41. Synthesis of Compound 103

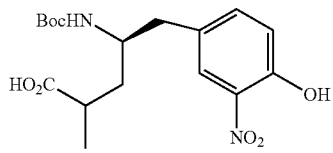

To a solution of ester 102 (15.3 g, 38.6 mmol, 1.0 eq.) in THF (100 mL) and methanol (100 mL) was added LiOH.H$_2$O (16.3 g, 389 mmol, 10.0 eq.) in water (190 mL) at room temperature.

The mixture was stirred at room temperature for 40 min. and then diluted with water (400 mL) and 1N KHSO$_4$ was added dropwise until pH 3-4 was reached. After extraction with EtOAc (3×300 mL), the organic phase was washed with brine, dried over anhydrous Na$_2$SO$_4$, filtered, concentrated to give 103 as a yellow solid (14.4 g, theoretical yield). $^1$H NMR (500 MHz, CDCl$_3$) δ 10.48 (s, 1H), 7.98-7.88 (m, 1H), 7.42 (dd, J=18.4, 8.2 Hz, 1H), 7.14-7.03 (m, 1H), 4.48 (d, J=8.6 Hz, 1H), 3.90 (s, 1H), 2.82-2.53 (m, 3H), 1.97-1.82 (m, 2H), 1.42-1.27 (m, 10H), 1.21 (d, J=6.7 Hz, 4H). MS ESI m/z calcd for $C_{17}H_{23}N_2O_7$ [M–H]$^-$ 367.16, found 367.14.

Example 42. Synthesis of Compound 104

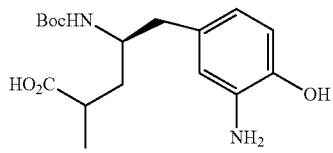

In a hydrogenation bottle, Pd/C (2.60 g, 10 wt %, 50% water) was added to a solution of compound 103 (26.0 g, 70.6 mmol, 1.0 eq.) in methanol (260 mL). The mixture was shaken overnight under 1 atm H$_2$ then filtered through Celite (filter aid), the filtrate was concentrated to afford compound 104 as a green oil (24.0 g, >100% yield).

Example 43. Synthesis of Compound 106

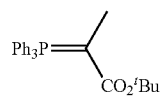

A mixture of tert-butyl-2-bromopropanoate (255 g, 1.22 mol, 1.0 eq.) and triphenyl phosphine (320 g, 1.22 mol, 1.0 eq.) in dry acetonitrile (1 L) was stirred at room temperature for 18 h. Acetonitrile was removed under reduced pressure and toluene was added to crash out a white precipitate. Toluene was then decanted off and the white solid was dissolved in dichloromethane (1 L) and transferred to a separatory funnel. 10% NaOH (1 L) was added to the funnel, and the organic layer immediately turned yellow after shaking. The organic layer was separated and the aqueous layer was extracted with dichloromethane (1 L) once. The dichloromethane layers were combined and washed with brine (400 mL) once, then dried over Na$_2$SO$_4$, filtered and concentrated, giving the ylide 106 as a yellow solid (280g, 58%).

Example 44. Synthesis of Compound 107

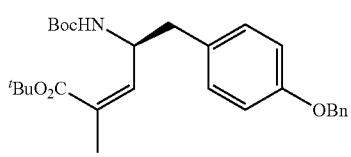

Aldehyde 99 (450 g, 1.27 mol, 1.0 eq.) was dissolved in dry dichloromethane (3 L), to which tert-butyl ester ylide 106 (546 g, 1.40 mmol, 1.1 eq.) was added and the solution was stirred at r.t. overnight as determined complete by TLC. Purification by column chromatography (10-50% EtOAc/hexanes) afforded compound 107 (444 g, 75% yield) as a white solid. ESI m/z calcd for $C_{28}H_{38}NO_5$ [M+H]$^+$: 468.27, found 468.22.

Example 45. Synthesis of Compound 108

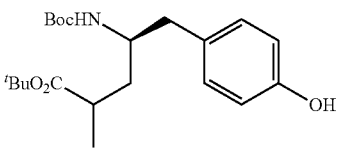

Compound 107 (63 g, 0.13 mol) was dissolved in methanol (315 mL) and hydrogenated (1 atm H$_2$) with Pd/C catalyst (10 wt %, 6.3 g) at r.t. overnight. The catalyst was filtered off and the filtrate were concentrated under reduced pressure to afford compound 108 (45.8 g, 93% yield).

Example 46. Synthesis of Compound 109

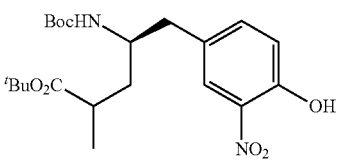

To a solution of compound 108 (390 g, 1.03 mol, 1.0 eq.) in THF (4 L) tert-butyl nitrite (1.06 kg, 10.3 mol, 10 eq.) was added at r.t. and the reaction was stirred overnight. After removal of THF, the residue was purified by column chromatography (10-50% EtOAc/hexanes) to afford compound 109 (314 g, 72% yield) as a light yellow solid.

Example 47. Synthesis of Compound 110

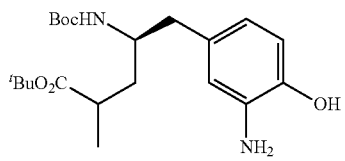

110

To a solution of 109 (166 g, 0.392 mol, 1.0 eq.) in EtOAc (500 mL) was added Pd/C (10 wt %, 16 g) under nitrogen, and the reaction flask was evacuated and purged with hydrogen for 3 times. The reaction mixture was stirred under hydrogen (1 atm) at r.t. for 16 h and then filtered over Celite and concentrated to afford product 110 (146 g, 97% yield) as a light yellow foam. $^1$H NMR (400 MHz, CDCl$_3$) δ 6.62 (d, J=7.9 Hz, 1H), 6.55 (s, 1H), 6.43 (d, J=7.3 Hz, 1H), 4.39 (dd, J=53.0, 44.2 Hz, 1H), 3.77 (s, 4H), 2.72-2.29 (m, 3H), 1.83-1.58 (m, 1H), 1.40 (d, J=7.6 Hz, 18H), 1.24 (s, 1H), 1.06 (t, J=5.7 Hz, 3H). MS ESI m/z calcd for $C_{21}H_{35}N_2O_5$ [M+H]$^+$394.25, found 395.25.

Example 48. Synthesis of Compound 114

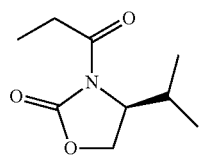

114

To a solution of (S)-4-isopropyloxazolidin-2-one (5.00 g, 38.7 mmol, 1.0 eq.) in anhydrous THF (200 mL) at −78° C. was added n-BuLi (2.5 M in hexanes, 17.0 mL, 1.2 eq.) in 30 min under N$_2$. The mixture was stirred at −78° C. for 1 h, and then propionyl chloride (4.0 mL, 42.58 mmol, 1.1 eq.) was added dropwise. After the mixture was stirred at −78° C. for another 1 h, TLC analysis indicated the reaction completed. Saturated ammonium chloride solution (250 mL) was added and extracted with EtOAc (3×100 mL). The combined organic layers were washed with 1N NaOH solution (200 mL) and brine (300 mL), dried over anhydrous Na$_2$SO$_4$, filtered, concentrated and purified by column chromatography (7:1 hexanes/EtOAc) to give compound 114 as a colorless oil (6.36 g, 89% yield). MS ESI m/z calcd for $C_9H_{16}NO_3$ [M+H]$^+$ 186.10, found 186.10. $^1$H NMR (400 MHz, CDCl$_3$) δ 4.48-4.39 (m, 1H), 4.27 (t, J=8.7 Hz, 1H), 4.21 (dd, J=9.1, 3.1 Hz, 1H), 3.06-2.82 (m, 2H), 2.38 (dtd, J=14.0, 7.0, 4.0 Hz, 1H), 1.17 (t, J=7.4 Hz, 3H), 0.90 (dd, J=17.0, 7.0 Hz, 6H).

Example 49. Synthesis of Compound 115

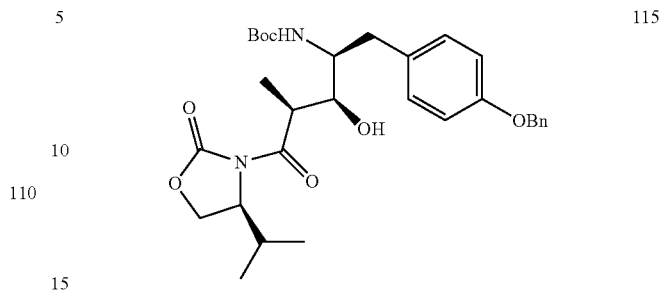

115

To a solution of (S)-4-isopropyl-3-propionyloxazolidin-2-one (2.00 g, 11.9 mmol, 1.1 eq.) in anhydrous dichloromethane (20 mL) at 0° C. was added DIPEA (2.3 mL, 12.9 mmol, 1.2 eq.) and n-Bu$_2$BOTf (1.0 M in dichloromethane, 12.0 mL, 1.1 eq.) under N$_2$. The mixture was stirred at 0° C. for 45 min, then cooled to −78° C., to which a solution of compound 99 (4.24 mL, 10.8 mmol, 1.0 eq.) in dichloromethane was added dropwise. The mixture was stirred at −78° C. for 1 h and then warmed slowly to room temperature. The mixture was stirred at room temperature overnight, and PBS (0.1M, pH 7.0, 100 mL) was added. After phase separation, the aqueous phase was further extracted with dichloromethane (3×50 mL). The combined organic layers were washed with brine (200 mL), dried over anhydrous Na$_2$SO$_4$, filtered and concentrated. The crude product was re-dissolved in methanol (100 mL) and treated with H$_2$O$_2$ (30% aqueous solution, 26 mL, 23 eq.) at 0° C. for 3 h. The methanol was removed by rotary evaporation and water (100 mL) was added. The resulting mixture was extracted with EtOAc (3×100 mL). The combined organic layers were washed with brine (300 mL), dried over anhydrous Na$_2$SO$_4$, filtered, concentrated and purified by SiO$_2$ column chromatography (3:1 hexanes/EtOAc) to give compound 115 as a foamy solid(2.70 g, 49% yield). $^1$H NMR (400 MHz, CDCl$_3$) δ7.52-7.26 (m, 5H), 7.15 (d, J=7.4 Hz, 2H), 6.93 (d, J=7.3 Hz, 2H), 5.05 (s, 2H), 4.69 (d, J=7.0 Hz, 1H), 4.47 (s, 1H), 4.36 (t, J=7.8 Hz, 1H), 4.17 (d, J=8.5 Hz, 1H), 3.93 (d, J=7.1 Hz, 1H), 3.85 (s, 2H), 2.84 (d, J=6.9 Hz, 2H), 2.31 (s, 1H), 1.40-1.37 (m, 9H), 1.31 (s, 3H), 0.92 (dd, J=13.4, 6.6 Hz, 6H). MS ESI m/z calcd for $C_{30}H_{41}N_2O_7$ [M+H]$^+$ 541.28, found 541.30.

Example 50. Synthesis of Compound 116

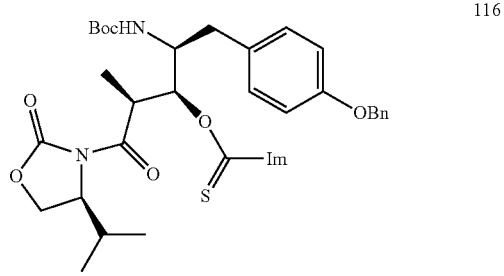

116

A mixture of compound 115 (2.50 g, 4.63 mmol, 1.0 eq.) and 1,1'-thiocarbonyldiimidazole (2.48 g, 13.89 mmol, 3.0 eq.) in anhydrous THF (46 mL) was refluxed overnight.

Water (100 mL) was added and the resulting mixture was extracted with EtOAc (3×50 mL). The combined organic layers were washed with brine (200 mL), dried over anhydrous Na$_2$SO$_4$, filtered, concentrated and purified by SiO$_2$ column chromatography (3:1 hexanes/EtOAc) to give compound 116 as a yellow foam (2.33 g, 77% yield). $^1$H NMR (400 MHz, CDCl$_3$) δ 8.41 (s, 1H), 7.67 (s, 1H), 7.36 (dt, J=16.0, 6.9 Hz, 6H), 7.09 (s, 1H), 7.05 (d, J=8.4 Hz, 2H), 6.86 (d, J=8.4 Hz, 2H), 6.32 (d, J=9.5 Hz, 1H), 5.01 (s, 2H), 4.56-4.43 (m, 2H), 4.32 (ddd, J=16.2, 15.6, 7.8 Hz, 3H), 4.19 (d, J=8.7 Hz, 1H), 2.96 (dd, J=14.6, 4.4 Hz, 1H), 2.49 (dd, J=14.5, 10.5 Hz, 1H), 2.29 (td, J=13.4, 6.7 Hz, 1H), 1.31 (s, 3H), 1.29 (s, 9H), 0.91 (dd, J=13.9, 6.9 Hz, 6H). MS ESI m/z calcd for C$_{34}$H$_{43}$N$_4$O$_7$S[M+H]$^+$ 651.27, found 651.39.

Example 51. Synthesis of Compound 117

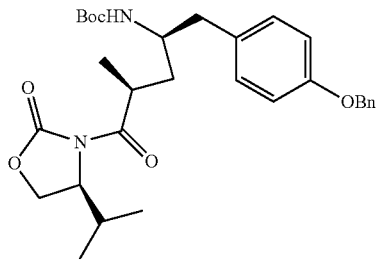

To a solution of compound 116 (1.90 g, 2.92 mmol, 1.0 eq.) in anhydrous toluene (30 mL) was added n-Bu$_3$SnH (1.6 mL, 5.84 mmol, 2.0 eq.) and azodiisobutyronitrile (0.05 g, 0.584 mmol, 0.1 eq.) in sequence. The mixture was refluxed for 2.5 h and then concentrated and purified by SiO$_2$ column chromatography (5:1 hexanes/EtOAc) to give compound 117 as a white foam (1.21 g, 79% yield). $^1$H NMR (400 MHz, CDCl$_3$) δ 7.36 (ddd, J=24.5, 14.5, 7.1 Hz, 5H), 7.08 (d, J=8.5 Hz, 2H), 6.90 (d, J=8.5 Hz, 2H), 5.04 (d, J=5.1 Hz, 2H), 4.48 (d, J=4.2 Hz, 1H), 4.33 (t, J=8.4 Hz, 1H), 4.22 (d, J=9.7 Hz, 1H), 4.15 (d, J=8.8 Hz, 1H), 3.81 (s, 2H), 2.73 (dd, J=14.1, 5.9 Hz, 1H), 2.61 (dd, J=14.0, 7.2 Hz, 1H), 2.29 (dq, J=13.5, 6.8 Hz, 1H), 2.11-2.00 (m, 1H), 1.35 (s, 9H), 1.20 (d, J=6.9 Hz, 3H), 0.89 (dd, J=14.0, 6.9 Hz, 6H). MS ESI m/z calcd for C$_{30}$H$_{41}$N$_2$O$_6$ [M+H]$^+$ 525.28, found 525.37.

Example 52. Synthesis of Compound 118

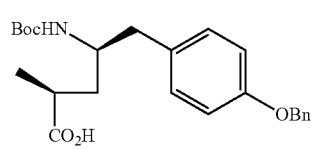

To a solution of compound 117 (1.20 g, 2.29 mmol, 1.0 eq) in THF (30 mL) were added LiOH (0.192 g, 4.58 mmol, 2.0 eq.) in water (6 mL) and H$_2$O$_2$ (30% aqueous solution, 1.4 mL, 6.0 eq.). After 3 h of stirring at 0° C., sodium bisulfite solution (1.5 M, 30 mL) was added to quench the reaction. After 30 min, 1 N KHSO$_4$ was added dropwise until pH 4 was reached. The reaction mixture was then extracted with EtOAc (3×50 mL). The EtOAc solution was washed with brine, dried over anhydrous Na$_2$SO$_4$, filtered, concentrated and purified by SiO$_2$ column chromatography (3:1 hexanes/EtOAc, containing 1% HOAc) to give compound 118 as a white solid (0.78 g, 82% yield). $^1$H NMR (400 MHz, CDCl$_3$) δ 7.46-7.28 (m, 5H), 7.07 (d, J=7.7 Hz, 2H), 6.91 (d, J=7.8 Hz, 2H), 4.52 (d, J=8.5 Hz, 1H), 3.87 (d, J=41.8 Hz, 1H), 2.82-2.43 (m, 3H), 1.85 (t, J=12.2 Hz, 1H), 1.41 (s, 9H), 1.17 (d, J=6.9 Hz, 3H). MS ESI m/z calcd for C$_{24}$H$_{32}$NO$_5$ [M+H]$^+$ 414.22, found 414.21.

Example 53. Synthesis of Compound 119

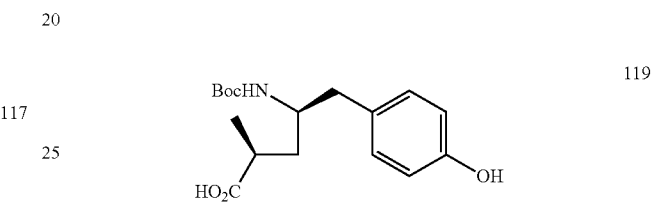

A mixture of compound 118 (0.77 g, 1.86 mmol, 1.0 eq.) and Pd/C (10%, 0.25 g) in methanol (15 mL) was hydrogenated under 1 atm H$_2$ pressure for 16 h and then filtered through Celite (filter aid). The filtrate was concentrated to afford compound 119 as a white solid (0.58 g, 96% yield). $^1$H NMR (400 MHz, CDCl$_3$) δ 7.00 (d, J=7.5 Hz, 2H), 6.80 (s, 2H), 4.51 (d, J=9.0 Hz, 1H), 3.88 (s, 1H), 2.66 (dd, J=65.6, 22.6 Hz, 4H), 1.88 (t, J=12.2 Hz, 1H), 1.42 (s, 9H), 1.14 (d, J=6.6 Hz, 3H). MS ESI m/z calcd for C$_{17}$H$_{26}$NO$_5$ [M+H]$^+$: 324.17, found 324.16.

Example 54. Synthesis of Compound 120

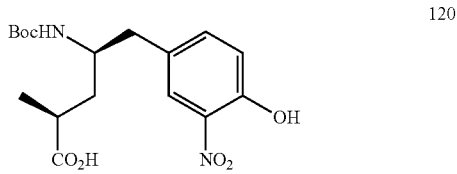 [SMILES: C[C@@H](C[C@H](Cc1ccc(O)c([N+](=O)[O-])c1)NC(=O)OC(C)(C)C)C(=O)O]

To a solution of compound 119 (0.57 g, 1.76 mmol, 1.0 eq.) in THF (10 mL) was added t-BuONO (0.63 mL, 5.28 mmol, 3.0 eq.) at 0° C. The reaction was stirred at 0° C. for 1 hr then room temperature 1 h. After water (50 mL) was added, the reaction mixture was extracted with EtOAc (3×30 mL). The combined organic layers were washed with brine (100 mL), dried over anhydrous Na$_2$SO$_4$, filtered, concentrated and purified by SiO$_2$ column chromatography (2:1 hexanes/EtOAc, containing 1% HOAc) to give compound 120 as a yellow solid (0.50 g, 77% yield). $^1$H NMR (400 MHz, DMSO) δ7.92 (s, 1H), 7.47 (d, J=8.3 Hz, 1H), 7.05 (d, J=8.5 Hz, 1H), 3.73 (s, 1H), 2.78 (dd, J=13.6, 5.3 Hz, 1H), 2.69-2.47 (m, 2H), 1.87 (t, J=11.9 Hz, 1H), 1.47-1.37 (m, 1H), 1.32 (s, 9H), 1.17 (d, J=7.2 Hz, 3H). MS ESI m/z calcd for C$_{17}$H$_{25}$N$_2$O$_7$ [M+H]$^+$ 369.15, found 369.14.

Example 55. Synthesis of Compound 121

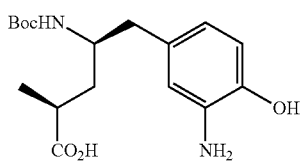

121

A mixture of compound 120 (0.50 g, 1.36 mmol, 1.0 eq.) and Pd/C (10 wt %, 0.02 g) in methanol (10 mL) was hydrogenated (1 atm $H_2$) at r.t. for 1 h, and then filtered through Celite (filter aid). The filtrate was concentrated to afford compound 121 as a white foam (0.43 g, 93% yield). MS ESI m/z calcd for $C_{17}H_{27}N_2O_5$ [M+H]$^+$ 339.18, found 339.17. $^1$H NMR (400 MHz, MeOD) δ 6.60 (d, J=7.9 Hz, 2H), 6.44 (d, J=7.3 Hz, 1H), 3.71 (d, J=6.3 Hz, 1H), 2.62-2.37 (m, 3H), 1.83 (ddd, J=13.7, 9.9, 3.7 Hz, 1H), 1.39 (s, 9H), 1.13 (d, J=7.1 Hz, 3H).

Example 56. Synthesis of Compound 124

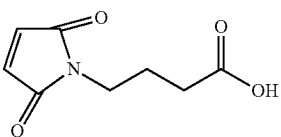

124

To a solution of maleic anhydride (268 g, 2.73 mol) in acetic acid (1 L) was added 4-aminobutanoic acid (285 g, 2.76 mol). After stirring at r.t. for 30 min, the reaction was refluxed for 1.5 h, cooled to r.t. and evaporated under vacuum to give a residue, which was taken up in EA, washed with water and brine, and dried over anhydrous $Na_2SO_4$, filtered and concentrated. The crude product was crystallized from EtOAc and PE to give a white solid (400 g, 80% yield). 1H NMR (500 MHz, CDCl$_3$) δ 6.71 (s, 2H), 3.60 (t, J=6.7 Hz, 2H), 2.38 (t, J=7.3 Hz, 2H), 2.00-1.84 (m, 2H).

Example 57. Synthesis of Compound 125

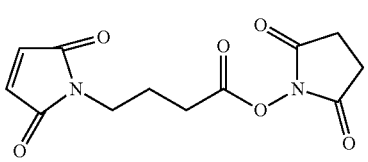

125

Compound 124 (400 g, 2.18 mol, 1.0 eq.) was dissolved in $CH_2Cl_2$ (1.5 L), to which N-hydroxysuccinimide (276 g, 2.40 mmol, 1.1 eq.) and DIC (303 g, 2.40 mol, 1.1 eq.) were added at r.t. and stirred overnight. The reaction was concentrated and purified by column chromatography (1:2 petroleum ether/EtOAc) to give NHS ester 125 as a white solid (382 g, 63% yield). $^1$H NMR (500 MHz, CDCl$_3$) δ 6.74 (s, 2H), 3.67 (t, J=6.8 Hz, 2H), 2.85 (s, 4H), 2.68 (t, J=7.5 Hz, 2H), 2.13-2.03 (m, 2H).

Example 58. Synthesis of Compound 126

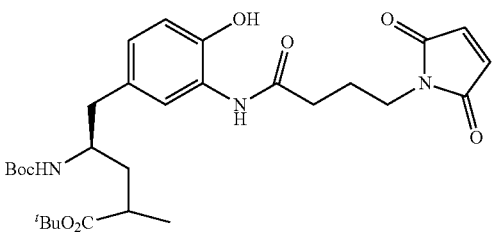

126

To a solution of 124 (60 g, 328 mmol, 1.3 eq.) in THF (600 mL) was added NMM (85.3 mL, 984 mmol, 3.0 eq.) at 0° C. with stirring, followed by isobutyl chloroformate (44.6 mL, 426 mmol, 1.3 eq.) dropwise. After stirring at 0° C. for 2 h, the resulting mixture was added dropwise to a solution of 104 (102 g, 259 mmol, 1.0 eq.) in THF (400 mL) while keeping the temperature at 0° C. After the addition was completed, the reaction was stirred for additional 30 min. and then quenched with water (300 mL), extracted with EtOAc (3×300 mL). The combined organic layers were dried, filtered, concentrated and purified by column chromatography with a gradient of 9-35% EtOAc/PE to afford compound 126 (104 g, 73% yield) as a light yellow solid. $^1$H NMR (400 MHz, CDCl$_3$) δ 8.86 (s, 1H), 8.40 (d, J=17.3 Hz, 1H), 6.87 (s, 3H), 6.70 (s, 2H), 4.53-4.16 (m, OH), 3.79 (s, 1H), 3.62 (t, J=6.1 Hz, 1H), 2.63 (s, 1H), 2.40 (t, J=6.9 Hz, 1H), 2.12-1.88 (m, 4H), 1.84-1.64 (m, 1H), 1.38 (t, J=9.6 Hz, 6H), 1.06 (t, J=6.0 Hz, 3H).

Example 59. Synthesis of Compound 127

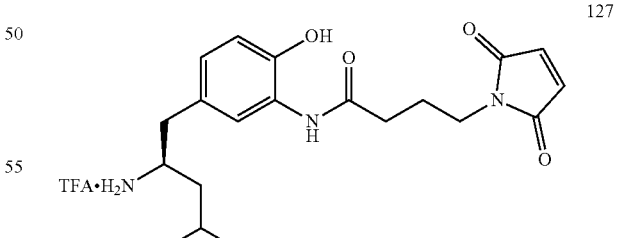

127

Compound 126 (12.7 g, 22.7 mmol) dissolved in $CH_2Cl_2$ (20 mL) was treated with TFA (40 mL) at 0° C. and the reaction was warmed to r.t. and stirred for 3h. The mixture was concentrated and co-evaporated with toluene three times. The residue was triturated with diethyl ether and a light yellow solid 127 was collected (11.4 g, theoretical yield).

Example 60. Synthesis of Compound 128

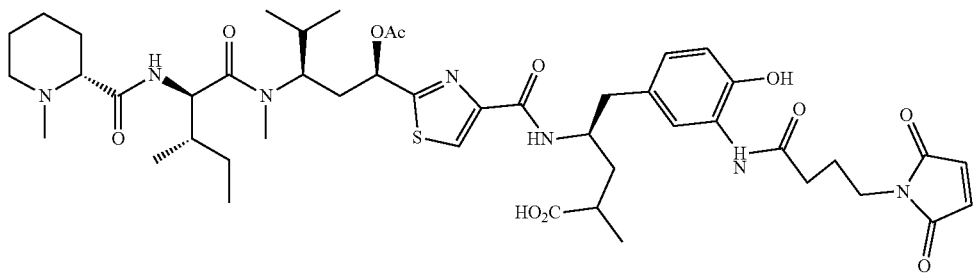

To a solution of carboxylic acid 33 (40 mg, 0.074 mmol, 1.0 eq.) in EtOAc was added pentafluorophenol (27 mg, 0.148 mmol, 2.0 eq.) and DCC (23 mg, 0.111 mmol, 1.5 eq.). The reaction mixture was stirred at r.t. for 16 h and then filtered over a Celite pad, with washing of the pad with EtOAc. The filtrate was concentrated and re-dissolved in DMA (6 mL), then compound 127 (56.6 mg, 0.13 mmol) and DIPEA (47.4 μL, 0.18 mmol) were added. The reaction mixture was stirred at r.t. for 24 h and then concentrated and purified by reverse phase HPLC (Cis column, 10-100% acetonitrile/water) to afford compound 128 (43 mg, 63% yield) as a white solid. MS ESI m/z calcd for $C_{46}H_{66}N_7O_{11}S$ [M+H]$^+$ 924.45, found 924.45.

Example 61. Synthesis of Compound 132

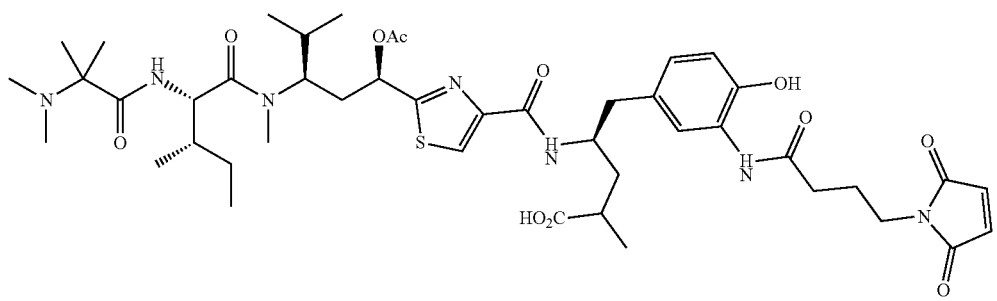

To a solution of compound 41a (11 g, 15.9 mmol, 1.0 eq.) and compound 127 (12.3 g, 23.8 mmol, 1.5 eq.) in DMF (100 mL) was added DIPEA (6.9 mL, 39.7 mmol, 2.5 eq.) at 0° C. The reaction mixture was warmed to r.t. and stirred for 1h. The mixture was concentrated under vacuum and purified on silica gel column (100% DCM to 10% MeOH/DCM) to give compound 132 (10 g, 69% yield) as an amorphous solid. MS ESI m/z calcd for $C_{45}H_{65}N_7O_{11}S$ [M+H]$^+$ 912.45, found 912.45.

Example 62. Synthesis of Compound 166

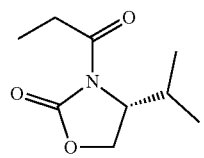

To a solution of (R)-4-isopropyloxazolidin-2-one (25.0 g, 0.194 mol, 1.0 eq) in anhydrous THF (1150 mL) was added n-BuLi (85.0 mL, 0.213 mol, 1.1 eq) at −78° C. under N$_2$ and the mixture was stirred at the same temperature for 1 h, a large number of white solids formed. Then propionyl chloride (20.0 mL, 0.232 mol, 1.2 eq) was added at −78° C. and the mixture was stirred at the same temperature for 1 h. After the consumption of (S)-4-isopropyloxazolidin-2-one monitored by TLC, the solution was poured into saturated ammonium chloride solution (1.2 L) and the mixture was extracted with EA (700 mL, 350 mL×2). The organic extract was washed with 1.0 N NaOH solution (1.0 L) and brine (1.0 L), dried over anhydrous sodium sulfate, filtered, concentrated in vacuo and purified by SiO$_2$ column chromatography (PE:EA=10:1) to give the title compound as a colorless oil (32.6 g, 90.8%). ESI m/z: calcd for $C_9H_{17}NO_3$ [M+H]$^+$: 186.1, found 186.1. $^1$H NMR (400 MHz, CDCl$_3$) δ 4.48-4.37 (m, 1H), 4.27 (t, J=8.7 Hz, 1H), 4.21 (dd, J=9.1, 3.1 Hz, 1H), 3.04-2.82 (m, 2H), 2.45-2.30 (m, 1H), 1.17 (t, J=7.4 Hz, 3H), 0.90 (dd, J=17.1, 7.0 Hz, 6H).

Example 63. Synthesis of Compound 167

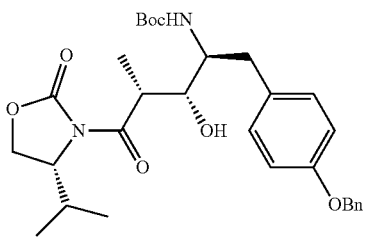

167

To a solution of (R)-4-isopropyl-3-propionyloxazolidin-2-one (18.4 g, 99.5 mmol, 1.1 eq) in anhydrous DCM (200 mL) were added Bu$_2$BOTf (1 M dichloromethane solution, 100 mL, 100 mmol, 1.1 eq) and DIPEA (19 mL, 108.6 mmol, 1.2 eq) at 0° C. under N$_2$, and the mixture was stirred at the same temperature for 45 min. A solution of aldehyde 99(32.2 g, 90.5 mmol, 1.0 eq) in dichloromethane (320 mL) was added at −78° C. and stirred at the same temperature for 1 h, then the solution was allowed to slowly warm to room temperature for 15 hours. The mixture was poured into 700 mL of potassium phosphate buffer (pH 7.0) and extracted with ethyl acetate. The organic extract was washed with brine, dried over anhydrous sodium sulfate, filtered, and then concentrated in vacuo. The residue was dissolved in methanol (730 mL) and cooled to 0° C., then 30% H$_2$O$_2$ aqueous solution (225 mL) was added slowly, and the mixture was stirred at the same temperature for 3 hours. After addition of water (750 mL), the mixture was concentrated in vacuo to remove methanol. The resulting aqueous solution was extracted with ethyl acetate (500 mL, 150 mL×2), and the organic extract was washed with 5% sodium hydrogen carbonate solution and brine, dried over anhydrous sodium sulfate, filtered, concentrated in vacuo and purified by SiO$_2$ column chromatography (PE:EA=3:1) to give the title compound as a white foam (31.7 g, 64.8%). ESI m/z: calcd for $C_{30}H_{41}N_2O_7$ [M+H]$^+$: 541.3, found 541.3. $^1$H NMR (400 MHz, CDCl$_3$) δ 7.49-7.29 (m, 5H), 7.17 (t, J=10.7 Hz, 2H), 6.93 (d, J=7.0 Hz, 2H), 5.06 (s, 2H), 4.28 (dd, J=44.4, 36.4 Hz, 3H), 4.04-3.52 (m, 3H), 3.11-2.73 (m, 2H), 2.35 (s, 1H), 1.41 (t, J=16.3 Hz, 9H), 0.91 (dd, J=15.6, 6.4 Hz, 5H).

Example 64. Synthesis of Compound 168

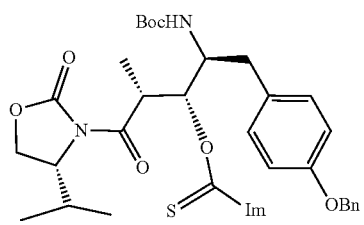

168

To a solution of compound 167 (28.3 g, 52.3 mmol, 1.0 eq) in anhydrous THF (350 mL) was added 1,1-thiocarbonyl diimidazole (TCDI) (35.1 g, 157.0 mmol, 3.0 eq), and the mixture was heated under reflux overnight. After the consumption of starting material monitored by TLC, the mixture was concentrated in vacuo and purified by SiO$_2$ column chromatography (PE:EA=3:1) to give the title compound as a pale yellow foam (26.1 g, 76.8%). ESI m/z: calcd for $C_{34}H_{43}N_4O_7S$ [M+H]$^+$: 651.3, found 651.3. $^1$H NMR (400 MHz, CDCl$_3$) δ 8.21 (s, 1H), 7.43 (d, J=11.8 Hz, 1H), 7.42-7.28 (m, 5H), 7.06 (d, J=8.3 Hz, 2H), 7.01 (s, 1H), 6.80 (d, J=8.3 Hz, 2H), 6.17 (dd, J=8.5, 2.9 Hz, 1H), 4.96 (s, 2H), 4.42-4.04 (m, 5H), 2.83 (dd, J=14.2, 6.2 Hz, 1H), 2.69 (dd, J=14.2, 7.1 Hz, 1H), 2.32 (dd, J=6.8, 4.2 Hz, 1H), 1.37 (s, 9H), 1.30 (d, J=6.9 Hz, 3H), 0.87 (dd, J=9.9, 7.0 Hz, 6H).

Example 65. Synthesis of Compound 169

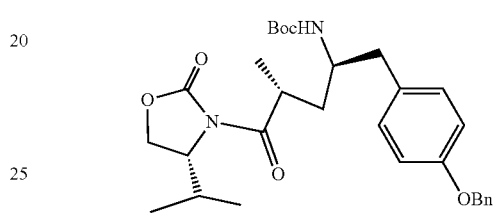

169

To a solution of compound 168(26.0 g, 40.0 mmol, 1.0 eq) in anhydrous toluene (350 mL) was added n-Bu$_3$SnH (21.5 mL, 80.0 mmol, 2.0 eq) and 2,2'-azobis(2-methylpropionitrile) (AIBN) (0.066 g, 0.01 eq) under N$_2$, and the mixture was heated under reflux for 1 hour. After the consumption of starting material monitored by TLC, the mixture was concentrated in vacuo and purified by SiO$_2$ column chromatography (PE:EA=5:1) to give the title compound as a white foam (6.0 g, 37.3%). ESI m/z: calcd for $C_{30}H_{41}N_2O_6$ [M+H]$^+$: 525.3, found 525.3. $^1$H NMR (400 MHz, CDCl$_3$) δ 7.37 (ddd, J=25.1, 15.1, 7.1 Hz, 5H), 7.08 (d, J=7.9 Hz, 2H), 6.89 (d, J=8.4 Hz, 2H), 5.03 (s, 2H), 4.61 (d, J=8.4 Hz, 1H), 4.40 (s, 1H), 4.32-4.08 (m, 2H), 3.91-3.66 (m, 2H), 2.83 (d, J=8.4 Hz, 1H), 2.60 (t, J=10.1 Hz, 1H), 2.33 (s, 1H), 1.71 (s, 1H), 1.41 (s, 9H), 1.15 (d, J=6.5 Hz, 3H), 0.87 (dd, J=17.0, 7.0 Hz, 6H).

Example 66. Synthesis of Compound 170

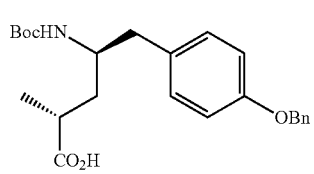

170

To a solution of compound 169(7.84 g, 15.0 mmol, 1.0 eq) in THF (90 mL) and water(30 mL) was added LiOH.H$_2$O (1.57 g, 37.5 mmol, 2.5 eq) in 30% H$_2$O$_2$ aqueous solution (11.4 mL, 112.5 mmol, 7.5 eq) at 0° C., and the mixture was stirred at the same temperature for 3 hours. After addition of 1.5M Na$_2$SO$_3$ solution (160 mL) at 0° C., the mixture was stirred at the same temperature for 30 min. then 1N KHSO$_4$ was added slowly until pH 4. The resulting aqueous solution was extracted with EA (200 mL, 75 mL×2), and the organic extract was washed with brine, dried over anhydrous sodium sulfate, filtered, concentrated in vacuo and purified by SiO$_2$ column chromatography (PE:EA=2:1) to give the title compound as a white solid (6.18 g, 100%). ESI m/z: calcd for $C_{24}H_{32}N_1O_5$ [M+H]$^+$: 414.2, found 414.2. $^1$H NMR (400

MHz, CDCl₃) δ 7.39 (ddd, J=24.5, 15.0, 7.2 Hz, 5H), 7.11 (d, J=7.8 Hz, 2H), 6.93 (d, J=8.3 Hz, 2H), 5.06 (s, 2H), 4.44 (t, J=8.3 Hz, 1H), 3.83 (d, J=69.4 Hz, 1H), 2.85-2.61 (m, 2H), 2.61-2.40 (m, 1H), 1.99-1.70 (m, 1H), 1.39 (d, J=26.1 Hz, 9H), 1.19 (s, 3H).

Example 67. Synthesis of Compound 171

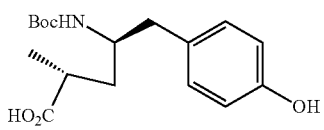
171

To a solution of compound 170 (6.18 g, 15.0 mmol, 1.0 eq) in MeOH (50 mL) was added Pd/C (0.6 g, 10% Pd/C) in a hydrogenation bottle. The mixture was shaken under 1 atm hydrogen atmosphere overnight, then filtered. The filtrate was concentrated to give the title compound as a colorless oil (4.8 g, 99% yield). ESI m/z: calcd for C₁₇H₂₆N₁O₅ [M+H]⁺: 324.2, found 324.2° ¹H NMR (400 MHz, CDCl₃) δ 6.97 (d, J=6.5 Hz, 2H), 6.74 (d, J=8.2 Hz, 2H), 3.93-3.66 (m, 1H), 2.58 (tdd, J=19.5, 12.9, 7.4 Hz, 3H), 1.75 (ddd, J=20.1, 16.3, 7.7 Hz, 1H), 1.37 (d, J=21.5 Hz, 9H), 1.11 (d, J=7.0 Hz, 3H).

Example 68. Synthesis of Compound 172

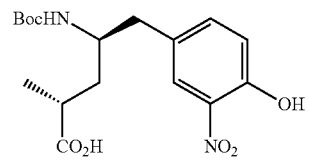
172

To a solution of compound 171 (4.8 g, 15.0 mmol, 1.0 eq) in anhydrous THF (75 mL) was added slowly t-BuONO (18.0 mL, 150 mmol, 10.0 eq) at 0° C. under N₂, and the mixture was stirred at the same temperature for 3 hours. After the consumption of starting material monitored by TLC, 1N KHSO₄ was added slowly to the mixture until pH 4. The resulting aqueous solution was extracted with EA (150 mL, 75 mL×2), and the organic extract was washed with brine, dried over anhydrous sodium sulfate, filtered, concentrated in vacuo and the residue was purified by SiO₂ column chromatography (PE:EA=3:1) to give the title compound as a yellow solid (3.6 g, 65.4%). ESI m/z: calcd for C₁₇H₂₅N₂O₇ [M+H]⁺: 369.2, found 369.2° ¹H NMR (400 MHz, MeOD) δ 7.93 (d, J=2.0 Hz, 1H), 7.48 (dd, J=8.6, 2.1 Hz, 1H), 7.06 (d, J=8.5 Hz, 1H), 3.83-3.71 (m, 1H), 2.82 (dd, J=13.6, 5.0 Hz, 1H), 2.66-2.41 (m, 2H), 1.84 (ddd, J=14.0, 10.6, 5.6 Hz, 1H), 1.65-1.51 (m, 1H), 1.28 (d, J=24.9 Hz, 9H), 1.15 (d, J=7.0 Hz, 3H).

Example 69. Synthesis of Compound 173

173

To a solution of compound 172 (3.2 g, 7.74 mmol, 1.0 eq) in MeOH (20 mL) was added Pd/C (0.2 g, 10% Pd/C) in a hydrogenation bottle. The mixture was shaken under 1 atm H₂ atmosphere for 3 h. After consumption of starting material monitored by TLC, the mixture was filtered and the filtrate was concentrated to give the title compound as a white foam (2.3 g, 92.0% yield). ESI m/z: calcd for C₁₇H₂₇N₂O₅ [M+H]⁺: 339.2, found 339.2. ¹H NMR (400 MHz, MeOD) δ 6.61 (d, J=8.0 Hz, 2H), 6.45 (d, J=6.3 Hz, 1H), 3.72 (d, J=7.3 Hz, 1H), 2.68-2.34 (m, 3H), 1.81-1.66 (m, 1H), 1.56-1.45 (m, 1H), 1.36 (d, J=29.0 Hz, 9H), 1.08 (d, J=6.9 Hz, 3H).

Example 70. Synthesis of Compound 187

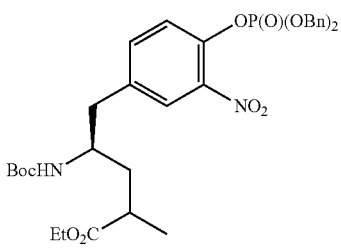
187

To a solution of compound 102 (1.00 g, 2.52 mmol) in acetonitrile (10 mL) was added CCl4 (2.2 mL, 22.7 mmol, 9.0 eq.) at −25° C. After stirring for 10 min, diisopropylethylamine (0.88 mL, 5.04 mmol, 2.0 eq.) and DMAP (0.03 g, 0.252 mmol, 0.1 eq.) were added, followed by dibenzyl phosphite (0.84 mL, 3.78 mmol, 1.5 eq.). The reaction mixture was allowed to reach r.t. over 1.5 h, and then quenched by a solution of KH₂PO₄ (0.5 M, 50 mL). The reaction mixture was extracted with EtOAc (3×50 mL). The combined organic extracts were dried over anhydrous Na₂SO₄ and concentrated under reduced pressure. The residue was purified by flash column chromatography (10-50% EtOAc/PE) to afford compound 187 (1.60 g, 96% yield) as a colorless oil. MS ESI m/z calcd for C₃₃H₄₁N₂O₁₀P [M+H]⁺ 657, found 657.

Example 71. Synthesis of Compound 188

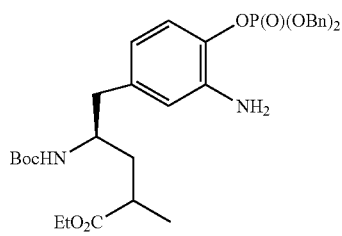

To a solution of compound 187 (1.60 g, 2.43 mmol) in methanol (20 mL) was added Pd/C (10 wt %, 160 mg). The reaction mixture was stirred under $H_2$ atmosphere (1 atm) at r.t. for 3 h, then filtered through Celite and concentrated under reduced pressure to afford compound 188 (1.00 g, 91% yield) as a white solid. MS ESI m/z calcd for $C_{19}H_{31}N_2O_8P$ [M−H]⁻ 447, found 447.

Example 72. Synthesis of Compound 189

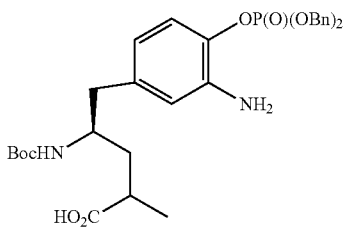

A solution of compound 188 (730 mg, 1.63 mmol) in ethanol (10 mL) was treated with 1 N NaOH (16 mL, 16.3 mmol, 10 eq.) at r.t. overnight, and then concentrated under reduced pressure. The residue was taken up in water (20 mL) and acidified to pH 6 by 1 N HCl. The aqueous solution was concentrated under reduced pressure and the residue was triturated with MeOH/EtOAc (80:20, 5 mL), compound 189 (0.68 g, 99% yield) was collected from filtration as a white solid. MS ESI m/z calcd for $C_{17}H_{27}N_2O_8P$ [M−H]⁻ 417, found 417.

Example 73. Synthesis of Compound 299

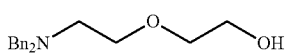

2-(2-aminoethoxy)ethanol (21.00 g, 200 mmol, 1.0 eq.) and $K_2CO_3$ (83.00 g, 600 mmol, 3.0 eq.) in acetonitrile (350 mL) was added BnBr (57.0 mL, 480 mmol, 2.4 eq.). The mixture was refluxed overnight. Water (1 L) was added and extracted with EtOAc (3×300 mL). The combined organic layers were washed with brine (1000 mL), dried over anhydrous $Na_2SO_4$, filtered, concentrated and purified by $SiO_2$ column chromatography (4:1 hexanes/EtOAc) to give a colorless oil (50.97 g, 89.2% yield). MS ESI m/z calcd for $C_{18}H_{23}NO_2Na$ [M+Na]⁺ 309.17, found 309.19.

Example 74. Synthesis of Compound 300

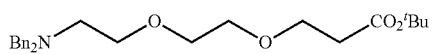

To a mixture of 2-(2-(dibenzylamino)ethoxy)ethanol (47.17 g, 165.3 mmol, 1.0 eq.), tert-butyl acrylate (72.0 mL, 495.9 mmol, 3.0 eq.) and n-$Bu_4NI$ (6.10 g, 16.53 mmol, 0.1 eq.) in DCM (560 mL) was added sodium hydroxide solution (300 mL, 50%). The mixture was stirred overnight. The organic layer was separated and the water layer was extracted with EtOAc (3×100 mL). The organic layers were washed with water (3×300 mL) and brine (300 mL), dried over anhydrous $Na_2SO_4$, filtered, concentrated and purified by $SiO_2$ column chromatography (7:1 hexanes/EtOAc) to give a colorless oil (61.08 g, 89.4% yield). MS ESI m/z calcd for $C_{25}H_{36}NO_4$ [M+H]⁺ 414.2566, found 414.2384.

Example 75. Synthesis of Compound 301

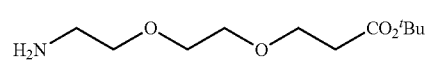

To a solution of tert-butyl 3-(2-(2-(dibenzylamino)ethoxy)ethoxy) propanoate (20.00 g, 48.36 mmol, 1.0 eq.) in THF (30 mL) and MeOH (60 mL) was added Pd/C (2.00 g, 10 wt %, 50% wet) in a hydrogenation bottle. The mixture was shaken overnight, filtered through Celite (filter aid), and the filtrate was concentrated to afford a colorless oil (10.58 g, 93.8% yield). MS ESI m/z calcd for $C_{11}H_{24}NO_4$ [M+H]⁺ 234.1627, found 234.1810.

Example 76. Synthesis of Compound 302

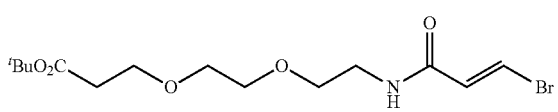

To a solution of (E)-3-bromoacrylic acid (0.15 g, 1 mmol), DMAP (0.15 g, 1.2 mmol) and DCC (0.21 g, 1 mmol) in DCM (10 ml), compound 301 (0.23g, 1 mmol) were added at 0° C. The reaction mixture was allowed to warm to r.t. and stirred overnight. The crude product was concentrated and purified by $SiO_2$ column chromatography with a gradient of EA/DCM to give the title product 302 (0.31g, 85% yield). ESI MS m/z: calcd for $C_{14}H_{25}BrNO_5$ [M+H]⁺: 366.08, found 366.08.

Example 77. Synthesis of Compound 303

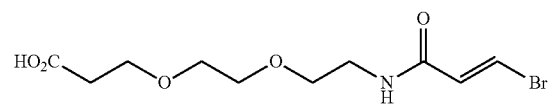

Compound 302 (0.31 g, 0.84 mmol) was dissolved in fomic acid (4 mL) at 0° C. then H₂O (2 mL) was added. The reaction mixture was allowed to warm to r.t. and stirred overnight. The crude product was concentrated and used for the next step without further purification. ESI MS m/z: calcd for $C_{10}H_{17}BrNO_5$ [M+H]⁺: 310.02, found 310.03.

Example 78. Synthesis of Compound 304

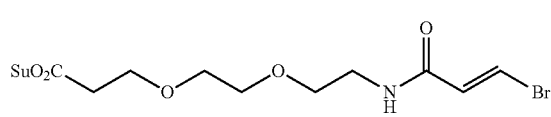

304

Compound 303 (0.12 g, 0.39 mmol), NHS (0.067 g, 0.58 mmol) and EDCI (0.11 g, 0.58 mmol) were dissolved in DCM (10 mL) and the mixture was stirred at r.t. overnight, concentrated and purified by SiO₂ column chromatography to give the title product 304 (0.13 g, 82% yield). ESI MS m/z: calcd for $C_{14}H_{20}BrN_2O_7$ [M+H]⁺:407.04, found 407.04.

Example 79. Synthesis of Compound 326

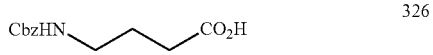

326

A solution of 4-aminobutyric acid (7.5 g, 75 mmol) and NaOH (6 g, 150 mmol) in H₂O (40 mL) was cooled to 0° C. and treated with a solution of CbzCl (16.1 g, 95 mmol) in THF (32 ml) dropwise. After 1 h, the reaction was allowed to warm to r.t. and stirred for 3 h. THF was removed under vacuum, the pH of the aqueous solution was adjusted to 1.5 by addition of 6 N HCl. The solution was extracted with ethyl acetate, and the organic layer was washed with brine, dried and concentrated to give compound 326 (16.4 g, 92% yield). MS ESI m/z calcd for $C_{12}H_{16}NO_5$ [M+H]⁺ 238.10, found 238.08.

Example 80. Synthesis of Compound 327

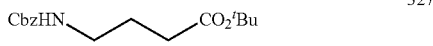

327

DMAP (0.8 g, 6.56 mmol) and DCC (17.1 g, 83 mmol) were added to a solution of 4-(((benzyloxy)carbonyl)amino)butanoic acid (16.4 g, 69.2 mmol) and t-BuOH (15.4 g, 208 mmol) in DCM (100 mL). After stirring at r.t. overnight, the reaction was filtered and filtrate concentrated. The residue was dissolved in ethyl acetate and the washed with 1N HCl, brine and dried over Na₂SO₄. Concentration and purification by column chromatography (10 to 50% EtOAc/hexanes) yielded compound 327 (7.5 g, 37% yield). MS ESI m/z calcd for $C_{16}H_{23}NO_4Na$ [M+Na]⁺316.16, found 316.13.

Example 81. Synthesis of Compound 328

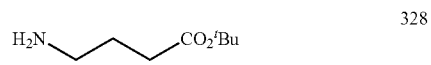

328 tert-Butyl 4-(((benzyloxy)carbonyl)amino)butanoate (560 mg, 1.91 mmol) was dissolved in MeOH (50 mL), and mixed with Pd/C catalyst (10 wt %, 100 mg) then hydrogenated (1 atm) at r.t. for 3 h. The catalyst was filtered off and all volatiles were removed under vacuum to afford compound 328 (272 mg, 90% yield). MS ESI m/z calcd for $C_8H_{18}NO_2$ [M+H]⁺ 160.13, found 160.13.

Example 82. Synthesis of Compound 330

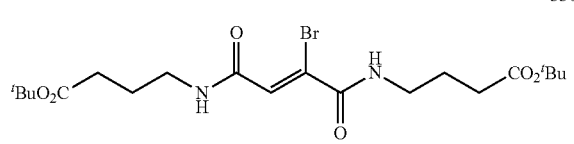

330 tert-Butyl 4-aminobutanoate (477 mg, 3 mmol) and 2,3-dibromosuccinic acid (414 mg, 1.5 mmol) was dissolved in DCM (35 mL), to which DIPEA (1.16 g, 9 mmol) and EDC (0.86 g, 4.5 mmol) were added. The resulting solution was stirred at r.t. overnight and then washed with brine, dried over Na₂SO₄. Filtration, concentration and purification by column chromatography (pure DCM to 10% MeOH/DCM) yielded compound 330 (160 mg, 22% yield). MS ESI m/z calcd for $C_{20}H_{34}BrN_2O_6$ [M+H]⁺ 477.15, found 477.16.

Example 83. Synthesis of Compound 331

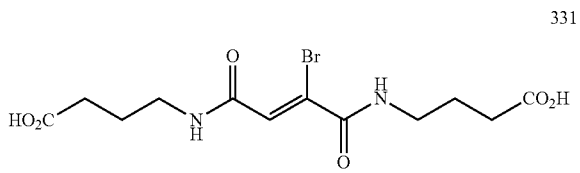 [SMILES: O=C(O)CCCNC(=O)/C=C(\Br)C(=O)NCCCC(=O)O]

331

Compound 330 (80 mg, 0.168 mmol) was dissolved in DCM (5 mL) and treated with formic acid (8 mL) at 38° C. overnight. All volatiles were removed under vacuum to afford compound 331 (61 mg, 99% yield). MS ESI m/z calcd for $C_{12}H_{18}BrN_2O_6$ [M+H]⁺ 365.03, found 365.05.

Example 84. Synthesis of Compound 332

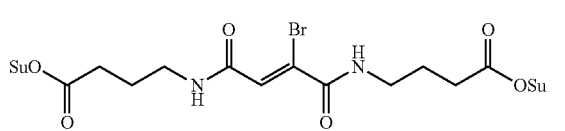

332

NHS (60 mg, 0.504 mmol) and EDCI (97 mg, 0.504 mmol) were added to a solution of compound 331 (61 mg, 0.168 mmol) in DCM (10 mL). After stirring at r.t. overnight, the reaction mixture was concentrated and purified by column chromatography (0 to 10% MeOH/DCM) to afford compound 332 (72 mg, 77% yield). MS ESI m/z calcd for $C_{20}H_{24}BrN_4O_{10}$ [M+H]$^+$ 559.06, found 559.78.

Example 85. Synthesis of Compound 333

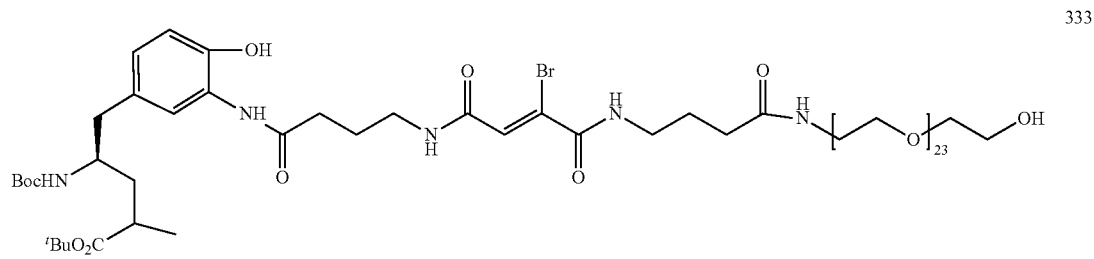

333

NaH$_2$PO$_4$ (0.1M in water, 1 mL) was added to a solution of compound 332 (36 mg, 0.065 mmol) and compound 110 (25 mg, 0.063 mmol) in EtOH (5 mL). The resulting solution was stirred at r.t. overnight and then HO-(PEG)$_{24}$-NH$_2$ (95 mg) was added to the mixture and stirred at r.t. overnight. All volatiles were removed under vacuum and the residue was purified by column chromatography (0 to 10% MeOH/DCM) to yield compound 333 (28 mg, 24% yield). MS ESI m/z 1798.93 ([M+H]$^+$).

Example 86. Synthesis of Compound 335

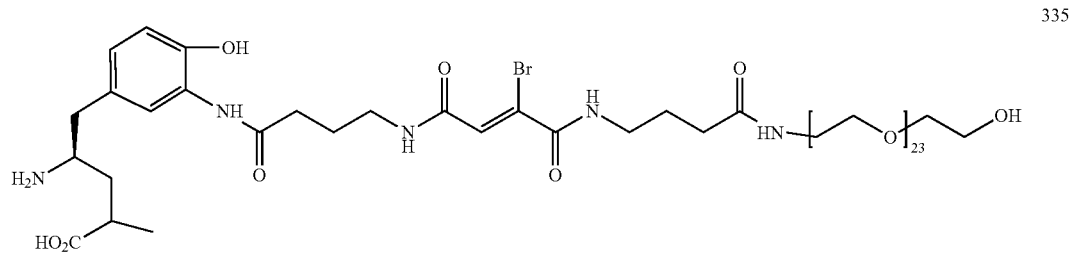

335

Compound 333 (28 mg, 0.0156 mmol) was dissolved in DCM (2 mL) and treated with TFA (2 mL) at r.t. for 2 h. All volatiles were removed under vacuum to afford compound 335 (25 mg, 98% yield), which was use directly in the next step. MS ESI m/z 1642.82 ([M+H]$^+$).

Example 87. Synthesis of Compound 337

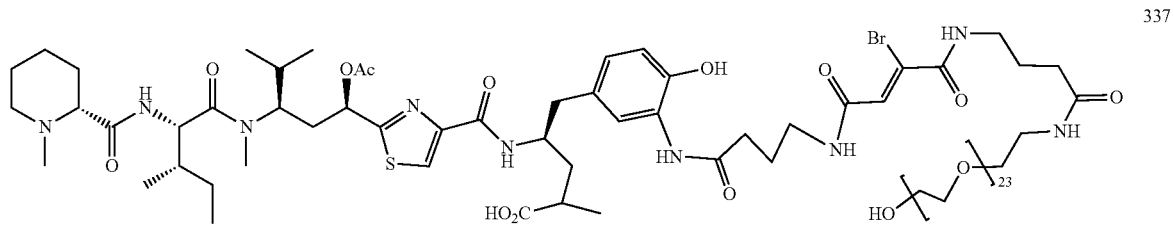

337

Compound 335 (25 mg, 0.0152 mmol) and perfluorophenyl ester 33a (15 mg, 0.0213 mmol) were dissolved in DMA (5 mL). To the mixture, DIPEA (10 mg, 0.077 mmol) was added. The resulting mixture was stirred at r.t. overnight, concentrated and purified by preparative HPLC (Cis column, 10-90% MeCN/H$_2$O) to afford compound 337 (13 mg, 40% yield). MS ESI m/z 2163.82 ([M+H]$^+$).

Example 88. Synthesis of Compound 341

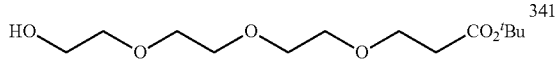 [SMILES: CC(C)(C)OC(=O)CCOCCOCCOCCO]

To a solution of 2,2'-(ethane-1,2-diylbis(oxy))diethanol (55.0 mL, 410.75 mmol, 3.0 eq.) in anhydrous THF (200 mL) was added sodium (0.1 g). The mixture was stirred until Na disappeared and then tert-butyl acrylate (20.0 mL, 137.79 mmol, 1.0 eq.) was added dropwise. The mixture was stirred overnight and then quenched by HCl solution (20.0 mL, 1N) at 0° C. THF was removed by rotary evaporation, brine (300 mL) was added and the resulting mixture was extracted with EtOAc (3×100 mL). The organic layers were washed with brine (3×300 mL), dried over anhydrous Na$_2$SO$_4$, filtered and concentrated to afford a colorless oil (30.20 g, 79.0% yield), which was used without further purification. MS ESI m/z calcd for C$_{13}$H$_{27}$O$_6$ [M+H]$^+$ 278.1729, found 278.1730.

Example 89. Synthesis of Compound 342

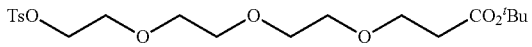

To a solution of tert-butyl 3-(2-(2-(2-hydroxyethoxy)ethoxy)ethoxy) propanoate (30.20 g, 108.5 mmol, 1.0 eq.) and TsCl (41.37 g, 217.0 mmol, 2.0 eq.) in anhydrous DCM (220 mL) at 0° C. was added TEA (30.0 mL, 217.0 mmol, 2.0 eq.). The mixture was stirred at room temperature overnight, and then washed with water (3×300 mL) and brine (300 mL), dried over anhydrous Na$_2$SO$_4$, filtered, concentrated and purified by SiO$_2$ column chromatography (3:1 hexanes/EtOAc) to give a colorless oil (39.4 g, 84.0% yield). MS ESI m/z calcd for C$_{20}$H$_{33}$O$_8$S [M+H]$^+$433.1818, found 433.2838.

Example 90. Synthesis of Compound 343

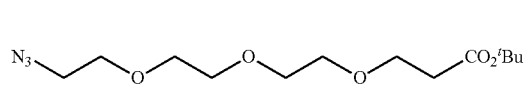

To a solution of tert-butyl 3-(2-(2-(2-(tosyloxy)ethoxy)ethoxy)ethoxy) propanoate (39.4 g, 91.1 mmol, 1.0 eq.) in anhydrous DMF (100 mL) was added NaN$_3$ (20.67 g, 316.6 mmol, 3.5 eq.).

The mixture was stirred at room temperature overnight. Water (500 mL) was added and extracted with EtOAc (3×300 mL). The combined organic layers were washed with water (3×900 mL) and brine (900 mL), dried over anhydrous Na$_2$SO$_4$, filtered, concentrated and purified by SiO$_2$ column chromatography (5:1 hexanes/EtOAc) to give a light yellow oil (23.8 g, 85.53% yield). MS ESI m/z calcd for C$_{13}$H$_{25}$O$_3$N$_5$Na [M+Na]$^+$326.2, found 326.2.

Example 91. Synthesis of Compound 344

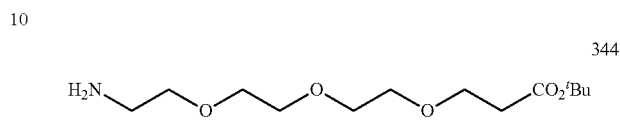

Raney-Ni (7.5 g, suspended in water) was washed with water (three times) and isopropyl alcohol (three times) and mixed with compound 343 (5.0 g, 16.5 mmol) in isopropyl alcohol. The mixture was stirred under a H$_2$ balloon at r.t. for 16 h and then filtered over a Celite pad, with washing of the pad with isopropyl alcohol. The filtrate was concentrated and purified by column chromatography (5-25% MeOH/DCM) to give a light yellow oil (2.60 g, 57% yield). MS ESI m/z calcd for C$_{13}$H$_{28}$NO$_5$ [M+H]$^+$ 279.19; found 279.19.

Example 92. Synthesis of Compound 345

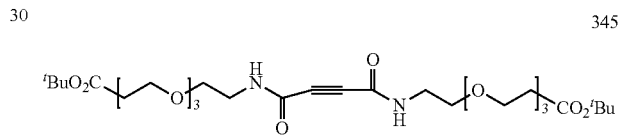

Acetylenedicarboxylic acid (0.35 g, 3.09 mmol, 1.0 eq.) was dissolved in NMP (10 mL) and cooled to 0° C., to which compound 344 (2.06 g, 7.43 mmol, 2.4 eq.) was added, followed by DMTMM (2.39 g, 8.65 mmol, 2.8 eq.) in portions. The reaction was stirred at 0° C. for 6 h and then diluted with ethyl acetate and washed with water and brine. The organic solution was concentrated and triturated with a mixture solvent of ethyl acetate and petroleum ether. The solid was filtered off and the filtrate was concentrated and purified by column chromatography (80-90% EA/PE) to give a light yellow oil (2.26 g, >100% yield), which was used without further purification. MS ESI m/z calcd for C$_{30}$H$_{53}$N$_2$O$_{12}$ [M+H]$^+$ 633.35; found 633.30.

Example 93. Synthesis of Compound 346

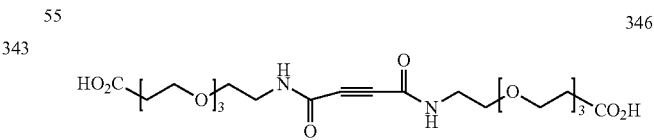

Compound 345 (2.26 g) was dissolved in dichloromethane (15 mL) and cooled to 0° C. then treated with TFA (15 mL). The reaction was warmed to r.t. and stirred for 45 min, and then the solvent and residual TFA was removed on rotovap. The crude product was purified by column chromatography (0-15% MeOH/DCM) to give a light yellow oil (1.39 g, 86% yield for two steps). MS ESI m/z calcd for $C_{22}H_{37}N_2O_{12}$ [M+H]$^+$ 521.23; found 521.24.

Example 94. Synthesis of Compound 380

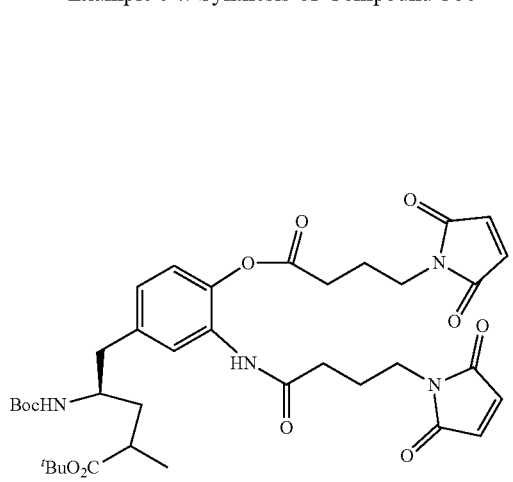

Compound 110 (68 mg, 0.17 mmol), compound 124 (94.5 mg, 0.52 mmol) and HATU (162 mg, 0.425 mmol) were dissolved in DCM (50 mL). TEA (73 ul, 0.52 mmol) was then added. The reaction mixture was stirred at r.t. overnight. Then the solvent was removed under reduced pressure and the residue was purified by SiO$_2$ column to give the title product 380 (98 mg, 80% yield). ESI m/z calcd for $C_{37}H_{49}N_4O_{11}$ [M+H]$^+$: 725.33, found 725.34.

Example 95. Synthesis of Compound 381

Example 96. Synthesis of Compound 384

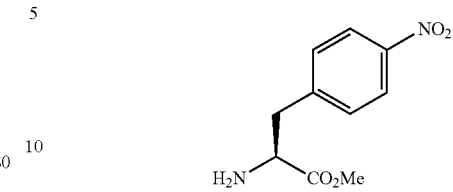

To a solution of (S)-2-amino-3-(4-nitrophenyl)propanoic acid (13.2 g, 62.8 mmol) in methanol (120 mL) was added thionyl chloride (9 mL, 125.6 mmol) at 0° C. The reaction mixture was heated to reflux and stirred for 1 h, then concentrated under vacuum and suspended in ethyl acetate (50 mL). The mixture was then filtered to afford the title compound as a white solid (14.5 g, 91% yield). ESI m/z calcd for $C_{10}H_{13}N_2O_4$ [M+H]$^+$: 225.08, found 225.08.

Example 97. Synthesis of Compound 385

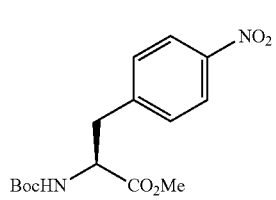

Compound 380 (98 mg, 0.135 mmol) dissolved in DCM (1.0 mL) was treated with TFA (1.0 mL) at r.t. for 2h, then concentrated and redissolved in DMA (1 mL), to which pentafluorophenyl ester 41a (44 mg, 0.06 mmol) and DIPEA (45.8 μL, 0.27 mmol) were added. The reaction was stirred overnight and then concentrated. The residue was purified by prep-HPLC with a gradient of MeCN/H$_2$O to give the title product 381 (37 mg, 55% yield). ESI m/z calcd for $C_{53}H_{73}N_8O_{14}S$ [M+H]$^+$: 1077.49, found 1077.50.

To a solution of compound 384 (9.5 g, 36.4 mmol) in THF (200 mL) was added triethylamine (12.6 mL, 91.1 mmol). After the mixture was stirred for 30 minutes, di-tert-butyl dicarbonate (12.5 mL, 54.7 mmol) was added, and the reaction mixture was stirred for 1 h, then diluted with ethyl acetate (200 mL), washed with 1 N HCl (30 mL), water (30 mL), dried over sodium sulfate, filtered and concentrated under vacuum to afford the title compound as a white solid (11.4 g, 97% yield). ESI m/z calcd for $C_{15}H_{21}N_2O_6$ [M+H]$^+$: 325.13, found 325.13.

Example 98. Synthesis of Compound 386

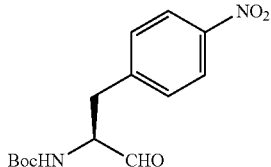

386

To a solution of compound 385 (14 g, 43.2 mmol) in anhydrous dichloromethane (150 mL) was added DIBAL-H (108 mL, 108 mmol) at −78° C. The reaction mixture was stirred at −78° C. for 30 min., then poured into ice water (200 mL), extracted with ethyl acetate (3×80 mL). The combined organic phase was washed with 1N HCl (2×50 mL), water (50 mL), dried over sodium sulfate, filtered, concentrated under vacuum, and purified by silica gel column chromatography to afford the title compound (8.6 g, 68% yield). ESI m/z calcd for $C_{14}H_{19}N_2O_5$ [M+H]$^+$: 295.12, found 295.12.

Example 99. Synthesis of Compound 387

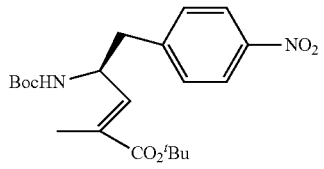

387

To a solution of compound 106 (8.1 g, 20.8 mmol) in DCM (100 mL) was added compound 386 (5.2 g, 17.8 mmol) at 0° C. The reaction mixture was warmed to r.t. and stirred for 30 min. then concentrated under vacuum and purified by silica gel column to afford the title compound as a yellow solid (5.9 g, 82% yield). ESI m/z calcd for $C_{21}H_{31}N_2O_6$ [M+H]$^+$: 406.21, found 406.21.

Example 100. Synthesis of Compound 388

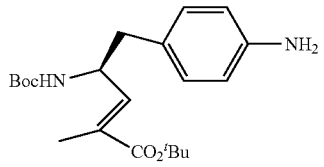

388

To a solution of compound 387 (4 g, 9.85 mmol) in MeOH (40 mL) was added Pd/C (0.4 g, 10 wt %) in a hydrogenation bottle. The mixture was stirred under 1 atm H$_2$ overnight, filtered through Celite (filter aid), and the filtrate was concentrated to afford compound 388 (3.6g, yield-100%). ESI m/z: calcd for $C_{21}H_{35}N_2O_4$ [M+H]$^+$: 379.25, found 379.25.

Example 101. Synthesis of Compound 389

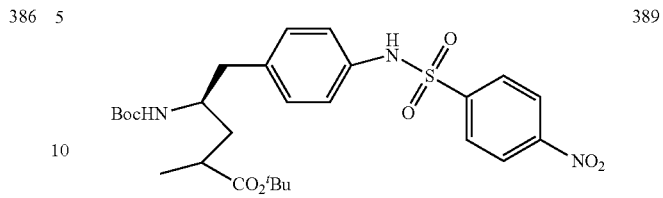

389

To a solution of compound 388 (3.6 g, 9.52 mmol) and triethylamine (1.3 mL, 9.52 mmol) in dichloromethane (50 mL) was added 4-nitrobenzenesulfonyl chloride (2.1 g, 9.52 mmol) at 0° C. The reaction mixture was warmed to r.t. and stirred for 1 h, then diluted with DCM (50 mL), washed with 1N HCl (20 mL), water (20 mL), dried over sodium sulfate, filtered and concentrated under vacuum, then purified by silica gel column chromatography to afford the title compound as a yellow solid (4 g, 75% yield). ESI m/z calcd for $C_{27}H_{38}N_3O_8S$ [M+H]$^+$: 564.23, found 564.23.

Example 102. Synthesis of Compound 390

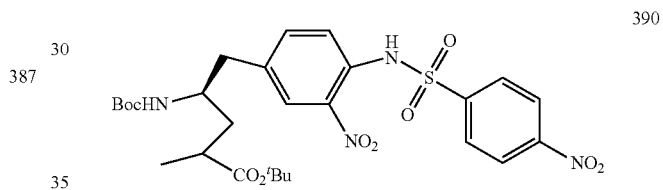

390

To a solution of compound 389 (3.6 g, 6.39 mmol) in acetonitrile (40 mL) was added tert-butyl nitrite (2.29 mL, 19.1 mmol). The reaction mixture was warmed to 45° C. and stirred for 6 hours. The reaction was then concentrated under vacuum and purified by silica gel column chromatography to afford the title compound (3 g, 79% yield). ESI m/z calcd for $C_{27}H_{37}N_4O_{10}S$ [M+H]$^+$: 609.22, found 609.22.

Example 103. Synthesis of Compound 391

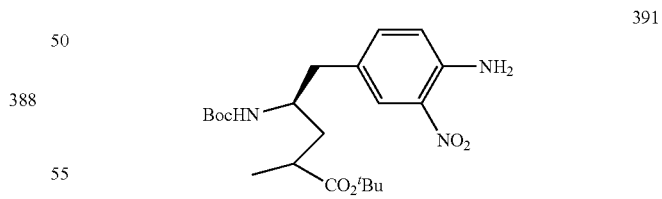

391

To a solution of compound 390 (3.0 g, 4.92 mmol) in acetonitrile/DMSO (30 mL/1 mL) were added 4-methoxy thiophenol (2.76 g, 19.7 mmol) and potassium carbonate (2.7 g, 19.7 mmol). The reaction mixture was stirred at the room temperature overnight, then diluted with ethyl acetate (100 mL), washed with water (20 mL), brine (20 mL), dried over sodium sulfate, filtered and concentrated under vacuum, and purified by silica gel column chromatography to afford the title compound (1.7 g, 85% yield). ESI m/z calcd for $C_{21}H_{34}N_3O_6$ [M+H]$^+$: 424.24, found 424.24.

Example 104. Synthesis of Compound 392

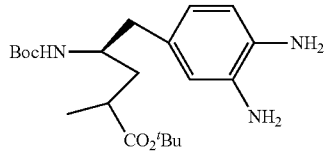

392

To a solution of compound 391 (100 mg, 0.236 mmol) in MeOH (4 mL) was added Pd/C (10 mg, 10 wt %) in a hydrogenation bottle. The mixture was stirred under 1 atm H$_2$ overnight, filtered through Celite (filter aid), and the filtrate was concentrated to afford the title compound (92.9 mg, ~100% yield). ESI m/z calcd for C$_{21}$H$_{36}$N$_3$O$_4$ [M+H]$^+$: 394.26, found 394.26.

Example 105. Synthesis of Compound 393

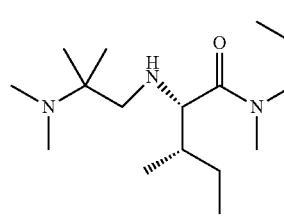

393

Compound 392 (66 mg, 0.17 mmol), compound 124 (94.5 mg, 0.52 mmol) and HATU (162 mg, 0.425 mmol) were dissolved in DCM (50 mL). TEA (73 ul, 0.52 mmol) was then added. The reaction mixture was stirred at r.t. overnight, the solvent was removed under reduced pressure and the residue was purified by SiO$_2$ column to give the title product 393 (98 mg, 80% yield). ESI m/z calcd for C$_{37}$H$_{50}$N$_5$O$_{10}$ [M+H]$^+$: 724.35, found 724.35.

Example 106. Synthesis of Compound 394

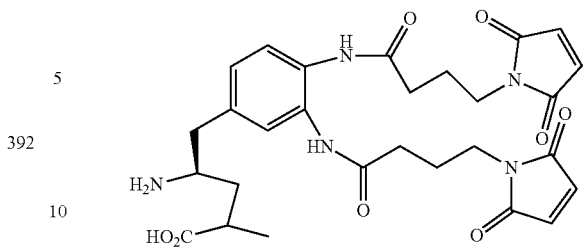

394

Compound 393 (98 mg, 0.135 mmol) dissolved in DCM (1.0 mL) was treated with TFA (1.0 mL) at r.t. for 2 h, then concentrated to give compound 394, which was used in the next step without further purification.

Example 107. Synthesis of Compound 395

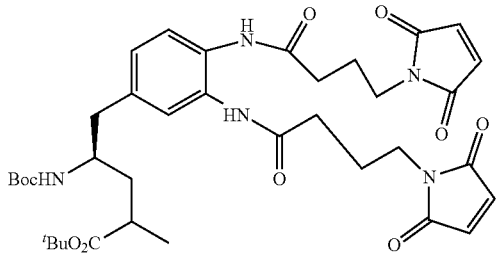

395

To a solution of compound 394 (76.9 mg, 0.135 mmol) in DMA (1 mL) was added pentafluorophenyl ester 41a (44 mg, 0.06 mmol) and DIPEA (45.8 µL, 0.27 mmol). The reaction was stirred overnight, then concentrated and the residue was purified by prep-HPLC with a gradient of MeCN/H$_2$O to give the title product 395 (37 mg, 55% yield). ESI m/z calcd for C$_{53}$H$_{74}$N$_9$O$_{13}$S [M+H]$^+$: 1076.50, found 1076.50.

Example 108. Synthesis of Compound 409

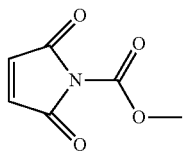

409

To a solution of maleimide (6.35 g, 65.4 mmol, 1.0 eq.) in EtOAc (120 mL) were added N-methyl morpholine (8.6 mL, 78.5 mmol, 1.2 eq.) and methyl chloroformate (6.0 mL, 78.5 mmol, 1.2 eq.) at 0° C. The reaction was stirred at 0° C. for 30 min and r.t. 1 h. The solid was filtered off and filtrate concentrated. The residue was dissolved in CH$_2$Cl$_2$ and filtered through a silica gel plug and eluated with CH$_2$Cl$_2$ to remove the color. The appropriate fractions were concentrated and resulted solid was triturated with 10% EtOAc/PE to give a white solid (9.00 g, 89% yield).

Example 109. Synthesis of Compound 410

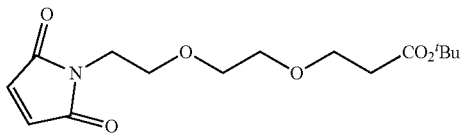

A mixture of compound 301 (8.16 g, 35.0 mmol, 1.0 eq.) and saturated NaHCO$_3$ (40 mL) was cooled to 0° C., to which compound 409 (5.43 g, 35.0 mmol, 1.0 eq.) was added in portions.

After stirring at 0° C. for 1 h, the reaction was warmed to r.t. and stirred for 1 h. The reaction was extracted with DCM (3×100 mL) and the organic extract was washed with brine, dried over anhydrous Na$_2$SO$_4$, concentrated and purified by SiO$_2$ column chromatography to give a white solid (6.76 g, 62% yield). MS ESI m/z calcd for C$_{15}$H$_{23}$NO$_6$ [M+H]$^+$ 314.15, found 314.15.

Example 110. Synthesis of Compound 411

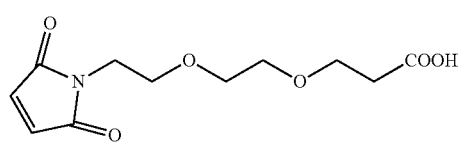

A solution of compound 410 (1.85 g, 5.9 mmol) was dissolved in DCM (20 mL) and treated with TFA (7 mL) at r.t. for 16 h, then concentrated and purified by SiO$_2$ column chromatography (11:1 DCM/MeOH) to give a white foam (1.47 g, 97% yield). MS ESI m/z calcd for C$_{11}$H$_{15}$NO$_6$ [M+H]$^+$ 258.09, found 258.09.

Example 111. Synthesis of Compound 412

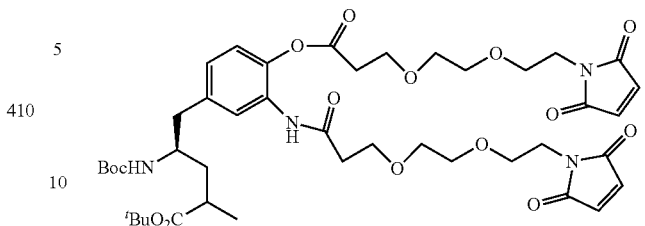

Compound 110 (100 mg, 0.25 mmol), compound 411 (65 mg, 0.25 mmol) and HATU (190 mg, 0.5 mmol) were dissolved in DCM (50 ml). TEA (73 μL, 0.5 mmol) was added and the reaction mixture was stirred at r.t. overnight. Then the solvent was removed under reduced pressure and the residue was purified by SiO$_2$ column to give the title product 412 (164 mg, 75% yield). ESI m/z calcd for C$_{43}$H$_{61}$N$_4$O$_{15}$ [M+H]$^+$: 873.41, found 873.41.

Example 112. Synthesis of Compound 413

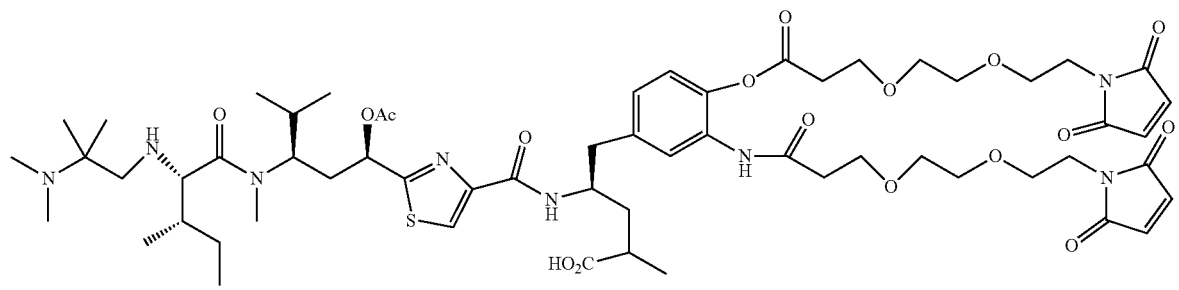

Compound 412 (52.4 mg, 0.06 mmol) dissolved in DCM (1.0 mL) was treated with TFA (1.0 mL) at r.t. for 2h, then concentrated and re-dissolved in DMA (1 mL), to which pentafluorophenyl ester 41a (44 mg, 0.06 mmol) and DIPEA (34 μL, 0.20 mmol) were added. The reaction was stirred overnight and then concentrated. The residue was purified by prep-HPLC with a gradient of MeCN/H$_2$O to give the title product 413 (33 mg, 45% yield). ESI m/z calcd for C$_{59}$H$_{85}$N$_8$O$_{18}$S [M+H]$^+$: 1225.56, found 1225.55.

Example 113. Synthesis of Compound 415

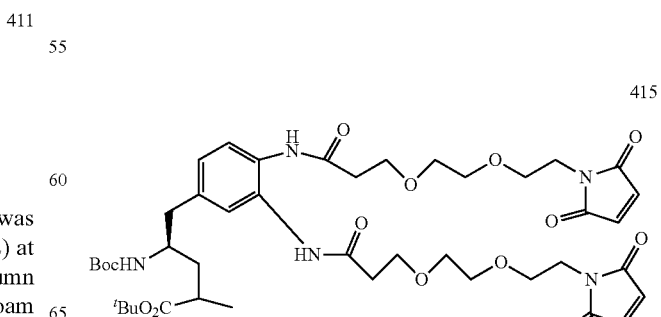

Compound 392 (98 mg, 0.25 mmol), compound 411 (130 mg, 0.5 mmol) and HATU (190 mg, 0.5 mmol) were dissolved in DCM (50 ml). TEA (73 µL, 0.5 mmol) was added and the reaction mixture was stirred at r.t. overnight. The reaction solvent was removed under reduced pressure and the residue was purified by SiO$_2$ column to give the title product 415 (163 mg, 75% yield). ESI m/z calcd for C$_{43}$H$_{62}$N$_5$O$_{14}$ [M+H]$^+$: 872.42, found 872.42.

Example 114. Synthesis of Compound 416

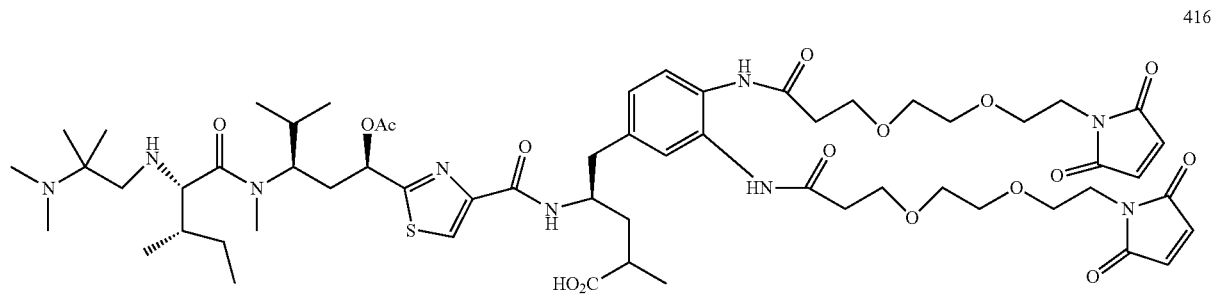 [SMILES: CC[C@H](C)[C@H](NCC(C)(C)N(C)C)C(=O)N(C)[C@H](C[C@@H](OC(C)=O)c1nc(C(=O)N[C@@H](Cc2ccc(NC(=O)CCOCCOCCN3C(=O)C=CC3=O)c(NC(=O)CCOCCOCCN3C(=O)C=CC3=O)c2)CC(C)C(=O)O)cs1)C(C)C]

416

Compound 415 (54.3 mg, 0.06 mmol) dissolved in DCM (1.0 mL) was treated with TFA (1.0 mL) at r.t. for 2 h, then concentrated and re-dissolved in DMA (1 mL), to which pentafluorophenyl ester 41a (44 mg, 0.06 mmol) and DIPEA (34 µL, 0.20 mmol) were added. The reaction was stirred overnight, then concentrated and the residue was purified by prep-HPLC with a gradient of MeCN/H$_2$O to give the title product 416 (33 mg, 45% yield). ESI m/z calcd for C$_{59}$H$_{86}$N$_9$O$_{17}$S [M+H]$^+$: 1224.58, found 1224.58.

Example 115. Synthesis of Compound 419

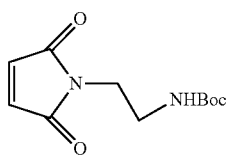

419

A mixture of N-Boc-ethylenediamine (5.6 mL, 35.4 mmol, 1.1 eq.) and saturated NaHCO$_3$ (60 mL) was cooled to 0° C., to which compound 409 (5.00 g, 32.2 mmol, 1.0 eq.) was added in portions. After stirring at 0° C. for 30 min, the reaction was warmed to r.t. and stirred for 1 h. The precipitate was collected by filtration and washed with cold water, then dissolved in EtOAc and washed with brine, dried over anhydrous Na$_2$SO$_4$ and concentrated to give a white solid (6.69 g, 87% yield).

Example 116. Synthesis of Compound 420

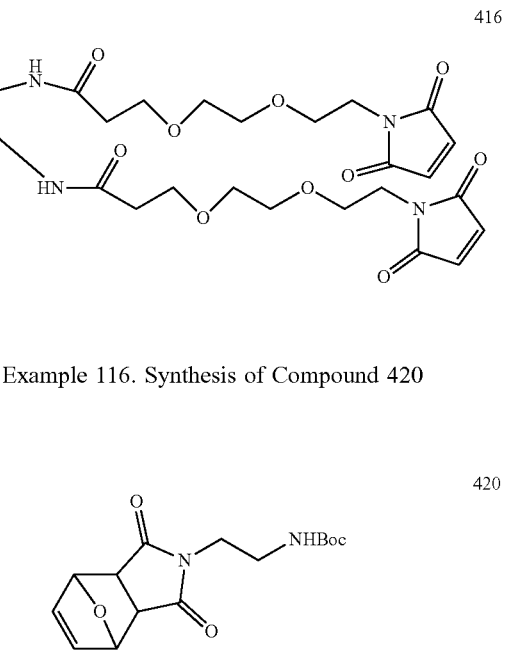

420

A solution of compound 419 (6.00 g, 25.0 mmol), furan (18.0 mL) in toluene (120 mL) in a high pressure tube was heated to reflux and stirred for 16 h. The colorless solution turned yellow during reaction. The mixture was then cooled to r.t. and concentrated. The resulting white solid was triturated with ethyl ether to give compound 420 (6.5 g, 84% yield).

Example 117. Synthesis of Compound 421

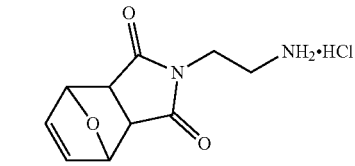

421

A solution of compound 420 (9.93 g, 32.2 mmol) was dissolved in dioxane (15 mL) and treated with concentrated HCl (15 mL) at r.t. for 3 h. The reaction was concentrated and the resulting solid was collected by filtration, with washing of the filter cake with EtOAc. The solid was dried in an oven (50° C.) overnight to give compound 421 (6.94 g, 88% yield).

Example 118. Synthesis of Compound 422

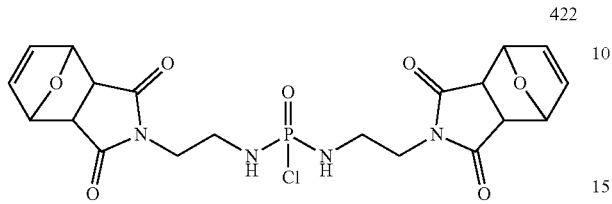

422

To a solution of compound 421 (0.85 g, 3.47 mmol) in THF (10 mL) was added POCl₃ (162 L, 1.73 mmol) at −10° C., followed by TEA (966 μL, 6.95 mmol). The reaction was stirred at −10° C. for 3h, and then the solution was diluted with DCM (20 mL) and filtered over Celite, the filtrate was concentrated to give compound 422, which was used in the next step directly. ESI m/z calcd for $C_{20}H_{23}C_1N_4O_7P$ [M+H]⁺: 497.09, found 497. 09.

Example 119. Synthesis of Compound 423

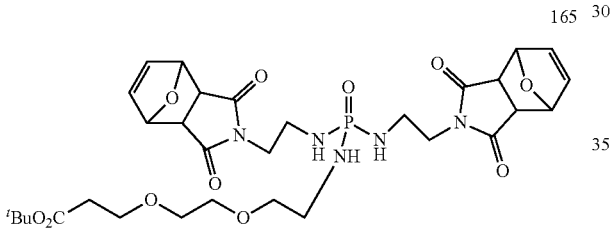

Compound 422 (0.50 g, 1.0 mmol) and DIPEA (0.4 mL, 2.4 mmol) were dissolved in DCM (5.0 mL) at 0° C., and then compound 301 (0.23 g, 1.0 mmol) was added. The reaction was stirred at 0° C. for 2.5h, then concentrated and purified by SiO₂ column to give the title product 423 (0.30 g, 43%). ESI m/z calcd for $C_{31}H_{45}N_5O_{11}P$ [M+H]⁺: 694.28, found 694.28.

Example 120. Synthesis of Compound 424

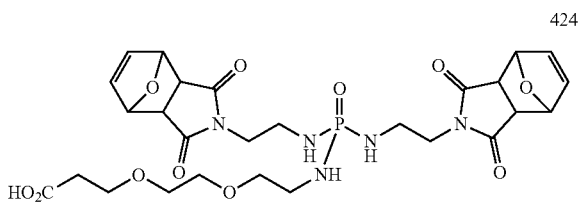 [SMILES: O=C(O)CCOCCOCCNP(=O)(NCCN1C(=O)C2C3C=CC(O3)C2C1=O)NCCN1C(=O)C2C3C=CC(O3)C2C1=O]

424

Compound 423 (0.30 g, 0.5 mmol) was dissolved in DCM (3 mL), and treated with TFA (3 mL) at r.t. for 2h, then concentrated to give compound 424, which was used in the next step without further purification.

Example 121. Synthesis of Compound 425

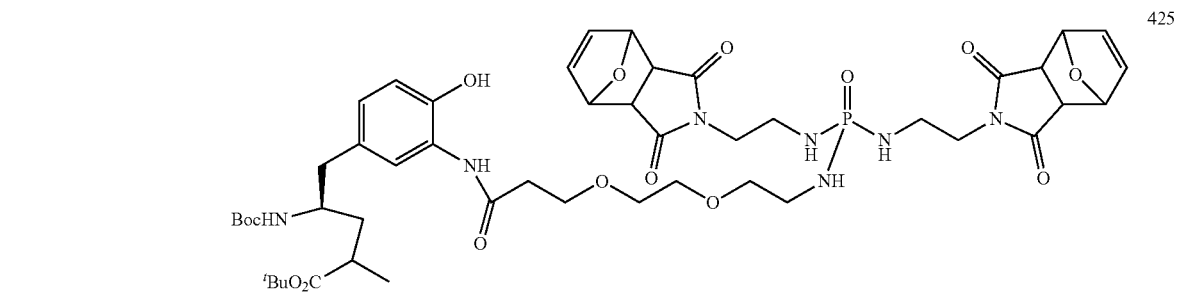 [SMILES: CC(C[C@H](Cc1ccc(O)c(NC(=O)CCOCCOCCNP(=O)(NCCN2C(=O)C3C4C=CC(O4)C3C2=O)NCCN2C(=O)C3C4C=CC(O4)C3C2=O)c1)NC(=O)OC(C)(C)C)C(=O)OC(C)(C)C]

425

Compound 424 (40 mg, 0.063 mmol), compound 110 (40 mg, 0.10 mmol), HATU (24 mg, 0.063 mmol) were dissolved in DCM (5 mL), and then TEA (27.8 μL, 0.2 mmol) was added. The reaction mixture was stirred at r.t. overnight. Then the solvent was removed under reduced pressure and the residue was purified by SiO₂ column to give the title product 425 (53.4 mg, 84% yield). ESI m/z calcd for $C_{48}H_{69}N_7O_{15}P$ [M+H]⁺: 1014.45, found 1014.45.

Example 122. Synthesis of Compound 426

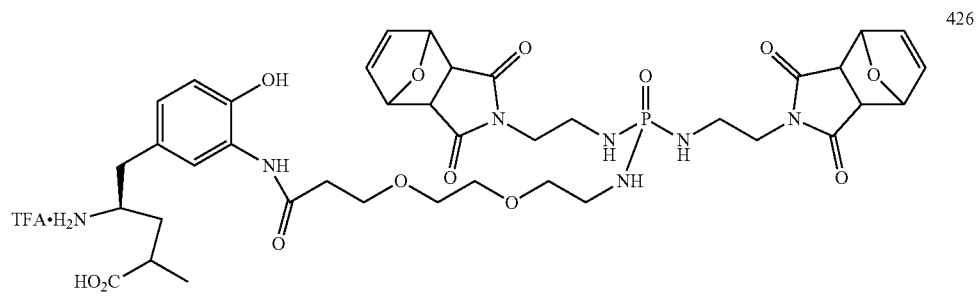

Compound 425 (53.4 mg, 0.053 mmol) was dissolved in DCM (2 mL), and treated with TFA (2 mL) at r.t. for 2 h, then concentrated to give compound 426, which was used in the next step without further purification.

Example 123. Synthesis of Compound 427

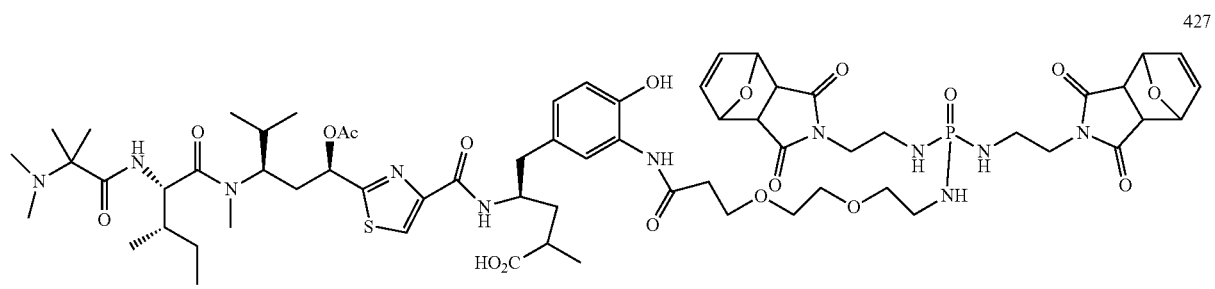 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCOCCOCCNP(=O)(NCCN3C(=O)C4C5C=CC(O5)C4C3=O)NCCN3C(=O)C4C5C=CC(O5)C4C3=O)c2)CC(C)C(=O)O)cs1)C(C)C]

To a solution of compound 426 (45.0 mg, 0.053 mmol) in DMA (1mL) were added pentafluorophenyl ester 41a (37.0 mg, 0.053 mmol) and DIPEA (17 μL, 0.1 mmol). The reaction was stirred overnight and concentrated. The residue was purified by prep-HPLC with a gradient of MeCN/H$_2$O to give the title product 427 (26.2 mg, 36% yield). ESI m/z calcd for $C_{64}H_{93}N_{11}O_{18}PS$ [M+H]$^+$: 1366.61, found 1366.61.

Example 124. Synthesis of Compound 428

Compound 427 (8.0 mg, 0.0058 mmol) was dissolved in toluene (5.0 mL) and heated to reflux overnight, then concentrated and purified by prep-HPLC with a gradient of MeCN/H$_2$O to give the title product 428 (6.4 mg, 90% yield). ESI m/z calcd for $C_{56}H_{85}N_{11}O_{16}PS$ [M+H]$^+$: 1230.56, found 1230.56.

Example 125. Synthesis of Compound 432

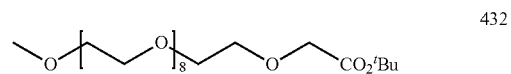

NaH (60%, 8.0 g, 200 mmol) was added to a solution of 2,5,8,11,14,17,20,23,26-nonaoxaoctacosan-28-ol (42.8 g, 100 mmol) in THF (1.0 L). After stirring at r.t. for 30 min,

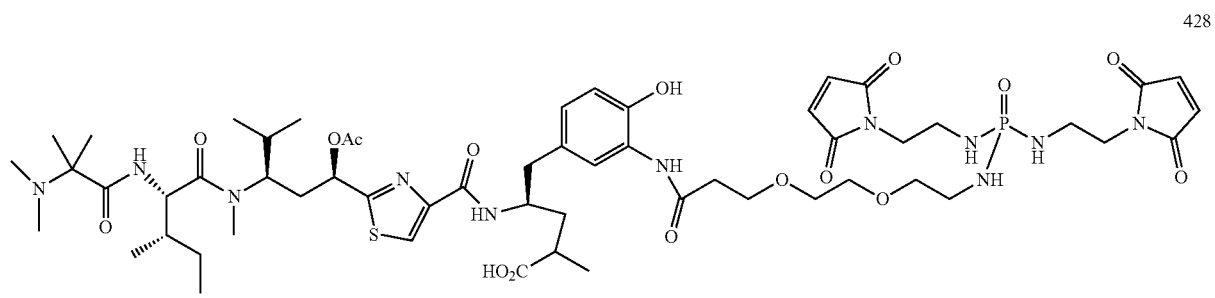 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCOCCOCCNP(=O)(NCCN3C(=O)C=CC3=O)NCCN3C(=O)C=CC3=O)c2)CC(C)C(=O)O)cs1)C(C)C]

tert-butyl 2-bromoacetate (48.8 g, 250 mmol) was added to the mixture, and stirred at r.t. for 1 h. The mixture was then poured onto ice water, extracted with DCM, and the organic layer was washed with brine, dried over anhydrous $Na_2SO_4$. Purification by column chromatography (0% to 5% MeOH: DCM) yielded compound 432 as a yellow oil(32 g, 59% yield).

Example 126. Synthesis of Compound 433

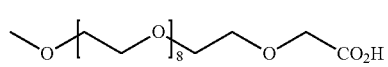

433

Compound 432 (40.0 g, 73.8 mmol) was dissolved in DCM (400 mL), and then formic acid (600 mL) was added. The resulting solution was stirred at 25° C. overnight. All volatiles were removed under vacuum, which afforded the title product as yellow oil (36.0 g, theoretical yield).

ESI m/z calcd for $C_{21}H_{43}O_{12}$ $[M+H]^+$: 487.27, found 487.24.

Example 127. Synthesis of Compound 434

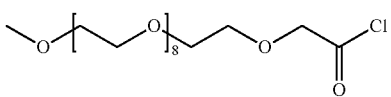

434

To the solution of compound 433 (36.0 g, 73.8 mmol) dissolved in DCM (640 mL), $(COCl)_2$ (100 mL) and DMF (52 g, 0.74 mmol) were added. The resulting solution was stirred at r.t. for 4 h. All volatiles were removed under vacuum to yield the title product as a yellow oil.

Example 128. Synthesis of Compound 436

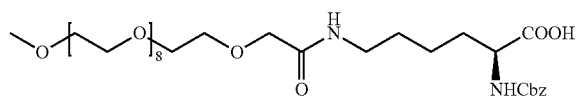

436

Z-L-Lys-OH (41.4 g, 147.6 mmol), $Na_2CO_3$ (23.4 g, 221.4 mmol) and NaOH (5.9 g, 147.6 mmol) were dissolved in water (720 mL). The mixture was cooled to 0° C., to which a solution of compound 434 (37.2 g, 73.8 mmol) in THF (20 mL) was added. The resulting mixture was stirred at r.t. for 1 h. THF was removed under vacuum, and concentrated HCl was added to the aqueous solution until pH reached 3 under ice cooling. After extraction with DCM, the organic layer was washed with brine, dried over $Na_2SO_4$ and concentrated to give the title product as yellow oil (55 g, 99% yield). ESI m/z calcd for $C_{35}H_{60}N_2O_{15}$ $[M+H]^+$: 749.40, found 749.39.

Example 129. Synthesis of Compound 437

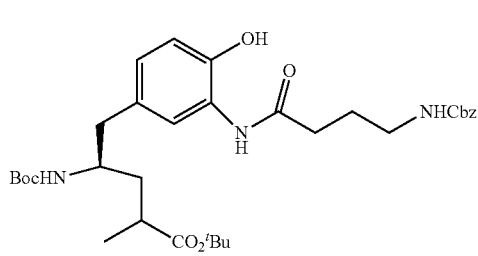

437

HATU (39.9 g, 105 mmol) was added to a solution of 4-(((benzyloxy)carbonyl)amino) butanoic acid (26.1 g, 110 mmol) in DMF (300 mL). After stirring at r.t. for 30 min, the mixture was added to a solution of compound 110 (39.4 g, 100 mmol) and TEA (20.2 g, 200 mmol) in DMF (300 mL). The resulting mixture was stirred at r.t. for 2 h. Water was then added, extracted with EtOAc, the organic layer was washed with brine, dried over $Na_2SO_4$. Purification by column chromatography (20% to 70% EA/PE) yielded the title product as a white solid (45 g, 73% yield).

ESI m/z calcd for $C_{33}H_{48}N_3O_8$ $[M+H]^+$: 614.34, found 614.15.

Example 130. Synthesis of Compound 438

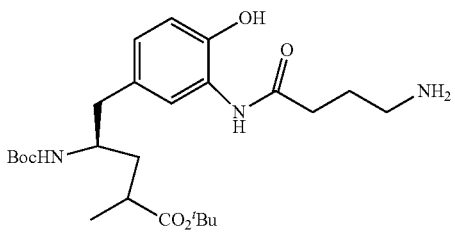

438

Compound 437 (100 g, 163 mmol) was dissolved in methanol (500 mL) and hydrogenated (1 atm) with Pd/C catalyst (10 wt %, 10 g) at r.t. overnight. The catalyst was filtered off and the filtrate were concentrated under reduced pressure to afford compound 438 (75.8 g, 97% yield) as a brown foamy solid. $^1$H NMR (400 MHz, $CDCl_3$) δ 7.11 (s, 1H), 6.83 (d, J=10.3 Hz, 2H), 5.04-4.52 (m, 6H), 3.90-3.56 (m, 1H), 2.81 (d, J=5.3 Hz, 2H), 2.63 (dd, J=12.5, 6.1 Hz, 2H), 2.54-2.26 (dd, J=14.0, 7.6 Hz, 4H), 1.94-1.64 (m, 3H), 1.44-1.36 (m, 18H), 1.08 (d, J=6.9 Hz, 3H). ESI m/z calcd for $C_{25}H_{42}N_3O_6$ $[M+H]^+$: 480.30, found 480.59.

Example 131. Synthesis of Compound 439

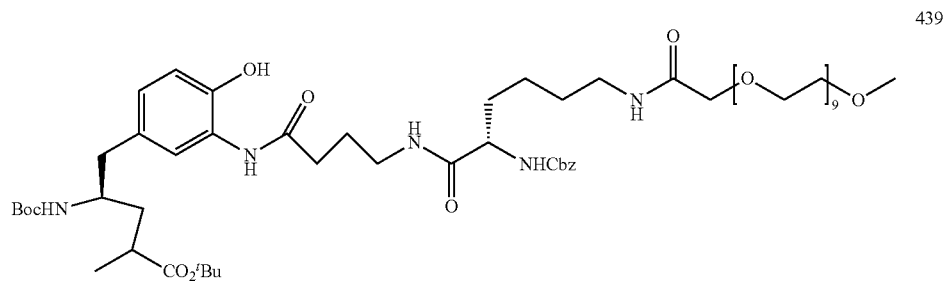

To a solution of compound 436 (130 g, 174 mmol, 1.1 eq.) in DMF (500 mL) were added TEA (66 mL, 474 mmol, 3 eq.) and HATU (72 g, 190 mmol, 1.2 eq.) in sequence at 0° C. Then the reaction mixture was warmed to r.t and stirred for 2 h. A solution of compound 438 (75.8 g, 158 mmol, 1.0 eq) in DMF (500 mL) was added to the above solution at 0° C., and the reaction mixture was stirred at r.t. for 1 h. The reaction mixture was poured into water (4 L), the aqueous layer was extracted with EtOAc (3×500 mL), and the organic layers were combined and washed with brine (2 L), dried over $Na_2SO_4$, concentrated and the crude product 439 (190 g) was used in the next step directly. ESI: m/z: calcd for $C_{60}H_{100}N_5O_{20}$ $[M+H]^+$: 1210.69, found 1210.69.

Example 132. Synthesis of Compound 440

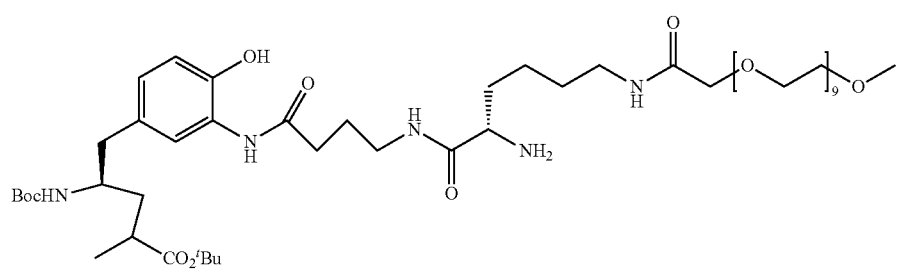

The crude product from previous reaction 439 (190 g) was dissolved in methanol (900 mL) and hydrogenated (1 atm) with Pd/C catalyst (10 wt %, 19 g) at r.t. overnight. The catalyst was filtered off and the filtrate were concentrated under reduced pressure, and the crude compound was purified by $SiO_2$ column with a gradient of DCM/MeOH to give the title product 440 (105 g 62% yield over two steps) as a brown oil. ESI m/z calcd for $C_{52}H_{95}N_5O_{18}$ $[M+H]^+$: 1077.65, found 1077.65.

Example 133. Synthesis of Compound 441

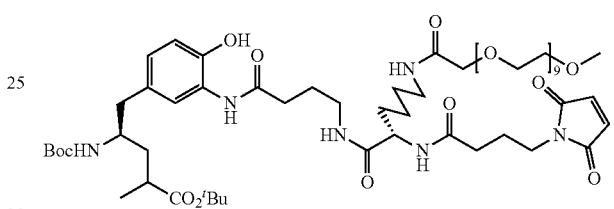

To a solution of compound 440 (105 g, 97.1 mmol, 1.0 eq.) in EtOH (5.3 L) was added compound 125 (54.4 g, 194.2 mmol, 2.0 eq) at r.t. Then 0.1M $NaH_2PO_4$ solution (1.1 L) was added, and the reaction mixture was stirred at r.t. overnight. EtOH was then evaporated under vacuum and the residue was poured onto water (3 L). The aqueous solution was extracted with EtOAc (4×500 mL), the organic layers were combined and washed with brine (2 L), dried over $Na_2SO_4$, concentrated and the crude product was purified by $SiO_2$ column with a gradient of DCM/MeOH to give the title compound 441 (100 g, 83% yield) as a yellow oil. $^1$H NMR (400 MHz, $CDCl_3$) δ 9.43 (s, 1H), 7.35 (s, 1H), 7.23 (t, J=5.1 Hz, 1H), 7.01 (d, J=4.5 Hz, 2H), 6.89 (s, 2H), 6.70 (s, 2H), 4.56-4.45 (m, 1H), 4.30 (t, J=9.7 Hz, 1H), 3.97 (s, 2H), 3.86-3.74 (m, 1H), 3.66-3.63 (m, 36H), 3.58-3.52 (m, 5H), 3.38 (s, 3H), 3.33-3.19 (m, 3H), 2.47 (d, J=6.2 Hz, 4H), 2.23 (dd, J=11.6, 6.1 Hz, 2H), 1.91 (dtd, J=26.8, 13.6, 6.5 Hz, 7H), 1.71 (d, J=7.7 Hz, 2H), 1.56-1.49 (m, 2H), 1.42 (s, 9H), 1.39 (s, 9H), 1.10 (d, J=6.5 Hz, 3H). ESI m/z calcd for $C_{60}H_{101}N_6O_{21}$ $[M+H]^+$: 1241.69, found 1241.69.

Example 134. Synthesis of Compound 442

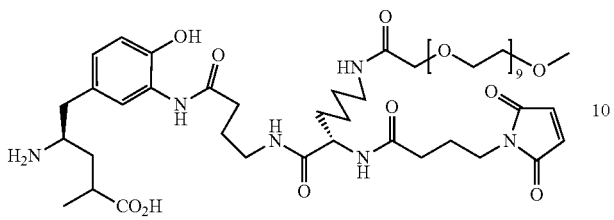

A solution of compound 441 (79.1 mg, 0.062 mmol) in DCM (2 mL) was treated with TFA (2 mL) at r.t. for 2 h then concentrated and co-evaporated with toluene to give a crude product 442, which was used directly in the next step.

Example 135. Synthesis of Compound 443

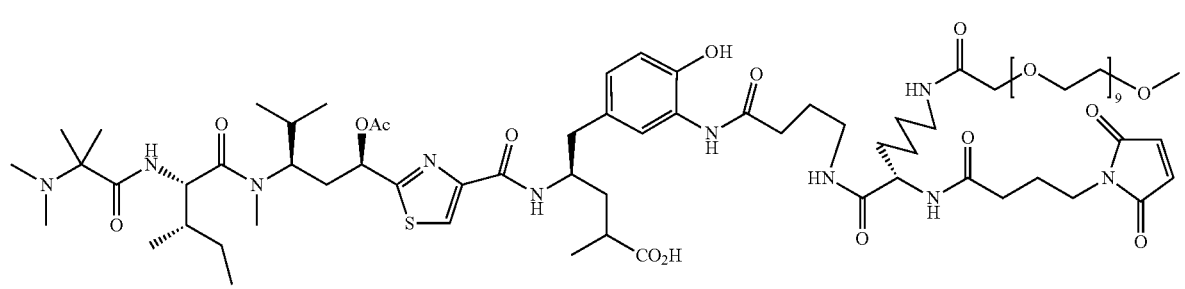

Compound 442 (67 mg, 0.062 mmol) and compound 41a (43 mg, 0.062 mmol) were dissolved in DMA (4 mL). And then DIPEA (43 µL, 0.248 mmol) was added. The resulting mixture was stirred at r.t. for 3 h. After the solvent was removed under vacuum, the residue was purified on preparative HPLC (Cis column, 10-90% MeCN/H$_2$O) to afford the title product 443 (59 mg, 60% yield). ESI m/z calcd for C$_{76}$H$_{125}$N$_{10}$O$_{24}$S [M+H]$^+$: 1594.92, found 1594.24.

Example 136. Synthesis of Compound 457

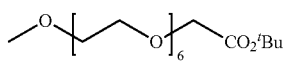

NaH (60%, 0.64 g, 16 mmol) was added to a solution of 2,5,8,11,14,17-hexaoxanonadecan-19-ol (2.37 g, 8 mmol) in THF (25 mL). After stirring at r.t. for 15 min, tert-butyl 2-bromoacetate (3.90 g, 20 mmol) was added and the reaction was stirred at r.t. overnight. The reaction mixture was poured onto ice water, extracted with DCM. The organic layer was washed with brine, dried over Na$_2$SO$_4$, purified by column chromatography (20% to 50% PE/EtOAc) to yield the title compound (1.47 g, 45%) as a colorless oil. ESI m/z calcd for C$_{19}$H$_{39}$O$_9$ [M+H]$^+$: 411.25, found 411.15.

Example 137. Synthesis of Compound 458

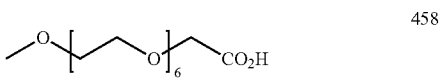

Compound 457 (1.47 g, 3.60 mmol) was dissolved in DCM (30 mL), and treated with formic acid (50 mL). The resulting solution was stirred at 38° C. overnight. All volatiles were removed under vacuum, which afforded the title compound (1.20 g, 94% yield) as a yellow oil.

ESI m/z calcd for C$_{15}$H$_{31}$O$_9$ [M+H]$^+$: 355.19, found 355.18.

Example 138. Synthesis of Compound 459

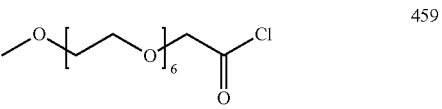

Compound 458 (1.10g, 3.20 mmol) was dissolved in DCM (20 mL), to the mixture, (COCl)$_2$ (4 mL) and DMF (3 drops) were added. The resulting solution was stirred at r.t. for 4 h. All volatiles were removed in vacuum to give the title compound as a yellow oil, which was used directly in the next step.

Example 139. Synthesis of Compound 460

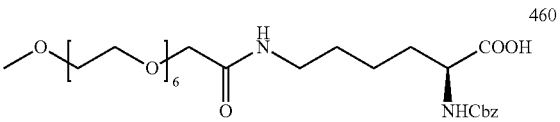

Z-L-Lys-OH (1.80 g, 6.4 mmol), Na$_2$CO$_3$ (1.00 g, 9.6 mmol) and NaOH (0.26 g, 6.4 mmol) were dissolved in water (30 mL) and cooled to 0° C., then a solution of compound 459 (1.20 g, 3.2 mmol) in THF (10 mL) was added. The resulting mixture was stirred at r.t. for 1 h. THF was removed under vacuum, and concentrated HCl was added to reach pH 3 under ice cooling. The solution was extracted with DCM, and the organic layer was washed with brine, dried over $Na_2SO_4$, concentrated to give the title compound (1.77 g, 90%) as a brown oil. ESI m/z calcd for $C_{29}H_{49}N_2O_{12}$ [M+H]$^+$: 617.32, found 617.31.

Example 140. Synthesis of Compound 461

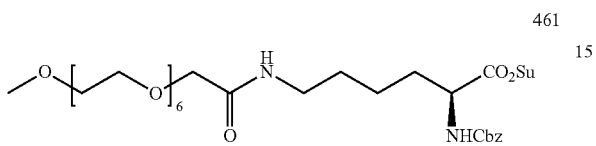

461

NHS (644 mg, 5.60 mmol) and EDC (1.08 g, 5.60 mmol) were added to a solution of compound 460 (2.30 g, 3.70 mmol) in DCM (100 mL). After stirring at r.t. overnight, the reaction mixture was loaded on silica gel column and purification by column chromatography (0% to 10% MeOH/DCM) yielded the title compound (2.10 g, 80% yield) as a brown oil. ESI m/z calcd for $C_{33}H_{52}N_3O_{14}$ [M+H]$^+$: 714.34, found 714.32.

Example 141. Synthesis of Compound 462

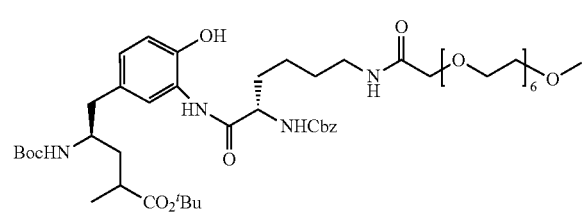

462

$NaH_2PO_4$ (0.1M, 3 mL) was added to a solution of compound 461 (357 mg, 0.50 mmol) and compound 110 (200 mg, 0.50 mmol) in EtOH (15 mL). The resulting solution was stirred at r.t. for 24 h. All volatiles were removed under vacuum, and the residue was purified by column chromatography (5% to 10% MeOH/DCM) to yield the title compound (216 mg, 44% yield) as a brown oil. ESI m/z calcd for $C_{50}H_{81}N_4O_{16}$ [M+H]$^+$: 993.56, found 993.57.

Example 142. Synthesis of Compound 463

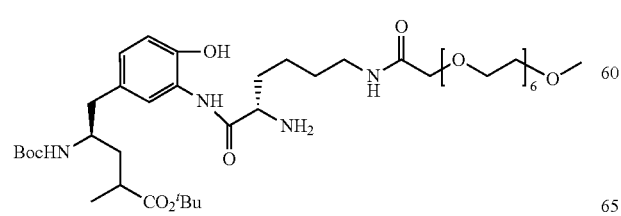

463

Compound 462 (108 mg, 0.109 mmol) was dissolved in MeOH (5 mL) and stirred with palladium catalyst (10% on carbon, 50 mg) under hydrogen atmosphere (1 atm) at r.t. for 3 h. The catalyst was filtered off and all volatiles were removed under vacuum, which afforded the title compound (94 mg, theoretical yield) as a yellow oil. ESI m/z calcd for $C_{42}H_{75}N_4O_{14}$ [M+H]$^+$: 859.52, found 859.93.

Example 143. Synthesis of Compound 464

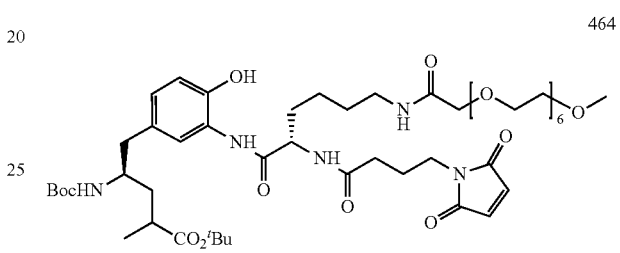

464

$NaH_2PO_4$ (0.1M, 2.0 mL) was added to a solution of compound 463 (94 mg, 0.109 mmol) and compound 125 (61 mg, 0.218 mmol) in EtOH (10 mL). The resulting solution was stirred at r.t. for 24 h. All volatiles were removed under vacuum, and purification by column chromatography (5% to 10% MeOH/DCM) yielded the title compound (40 mg, 36% yield) as a yellow oil. ESI m/z calcd for $C_{50}H_{82}N_5O_{17}$ [M+H]$^+$: 1024.56, found 1024.98.

Example 144. Synthesis of Compound 465

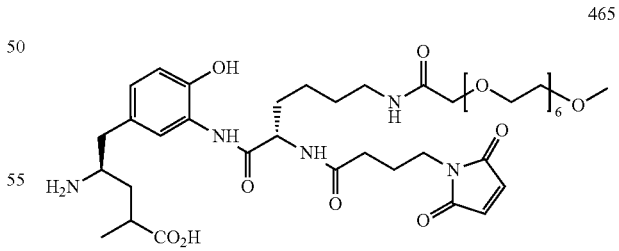

465

Compound 464 (20 mg, 0.0196 mmol) was dissolved in DCM (3 mL) and treated with TFA (3 mL) at r.t. for 2 h. All volatiles were removed in vacuum, which afforded the title compound (17.0 mg, theoretical yield) as a yellow oil. ESI m/z calcd for $C_{41}H_{66}N_5O_{15}$ [M+H]$^+$: 868.45, found 868.47.

Example 145. Synthesis of Compound 466

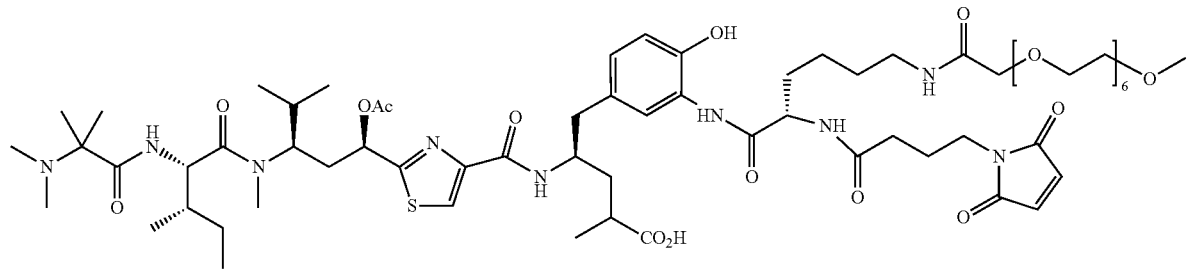

466

Compound 465 (17.0 mg, 0.0196 mmol) and compound 41a (14 mg, 0.0196 mmol) were dissolved in DMA (3 mL). To the mixture, DIPEA (10 µL, 0.0588 mmol) was added. The resulting mixture was stirred at r.t. for 3 h. The solvent was then removed under vacuum, and the residue was purified on preparative HPLC (Cis column, 10-90% MeCN/H$_2$O) to afford the title compound 466 (15 mg, 64% yield) as a yellow oil. ESI m/z calcd for $C_{66}H_{106}N_9O_{20}S$ [M+H]$^+$: 1376.72, found 1376.72.

Example 146. Synthesis of Compound 487

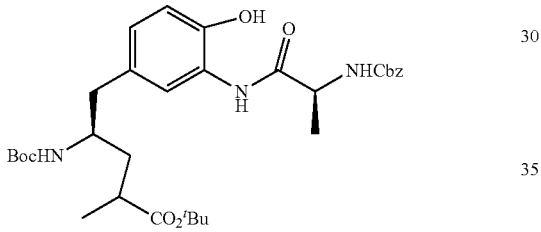

487

Compound 110 (0.30 g, 0.76 mmol), compound Z-L-Ala-OH (0.17 g, 0.76 mmol) and HATU (0.29 g, 0.76 mmol) were dissolved in DCM (20 mL), to which TEA (110 µL, 0.8 mmol) was added. The reaction mixture was stirred at r.t. overnight. Then the solvent was removed under reduced pressure and the residue was purified by SiO$_2$ column to give the title product 487 (0.43 g, 95% yield). ESI m/z calcd for $C_{32}H_{46}N_3O_8$ [M+H]$^+$: 600.32, found 600.32.

Example 147. Synthesis of Compound 488

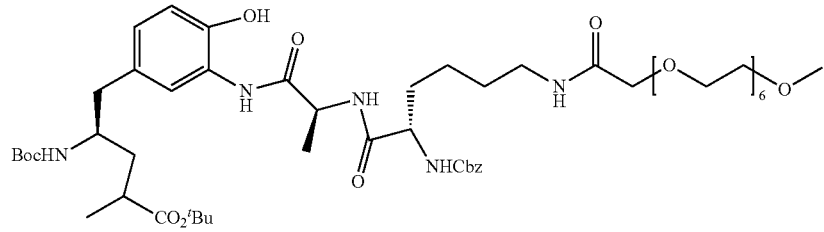

488

In a hydrogenation bottle, Pd/C (0.10 g, 33 wt %, 50% wet) was added to a solution of compound 487 (0.3 g, 0.5 mmol) in MeOH (10 mL). The mixture was shaken overnight under 1 atm H$_2$ then filtered through Celite (filter aid), the filtrate was concentrated and mixed with compound 461 (357 mg, 0.5 mmol) in EtOH (20 mL). NaH$_2$PO$_4$ (0.1M, 4 mL) was added and the resulting solution was stirred at r.t. for 24 h. All volatiles were removed under vacuum, and purification of the residue by column chromatography (5% to 10% MeOH/DCM) yielded the title compound (176 mg, 33%) as a yellow oil. ESI m/z calcd for $C_{53}H_{86}N_5O_{17}$ [M+H]$^+$: 1064.59, found 1064.60.

Example 148. Synthesis of Compound 489

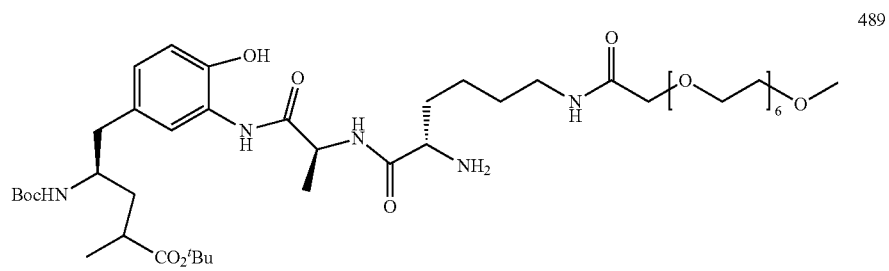

489

Compound 488 (176 mg, 0.166 mmol) was dissolved in MeOH (15 mL), and was hydrogenated (1 atm) with palladium catalyst (10%, 80 mg) at r.t. for 3h. The catalyst was filtered off and all volatiles were removed under vacuum, which afforded the title compound (154 mg, theoretical yield) as a yellow oil. ESI m/z calcd for $C_{45}H_{80}N_5O_{15}$ $[M+H]^+$: 930.56, found 930.56.

Example 149. Synthesis of Compound 490

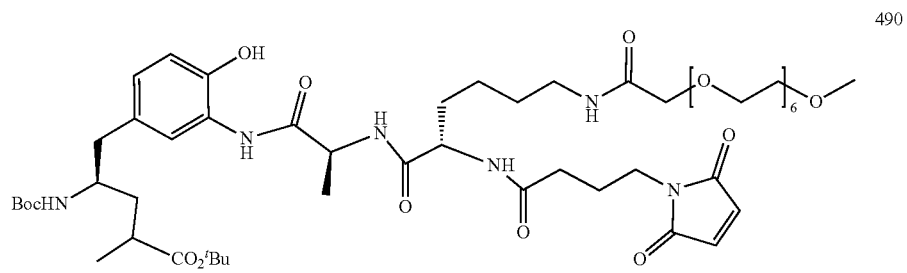

490

NaH$_2$PO$_4$ (0.1 M, 4 ml) was added to a solution of compound 489 (154 mg, 0.166 mmol) and compound 125 (93 mg, 0.332 mmol) in EtOH (20 mL). The resulting solution was stirred at r.t. for 24 h. All volatiles were removed under vacuum, purification by column chromatography (5% to 10% MeOH: DCM) yielded the title compound (117 mg, 64%) as a yellow oil. ESI m/z calcd for $C_{53}H_{87}N_6O_{18}$ $[M+H]^+$: 1095.60, found 1095.61.

Example 150. Synthesis of Compound 491

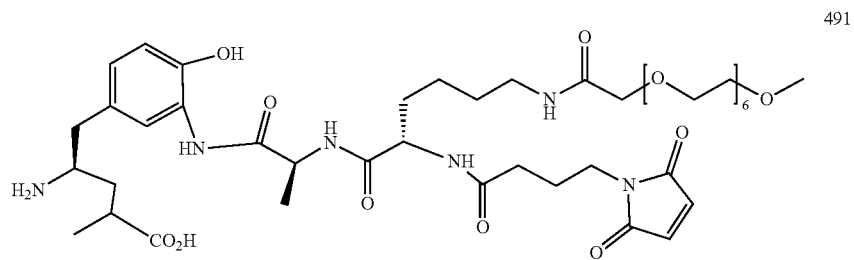

491

Compound 490 (39 mg, 0.0356 mmol) was dissolved in DCM (3 mL) and treated with TFA (3 mL) at r.t. for 2 h. All volatiles were removed under vacuum, which afforded the title compound (33 mg, theoretical yield) as a yellow oil. ESI m/z calcd for $C_{44}H_{71}N_6O_{16}$ $[M+H]^+$: 939.48, found 939.49.

Example 151. Synthesis of Compound 492

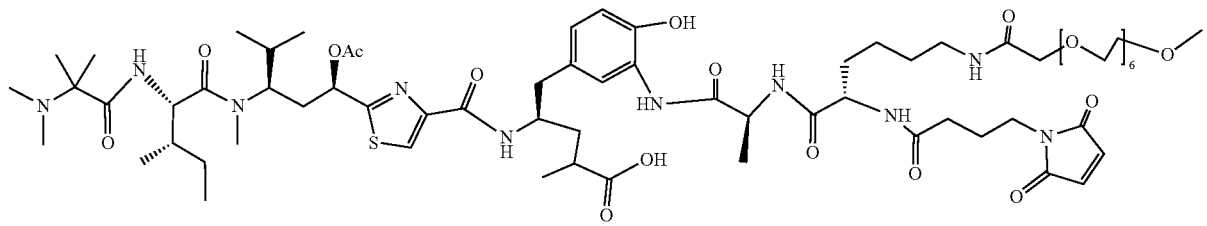
492

Compound 491 (33 mg, 0.0356 mmol) and compound 41a (25 mg, 0.0356 mmol) was dissolved in DMA (3 mL), to which DIPEA (15 mg, 0.116 mmol) was added. The resulting mixture was stirred at r.t. for 3 h. The solvent was removed under vacuum, and the residue was purified on preparative HPLC ($C_{18}$ column, 10-90% $MeCN/H_2O$) to afford the title compound 492 (17 mg, 33%) as a yellow oil. ESI m/z calcd for $C_{69}H_{111}N_{10}O_{21}S$ $[M+H]^+$: 1447.76, found 1448.78.

Example 152. Synthesis of Compound 495

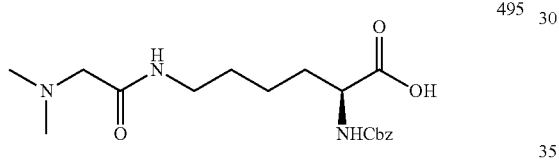
495

2-(Dimethylamino)acetic acid(0.60 g, 4.30 mmol) and HATU (1.08 g, 2.86 mmol) were dissolved in DMF (2 mL), to which TEA (1 mL, 7.16 mmol) was added. After stirring at r.t. for 1 h, a solution of Z-L-Lys-OH (0.80 g, 2.86 mmol) in DMF (2 mL) was added. The reaction mixture was stirred at r.t. for 2 h and then concentrated under reduced pressure. The residue was purified by prep-HPLC with a gradient of $MeCN/H_2O$ to give the title compound 495 (0.50 g, 50% yield) as a colorless oil. ESI m/z calcd for $C_{18}H_{28}N_3O_5$ $[M+H]^+$:366.20, found 366.20.

Example 153. Synthesis of Compound 496

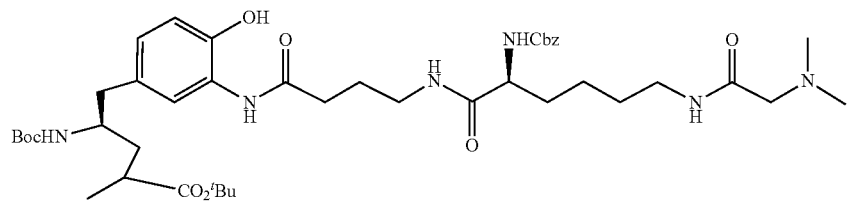
496

To a solution of carboxylic acid 495 (0.50 g, 1.37 mmol) in DCM (15 mL) were added pentafluorophenol (0.38 g, 2.05 mmol) and EDCI (0.52 g, 2.74 mmol). The reaction mixture was stirred at r.t. overnight, and then filtered over Celite, with washing of the filter cake with DCM. The filtrate was concentrated and the resulting PFP-ester was dissolved in 10 mL DCM. Compound 438 (0.44 g, 0.91 mmol) and i-$Pr_2EtN$ (0.32 mL, 1.82 mmol) were added and the reaction mixture was stirred at r.t. for 2 h, then concentrated. The residue was purified by $SiO_2$ column using a gradient of MeOH/DCM to deliver product 496 (1.02 g, theoretical yield). ESI m/z calcd for $C_{43}H_{67}N_6O_{10}$ $[M+H]^+$: 827.48, found 827.48.

Example 154. Synthesis of Compound 497

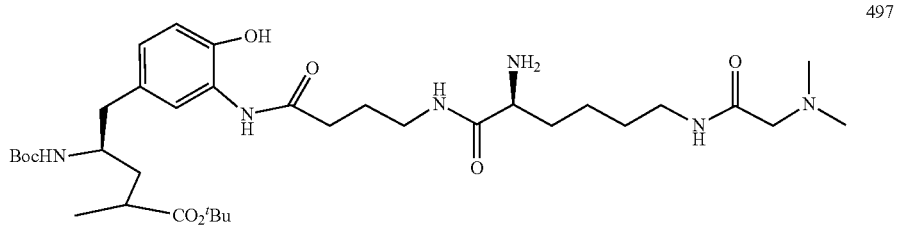 [SMILES: CC(C[C@H](Cc1ccc(O)c(NC(=O)CCCNC(=O)[C@@H](N)CCCCNC(=O)CN(C)C)c1)NC(=O)OC(C)(C)C)C(=O)OC(C)(C)C]
497

Compound 496 (1.02 g, 1.23 mmol) was dissolved in MeOH (10 mL) and stirred with palladium catalyst (10% on carbon, 100 mg) under hydrogen atmosphere (1 atm) at r.t. overnight. The catalyst was filtered off and all volatiles were removed under vacuum, which afforded the title compound (0.76 g, 89% yield). ESI m/z calcd for $C_{35}H_{61}N_6O_8$ [M+H]$^+$: 693.45, found 693.45.

Example 155. Synthesis of Compound 498

Compound 498 (0.15 g, 0.175 mmol) was dissolved in DCM (1 mL) and treated with TFA (2 mL) at r.t. for 2 h. All volatiles were removed in vacuum, and the residue was dissolved in DMA (2 mL), to which pentafluorophenyl ester 41a (121.1 mg, 0.175 mmol) was added, followed by DIPEA (91 µL, 0.525 mmol). The reaction was stirred overnight and concentrated, purified by prep-HPLC with a gradient of MeCN/H$_2$O to give the title product 499 (30.7 mg, 14%). ESI m/z calcd for $C_{59}H_{92}N_{11}O_{14}S$ [M+H]$^-$: 1210.65, found 1210.62.

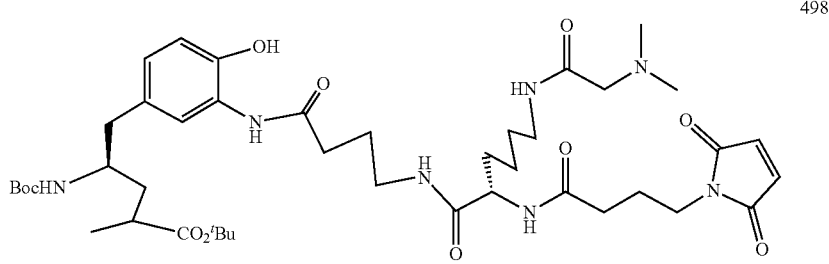 [SMILES: CC(C[C@H](Cc1ccc(O)c(NC(=O)CCCNC(=O)[C@H](CCCCNC(=O)CN(C)C)NC(=O)CCCN2C(=O)C=CC2=O)c1)NC(=O)OC(C)(C)C)C(=O)OC(C)(C)C]
498

NaH$_2$PO$_4$ (0.1M, 1 mL) was added to a solution of compound 497 (0.25 g, 0.36 mmol, 1 eq) and compound 125 (0.15 g, 0.54 mmol, 1.5 eq) in EtOH (5 mL). The resulting solution was stirred at r.t. overnight. All volatiles were removed under vacuum, and purification by column chromatography (5% to 10% MeOH/DCM) yielded the title compound (0.15 g, 48% yield). ESI m/z calcd for $C_{43}H_{68}N_7O_{11}$ [M+H]$^+$: 858.49, found 858.49.

Example 156. Synthesis of Compound 499

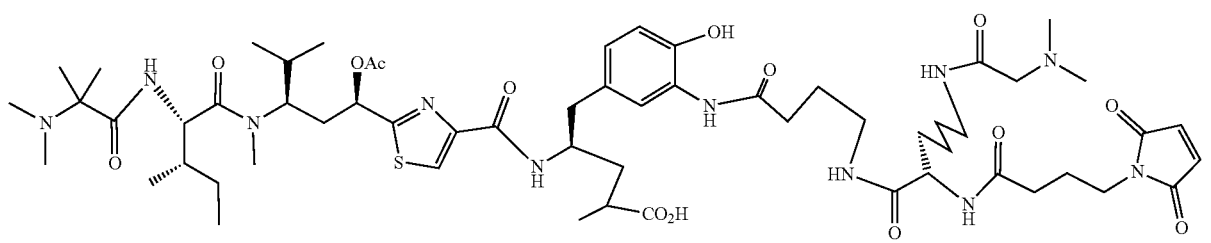
499

Example 157. Synthesis of Compound 501

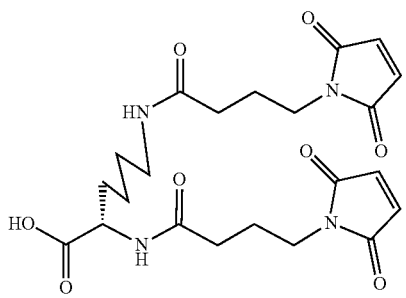

To a solution of H-Lys-OH (0.31 g, 2.14 mmol, 1 eq) in EtOH (20 mL) was added compound 125 (1.80 g, 6.42 mmol, 3 eq) at r.t. Then 0.5 M Na₂HIPO₄ (4 mL) was added, and the reaction mixture was stirred at r.t. overnight. After solvents were evaporated under vacuum, the residue was purified by prep-HPLC with a gradient of H₂O/MeCN to give the title compound 501 (0.26 g, 26%). ESI m/z calcd for $C_{22}H_{29}N_4O_8$ [M+H]⁺:477.19, found 477.19.

Example 158. Synthesis of Compound 502

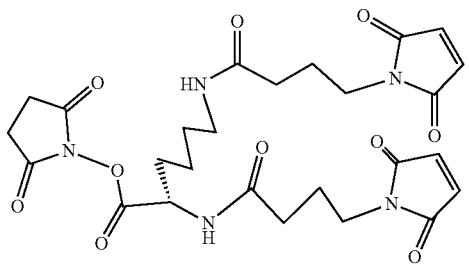

To a solution of carboxylic acid 501 (0.26 g, 0.55 mmol) in DCM (10 mL) were added NHS (0.095 g, 0.825 mmol) and EDCI (0.16 g, 0.825 mmol). The reaction mixture was stirred at r.t. overnight, then concentrated and diluted with H₂O (50 mL), extracted with EtOAc (2×20 mL).

Combined organic layers were dried over Na₂SO₄, filtered and concentrated to give a crude product 502 (0.34 g), which was used in the next step directly. ESI m/z calcd for $C_{26}H_{32}N_5O_{10}$ [M+H]⁺:574.21, found 574.21.

Example 159. Synthesis of Compound 503

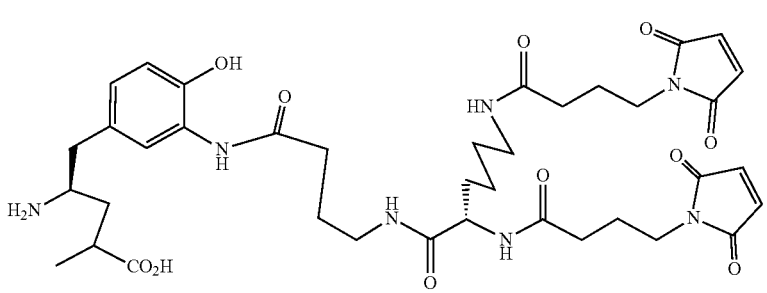

To a solution of compound 438 (0.19 g, 0.4 mmol, 1.0 eq.) in EtOH (30 mL) were added compound 502 (0.34 g, 0.6 mmol, 1.5 eq.) and 0.1 M NaH₂PO₄ (6 mL). The reaction mixture was stirred at r.t. overnight and then concentrated under vacuum. The residue was diluted with H₂O (100 mL), extracted with EtOAc (2×40 mL). The combined organic layers were dried over Na₂SO₄, then purified by SiO₂ column with a gradient of DCM/MeOH to give the title product 503 (0.115 g, 31%). ESI m/z calcd for $C_{47}H_{68}N_7O_{13}$ [M+H]⁺: 938.48, found 938.49.

Example 160. Synthesis of Compound 504

To a solution of compound 503 (0.115 g, 0.12 mmol) in 1 mL of DCM was added 2 mL of TFA, and the reaction mixture was stirred at r.t. for 2h, then concentrated and purified by prep-HPLC with a gradient of H₂O/MeCN to give the title compound 504 (0.0312 g, 33%). ESI m/z calcd for $C_{22}H_{29}N_4O_8$ [M+H]⁺:477.19, found 477.19.

Example 161. Synthesis of Compound 505

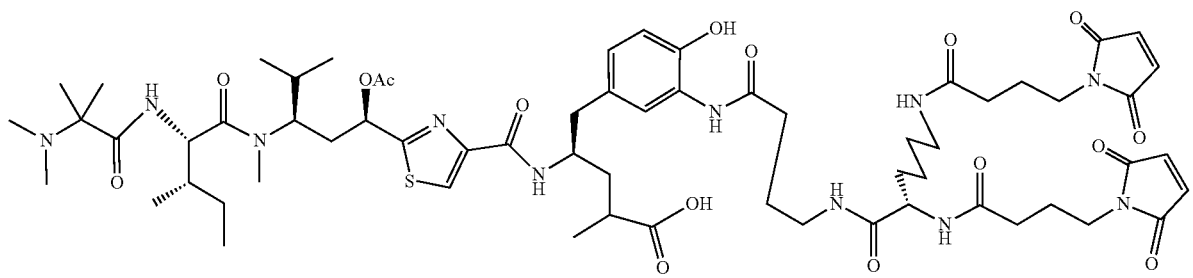

To the solution of compound 504 (31.2 mg, 0.04 mmol) in DMA (2 mL) was added pentafluorophenyl ester 41a (27 mg, 0.04 mmol), followed by DIPEA (16 µL, 0.08 mmol). The reaction was stirred overnight and concentrated, purified by prep-HPLC with a gradient of MeCN/H$_2$O to give the title product 505 (11.9 mg, 24%). ESI: m/z: calcd for C$_{63}$H$_{92}$N$_{11}$O$_{16}$S [M+H]$^+$: 1290.64, found 1290.64.

Example 162. Synthesis of Compound 508

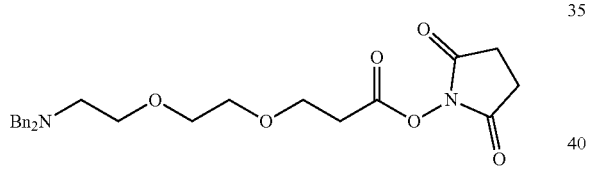

To a solution of compound 300 (5.00 g, 12.1 mmol) in 10 mL DCM was added 5 mL of TFA. The reaction mixture was stirred at r.t. for 1 h, and then concentrated. The crude product was dissolved in DCM (50 mL), to which NHS (4.25 g, 37 mmol) and EDCI (7.10 g, 37 mmol) were added. The reaction mixture was stirred at r.t. overnight, then concentrated and purified by SiO$_2$ column with a gradient of DCM/MeOH to give the title compound 508 (5.00 g, 91%). ESI m/z calcd for C$_{25}$H$_{31}$N$_2$O$_6$ [M+H]$^+$: 455.21, found 455.21.

Example 163. Synthesis of Compound 509

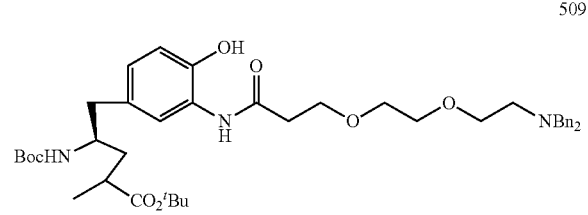

To a solution of compound 110 (1.00 g, 2.5 mmol, 1.0 eq.) in EtOH (10 mL) were added compound 508 (1.80 g, 3.9 mmol, 1.5 eq.) and 0.1M NaH$_2$PO$_4$ (2 mL) at r.t. The reaction mixture was stirred at r.t. overnight, and then concentrated. The residue was diluted with H$_2$O (100 mL), then extracted with EtOAc (3×50 mL). The combined the organic layers were dried over Na$_2$SO$_4$, filtered and concentrated, purified by SiO$_2$ column with a gradient of DCM/MeOH to give the title compound 509 (0.93 g, 50%). ESI m/z calcd for C$_{42}$H$_{60}$N$_3$O$_8$ [M+H]$^+$: 734.43, found 734.43.

Example 164. Synthesis of Compound 510

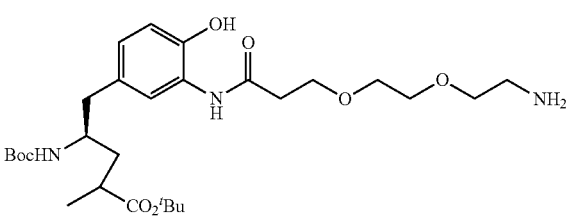

In a hydrogenation bottle, Pd/C (0.093 g, 10 wt %) was added to a solution of compound 509 (0.93 g, 1.27 mmol) in EtOAc (20 mL). The mixture was shaken overnight under 1 atm H$_2$ then filtered through Celite (filter aid), the filtrate was concentrated to afford compound 510 (0.57 g, 81%) and used in the next step without further purification. ESI m/z calcd for C$_{28}$H$_{48}$N$_3$O$_8$ [M+H]$^+$:554.34, found 554.34.

Example 165. Synthesis of Compound 511

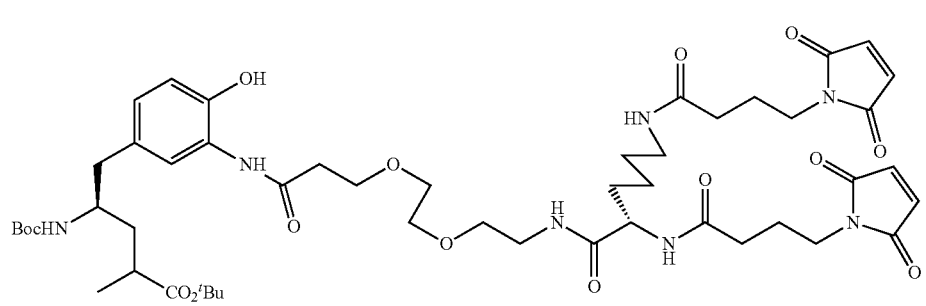

511

To a solution of compound 510 (0.25 g, 0.45 mmol, 1.0 eq.) in EtOH (5 mL) was added compound 502 (0.39 g, 0.68 mmol, 1.5 eq.) at r.t. Then 0.1M $NaH_2PO_4$ (1 mL) was added, and the reaction mixture was stirred at r.t. overnight. The reaction mixture was concentrated under vacuum, and the residue was diluted with $H_2O$ (100 mL), then extracted with EtOAc (2×50 mL).

The combined organic layers were dried over $Na_2SO_4$, filtered and concentrated, purified by $SiO_2$ column with a gradient of DCM/MeOH to give the title compound 511 (0.076 g, 17%). ESI m/z calcd for $C_{50}H_{74}N_7O_{15}$ $[M+H]^+$: 1012.52, found 1012.53.

Example 166. Synthesis of Compound 512

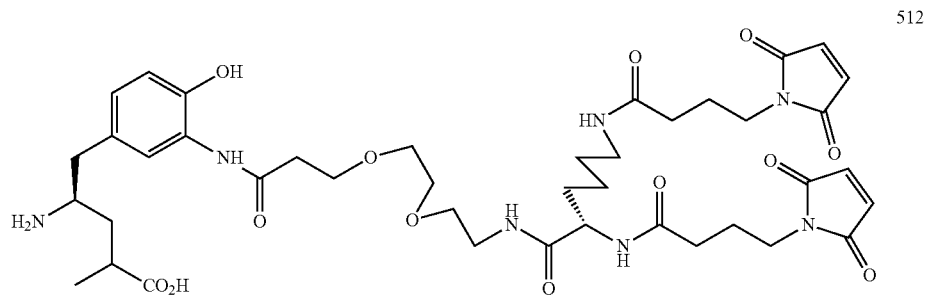 [SMILES: CC(C[C@@H](N)Cc1ccc(O)c(NC(=O)CCOCCOCCNC(=O)[C@H](CCCCNC(=O)CCCN2C(=O)C=CC2=O)NC(=O)CCCN2C(=O)C=CC2=O)c1)C(=O)O]

512

To a solution of compound 511 (0.076 g, 75 mmol) in 2 mL DCM was added 4 mL of TFA. The reaction mixture was stirred at r.t. for 1 h, concentrated, and the crude product 512 was used in the next step without further purification. ESI m/z calcd for $C_{41}H_{58}N_7O_{13}$ $[M+H]^+$: 856.40, found 856.40.

Example 167. Synthesis of Compound 513

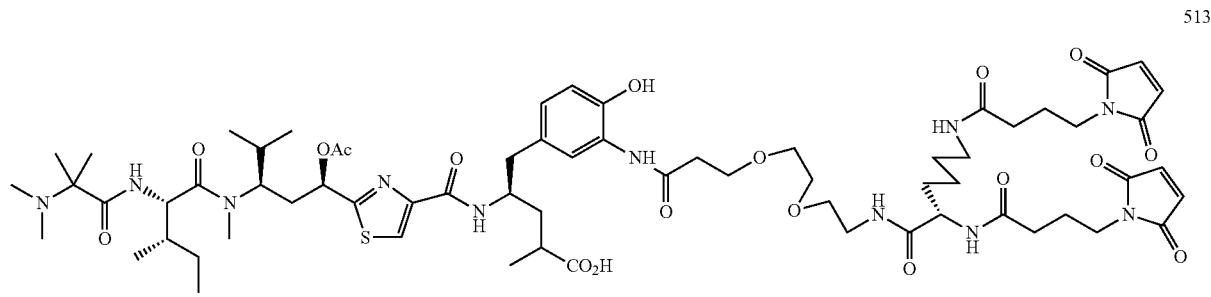 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCOCCOCCNC(=O)[C@H](CCCCNC(=O)CCCN3C(=O)C=CC3=O)NC(=O)CCCN3C(=O)C=CC3=O)c2)CC(C)C(=O)O)cs1)C(C)C]

513

To a solution of above compound 512 in DMA (2 mL) were added compound 41a (33 mg, 0.048 mmol) and DIPEA (25 uL, 0.144 mmol). The reaction was stirred at r.t. for 3 h, then concentrated and purified by prep-HPLC with a gradient of MeCN/H$_2$O to give the title compound 513 (21.3 mg, 32%). ESI m/z calcd for $C_{66}H_{98}N_{11}O_{18}S$ [M+H]$^+$: 1364.67, found 1364.67.

Example 168. Synthesis of Compound 515

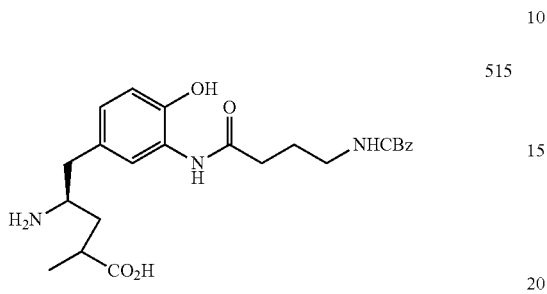

515

To a solution of compound 437 (1.00 g, 1.63 mmol) in 1 mL DCM was added 2 mL TFA, the reaction mixture was stirred at r.t. for 1 h, and then concentrated. The resulting crude product 515 was used in the next step without further purification. ESI m/z calcd for $C_{24}H_{32}N_3O_6$ [M+H]$^+$:458.22, found 458.22.

Example 169. Synthesis of Compound 516

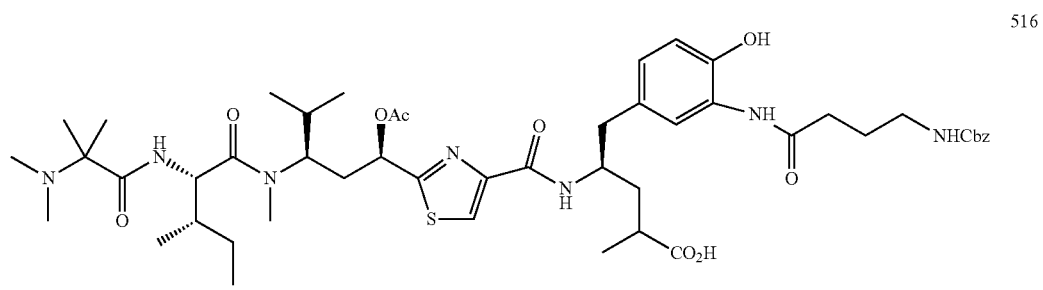 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCNC(=O)OCc3ccccc3)c2)CC(C)C(=O)O)cs1)C(C)C]

516

To a solution of compound 515 in DMF (3 mL) were added pentafluorophenyl ester 41a (0.63 g, 0.91 mmol) and DIPEA (0.46 mL, 2.73 mmol). The reaction was stirred at r.t. overnight, then concentrated and purified by SiO$_2$ column with a gradient of DCM/MeOH to give the title compound 516 (1.75 g, theoretical yield) as a yellow oil. ESI m/z calcd for $C_{49}H_{72}N_7O_{11}S$ [M+H]$^+$:966.49, found 966.49.

Example 170. Synthesis of Compound 517

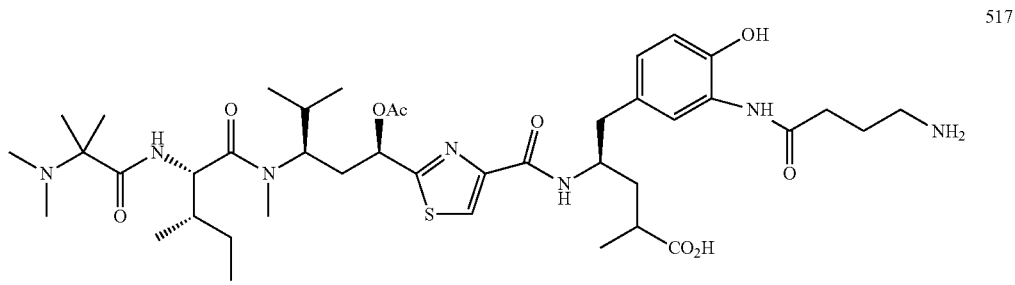 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN)c2)CC(C)C(=O)O)cs1)C(C)C]

517

In a hydrogenation bottle, Pd/C (0.02 g, 10 wt %) was added to a solution of compound 516 (0.20 g, 0.20 mmol) in MeOH (15 mL). 1N HCl was then added to adjust pH to around 4. The mixture was shaken overnight under 1 atm $H_2$ then filtered through Celite (filter aid), the filtrate was concentrated to afford compound 517, which was used in the next step without further purification. ESI m/z calcd for $C_{41}H_{66}N_7O_9S$ [M+H]$^+$:832.46, found 832.46.

Example 171. Synthesis of Compound 519

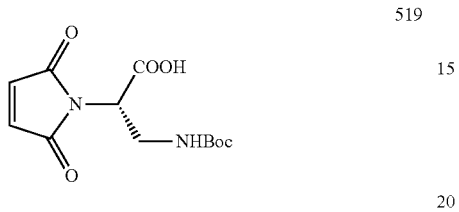

To a solution of H-Dap(Boc)-OH (1.00 g, 4.9 mmol) in saturated $NaHCO_3$ (20 mL) at 0° C. was added compound 409 (2.30 g, 14.7 mmol). The reaction was stirred at 0° C. for 1 h, then warmed to r.t. and stirred for another hour. Then 1N $KHSO_4$ was added to adjust pH to ~6 and the resulting mixture was extracted with EtOAc (2×50 mL). Combined organic layers were dried over $Na_2SO_4$, filtered, and concentrated to give compound 519 (0.42 g, 30% yield). ESI m/z calcd for $C_{12}H_{15}N_2O_6$ [M–H]$^-$: 283.10, found 283.10.

Example 172. Synthesis of Compound 520

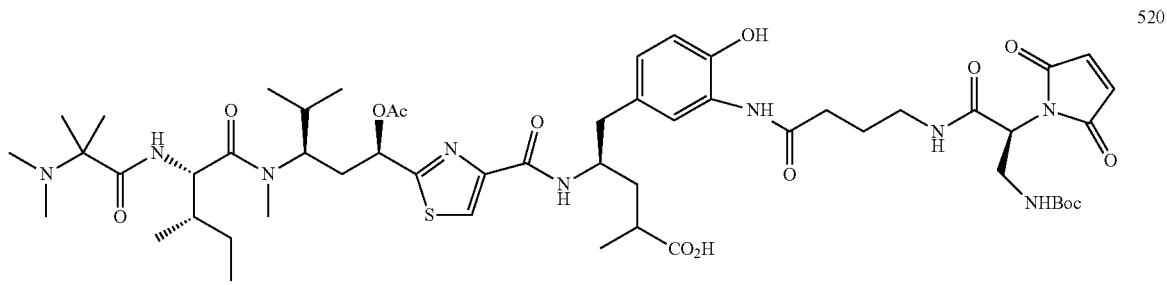 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCNC(=O)[C@H](CNC(=O)OC(C)(C)C)N3C(=O)C=CC3=O)c2)CC(C)C(=O)O)cs1)C(C)C]

To a solution of carboxylic acid 519 (0.21 g, 0.74 mmol) in EtOAc (10 mL) were added pentafluorophenol (0.27 g, 1.48 mmol) and DCC (0.30 g, 1.48 mmol). The reaction mixture was stirred at r.t. overnight and then filtered, with washing of the filter cake with EtOAc. The filtrate was concentrated to give the PFP-ester (0.17 g, 0.37 mmol), which was dissolved in 1 mL DMF. Compound 517 (0.36 g, 0.43 mmol) and DIPEA (0.13 mL, 0.74 mmol) were added and the reaction mixture was stirred at r.t. for 2 h. The reaction was concentrated and purified by prep-HPLC with a gradient of MeCN/$H_2O$ to give the title compound 520 (50 mg, 13%). ESI m/z calcd for $C_{53}H_{80}N_9O_{14}S$ [M+H]$^+$: 1098.55, found 1098.55.

Example 173. Synthesis of Compound 521

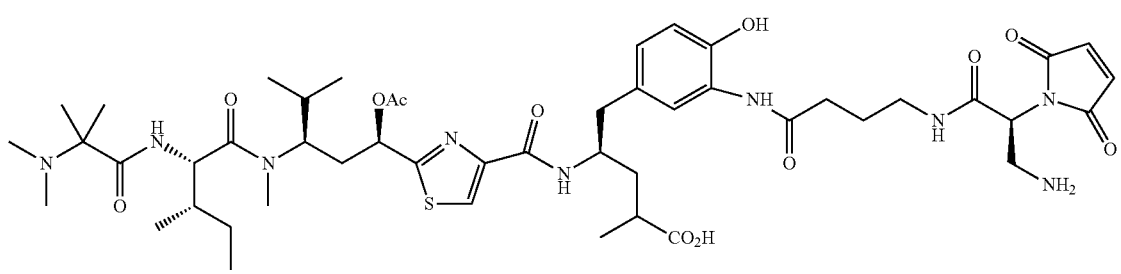

To a solution of compound 520 (50 mg, 0.046 mmol) in 0.5 mL DCM was added 1 mL TFA. The reaction mixture was stirred at r.t. for 1 h, then concentrated, and purified by prep-HPLC with a gradient of MeCN/H$_2$O to give the title compound 521 (11 mg, 25%). ESI m/z calcd for C$_{48}$H$_{72}$N$_9$O$_{12}$S [M+H]$^+$: 998.49, found 998.49.

Example 174. Synthesis of Compound 523

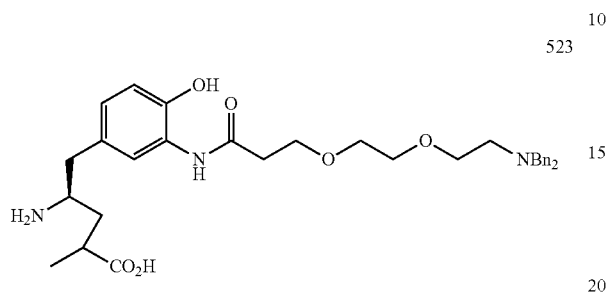

To a solution of compound 509 (1.00 g, 1.36 mmol) in 2 mL DCM was added 4 mL TFA and the reaction mixture was stirred at r.t. for 1 h, then concentrated to give compound 523, which was used in the next step without further purification. ESI m/z calcd for C$_{33}$H$_{44}$N$_3$O$_6$ [M+H]$^+$:578.32, found 578.32.

Example 175. Synthesis of Compound 524

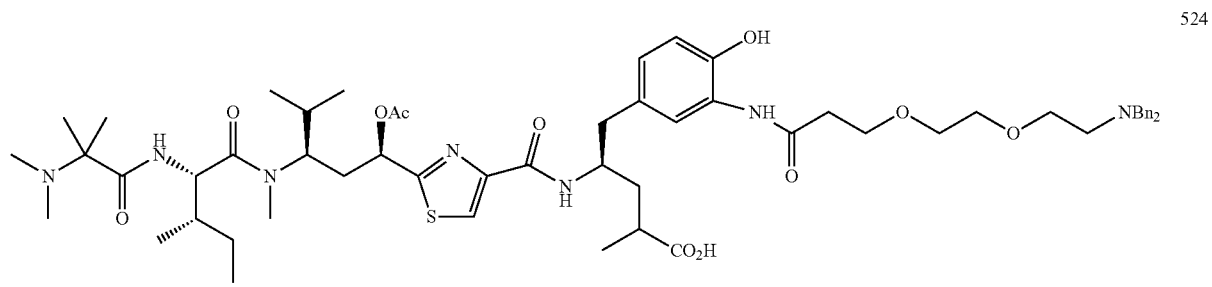

To the solution of compound 523 in DMF (5 mL) were added pentafluorophenyl ester 41a (0.78 g, 1.13 mmol) and DIPEA (0.8 mL, 4.52 mmol). The reaction was stirred at r.t. overnight and then concentrated, purified by SiO$_2$ column with a gradient of DCM/MeOH to give the title compound 524 (1.64 g, theoretical yield). ESI m/z calcd for C$_{58}$H$_{84}$N$_7$O$_{11}$S [M+H]$^+$:1086.59, found 1086.58.

Example 176. Synthesis of Compound 525

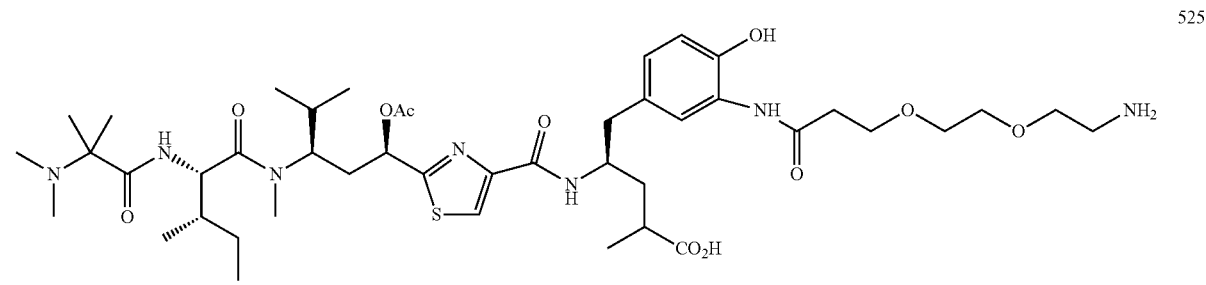 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCOCCOCCN)c2)CC(C)C(=O)O)cs1)C(C)C]

In a hydrogenation bottle, Pd/C (0.08 g, 10 wt %, 65.9% wet) was added to a solution of compound 524 (0.80 g, 0.20 mmol) in MeOH (10 mL), and 1N HCl was added to adjust pH to ~4. The mixture was shaken overnight under 1 atm $H_2$ then filtered through Celite (filter aid), the filtrate was concentrated to afford compound 525, which contained some un-reacted starting material and was used in the next step without further purification. ESI: m/z: calcd for $C_{41}H_{66}N_7O_9S$ $[M+H]^+$:832.46, found 832.46.

Example 177. Synthesis of Compound 527

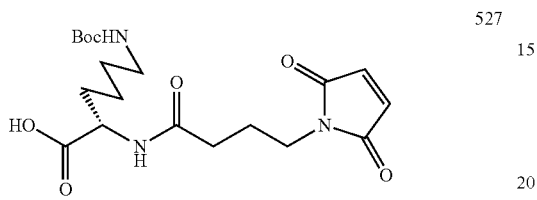

527

To a solution of H-Lys(Boc)-OH (1.00 g, 3.8 mmol, 1.0 eq.) in EtOH (16 mL) was added compound 125 (1.00 g, 5.6 mmol, 1.5 eq.) at r.t. After 0.1 M $NaH_2PO_4$ (3 mL) was added, the reaction mixture was stirred at r.t. overnight. The reaction was concentrated under vacuum, and the residues was purified by $SiO_2$ column with a gradient of DCM/MeOH to give the title compound 527 (1.62 g, theoretical yield). ESI m/z calcd for $C_{19}H_{30}N_3O_7$ $[M+H]^+$: 412.20, found 412.20.

Example 178. Synthesis of Compound 528

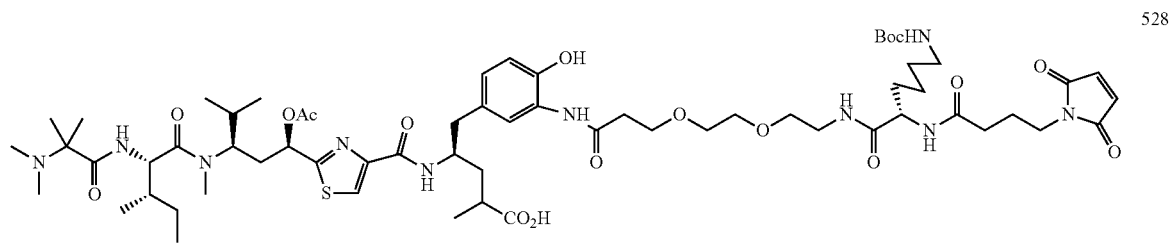 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCOCCOCCNC(=O)[C@H](CCCCNC(=O)OC(C)(C)C)NC(=O)CCCN3C(=O)C=CC3=O)c2)CC(C)C(=O)O)cs1)C(C)C]

528

To a solution of carboxylic acid 527 (0.24 g, 0.58 mmol) in EtOAc (10 mL) were added pentafluorophenol (0.21 g, 1.17 mmol) and DCC (0.24 g, 1.17 mmol). The reaction mixture was stirred at r.t. overnight, and then filtered with washing of the filter cake with EtOAc, and the filtrate was concentrated. The resulting PFP-ester(32 mg, 0.056 mmol) was dissolved in 1 mL DMF, to which compound 525 (50 mg, 0.056 mmol) and i-$Pr_2$EtN (29 μL, 0.168 mmol) were added. The reaction mixture was stirred at r.t. for 2 h and concentrated. The residue was purified by HPLC with a gradient of MeCN/$H_2O$ to give the title compound 528 (3 mg, 4% yield). ESI m/z calcd for $C_{63}H_{99}N_{10}O_{17}S$ $[M+H]^+$: 1299.68, found 1299.68.

Example 179. Synthesis of Compound 529

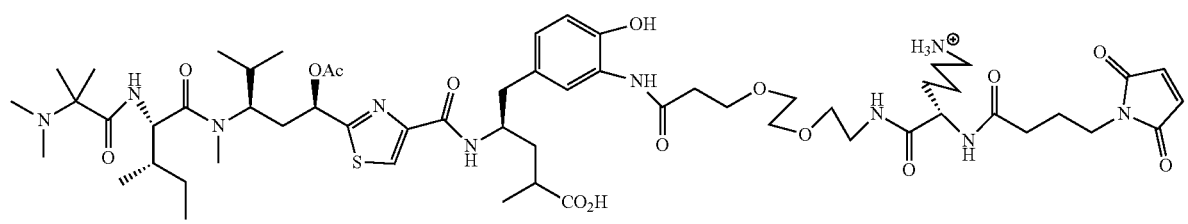

529

To a solution of compound 528 (3 mg, 0.002 mmol) in 0.5 mL DCM was added 1 mL TFA, the reaction mixture was stirred at r.t. for 1 h, then concentrated. The crude product was purified by HPLC with a gradient of MeCN/H$_2$O to give the title compound 529 (1.43 mg, 52% yield). ESI m/z calcd for C$_{58}$H$_{91}$N$_{10}$O$_{15}$S [M+H]$^+$:1199.63, found 1199.62.

Example 180. Synthesis of Compound 532

To a solution of H-Dap(Boc)-OH (1.00 g, 4.9 mmol, 1.0 eq.) in EtOH (30 mL) was added compound 125 (2.00 g, 7.3 mmol, 1.5 eq.) at r.t. Then 0.1M NaH$_2$PO$_4$ (6 mL) was added, and the reaction mixture was stirred at r.t. overnight. The solvents were removed under vacuum, and the residues was purified by SiO$_2$ column with a gradient of DCM/MeOH to give the title compound 536 (1.41 g, 78%). ESI m/z calcd for C$_{16}$H$_{24}$N$_3$O$_7$ [M+H]$^+$: 370.15, found 370.15.

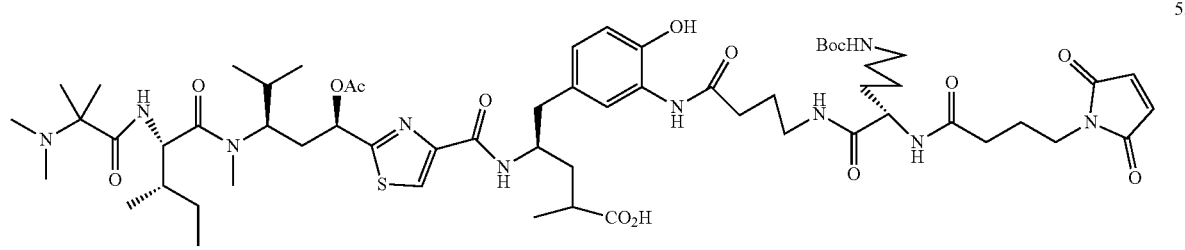

532

The pentafluorophenyl ester of compound 527 (0.11 g, 0.19 mmol) was dissolved in 1 mL DMF, to which compound 517 (0.21 g, 0.25 mmol) and i-Pr$_2$EtN (86 uL, 0.5 mmol) were added. The reaction mixture was stirred at r.t. for 2 h and concentrated. The residue was purified by prep-HPLC with a gradient of MeCN/H$_2$O to give the title product 532 (20 mg, 9%). ESI m/z calcd for C$_{60}$H$_{93}$N$_{10}$O$_{15}$S [M+H]$^+$: 1225.65, found 1225.66.

Example 181. Synthesis of Compound 533

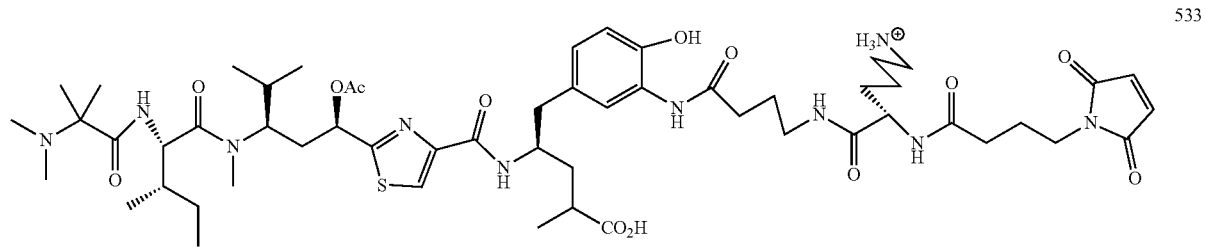 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCNC(=O)[C@H](CCCC[NH3+])NC(=O)CCCN3C(=O)C=CC3=O)c2)CC(C)C(=O)O)cs1)C(C)C]

533

To a solution of compound 532 (20 mg, 0.016 mmol) in 1 mL DCM was added 2 mL TFA. The reaction mixture was stirred at rt for 1 h, then concentrated, and the crude product was purified by prep-HPLC with a gradient of MeCN/H$_2$O to give the title compound 533 (8.9 mg, 18% yield). ESI m/z calcd for C$_{55}$H$_{85}$N$_{10}$O$_{13}$S [M+H]$^+$:1125.59, found 1125.59.

Example 182. Synthesis of Compound 536

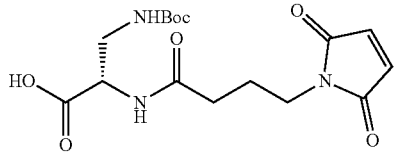

536

Example 183. Synthesis of Compound 537

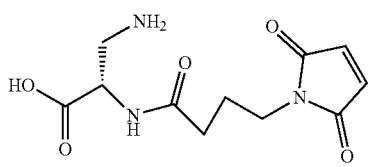

537

To a solution of compound 536 (1.41 g, 3.8 mmol) in 2 mL DCM was added 5 mL TFA.
The reaction mixture was stirred at r.t. for 1 h, and then concentrated. The crude product 537 was used in the next step without further purification. ESI m/z calcd for C$_{11}$H$_{16}$N$_3$O$_5$ [M+H]$^+$:270.10, found 270.10.

Example 184. Synthesis of Compound 538

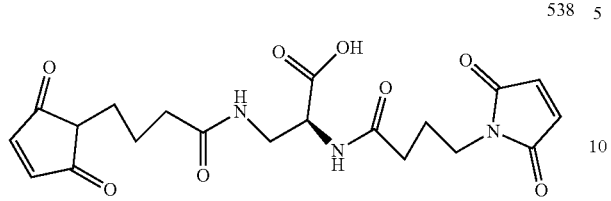
538

To a solution of above compound 537 in EtOH (20 mL) was added compound 125 (1.90 g, 6.9 mmol, 1.5 eq.) at r.t. Then 0.1M NaH$_2$PO$_4$ (4 mL) was added, and the reaction mixture was stirred at r.t. overnight. After the solvents were removed under vacuum, then the residues was purified by HPLC with a gradient of H$_2$O/MeCN to give the title compound 538 (0.45 g, 22% yield). ESI m/z calcd for C$_{19}$H$_{23}$N$_4$O$_8$ [M+H]$^+$: 435.14, found 435.14.

Example 185. Synthesis of Compound 539

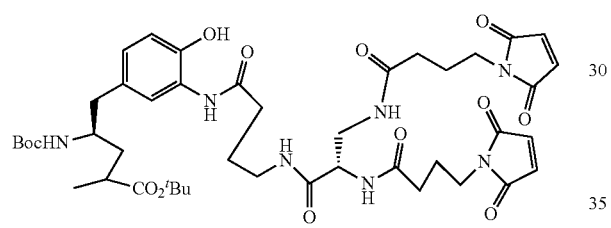
539

To a solution of compound 538 (0.15 g, 0.34 mmol), compound 438 (0.17 g, 0.34 mmol) and HATU (0.16 g, 0.41 mmol) in DMF (2 mL), TEA (95 µL, 0.68 mmol) was added. After stirring at r.t. for 1 h, the reaction was concentrated under reduced pressure and the residue was purified by prep-HPLC with a gradient of MeCN/H$_2$O to give the title compound 539 (34 mg, 11% yield). ESI m/z calcd for C$_{44}$H$_{62}$N$_7$O$_{13}$ [M+H]$^+$: 896.43, found 896.42.

Example 186. Synthesis of Compound 540

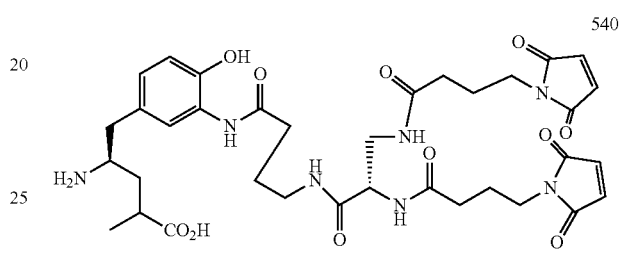
540

To a solution of compound 539 (34 mg, 0.04 mmol) in 0.5 mL DCM was added 1 mL TFA.

The reaction mixture was stirred at r.t. for 2h, and then concentrated to afford the title compound 540, which was used in the next step without further purification. ESI m/z calcd for C$_{35}$H$_{46}$N$_7$O$_{11}$ [M+H]$^+$: 740.30, found 740.32.

Example 187. Synthesis of Compound 541

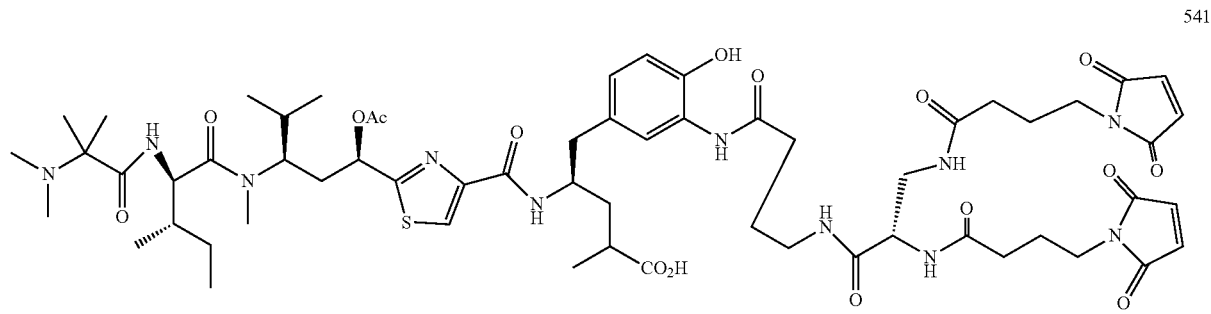 [SMILES: CC[C@H](C)[C@@H](NC(=O)C(C)(C)N(C)C)C(=O)N(C)[C@H](C[C@@H](OC(C)=O)c1nc(C(=O)N[C@@H](Cc2ccc(O)c(NC(=O)CCCNC(=O)[C@H](CNC(=O)CCCN3C(=O)C=CC3=O)NC(=O)CCCN3C(=O)C=CC3=O)c2)CC(C)C(=O)O)cs1)C(C)C]
541

To the solution of compound 540 in DMA (2 mL) was added pentafluorophenyl ester 41a (28 mg, 0.04 mmol), followed by DIPEA (21 µL, 0.12 mmol). The reaction was stirred overnight and then concentrated and purified by prep-HPLC with a gradient of MeCN/H$_2$O to give the title compound 541 (14.4 mg, 29%). ESI m/z calcd for C$_{60}$H$_{86}$N$_{11}$O$_{16}$S [M+H]$^+$: 1248.59, found 1248.60.

Example 188. Synthesis of Compound 544

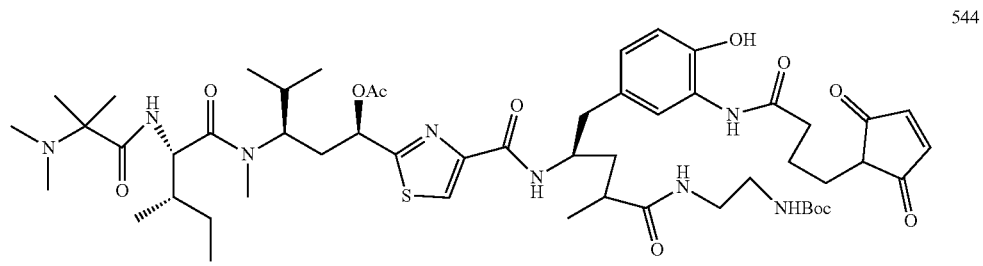 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCC3C(=O)C=CC3=O)c2)CC(C)C(=O)NCCNC(=O)OC(C)(C)C)cs1)C(C)C]

To a solution of compound 132 (0.300 g, 0.329 mmol, 1.0 eq.) and tert-butyl (2-aminoethyl)carbamate hydrochloride (0.063 g, 0.395 mmol, 1.2 eq.) in anhydrous DCM (30 mL) at 0° C. was added EDCI (0.189 g, 0.988 mmol, 3.0 eq.). After stirring for 10 minutes, the reaction was warmed to room temperature and stirred overnight. The reaction was diluted with DCM and washed with water and brine, dried over anhydrous $Na_2SO_4$, concentrated and purified by $SiO_2$ column chromatography (DCM/MeOH) to give compound 544 as a yellow foamy solid (0.132 g, 54% yield). ESI m/z calcd for $C_{52}H_{80}N_9O_{12}S[M+H]^+$: 1054.6, found:1054.6.

Example 189. Synthesis of Compound 545

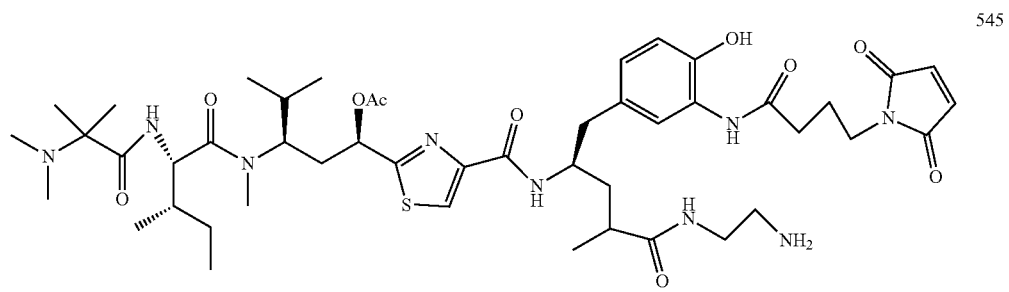 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)NCCN)cs1)C(C)C]

To a solution of compound 544 (0.132 g, 0.125 mmol, 1.0 eq.) in DCM (4.5 mL) at r.t. was added TFA (1.5 mL) and stirred for 1 h. The reaction was diluted with anhydrous toluene and concentrated, and this operation was repeated for three times to give a yellow oil which was purified on prep-HPLC (Cis column, mobile phase A: water, mobile phase B: acetonitrile, from 10% of B to 80% of B in 60 min). The fractions were pooled and lyophilized to give compound 545 (111 mg, 93% yield). ESI m/z calcd for $C_{47}H_{72}N_9O_{10}S$ $[M+H]^+$: 954.5, found: 954.5.

Example 190. Synthesis of Compound 548

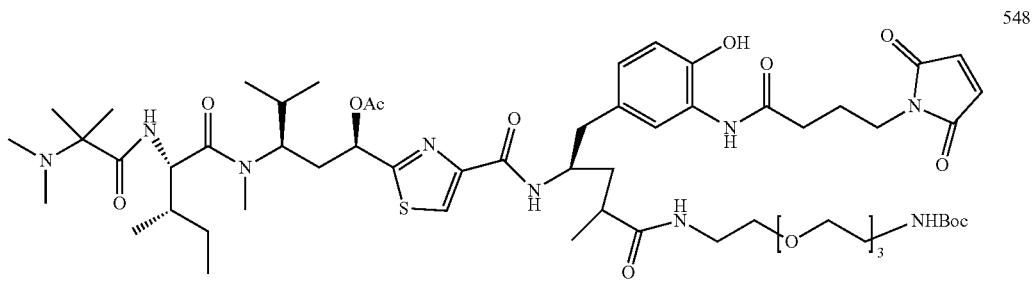

To a solution of compound 132 (0.050 g, 0.0549 mmol, 1.0 eq.) and tert-butyl (2-(2-(2-(2-aminoethoxy)ethoxy)ethoxy)ethyl)carbamate (0.024 g, 0.0824 mmol, 1.5 eq.) in anhydrous DCM (10 mL) at 0° C. was added EDCI (0.032 g, 0.1647 mmol, 3.0 eq.). After stirring for 10 minutes, the reaction was warmed to r.t. and stirred overnight. The mixture was then diluted with DCM and washed with water and brine, dried over anhydrous $Na_2SO_4$, concentrated and purified by $SiO_2$ column chromatography (DCM/MeOH) to give the title compound as a yellow foamy solid (0.030 g, 46% yield). ESI m/z calcd for $C_{58}H_{92}N_9O_{15}S$ $[M+H]^+$: 1186.6, found:1186.6.

Example 191. Synthesis of Compound 549

Example 192. Synthesis of Compound 552

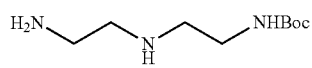

552

To a solution of N-(2-aminoethyl)ethane-1,2-diamine (28.7 g, 275 mmol, 10.0 eq.) and DMAP (0.034 g, 0.000275 mmol, 0.01 eq.) in anhydrous DCM (350 mL) at 0° C. was added $Boc_2O$ (6.0 g, 0.0275 mmol, 1.0 eq.) in anhydrous DCM (100 mL) over 3 h. The reaction was then warmed to

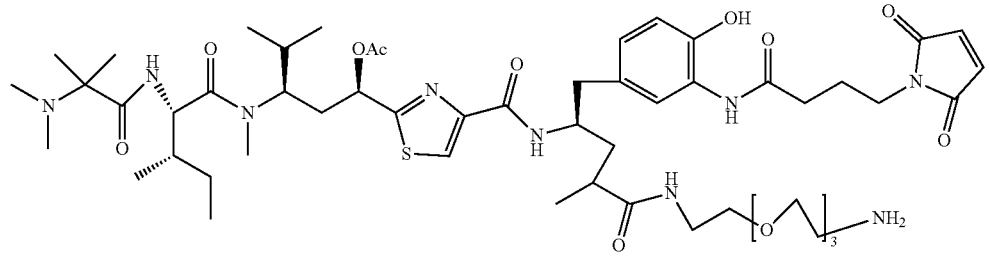

549 r.t. and stirred overnight, concentrated and purified by $SiO_2$ column chromatography (DCM/MeOH) to give the title compound as a yellow oil (4.5 g, 80% yield). ESI m/z calcd for $C_9H_{22}N_3O_2$ $[M+H]^+$: 204.2, found:204.2.

Example 193. Synthesis of Compound 553

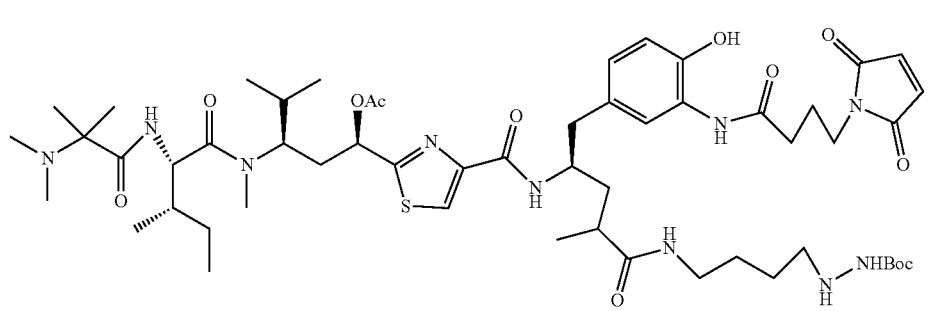

553

To a solution of compound 548 (0.030 g, 0.0253 mmol, 1.0 eq.) in DCM (3.0 mL) at r.t. was added TFA (1.0 mL). The reaction was stirred for 1 h and then diluted with anhydrous toluene and concentrated, this operation was repeated for three times to give a yellow oil, which was purified on prep-HPLC ($C_{18}$ column, mobile phase A: water, mobile phase B: acetonitrile, from 10% of B to 80% of B in 60 min). The fractions were pooled and lyophilized to give compound 549 (11.7 mg, 43% yield). ESI m/z calcd for $C53H_4N_9O_{13}S$ $[M+H]^+$: 1086.6, found:1086.6.

To a solution of compound 132 (0.060 g, 0.0658 mmol, 1.0 eq.) and tert-butyl (2-((2-aminoethyl)amino)ethyl)carbamate (0.016 g, 0.0790 mmol, 1.2 eq.) in anhydrous DCM (6 mL) at 0° C. was added EDCI (0.038 g, 0.1974 mmol, 3.0 eq.). After stirring for 10 minutes, the reaction was warmed to r.t. and stirred overnight. The mixture was concentrated and purified on prep-HPLC (Cis column, mobile phase A: water, mobile phase B: acetonitrile, from 10% of B to 80% of B in 60 min). The fractions were pooled and lyophilized to give the title compound 553 (48 mg, 66% yield). ESI m/z calcd for $C_{54}H_{85}N_{10}O_{12}S$ $[M+H]^+$: 1097.6, found:1097.6.

Example 194. Synthesis of Compound 554

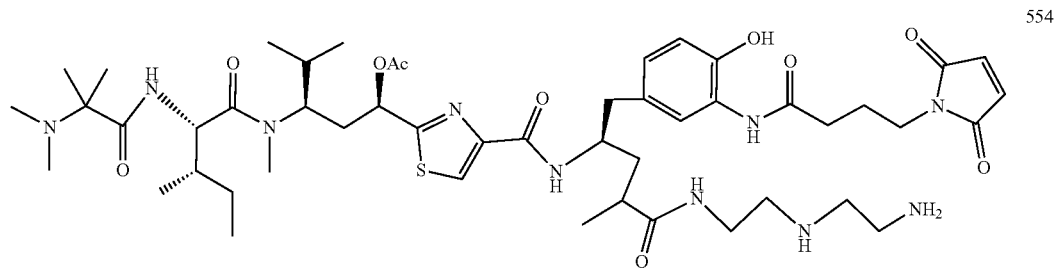 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)NCCNCCN)cs1)C(C)C]

To a solution of compound 553 (0.048g, 0.0437 mmol, 1.0 eq.) in DCM (3.0 mL) at r.t. was added TFA (1.0 mL). After stirring for 1 h, the reaction was diluted with anhydrous toluene and concentrated, and this operation was repeated for three times to give a yellow oil, which was purified on prep-HPLC ($C_{18}$ column, mobile phase A: water, mobile phase B: acetonitrile, from 10% of B to 80% of B in 60 min). The fractions were pooled and lyophilized to give the title compound 554 (111 mg, 93% yield). ESI m/z calcd for $C_{49}H_{77}N_{10}O_{10}S[M+H]^+$: 997.5, found: 997.5.

Example 195. Synthesis of Compound 558

To a solution of compound 132 (0.400 g, 0.439 mmol, 1.0 eq.) and H-Lys(Boc)-O$^t$Bu.HCl (0.135 g, 0.528 mmol, 1.2 eq.) in anhydrous DCM (40 mL) at 0° C. was added EDCI (0.189 g, 1.317 mmol, 3.0 eq.). After stirring for 10 min, the reaction was warmed to r.t. and stirred overnight. The mixture was diluted with DCM and washed with water and brine, dried over anhydrous $Na_2SO_4$, concentrated and purified by $SiO_2$ column chromatography (DCM/MeOH) to give compound 558 as a yellow oil (0.43 g, 82% yield). ESI m/z calcd for $C_{60}H_{94}N_9O_{14}S$ [M+H]$^+$: 1196.7, found:1196.7.

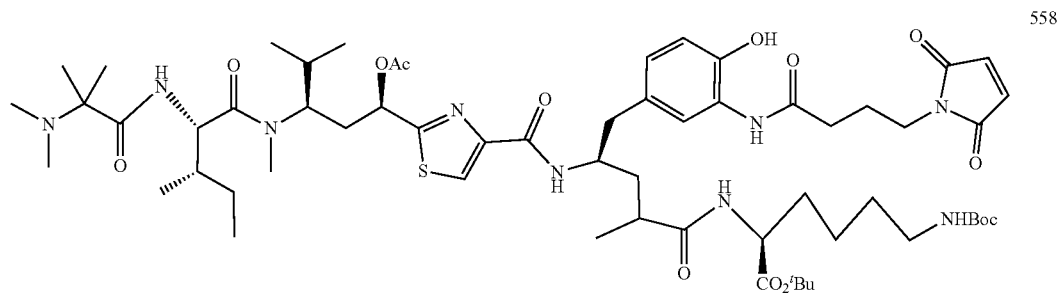 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)N[C@@H](CCCCNC(=O)OC(C)(C)C)C(=O)OC(C)(C)C)cs1)C(C)C]

Example 196. Synthesis of Compound 559

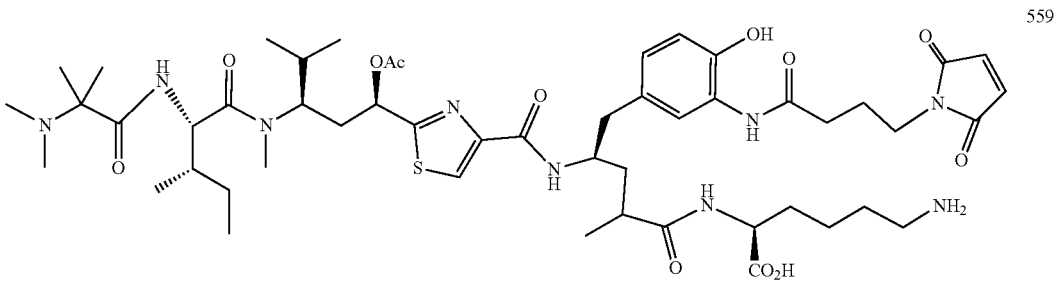 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)N[C@@H](CCCCN)C(=O)O)cs1)C(C)C]

To a solution of compound 558 (0.230 g, 0.192 mmol, 1.0 eq.) in DCM (6.0 mL) at r.t. was added TFA (2.0 mL) and the reaction was stirred for 3 h and then diluted with toluene and concentrated, this operation was repeated for three times to give a yellow oil, which was purified on prep-HPLC ($C_{18}$ column, mobile phase A: water, mobile phase B: acetonitrile, from 10% of B to 80% of B in 60 min). The fractions were pooled and lyophilized to give the title compound (153 mg, 76% yield). ESI m/z calcd for $C_{51}H_{78}N_9O_{12}S$ [M+H]$^+$: 1040.5, found:1040.5.

Example 197. Synthesis of Compound 562

To a solution of compound 562 (0.270 g, 0.177 mmol, 1.0 eq.) in DCM (6.0 mL) at r.t. was added TFA (2.0 mL) and stirred for 4 h. The mixture was diluted with anhydrous toluene and concentrated, this operation was repeated for three times to give a yellow oil, which was purified on prep-HPLC ($C_{18}$ column, mobile phase A: water, mobile phase B: acetonitrile, from 10% of B to 80% of B in 60 min). The fractions were pooled and lyophilized to give the title compound (172 mg, 83% yield). ESI m/z calcd for $C_{57}H_{90}N_{11}O_{13}S$ [M+H]$^+$: 1168.6, found: 1168.6.

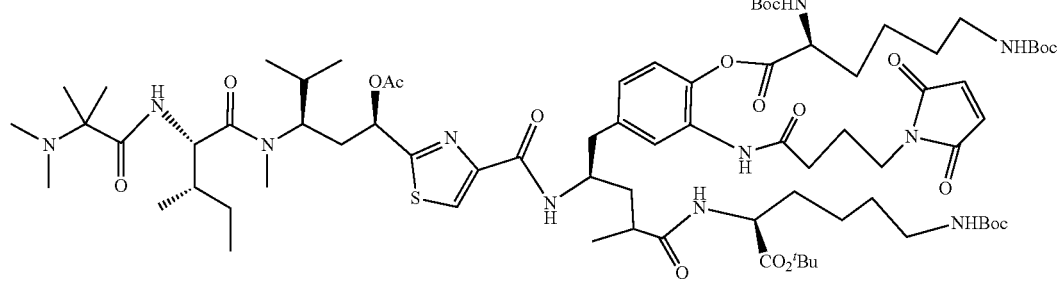

562

To a solution of compound 558 (0.200 g, 0.167 mmol, 1.0 eq.) and Boc-L-Lys(Boc)-OH (0.070 g, 0.200 mmol, 1.2 eq.) in anhydrous DCM (10 mL) at 0° C. was added HATU (0.095 g, 0.250 mmol, 1.5 eq.) and TEA (46 µL, 0.334 mmol, 2.0 eq.). The reaction was stirred for 10 min at 0° C. and stirred for 10 minutes, then warmed to r.t. and stirred overnight. The mixture was diluted with DCM and washed with water and brine, dried over anhydrous $Na_2SO_4$, concentrated and purified by $SiO_2$ column chromatography (DCM/MeOH) to give compound 562 as a colorless oil (0.270 g, theoretical yield). ESI m/z calcd for $C_{76}H_{122}N_{11}O_{19}S$ [M+H]$^+$: 1524.9, found:1524.9.

Example 198. Synthesis of Compound 563

Example 199. Synthesis of Compound 566

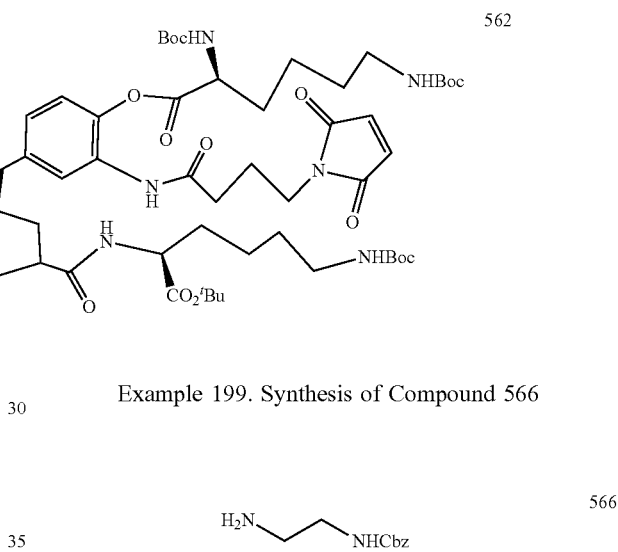

566

To a solution of ethane-1,2-diamine (30.0 g, 0.5 mol, 10.0 eq.) in anhydrous DCM (500 mL) at 0° C. was added CbzCl (8.53 g, 0.050 mol, 1.0 eq.) in anhydrous DCM (250 mL) over 7 h. The reaction was then warmed to r.t. and stirred overnight. The mixture was washed with water and brine, dried over anhydrous $Na_2SO_4$, and concentrated to give benzyl (2-aminoethyl)carbamate as a white solid (7.0 g, 94% yield). ESI m/z calcd for $C_{10}H_{14}N_2O_2$ [M+H]$^+$: 195.1, found: 195.2.

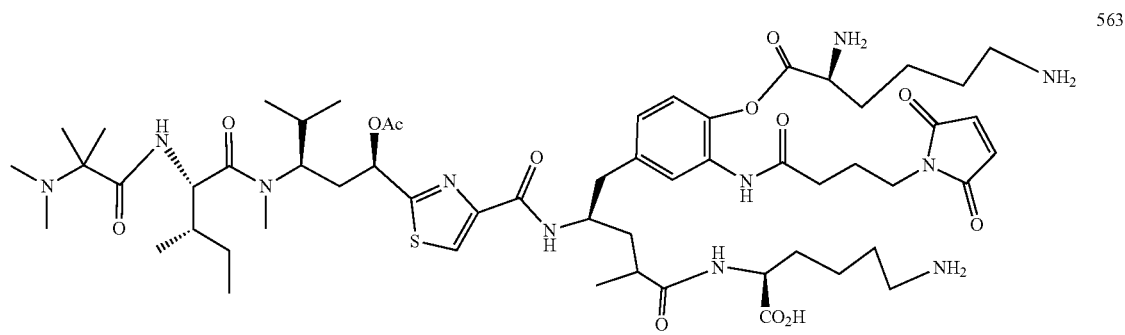 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(OC(=O)[C@@H](N)CCCCN)c(NC(=O)CCCN3C(=O)C=CC3=O)c2)CC(C)C(=O)N[C@@H](CCCCN)C(=O)O)cs1)C(C)C]

563

Example 200. Synthesis of Compound 567

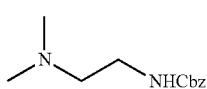
567

To a solution of compound 566 (7.0 g, 35.8 mmol, 1.0 eq.) and 37% HCHO (aq) (14 mL, 0.1772 mmol, 5.0 eq.) in MeOH (120 mL) at 0° C. was added $NaBH_3CN$ (3.9 g, 0.0620 mol, 1.6 eq.), then HOAc (3 mL) was added to adjust pH~7.0. The mixture was warmed to r.t. and stirred overnight, then concentrated. The residue was dissolved in DCM (200 mL), and washed with water and brine, dried over anhydrous $Na_2SO_4$, concentrated and purified by $SiO_2$ column chromatography (DCM/MeOH) to give the title compound as a light yellow oil (6.4 g, 80% yield).

ESI m/: calcd for $C_{12}H_{18}N_2O_2$ $[M+H]^+$: 224.1, found: 224.1.

Example 201. Synthesis of Compound 568

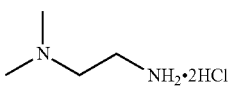
568

Compound 567 (3.0 g, 13.4 mmol, 1.0 eq.) and Pd/C (0.3 g, 10% Pd/C, 50% wet) were mixed with HCl (3 mL) and MeOH (100 mL) in a hydrogenation bottle and shaken at 100 psi $H_2$ atmosphere for 5 h. Then the mixture was filtered over Celite and the filtrate was concentrated to give the title compound as a yellow solid (2.1 g, 98% yield). $^1$H NMR (400 MHz, D2O) δ 3.33 (d, J=4.6 Hz, 2H), 3.27 (s, 2H), 2.79 (s, 6H).

Example 202. Synthesis of Compound 569

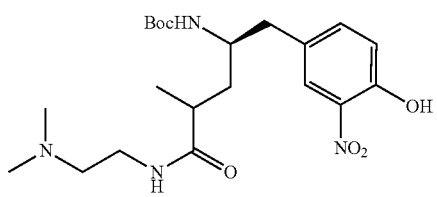
569

To a solution of compound 103 (0.58 g, 1.58 mmol, 1.0 eq.) and compound 568 (0.051 g, 3.15 mmol, 2.0 eq.) in anhydrous DMF (10 mL) at 0° C. were added HATU (0.090 g, 2.37 mmol, 1.5 eq.) and TEA (0.656 mL, 4.74 mmol, 3.0 eq.). After stirring for 10 minutes, the reaction was warmed to r.t. and stirred for 90 minutes. The mixture was diluted with $H_2O$ and extracted with EA (3×100 mL). The combined organic layers were washed with water and brine, dried over anhydrous $Na_2SO_4$, concentrated to give the title compound as a yellow foamy solid (0.67 g, 97% yield). ESI m/z calcd for $C_{21}H_{35}N_4O_6$ $[M+H]^+$: 439.2, found:439.2.

Example 203. Synthesis of Compound 570

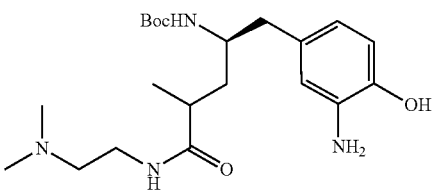
570

Pd/C (0.2 g, 10% Pd/C, 50% wet) was added to a solution of compound 569 (0.60 g, 13.7 mmol, 1.0 eq.) in EA (10 mL). The mixture was shaken at 100 psi $H_2$ atmosphere for 4 h. Then the mixture was filtered over Celite and the filtrate was concentrated to give the title compound as a green oil (5.50 g, 98% yield). ESI m/z calcd for $C_{21}H_{37}N_4O_{64}$ $[M+H]^+$: 409.3, found:409.3.

Example 204. Synthesis of Compound 571

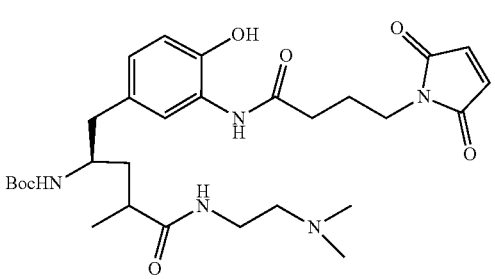
571

To a solution of compound 570 (0.50 g, 1.22 mmol, 1.0 eq.) in 95% EtOH (10 mL) and 0.1M $NaH_2PO_4$ (2 mL) was added compound 125 (0.683 g, 2.44 mmol, 2.0 eq.) and the reaction was stirred overnight and then concentrated and purified by $SiO_2$ column chromatography (DCM/MeOH) to give the title compound as a light yellow oil (0.624 g, 89% yield). ESI m/z calcd for $C_{29}H_{44}N_5O_7$ $[M+H]^+$: 574.3, found:574.3.

Example 205. Synthesis of Compound 572

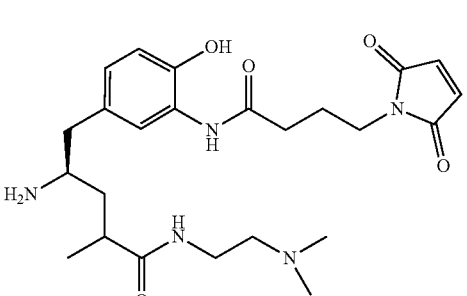
572

To a solution of compound 571 (0.20 g, 0.349 mmol, 1.0 eq) in DCM (6.0 mL) at r.t. was added TFA (2.0 mL) and the reaction was stirred for 2 h, then diluted with anhydrous toluene and concentrated, this operation was repeated for three times to give the title compound as a yellow oil (165 mg, theoretical yield). ESI m/z calcd for $C_{24}H_{36}N_5O_5$ $[M+H]^+$: 474.3, found:474.3.

Example 206. Synthesis of Compound 573

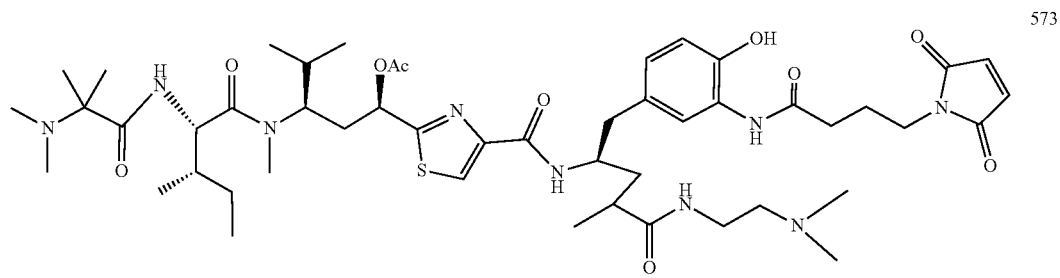 [SMILES: CC[C@H](C)[C@H](NC(=O)C(C)(C)N(C)C)C(=O)N(C)[C@H](C[C@@H](OC(C)=O)c1nc(C(=O)N[C@@H](Cc2ccc(O)c(NC(=O)CCCN3C(=O)C=CC3=O)c2)CC(C)C(=O)NCCN(C)C)cs1)C(C)C]

To a solution of compound 572 (0.165 g, 0.349 mmol, 1.0 eq.) in anhydrous DMF (2 mL) at 0° C. was added compound 41a (0.290 g, 1.047 mmol, 1.2 eq.) in anhydrous DMF (3 mL) and the reaction was stirred for 10 minutes, then warmed to r.t. and stirred for 1 h. The reaction mixture was concentrated and purified on prep-HPLC ($C_{18}$ column, mobile phase A: water, mobile phase B: acetonitrile, from 10% of B to 80% of B in 60 min). The fractions were pooled and lyophilized to give the title compound (58 mg, 17% yield) as a light yellow foamy solid. ESI m/z calcd for $C_{49}H_{76}N_9O_{10}S$ [M+H]$^+$: 982.5, found: 982.5.

Example 207. Synthesis of Compound 576

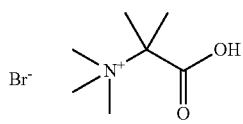

To a solution of 2-bromo-2-methylpropanoic acid (3.00 g, 17.9 mmol) in THF (30 mL) was added trimethylamine (1M solution in THF, 17.9 mL, 35.9 mmol). The reaction mixture was stirred overnight at r.t. The precipitate was collected by filtration and washed with EA to give compound 576 (4.00 g, theoretical yield) as a white solid. ESI m/z calcd for $C_7H_{16}NO_2$ [M+H]$^+$: 146, found 146.

Example 208. Synthesis of Compound 577

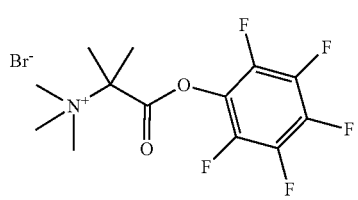

To a solution of compound 576 (1.55 g, 6.9 mmol) and PFP (2.50 g, 13.8 mmol) in DCM (20 mL) was added DCC (2.80 g, 13.8 mmol). The reaction mixture was stirred at r.t. overnight.

The reaction was filtered and the filtrate was concentrated under vacuum to give compound 577 as a colorless oil, which was used directly in the next step. ESI m/: calcd for $C_{13}H_{15}F5NO_2$ [M+H]$^+$: 312, found 312.

Example 209. Synthesis of Compound 578

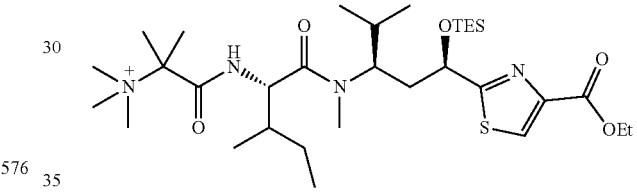

To a solution of compound 17 (1.78 g, 3.4 mmol) and the compound 577 (6.9 mmol) in DMF (20 mL) was added DIPEA (1.8 mL, 10.4 mmol) at 0° C. The reaction mixture was warmed to r.t. and stirred for 1 h, then concentrated under vacuum and purified by silica column (100:1 to 5:1 DCM/MeOH) to give compound 578 (1.20 g, 54% yield) as a foamy solid. ESI m/z calcd for $C_{32}H_{61}N_4O_5SSi$ [M+H]$^+$: 642, found 642.

Example 210. Synthesis of Compound 579

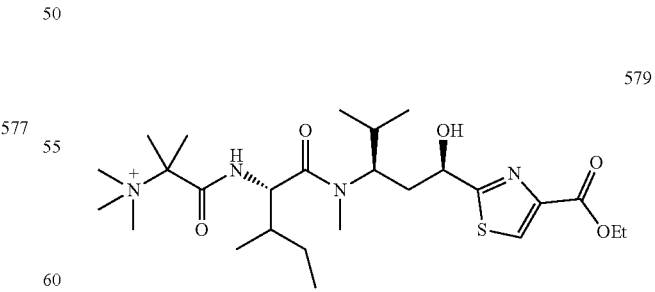

Compound 578 (1.20 g, 1.86 mmol) was dissolved in AcOH/THF/H$_2$O (v/v/v 3:1:1, 20 mL) and stirred overnight. The reaction was then concentrated under vacuum, and used for the next step without further purification. ESI m/z calcd for $C_{26}H_{47}N_4O_5S$ [M+H]$^+$: 527, found 527.

Example 211. Synthesis of Compound 580

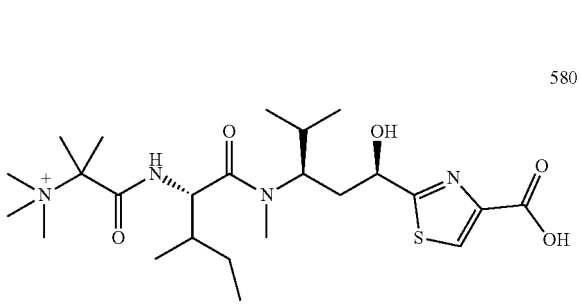

To a solution of compound 579 (1.86 mmol) in 1,4-dioxane (10 mL) was added 1N NaOH (9.3 mL). And the reaction mixture was stirred for 2 h and concentrated under vacuum. The residue was diluted with water (10 mL) and 1N HCl was added to adjust pH to ~4. The mixture was concentrated under vacuum to give compound 580 as a white solid. ESI m/z calcd for $C_{24}H_{43}N_4O_5S$ $[M+H]^+$: 499, found 499.

Example 212. Synthesis of Compound 581

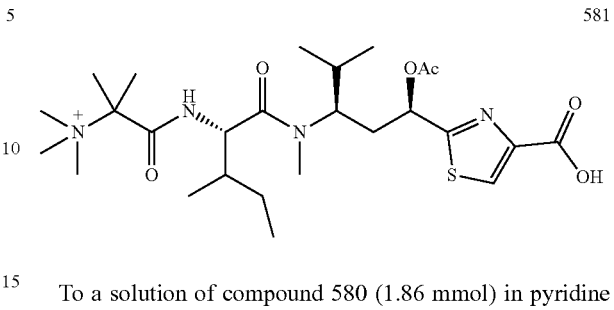

To a solution of compound 580 (1.86 mmol) in pyridine (10 mL) was added acetic anhydride (884 μL, 9.36 mmol) at 0° C. Then the reaction mixture was warmed to r.t. and stirred overnight. The reaction was concentrated under vacuum and then diluted with $H_2O$ (20 mL) and washed with EA (3×10 mL). The aqueous layer was concentrated under vacuum to give compound 581 as a yellow solid. ESI m/z calcd for $C_{26}H_{45}N_4O_6S$ $[M+H]^+$: 541, found 541.

Example 213. Synthesis of Compound 582

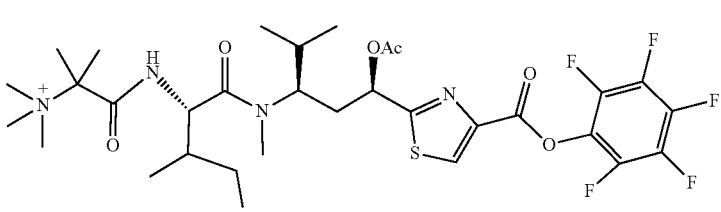

To a solution of compound 581 (150 mg, 0.277 mmol) and pentafluorophenol (76.5 mg, 0.415 mmol) in DCM (2 mL) was added EDCI (63.7 mg, 0.33 mmol). The reaction mixture was stirred for 3 h and concentrated under vacuum to give compound 582 as a yellow oil. ESI m/z calcd for $C_{32}H_{44}F_5N_4O_6S$ $[M+H]^+$:707, found 707.

Example 214. Synthesis of Compound 583

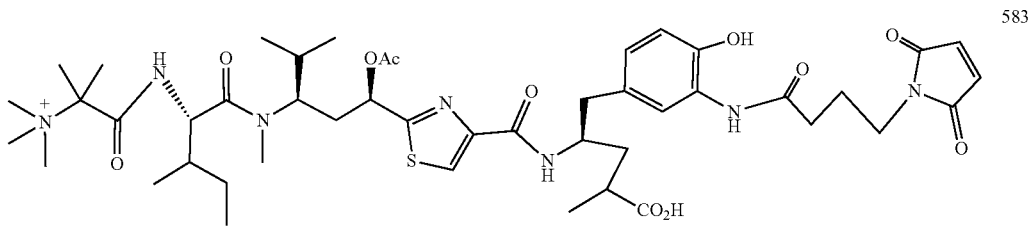

To a solution of compound 127 (50 mg, 0.07 mmol) and compound 582 (0.14 mmol) in DMF (2 mL) was added DIPEA (49 μL, 0.28 mmol) at 0° C. Then the reaction mixture was warmed to r.t. and stirred for 1 h, then concentrated under vacuum and purified by prep-HPLC (10-90% MeCN/$H_2O$) to give compound 583 (30 mg, 46% yield) as a white solid. ESI m/z calcd for $C_{46}H_{68}N_7O_{11}S$ $[M+H]^+$: 926, found 926.

Example 215. Synthesis of Compound 586

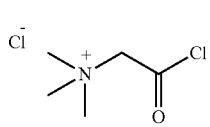
586

A suspension of betaine (870 mg, 7.4 mmol) in thionyl chloride (10 mL) was heated to 70° C. and stirred for 2 h. The reaction was concentrated under vacuum and co-evaporated with toluene (3×10 mL) to afford compound 586 as a yellow solid, which was used in the next step without further purification.

Example 216. Synthesis of Compound 587

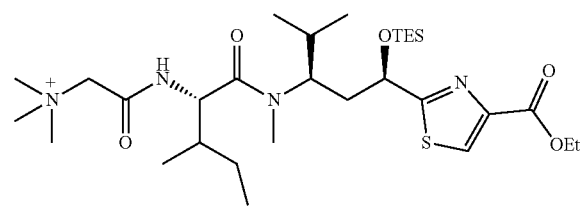
587

To a suspension of compound 17 (1.90 g, 3.71 mmol) in DCM (20 mL) was added DIPEA (2.58 mL, 14.8 mmol). Then the solution was cooled to 0° C. and the above compound 586 in DCM (20 mL) was added. The reaction mixture was warmed to r.t. and stirred for 1 h, concentrated under vacuum and purified by silica column (100:1 to 5:1 DCM/MeOH) to give compound 587 (2.3 g, theoretical yield) as a yellow solid. ESI m/z calcd for $C_{30}H_{57}N_4O_5SSi$ [M+H]$^+$:613, found 613.

Example 217. Synthesis of Compound 588

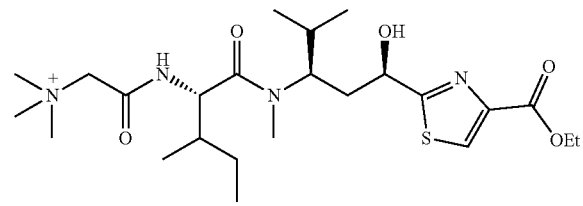
588

Compound 587 (2.3 g, 3.7 mmol) was dissolved in AcOH/THF/H$_2$O (v/v/v 3:1:1, 40 mL) and stirred overnight. The reaction was concentrated to give compound 588, which was used in next step without any purification. ESI m/z calcd for $C_{24}H_{43}N_4O_5S$ [M+H]$^+$: 499, found 499.

Example 218. Synthesis of Compound 589

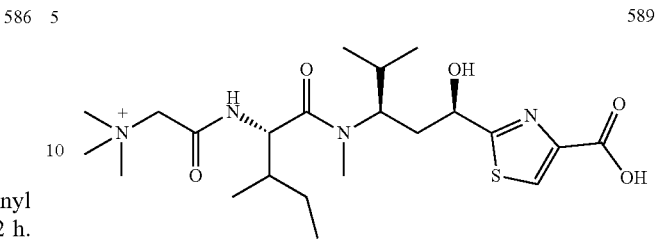
589

To a solution of compound 588 (3.7 mmol) in 1,4-dioxane (20 mL) was added 1N NaOH (18.5 mL), and the reaction mixture was stirred at r.t. for 2 h and concentrated under vacuum. The residue was diluted with 10 mL water and acidified to pH~4 with 1N HCl, then concentrated to give compound 589 (1.00 g, 57% yield) as a white solid. ESI m/z calcd for $C_{22}H_{39}N_4O_5S$ [M+H]$^+$: 471, found 471.

Example 219. Synthesis of Compound 590

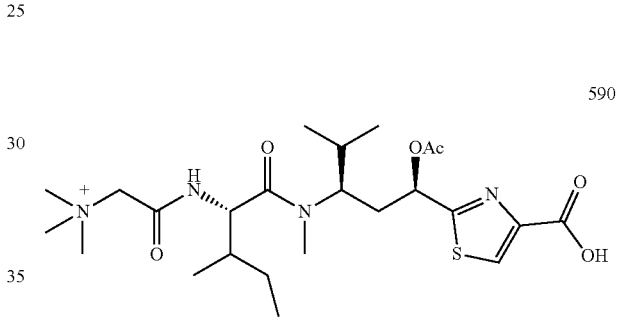
590

To a solution of compound 589 (1.00 g, 2.12 mmol) in pyridine (10 mL) was added acetic anhydride (1 mL, 10.6 mmol) at 0° C. Then the reaction mixture was warmed to r.t. and stirred overnight. The reaction was concentrated under vacuum then diluted with water (20 mL) and washed with EA (3×10 mL). The aqueous phase was concentrated under vacuum to give compound 590 as a yellow solid. ESI m/z calcd for $C_{24}H_{41}N_4O_6S$ [M+H]$^+$: 513, found 513.

Example 220. Synthesis of Compound 591

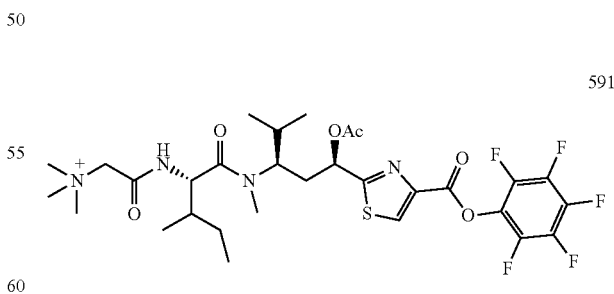
591

To a solution of compound 590 (70 mg, 0.136 mmol) and pentafluorophenol (30 mg, 0.163 mmol) in DCM (2 mL) was added DCC (33.7 mg, 0.163 mmol). The reaction mixture was stirred for 3 h and concentrated under vacuum to give the compound 591 as a yellow oil. ESI m/z calcd for $C_{30}H_{40}F_5N_4O_6S$ [M+H]$^+$:679, found 679.

Example 221. Synthesis of Compound 592

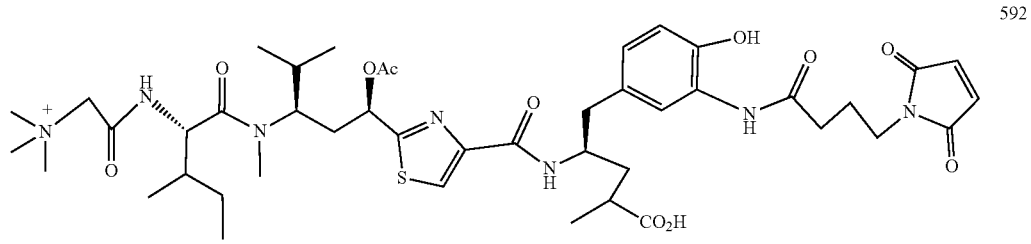

To a solution of compound 591 (0.136 mmol) and compound 127 (0.11 g, 0.273 mmol) in DMF (2 mL) was added DIPEA (71 μL, 0.408 mmol) at 0° C. The reaction mixture was warmed to r.t. and stirred for 1 h, concentrated under vacuum and purified by prep-HPLC to give compound 592 (30.9 mg, 25% yield) as a yellow solid. ESI m/z calcd for $C_{44}H_{64}N_7O_{11}S$ [M+H]$^+$:899, found 899.

Example 222. Synthesis of Compound 604

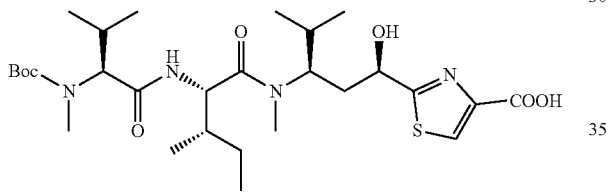

(S)-2-((tert-butoxycarbonyl)(methyl)amino)-3-methylbutanoic acid (33 mg, 0.14 mmol), DCC (32 mg, 0.154 mmol) and pentafluorophenol (39 mg, 0.21 mmol) were dissolved in ethyl acetate (20 mL) and the reaction was stirred at room temperature overnight. The reaction was then concentrated to dryness to give compound 602, which was dissolved in 2 mL of DMA, and a solution of compound 603 (52 mg, 0.14 mmol) in 3 mL of DMA and DIPEA (48.5 μL, 0.28 mmol) were added. The reaction was stirred at room temperature overnight and then concentrated. The residue was diluted with 1 mL of acetonitrile and purified by reverse phase HPLC with a gradient of MeCN/H$_2$O to afford compound 604 (40.2 mg, 49% yield) o ESI: m/z: calcd for $C_{28}H_{49}N_4O_7S$ [M+H]$^+$: 585.32, found 585.32.

Example 223. Synthesis of Compound 605

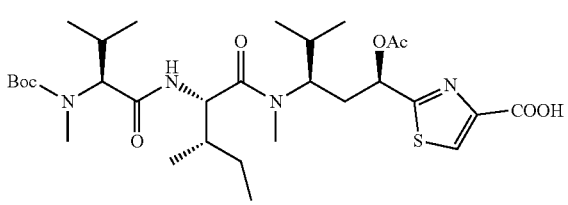

To a solution of compound 604 (40 mg, 0.069 mmol) in pyridine (8 mL) at 0° C. was added acetic anhydride (20.4 mg, 0.2 mmol), and the reaction was warmed to room temperature and stirred overnight, then concentrated. The residue was purified by column chromatography (MeOH/DCM) to afford the title compound 605 (48.1 mg, ~100% yield). ESI: m/z: calcd for $C_{30}H_{51}N_4O_9S$ [M+H]$^+$: 627.33, found 627.33.

Example 224. Synthesis of Compound 608

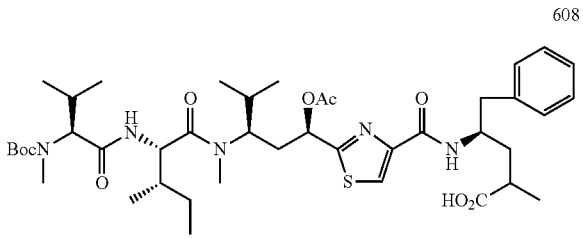 [SMILES: CC[C@H](C)[C@H](NC(=O)[C@H](C(C)C)N(C)C(=O)OC(C)(C)C)C(=O)N(C)[C@H](C[C@@H](OC(C)=O)c1nc(C(=O)N[C@@H](Cc2ccccc2)CC(C)C(=O)O)cs1)C(C)C]

Compound 605 (48.1 mg, 0.077 mmol), DCC (17.4 mg, 0.085 mmol) and pentafluorophenol (21.2 mg, 0.115 mmol) were dissolved in ethyl acetate (10 mL) and the reaction was stirred overnight at room temperature, then concentrated to dryness to give compound 606, which was dissolved in 4 mL of DMA, and a solution of compound 607 (20.7 mg, 0.1 mmol) in 3 mL of DMA and DIPEA (26.8 μL, 0.154 mmol) were added. The reaction was stirred at room temperature overnight and then concentrated. The residue was diluted with 1 mL of acetonitrile and purified by reverse phase HPLC with a gradient of MeCN/H$_2$O to afford compound 608(63 mg, ~100% yield). ESI: m/z: calcd for $C_{42}H_{66}N_5O_9S$ [M+H]$^+$: 816.45, found 816.45.

Example 225. Synthesis of Compound 609

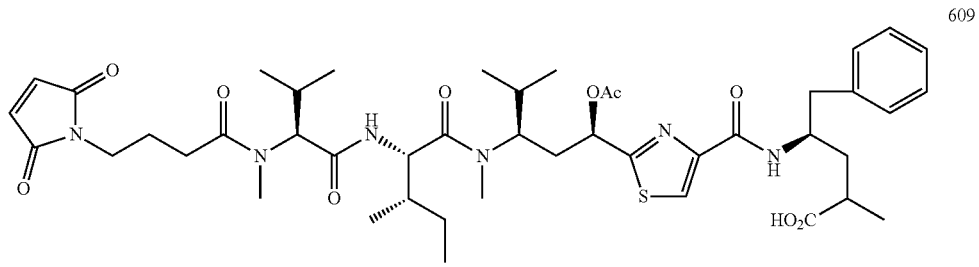 [SMILES: CC[C@H](C)[C@H](NC(=O)[C@H](C(C)C)N(C)C(=O)CCCN1C(=O)C=CC1=O)C(=O)N(C)[C@H](C[C@@H](OC(C)=O)c1nc(C(=O)N[C@@H](Cc2ccccc2)CC(C)C(=O)O)cs1)C(C)C]

Compound 608 from previous step was dissolved in DCM (1 mL) and treated with TFA (1 mL) at r.t. for 2 h. The reaction was concentrated and the residue was dissolved in EtOH (20 mL). Compound 125 (30.8 mg, 0.11 mmol) and 0.1 M NaH$_2$PO$_4$ (4 mL) were added and the resulting mixture was stirred at r.t. overnight, then concentrated and the residue was purified by column chromatography (MeOH/DCM) to afford the title compound 609 (28.5 mg, 42% yield). ESI m/z: calcd for C$_{45}$H$_{65}$N$_6$O$_{10}$S [M+H]$^+$: 881.44, found 881.44.

Example 226. Synthesis of Compound 612

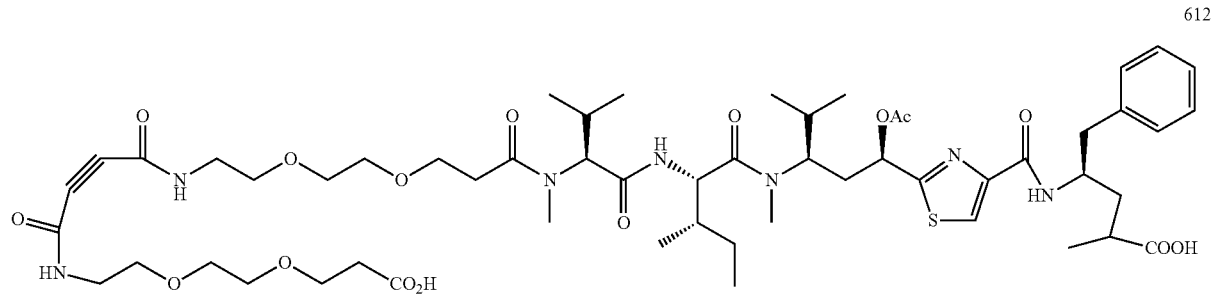 [SMILES: CC[C@H](C)[C@H](NC(=O)[C@H](C(C)C)N(C)C(=O)CCOCCOCCNC(=O)C#CC(=O)NCCOCCOCCC(=O)O)C(=O)N(C)[C@H](C[C@@H](OC(C)=O)c1nc(C(=O)N[C@@H](Cc2ccccc2)CC(C)C(=O)O)cs1)C(C)C]

To a solution of compound 608 (63 mg, 0.077 mmol) in DCM (1 mL) was treated with TFA (1 mL) at room temperature for 2 h, then concentrated and the residue was dissolved in DMA (4 mL). Compound 611 (65.8 mg, 0.11 mmol) and DIPEA (27 µL, 0.154 mmol) were added and the reaction was stirred at room temperature overnight, then concentrated and the residue was purified by reverse phase HPLC with a gradient of MeCN/H$_2$O to afford compound 612 (14 mg, 16% yield). ESI: m/z: calcd for C$_{55}$H$_{84}$N$_7$O$_{16}$S [M+H]$^+$: 1130.56, found 1130.57.

Example 227. Synthesis of Compound 614

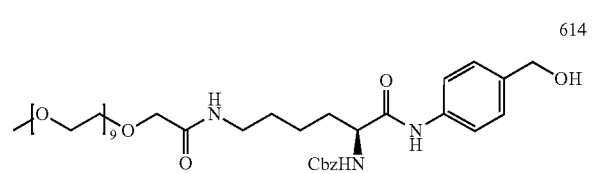

To a solution of compound 436 (3.0 g, 4.00 mmol) in DMF (50 mL) were added HATU (2.3 g, 6 mmol) and TEA (1.7 mL, 12 mmol). The reaction was stirred at 0° C. for 20 min and allowed to warm to r.t. and stirred for 3h. After that, a solution of (4-aminophenyl)methanol (0.99 g, 8 mmol) in DMF (10 mL) was added, and the reaction was stirred at r.t. for 1.5 h, then poured into a separatory funnel containing 150 mL of water and extracted with 50 mL of EtOAc twice. The organic phases were collected and dried over anhydrous Na$_2$SO$_4$, filtered and concentrated. The residue was purified by column chromatography (MeOH/DCM) to afford the title compound 614 (3.9 g, -100% yield). ESI: m/z: calcd for C$_{42}$H$_{68}$N$_3$O$_{15}$ [M+H]$^+$: 854.46, found 854.46.

Example 228. Synthesis of Compound 615

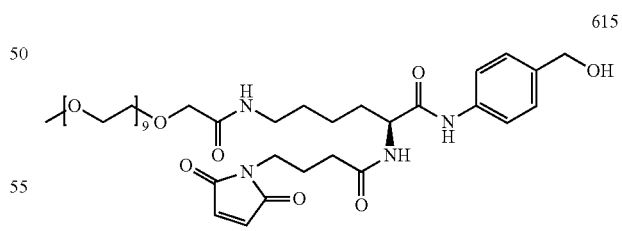

To a solution of compound 614 (1.9 g, 2.22 mmol) in MeOH (20 mL) was added Pd/C (0.19 g, 10 wt %) in a hydrogenation bottle. The mixture was shaken for 50 min, filtered through Celite (filter aid), and the filtrate was concentrated then dissolved in EtOH (100 mL). Compound 125 (0.61 g, 2.20 mmol) and 0.1 M NaH$_2$PO$_4$ (20 mL) were added and the reaction was stirred overnight at room temperature, then concentrated. The residue was diluted with MeOH and purified by reverse phase HPLC with a gradient of MeCN/H$_2$O to afforded compound 615 (0.30 g 19% yield). ESI: m/z: calcd for C$_{42}$H$_{69}$N$_4$O$_{16}$ [M+H]$^+$: 885.46, found 885.44.

Example 229. Synthesis of Compound 616

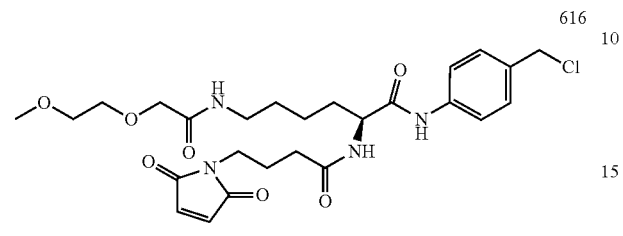

To a solution of compound 615 (0.12 g, 0.14 mmol) in DMF (50 mL) was added SOCl$_2$ (11 μL, 0.154 mmol) at 0° C. The reaction was stirred for 1 hour at 0° C. and then concentrated to dryness to give crude product compound 616 (0.13 g, 0.14 mmol). ESI: m/z: calcd for C$_{42}$H$_{68}$ClN$_4$O$_{15}$ [M+H]$^+$: 903.43, found 903.44.

Example 230. Synthesis of Compound 618

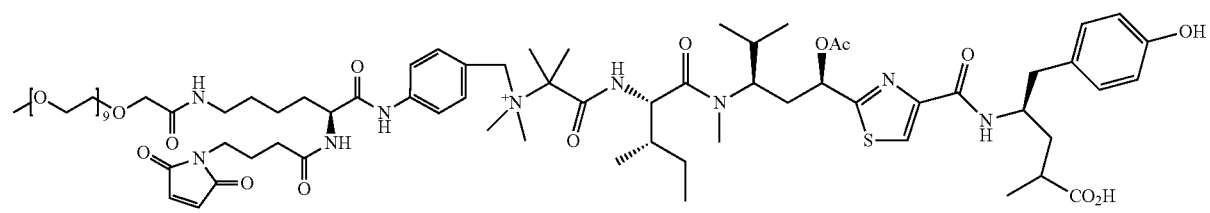

To a solution of compound 616 (0.13 g, 0.14 mmol) and compound 617 (0.06 g, 0.07 mmol) in DMF (10 mL) were added TBAI (16 mg, 0.042 mmol) and DIPEA (64 μL, 0.35 mmol). The reaction was stirred at r.t. for 1 h and then concentrated. The residue was purified by reverse phase HPLC with a gradient of MeCN/H$_2$O to afford compound 618 (10 mg, 8.9% yield0. ESI: m/z: calcd for C$_{79}$H$_{125}$N$_9$O$_{23}$S [M+H]$^-$: 1599.85, found 1599.82.

Example 231. Synthesis of Compound 620

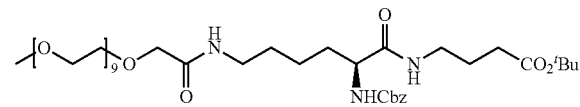

A mixture of tert-butyl 4-aminobutanoate (1.03 g, 6.12 mmol) and compound 436 (4.16 g, 5.56 mmol) in DMF (18 mL) was cooled to 0° C. and HATU (2.32 g, 6.12 mmol) and TEA (1.2 mL, 8.34 mmol) were added in sequence. The reaction was stirred for 50 min, then diluted with water (300 mL), and extracted with EtOAc (3×250 mL). The EtOAc solution was washed with brine, dried over anhydrous Na$_2$SO$_4$, filtered, concentrated and purified by SiO$_2$ column chromatography (32:1 DCM/MeOH) to give compound 620 (5.98 g). MS ESI m/z calcd for C$_{43}$H$_{75}$N$_3$O$_{16}$ [M+H]$^+$ 890.51, found 891.09.

Example 232. Synthesis of Compound 621

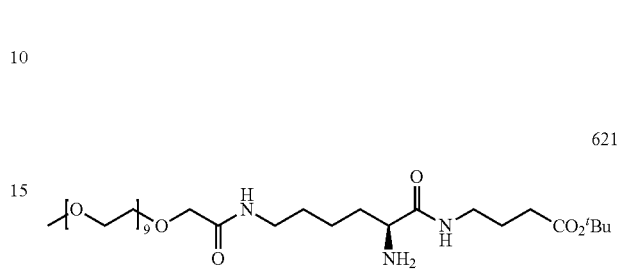

To a solution of compound 620 (1.0 g, 1.13 mmol) in MeOH (50 mL) was added Pd/C (10 wt %, 0.10 g) in a hydrogenation bottle. The mixture was shaken for 2 h, filtered through Celite (filter aid), and the filtrate was concentrated to afford compound 621(1.0 g, 1.32 mmol, yield>100%). ESI: m/z: calcd for C$_{35}$H$_{70}$N$_3$O$_{14}$ [M+H]$^+$: 756.48, found 756.47.

Example 233. Synthesis of Compound 622

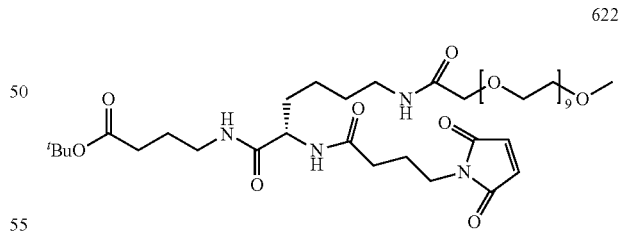

To a solution of compound 621 (0.93 g, 1.23 mmol, 1.0 eq) and compound 125 (0.95 g, 1.84 mmol, 1.5 eq) in 95% EtOH (50 mL) at room temperature was added NaH$_2$PO$_4$ solution (0.1M, pH 5.0, 10 mL). The mixture was stirred overnight, then concentrated and diluted with water (50 mL) and extracted with DCM (80 mL×3), dried over anhydrous Na$_2$SO$_4$, filtered, concentrated and purified by SiO$_2$ column chromatography (DCM:MeOH=25:1) to give the title compound as a light yellow oil (0.90 g, 80%). ESI m/z: calcd for C$_{43}$H$_{77}$N$_4$O$_{17}$ [M+H]$^+$: 921.5, found: 921.5.

Example 234. Synthesis of Compound 623

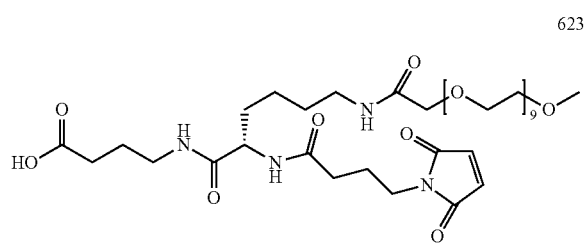

Compound 622 (0.90 g, 0.98 mmol) was dissolved in HCOOH (50 mL) and stirred at room temperature for 1 hour. The reaction mixture was concentrated and co-evaporated with toluene twice, and the residue was placed on a vacuum pump to give compound 623 (0.85 g, 0.98 mmol, crude product). ESI: m/z: calcd for $C_{39}H_{69}N_4O_{17}$ [M+H]$^+$: 865.46, found 865.44.

Example 235. Synthesis of Compound 624

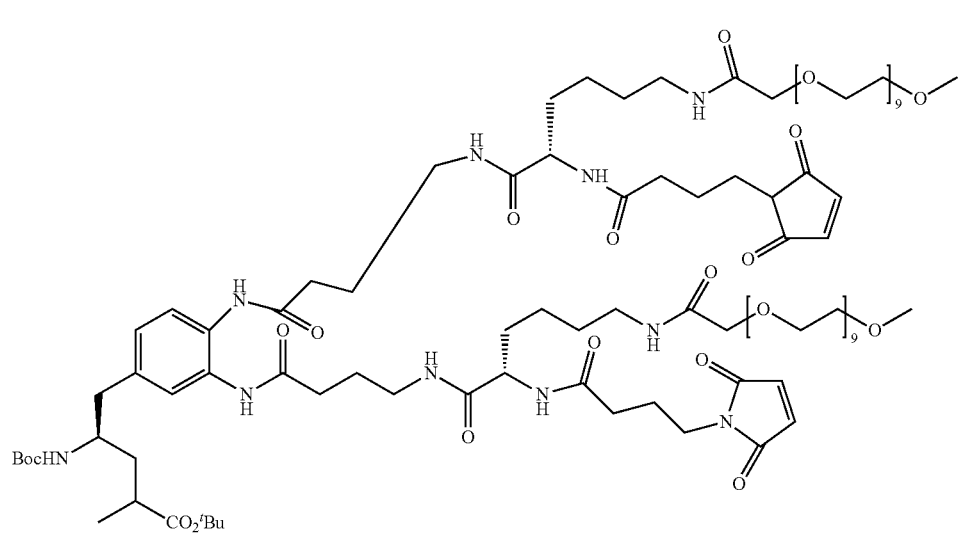

To a solution of compound 392 (92.9 mg, 0.236 mmol) and compound 623 (510 mg, 0.59 mmol) in DMF (3 mL), were added HATU (179 mg, 0.472 mmol) and triethylamine (82 μL, 0.59 mmol) at 0° C. The reaction mixture was warmed to r.t. and stirred for 1 h, then diluted with dichloromethane (50 mL), washed with 1N HCl (5 mL), water (5 mL), dried over sodium sulfate, filtered and concentrated under vacuum and purified by silica gel column chromatography to afford the title product (295 mg, 60% yield). ESI m/z calcd for $C_{99}H_{168}N_{11}O_{36}$ [M+H]$^+$: 2087.16, found 2087.14.

Example 236. Synthesis of Compound 625

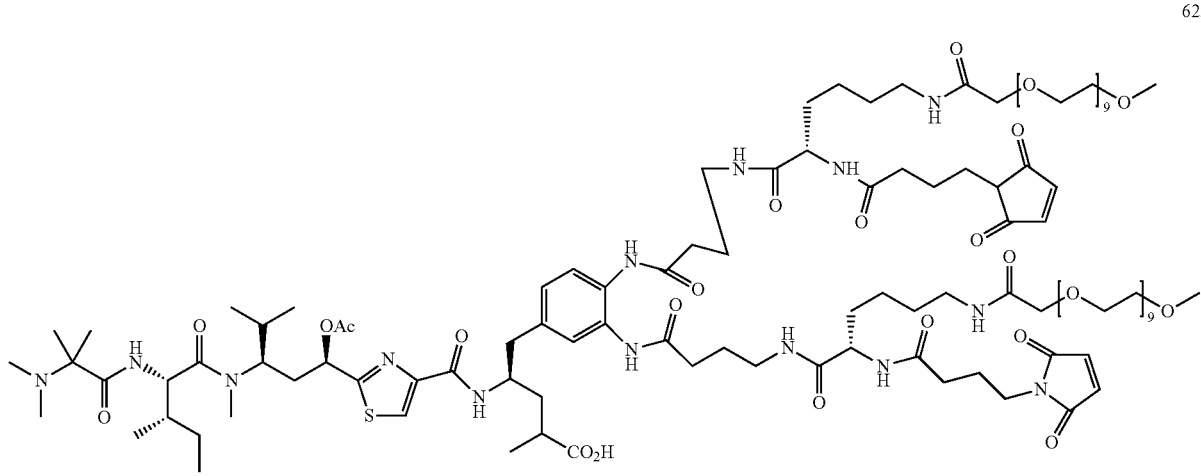

To a solution of compound 624 (100 mg, 0.047 mmol) in DCM (3 mL) was added trifluoroacetic acid (3 mL), and the reaction mixture was stirred at room temperature for 2 hours, and then concentrated. The residue was dissolved in DMF (3 mL), to which compound 41a (49.7 mg, 0.071 mmol) and DIPEA (12 µL, 0.071 mmol) were added. The reaction mixture was stirred at r.t. for 1 h, then concentrated under vacuum and purified by prep-HPLC to afford the title compound (57 mg, 50% yield). ESI m/z calcd for $C_{115}H_{192}N_{11}O_{39}S$ [M+H]$^+$: 2439.31, found 2439.30.

Example 237. Synthesis of Compound 627

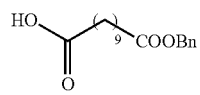

627

To a solution of undecanedioic acid (1.73 g, 8 mmol) in DMF (30 mL) were added $K_2CO_3$ (1.1 g, 8 mmol) and BnBr (1.36 g, 8 mmol). The mixture was stirred at r.t. overnight, then concentrated and purified by column chromatography (PE/EtOAc) to afford the title compound 627 (1.1 g, 45% yield). ESI m/z: calcd for $C_{18}H_{27}O_4$ [M+H]$^+$: 307.18, found 307.15.

Example 238. Synthesis of Compound 628

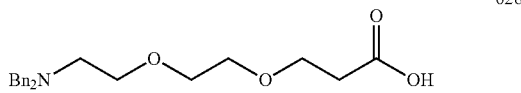

628

To a solution of compound 300 (2.00 g, 4.84 mmol) in DCM (5 mL) was added $HCO_2H$ (5 mL). The reaction was stirred at room temperature overnight, then concentrated to dryness and co-evaporated twice with DCM, and the residue was placed on a pump to give compound 628 (1.72 g, ~100% yield). ESI m/z calcd for $C_{21}H_{27}NO_4$ [M+H]$^+$: 358.19, found 358.19.

Example 239. Synthesis of Compound 629

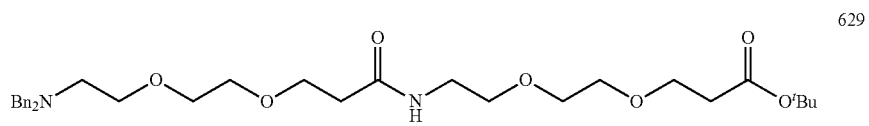

629

To a solution of compound 301 (1.12 g, 4.83 mmol) and compound 628 (1.72 g, 4.83 mmol) in DCM (30 mL) were added HATU (1.83 g, 4.83 mmol) and TEA (0.68 mL, 4.83 mmol) at 0° C. The reaction was warmed to r.t. and stirred for 1 h, then diluted with 50 mL DCM and poured into a separatory funnel containing 50 mL of water. The organic phase was separated, and washed with brine (50 mL), dried over anhydrous $Na_2SO_4$, filtered and concentrated. The residue was purified by column chromatography (MeOH/DCM) to afford the title compound 629 (2.21 g, 80% yield). ESI m/z calcd for $C_{32}H_{48}N_2O_7$ [M+H]$^+$: 573.35, found 573.35.

Example 240. Synthesis of Compound 630

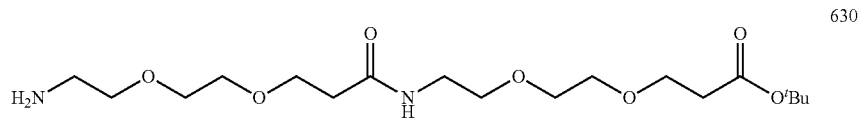 [SMILES: CC(C)(C)OC(=O)CCOCCOCCNC(=O)CCOCCOCCN]

630

To a solution of compound 629 (2.21 g, 3.86 mmol) in MeOH (20 mL) was added Pd/C (10 wt %, 0.2 g) in a hydrogenation bottle. The mixture was stirred under 1 atm $H_2$ overnight, filtered through Celite (filter aid), and the filtrate was concentrated to afford compound 630 (1.5 g, ~100% yield). ESI m/z calcd for $C_{18}H_{36}N_2O_7$ $[M+H]^+$: 393.25, found 393.25

Example 241. Synthesis of Compound 631

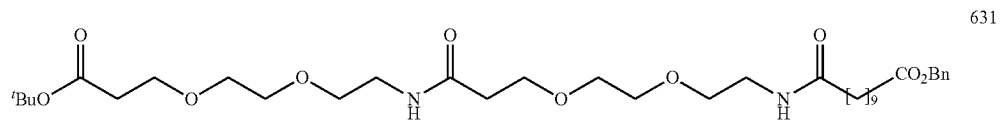

631

To a solution of compound 630 (1.50 g, 3.86 mmol) and compound 627 (1.10 g, 3.6 mmol) in DCM (50 mL) were added HATU (1.48 g, 3.9 mmol) and TEA (0.55 mL, 3.9 mmol) at 0° C. The reaction mixture was stirred at r.t. for 1 h, then diluted with 50 mL DCM and poured into a separatory funnel containing 50 mL of water. The organic phase was separated, washed with brine (50 mL), dried over anhydrous $Na_2SO_4$, filtered and concentrated. The residue was purified by column chromatography (MeOH/DCM) to afford the title compound 631 (1.50 g, 61% yield). ESI m/z calcd for $C_{36}H_{61}N_2O_{10}$ $[M+H]^+$: 681.42, found 681.42.

Example 242. Synthesis of Compound 632

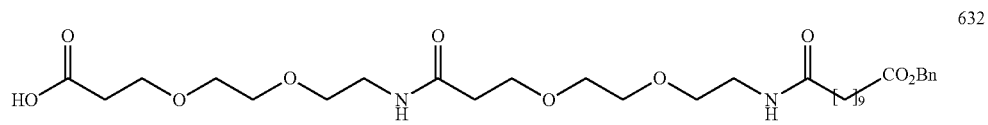

632

To a solution of compound 631 (1.50 g, 2.2 mmol) in DCM (1 mL) was added TFA (3 mL). The reaction was stirred at room temperature for 1 h, then concentrated to dryness and co-evaporated twice with DCM, and the residue was placed on a pump to give compound 632 (0.09 g, 2.2 mmol, crude product). ESI m/z: calcd for $C_{32}H_{53}N_2O_{10}$ $[M+H]^+$: 625.36, found 625.35.

Example 243. Synthesis of Compound 633

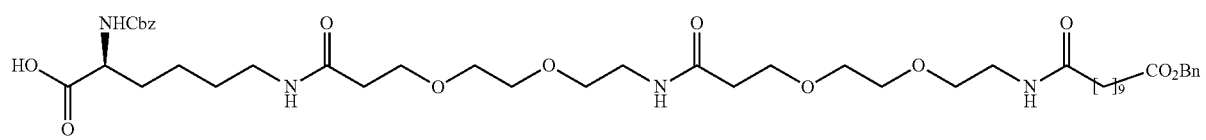

633

To a solution of compound 632 (1.50 g, 2.20 mmol) and Z-Lys-OH (0.62 g, 2.20 mmol) in DCM (50 mL) were added HATU (0.84 g, 2.20 mmol) and TEA (0.31 mL, 2.20 mmol) at 0° C. The reaction mixture was stirred at r.t. for 1 h, then diluted with 50 mL DCM and poured into a separatory funnel containing 100 mL of water. The organic phase was separated, and washed with brine (100 mL), dried over anhydrous $Na_2SO_4$, filtered and concentrated. The residue was purified by column chromatography (MeOH/DCM) to afford the title compound 633 (1.00 g, 53% yield). ESI m/z calcd for $C_{46}H_{71}N_4O_{13}$ $[M+H]^+$: 887.49, found 887.50.

Example 244. Synthesis of Compound 634

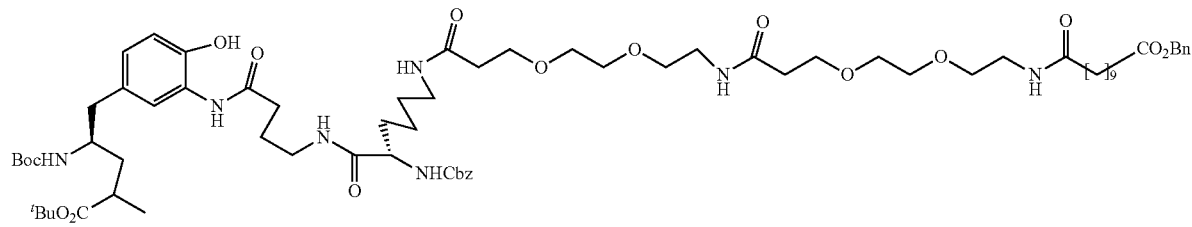

634

To a solution of compound 633 (0.50 g, 0.56 mmol) in DMF (5 mL) was added HATU (0.21g, 0.56 mmol) and the reaction was stirred at room temperature for 30 min. After that, a solution of compound 438 (0.27 g, 0.56 mmol) in DMF (5 mL) and TEA (85 µL, 0.6 mmol) were added in sequence at 0° C., and the reaction was stirred for 1 h. The reaction mixture was poured into a separatory funnel containing 100 mL of water and extracted with 50 mL of EtOAc twice. The organic phase was washed once with 100 mL of brine, dried over anhydrous $Na_2SO_4$, filtered and concentrated. The residue was purified by column chromatography (MeOH/DCM) to afford the title compound 634 (0.40 g, 55% yield). ESI m/z: calcd for $C_{71}H_{11}N_7O_{18}S$ $[M+H]^+$: 1348.78, found 1348.78.

Example 245. Synthesis of Compound 635

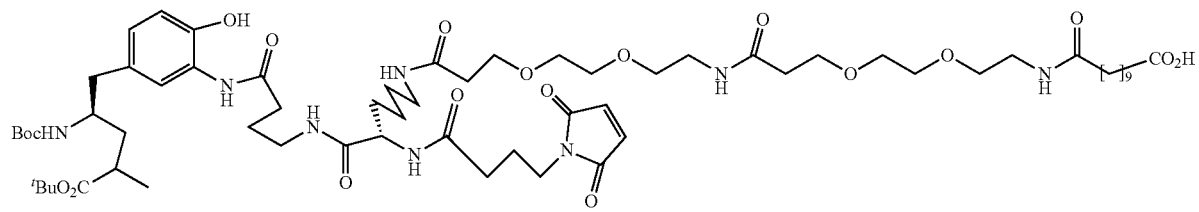

635

To a solution of compound 634 (0.40 g, 0.30 mmol) in MeOH (20 mL) was added Pd/C (10 wt %, 0.2 g) in a hydrogenation bottle. The mixture was stirred under 1 atm $H_2$ overnight, filtered through Celite (filter aid), and the filtrate was concentrated and re-dissolved in EtOH (20 mL) Compound 125 (88.5 mg, 0.30 mmol) and 0.1 M $NaH_2PO_4$ (4 mL) were added. The mixture was stirred at r.t. overnight, then concentrated and the residue was purified by column chromatography (MeOH/DCM) to afford the title compound 635 (0.10 g, 26% yield). ESI m/z: calcd for $C_{64}H_{106}N_9O_{19}$ $[M+H]^+$: 1304.75, found 1304.75.

Example 246. Synthesis of Compound 636

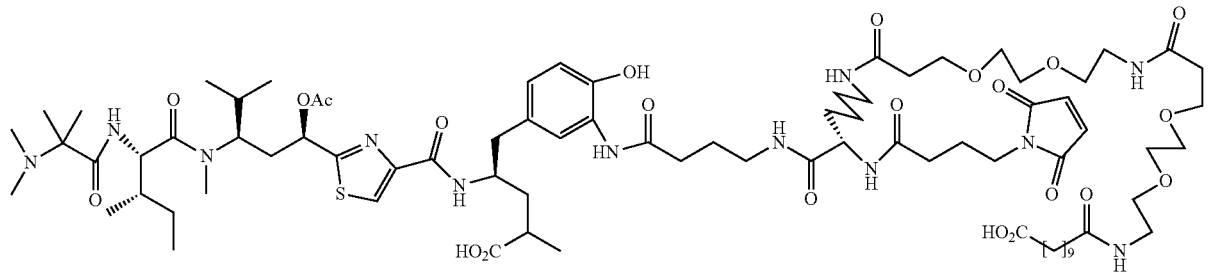

636

To a solution of compound 635 (0.10 g, 0.077 mmol) in DCM (1 mL) was added TFA (3 mL). The reaction was stirred at room temperature for 30 min, then concentrated to dryness and co-evaporated twice with DCM, and the residue was dissolved in DMA (4 mL). Compound 41a (65.8 mg, 0.11 mmol) and DIPEA (26 µL, 0.15 mmol) were added. The reaction mixture was stirred at room temperature for 1 h and then concentrated. The residue was diluted with 2 mL MeCN and purified by reverse phase HPLC with a gradient of MeCN/H$_2$O to afforded compound 636 (20 mg, 15% yield). ESI m/z: calcd for C$_{80}$H$_{130}$N$_{13}$O$_{22}$S [M+H]$^+$: 1656.90, found 1656.91.

Example 247. Synthesis of Compound 638

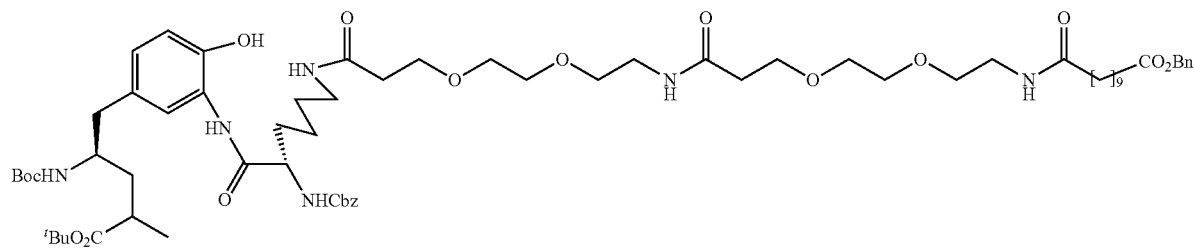

To a solution of compound 633 (0.50 g, 0.56 mmol) in DMF (5 mL) was added HATU (0.21 g, 0.56 mmol) and the reaction was stirred at room temperature for 30 min. After that, a solution of compound 110 (0.22 g, 0.56 mmol) in DMF (5 mL) and TEA (85 µL, 0.60 mmol) were added at 0° C. After stirring for 1 h, the reaction mixture was poured into a separatory funnel containing 100 mL of water and extracted with 50 mL of EtOAc twice. The organic phase was separated and washed with 100 mL of brine, dried over anhydrous Na$_2$SO$_4$, filtered and concentrated. The residue was purified by column chromatography (MeOH/DCM) to afford the title compound 638 (0.20 g, 26% yield). ESI m/z: calcd for C$_{67}$H$_{103}$N$_6$O$_{17}$ [M+H]$^+$: 1263.73, found 1263.73.

Example 248. Synthesis of Compound 639

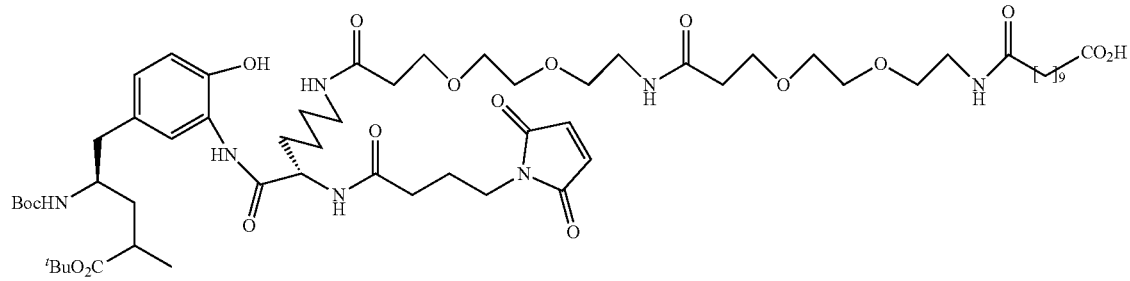

To a solution of compound 638 (0.20 g, 0.16 mmol) in MeOH (20 mL) was added Pd/C (10 wt %, 0.2 g) in a hydrogenation bottle. The mixture was stirred under 1 atm H$_2$ overnight, filtered through Celite (filter aid), and the filtrate was concentrated then dissolved in EtOH (20 mL) Compound 125 (47.2 mg, 0.30 mmol) and 0.1 M NaH$_2$PO$_4$ (4 mL) were added. The mixture was stirred at r.t. overnight, then concentrated and the residue was purified by column chromatography (MeOH/DCM) to afford the title compound 639 (75 mg, 40% yield). ESI m/z: calcd for C$_{60}$H$_{98}$N$_7$O$_{18}$ [M+H]$^+$: 1204.69, found 1204.68.

Example 249. Synthesis of Compound 640

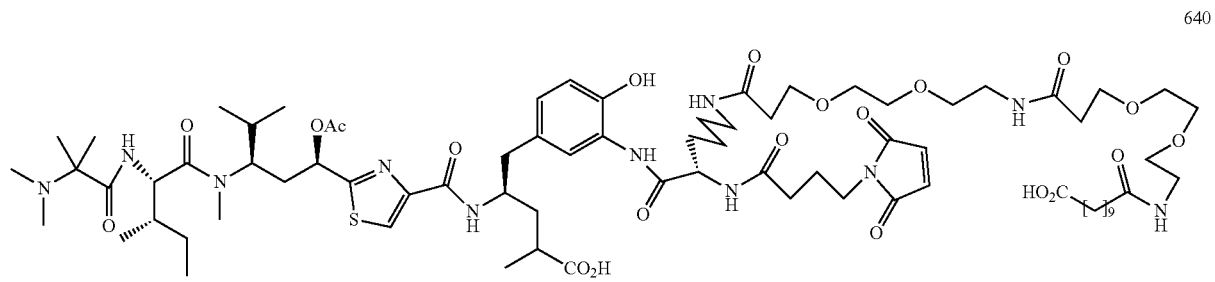

640

To a solution of compound 639 (75 mg, 0.06 mmol) in DCM (1 mL) was added TFA (3 mL). The reaction was stirred at room temperature for 30 min, then concentrated to dryness and co-evaporated twice with DCM, and the residue was dissolved in DMA (2 mL). Compound 41a (41 mg, 0.06 mmol) and DIPEA (26 µL, 0.15 mmol) were added and the reaction mixture was stirred at room temperature for 1 h, then concentrated. The residue was diluted with 2 mL MeCN and purified by reverse phase HPLC with a gradient of MeCN/H$_2$O to afford compound 640 (34 mg, 37% yield). ESI m/z: calcd for C$_{76}$H$_{122}$N$_{11}$O$_{21}$S [M+H]$^+$: 1556.85, found 1556.85.

Example 250. Synthesis of Compound 642

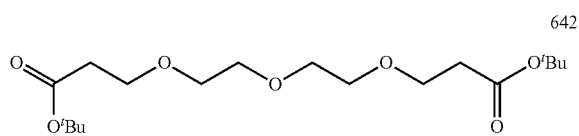 [SMILES: CC(C)(C)OC(=O)CCOCCOCCOCCC(=O)OC(C)(C)C]

642

To a solution of diethylene glycol (20 g, 0.188 mol) in THF (200 mL) was added Na (0.43 g, 0.018 mol). After stirring at r.t. for 1 h, tert-butyl acrylate (48 g, 0.376 mol) was added and the reaction mixture was stirred at r.t. for 2 days. The reaction was concentrated under vacuum and purified by column chromatography to afford the title compound (34 g, 50% yield). ESI m/z calcd for C$_{18}$H$_{35}$O$_7$ [M+H]$^+$: 363.23, found 363.23.

Example 251. Synthesis of Compound 643

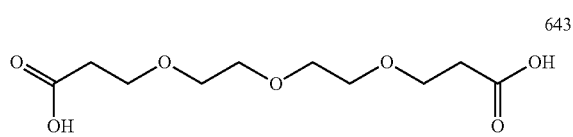 [SMILES: O=C(O)CCOCCOCCOCCC(=O)O]

643

Compound 642 (34 g, 0.093 mol) was dissolved in formic acid (100 mL) at room temperature and stirred overnight. The reaction was concentrated under vacuum to afford the title compound. ESI m/z calcd for C$_{10}$H$_{19}$O$_7$ [M+H]$^-$: 251.11, found 251.11.

Example 252. Synthesis of Compound 644

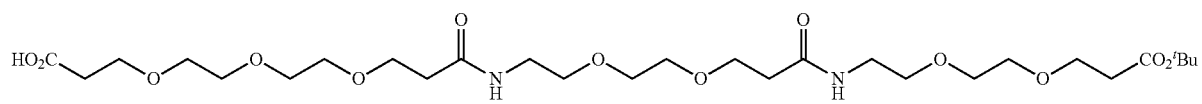

644

To a solution of amine 630 (1.50 g, 3.82 mmol) and diacid 643 (1.90 g, 7.64 mmol) in DMF (10 mL) were added HATU (1.45 g, 3.82 mmol) and DIPEA (0.66 mL, 3.82 mmol) at 0° C. The reaction mixture was warmed to r.t. and stirred for 1 h, then diluted with DCM (80 mL), washed with water (10 mL), dried over sodium sulfate, filtered, concentrated and purified by silica gel column chromatography to afford a colorless liquid (1.75 g, 75% yield). ESI m/z calcd for C$_{28}$H$_{53}$N$_2$O$_{13}$ [M+H]$^+$: 625.35, found 625.35.

Example 253. Synthesis of Compound 645

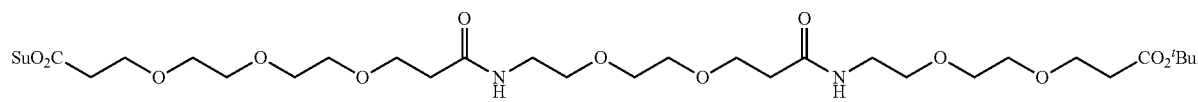

645

To a solution of compound 644 (1.75 g, 2.8 mmol) in DCM (20 mL) were added EDCI (1.07 g, 5.6 mmol) and NHS (0.64 g, 5.6 mmol) at 0° C. The reaction was warmed to room temperature and stirred overnight, then diluted with DCM (80 mL), washed with water (10 mL), dried over sodium sulfate, filtered and concentrated under vacuum to afford the title compound (2.00 g, ~100% yield). ESI m/z calcd for $C_{32}H_{56}N_3O_{15}$ [M+H]$^+$: 722.36, found 722.36.

To a solution of amine 438 (1.87 g, 3.9 mmol) and acid 646 (2.3 g, 2.59 mmol) in dichloromethane (30 mL) were added HATU (0.98 g, 2.59 mmol) and DIPEA (450 μL, 2.59 mmol) at 0° C. The reaction mixture was warmed to r.t. and stirred for 1 h, then concentrated under vacuum and purified by silica gel column chromatography to afford the title compound (2.4 g, 70% yield). ESI m/z calcd for $C_{67}H_{110}N_7O_{21}$ [M+H]$^+$: 1348.77, found 1348.77.

Example 254. Synthesis of Compound 646

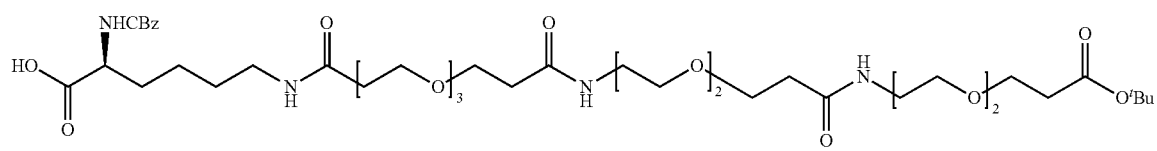

646

To a solution of N-α-Cbz-L-lysine (1.17 g, 4.2 mmol) in water (10 mL) was added sodium bicarbonate (0.47 g, 5.6 mmol), and the reaction mixture was cooled to 5° C., and compound 645 (2.00 g, 2.8 mmol) dissolved in 1,4-Dioxane (10 mL) was added. The reaction was warmed to r.t. and stirred for 1 h, then acidified to pH 3 by addition of 1 N HCl, extracted with DCM (50 mL×3). The organic extracts were washed with water (20 mL), dried over sodium sulfate, filtered and concentrated to afford the title product (2.3 g, 92% yield). ESI m/z calcd for $C_{42}H_{71}N_4O_{16}$ [M+H]$^+$: 887.48, found 887.48.

Example 255. Synthesis of Compound 647

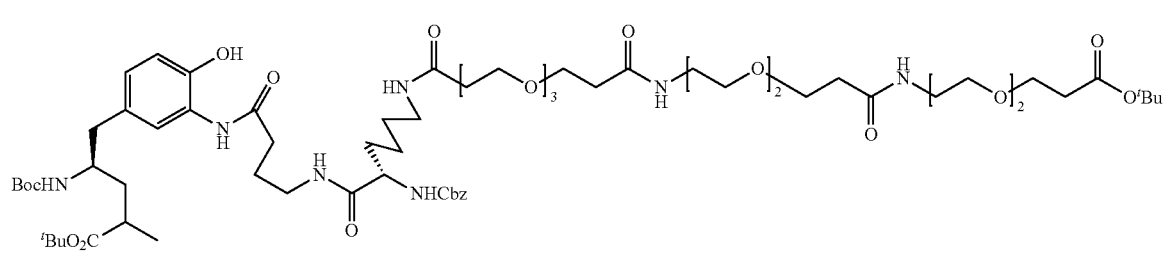

647

Example 256. Synthesis of Compound 648

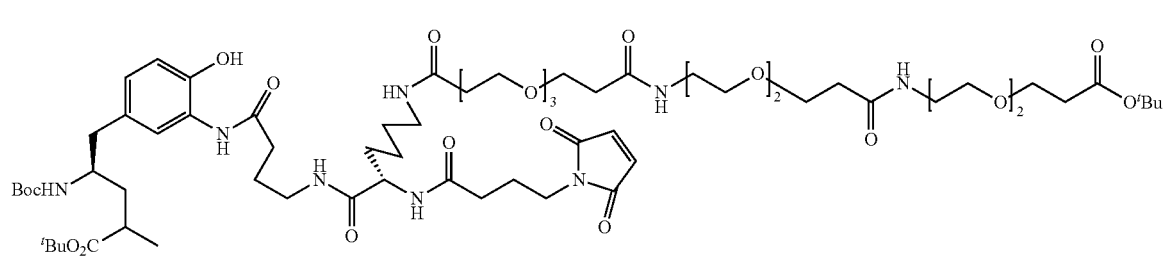

648

To a solution of compound 647 (2.4 g, 1.78 mmol) in MeOH (20 mL) was added Pd/C (10 wt %, 0.2 g) in a hydrogenation bottle. The mixture was stirred under 1 atm H$_2$ overnight, filtered through Celite (filter aid), and the filtrate was concentrated and re-dissolved in EtOH (20 mL) Compound 125 (0.79 g, 2.67 mmol) and 0.1 M NaH$_2$PO$_4$ (10 mL) were added and the mixture was stirred at r.t. overnight, then concentrated and the residue was purified by column chromatography (MeOH/DCM) to afford the title compound 648 (1.52 g, 62% yield). ESI m/z: calcd for C$_{67}$H$_{111}$N$_8$O$_{22}$ [M+H]$^+$: 1379.77, found 1379.75.

Example 257. Synthesis of Compound 649

Example 259. Synthesis of Compound 652

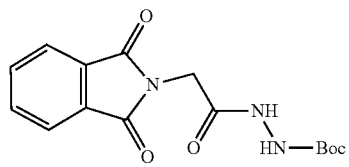

652

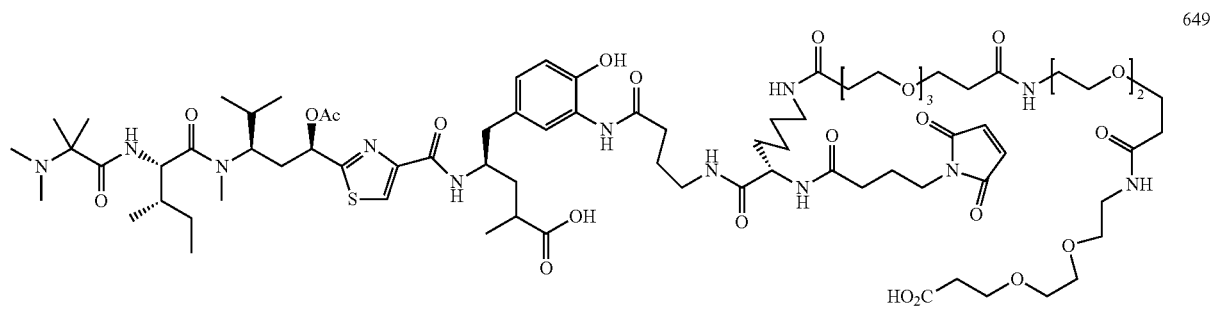

649

To a solution of the compound 648 (51 mg, 0.037 mmol) in dichloromethane (2 mL) was added trifluoroacetic acid (2 mL), and the reaction mixture was stirred at room temperature for 2 hours, then concentrated and re-dissolved in DMF (1.0 mL). A solution of compound 41a (38.4 mg, 0.055 mmol) in DMF (1.0 mL) was added at 0° C., followed by DIPEA (13 μL, 0.074 mmol). The reaction mixture was then warmed to r.t. and stirred for 1 h, concentrated under vacuum and purified by prep-HPLC to afford the title compound 649 (36.5 mg, 60% yield). ESI m/z calcd for C$_{79}$H$_{127}$N$_{12}$O$_{25}$S [M+H]$^+$: 1675.86, found 1675.86.

To a solution of Boc-hydrazine (7.08. g, 53.5 mmol) in DCM (200 mL) was added Et$_3$N (13.5 mL, 97.4 mmol), and then compound 651 (10.8 g, 48.7 mmol) was added at 0° C. After that the reaction was stirred at r.t. for 30 min. and poured into ice-water (100 mL) and extracted with DCM (3×100 mL). The combined organic phases were washed with water (100 mL) and brine (100 mL), dried over anhydrous Na$_2$SO$_4$, filtered and concentrated to give a white solid (15.5 g, 100% yield). ESI m/z calcd for C$_{15}$H$_{18}$N$_3$O$_5$ [M+H]$^+$: 320.12, found: 320.12.

Example 260. Synthesis of Compound 653

Example 258. Synthesis of Compound 651

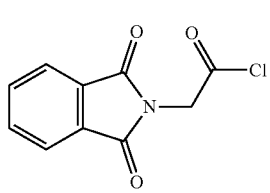

651

653

To a solution of N-Phthaloylglycine (10.0 g, 48.7 mmol) in DCM (100 mL) was added oxalyl chloride (6.3 mL, 73.1 mmol) at r.t., followed by a drop of DMF. The reaction was stirred for 2 h and then concentrated to give compound 651 (10.8 g) as a yellow solid.

Compound 652 (15.5 g, 48.7 mmol) was dissolved in DCM (150 mL) and treated with TFA (50 mL) at r.t. for 1 h, then concentrated to give a white solid (10.6 g, 100% yield). ESI m/z calcd for C$_{10}$H$_{10}$N$_3$O$_3$ [M+H]$^+$: 220.06, found: 220.06.

Example 261. Synthesis of Compound 654

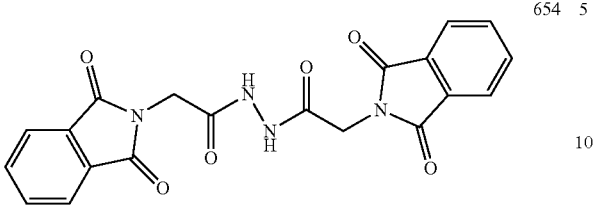
654

To a solution of compound 653 (10.6 g, 48.7 mmol) in DCM (200 mL) was added Et$_3$N (13.5 mL, 97.4 mmol) and compound 651 (10.8 g, 48.7 mmol) at 0° C. The reaction was warmed to r.t. and stirred overnight. The precipitate was collected by filtration and suspended in water (100 mL) and stirred for 20 min. The mixture was filtered again to give a white solid (15.7 g, 80% yield). ESI m/z calcd for C$_{20}$H$_{15}$N$_4$O$_6$ [M+H]$^+$: 407.09, found: 407.09.

Example 262. Synthesis of Compound 655

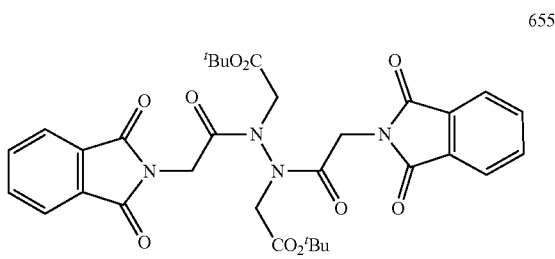 [SMILES: CC(C)(C)OC(=O)CN(C(=O)CN1C(=O)c2ccccc2C1=O)N(CC(=O)OC(C)(C)C)C(=O)CN1C(=O)c2ccccc2C1=O]
655

NaH (0.5 g, 12.3 mmol) was added to a solution of compound 654 (2.0 g, 4.92 mmol) in DMF (40 mL) in portions at 0° C. The mixture was warmed to r.t. and stirred for 3 h. After that tert-butyl bromoacetate (2.0 g, 10.3 mmol) was added and the reaction was stirred overnight before pouring into ice-water (100 mL) and extraction with DCM (3×50 mL). The combined organic phase was washed with water (50 mL), brine (50 mL), dried over anhydrous Na$_2$SO$_4$, filtered and concentrated, purified by silica gel chromatography to give a white solid (1.5 g, 50% yield). ESI m/z calcd for C$_{32}$H$_{35}$N$_4$O$_{10}$ [M+H]$^+$: 635.23, found: 635.23.

Example 263. Synthesis of Compound 656

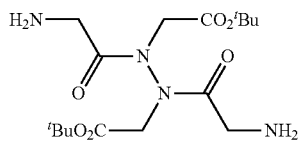
656

A mixture of compound 655 (1.5 g, 2.36 mmol) and hydrazine (442 mg, 7.08 mmol) in ethanol (30 mL) was refluxed for 1 h, then cooled to r.t. and filtered. The filtrate was concentrated and taken up in ethyl acetate (20 mL), filtered again. The filtrate was concentrated to give a white solid (750 mg, 85% yield). ESI m/z calcd for C$_{16}$H$_{31}$N$_4$O$_6$ [M+H]$^+$: 375.22, found: 375.22.

Example 264. Synthesis of Compound 657

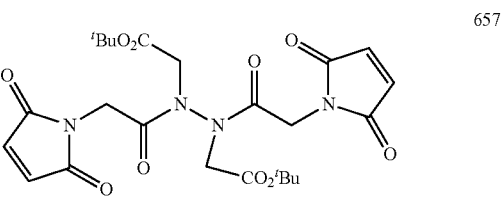 [SMILES: CC(C)(C)OC(=O)CN(C(=O)CN1C(=O)C=CC1=O)N(CC(=O)OC(C)(C)C)C(=O)CN1C(=O)C=CC1=O]
657

A solution of compound 656 (750 mg, 2 mmol) in THF (2 mL) was added to saturated NaHCO$_3$ aqueous solution (30 mL) and then cooled to 0° C., compound 409 (622 mg, 4 mmol) was then added and the reaction was stirred at 0° C. for 1 h. A white solid was collected by filtration (854 mg, 80% yield). ESI m/z calcd for C$_{24}$H$_{31}$N$_4$O$_{10}$ [M+H]$^+$: 535.20, found: 535.20.

Example 265. Synthesis of Compound 658

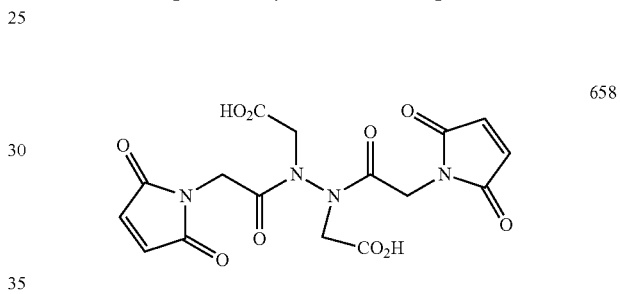
658

Compound 657 (854 mg, 1.6 mmol) was dissolved in DCM (3 mL) and treated with TFA (3 mL) at r.t. for 2 h. The reaction was then concentrated to give compound 658 (675 mg, 100% yield). ESI m/z calcd for C$_{16}$H$_{15}$N$_4$O$_{10}$ [M+H]$^+$: 423.07, found: 423.07.

Example 266. Synthesis of Compound 659

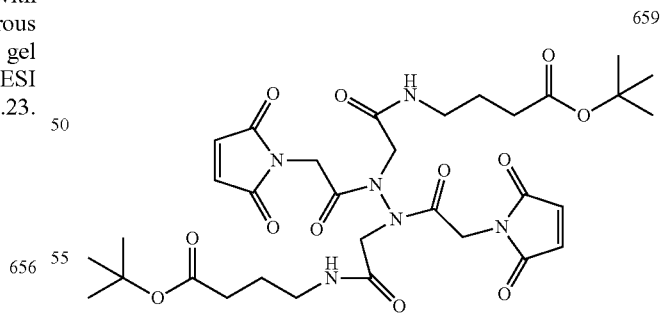
659

To a solution of compound 658 (200 mg, 0.47 mmol) in DMF (5 mL) was added tert-butyl 4-Aminobutanoate (158 mg, 0.99 mmol) and EDC (189.7 mg, 0.99 mmol) at 0° C. The reaction was warmed to r.t. and stirred overnight, poured into ice-water, and extraction with DCM (3×10 mL). The combined organic phase was washed with 1 N HCl (5 mL), water (5 mL), brine (5 mL), dried over anhydrous Na$_2$SO$_4$, filtered and concentrated to give a white solid (330 mg, 100% yield).

Example 267. Synthesis of Compound 660

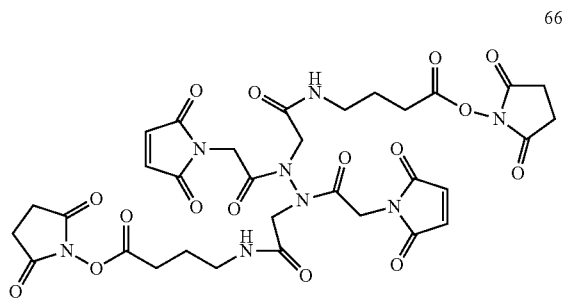

Compound 659 (330 mg, 0.47 mmol) was dissolved in DCM (3 mL) and treated with TFA (3 mL) at r.t. for 2 h. The reaction was concentrated and re-dissolved in DMF (5 mL) and cooled to 0° C., NHS (113 mg, 0.98 mmol) and EDC (189 mg, 0.98 mmol) were added in sequence. The reaction was warmed to r.t. and stirred overnight, poured into ice-water, and extraction with DCM (3×20 mL). The combined organic phase was washed with water (5 mL), brine (5 mL), dried over anhydrous $Na_2SO_4$, filtered and concentrated to give a white solid (369 mg, 100% yield). ESI m/z calcd for $C_{32}H_{35}N_8O_{16}$ [M+H]: 787.21, found: 787.21.

Example 268. Synthesis of Compound 663

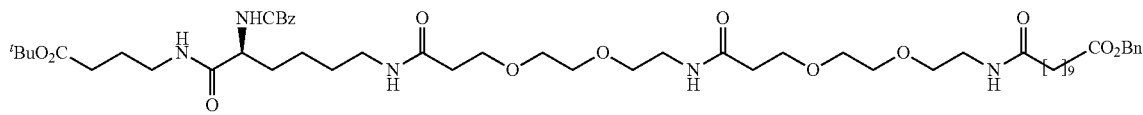

Compound 633 (200 mg, 0.225 mmol) was dissolved in DMF (5 mL) and cooled to 0° C., tert-butyl 4-Aminobutanoate (71.8 mg, 0.45 mmol) and EDC (86.2 mg, 0.45 mmol) were added in sequence. The reaction was warmed to r.t. and stirred overnight, poured into ice-water, and extraction with DCM (3×10 mL). The combined organic phase was washed with water (5 mL), brine (5 mL), dried over anhydrous $Na_2SO_4$, filtered and concentrated to give compound 663 (231 mg, 100% yield). ESI m/z calcd for $C_{54}H_{86}N_5O_{14}$ [M+H]$^+$:1028.61, found: 1028.61.

Example 269. Synthesis of Compound 664

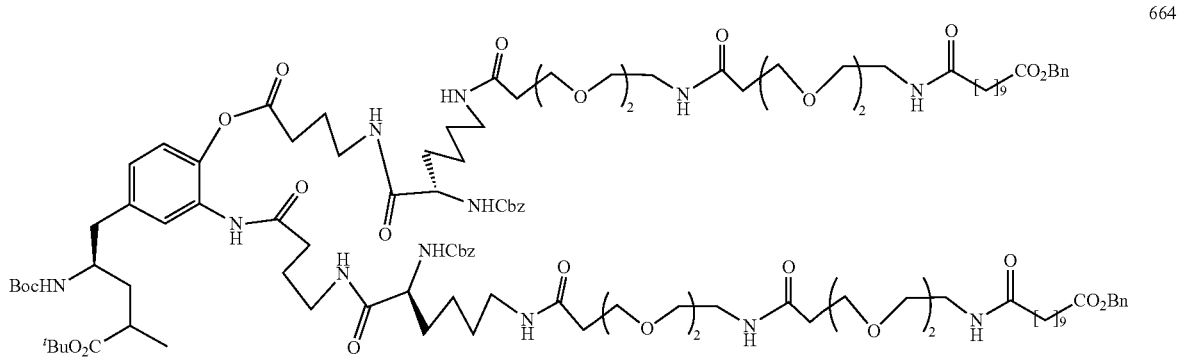

Compound 663 (231 mg, 0.225 mmol) was dissolved in DCM (3 mL) and treated with TFA (3 mL) at r.t. for 1 h. The reaction was concentrated and re-dissolved in DMF (5 mL) and cooled to 0° C., compound 110 (44 mg, 0.112 mmol), HATU (85.5 mg, 0.225 mmol) and DIPEA (39 µL, 0.225 mmol) were added in sequence. The reaction was warmed to r.t. and stirred overnight, poured into ice-water, and extraction with DCM (3×10 mL). The combined organic phase was washed with 1 N HCl (5 mL), water (5 mL), brine (5 mL), dried over anhydrous $Na_2SO_4$, filtered and concentrated, purified by silica gel column chromatography (0-5% MeOH/DCM) to give a white foam (206 mg, 80% yield). ESI m/z calcd for $C_{121}H_{185}N_{12}O_{31}$ $[M+H]^+$: 2302.32, found: 2302.34.

Example 270. Synthesis of Compound 665

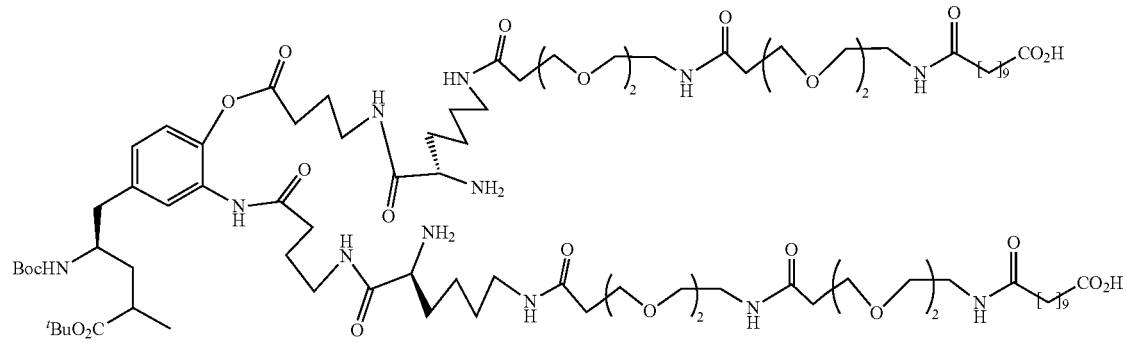

Compound 664 (206 mg, 0.089 mmol) was dissolved in MeOH (5 mL) and mixed Pd/C (10 wt %, 20 mg), hydrogenated under 1 atm $H_2$ pressure overnight. The mixture was then filtered through Celite (filter aid), and the filtrate was concentrated to afford compound 665 (165 mg, 100% yield). ESI m/z calcd for $C_{91}H_{161}N_{12}O_{27}$ $[M+H]^+$: 1854.15, found 1854.15.

Example 271. Synthesis of Compound 666

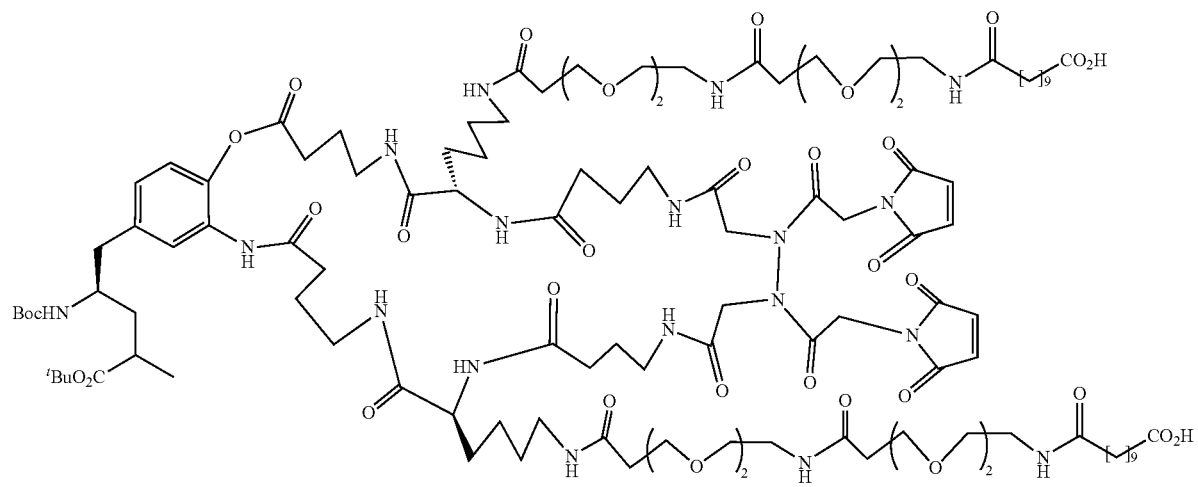

To a solution of compound 665 (165 mg, 0.089 mmol) in ethanol (10 mL) were added compound 660 (140 mg, 0.178 mmol) and phosphate buffer (0.5M, pH 7.5, 3 mL) at 0° C. The reaction was stirred at r.t. overnight and then concentrated and purified by silica gel column chromatography (0-5% MeOH/DCM) to give compound 666 (128 mg, 61% yield). ESI m/z calcd for $C_{115}H_{185}N_{18}O_{37}$ [M+H]$^+$: 2410.31, found: 2410.31.

Example 272. Synthesis of Compound 667

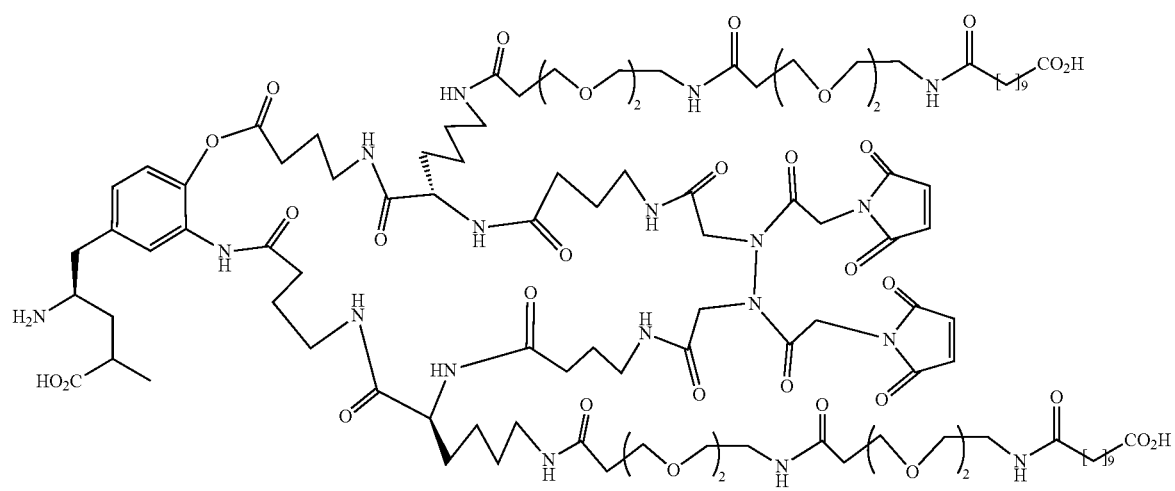

667

Compound 666 (128 mg, 0.053 mmol) was dissolved in DCM (3 mL) and treated with TFA (3 mL) at r.t. for 2 h. The reaction was concentrated and co-evaporated with DCM for three times to give compound 667 (120 mg, 100% yield). ESI m/z calcd for $C_{106}H_{169}N_{18}O_{35}$ [M+H]$^+$: 2254.19, found: 2254.19.

Example 273. Synthesis of Compound 668

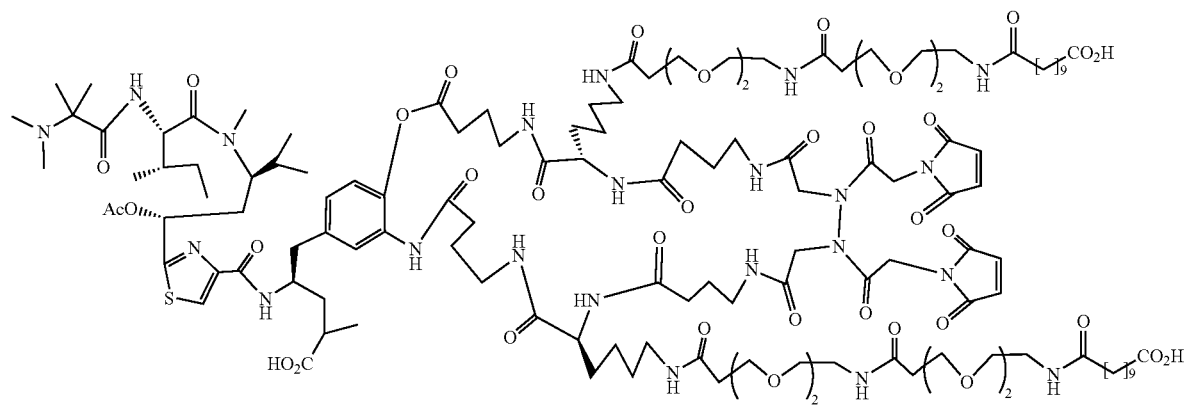

668

Compound 667 (120 mg, 0.053 mmol) and compound 41a (36.6 mg, 0.053 mmol) were dissolved in DMA (5 mL) and cooled to 0° C. DIPEA (18 μL, 0.106 mmol) was added and the reaction was warmed to r.t. and stirred for 1 h. After the reaction mixture was concentrated, the residue was purified by prep-HPLC ($C_{18}$, 10-90% acetonitrile/water) to give compound 668 (73 mg, 50% yield). ESI m/z calcd for $C_{131}H_{209}N_{22}O_{40}S$ [M+H]$^+$: 2762.46, found: 2762.46.

Example 274. Synthesis of Compound 670

To the solution of compound 621 (1 g, 1.32 mmol) in a saturated solution of NaHCO$_3$(20 mL) was added compound 409 (0.4 g, 2.64 mmol) in ice-water bath. The reaction was stirred for 30 min and then poured into a separatory funnel containing 100 mL of ethyl acetate and the organic phase was separated, washed with 50 mL of water and 50 mL of brine, dried over anhydrous Na$_2$SO$_4$, filtered and concentrated to give compound 670 (0.8 g, yield 72%). ESI: m/z: calcd for $C_{39}H_{70}N_3O_{16}$ [M+H]$^+$: 836.47, found 836.47.

Example 275. Synthesis of Compound 671

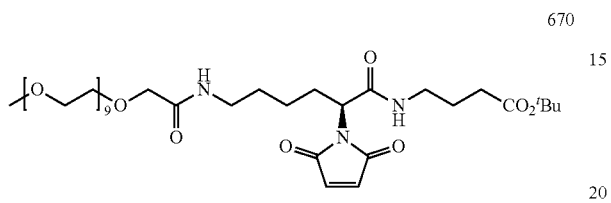

670

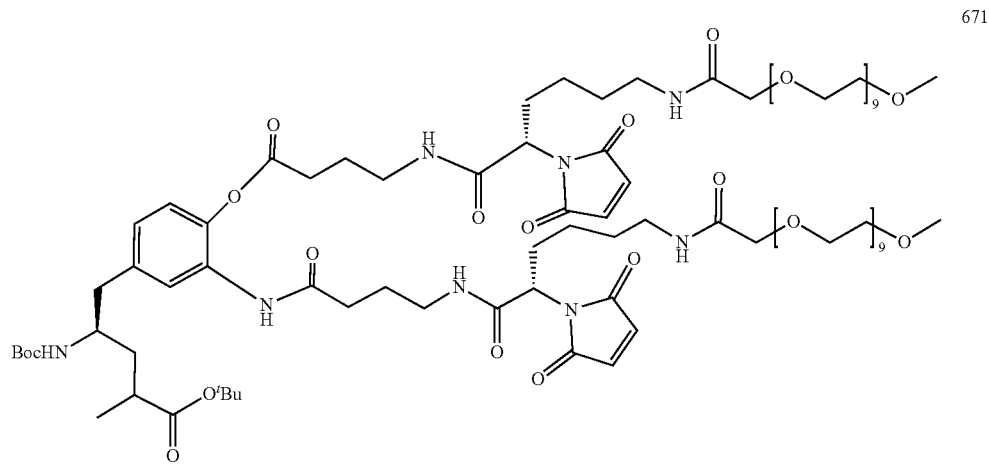

671

Compound 670 (0.9 g, 0.98 mmol) was dissolved in HCOOH (50 mL) and stirred at room temperature for 1 hour. The reaction mixture was concentrated and co-evaporated with toluene twice, and the residue was placed on a vacuum pump to give an oil. Half of the material was dissolved in DMF (10 mL) and compound 110 (0.35 g, 0.48 mmol), HATU (0.36 g, 0.96 mmol) and TEA (0.15 mL, 1.44 mmol) were added at 0° C. After stirring for 30 min, the reaction mixture was poured into a separatory funnel containing 100 mL of water and extracted twice with 50 mL of ethyl acetate. The organic phases were combined, dried over anhydrous Na$_2$SO$_4$, filtered and concentrated. The residue was purified by column chromatography (MeOH/DCM) to afford the title compound 671 (21 mg, 2%). ESI: m/z: calcd for $C_{91}H_{153}N_8O_{35}$ [M+H]$^+$: 1919.04, found 1919.04.

Example 276. Synthesis of Compound 672

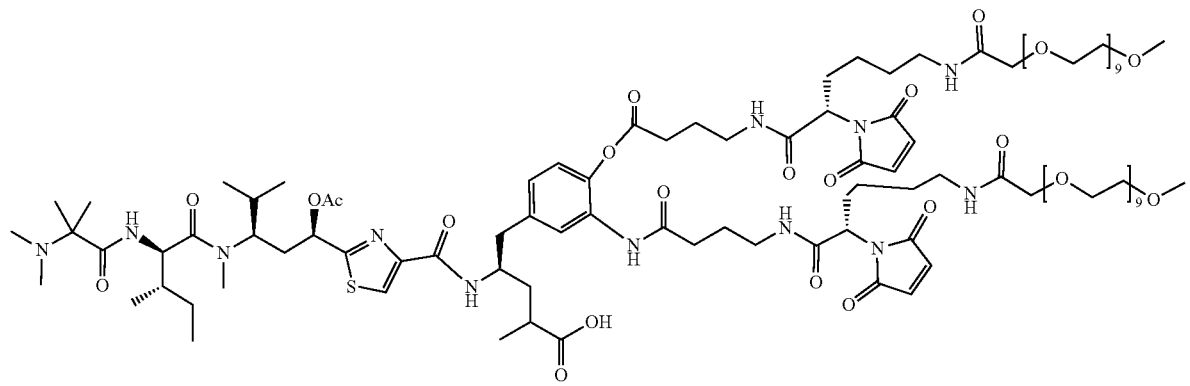

672

To a solution of compound 671 (21 mg, 0.01 mmol) in DCM (0.5 mL) was added TFA (1 mL). The reaction was stirred at room temperature for 1 hour, and then concentrated and co-evaporated twice with DCM, and the residue was placed on a vacuum pump for 2 h, and then dissolved in DMA (2 mL). Compound 41a (6.9 mg, 0.01 mmol) was added, followed by DIPEA (17 µL, 0.1 mmol). The reaction mixture was stirred at room temperature for 30 min and then concentrated. The residue was purified by reverse phase HPLC with a gradient of MeCN/H$_2$O to afforded compound 672 (10 mg, 44% yield). ESI: m/z: calcd for $C_{107}H_{177}N_{12}O_{38}S$ [M+H]$^+$:2271.20, found 2271.20.

Example 277. Synthesis of Compound 675

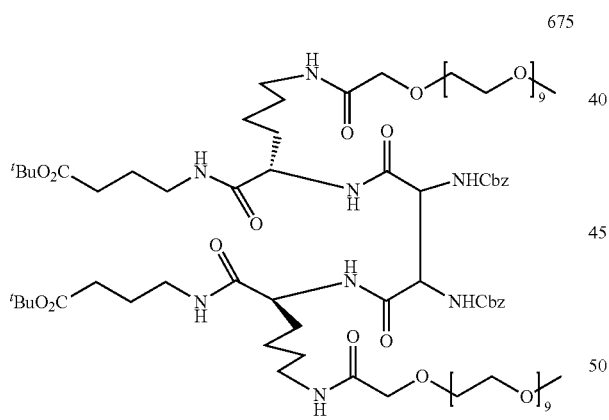

675

A mixture of compound 621 (5.98 g, 6.73 mmol) and Pd/C (10 wt %, 0.6 g) in methanol (30 mL) was hydrogenated under 1 atm H$_2$ pressure overnight and then filtered through Celite (filter aid). The filtrate was concentrated and re-dissolved in THF (60 mL), compound 674 (1.01 g, 2.42 mmol) and HOBt (817 mg, 6.05 mmol) were added at 0° C. DCC (1.25 g, 6.05 mmol) and DIPEA (2.1 mL, 12.10 mmol) were added in sequence. The reaction was stirred at r.t. overnight, then diluted with EtOAc (400 mL), and washed with 1N HCl, saturated sodium bicarbonate and brine, dried over anhydrous Na$_2$SO$_4$, filtered, concentrated and purified by SiO$_2$ column chromatography (24:1 DCM/MeOH) to give compound 675 (5.65 g, 49% yield). MS ESI m/z calcd for $C_{90}H_{154}N_8O_{34}$ [M+H]$^+$ 1892.06, found 1892.83.

Example 278. Synthesis of Compound 676

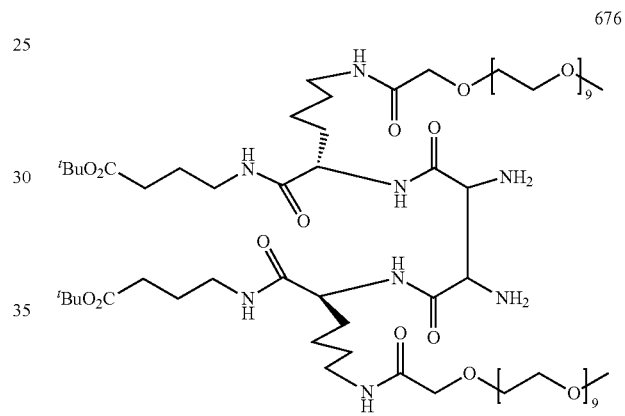

676

A mixture of compound 675 (3.71 g, 1.96 mmol) and Pd/C (10 wt %, 0.40 g) in methanol (50 mL) was hydrogenated under 1 atm H$_2$ pressure overnight and then filtered through Celite (filter aid). The filtrate was concentrated to afford compound 676 (4.57 g, 51% yield). MS ESI m/z calcd for $C_{74}H_{142}N_8O_{30}$ [M+H]$^+$ 1623.98, found 1624.42.

Example 279. Synthesis of Compound 677

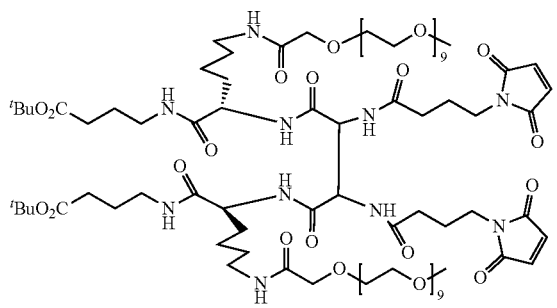

677

To a solution of compound 676 (315 mg, 0.194 mmol) in EtOH (10 mL) were added Na$_2$HPO$_4$ aqueous solution (0.5

M, 2.5 mL) and compound 125 (136 mg, 0.485 mmol). The mixture was stirred at room temperature for 3 days, concentrated and purified by SiO$_2$ column chromatography (3:2 H$_2$O/MeCN) to give an oil (50 mg, 13% yield), which was dissolved in dichloromethane (5 mL) and treated with TFA (5 mL) at r.t. overnight, and then concentrated to afford compound 677 (47 mg, 98% yield). MS ESI m/z calcd for C$_{82}$H$_{140}$N$_{10}$O$_{36}$ [M+H]$^+$ 1841.94, found 1841.88.

Example 280. Synthesis of Compound 678

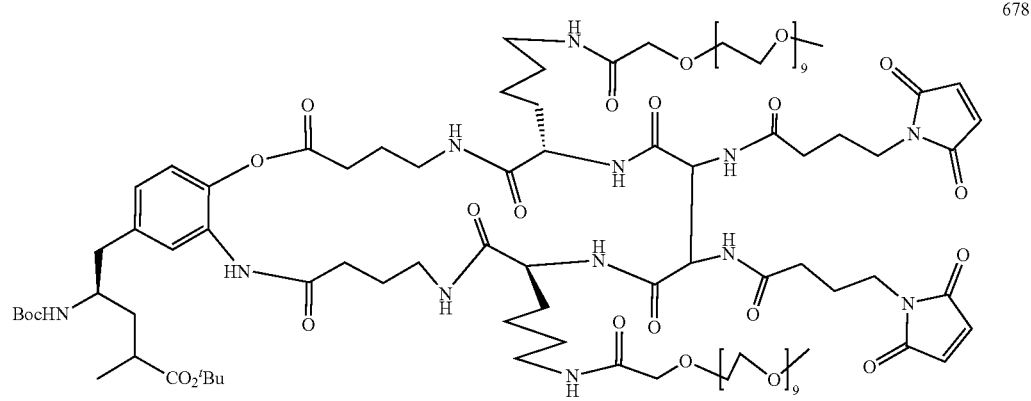

678

A mixture of compound 677 (154 mg, 0.0837 mmol) and compound 110 (33 mg, 0.0837 mmol) in DMF (6 mL) was cooled to 0° C. and HATU (64 mg, 0.167 mmol,) and TEA (46 µL, 0.335 mmol) were added in sequence. The reaction was stirred for 1 h then diluted with water (100 mL), and extracted with EtOAc (3×100 mL). The EtOAc solution was washed with brine, dried over anhydrous Na$_2$SO$_4$, filtered, concentrated and purified by SiO$_2$ column chromatography (6:1 DCM/MeOH) to give compound 678 (98 mg, 53% yield). MS ESI m/z calcd for C$_{103}$H$_{170}$N$_{12}$O$_{39}$ [M+H]$^+$ 2200.17, found 2200.15.

Example 281. Synthesis of Compound 679

To a solution of compound 678 (98 mg, 0.045 mmol) in dichloromethane (3 mL) was added TFA (6 mL). The reaction mixture was stirred at r.t. for 1 h, and then concentrated and re-dissolved in DMA (1 mL), compound 41a (31 mg, 0.045 mmol) and DIPEA (12 µL, 0.068 mmol) were added. The reaction mixture was stirred at r.t. for 90 min, then concentrated and purified by reverse phase HPLC (Cis column, 10-100% acetonitrile/water) to afford compound 679 (33.6 mg, 30% yield). MS ESI m/z calcd for C$_{119}$H$_{194}$N$_{16}$O$_{42}$S [M+H]$^+$ 1276.66, found 1276.65.

Example 282. Synthesis of Compound 681

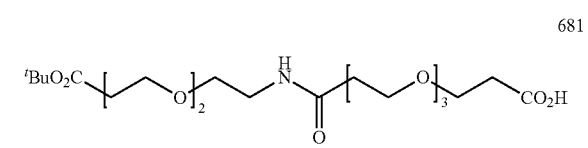

681

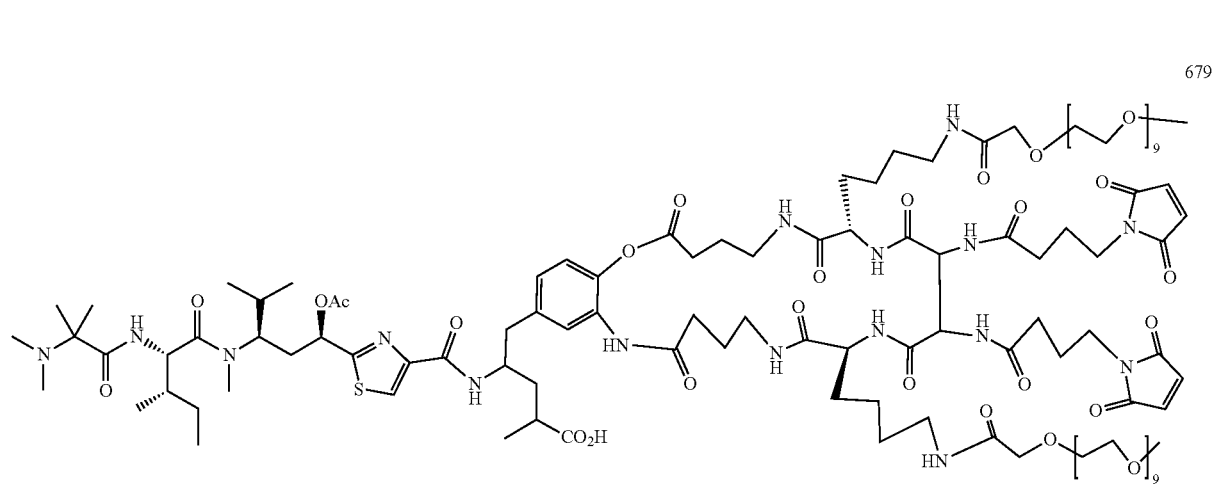

679

To the solution of compound 301 (1.0 g, 4.3 mmol) and compound 643 (1.6 g, 6.4 mmol) in DCM (15 mL) were added HATU (1.83 g, 4.83 mmol) and TEA (0.68 mL, 4.83 mmol) at 0° C.

The reaction mixture was allowed to stir at 0° C. for 90 min, then concentrated and purified by column chromatography (MeOH/DCM) to afford the title compound 681 (2.0 g, >100% yield, containing silica gel). ESI m/z $C_{21}H_{40}NO_{10}$ [M+H]$^+$: 466.26, found 466.23.

Example 283. Synthesis of Compound 682

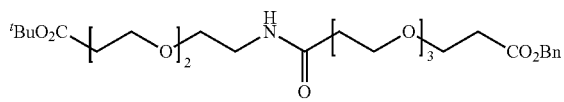

682

To a solution of compound 681 (2.0 g, 4.3 mmol) in DMF (30 mL) were added $K_2CO_3$ (1.2 g, 8.6 mmol) and BnBr (1.47 g, 8.6 mmol). The mixture was stirred at r.t. overnight, then poured into a separatory funnel containing 100 mL of water and extracted with EtOAc (3×50 mL). The organic phase was combined and dried over anhydrous $Na_2SO_4$, filtered, concentrated and purified by column chromatography (MeOH/DCM) to afford the title compound 682 (1.0 g, 42% yield).

ESI: m/z: calcd for $C_{28}H_{46}NO_{10}$ [M+H]$^+$: 556.30, found 556.30.

Example 284. Synthesis of Compound 683

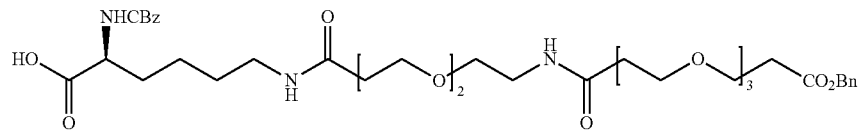

683

To a solution of compound 682 (1.0 g, 1.8 mmol) in DCM (1 mL) was added TFA (3 mL).

The reaction was stirred at room temperature for 1 h, then concentrated to dryness and co-evaporated twice with DCM, dissolved in DCM (50 mL). Z-Lys-OH (0.5 g, 1.8 mmol), HATU (1.83 g, 4.83 mmol) and TEA (0.68 mL, 4.83 mmol) were added at 0° C. The reaction mixture was allowed to stir at r.t. for 1 h, then poured into a separatory funnel containing 100 mL of water and extracted with 50 mL of DCM three times. The organic phase was combined and washed once with 100 mL of brine, then dried over anhydrous $Na_2SO_4$, filtered and concentrated. The residue was purified by column chromatography (MeOH/DCM) to afford the title compound 683 (1.0 g, 71% yield). ESI m/z $C_{38}H_{56}N_3O_{13}$ [M+H]$^+$:762.37, found 762.37.

Example 285. Synthesis of Compound 684

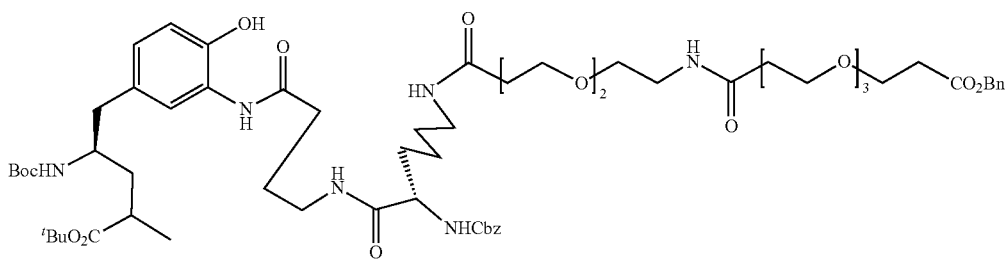

684

To a solution of compound 683 (1.0 g, 1.3 mmol) in DMF (10 mL) was added HATU (0.60 g, 1.56 mmol), the reaction was stirred at room temperature for 30 min. After that, a solution of compound 438 (0.51g, 1.3 mmol) in DMF (10 mL) and TEA (0.28 mL, 2 mmol) were added at 0° C., and the reaction was stirred at 0° C. for 1 h, then poured into a separatory funnel containing 100 mL of water and extracted with EtOAc (50 mL) twice. The organic phases were combined and washed with 100 mL of brine, dried over anhydrous $Na_2SO_4$, filtered and concentrated. The residue was purified by column chromatography (MeOH/DCM) to afford the title compound 684 (1.20 g, 73% yield). ESI: m/z: calcd for $C_{63}H_{95}N_6O_{18}$ [M+H]$^+$: 1223.66, found 1223.66.

Example 286. Synthesis of Compound 685

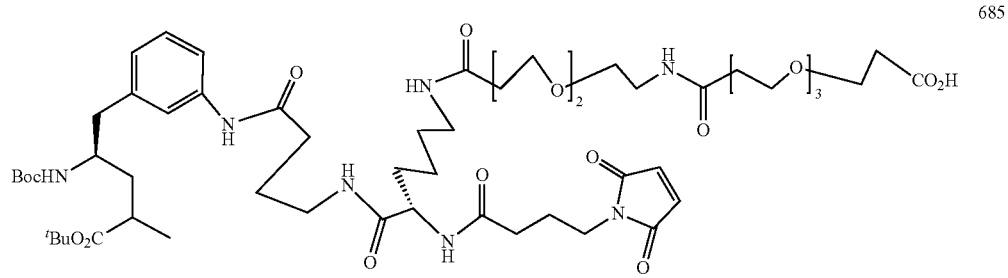

685

To a solution of compound 684 (1.20 g, 0.98 mmol) in MeOH (20 mL) was added Pd/C (0.1 g, 10 wt %, 50% wet) in a hydrogenation bottle. The mixture was shaken overnight, filtered through Celite (filter aid), and the filtrate was concentrated and then dissolved in EtOH (50 mL). Compound 125 (0.32 g, 1.16 mmol) and 0.1 M $NaH_2PO_4$ (10 mL) were added and the mixture was stirred at r.t. overnight. After concentration, the residue was purified by column chromatography (MeOH/DCM) to afford the title compound 685 (0.57g, 50% yield). ESI: m/z: calcd for $C_{56}H_{90}N_7O_{19}$ [M+H]$^+$: 1164.62, found 1164.62.

Example 287. Synthesis of Compound 686

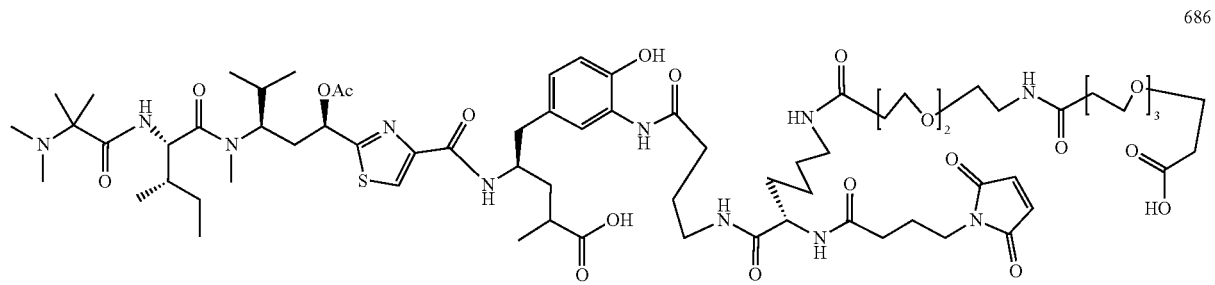

686

To a solution of compound 685 (0.10 g, 0.086 mmol) in DCM (1 mL) was added TFA (3 mL). The reaction was stirred at room temperature for 30 min, then concentrated to dryness and co-evaporated twice with DCM, then dissolved in DMA (2 mL) and compound 41a (59 mg, 0.086 mmol) and DIPEA (26 μL, 0.15 mmol) were added. The reaction mixture was stirred at room temperature for 1 h and then concentrated, dissolved in 2 mL acetonitrile and purified by reverse phase HPLC with a gradient of MeCN/$H_2O$ to afforded compound 686 (34 mg, 26% yield). ESI: m/z: calcd for $C_{72}H_{114}N_{11}O_{22}S$ [M+H]$^+$: 1516.78, found 1516.78.

Example 288. Synthesis of Compound 688

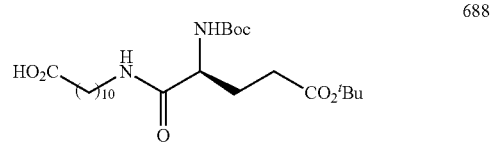

688

To a solution of Boc-Glu(OtBu)-OH (0.50 g, 1.65 mmol) in DMF (10 mL) were added HATU (0.69 g, 1.82 mmol) and TEA (0.26 mL, 1.82 mmol). After stirring for 30 min, a solution of 11-aminoundecanoic acid (0.33 g, 1.65 mmol) in DMF (10 mL) was added and the reaction was stirred at r.t. for 1 h, then poured into a separatory funnel containing 200 mL of 1N HCl and extracted with DCM (3×50 mL). The organic phase was washed once with 100 mL of brine, then dried over anhydrous $Na_2SO_4$, filtered and concentrated. The residue was purified by column chromatography (MeOH/DCM) to afford the title compound 688 (1.0 g, >100% yield). ESI: m/z: calcd for $C_{25}H_{47}N_2O_7$ [M+H]$^+$: 487.33, found 487.34.

Example 289. Synthesis of Compound 689

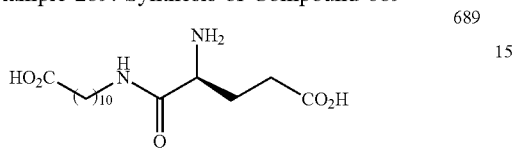

689

To a solution of compound 688 (1.0 g) in DCM (1 mL) was added TFA (3 mL). The reaction was stirred at room temperature for 30 min, then concentrated to dryness and dried twice with DCM. Finally, placed on a vacuum pump give compound 689 (0.68 g, 2.06 mmol). ESI: m/z: calcd for $C_{16}H_{31}N_2O_5$ [M+H]$^+$: 331.22, found 331.22.

Example 290. Synthesis of Compound 690

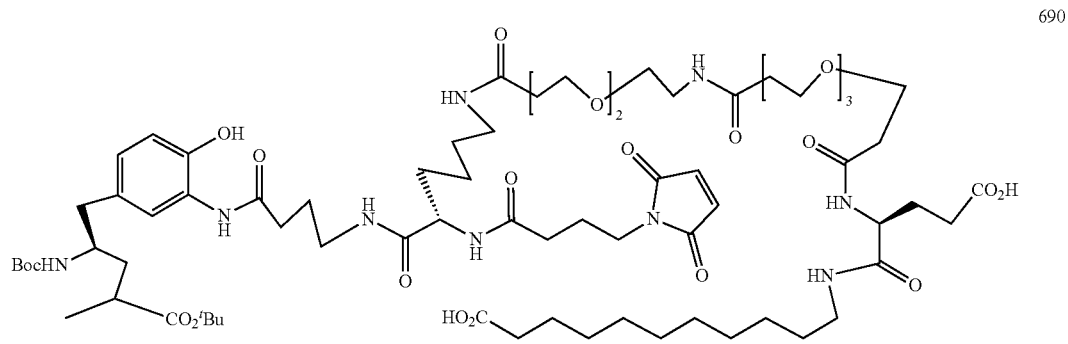

690

To a solution of compound 685 (0.10 g, 0.086 mmol) in EtOAc (6 mL) was added pentafluorophenol (18.4 mg, 0.1 mmol) and EDC (19.1 mg, 0.1 mmol). The reaction was stirred at room temperature for 1 h, and then poured into a separatory funnel containing 100 mL of water and extracted with 50 mL of EtOAc. The organic phase was collected and dried over anhydrous $Na_2SO_4$, filtered and concentrated. The residue was re-dissolved in 5 mL DMF, and a solution of compound 125 (43 mg, 0.13 mmol) in DMF (5 mL) and DIPEA (35 μL, 0.222 mmol) were added.

The reaction was stirred at r.t. for 90 min., then poured into a separatory funnel containing 100 mL of 1N HCl and extracted with DCM (2×50 mL). The organic phase was washed once with 100 mL of brine, then dried over anhydrous $Na_2SO_4$, filtered and concentrated. The residue was purified by column chromatography (MeOH/DCM) to afford the title compound 690 (0.11 g, 87% yield). ESI: m/z: calcd for $C_{72}H_{118}N_9O_{23}$ [M+H]$^+$: 1476.83, found 1476.84.

Example 291. Synthesis of Compound 691

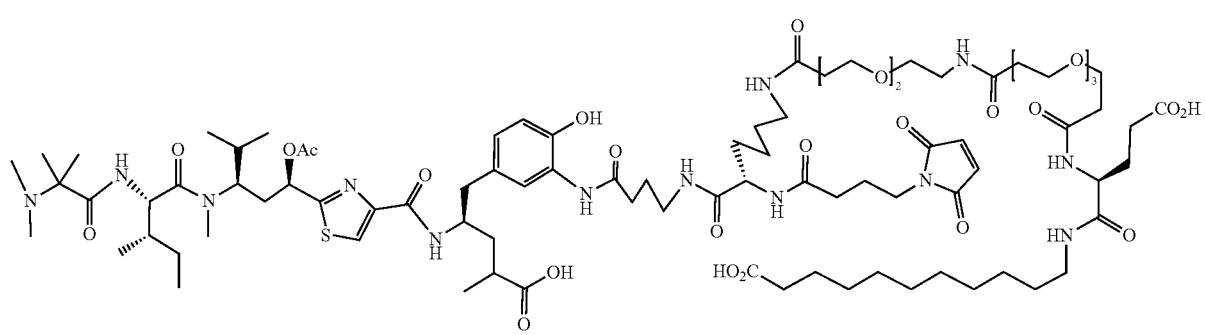

691

To a solution of compound 691 (0.11 g, 0.074 mmol) in DCM (1 mL) was added TFA (3 mL). The reaction was stirred at room temperature for 30 min, then concentrated to dryness and co-evaporated twice with DCM, then dissolved in DMA (6 mL). Compound 41a (100 mg, 0.148 mmol) and DIPEA (35 µL, 0.222 mmol) were added and the reaction mixture was stirred at room temperature for 2 h and concentrated. The residue was dissolved in 2 mL acetonitrile and purified by reverse phase HPLC with a gradient of MeCN/$H_2O$ to afforded compound 691 (28.6 mg, 21% yield). ESI: m/z: calcd for $C_{88}H_{142}N_{13}O_{26}S$ [M+H]$^+$: 1828.98, found 1828.98.

Example 292

General method of Preparation of Conjugate 133, 339, 382, 396, 414, 444,
455, 467, 474, 480, 486, 493, 500, 522, 530, 534, 546, 550, 556, 560, 564, 574, 584, 593, 601, 613, 619, 626, 637, 641, 650, 669, 673, 680, 687, 692, E1, E2, E3, E4, E5, E6 and E7.

To a mixture of 2.0 mL of 10 mg/ml Herceptin in pH 6.0-8.0, were added of 0.70-2.0 mL PBS buffer of 100 mM $NaH_2PO_4$, pH 6.5-8.5 buffers, TCEP (14-35 µL, 20 mM in water) and the compound 132, mixture of 337 and 338, 381, 395, 413, 443, 454, 466, 473, 479, 485, 492, 499, 521, 529, 533, 545, 549, 554, 559, 563, 573, 583, 592, 600, 612, 618, 625, 636, 640, 649, 668, 672, 679, 686, 691, or maleimide precursor of E1, E2, E3, E4, E5, E6 and E7 (14-28 µL, 20 mM in DMA independently, followed by addition of 4-(azidomethyl)benzoic acid (14-50 µL, 20 mM in pH 7.5, PBS buffer). The mixture was incubated at RT for 4-18 h, then DHAA (135 µL, 50 mM) was added in. After continuous incubation at RT overnight, the mixture was purified on G-25 column eluted with 100 mM $NaH_2PO_4$, 50 mM NaCl pH 6.0-7.5 buffer to afford 12.2-18.6 mg of the conjugate compound 133, 339, 382, 396, 414, 444, 455, 467, 474, 480, 486, 493, 500, 522, 530, 534, 546, 550, 556, 560, 564, 574, 584, 593, 601, 613, 619, 626, 637, 641, 650, 669, 673, 680, 687, 692, E1, E2, E3, E4, E5, E6 and E7 (60%-93% yield) accordingly in 13.4-15.8 ml of the $NaH_2PO_4$, buffer. The drug/antibody ratio (DAR) was 3.4-4.1 for conjugate, wherein DAR was determined via UPLC-QTOF mass spectrum. It was 94-99% monomer analyzed by SEC HPLC (Tosoh Bioscience, Tskgel G3000SW, 7.8 mm ID×30 cm, 0.5 ml/min, 100 min) and a single band measured by SDS-PAGE gel.

Example 293

In vitro cytotoxicity evaluation of conjugate 133, 339, 382, 396, 414, 444, 455, 467, 474, 480, 486, 493, 500, 522, 530, 534, 546, 550, 556, 560, 564, 574, 584, 593, 601, 613, 619, 626, 637, 641, 650, 669, 673, 680, 687, 692, E1, E2, E3, E4, E5, E6 and E7 in comparison with T-DM1: The cell line used in the cytotoxicity assays was NCI-N87, a human gastric carcinoma cell line; The cells were grown in RPMI-1640 with 10% FBS. To run the assay, the cells (180 l, 6000 cells) were added to each well in a 96-well plate and incubated for 24 hours at 37° C. with 5% $CO_2$. Next, the cells were treated with test compounds (20 µl) at various concentrations in appropriate cell culture medium (total volume, 0.2 mL). The control wells contain cells and the medium but lack the test compounds. The plates were incubated for 120 hours at 37° C. with 5% $CO_2$. MTT (5 mg/ml) was then added to the wells (20 µl) and the plates were incubated for 1.5 hr at 37° C. The medium was carefully removed and DMSO (180 µl) was added afterward. After it was shaken for 15 min, the absorbance was measured at 490 nm and 570 nm with a reference filter of 620 nm. The inhibition % was calculated according to the following equation: inhibition %=[1-(assay-blank)/(control-blank)]×100. The results are listed in Table 1.

TABLE 1

The Structures of the Her2-tubulysin analog conjugates of the patent application along with their cytotoxicity IC50 results:

Conjugate # Structures and its IC50 against NCI-N87 cells

133

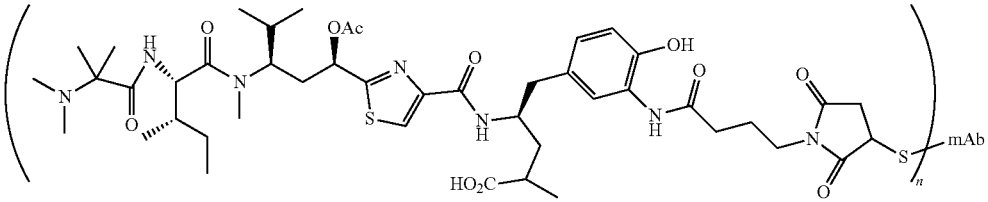

IC$_{50}$ = 0.17 nM, (DAR = 3.6).

339

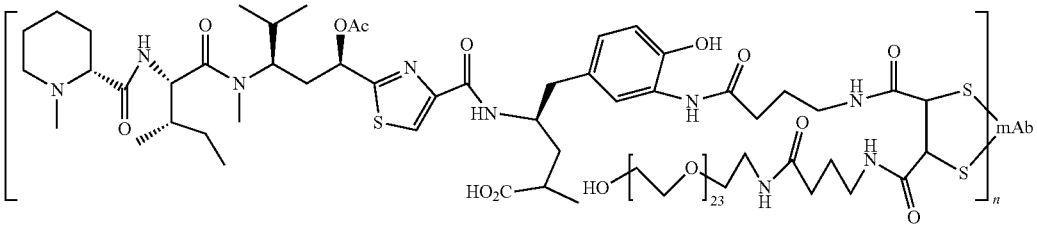

IC$_{50}$ = 9.17 nM, (DAR = 3.6).

TABLE 1-continued
The Structures of the Her2-tubulysin analog conjugates of the patent application along with their cytotoxicity IC50 results:
| Conjugate # | Structures and its IC50 against NCI-N87 cells |
|---|---|
| 382 | 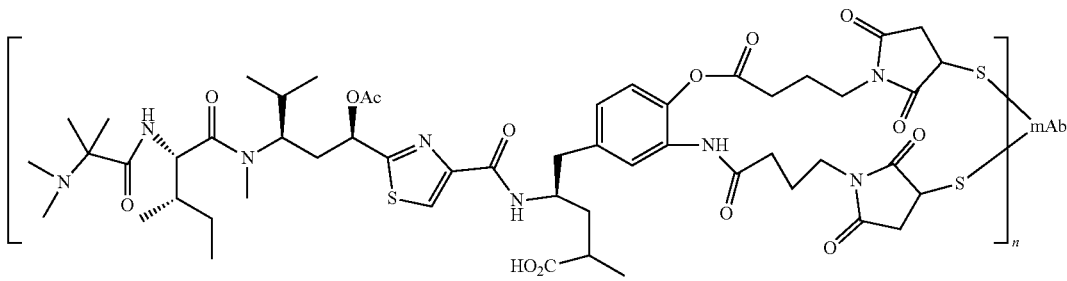<br>IC$_{50}$ = 0.73 nM, (DAR = 3.8). |
| 396 | 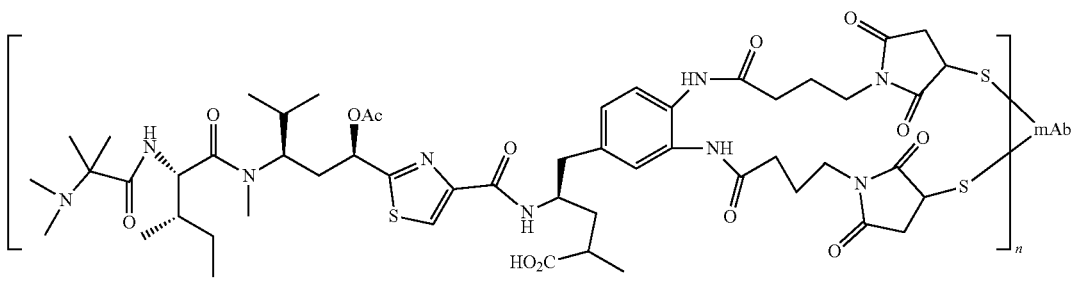<br>IC$_{50}$ = 13.06 nM, (DAR = 3.9). |
| 414 | 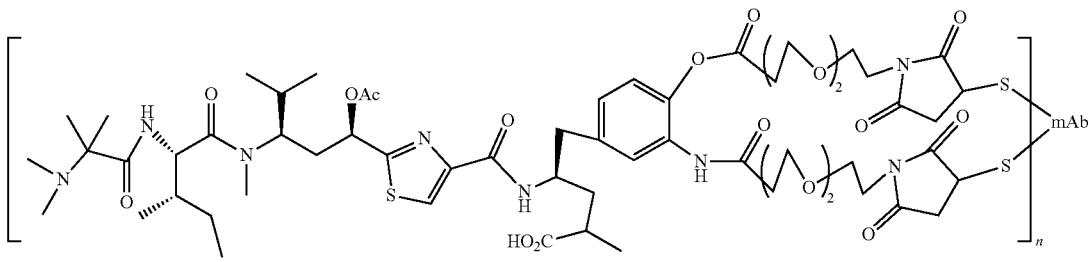<br>IC$_{50}$ = 0.51 nM, (DAR = 3.8). |
| 444 | 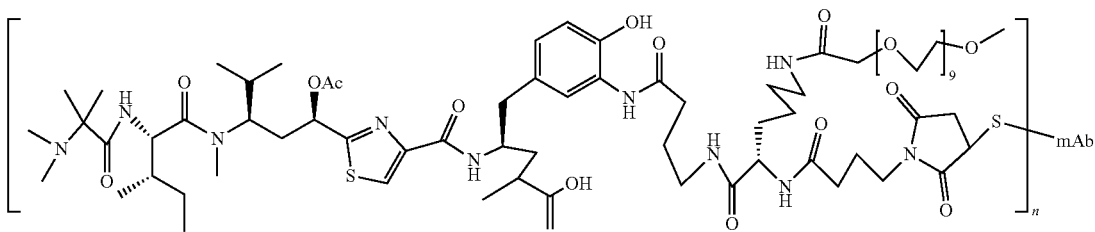<br>IC$_{50}$ = 0.22 nM, (DAR = 3.7). |

TABLE 1-continued
The Structures of the Her2-tubulysin analog conjugates of the patent application along with their cytotoxicity IC50 results:
| Conjugate # | Structures and its IC50 against NCI-N87 cells |
|---|---|
| 455 | 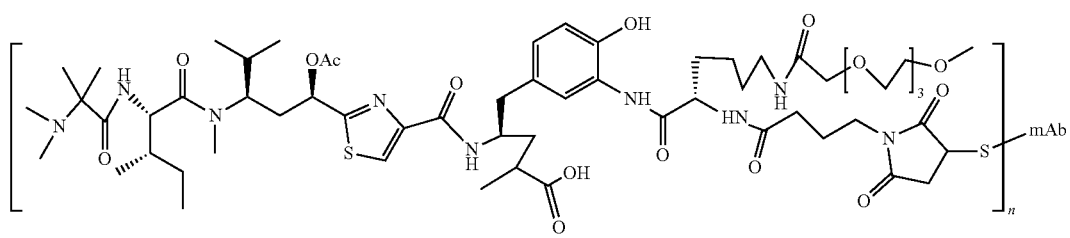<br>IC$_{50}$ = 0.06 nM, (DAR = 3.8). |
| 467 | 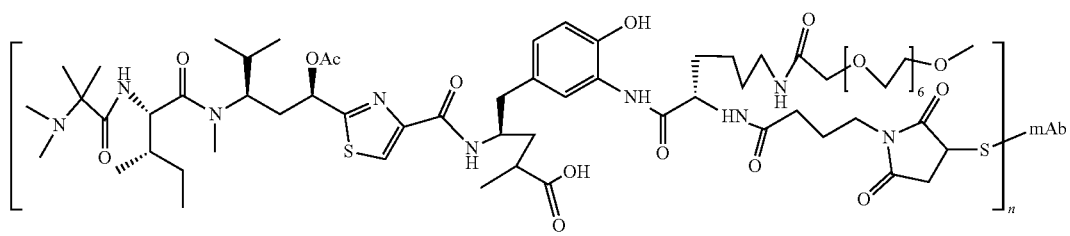<br>IC$_{50}$ = 0.07 nM, (DAR = 3.6). |
| 474 | 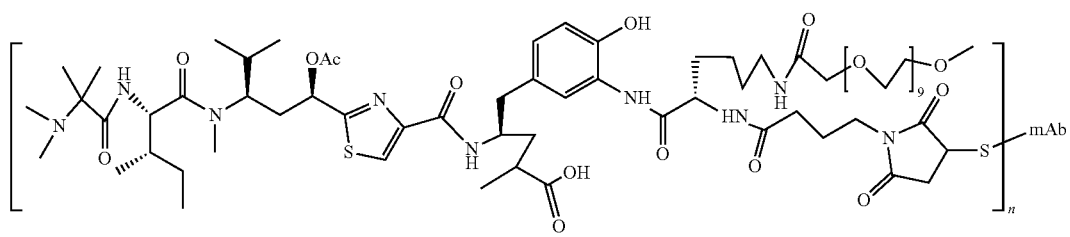<br>IC$_{50}$ = 0.31 nM, (DAR = 3.8). |
| 480 | 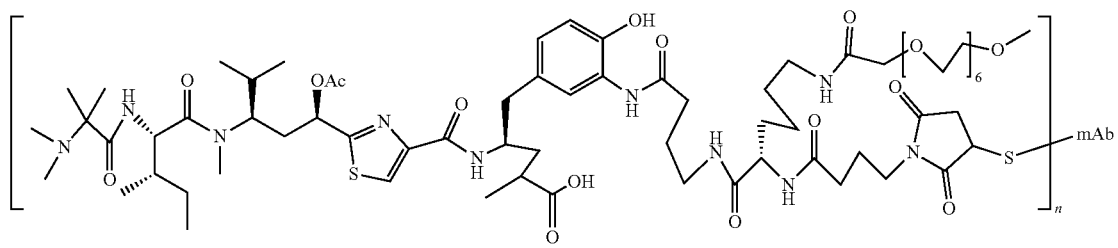<br>IC$_{50}$ = 0.24 nM, (DAR = 3.7). |
| 486 | 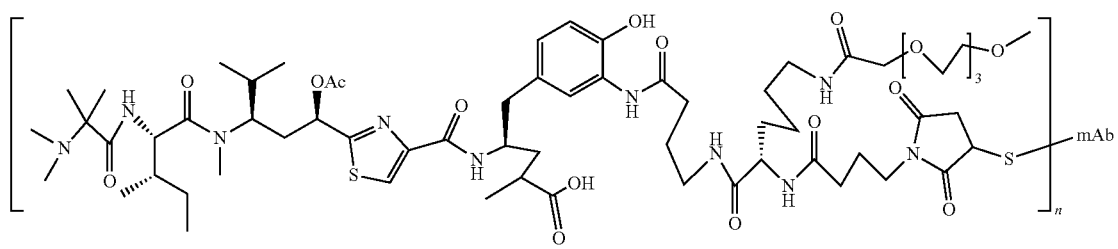<br>IC$_{50}$ = 0.62 nM, (DAR = 3.5). |

TABLE 1-continued
The Structures of the Her2-tubulysin analog conjugates of the patent application along with their cytotoxicity IC50 results:
| Conjugate # | Structures and its IC50 against NCI-N87 cells |
|---|---|
| 493 | 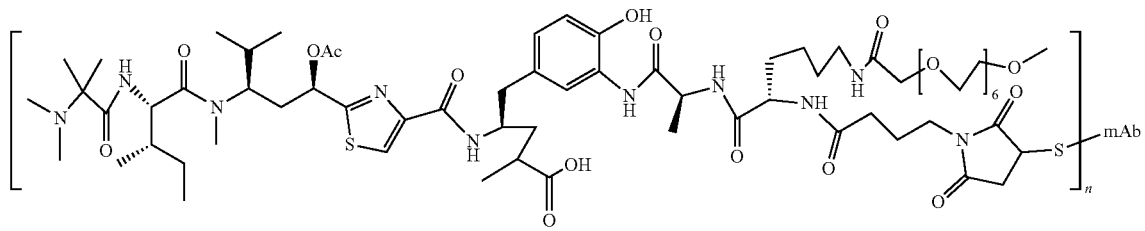<br>IC$_{50}$ = 0.15 nM, (DAR = 3.8). |
| 500 | 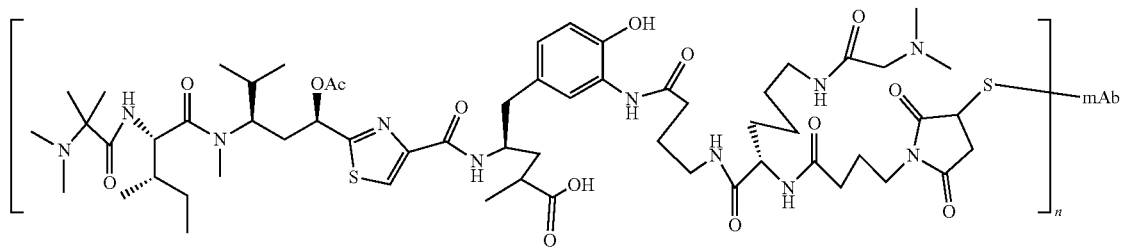<br>IC$_{50}$ = 0.37 nM, (DAR = 3.6). |
| 522 | 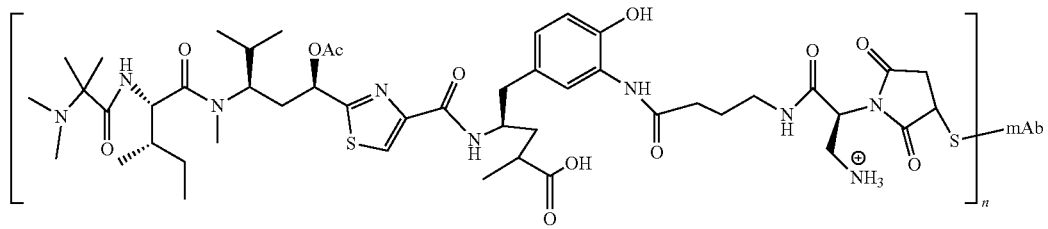<br>IC$_{50}$ = 0.51 nM, (DAR = 3.5). |
| 530 | 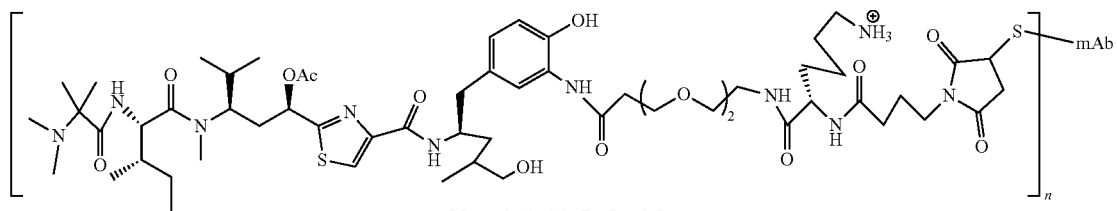<br>IC$_{50}$ = 0.18 nM, (DAR = 3.7). |

TABLE 1-continued
The Structures of the Her2-tubulysin analog conjugates of the patent application along with their cytotoxicity IC50 results:
Conjugate # | Structures and its IC50 against NCI-N87 cells
534
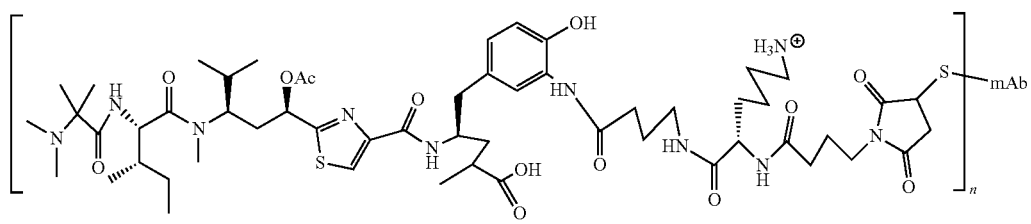
IC$_{50}$ = 0.11 nM, (DAR = 3.6).
546
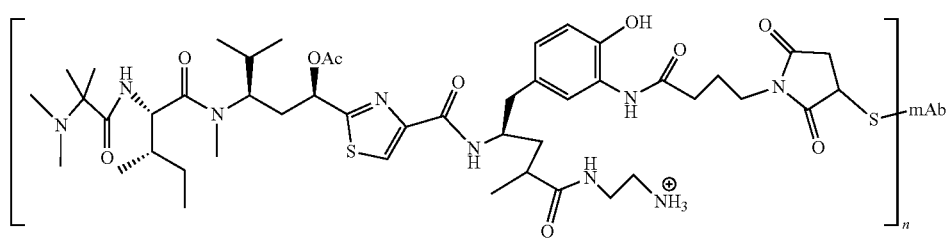
IC$_{50}$ = 3.56 nM, (DAR = 3.8).
550
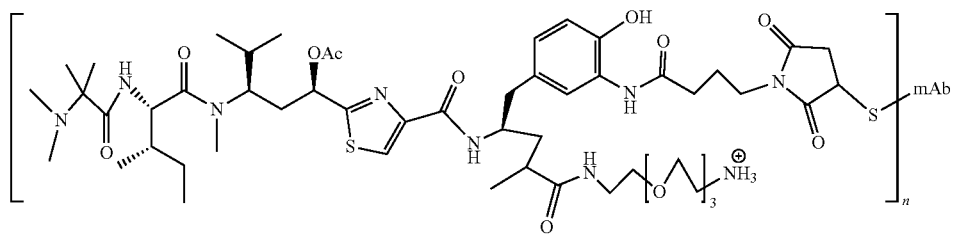
IC$_{50}$ = 9.01 nM, (DAR = 3.8).
556
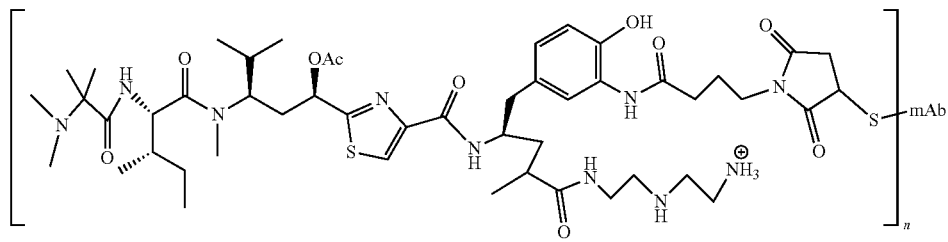
IC$_{50}$ = 3.51 nM, (DAR = 3.6).
560
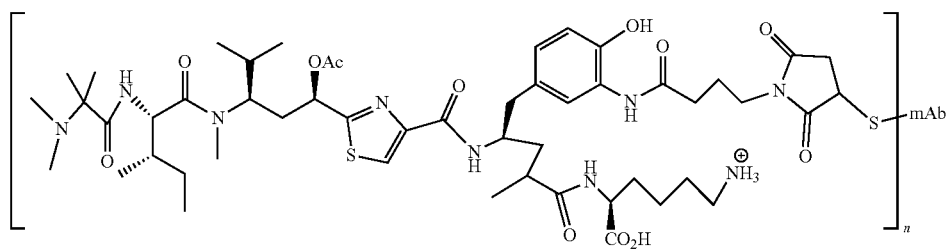
IC$_{50}$ = 2.3 nM, (DAR = 3.8).

TABLE 1-continued
The Structures of the Her2-tubulysin analog conjugates of the patent application along with their cytotoxicity IC50 results:
Conjugate # | Structures and its IC50 against NCI-N87 cells
564
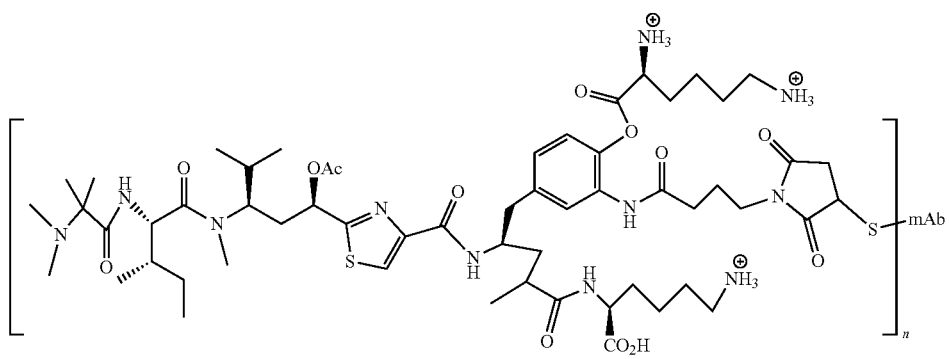
IC$_{50}$ = 4.21 nM, (DAR = 3.8).
574
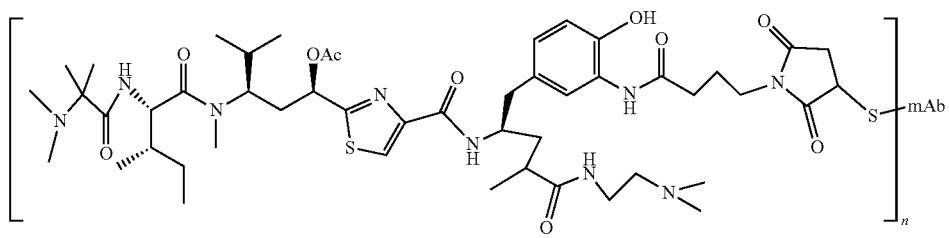
IC$_{50}$ = 1.35 nM, (DAR = 3.7).
584
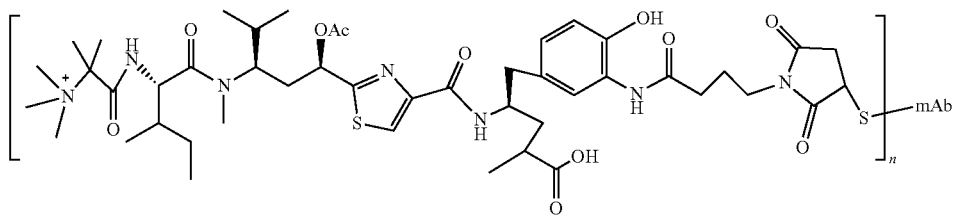
IC$_{50}$ = 0.32 nM, (DAR = 3.7).
593
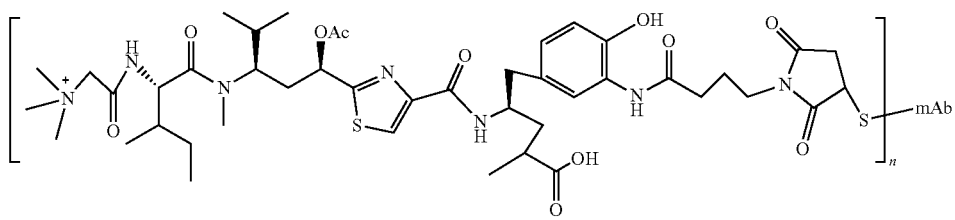
IC$_{50}$ = 0.22 nM, (DAR = 3.8).

TABLE 1-continued
The Structures of the Her2-tubulysin analog conjugates of the patent application along with their cytotoxicity IC50 results:
Conjugate # Structures and its IC50 against NCI-N87 cells
601
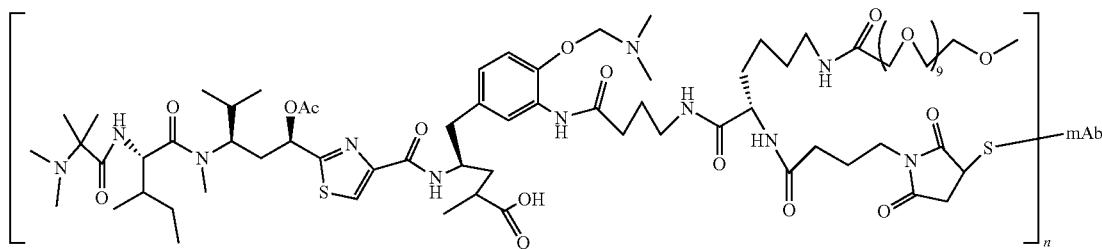
IC$_{50}$ = 2.31 nM, (DAR = 3.6).
613
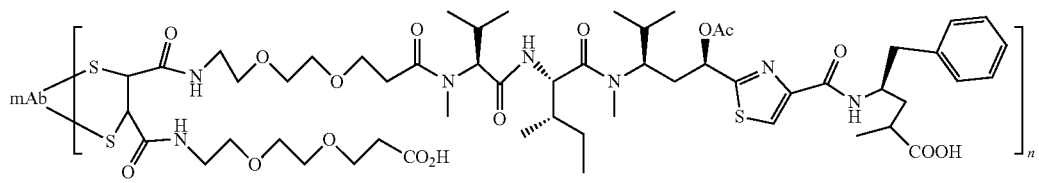
IC$_{50}$ = 11.2 nM, (DAR = 3.6).
619
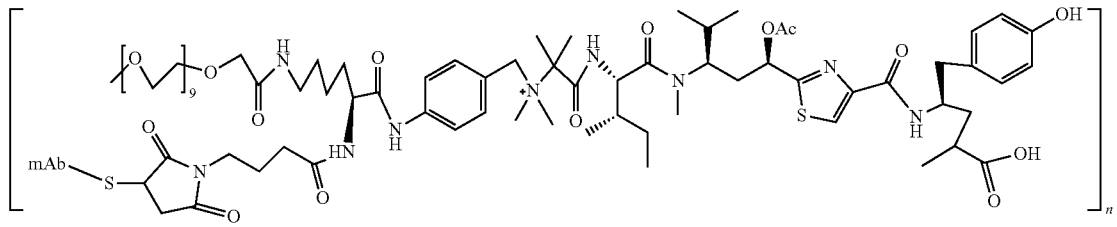
IC$_{50}$ = 0.98 nM, (DAR = 3.7).
626
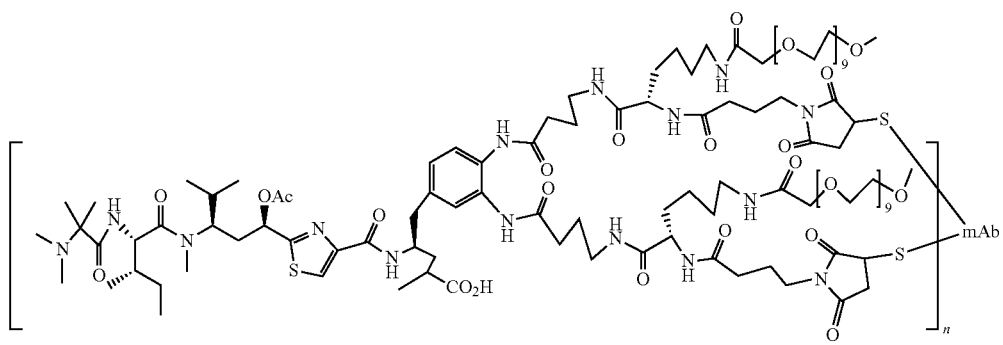
IC$_{50}$ = 10.5 nM, (DAR = 3.8).

TABLE 1-continued
The Structures of the Her2-tubulysin analog conjugates of the patent application along with their cytotoxicity IC50 results:
Conjugate # | Structures and its IC50 against NCI-N87 cells
637
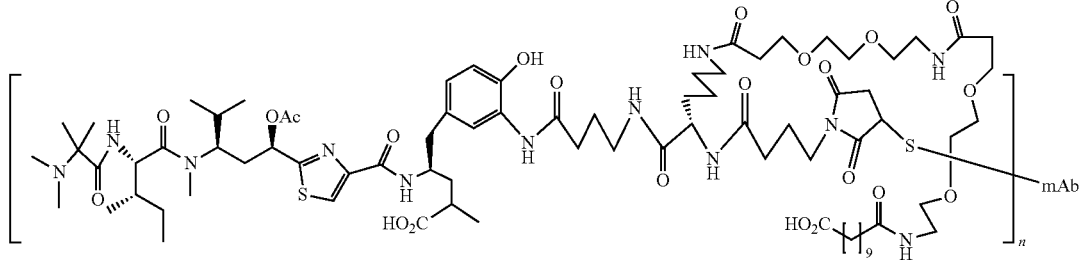
IC$_{50}$ = 0.23 nM, (DAR = 3.6).
641
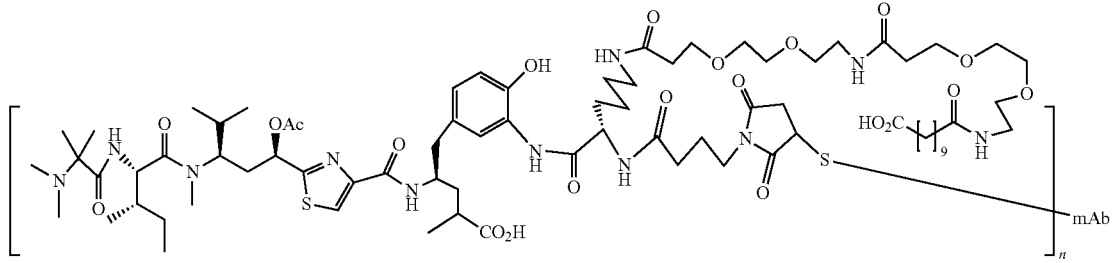
IC$_{50}$ = 1.35 nM, (DAR = 3.6).
650
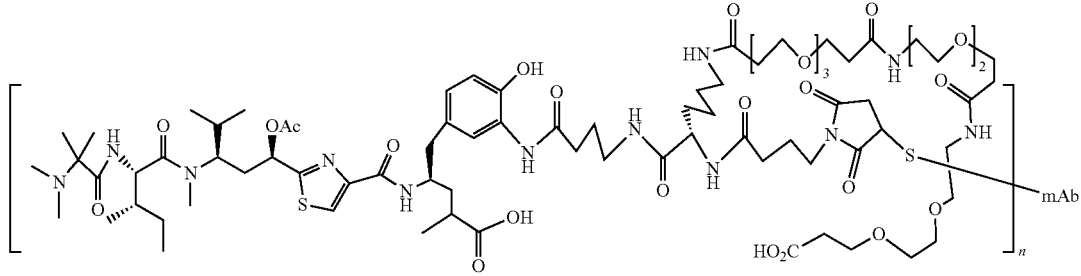
IC$_{50}$ = 0.73 nM, (DAR = 3.6).
669
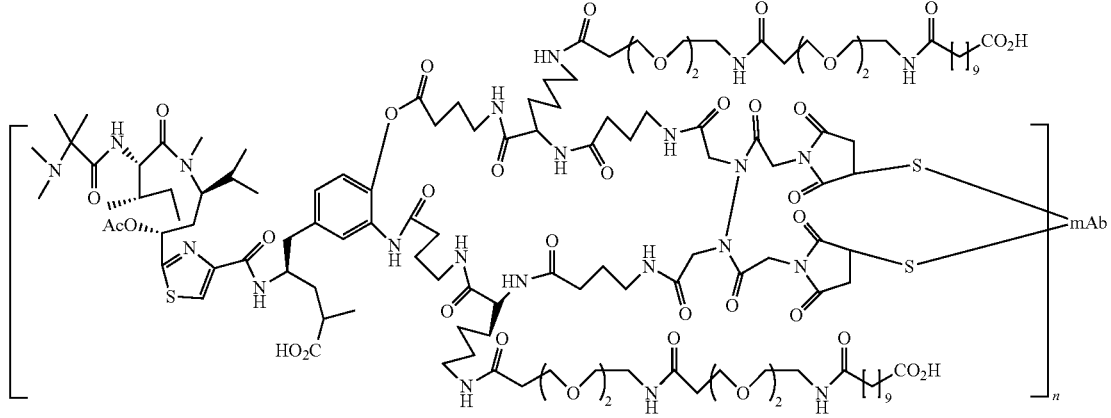
IC$_{50}$ = 1.08 nM, (DAR = 3.9).

TABLE 1-continued
The Structures of the Her2-tubulysin analog conjugates of the patent application along with their cytotoxicity IC50 results:
Conjugate # | Structures and its IC50 against NCI-N87 cells
673
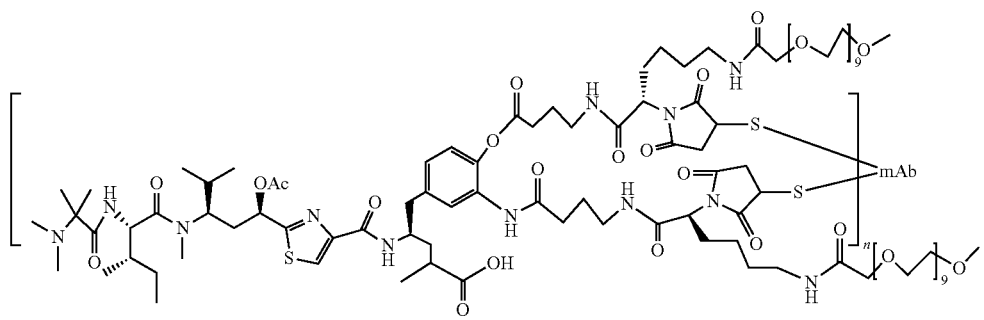
IC$_{50}$ = 0.42 nM, (DAR = 3.8).
680
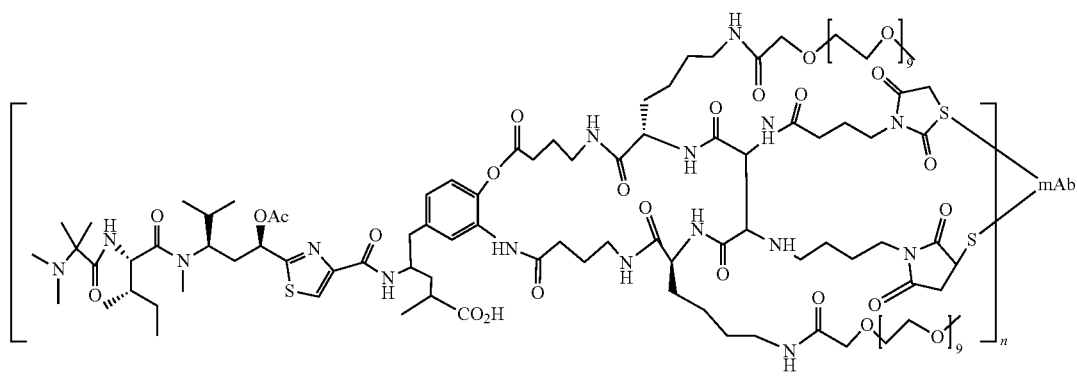
IC$_{50}$ = 2.7 nM, (DAR = 3.9).
687
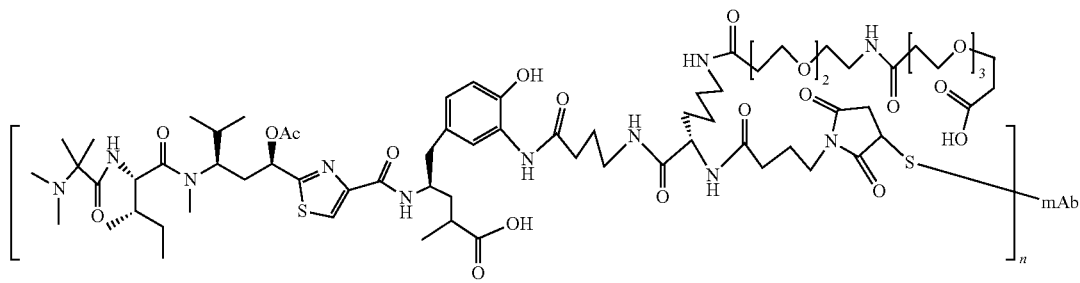
IC$_{50}$ = 0.87 nM, (DAR = 3.8).
692
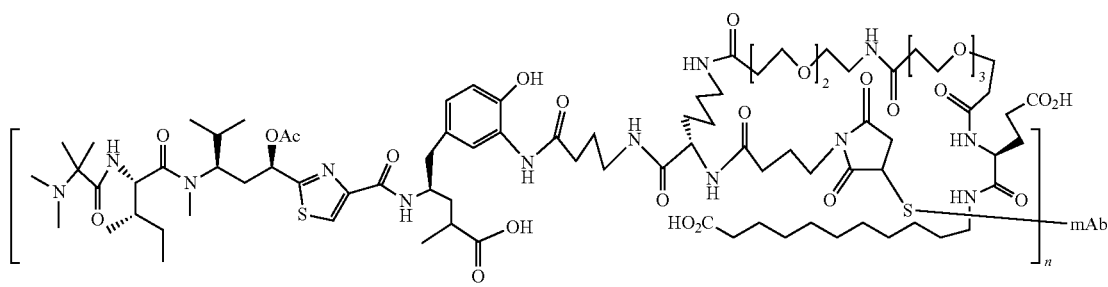
IC$_{50}$ = 1.36 nM, (DAR = 3.6).

TABLE 1-continued
The Structures of the Her2-tubulysin analog conjugates of the patent application along with their cytotoxicity IC50 results:
| Conjugate # | Structures and its IC50 against NCI-N87 cells |
|---|---|
| E1 | 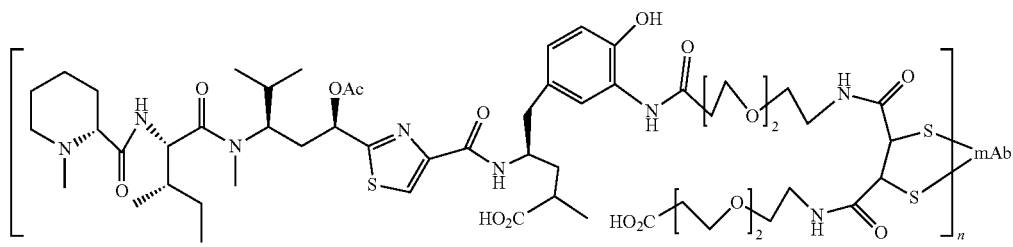 $IC_{50}$ = 8.21 nM, (DAR = 3.6). |
| E2 | 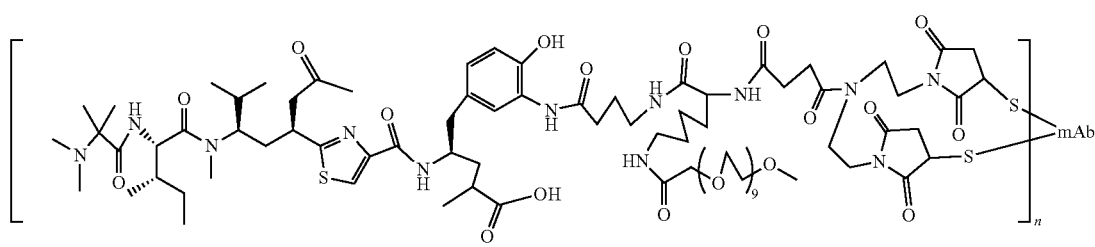 $IC_{50}$ = 0.47 nM, (DAR = 3.9). |
| E3 | 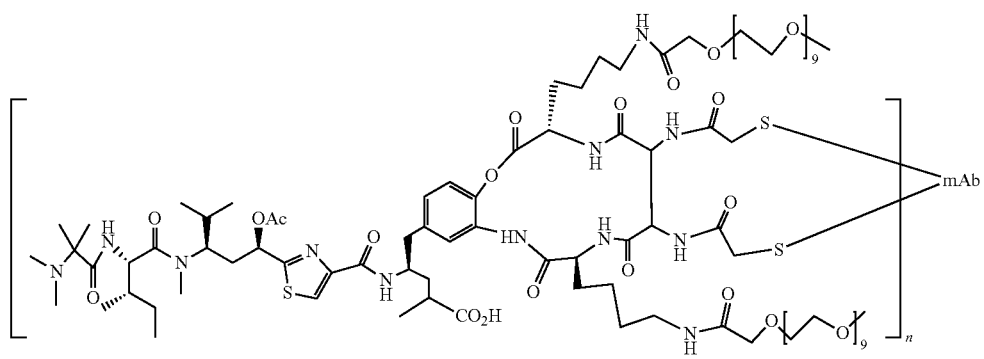 $IC_{50}$ = 11.5 nM, (DAR = 3.6). |
| E4 | 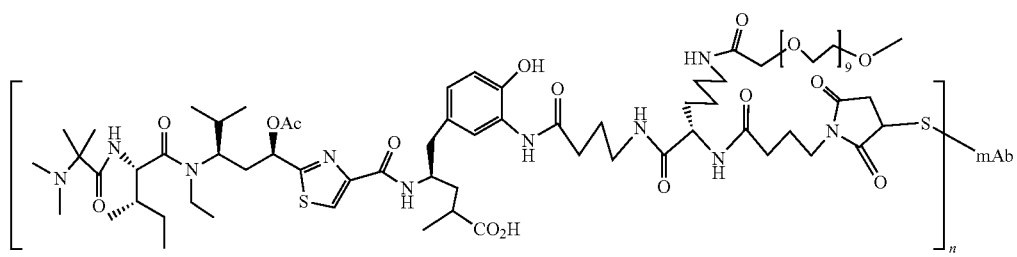 $IC_{50}$ = 0.27 nM, (DAR = 3.6). |

TABLE 1-continued

The Structures of the Her2-tubulysin analog conjugates of the patent application along with their cytotoxicity IC50 results:

| Conjugate # | Structures and its IC50 against NCI-N87 cells |
|---|---|
| E5 | 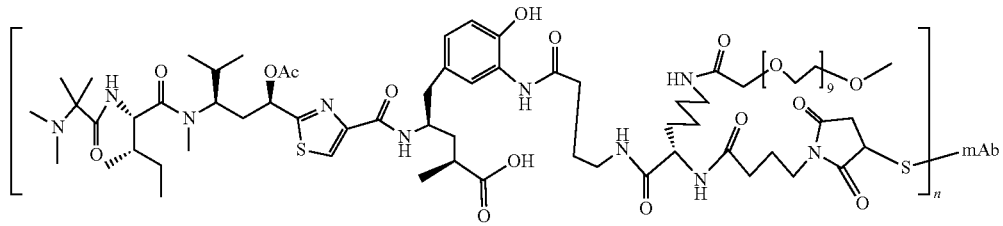<br>IC$_{50}$ = 0.17 nM, (DAR = 3.7). |
| E6 | 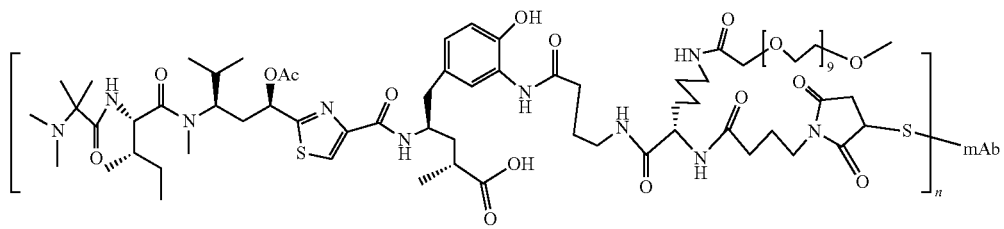<br>IC$_{50}$ = 0.43 nM, (DAR = 3.6). |
| E7 | 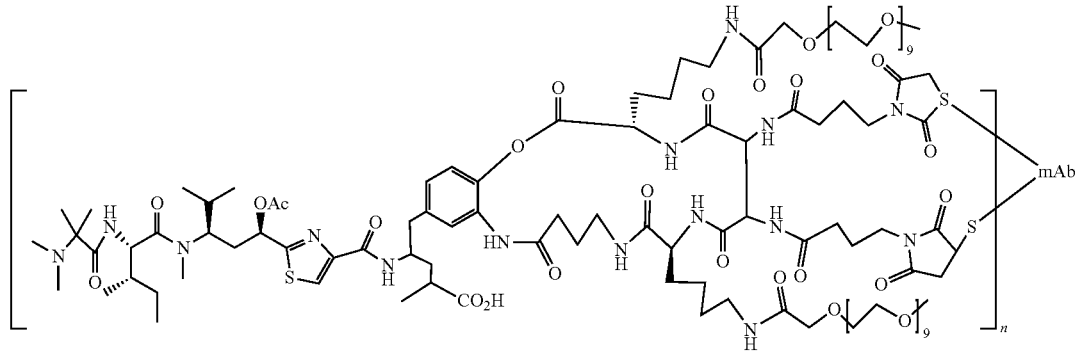<br>IC$_{50}$ = 1.65 nM, (DAR = 3.8). |

Example 294. Antitumor Activity In Vivo (BALB/c Nude Mice Bearing NCI-N87 Xenograft Tumor)

The in vivo efficacy of conjugates 474, 486, 493, 601, 626, 637, 641, 669, 673, 680, and 692 along with T-DM1 were evaluated in a human gastric carcinoma N-87 cell line tumor xenograft models. Five-week-old female BALB/c Nude mice (78 animals) were inoculated subcutaneously in the area under the right shoulder with N-87 carcinoma cells (5×10$^6$ cells/mouse) in 0.1 mL of serum-free medium. The tumors were grown for 8 days to an average size of 140 mm$^3$. The animals were then randomly divided into 13 groups (6 animals per group). The first group of mice served as the control group and was treated with the phosphate-buffered saline (PBS) vehicle. 12 groups were treated with conjugates 474, 486, 493, 601, 626, 637, 641, 669, 673, 680, 692 and T-DM1 respectively at dose of 6 mg/Kg administered intravenously. Three dimensions of the tumor were measured every 3 or 4 days (twice a week) and the tumor volumes were calculated using the formula tumor volume=½(length×width×height). The weight of the animals was also measured at the same time. A mouse was sacrificed when any one of the following criteria was met: (1) loss of body weight of more than 20% from pretreatment weight, (2) tumor volume larger than 1500 mm$^3$, (3) too sick to reach food and water, or (4) skin necrosis. A mouse was considered to be tumor-free if no tumor was palpable.

Figure 63:
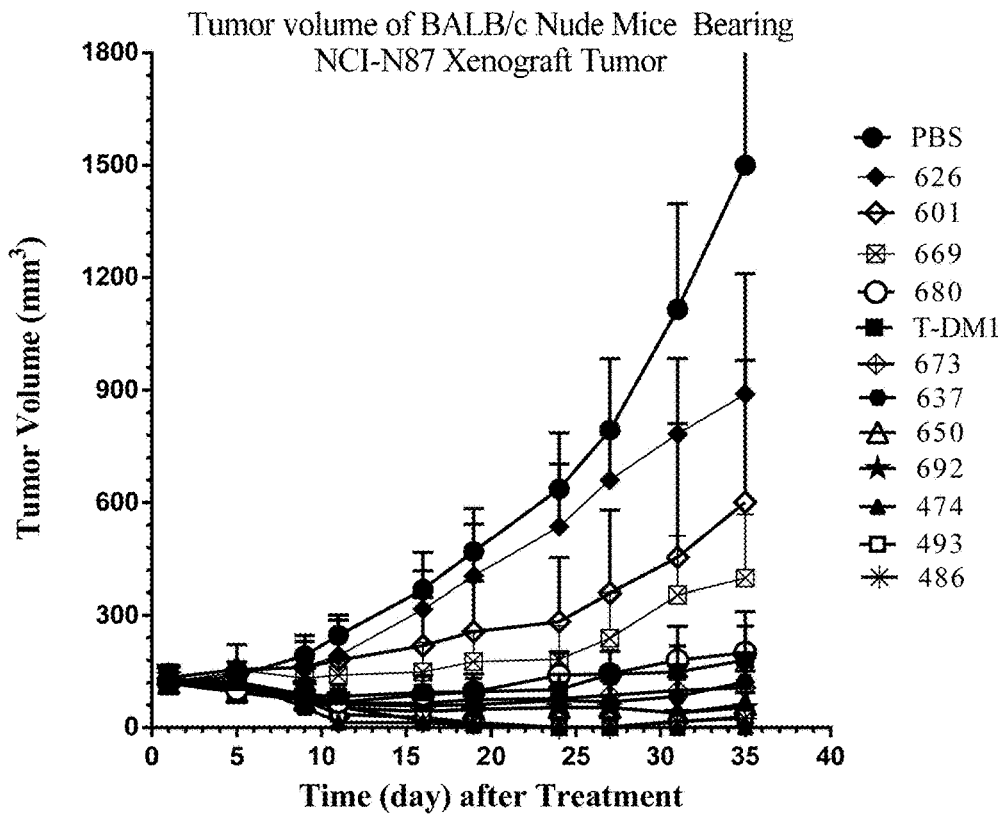
FIG. 63 shows the comparison of the anti-tumor effect of conjugate compounds 474, 486, 493, 601, 626, 637, 641, 669, 673, 680, and 692 with T-DM1 using human gastric tumor N87 cell model, i.v., one injection at dosing of 6 mg/kg.

The results were plotted in FIG. 63. All the 12 conjugates did not cause the animal body weight loss. Here 7 conjugates (673, 637, 650, 692, 474, 493 and 486) tested demonstrated better anti-tumor activity than T-DM1. All 6/6 animals at the groups of compounds 474, 493, and 486 had almost no tumor measurable at day 16 till day 28. In contrast T-DM1 at dose of 6 mg/Kg was not able to eliminate the tumors and it only inhibited the tumor growth for 26 days. In addition, conjugate compounds 601, 669, 680, 673, 637, 650, and 692 did not eradicate the tumor at dose of 6 mg/Kg completely. The inhibition of the tumor growth at dose of 6 mg/Kg are:

| Conjugate | Tumor growth delay |
|---|---|
| T-DM1 | 26 days |
| 626 | <4 days |
| 601 | 13 days |
| 669 | 18 days |
| 680 | 25 days |
| 673 | >30 days |
| 637 | >30 days |
| 650 | >30 days |
| 692 | >30 days |
| 474 | >30 days |
| 493 | >30 days |
| 486 | >30 days |

Example 295. Stability study of the conjugates having a side chain-linkage in comparison with T-DM1 and a regular conjugate (compound 133) having a mono-linkage in the mouse serum.

Sixty female ICR mice, 6-7 weeks old, were separated into 4 groups. Each group included 15 mice for the PK study of one out of four ADCs. These 15 mice were further randomly divided into three groups (n=5). Each mouse was given conjugates T-DM$_1$, 133, 680 and 692, respectively at dose of 10 mg/Kg/per rat, i.v. bolus. The blood collection was followed the NCI's Guidelines for Rodent Blood Collection. Basically, mice in each group were taken turn for bleeding in order to avoid more than twice bleedings in a period of 24 hr. Blood was taken from retro-orbital blood sinus with a 70 uL capillary at time 0 (pre-dosing), 0.083, 0.25, 0.5, 1, 4, 8, 24, 48, 96, 168, 312 and 504 hrs post dosing. Plasma samples were analyzed for total antibodies and drug-conjugated antibodies by specific ELISA techniques. In brief, the conjugated antibody or the total antibody concentration in the mouse serum was measured as follows: 96-well ELISA plates were respectively coated overnight at 4° C. with anti-DM1 antibody, anti-tubulysin antibody or anti-Her-2's Fab antibody (1 ug/mL in 10 mM PBS, pH7.2). The plates were then washed three times with a washing buffer PBS-T (PBS/0.02% Tween20), and then blocked with a dilution buffer 1% (w/v) BSA/PBS-T for 1 hour at 37° C. After the blocking buffer was removed, the standards or mouse serum samples each with triple replicates were diluted in 1% BSA/PBS-T buffer, incubated at 37° C. for 1 hour, then the AP-conjugated donkey anti-human antibody was added for 30 minutes at 37° C. after the plates were washed. Plates were washed again, followed by the addition of pNPP substrate for the color development and then read on a microplate reader at 405 nm wavelength once the color development reaction was quenched with the 1 mol/L sodium hydroxide. The concentration of the conjugated antibody or the total antibody was obtained from a four-parameter curve fitting of the standard curve.

Figure 64:
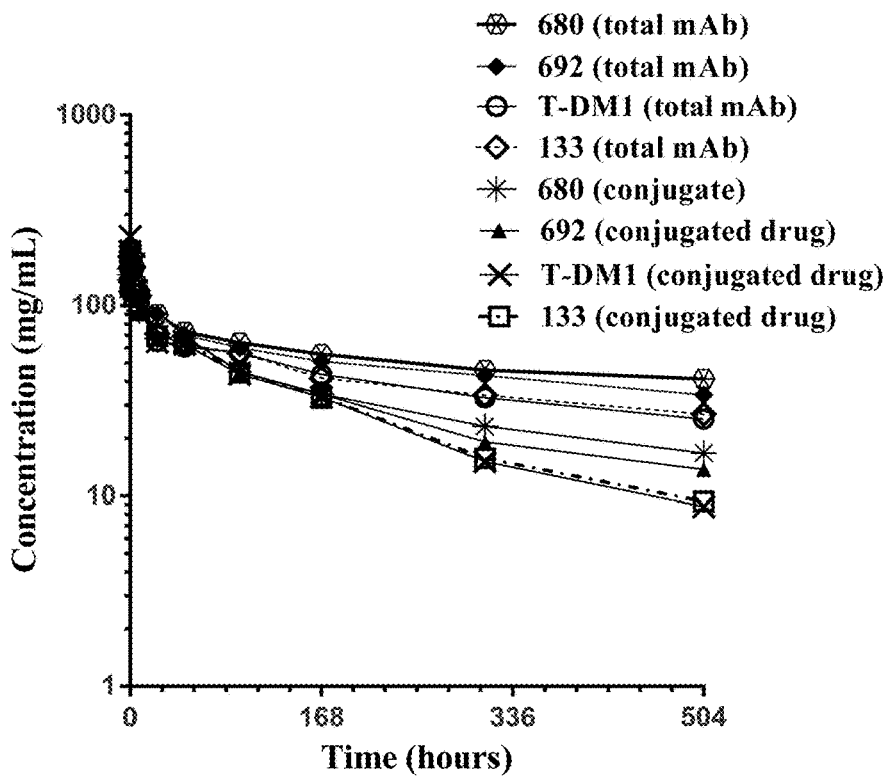
FIG. 64 shows the stability study of the conjugates (680 and 692) having a side chain-linkage in comparison with T-DM1 and a regular conjugate (compound 133) having a mono-linkage in the mouse serum.

The result as shown in FIG. 64, the PK behaviors of total antibodies and drug-conjugated antibodies after dosing four ADCs presented as typical two-phase clearance curves. Equivalences between plasma and peripheral tissues were reached 8 hrs post-dosing. Elimination phase emerged 24 hr post-dosing and continued until the last sampling time point. In summary, the values of conjugate exposures (Auciast) for these three ADCs are 14981, 14857, 17212 and 17638 hr·ug/kg for T-DM1, 133, 680 and 692 respectively. Distribution volumes for all these three conjugates are double of total blood volumes. The clearances (CL) of the conjugates are 0.59, 0.59, 0.48, and 0.45 mL/hr/kg, which are almost halves of those for total antibodies. The clearance of 692 and 680 both their conjugates and total antibodies, are smaller than T-DM1 and the regular conjugate 133, which indicates that the conjugates having the branched-linkage are more stable than the regular mono-linked conjugates in the mouse serum.

Example 296. Liver toxicity Study of the conjugate having a branched-linkage in comparison with regular conjugates (compound 133 and T-DM1) having a regular linkage. Eight-four female ICR mice, 6-7 weeks old, were separated into 14 groups. Each group included 6 mice for the liver toxicity study. The first group of mice served as the control group and was treated with the phosphate-buffered saline (PBS) vehicle. 13 groups were treated with conjugates 133, 474, 486, 493, 601, 626, 637, 641, 669, 673, 680, 692 and T-DM1 respectively at dose of 200 mg/Kg administered intravenously. The blood collection was followed the NCI's Guidelines for Rodent Blood Collection. Basically, Blood samples were collected through retro-orbital sinuses of the mice, and centrifuged to obtain the sera on Day 5 and 12 after administration. The levels of aspartate aminotransferase (AST), alanine aminotransferase (ALT) and alkaline phosphatase (ALP) were analyzed using PUS-2018 semi-automatic biochemistry analyzer with a commercial kid (using aspartate and alanine as substrates, respectively). Reference values were established by following reactive dynamics, according to manufacturer's recommendations. The results on average are show in Table 2 below:

| Compound | AST (IU/mL) | | ALT(IU/mL) | | ALP(IU/mL) | |
|---|---|---|---|---|---|---|
| | Day 5 | Day 12 | Day 5 | Day 12 | Day 5 | Day 12 |
| PBS | 91 | 95 | 46 | 36 | 186 | 179 |
| T-DM1 | 3276 | 1509 | 412 | 453 | 495 | 502 |
| 133 | 3683 | 1762 | 461 | 523 | 498 | 382 |
| 474 | 1283 | 276 | 184 | 125 | 288 | 228 |
| 486 | 1873 | 1539 | 201 | 263 | 381 | 301 |
| 493 | 1521 | 602 | 197 | 165 | 323 | 287 |
| 601 | 111 | 105 | 86 | 46 | 206 | 189 |
| 626 | 151 | 108 | 96 | 49 | 197 | 193 |
| 637 | 851 | 178 | 186 | 79 | 267 | 187 |
| 641 | 918 | 183 | 186 | 87 | 287 | 172 |
| 650 | 832 | 173 | 186 | 78 | 279 | 167 |
| 673 | 653 | 158 | 136 | 59 | 207 | 181 |
| 680 | 193 | 98 | 76 | 39 | 256 | 189 |
| 692 | 238 | 91 | 106 | 37 | 273 | 189 |

The liver toxicity results indicate that at the much higher dose of 150 mg/Kg the conjugates (474, 486, 493, 601, 626, 637, 641, 669, 673, 680, and 692) with the side chain linker are much less toxic than both T-DM1 and the regular mono-linked conjugate 133. Since conjugates 474, 486, 493, 637, 641, 669, 673, 680, and 692 have better in vivo activity than T-DM1, therefore the overall therapeutical windows for conjugates 474, 486, 493, 637, 641, 669, 673, 680, and 692 would be much wider than T-DM1.

What is claimed is:

1. A composition comprising at least one side chain-linkaged conjugate compound of the Formula (I):

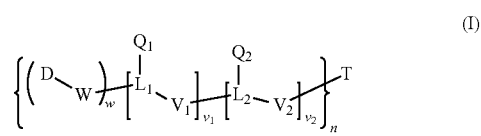

wherein
"-" represents a single bond; n is 1 to 30;
T is a cell-binding molecule, which is an antibody;
$L_1$ and $L_2$ are, the same or different, independently selected from O, NH, N, S, P, NNH, NHNH, N($R_3$), N($R_3$)N($R_{3'}$), CH, CO, C(O)NH, C(O)O, NHC(O)NH, NHC(O)O, polyethyleneoxy unit of formula ($OCH_2CH_2$)$_p$$OR_3$, or ($OCH_2CH-(CH_3)$)$_p$$OR_3$, or NH($CH_2CH_2O$)$_p$$R_3$, or NH($CH_2CH(CH_3)O$)$_p$$R_3$, or N[($CH_2CH_2O$)$_p$$R_3$]—[($CH_2CH_2O$)$_p$$R_{3'}$], or ($OCH_2CH_2$)$_p$$COOR_3$, or $CH_2CH_2$($OCH_2CH_2$)$_p$$COOR_3$, wherein p and p' are independently an integer selected from 0 to about 1000, or combination thereof; $C_1$-$C_8$ alkyl; $C_2$-$C_8$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; or (Aa)$_r$, r=1-12 (one to 12 amino acid units), which is composed from natural or unnatural amino acids, or the same or different sequences of dipeptide, tripeptide, tetrapeptide, pentapeptide, hexapeptide, heptapeptide, octapeptide, nonapeptide, decapeptide, undecapeptide or dodecapeptide unit;
$R_3$ and $R_{3'}$ are independently H, $C_1$-$C_8$ alkyl; $C_2$-$C_8$ heteroalkyl, or heterocyclic; $C_3$-$C_8$ aryl, Ar-alkyl, cycloalkyl, alkylcycloalkyl, heterocycloalkyl, heteroalkylcycloalkyl, carbocyclic, or alkylcarbonyl;
W is a stretcher unit having $C_1$-$C_{18}$, normally a self-immolative spacer, a peptidic unit, a hydrazone, a disulfide, a thioether, an ester, or an amide bond; w is 1 or 2 or 3;
$V_1$ and $V_2$ are independently a spacer unit and selected from O, NH, S, $C_1$-$C_8$ alkyl, $C_2$-$C_8$ heteroalkyl, alkenyl, or alkynyl, $C_3$-$C_8$ aryl, heterocyclic, carbocyclic, cycloalkyl, alkylcycloalkyl, heterocycloalkyl, heteroaralkyl, heteroalkylcycloalkyl, or alkylcarbonyl, or (Aa)$_r$, r=1-12 (one to 12 amino acid units), which is composed from a natural or unnatural amino acid, or the same or different sequences of dipeptide, tripeptide, tetrapeptide, pentapeptide, hexapeptide, heptapeptide, octapeptide, nonapeptide, decapeptide, undecapeptide or dodecapeptide unit; or ($CH_2CH_2O$)$_p$, p is 0-1000; and $v_1$ and $v_2$ are independently 0, 1 or 2, but $v_1$ and $v_2$ are not 0 at the same time; when $v_1$ or $v_2$ is 0, it means one of the side chain $Q_1$ or $Q_2$ fragment is absent;
$Q_1$ and $Q_2$ are independently a $C_2$-$C_{100}$ polycarboxylacid; a $C_2$-$C_{100}$ polyalkylamine; a $C_6$-$C_{100}$ oligosaccharide or polysaccharide, a $C_6$-$C_{100}$ zwitterionic betaines or zwitterionic poly(sulfobetaine)) (PSB)s that consist of a quaternary ammonium cation and a sulfonate anion; a $C_6$-$C_{100}$ biodegradable polymer composed of poly(lactic/glycolic acid) (PLGA), poly(acrylates), chitosan, copolymer of N-(2-hydroxypropyl)methacrylamide, poly[2-(methacryloyloxy)ethyl phosphorylcholine] (PMPC), poly-L-glutamic acid, poly(lactide-co-glycolide) (PLG), poly(lactide-co-glycolide), poly(ethylene glycol)(PEG), poly(propylene glycol)(PPG), poly(lactide-co-glycolide), poly(ethylene glycol)-modified peptides, poly(ethylene glycol)-containing an amino acid or peptides, poly(ethylene glycol)-modified lipids, poly(ethylene glycol)-modified alkylcarboxic acid, poly(ethylene glycol)-modified alkylamine, poly(lactide-co-glycolide, hyaluronic acid (HA) (glycosaminoglycan), heparin/heparan sulfate (HSGAGs), chondroitin sulfate/dermatan sulfate (CSGAGs), poly(ethylene glycol)-modified alkylsulfate, poly(ethylene glycol)-modified alkylphosphate, or poly(ethylene glycol)-modified alkyl quaternary ammonium;

alternatively, any one or more of W, $Q_1$, $Q_2$, $L_1$, $L_2$, $V_1$, or $V_2$ can be independently absent but $Q_1$, and $Q_2$ are not absent at the same time;
D is tubulysin analog having the following formula (II):

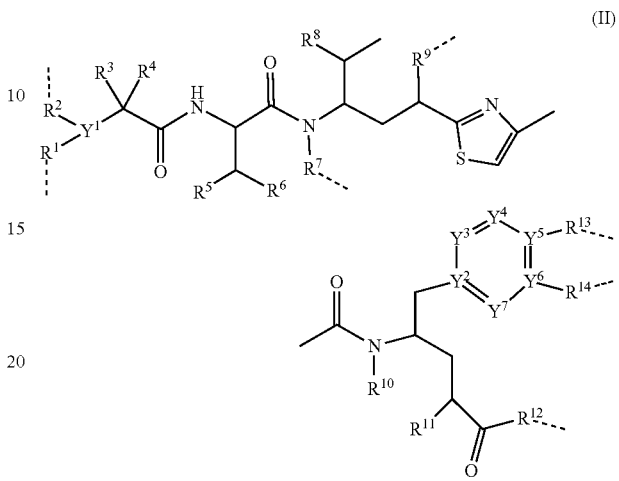

(II)

or a pharmaceutically acceptable salt, hydrates, or hydrated salt; or a polymorphic crystalline structure; or an optical isomer, racemate, diastereomer or enantiomer thereof,
wherein - - - - - is a linkage site that links to W independently;
wherein $R^1$, $R^2$, $R^3$, and $R^4$ are independently H, $C_1$~$C_8$ alkyl; $C_2$~$C_8$ heteroalkyl, or heterocyclic; $C_3$~$C_8$ aryl, Ar-alkyl, cycloalkyl, alkylcycloalkyl, heterocycloalkyl, heteroalkylcycloalkyl, carbocyclic, or alkylcarbonyl; or $R^1R^2$, $R^1R^3$, $R^2R^3$, $R^3R^4$, $R^5R^6$, $R^{11}R^{12}$ or $R^{13}R^{14}$ form a 3~7 membered carbocyclic, cycloalkyl, heterocyclic, heterocycloalkyl, aromatic or heteroaromatic ring system; $R^1$ and $R^2$ can be independently absent when they link to W independently or simultaneously, $Y^1$ is N or CH;
wherein $R^5$, $R^6$, $R^8$, $R^{10}$ and $R^{11}$ are independently H, or $C_1$~$C_4$ alkyl or heteroalkyl;
wherein $R^7$ is independently H, $R^{14}$, —$R^{14C}$(=O)$X^1R^{15}$; or —$R^{14}X^1R^{15}$; $X^1$ is O, S, S—S, NH, $CH_2$ or $NR^{14}$;
wherein $R^9$ is selected from H, OH, —O—, =O, —$OR^{14}$, —OC(=O)$R^{14}$, —OC(=O)$NHR^{14}$—, —OC(=O)$R^{14}SSR^{15}$—, OP(=O)($OR^{14}$)—, —OC(=O)$NR^{14}R^{15}$, OP(=O)($OR^{14}$), or $OR^{14}OP$(=O)($OR^{15}$);
wherein $R^{11}$ is independently H, $R^{14}$, —$R^{14}C$(=O)$R^{16}$, —$R^{14}X^2R^{16}$, —$R^{14}C$(=O)$X^2$; wherein $X^2$ is —O—, —S—, —NH—, —N($R^{14}$)—, —O—$R^{14}$—, —S—$R^{14}$—, —S(=O)—$R^{14}$—, or —$NHR^{14}$;
wherein $R^{12}$ is $R^{15}$, —OH, —SH, —$NH_2$, NH, $NHNH_2$, —NH($R^{15}$), —$OR^{15}$, —$R^{15}COR^{16}$, —$R^{15}COOR^{16}$, —$R^{15}C$(O)$NH_2$, —$R^{15}C$(O)$NHR^{17}$, —$SR^{16}$, $R^{15}S$(=O)$R^{16}$, —$R^{15}P$(=O)($OR^{17}$)$_2$, —$R^{15}OP$(=O)($OR^{17}$)$_2$, —$CH_2OP$(=O)($OR^{17}$)$_2$, —$R^{15}SO_2R^{17}$, —$R^{15}X_2R^{16}$, or —$R^{15}C$(=O)$X^2$, where $X^2$ is —O—, OH, SH, —S—, $NH_2$, —NH—, —N($R^{15}$)—, —O—$R^{15}$—, —S—$R^{15}$—, —S(=O)—$R^{15}$—, $CH_2$ or —$NHR^{15}$—;
$R^{13}$ and $R^{14}$ are independently H, O, S, NH, N($R^{15}$), NHNH, —OH, —SH, —$NH_2$, NH, $NHNH_2$, —NH($R^{15}$), —$OR^{15}$, CO, —$COX^2$, —$COX^2R^{16}$, $R^{17}$, F, Cl, Br, I, $SR^{16}$, $NR^{16}R^{17}$, N=$NR^{16}$, N=$R^{16}$, $NO_2$, $SOR^{16}R^{17}$, $SO_2R^{16}$, $SO_3R^{16}$, $OSO_3R^{16}$, $PR^{16}R^{17}$, $POR^{16}R^{17}$; $PO_2R^{16}R^{17}$, $OP(O)(OR^{17})_2$, $OCH_2OP(O)(OR^{17})_2$, $OC(O)R^{17}$, $OC(O)OP(O)(OR^{17})_2$, $PO(OR^{16})(OR^{17})$, $OP(O)(OR^{17})OP(O)(OR^{17})_2$, $OC(O)NHR^{17}$, —O—($C_4$-$C_{12}$ glycoside), —N—($C_4$-$C_{12}$ glycoside); $C_1$~$C_8$ alkyl, heteroalkyl; $C_2$-$C_8$ alkenyl, alkynyl, heteroalkyl, or heterocycloalkyl; $C_3$-$C_8$ aryl, Ar-alkyl, carbocyclic, cycloalkyl, heteroalkylcycloalkyl, alkylcarbonyl, or heteroaryl, or $C_2$-$C_8$ ester, ether, or amide; or peptide containing 1-8 amino acids $(NH(Aa)_{1\sim 8}$ or $CO(Aa)_{1\sim 8}$ (N-terminal or C-terminal 1-8 the same or different amino acids), or polyethyleneoxy unit of formula $(OCH_2CH_2)_p$ or $(OCH_2CH(CH_3))_p$, wherein p is an integer from 0 to about 1000, or any combination of above groups thereof; $X^2$ is O, S, S—S, NH, $CH_2$, OH, SH, $NH_2$, $CHR^{14}$ or $NR^{14}$;

$R^{15}$, $R^{16}$ and $R^{17}$ is independently H, $C_1$~$C_8$ alkyl, heteroalkyl; $C_2$-$C_8$ alkenyl, alkynyl, heteroalkyl, or heterocycloalkyl; $C_3$-$C_8$ aryl, Ar-alkyl, carbocyclic, cycloalkyl, heteroalkylcycloalkyl, alkylcarbonyl, heteroaryl, alkylcarbonyl, or $Na^+$, $K^+$, $Cs^+$, $Li^+$, $Ca^{2+}$, $Mg^+$, $Zn^{2+}$, $N^+(R^1)(R^2)(R^3)(R^4)$, or $HN^+(C_2H_5OH)_3$ salt;

$Y^1$ and $Y^2$ are independently N or CH; q is 0 or 1; when q=0, $Y^3$ does not exist, $Y^4$, $Y^5$, $Y^6$ and $Y^7$ are independently CH, N, NH, O, S, or $N(R^1)$, thus $Y^2$, $Y^4$, $Y^5$, $Y^6$ and $Y^7$ form a heteroaromatic ring of furan, pyrrole, thiophene, thiazole, oxazole, imidazole, pyrazole, triazole, tetrazole, thiadiazole; when q=1, $Y^3$, $Y^4$, $Y^5$, $Y^6$ and $Y^7$ are independently CH or N, thus $Y^2$, $Y^3$, $Y^4$, $Y^5$, $Y^6$ and $Y^7$ form aromatic ring of benzene, pyridine, pyridazine, pyrimidine, pyrazine, triazine, tetrazine, or pentazine; and wherein D/T ratio is 3.4 to 4.1.

2. The composition according to claim 1, wherein $Q_1$ and $Q_2$ are independently selected from Iq-01 to Iq-35:

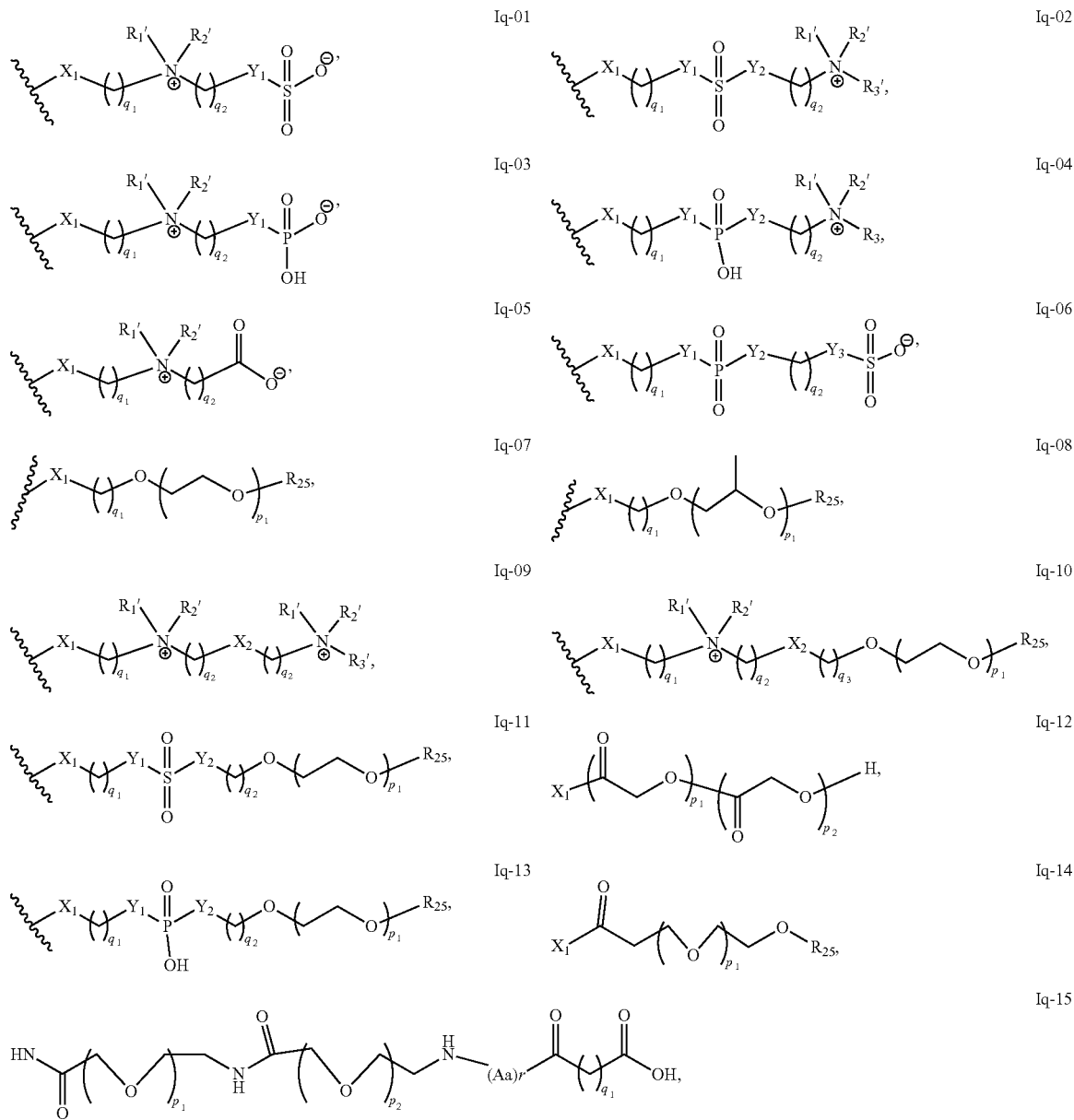

-continued
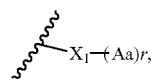 Iq-16
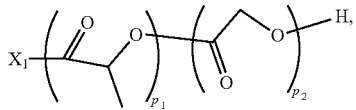 Iq-17
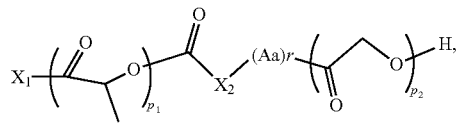 Iq-18
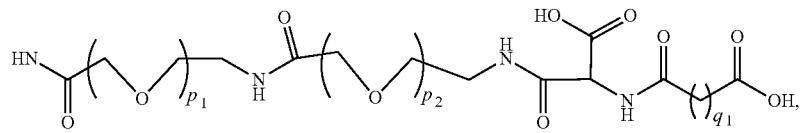 Iq-19
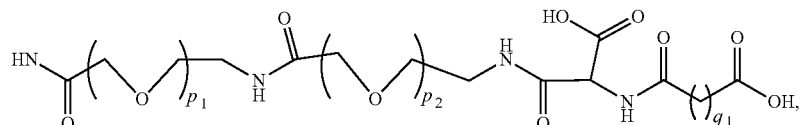 Iq-20
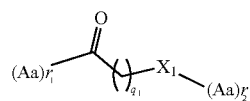 Iq-21
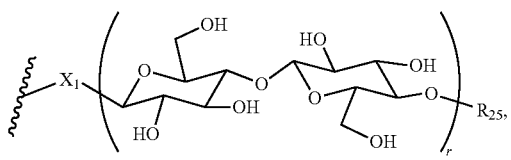 Iq-22
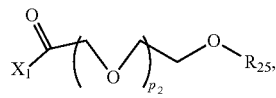 Iq-23
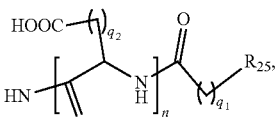 Iq-24
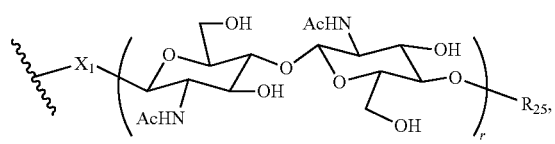 Iq-25
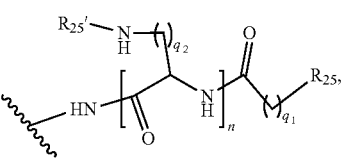 Iq-26
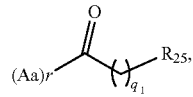 Iq-27
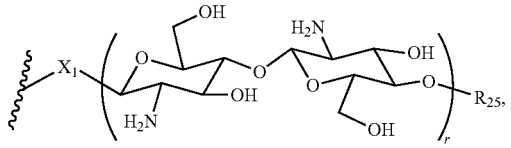 Iq-28
 Iq-29
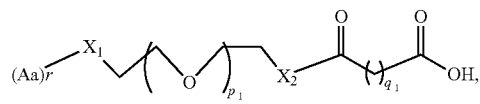 Iq-30
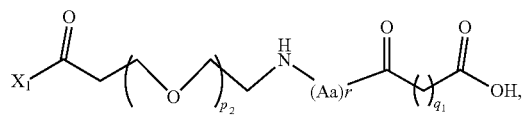 Iq-32
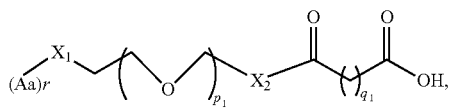 Iq-33

-continued

Iq-34

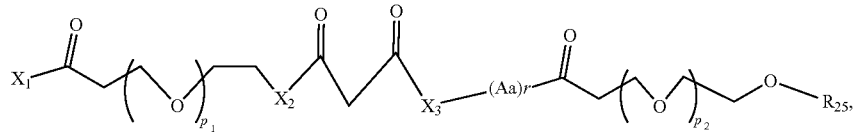

Iq-35

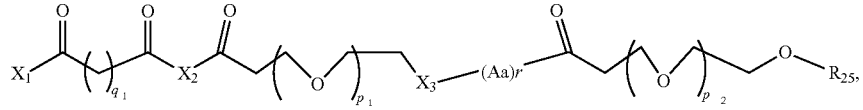

wherein $R_{25}$ and $R_{25'}$ are independently selected from H; HC(O), CH$_3$C(O), CH$_3$C(NH), C$_1$-C$_{18}$ alkyl, C$_1$-C$_{18}$ alkyl, alkyl-Y$_1$—SO$_3$H, C$_1$-C$_{18}$ alkyl-Y$_1$—PO$_3$H$_2$, C$_1$-C$_{18}$ alkyl-Y$_1$—CO$_2$H, C$_1$-C$_{18}$ alkyl-Y$_1$—N$^+$R$_1$'R$_2$'R$_3$'R$_4$', C$_1$-C$_{18}$ alkyl-Y$_1$—CONH$_2$, C$_2$-C$_{18}$ alkylene, C$_2$-C$_{18}$ ester, C$_2$-C$_{18}$ ether, C$_2$-C$_{18}$ amine, C$_2$-C$_{18}$ alkyl carboxylamide, C$_3$-C$_{18}$ Aryl, C$_3$-C$_{18}$ cyclic alkyl, C$_3$-C$_{18}$ heterocyclic, 1~24 amino acids; C$_2$-C$_{18}$ lipid, a C$_2$-C$_{18}$ fatty acid or a C$_2$-C$_{18}$ fatty ammonium lipid; X$_1$ and X$_2$ are independently selected from NH, N(R1'), O, CH$_2$, S, C(O), S(O), S(O$_2$), P(O)(OH), NHNH, CH=CH, Ar or (Aa)q$_1$, q$_1$=0-24 (0-24 amino acids, q$_1$=0 means absent); X$_1$, X$_2$, X$_3$, Y$_1$, Y$_2$ and Y$_3$ are independently selected from NH, N(R$_1$'), O, C(O), CH$_2$, S, S(O), NHNH, C(O), OC(O), OC(O)O, OC(O)NH, NHC(O)NH, Ar or Ar or (Aa)q$_1$, X$_1$, X$_2$, X$_3$, Y$_1$, Y$_2$ and Y$_3$ can be independently absent; p$_1$, and p$_2$ are independently 0-100 but are not 0 at the same time; q$_1$, q$_2$ and q$_3$ are independently 0-24; R$_1$', R$_2$', R$_3$' and R$_4$' are independently selected from H and C$_1$-C$_6$ alkyl; Aa is natural or unnatural amino acid; Ar or (Aa)q$_1$, is the same or different sequence of peptides; q$_1$=0 means (Aa)q$_1$ absent; and r and n are defined the same as in claim 1.

3. The composition according to claim 1, wherein D (tubulysin structure) is selected from I-01 to I-75:

I-01

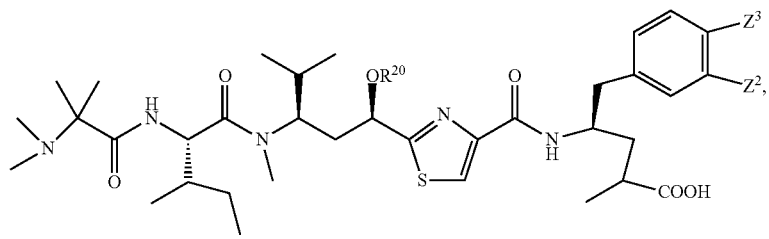

I-02

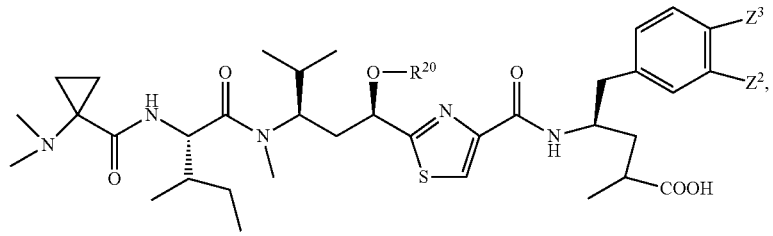

I-03

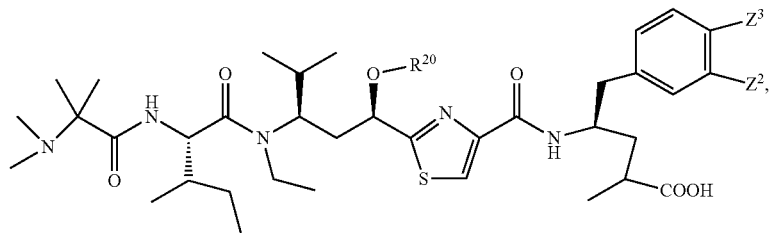

I-04
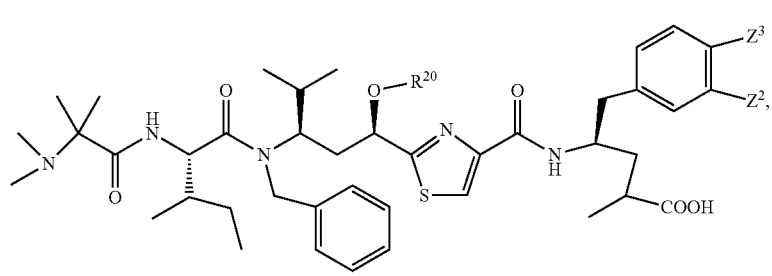
I-05
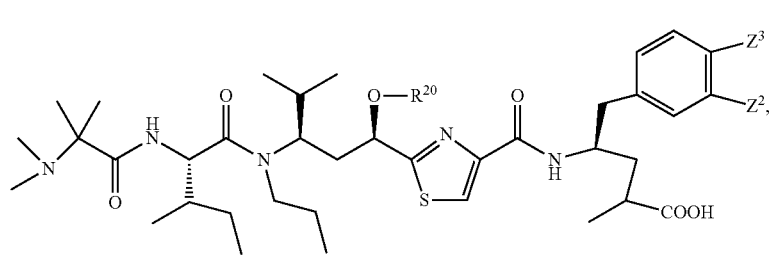
I-06
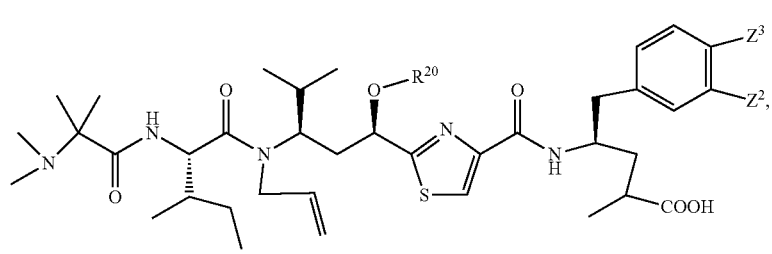
I-07
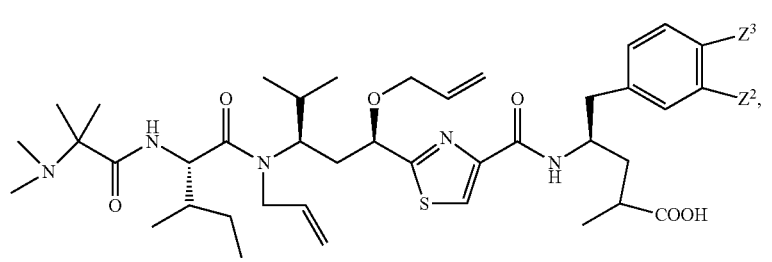
I-08
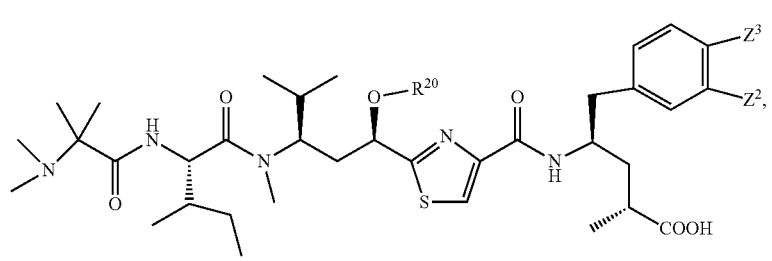
I-09
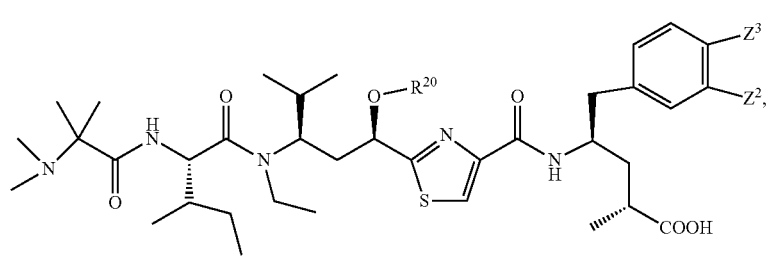

-continued
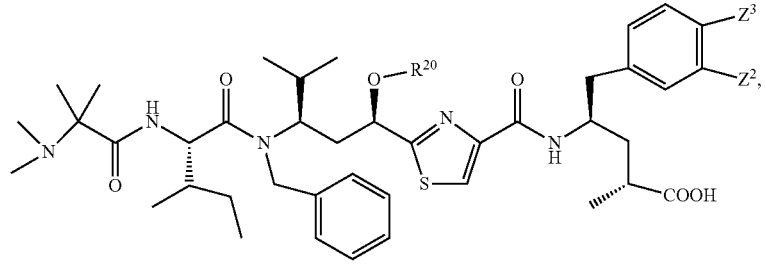
I-10
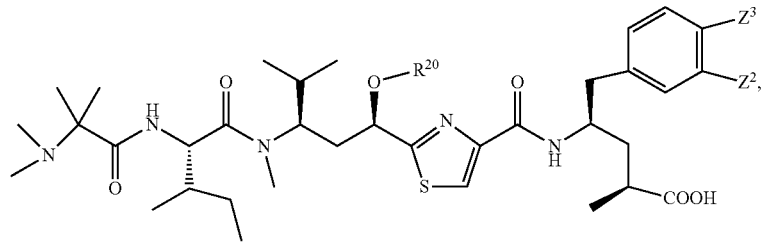
I-11
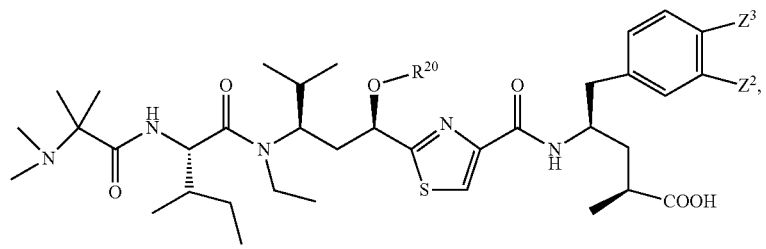
I-12
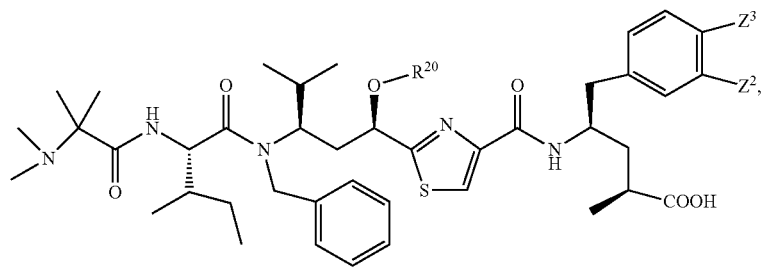
I-13
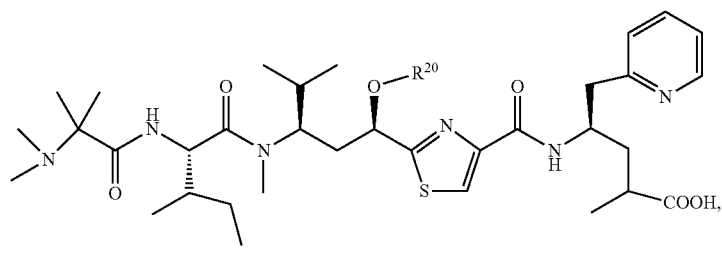
I-14
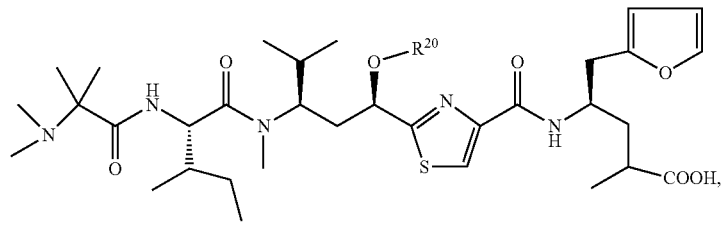
I-15

-continued
I-16
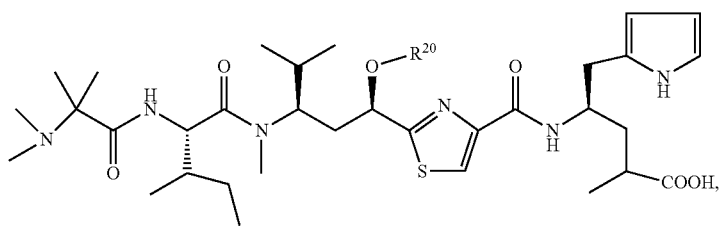
I-17
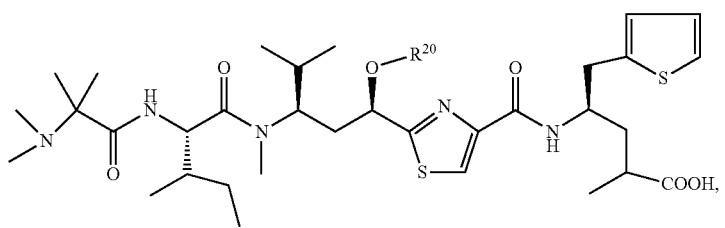
I-18
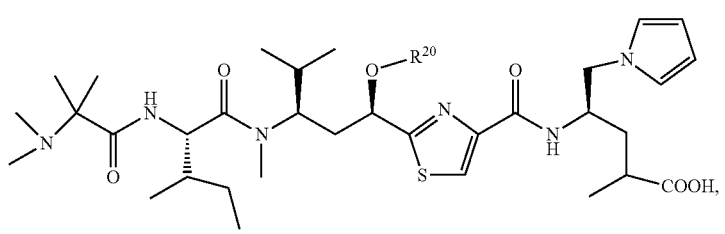
I-19
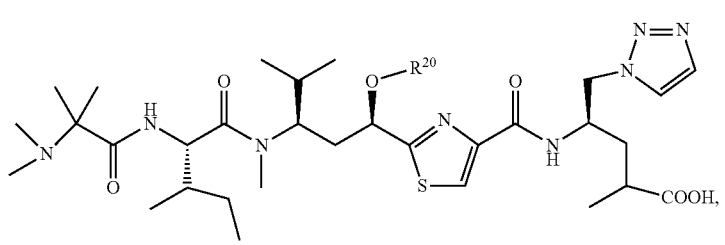
I-20
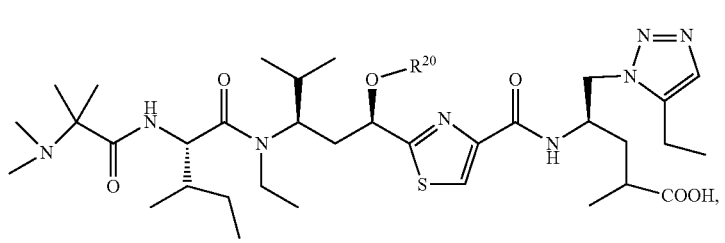
I-21
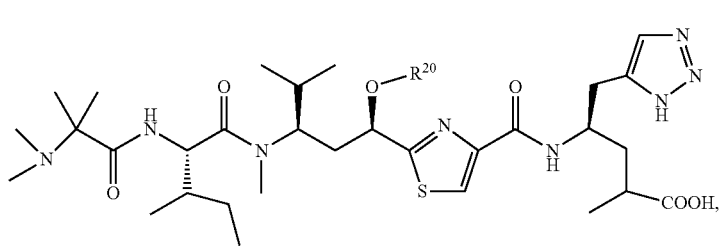
I-22
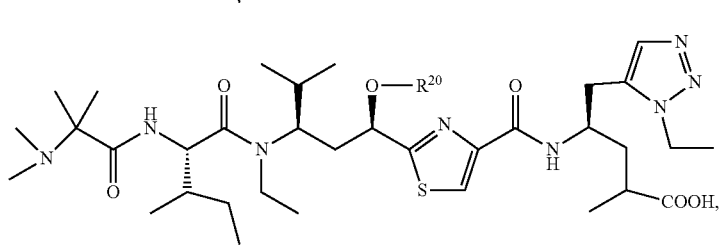

I-23
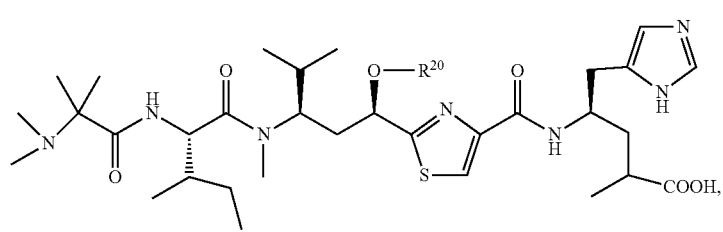
I-24
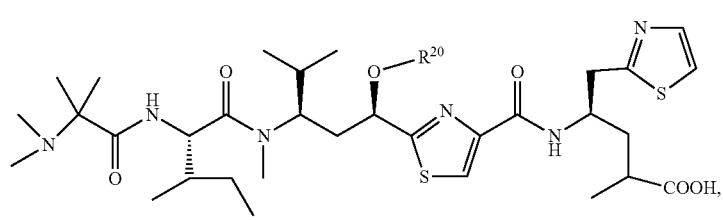
I-25
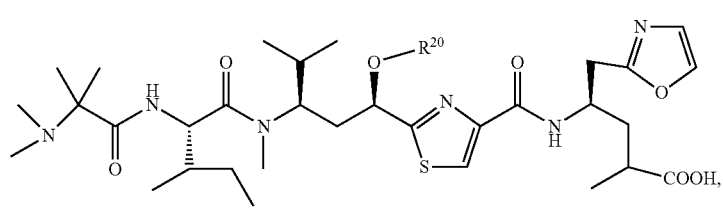
I-26
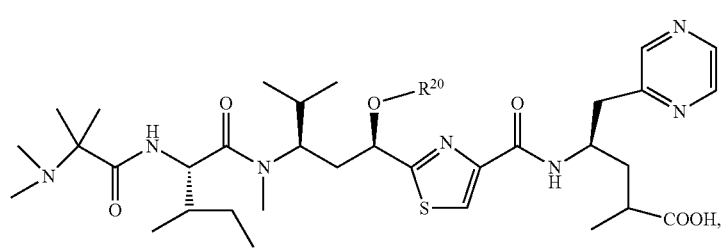
I-27
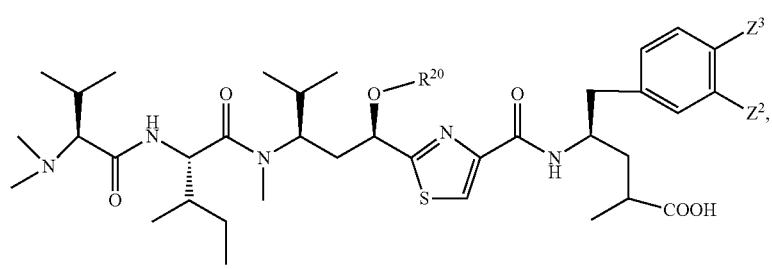
I-28
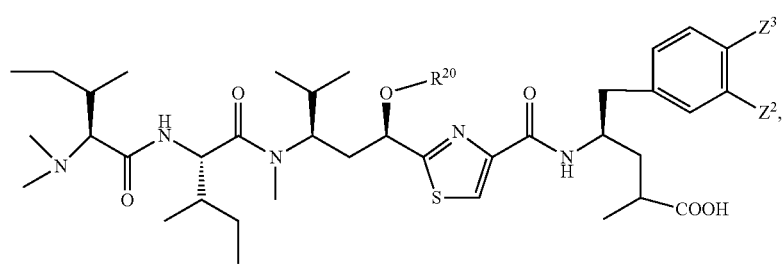

I-29
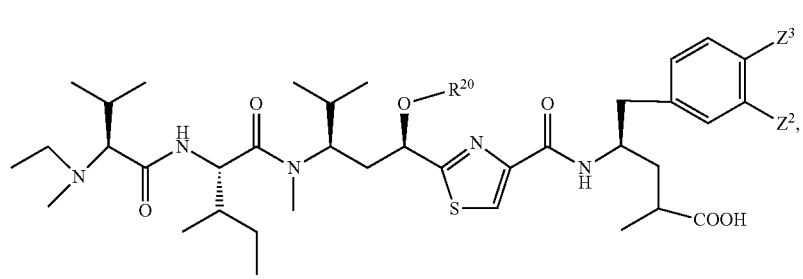
I-30
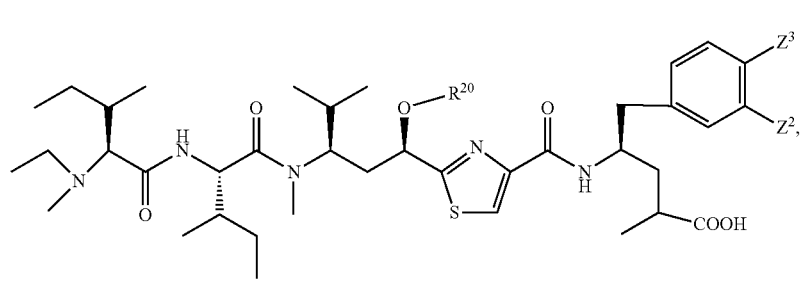
I-31
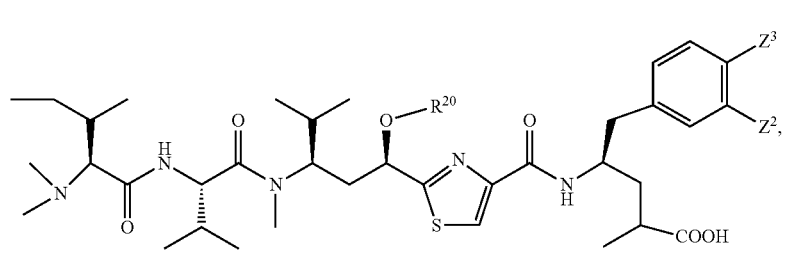
I-32
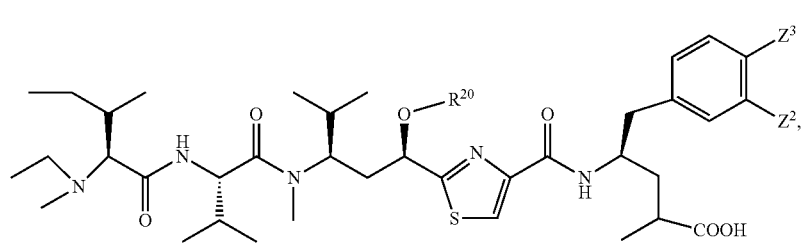
I-33
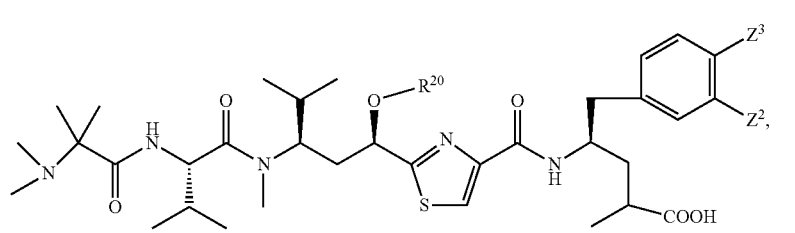
I-34
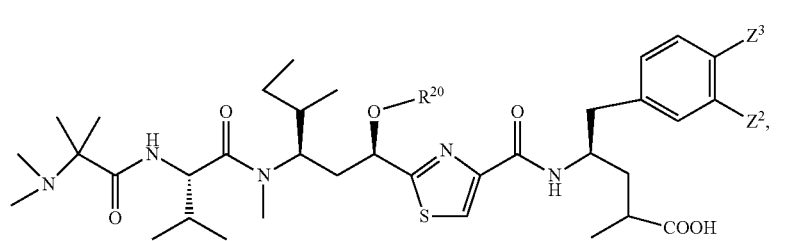

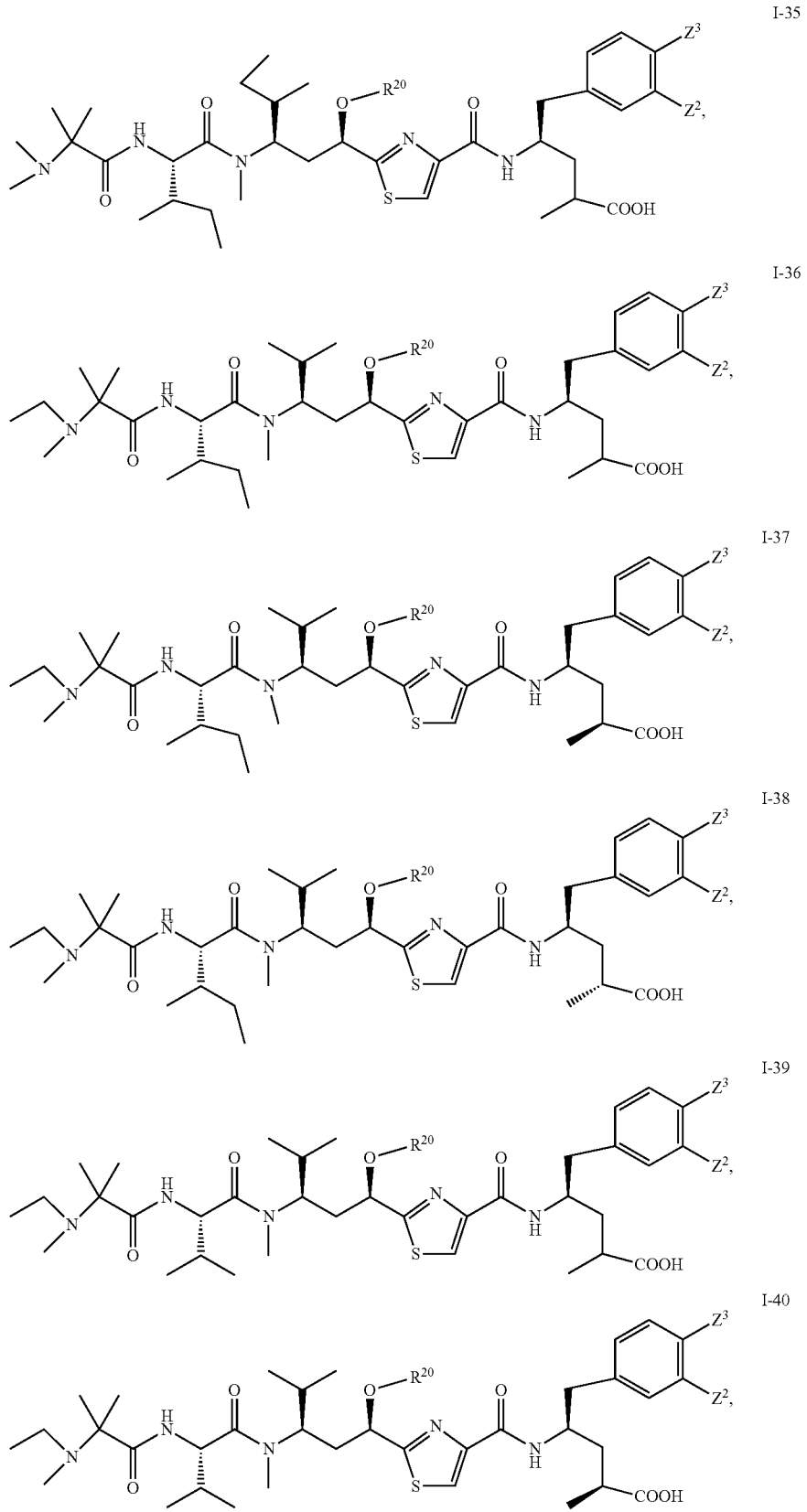

-continued
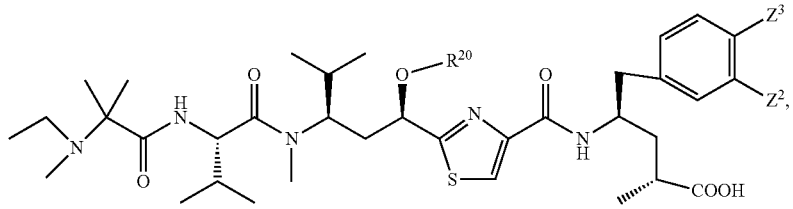
I-41
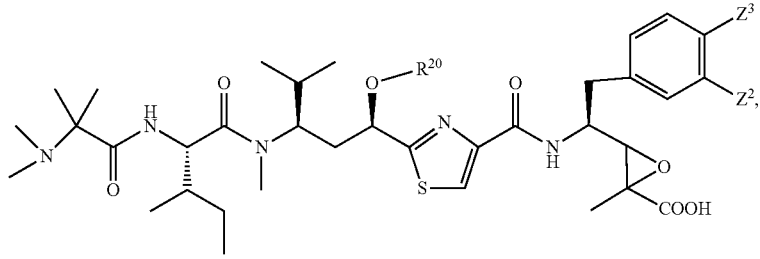
I-42
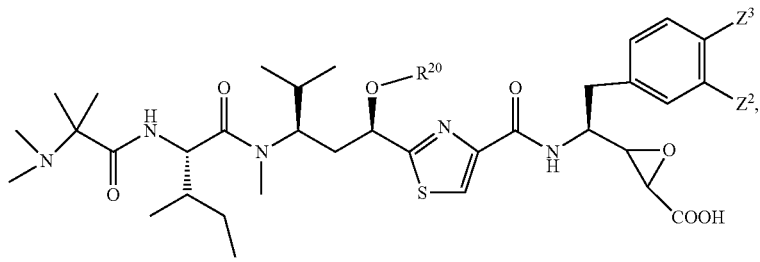
I-43
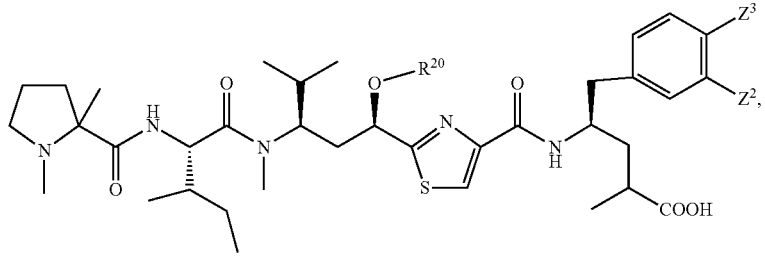
I-44
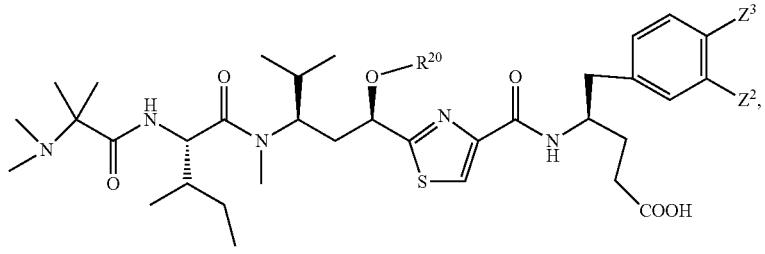
I-45
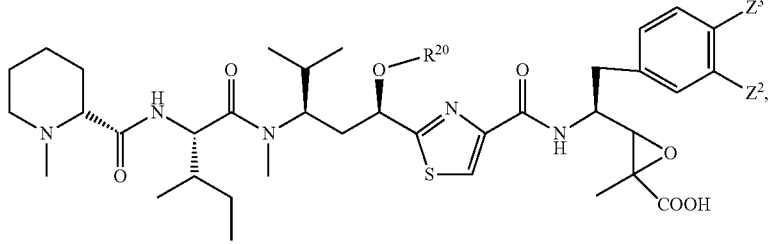
I-46

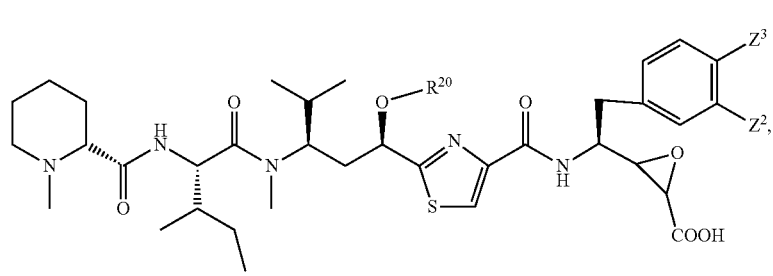
I-47
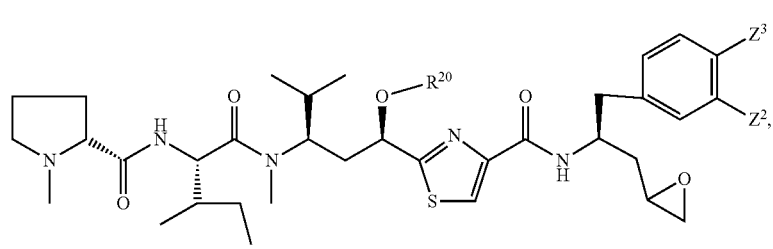
I-48
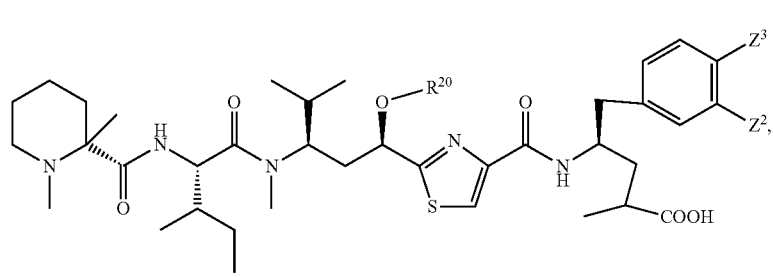
I-49
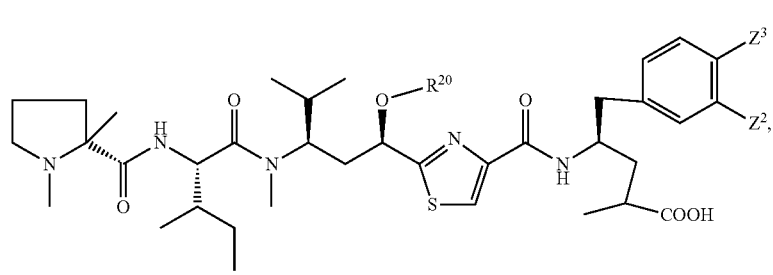
I-50
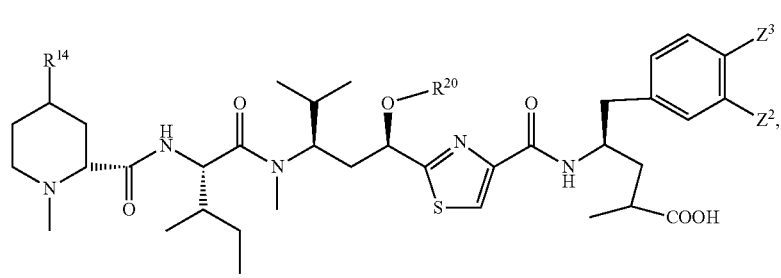
I-51
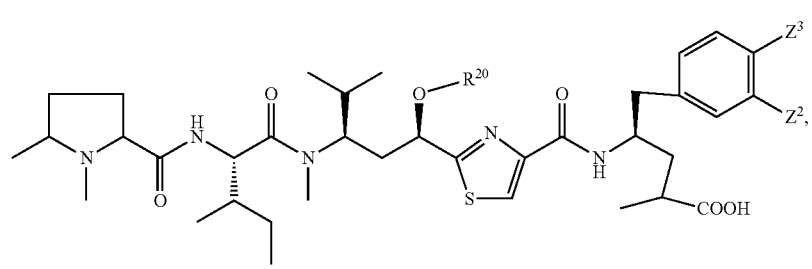
I-52

-continued
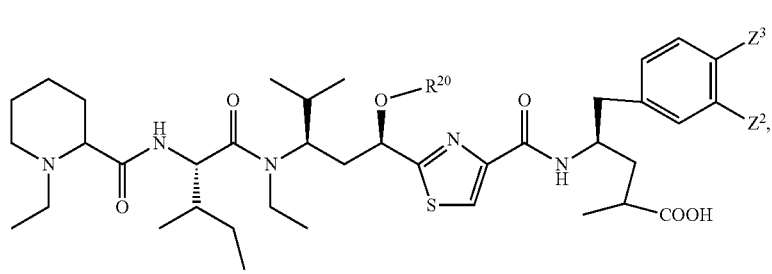
I-53
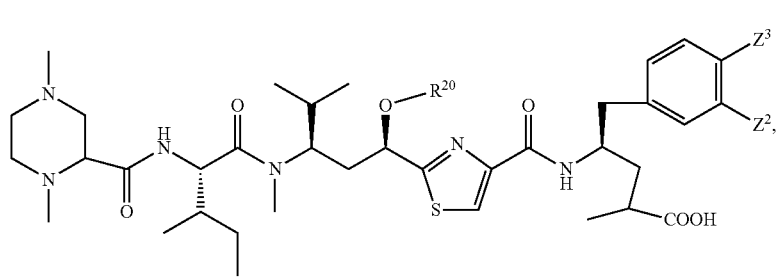
I-54
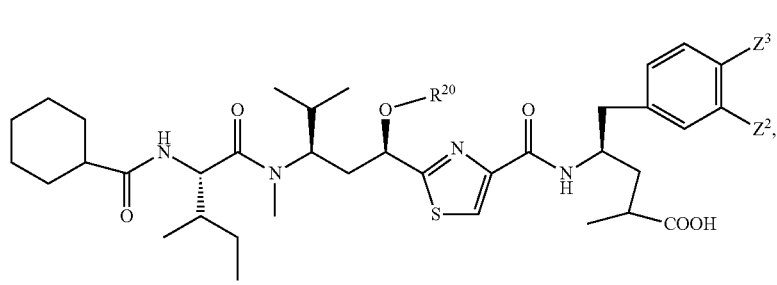
I-55
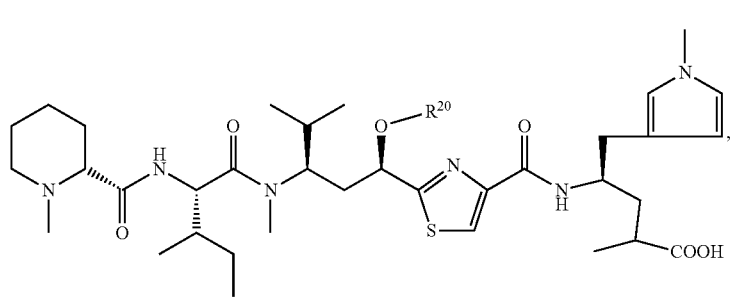
I-56
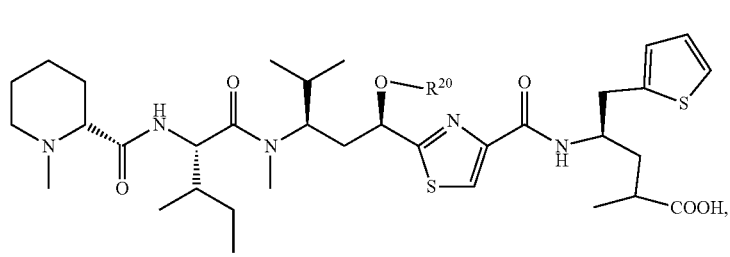
I-57
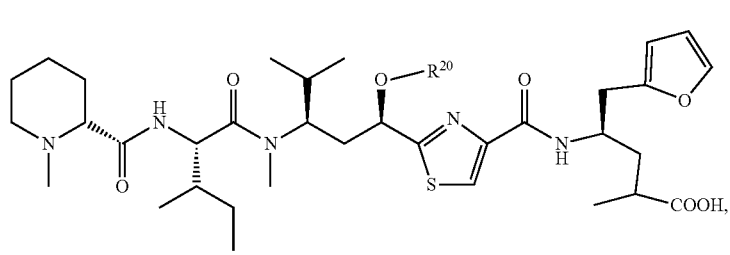
I-58

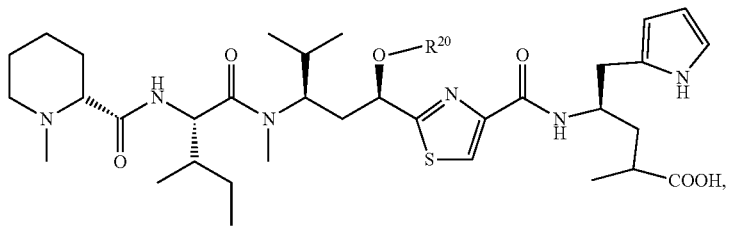
I-59
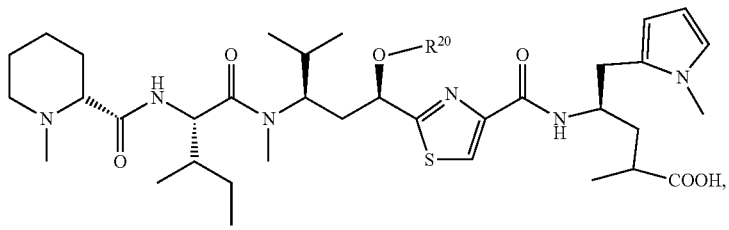
I-60
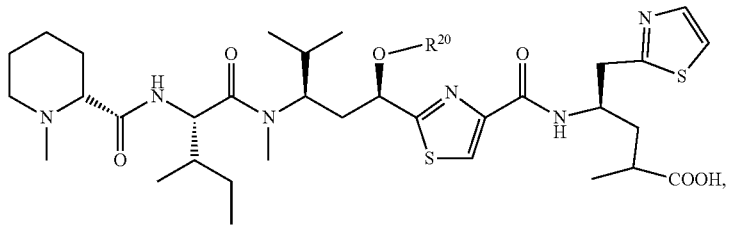
I-61
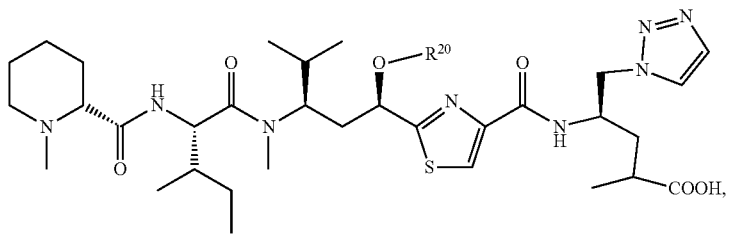
I-62
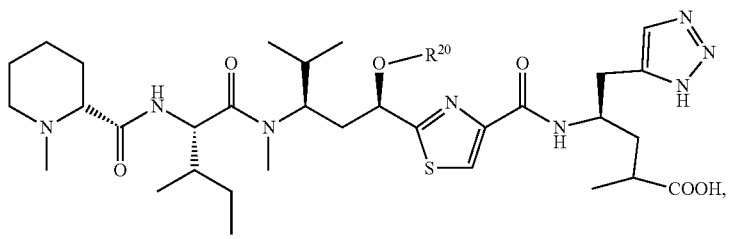
I-63
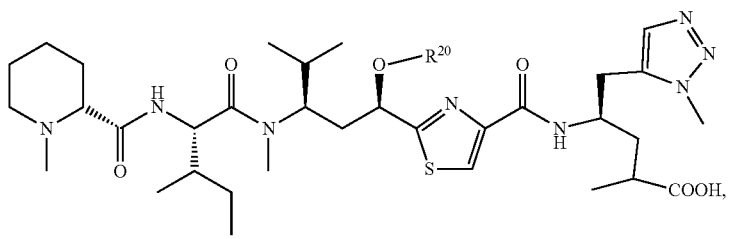
I-64

I-65
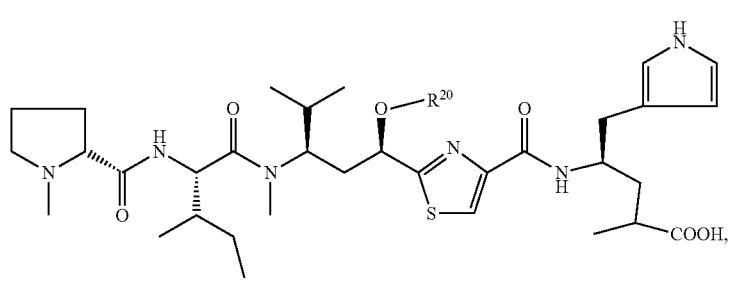
I-66
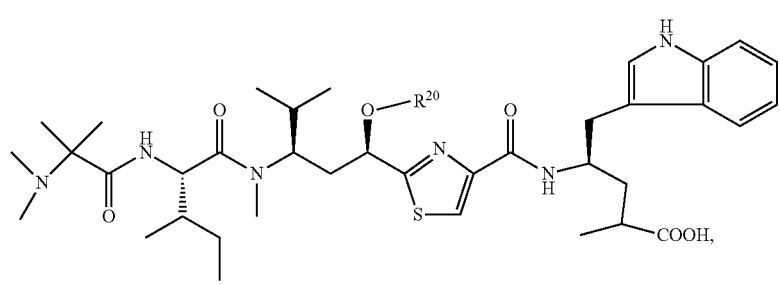
I-67
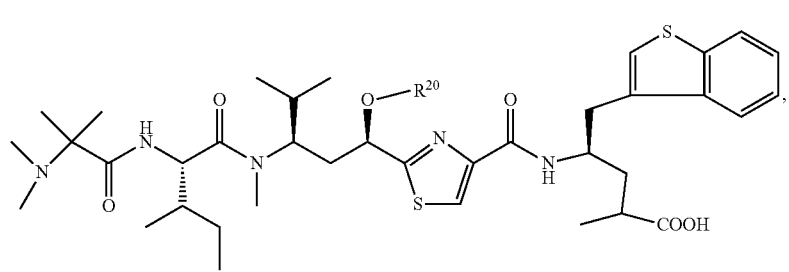
I-68
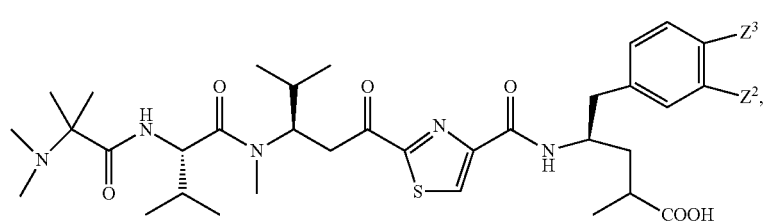
I-69
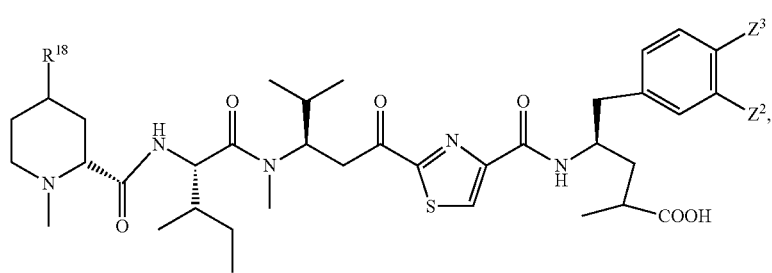
I-70
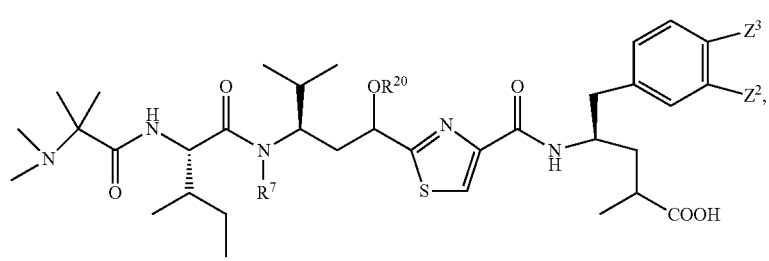

-continued

I-71
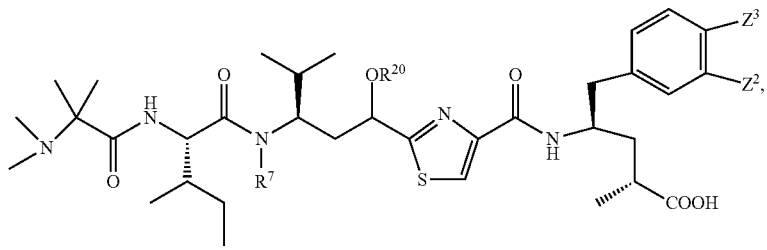

I-72
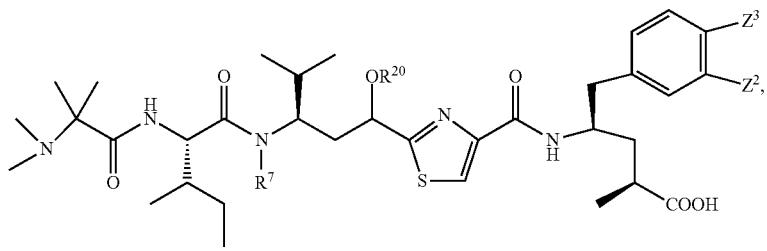

I-73
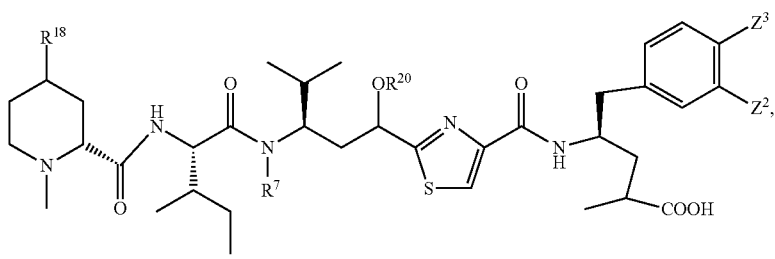

I-74
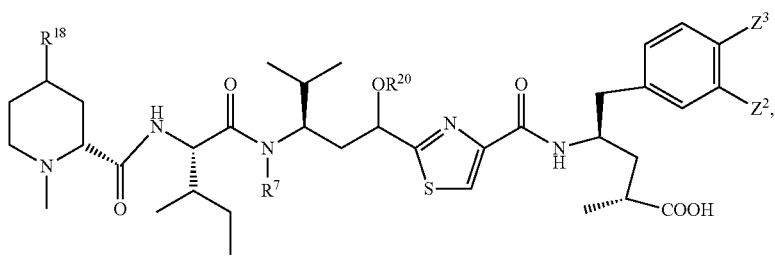

I-75
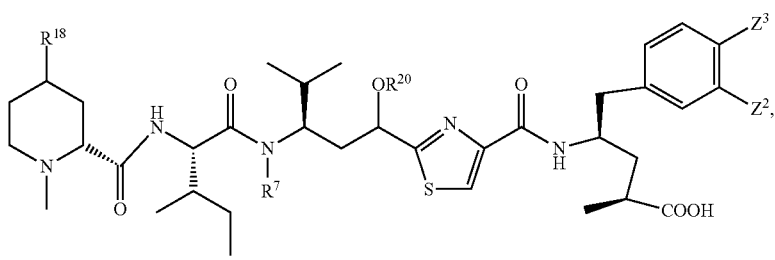

or their pharmaceutically acceptable salts, hydrates, or hydrated salts; or the polymorphic crystalline structures of these compounds; or their optical isomers, racemates, diastereomers or enantiomers; wherein $R^{20}$ is H; $C_1$-$C_8$ linear or branched alkyl or heteroalkyl; $C_2$-$C_8$ linear or branched alkenyl, alkynyl, alkylcycloalkyl, or heterocycloalkyl; $C_3$-$C_8$ linear or branched aryl, Ar-alkyl, heterocyclic, carbocyclic, cycloalkyl, heteroalkylcycloalkyl, alkylcarbonyl, heteroaryl; carbonate (—C(O)O$R^{17}$), or carbamate (—C(O)N$R^{17}R^{18}$); or $C_1$-$C_8$ carboxylate, ester, ether, or amide; or 1~8 amino acids; or polyethyleneoxy unit of formula $(OCH_2CH_2)_p$ or $(OCH_2CH(CH_3))_p$, wherein p is an integer from 0 to about 1000; or $R^{20}$ is absent and the oxygen forms a ketone, or combination above thereof; $Z^3$ and $Z^3$ are independently H, OH, NH$_2$, O, NH, COOH, COO, C(O), C(O), C(O)NH, C(O)NH$_2$, $R^{18}$, OCH$_2$OP(O)(O$R^{18}$)$_2$, OC(O)OP(O)(O$R^{18}$)$_2$, OPO(O$R^{18}$)$_2$, NHPO(O$R^{18}$)$_2$, OP(O)(O$R^{18}$)OP(O)(O$R^{18}$)$_2$, OC(O)$R^{18}$, OC(O)NH$R^{18}$, OSO$_2$(O$R^{18}$), O—(C$_4$-C$_{12}$-glycoside), $C_1$-$C_8$ linear or branched alkyl or heteroalkyl; $C_2$-$C_8$ linear or branched alkenyl, alkynyl, alkylcycloalkyl, or heterocycloalkyl; $C_3$-$C_8$ linear or branched aryl, Ar-alkyl, heterocyclic, carbocyclic, cycloalkyl, heteroalkylcycloalkyl, alkylcarbonyl, heteroaryl; carbonate (—C(O)O$R^{17}$), or carbamate (—C(O)N$R^{17}R^{18}$); $R^{17}$ and $R^{18}$ are independently H, $C_1$-$C_8$ linear or branched alkyl or heteroalkyl; $C_2$-$C_8$ linear or branched alkenyl, alkynyl, alkylcycloalkyl, or heterocycloalkyl; $C_3$-$C_8$ linear or branched aryl, Ar-alkyl, heterocyclic, carbocyclic, cycloalkyl, heteroalkylcycloalkyl, alkylcarbonyl, heteroaryl; carbonate, or carbamate; X is O, S, NH, NHNH, or $CH_2$; $R^7$ and $R^{14}$ are defined the same as in claim 1.

4. The composition according to claim 1, wherein W, $L_1$, $L_2$, $V_1$, and $V_2$ independently is composed of one or more linker components of the following structures:

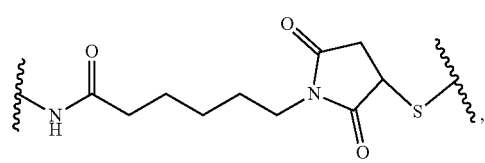

6-maleimidocaproyl (MC)

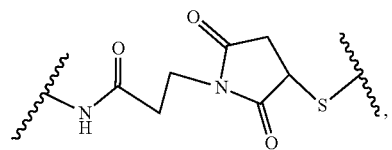

maleimido propanoyl (MP)

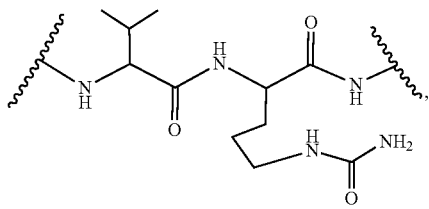

valine-citrulline (val-cit)

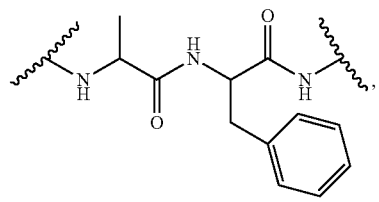

alanine-phenylalanine (ala-phe)

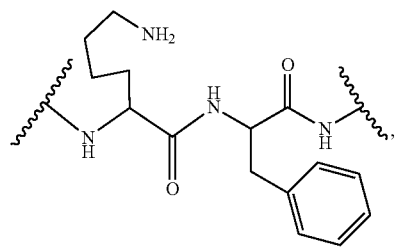

lysine-phenylalanine (lys-phe)

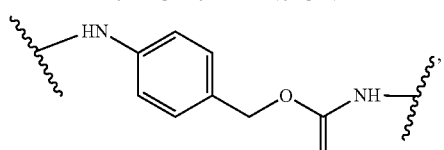

p-aminobenzyloxycarbonyl (PAB)

-continued

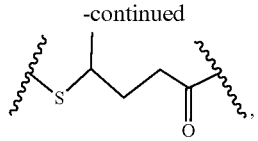

4-thio-pentanoate (SPP)

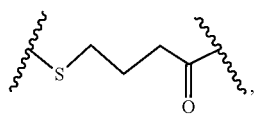

4-thio-butyrate (SPDB)

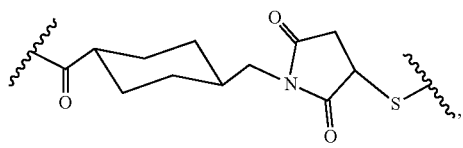

4-(N-malemidomethyl)cyclo-hexane-1-carboxylate (MCC)

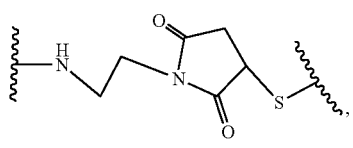

maleimidoethyl (ME)

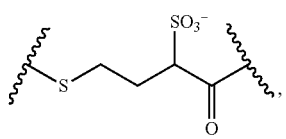

4-thio-2-hydroxysulfonyl-butyrate (2-Sulfo-SPDB)

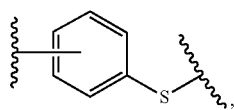

aryl-thiol (PySS)

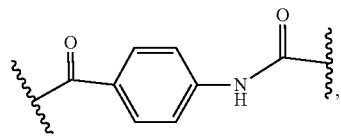

(4-acetyl)aminobenzoate (SIAB)

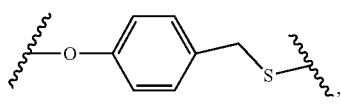

oxylbenzylthio

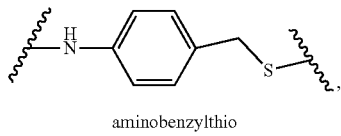

aminobenzylthio

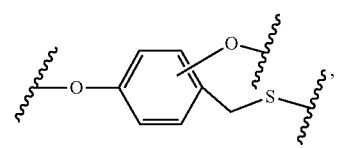

dioxylbenzylthio

431
-continued
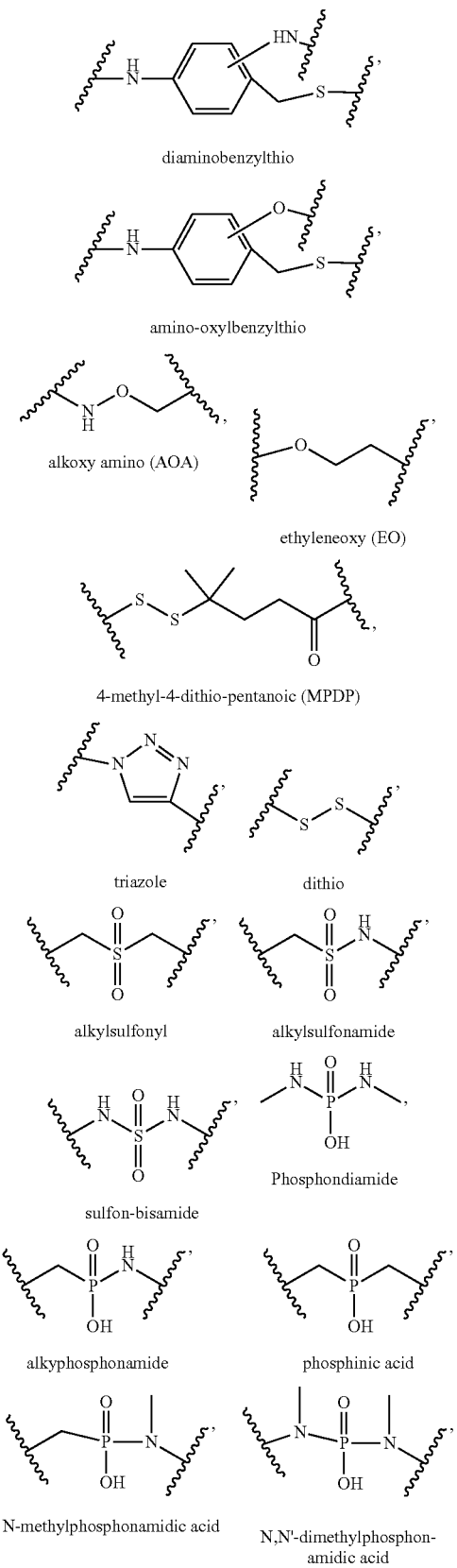
432
-continued
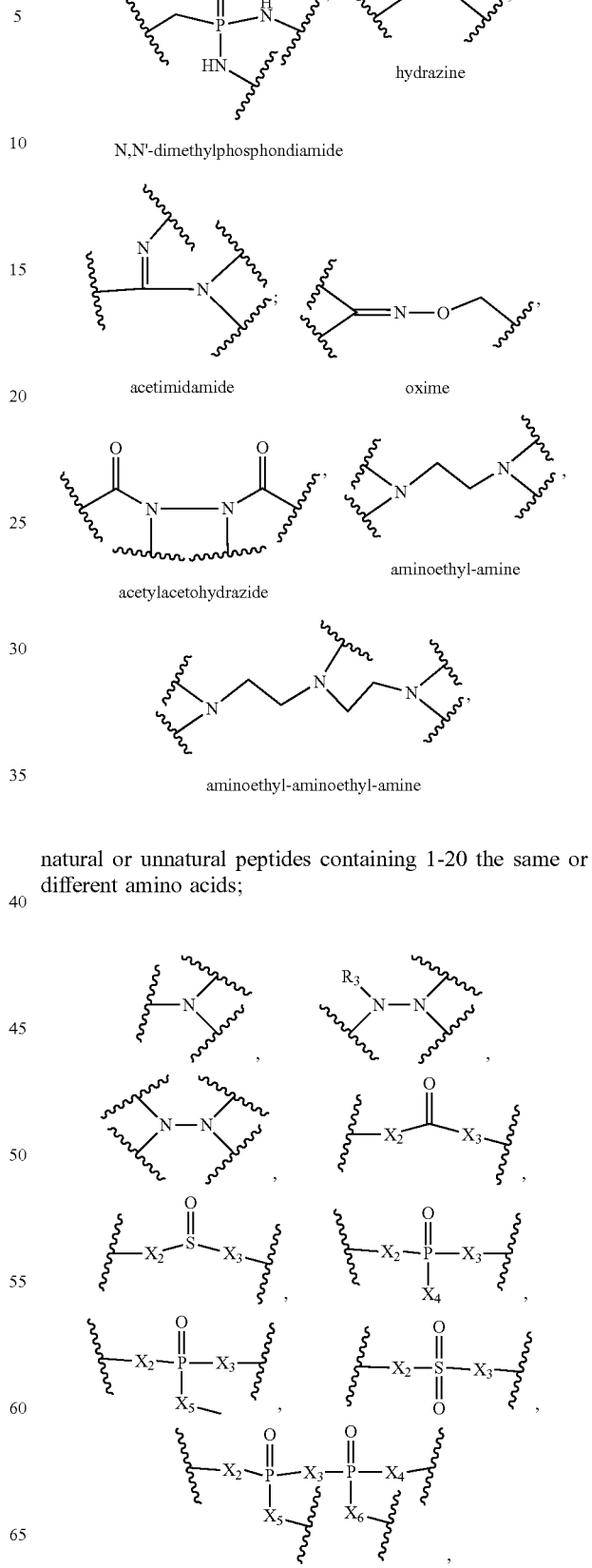
natural or unnatural peptides containing 1-20 the same or different amino acids;

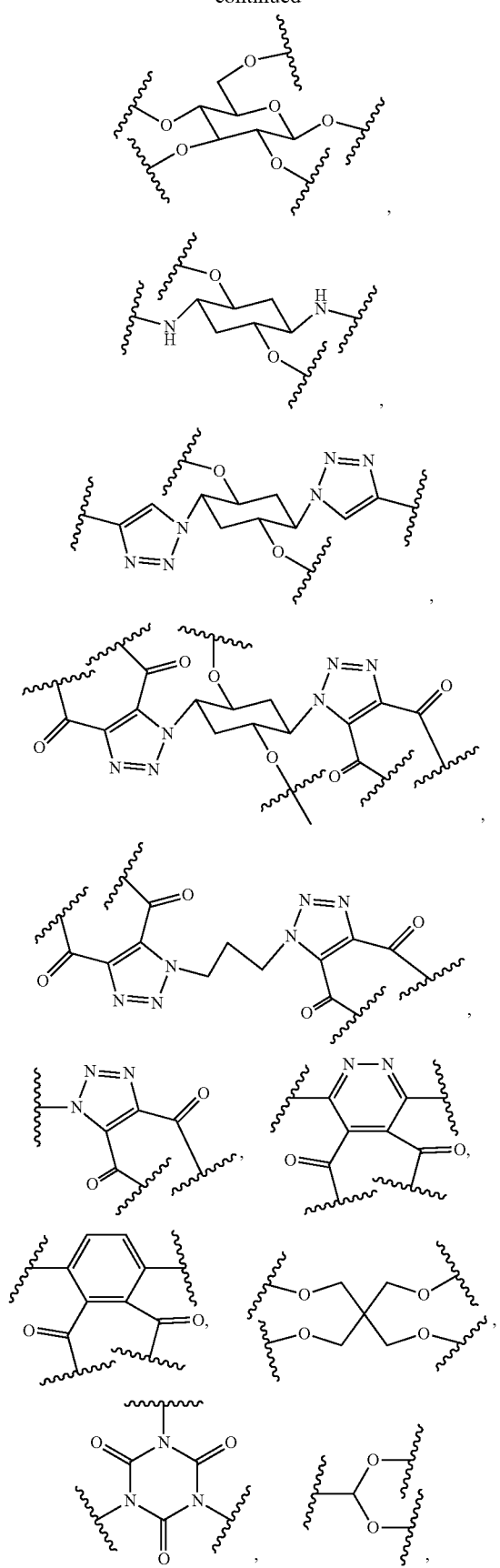
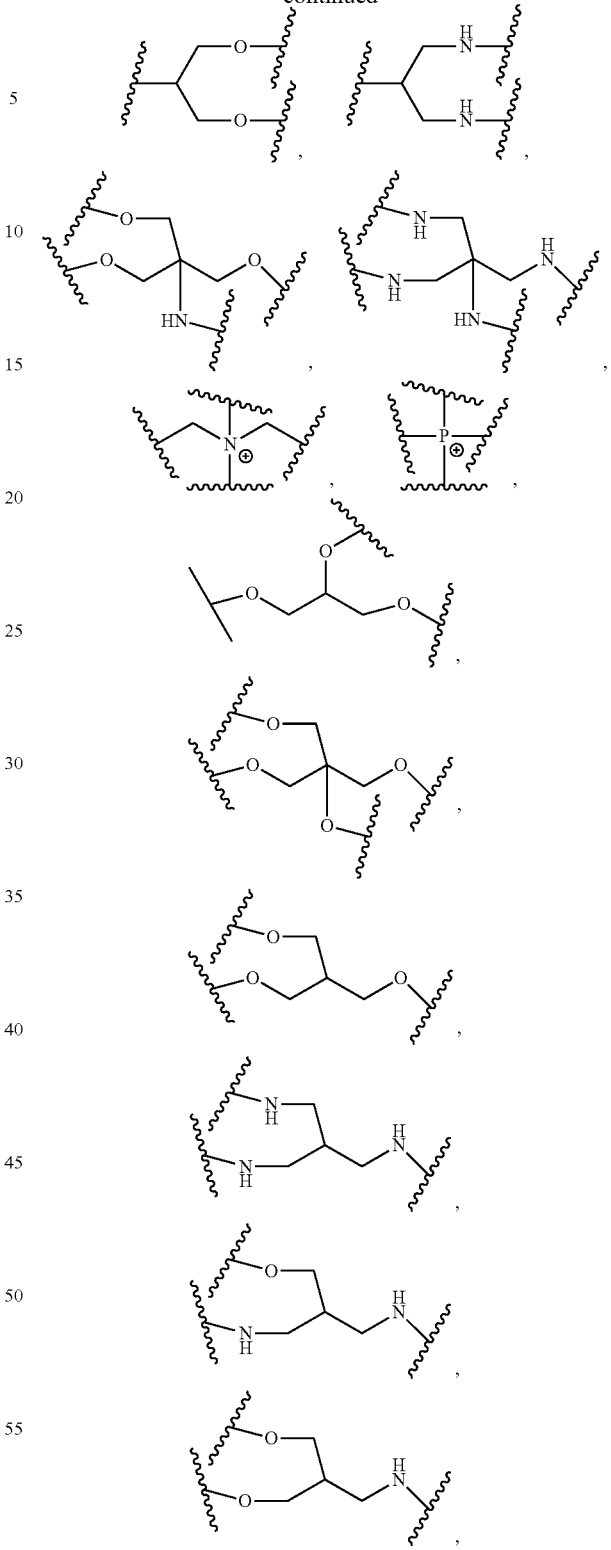
wherein ⌇ is the site of linkage; $X_2$, $X_3$, $X_4$, $X_5$, or $X_6$, are independently selected from NH; NHNH; N($R_3$); N($R_3$)N ($R_3$); O; S; $C_1$-$C_6$ alkyl; $C_2$-$C_6$ heteroalkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; or 1-8 amino acids; wherein $R_3$ and $R_{3'}$ are independently H; $C_1$-$C_8$ alkyl; $C_2$-$C_8$ hetero-alkyl, alkylcycloalkyl, or heterocycloalkyl; $C_3$-$C_8$ aryl, Ar-alkyl, heterocyclic, carbocyclic, cycloalkyl, heteroalkylcycloalkyl, alkylcarbonyl, or heteroaryl; or $C_1$-$C_8$ ester, ether, or amide; or polyethyleneoxy unit of formula $(OCH_2CH_2)_p$ or $(OCH_2CH(CH_3))_p$, wherein p is an integer from 0 to about 1000, or any combination thereof.

5. The composition according to claim 1, wherein W, $L_1$, $L_2$, $V_1$, and $V_2$ independently is composed of:

(A): a self-immolative component, peptidic unit, a hydrazone bond, a disulfide, an ester, an oxime, an amide, or a thioether bond the self-immolative unit including aromatic compounds that are electronically similar to the para-aminobenzyl-carbamoyl (PAB) groups, 2-aminoimidazol-5-methanol derivatives, heterocyclic PAB analogs, beta-glucuronide, and ortho or para-aminobenzylacetals; or one of the following structures:

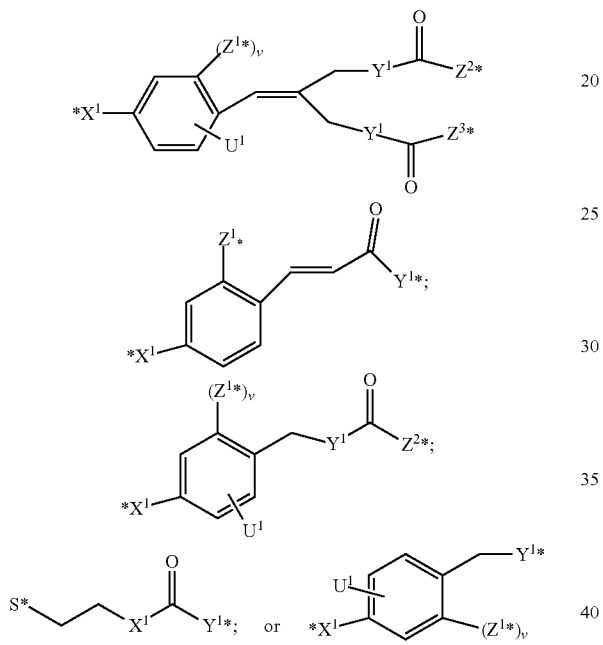

wherein the (*) atom is the point of attachment of another component; $X^1$, $Y^1$, $Z^2$ and $Z^3$ are independently NH, O, or S; $Z^1$ is independently H, $NHR_1$, $OR_1$, $SR_1$, or $COX_1R_1$, wherein $X_1$ and $R_1$ are defined above; v is 0 or 1; $U^1$ is independently H, OH, $C_1$~$C_6$ alkyl, $(OCH_2CH_2)_n$, F, Cl, Br, I, $OR_5$, $SR_5$, $NR_5R_5'$, $N=NR_5$, $N=R_5$, $NR_5R_5'$, $NO_2$, $SOR_5R_5'$, $SO_2R_5$, $SO_3R_5$, $OSO_3R_5$, $PR_5R_5'$, $POR_5R_5'$, $PO_2R_5R_5'$, $OPO(OR_5)(OR_5')$, or $OCH_2PO(OR_5(OR_5'))$, wherein $R_5$ and $R_5'$ are independently selected from H, $C_1$~$C_8$ alkyl; $C_2$~$C_8$ alkenyl, alkynyl, heteroalkyl, or amino acid; $C_3$~$C_8$ aryl, heterocyclic, carbocyclic, cycloalkyl, heterocycloalkyl, heteroaralkyl, alkylcarbonyl, or glycoside; or pharmaceutical cation salts;

(B): a non-self-immolative linker component containing one of the following structures:

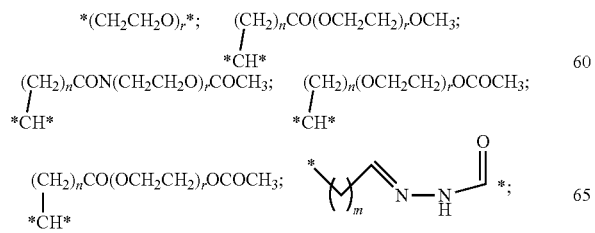

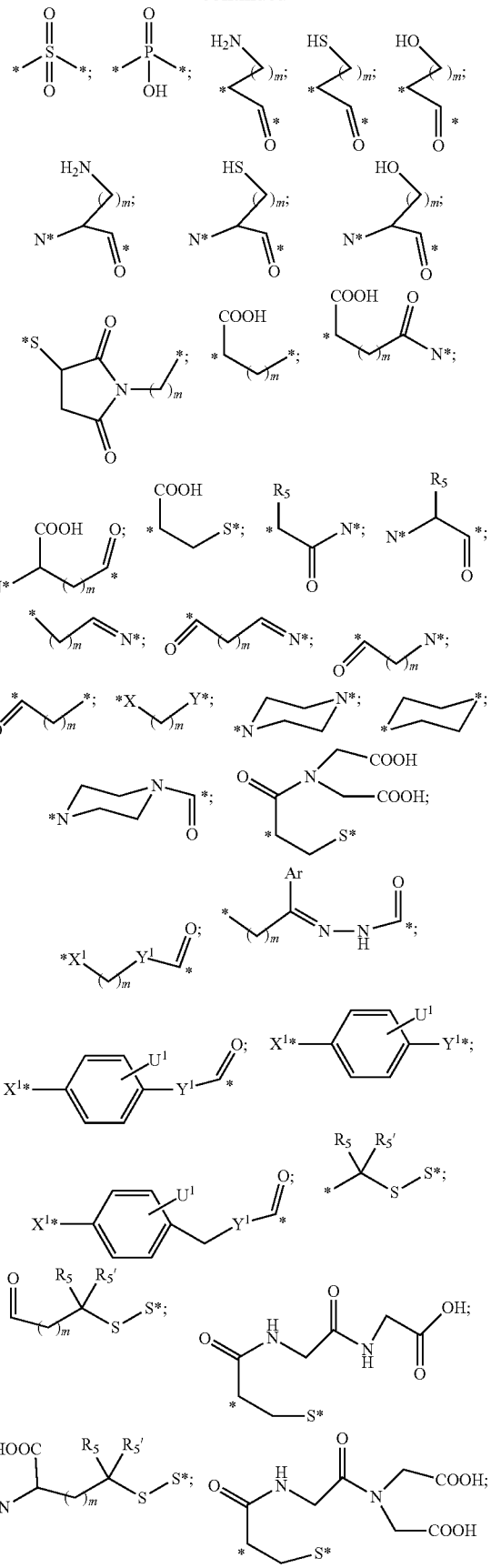

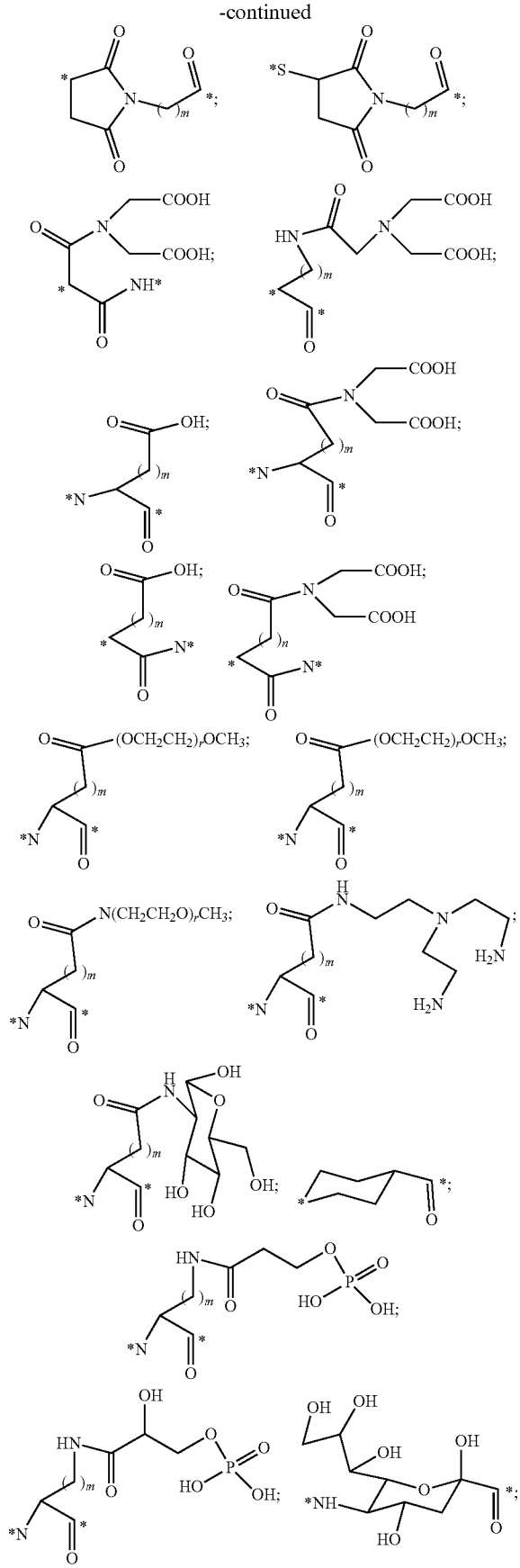

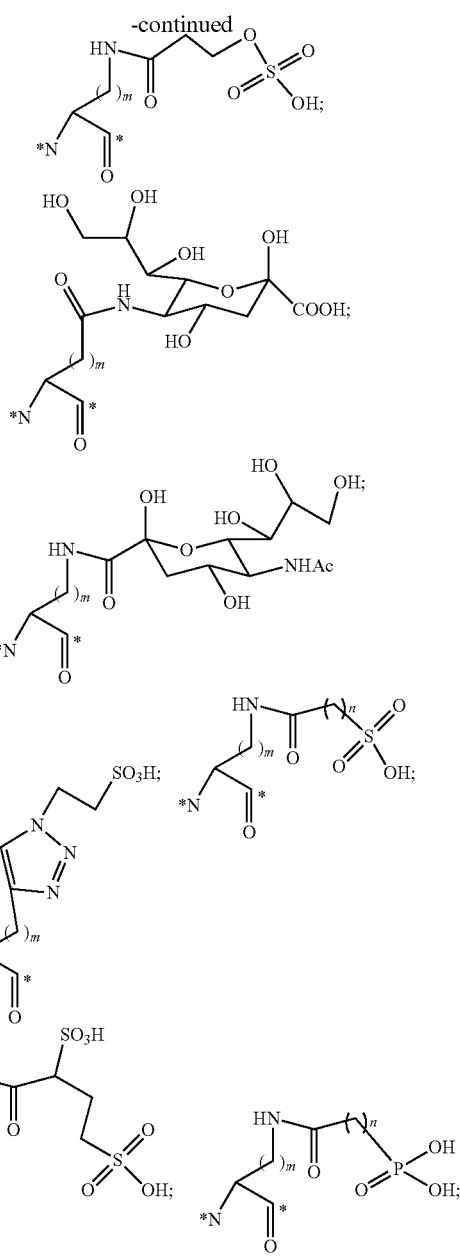

wherein the (*) atom is the site of attachment. $X^1$, $Y^1$, $U^1$, $R_5$, $R_5'$ are defined as above; r is 0~100; m and n are 0~20 independently;

(C): a releasable component that at least one bond that can be broken under physiological conditions: a pH-labile, acid-labile, base-labile, oxidatively labile, metabolically labile, biochemically labile or enzyme-labile bond, which having one of the following structures:
—$(CR_5R_6)_m(Aa)_r(CR_7R_8)_n(OCH_2CH_2)_t$—,
—$(CR_5R_6)_m(CR_7R_8)_n(Aa)_r(OCH_2CH_2)_t$—, -$(Aa)_r$-$(CR_5R_6)_m(CR_7R_8)_n(OCH_2CH_2)_t$—, —$(CR_5R_6)_m(CR_7R_8)_n(OCH_2CH_2)_r(Aa)_t$-, —$(CR_5R_6)_m$—$(CR_7=CR_8)(CR_9R_{10})_n(Aa)_t(OCH_2CH_2)_r$—,
—$(CR_5R_6)_m(NR_{11}CO)(Aa)_t(CR_9R_{10})_n$—$(OCH_2CH_2)_r$—, —$(CR_5R_6)_m(Aa)_t(NR_{11}CO)(CR_9R_{10})_n$ $(OCH_2CH_2)_r$—,—$(CR_5R_6)_m(OCO)(Aa)_t(CR_9R_{10})_n$—$(OCH_2CH_2)_r$—, —$(CR_5R_6)_m(OCNR_7)(Aa)_t(CR_9R_{10})_n$ $(OCH_2CH_2)_r$—, —$(CR_5R_6)_m(CO)(Aa)_t$-$(CR_9R_{10})_n$ —(OCH₂CH₂)ᵣ—, —(CR₉R₁₀)ₙ(OCH₂CH₂)ᵣ—, —(CR₉R₁₀)ₙ—(OCH₂CH₂)ᵣ—, (Aa)ₜ(CR₉R₁₀)ₙ(OCH₂CH₂)ᵣ—, (CO)(Aa)ₜ(CR₉R₁₀)ₙ—(OCH₂CH₂)ᵣ—, -phenyl-CO(Aa)ₜ(CR₇R₈)ₙ—, —(CR₅R₆)ₘ-oxazolyl-CO(Aa)ₜ(CR₇R₈)ₙ—, —(CR₅R₆)ₘ-thiazolyl-CO(Aa)ₜ(CCR₇R₈)ₙ—, —(CR₅R₆)ₜ-imidazolyl-CO—(CR₇R₈)ₙ—, —(CR₅R₆)ₜ-morpholino-CO(Aa)ₜ-(CR₇R₈)ₙ—, —(CR₅R₆)ₜ-piperazino-CO(Aa)ₜ-(CR₇R₈)ₙ—, —(CR₅R₆)ₜ-N-methylpiperazin-CO(Aa)ₜ-(CR₇R₈)ₙ—, —(CR₅R)ₘ-(Aa)ₜphenyl-, —(CR₅R₆)ₘ-(Aa)ₜfuryl-, —(CR₅R₆)ₘ-oxazolyl(Aa)ₜ-, —(CR₅R₆)ₘ-thiazolyl(Aa)ₜ-, —(CR₅R₆)ₘ-thienyl-(Aa)ₜ-, —(CR₅R₆)ₘ-imidazolyl(Aa)ₜ-, —(CR₅R₆)ₘ-morpholino-(Aa)ₜ-, —(CR₅R₆)ₘ-piperazino-(Aa)ₜ-, —(CR₅R₆)ₘ—N-methylpiperazino-(Aa)ₜ-, —K(CR₅R₆)ₘ(Aa)r(CR₇R₈)ₙ(OCH₂CH₂)ₜ—, —K(CR₅R₆)ₘ(CR₇R₈)ₙ-(Aa)ₜ(OCH₂CH₂)ₜ—, —K(Aa)ᵣ-(CR₅R₆)ₘ(CR₇R₈)ₙ(OCH₂CH₂)ₜ—, —K(CR₅R₆)ₘ—(CR₇R₈)ₙ(OCH₂—CH₂)ᵣ(Aa)ₜ-, —K(CR₅R₆)ₘ—(CR₇=CR₈)(CR₉R₁₀)ₙ(Aa)ₜ(OCH₂CH₂)ᵣ—, R₅R₆)ₘ—(NR₁₁CO—)(Aa)ₜ(CR₉R₁₀)ₙ (OCH₂CH₂)ᵣ—, —K(CR₅R₆)ₘ(Aa)ₜ(NR₁₁CO)(CR₉R₁₀)ₙ(OCH₂CH₂)ᵣ—, —K(CR₅R₆)ₘ(OCO)(Aa)t(CR₉R₁₀)ₙ—(OCH₂CH₂)ᵣ—, —K(CR₅R₆)ₘ(OCNR₇)(Aa)ₜ(CR₉R₁₀)ₙ—(OCH₂CH₂)ᵣ—, —K(CR₅R₆)ₘ(CO)(Aa)ₜ-(CR₉R₁₀)ₙ(OCH₂CH₂)ᵣ—, —K(CR₅R₆)ₘ(NR₁₁CO)(Aa)ₜ-(CR₉R₁₀)ₙ(OCH₂CH₂)ᵣ—, —K(CR₅R₆)ₘ—(OCO)(Aa)ₜ(CR₉R₁₀)ₙ(OCH₂CH₂)ᵣ—, —K(CR₅R₆)ₘ—(OCNR₇)(Aa)ₜ(CR₉R₁₀)ₙ(OCH₂CH₂)ᵣ—, —K—(CR₅R₆)ₘ(CO)(Aa)ₜ(CR₉R₁₀)ₙ(OCH₂CH₂)ᵣ—, —K(CR₅R₆)ₘ-phenyl-CO(Aa)ₜ(CR₇R₈)ₙ—, —K—(CR₅R₆)ₘ-furyl-CO(Aa)ₜ-(CR₇R₈)ₙ—, —K(CR₅R₆)ₘ-oxazolyl-CO(Aa)ₜ-(CR₇R₈)ₙ—, —K(CR₅R₆)ₘ-thiazolyl-CO(Aa)ₜ-(CR₇R₈)ₙ—, —K(CR₅R₆)ₜ-thienyl-CO(CR₇R₈)ₙ—, —K(CR₅R₆)ₜimidazolyl-CO—(CR₇R₈)ₙ—, —K(CR₅R₆)ₜ-morpholino-CO-(Aa)ₜ(CR₇R₈)ₙ—, —K(CR₅R₆)ₜ-piperazino-CO(Aa)ₜ-(CR₇R₈)ₙ—, —K(CR₅R₆)ₜ—N-methylpiperazin-CO(Aa)ₜ(CR₇R₈)ₙ—, —K(CR₅R)ₘ—(Aa)ₜphenyl, —K—(CR₅R₆)ₘ-(Aa)ₜfuryl-, —K(CR₅R₆)ₘ-oxazolyl(Aa)ₜ-, —K(CR₅R₆)ₘ-thiazolyl(Aa)ₜ-, —K(CR₅R₆)ₘ-thienyl-(Aa)ₜ-, —K(CR₅R₆)ₘ-imidazolyl(Aa)ₜ-, —K(CR₅R₆)ₘ-morpholino(Aa)ₜ-, —K(CR₅R₆)ₘ-piperazino-(Aa)ₜ-, —K(CR₅R₆)ₘ—N-methylpiperazino(Aa)ₜ-; wherein m, Aa, m, and n are described above; t and r are 0-100 independently; $R_3$, $R_4$, $R_5$, $R_6$, $R_7$, and $R_8$ are independently chosen from H; halide; $C_1$~$C_8$ alkyl; $C_2$~$C_8$ aryl, alkenyl, alkynyl, ether, ester, amine or amide, which is optionally substituted by one or more halide, CN, $NR_1R_2$, $CF_3$, OR, Aryl, heterocycle, $S(O)R_1$, $SO_2R_1$, —$CO_2H$, —$SO_3H$, —$OR_1$, —$CO_2R_1$, —$CONR_1$, —$PO_2R_1R_2$, —$PO_3H$ or $P(O)R_1R_2R_3$; K is $NR_1$, —SS—, —C(=O)—, —C(=O)NH—, —C(=O)O—, —C=NH—O—, —C=N—NH—, —C(=O)NH—NH—, O, S, Se, B, Het (heterocyclic or heteroaromatic ring having $C_3$-$C_8$), or a peptide containing 1-20 amino acids.

6. The composition according to claim 1, wherein the conjugate compound of Formula (I) has one of the following structures of a-01 to a-100:

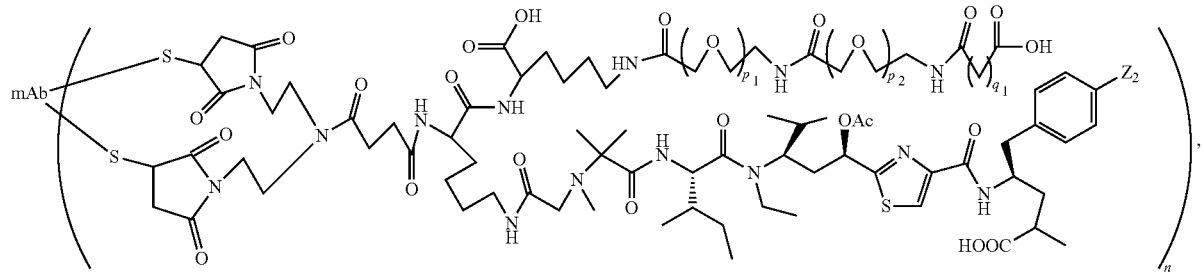

a-01

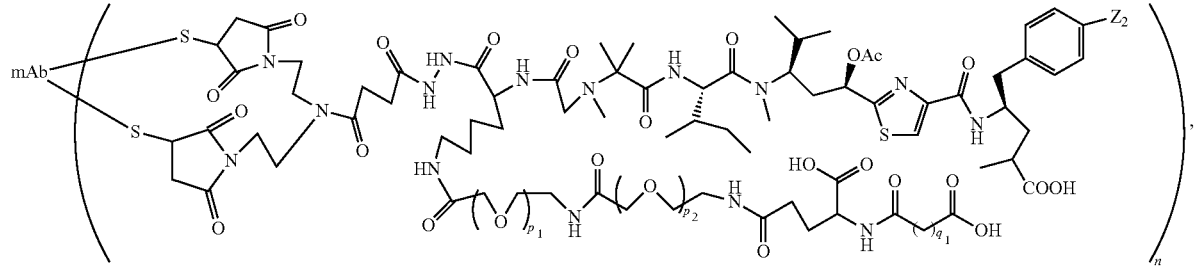

a-02

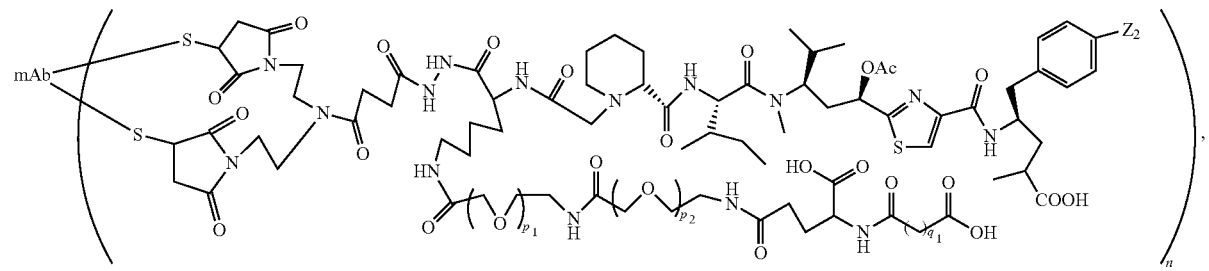
a-03
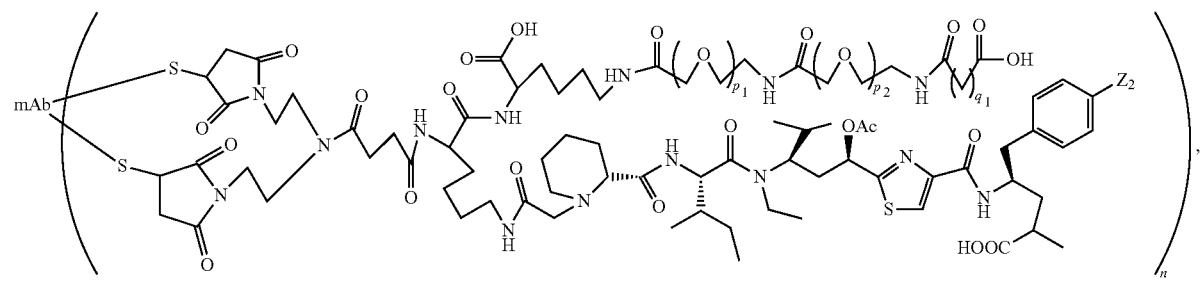
a-04
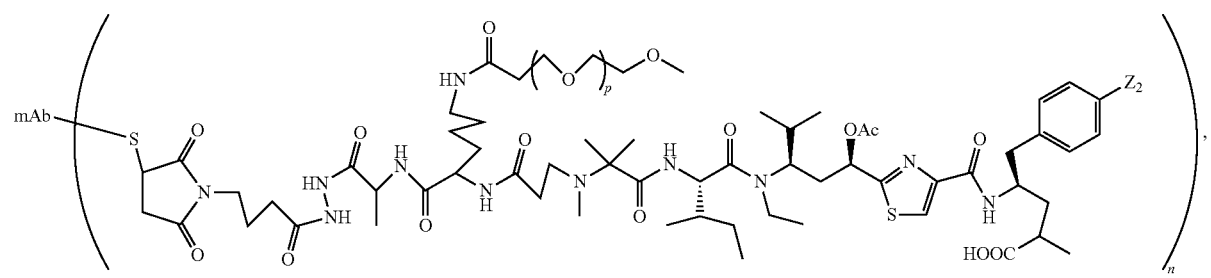
a-05
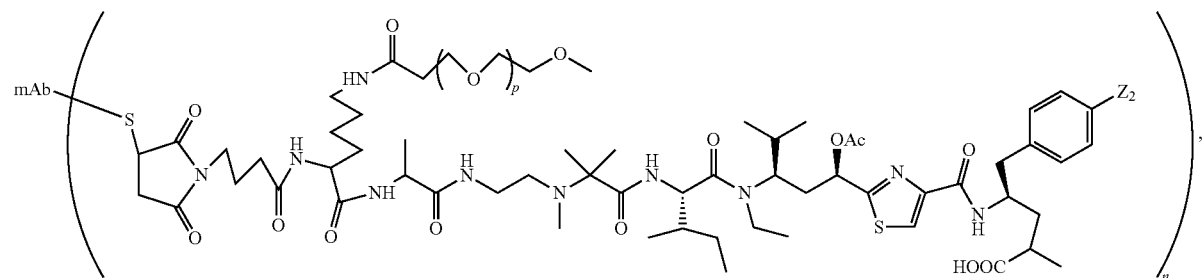
a-06
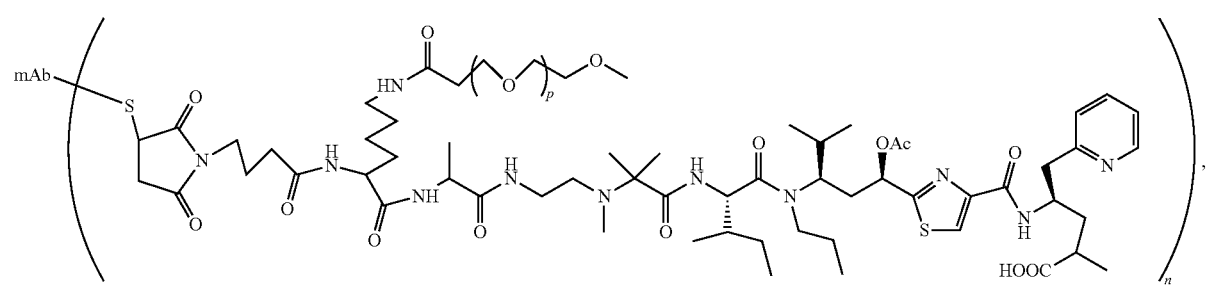
a-07

-continued
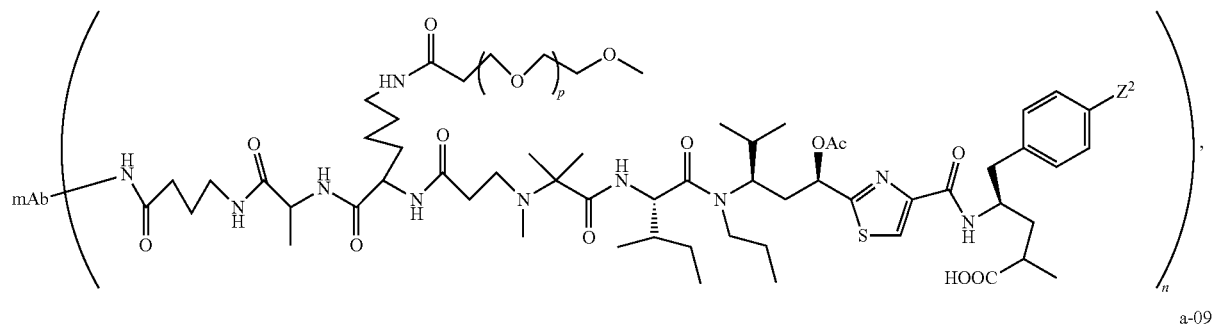
a-08
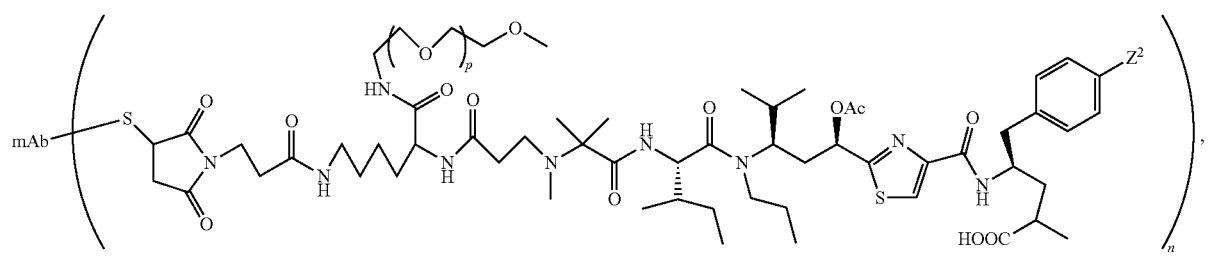
a-09
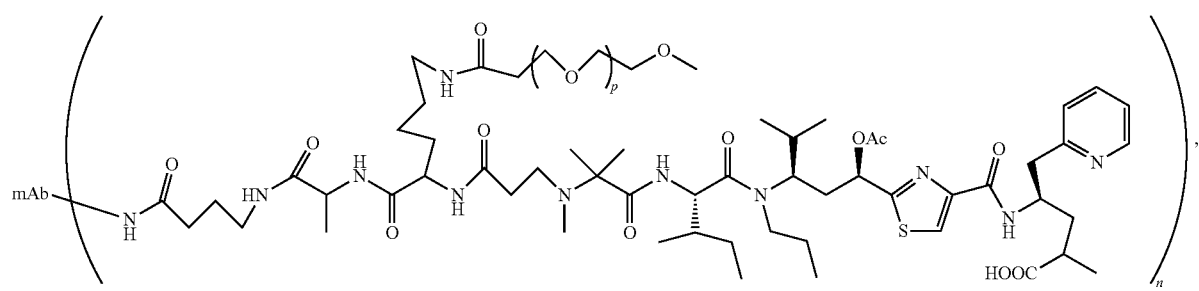
a-10
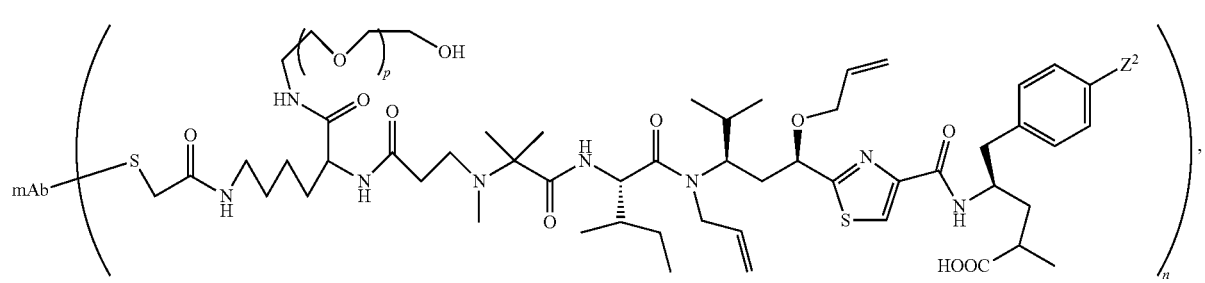
a-11
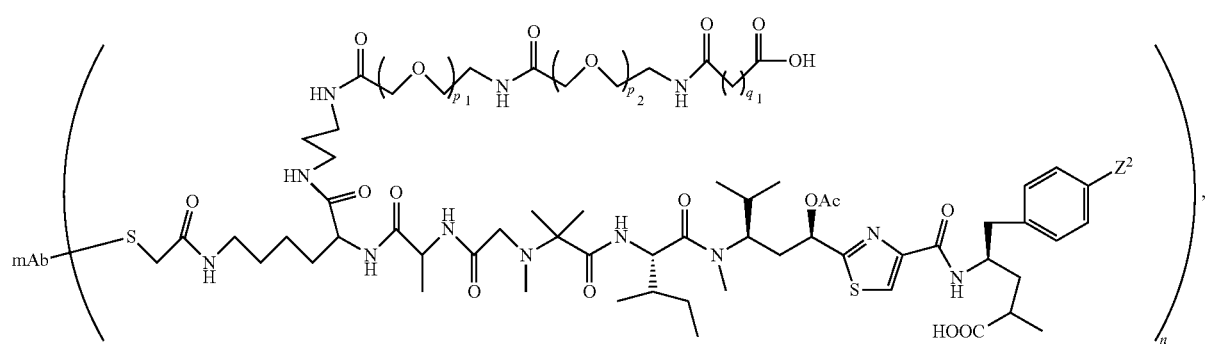
a-12

-continued
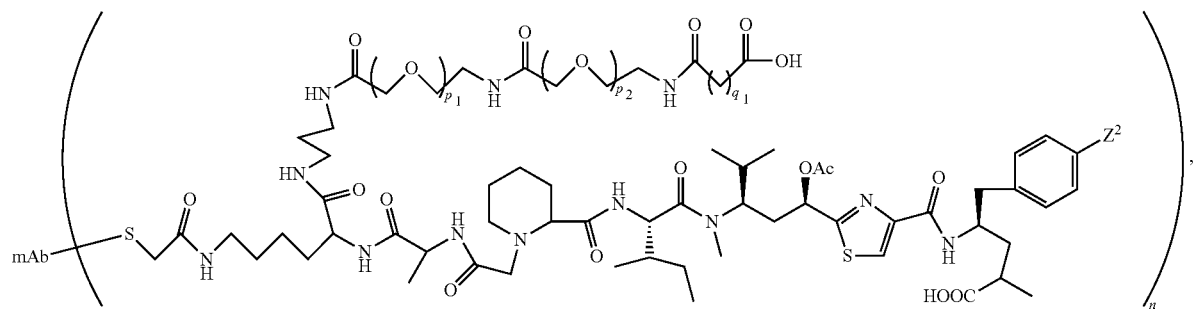
a-13
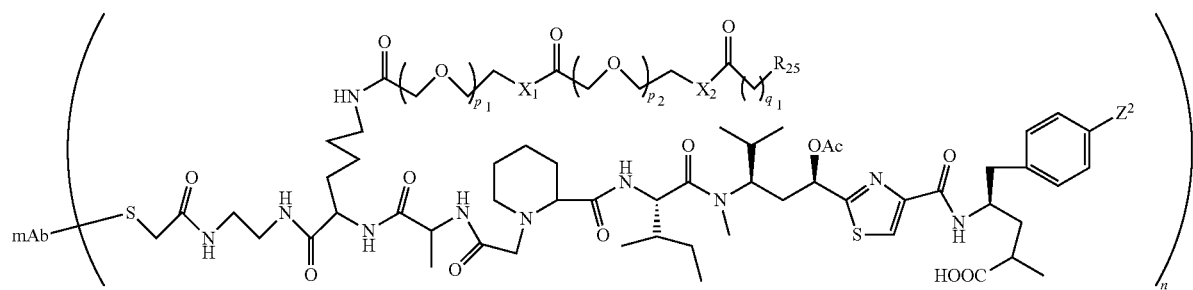
a-14
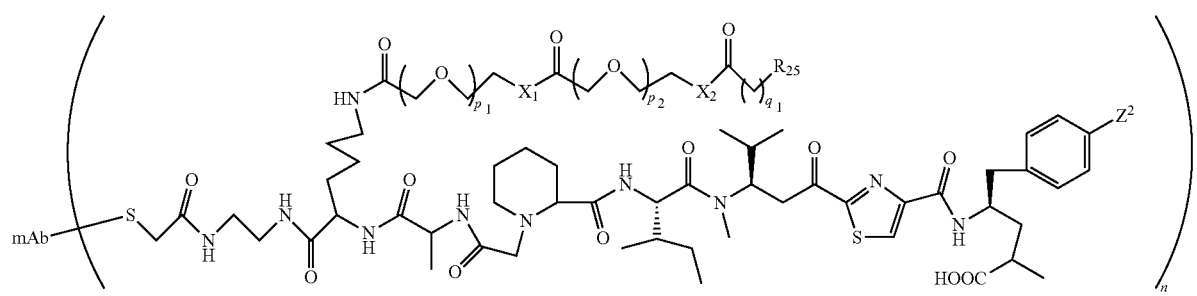
a-15
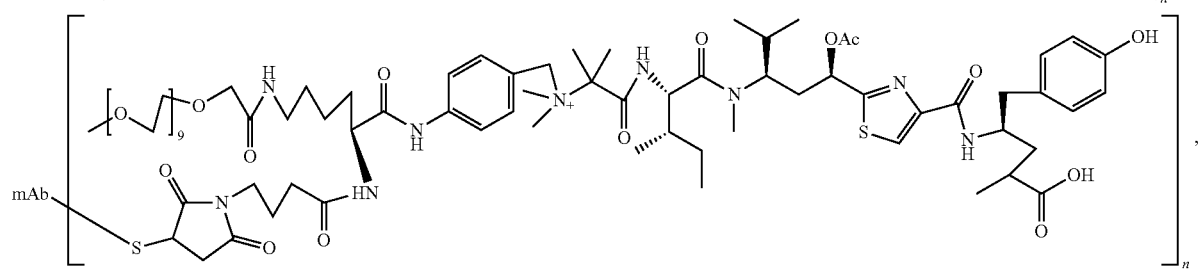
a-16
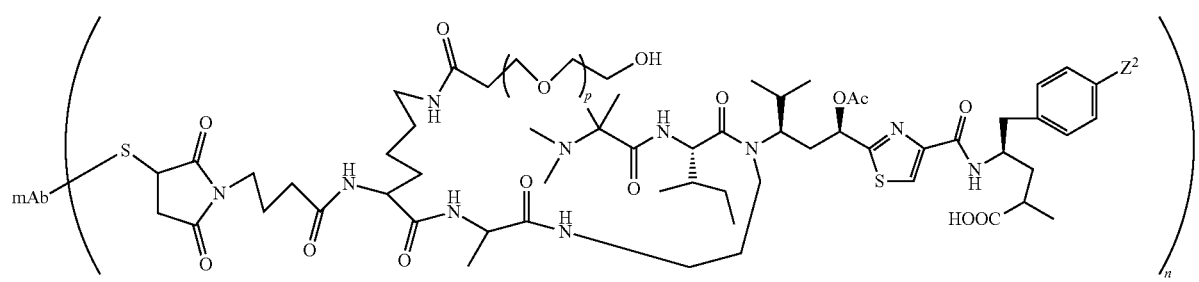
a-17 a-18
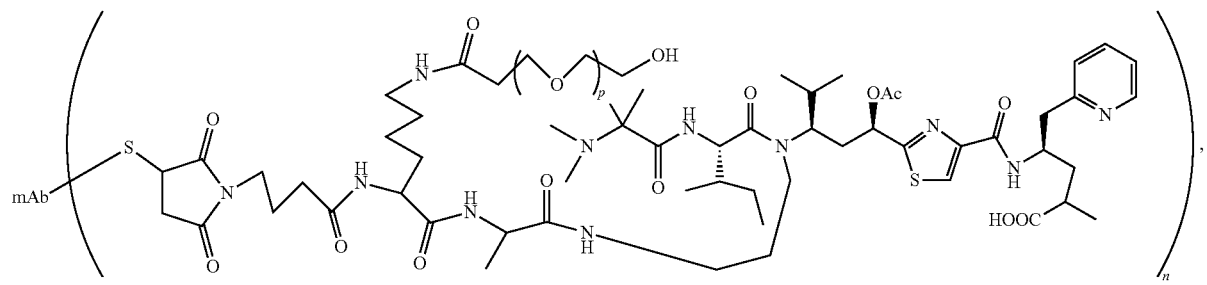
a-19
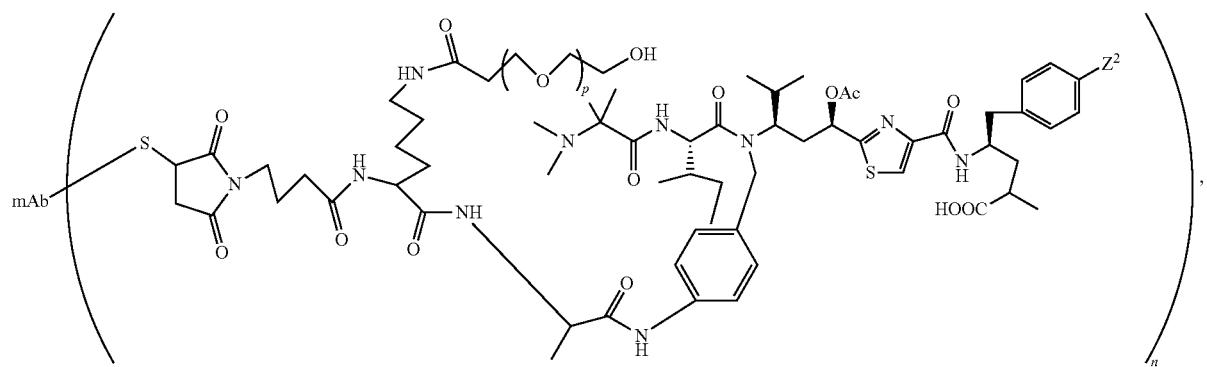
a-20
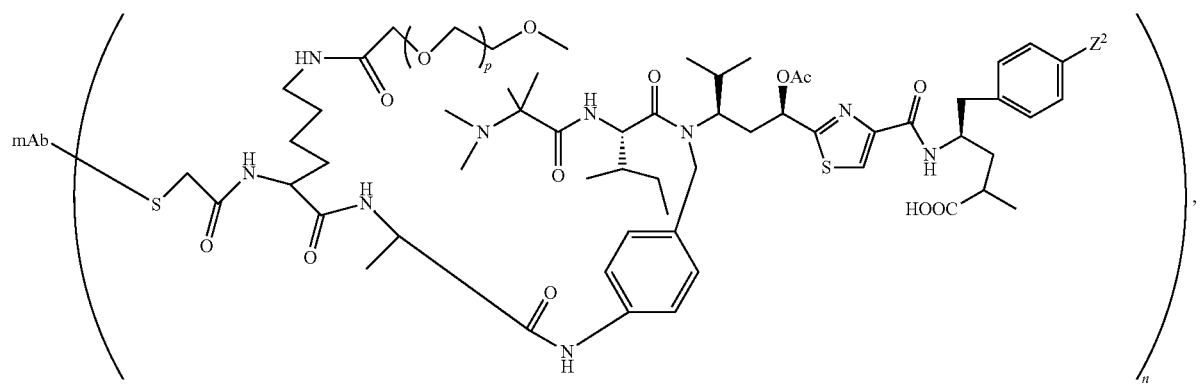
a-21
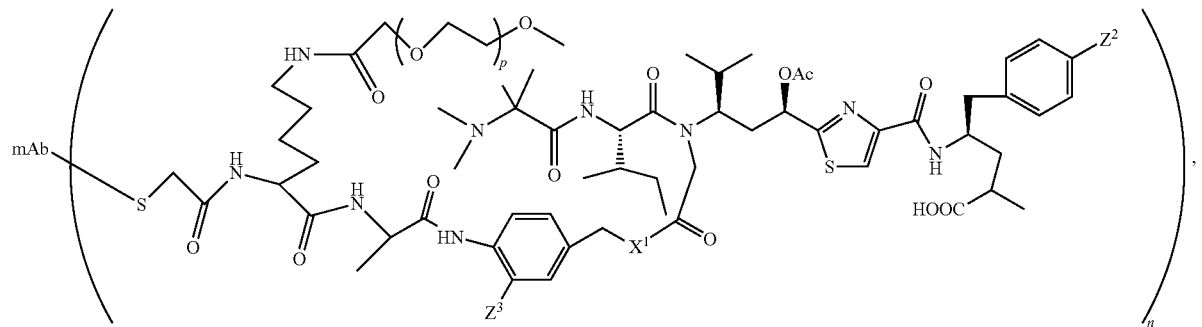

a-22
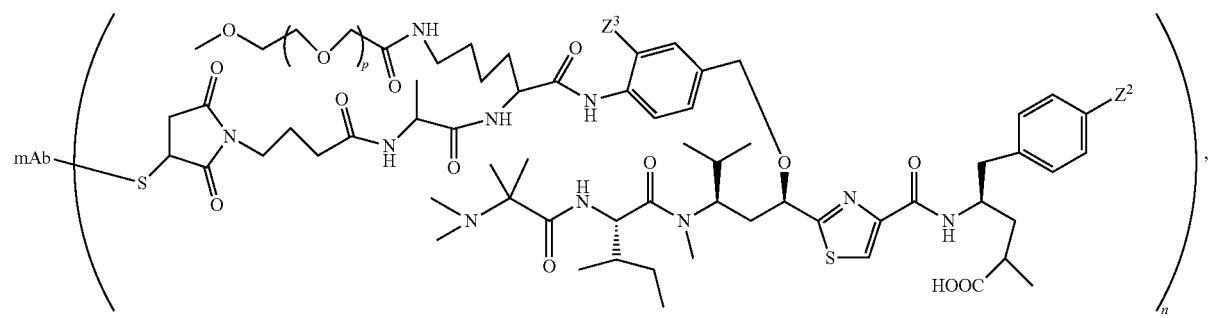
a-23
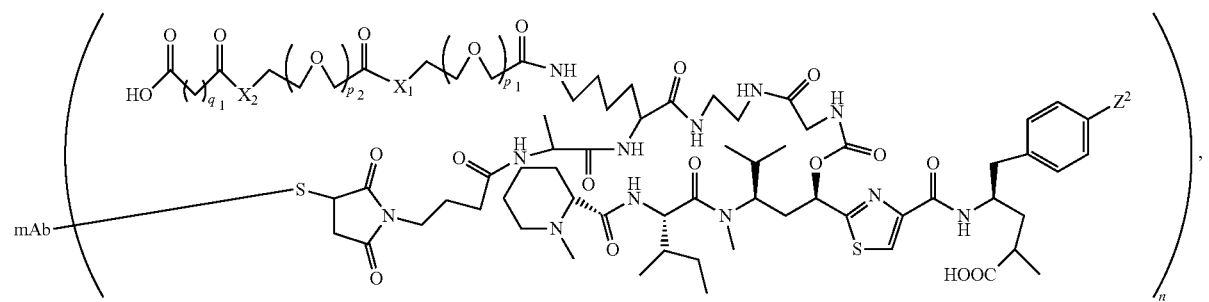
a-24
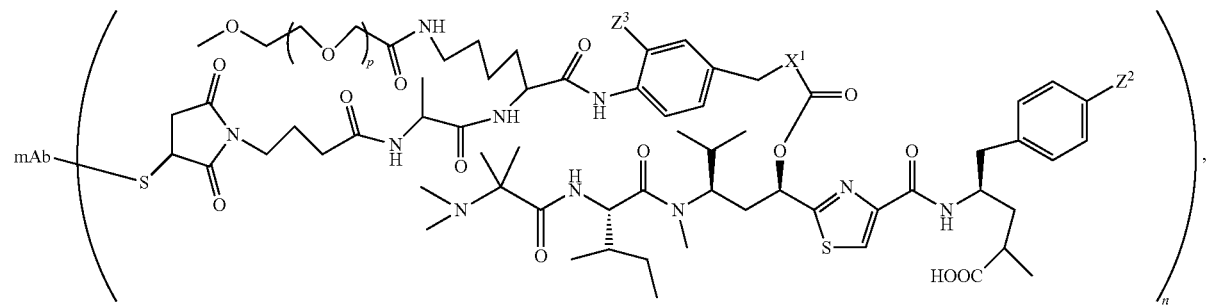
a-25
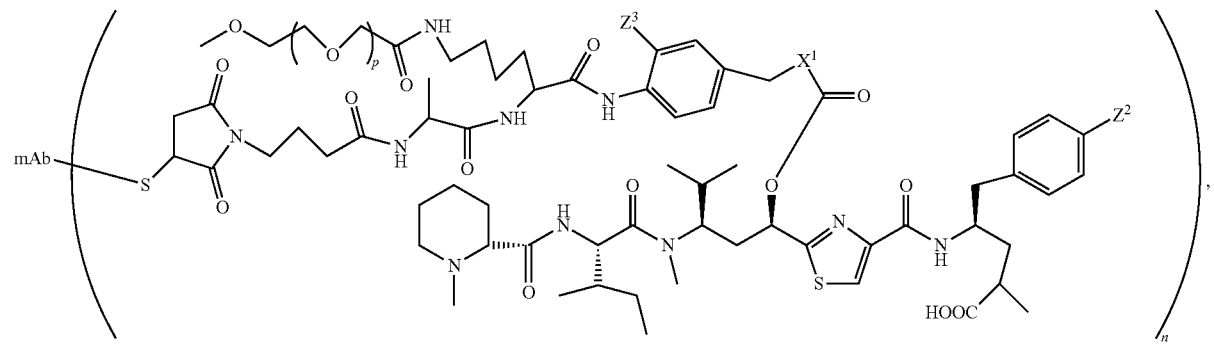

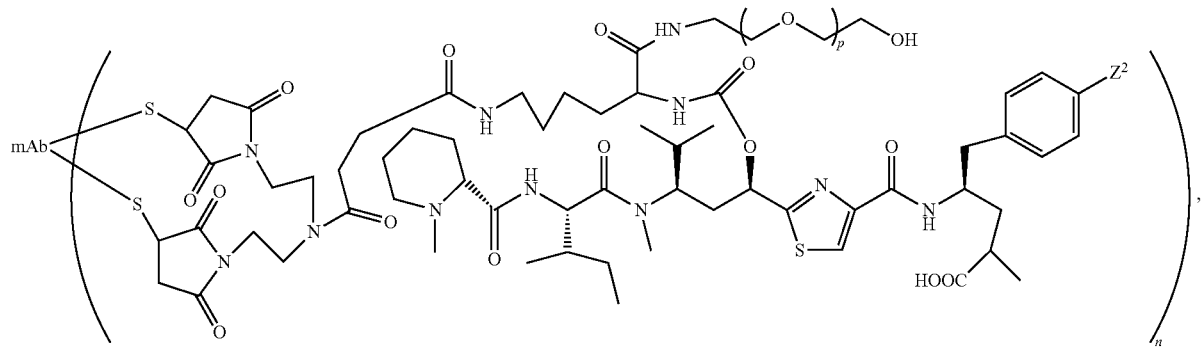
a-26
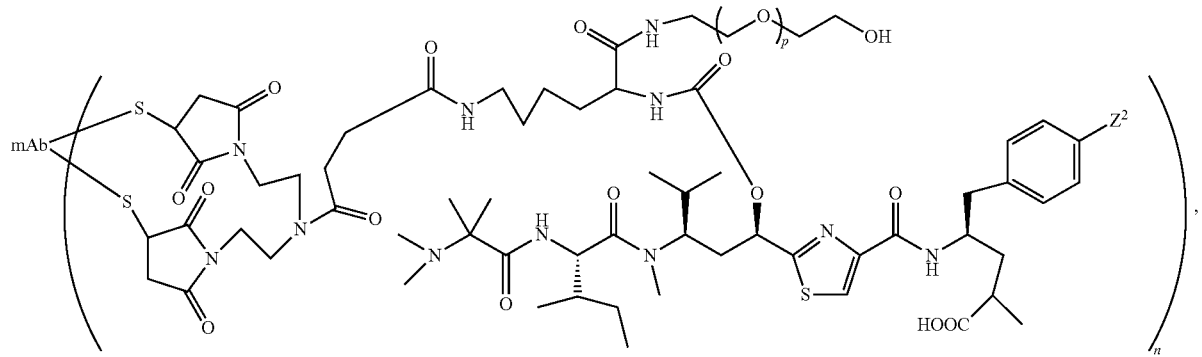
a-27
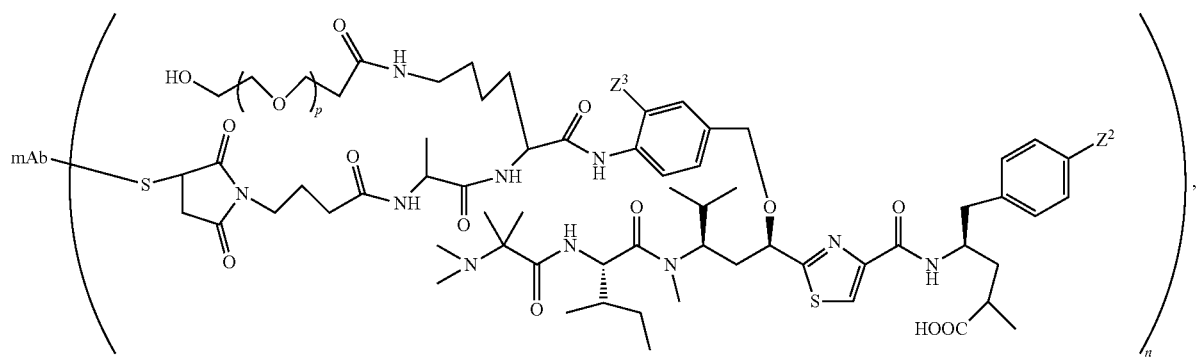
a-28
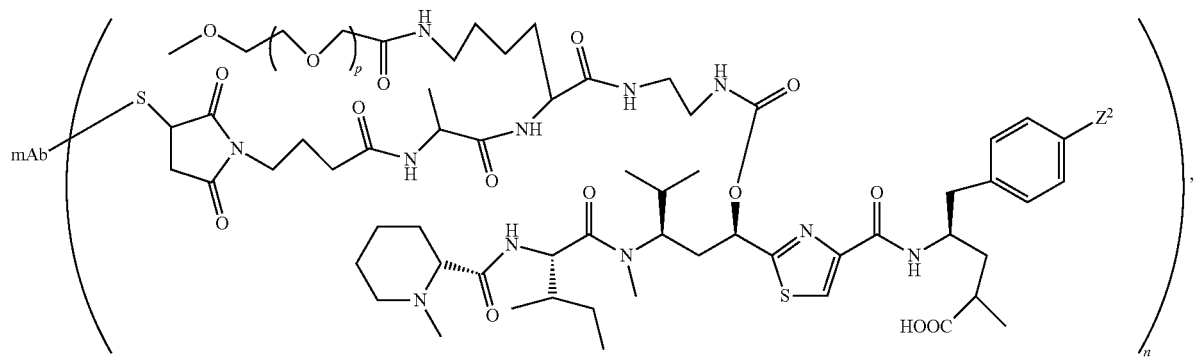
a-29

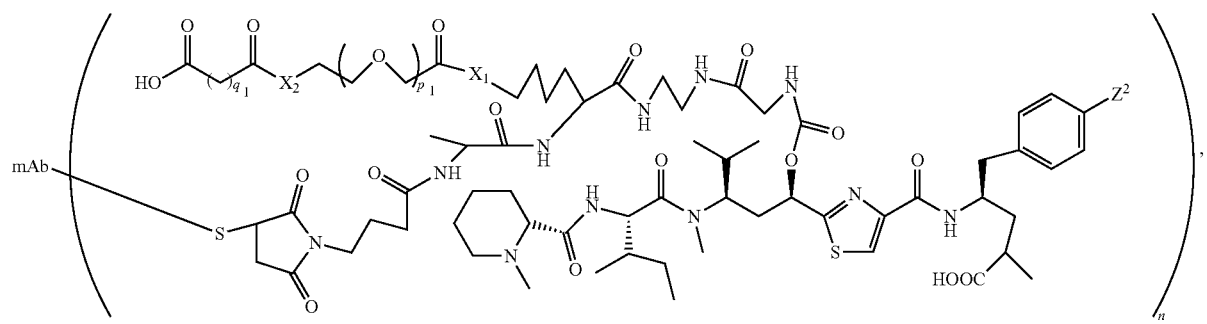
a-30
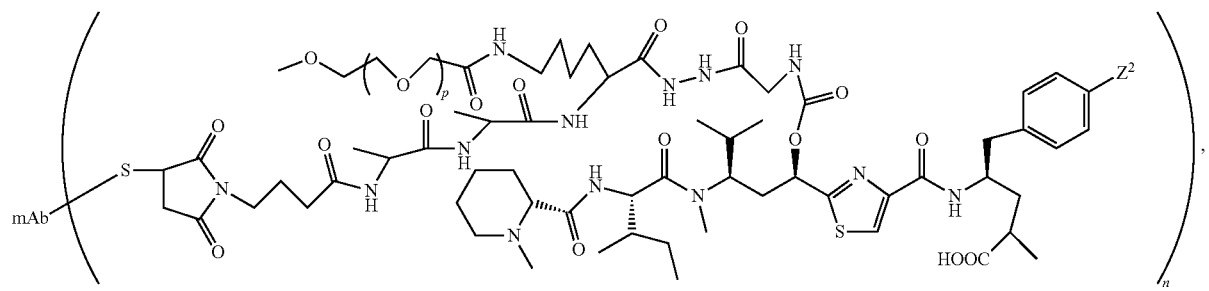
a-31
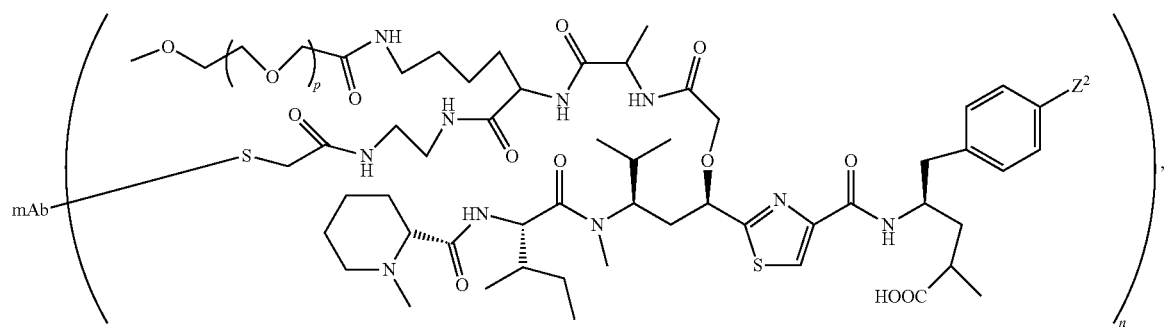
a-32
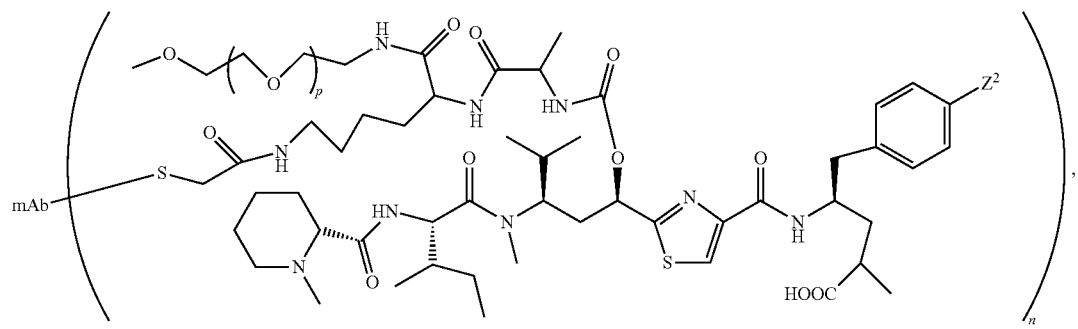
a-33

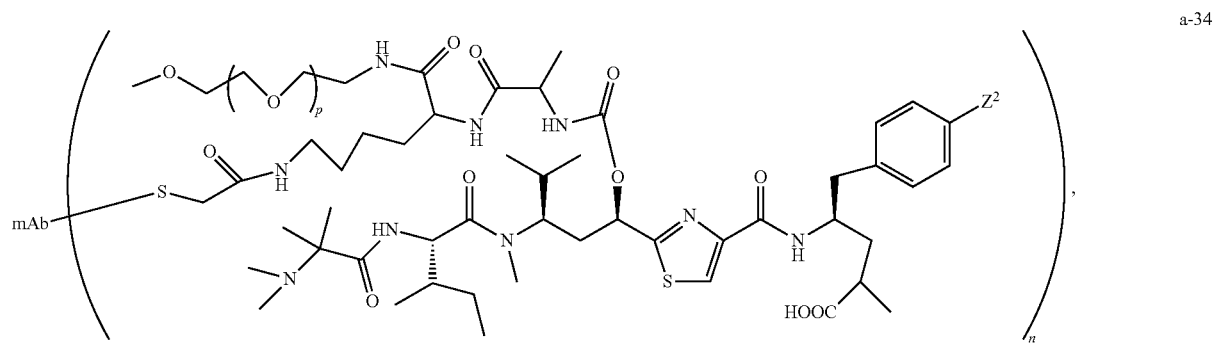
a-34
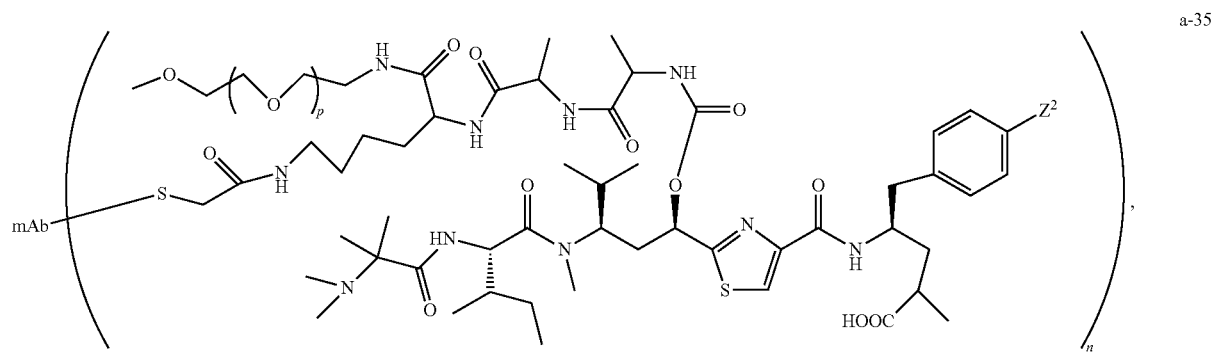
a-35
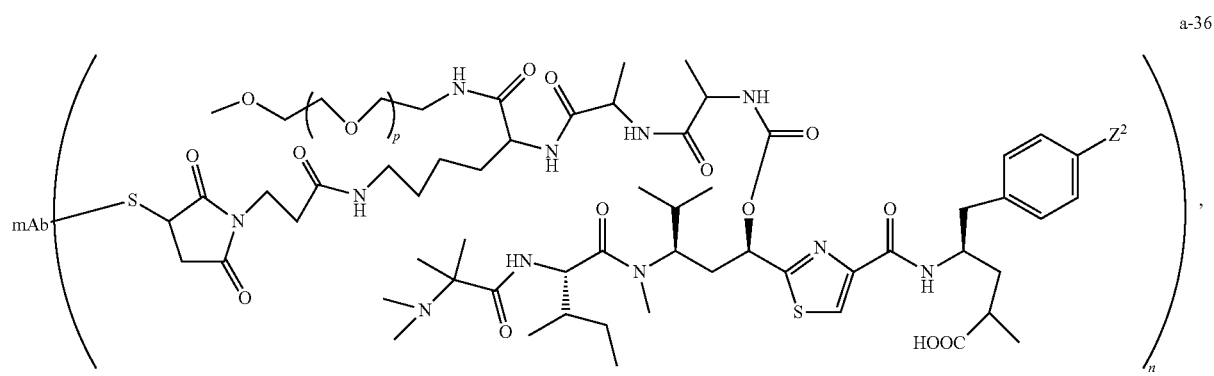
a-36
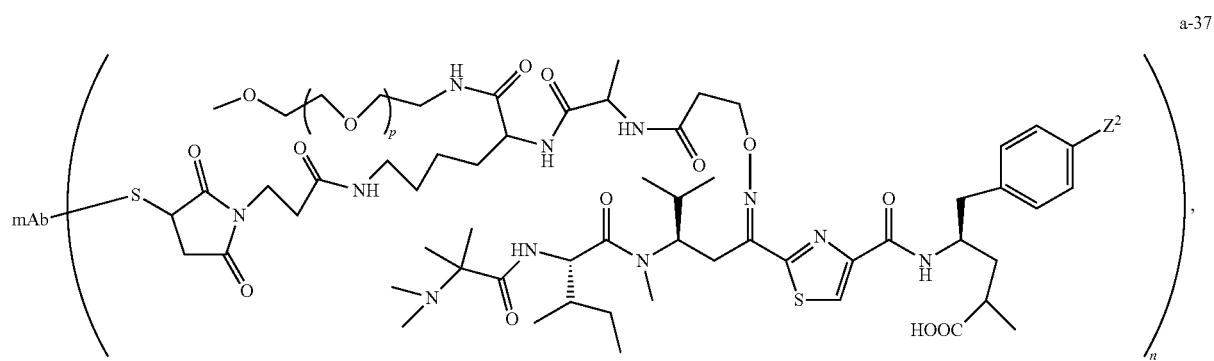
a-37 a-38
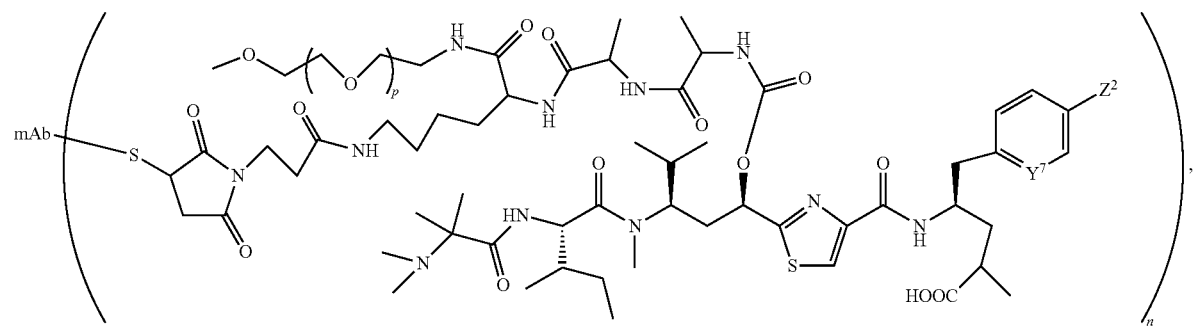
a-39
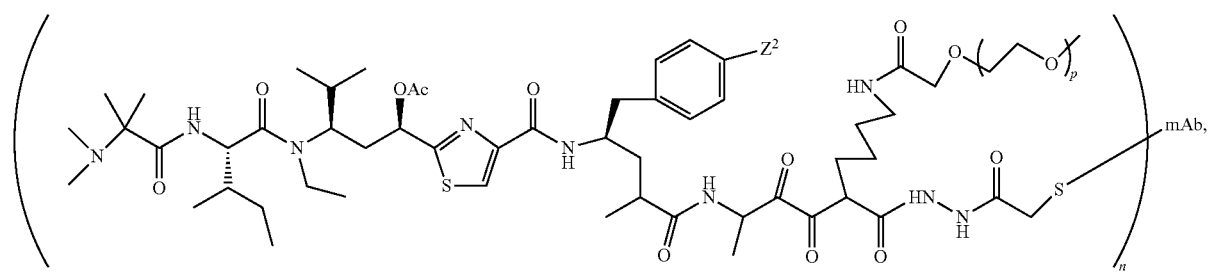
a-40
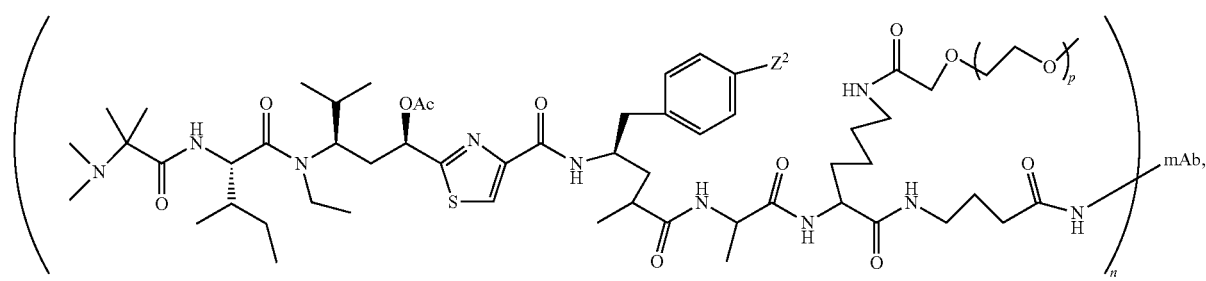
a-41
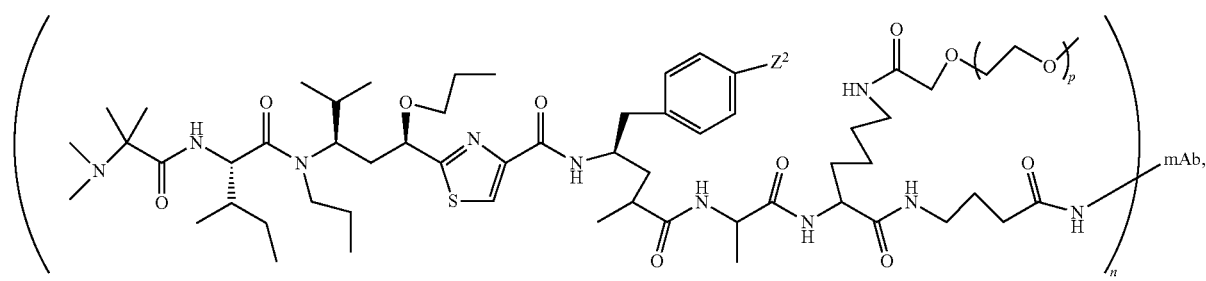
a-42
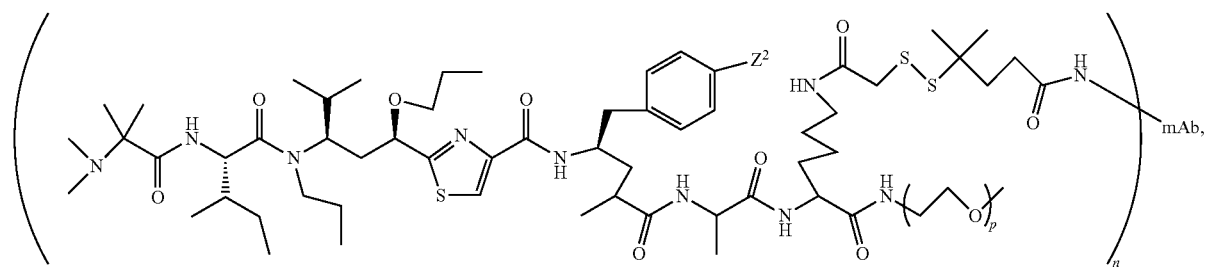

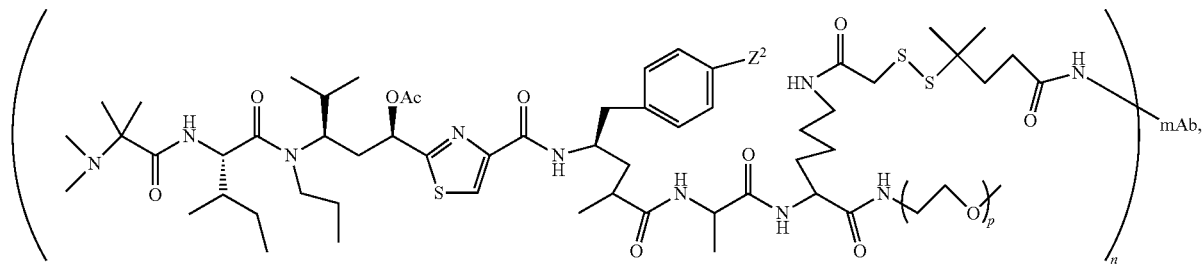
a-43
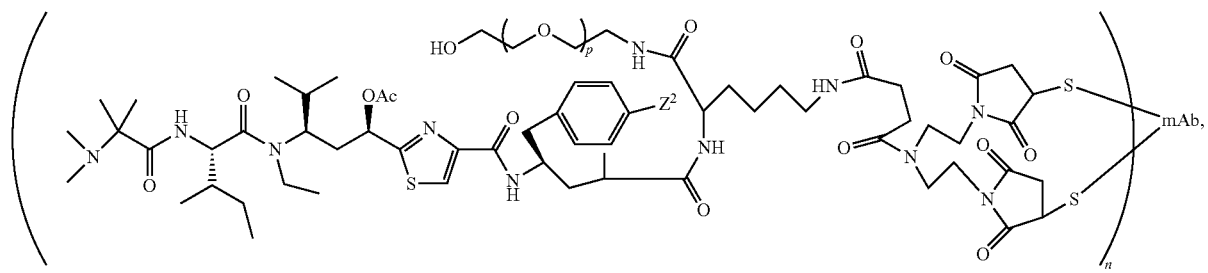
a-44
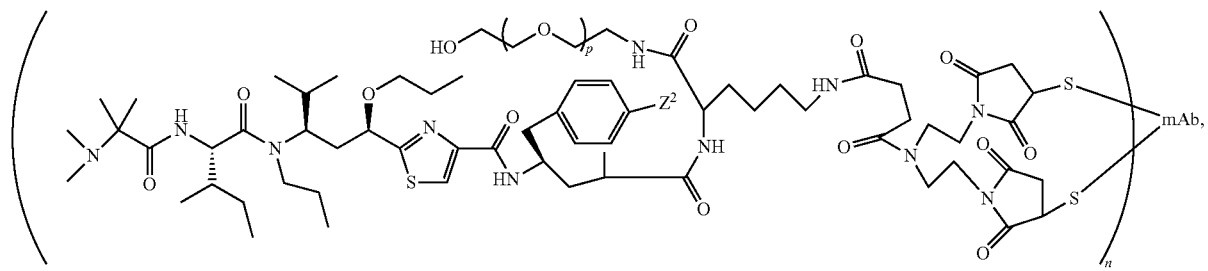
a-45
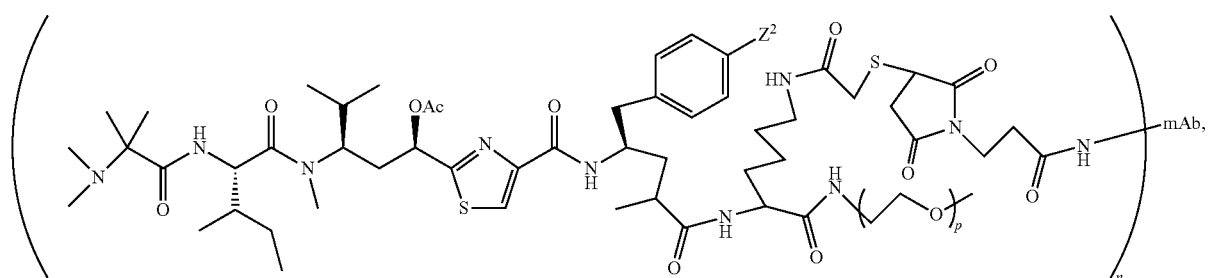
a-46
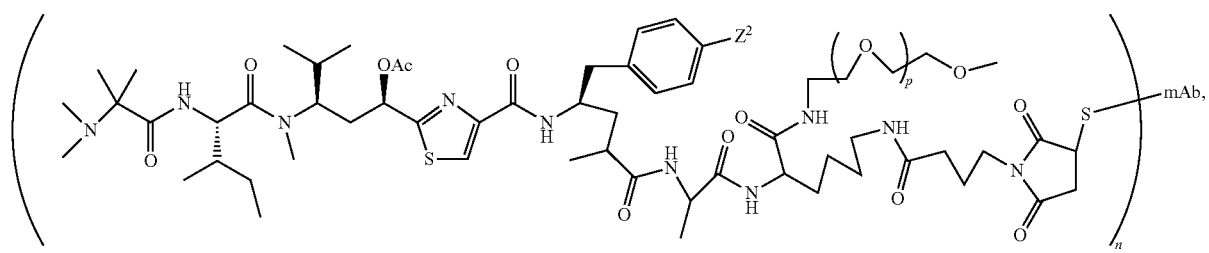
a-47 a-48
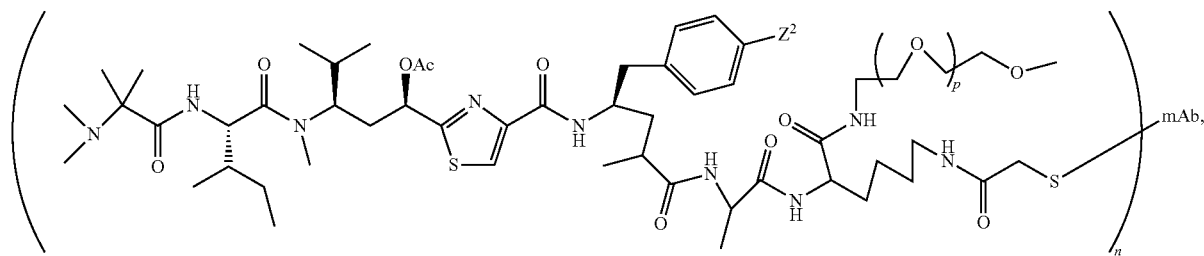
a-49
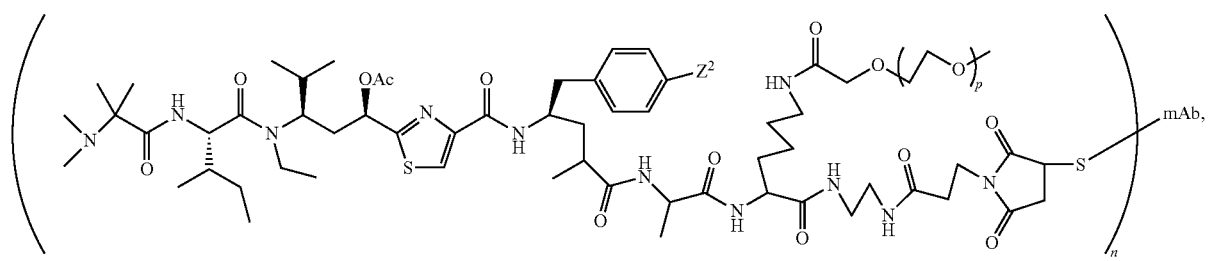
a-50
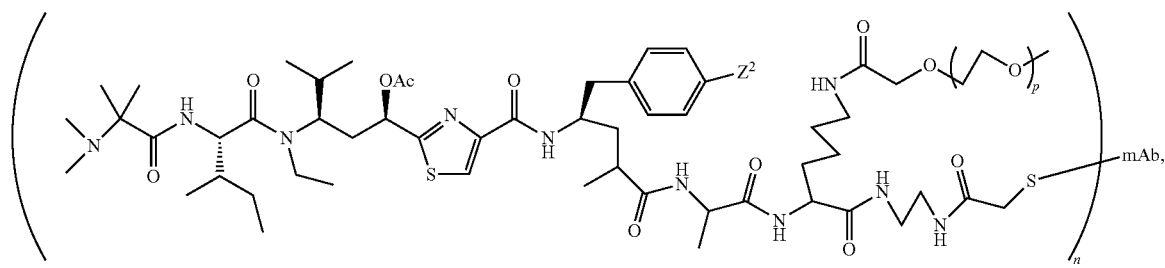
a-51
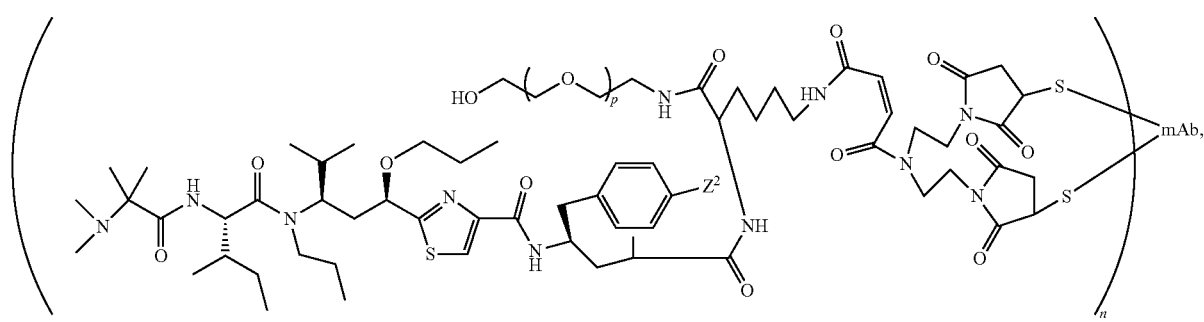
a-52
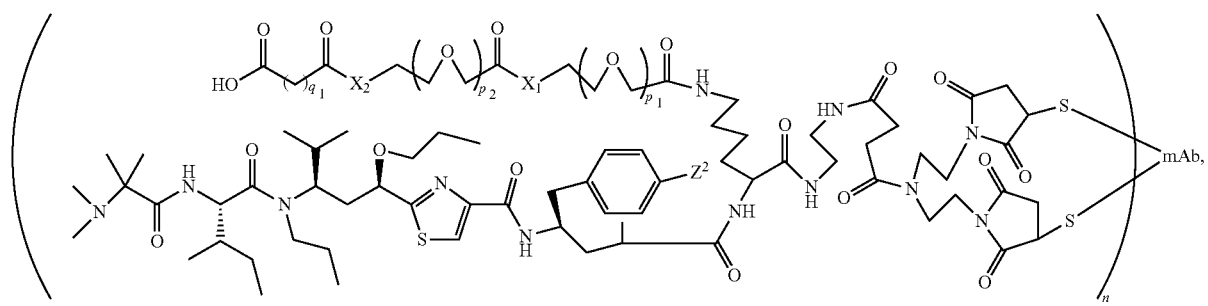

-continued
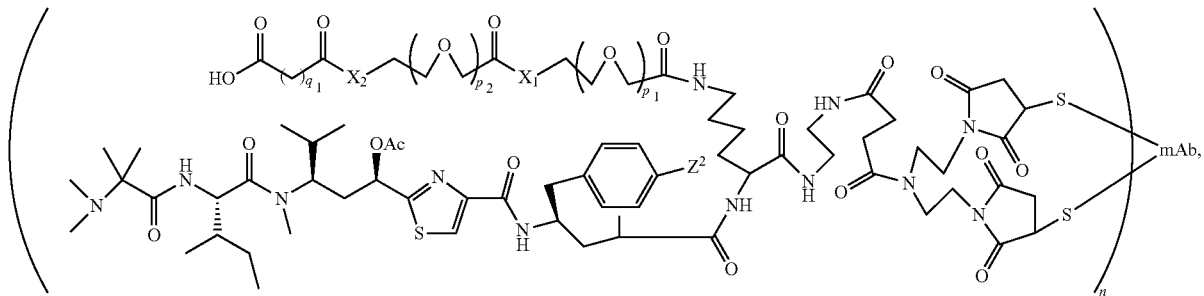
a-53
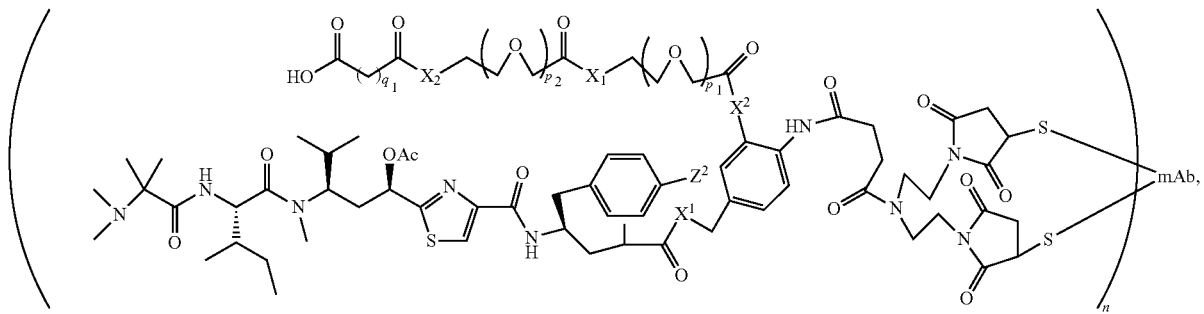
a-54
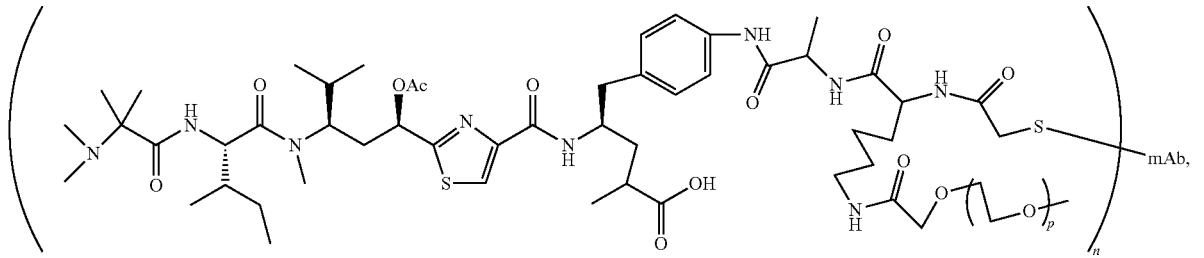
a-55
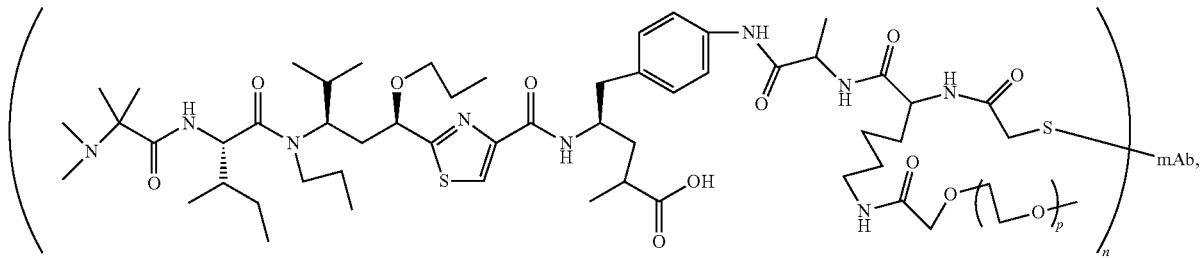
a-56
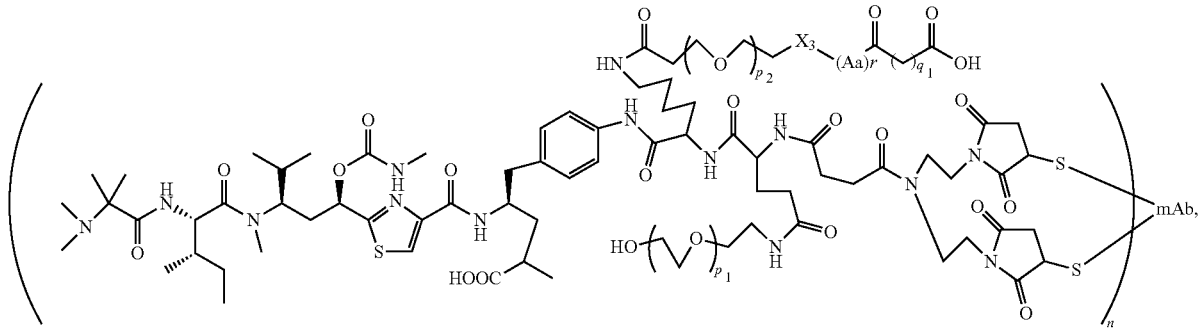
a-57

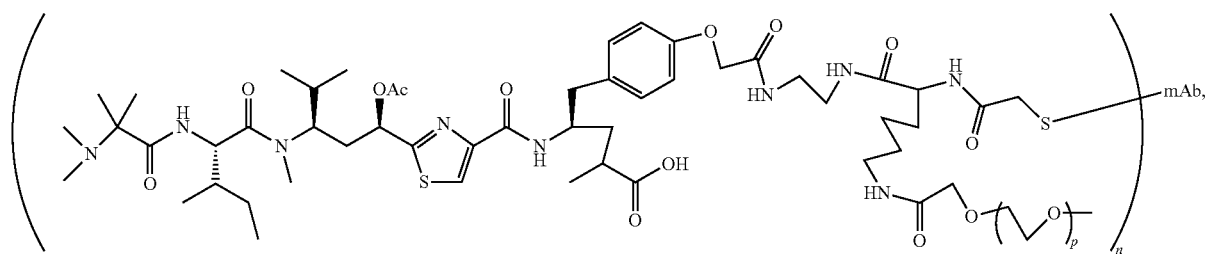
a-58
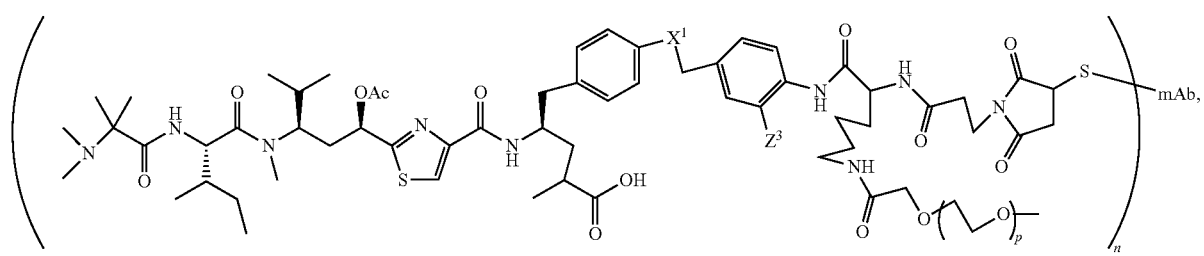
a-59
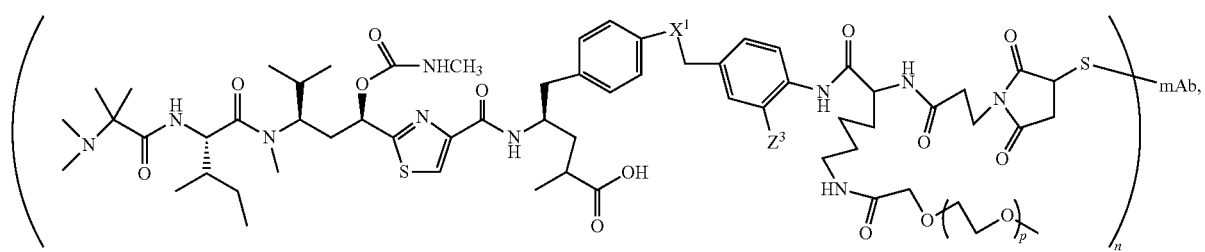
a-60
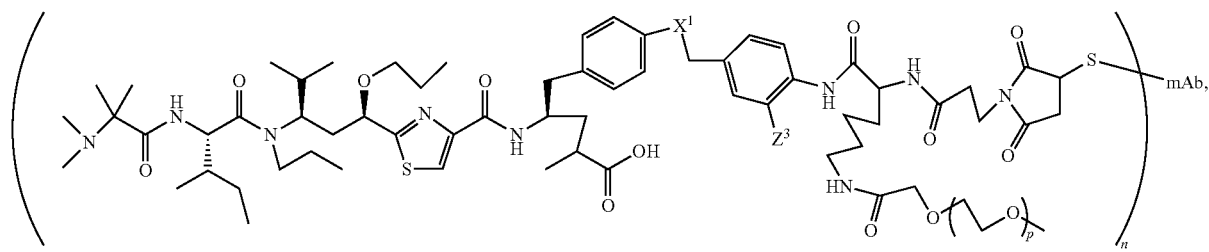
a-61
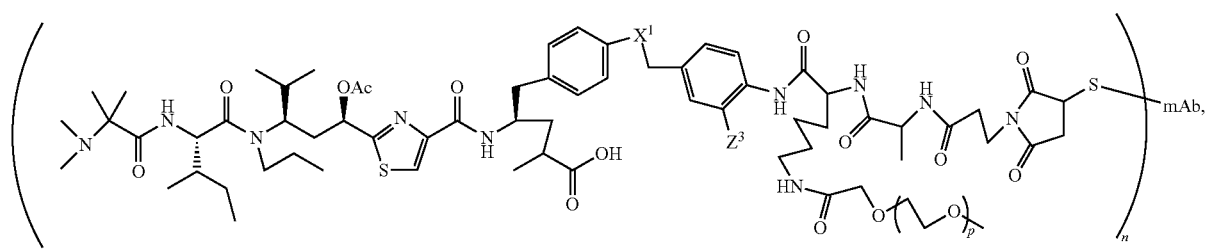
a-62

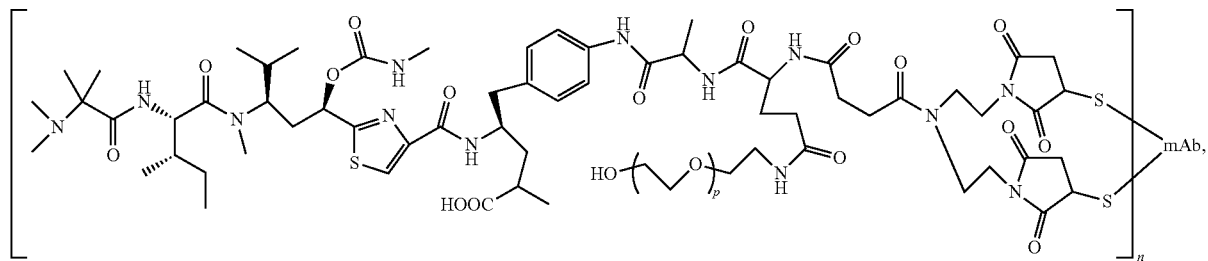
a-63
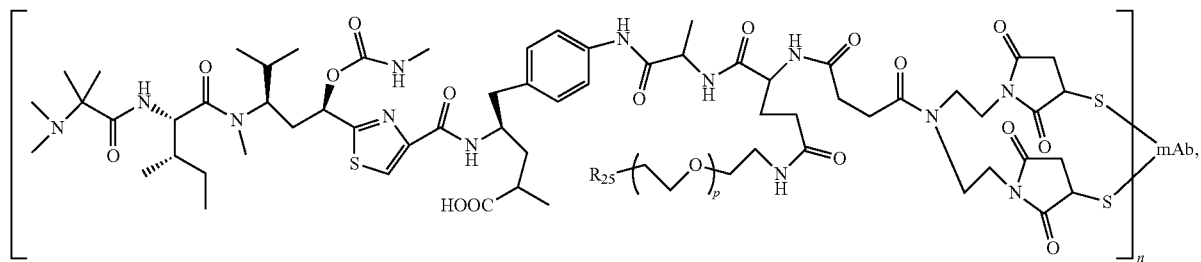
a-64
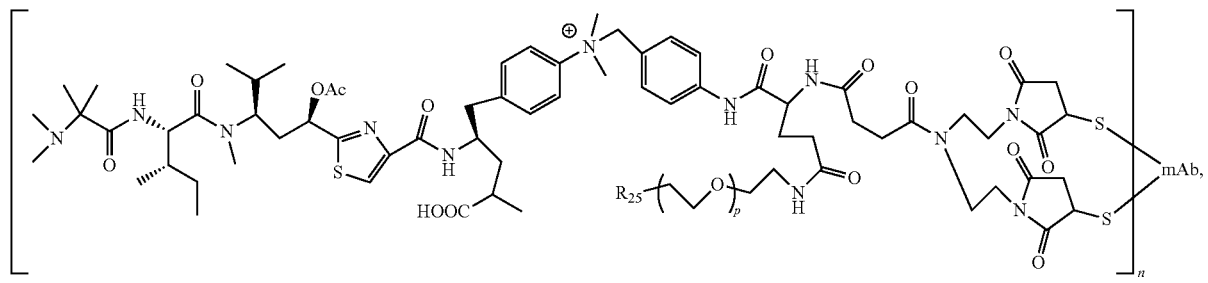
a-65
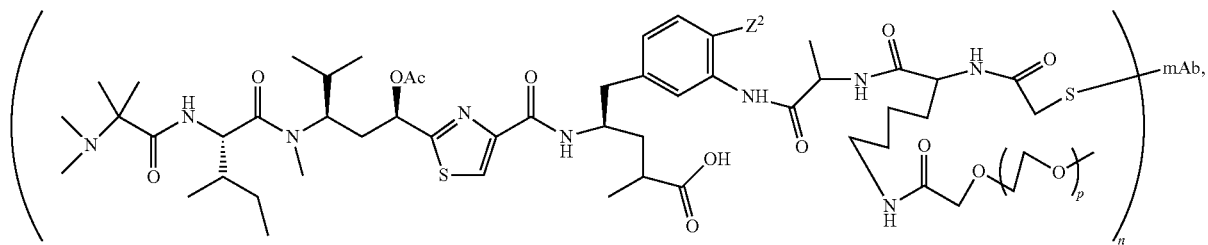
a-66
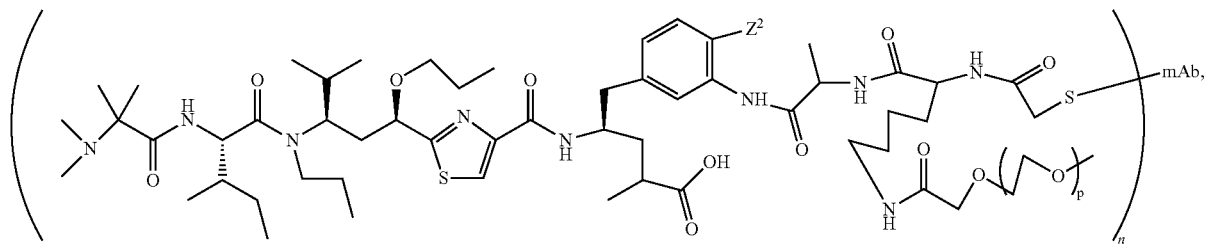
a-67

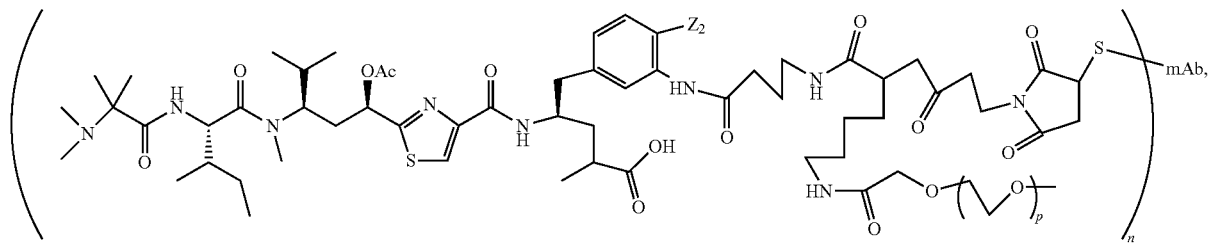
a-68
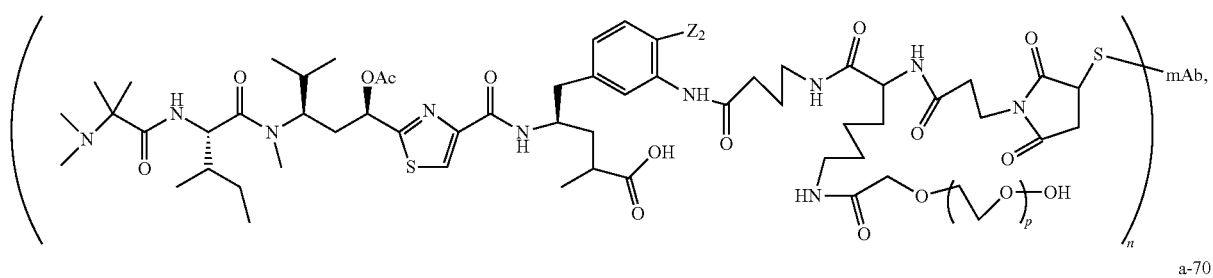
a-69
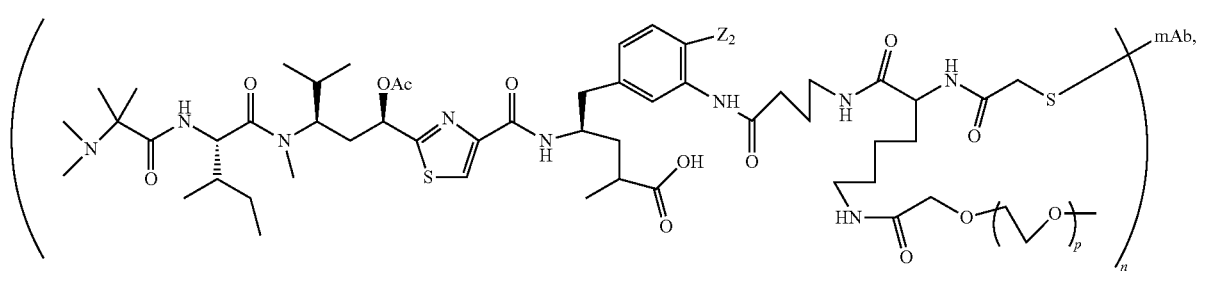
a-70
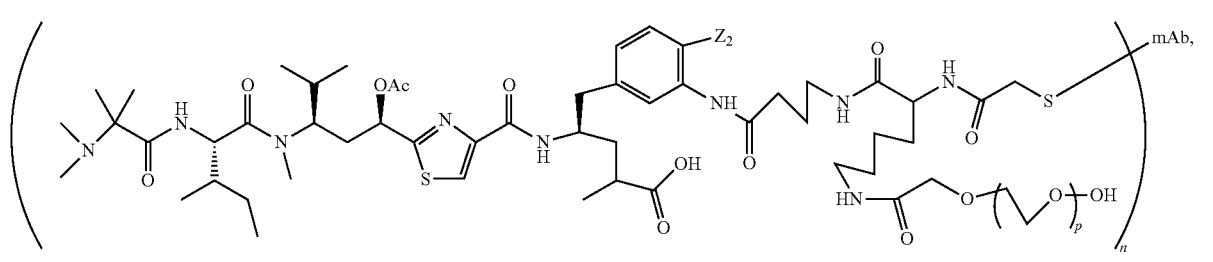
a-71
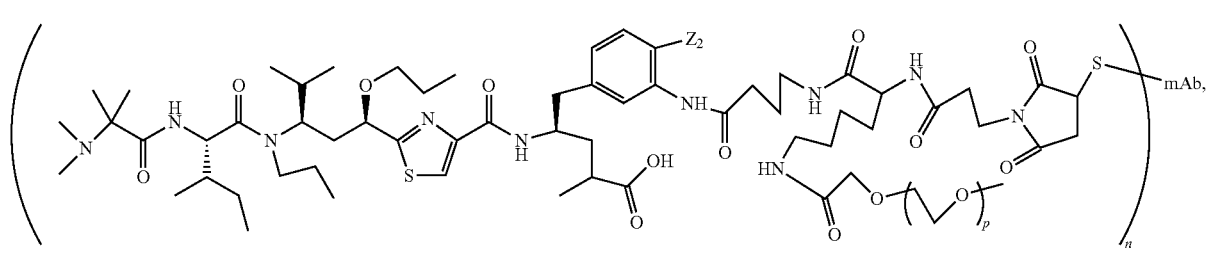
a-72
a-73

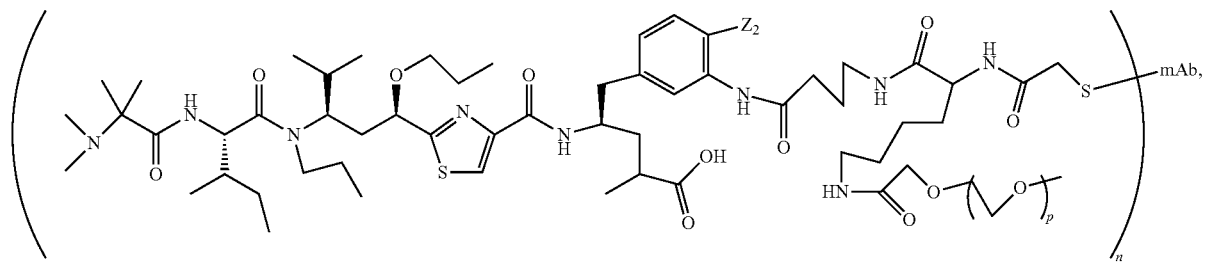
a-74
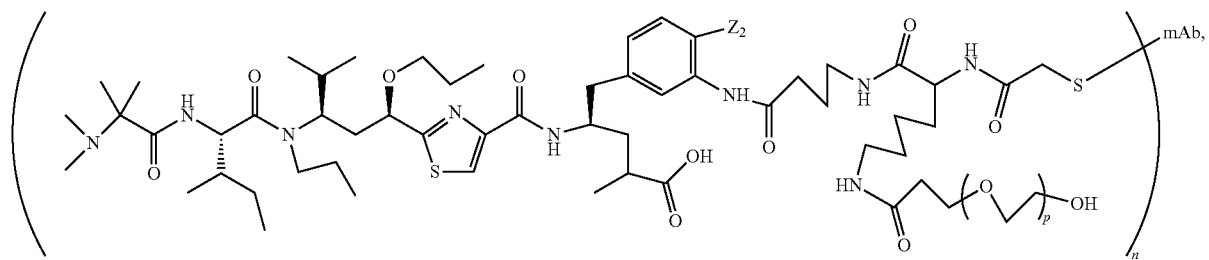
a-75
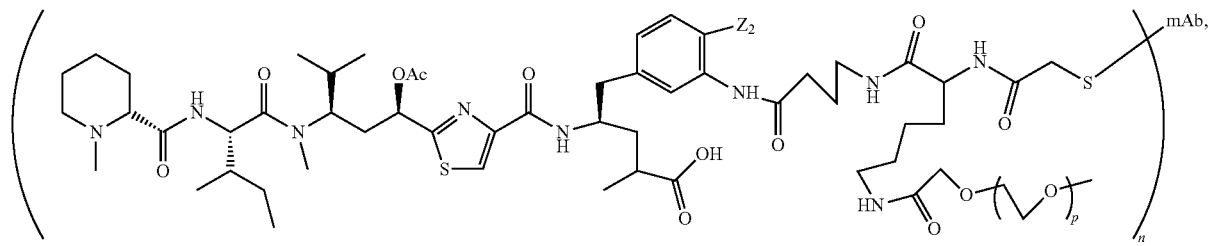
a-76
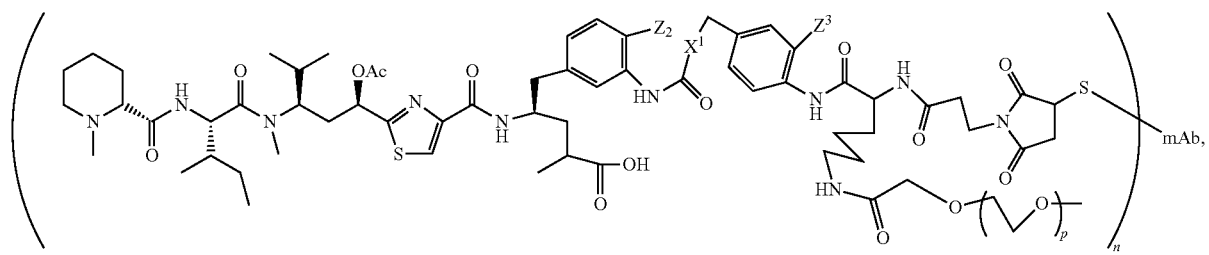
a-77
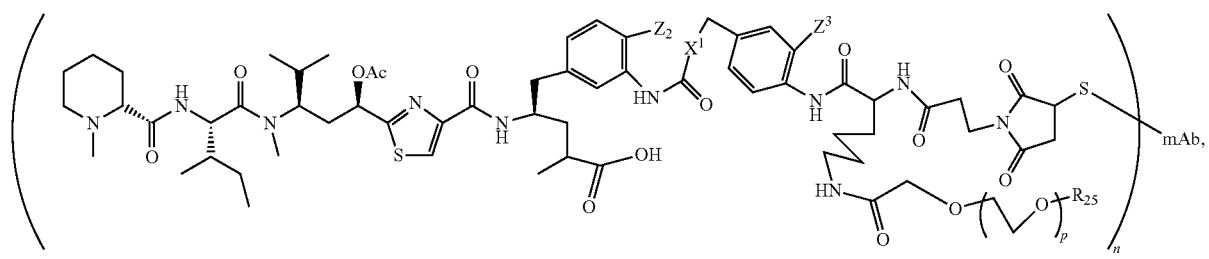
a-78

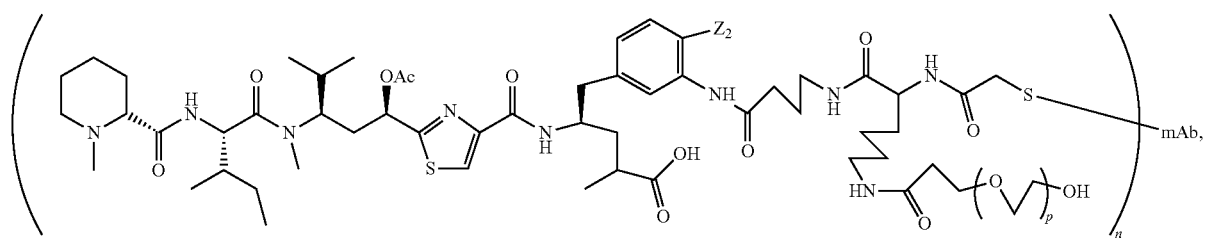
a-79
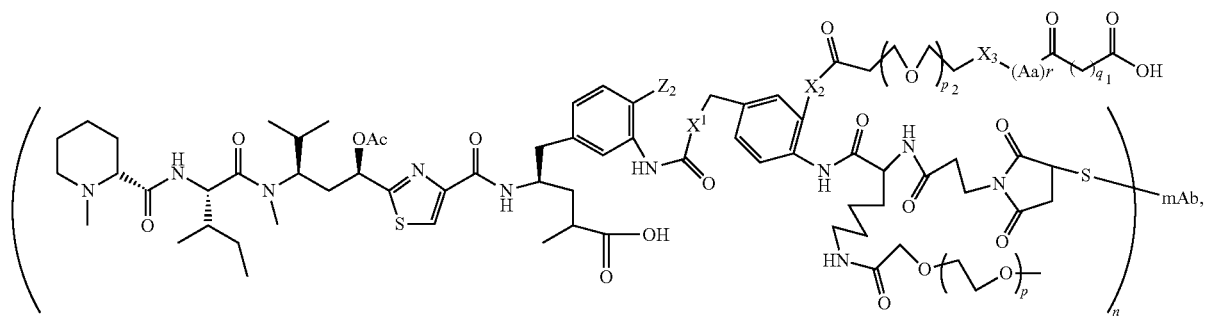
a-80
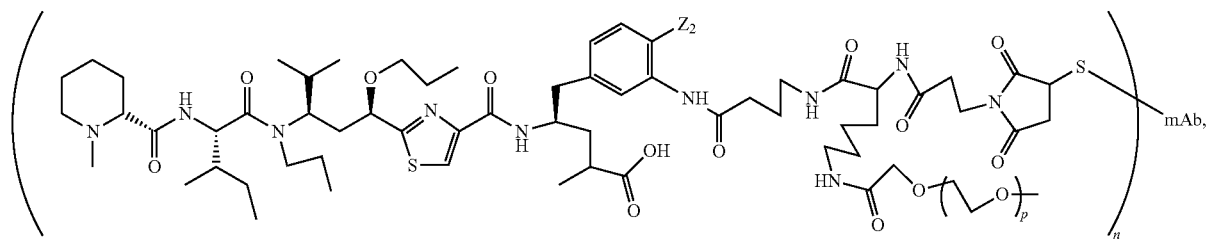
a-81
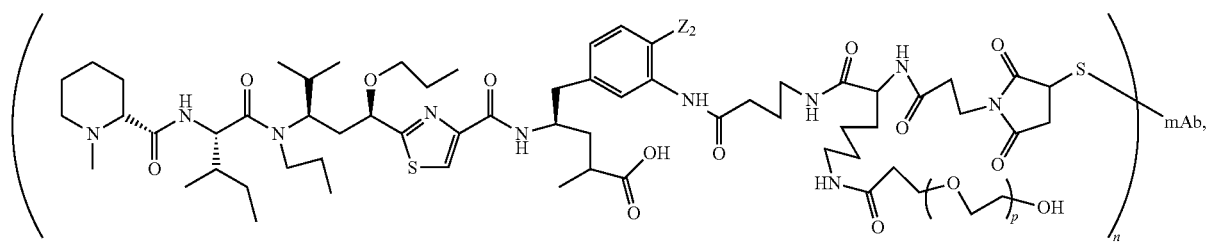
a-82
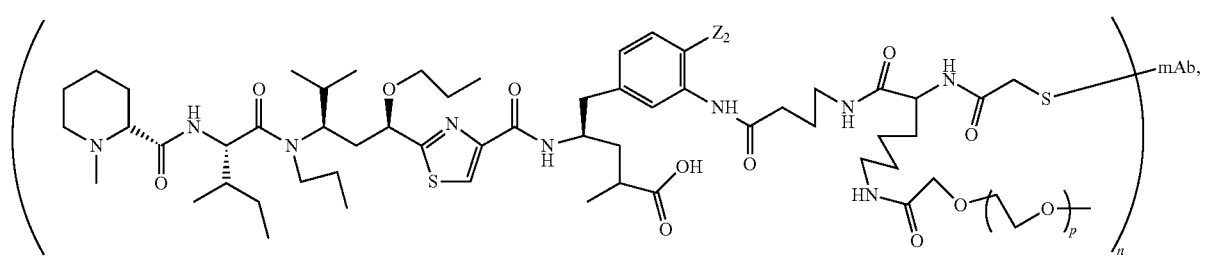
a-83

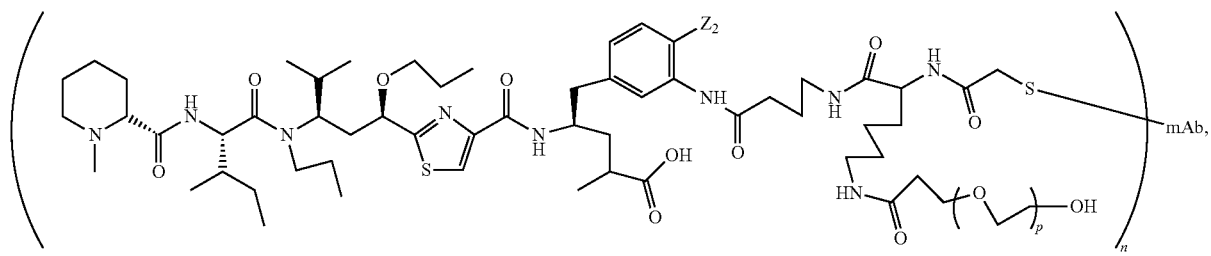
a-84
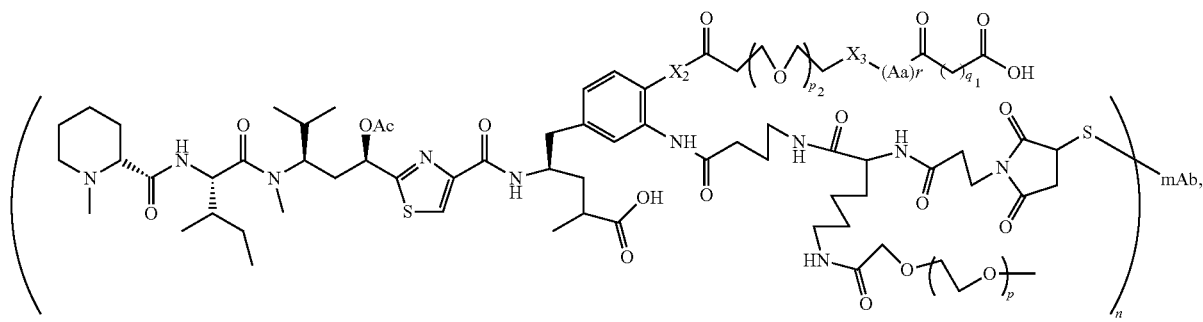
a-85
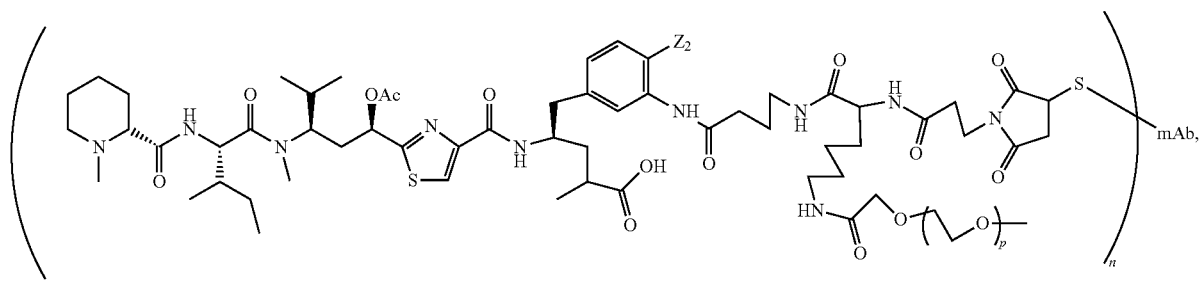
a-86
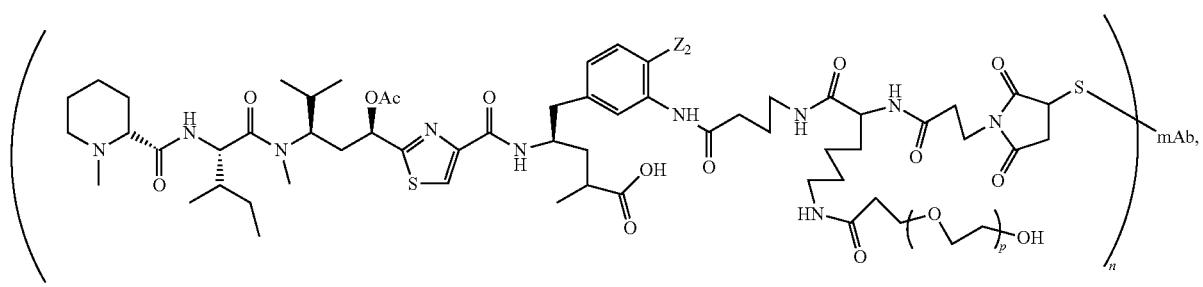
a-87
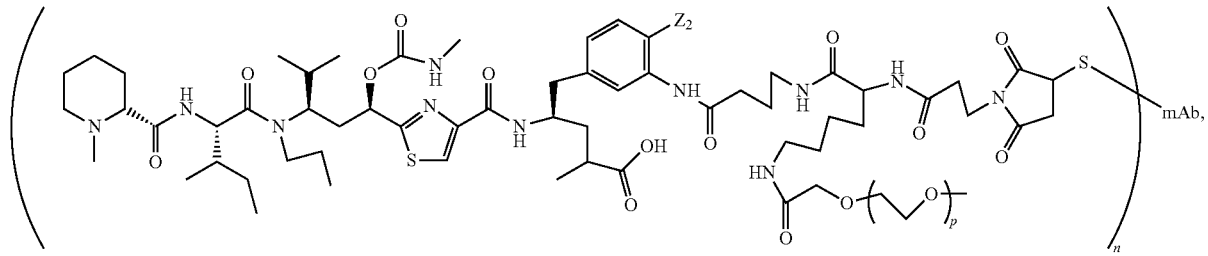
a-88

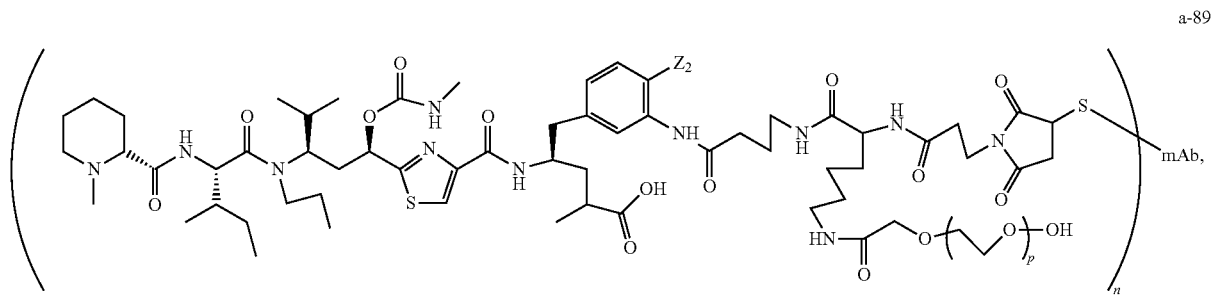
a-89
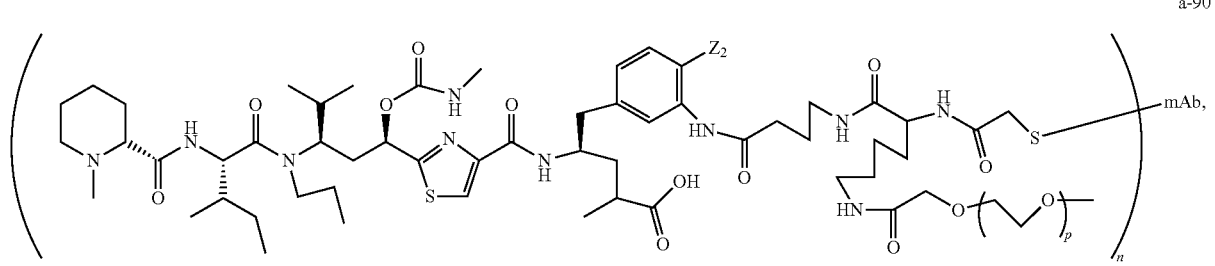
a-90
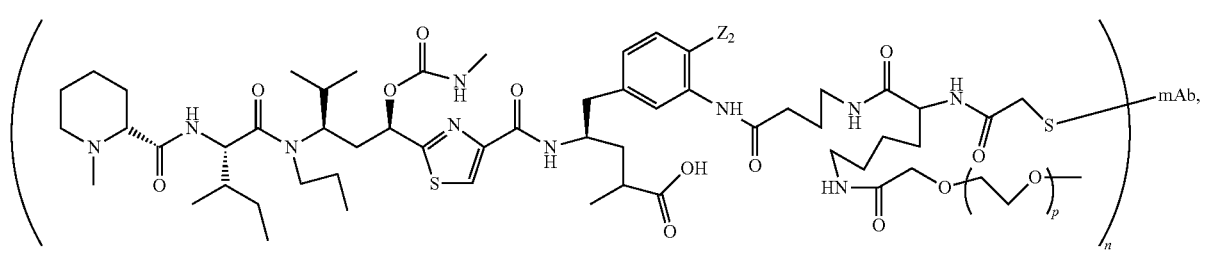
a-91
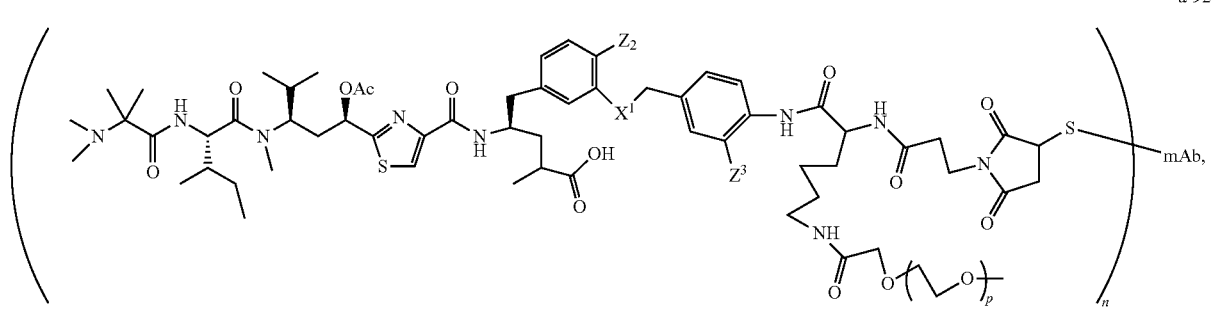
a-92
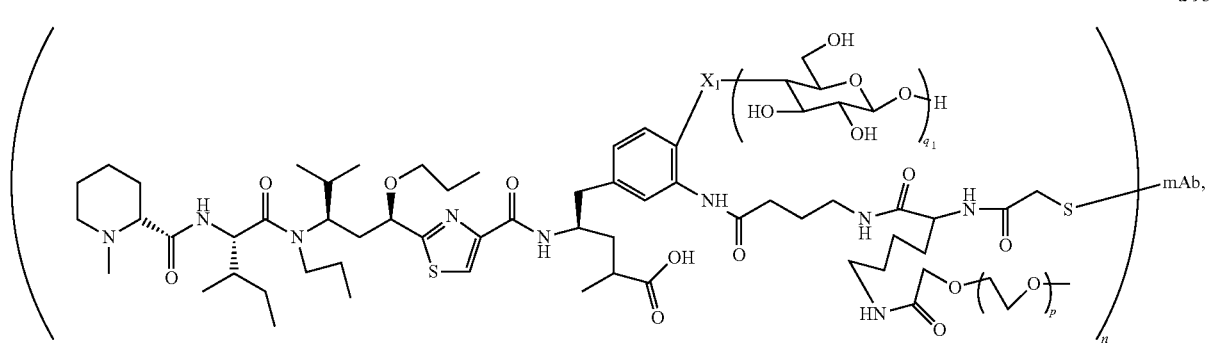
a-93

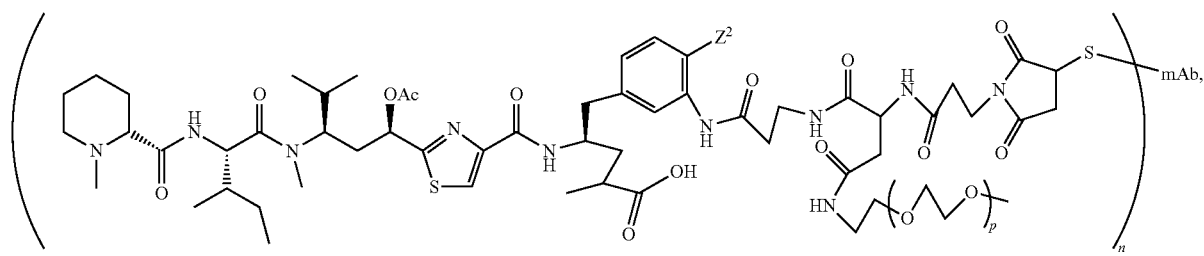
a-94
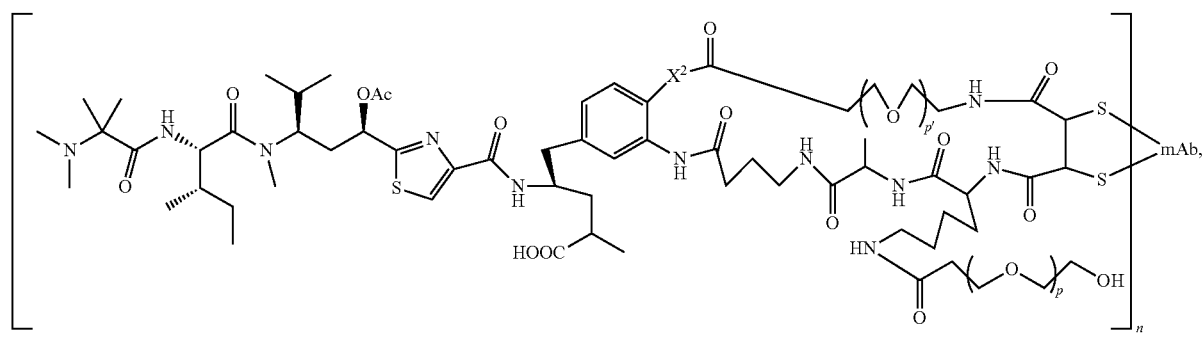
a-95
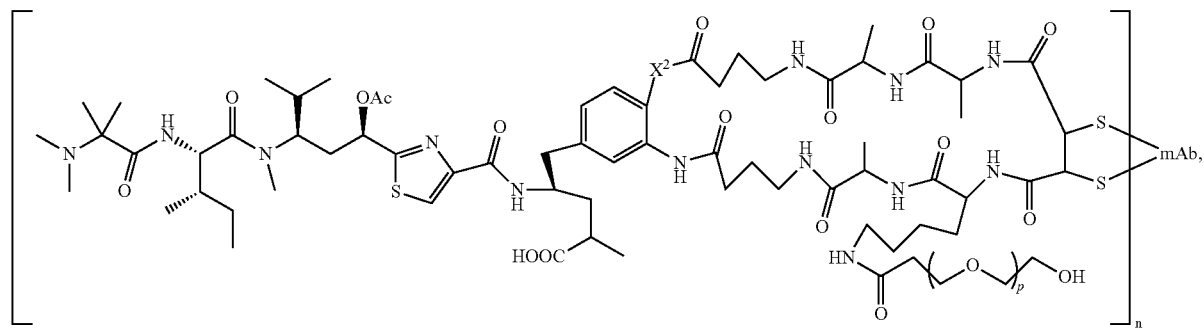
a-96
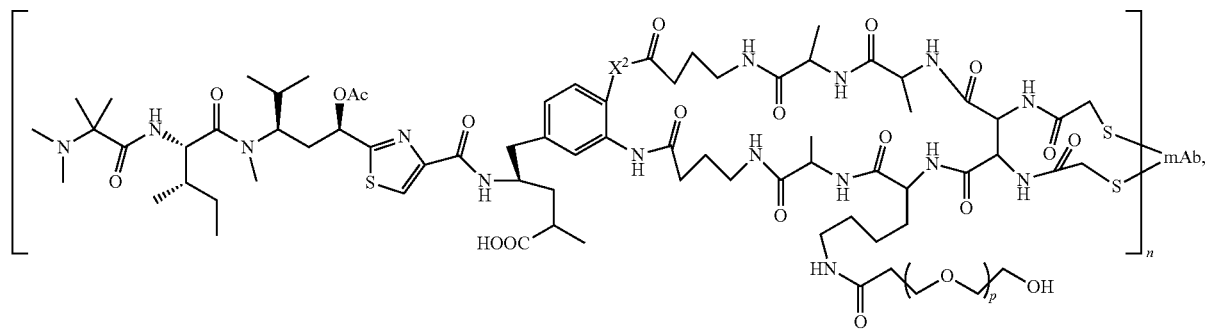
a-97

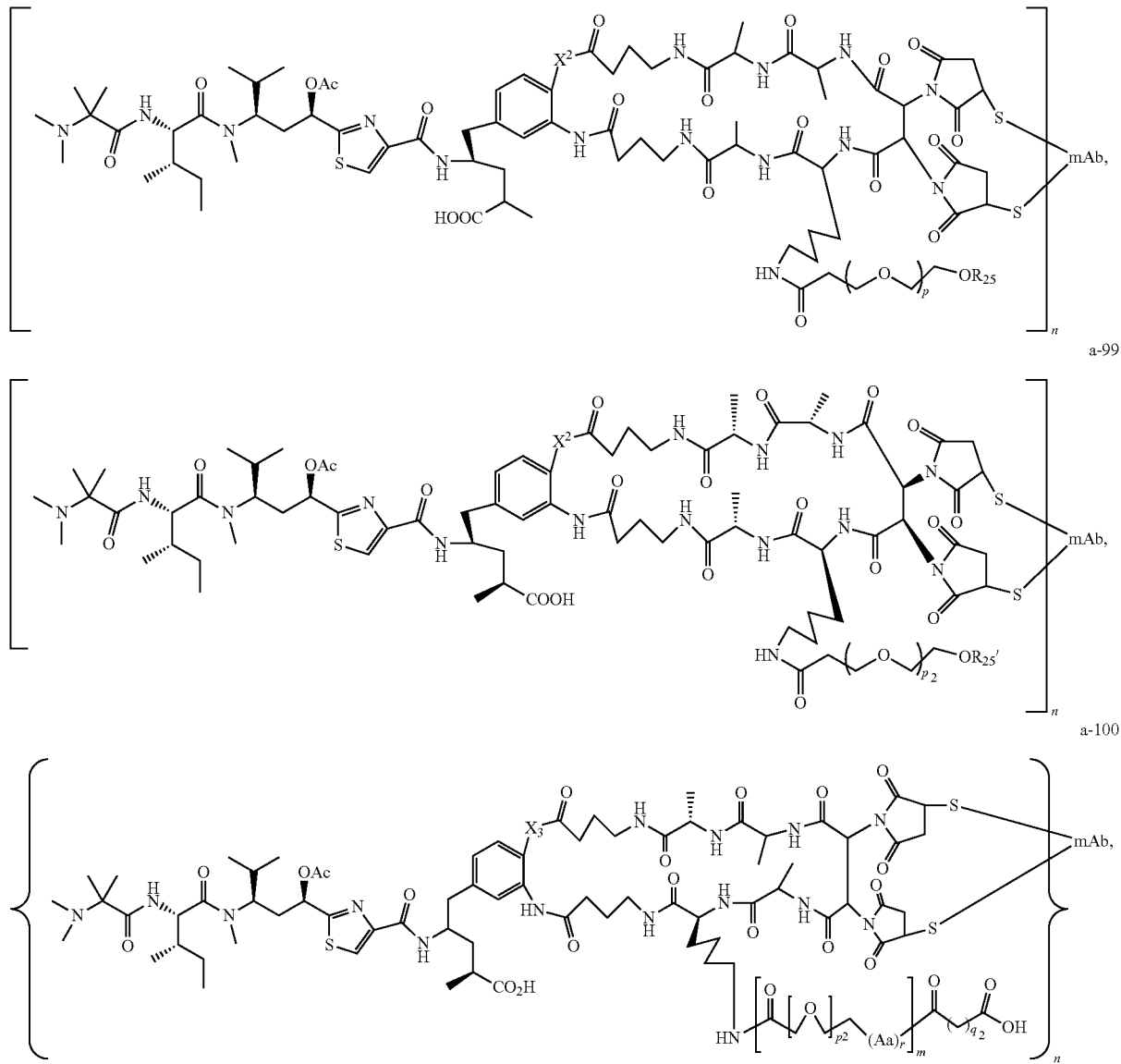

or their pharmaceutically acceptable salts, hydrates, or hydrated salts; or the polymorphic crystalline structures of these compounds; or their optical isomers, racemates, diastereomers or enantiomers; wherein mAb is an antibody or a cell-binding molecule; $Z^3$ and $Z^3$ are independently H, OH, $NH_2$, O, NH, COOH, COO, C(O), C(O), C(O)NH, C(O)$NH_2$, $R^{18}$, $OCH_2OP(O)(OR^{18})_2$, $OC(O)OP(O)(OR^{18})_2$, $OPO(OR^{18})_2$, NHPO$(OR^{18})_2$, $OP(O)(OR^{18})O$—$P(O)(OR^{18})_2$, $OC(O)R^{18}$, $OC(O)NHR^{18}$, $OSO_2(OR^{18})$, O—($C_4$-$C_{12}$-glycoside), $C_1$-$C_8$ linear or branched alkyl or heteroalkyl; $C_2$-$C_8$ linear or branched alkenyl, alkynyl, alkylcycloalkyl, or heterocycloalkyl; $C_3$-$C_8$ linear or branched aryl, Ar-alkyl, heterocyclic, carbocyclic, cycloalkyl, heteroalkylcycloalkyl, alkylcarbonyl, heteroaryl; carbonate (—C(O)$OR^{17}$), carbamate (—C(O) $NR^{17}R^{18}$); or a polyalkylene glycol having a molecular weight of from about 88 Daltons to about 20 kDa; $R^{17}$ and $R^{18}$ are independently H, $C_1$-$C_8$ linear or branched alkyl or heteroalkyl; $C_2$-$C_8$ linear or branched alkenyl, alkynyl, alkylcycloalkyl, or heterocycloalkyl; $C_3$-$C_8$ linear or branched aryl, Ar-alkyl, heterocyclic, carbocyclic, cycloalkyl, heteroalkylcycloalkyl, alkylcarbonyl, heteroaryl; carbonate, or carbamate; $R^{19}$ is H, OH, $NH_2$, $OSO_2(OR^{18})$, $XCH_2OP(O)(OR^{18})_2$, $XPO(OR^{18})_2$, $XC(O)OP(O)(OR^{18})_2$, $XC(O)R^{18}$, $XC(O)NHR^{18}$, $C_1$~$C_8$ alkyl or carboxylate; $C_2$~$C_8$ alkenyl, alkynyl, alkylcycloalkyl, or heterocycloalkyl; $C_3$~$C_8$ alkyl or alkylcarbonyl; or pharmaceutical salts; X, $X_1$, $X_2$ and $X_3$ are independently O, S, NH, NHNH, or $CH_2$; $q_1$, $q_2$ and $q_3$ are independently selected from 0-24; p, $p_1$ and $p_2$ are independently 1-100; $R_1'$, $R_2'$, $R_3'$ and $R_4'$ are independently selected from H and $C_1$-$C_6$ alkyl; Aa is natural or unnatural amino acid; r is 0-12; (Aa)r is a peptide containing the same or different sequence of amino acids when r>2; r=0 means (Aa)r absent; m and n are independently 1-30.

7. The composition according to claim 1, wherein the cell binding molecule is selected from:

a full-length antibody (polyclonal antibody, monoclonal antibody, antibody dimer, antibody multimer), multi-specific antibody (selected from, bispecific antibody, trispecific antibody, or tetraspecific antibody); a single chain antibody, an antibody fragment that binds to the target cell, a monoclonal antibody, a single chain monoclonal antibody, a monoclonal antibody fragment that binds the target cell, a chimeric antibody, a chimeric antibody fragment that binds to the target cell, a domain antibody, a domain antibody fragment that binds to the target cell, a resurfaced antibody, a resurfaced single chain antibody, or a resurfaced antibody fragment that binds to the target cell, a humanized antibody or a resurfaced antibody, a humanized single chain antibody, or a humanized antibody fragment that binds to the target cell, anti-idiotypic (anti-Id) antibodies, CDR's, diabody, triabody, tetrabody, miniantibody, a probody, and a probody fragment.

8. The composition according to claim 1, wherein the cell-binding molecule, T, when linking to $V_1$ and/or $V_2$, of Formula (I) and (III), or when T directly linking to $L_1$ and/or $L_2$ of Formula (I) and (III), wherein $V_1$, and/or $V_2$, are absent, having one or more of the following the linkage structures:

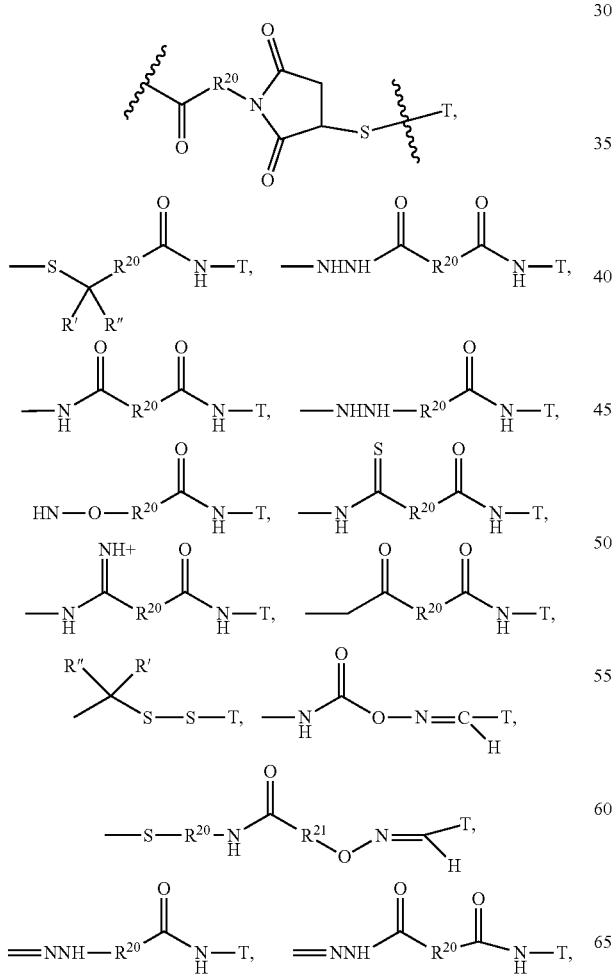
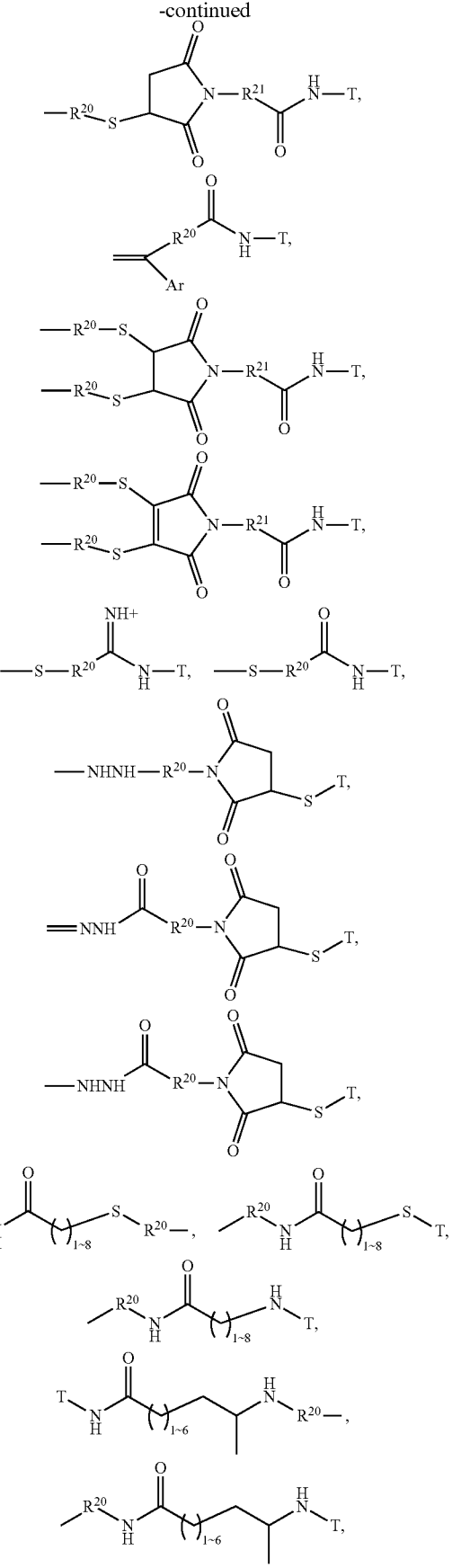

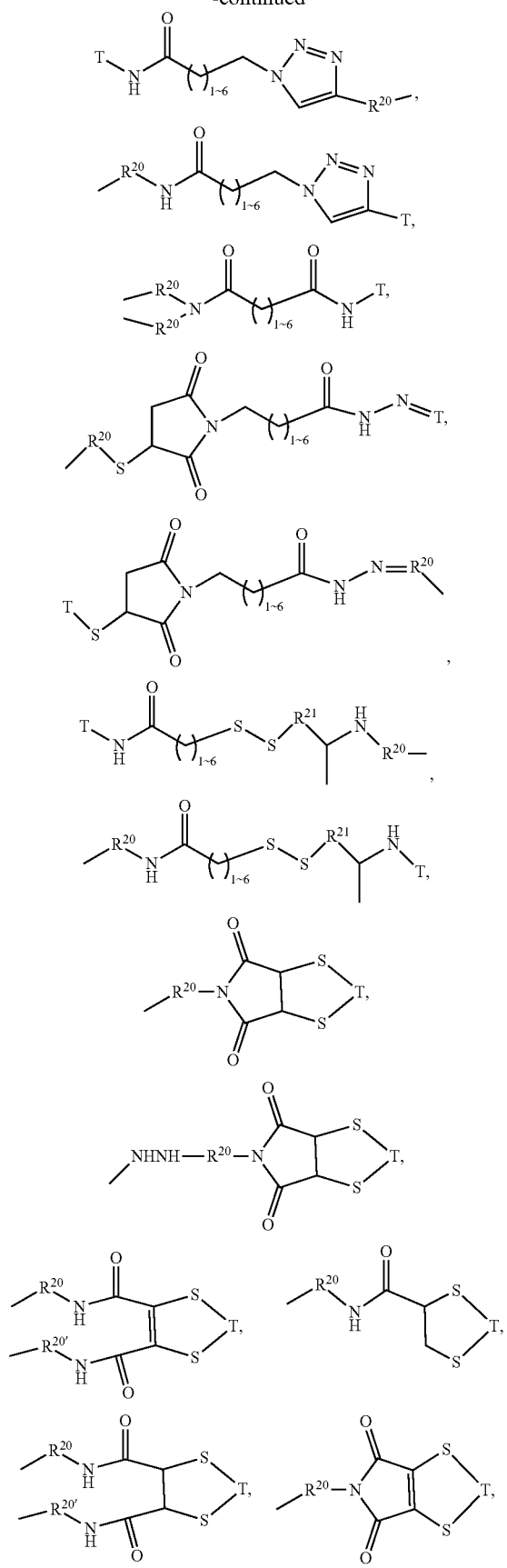
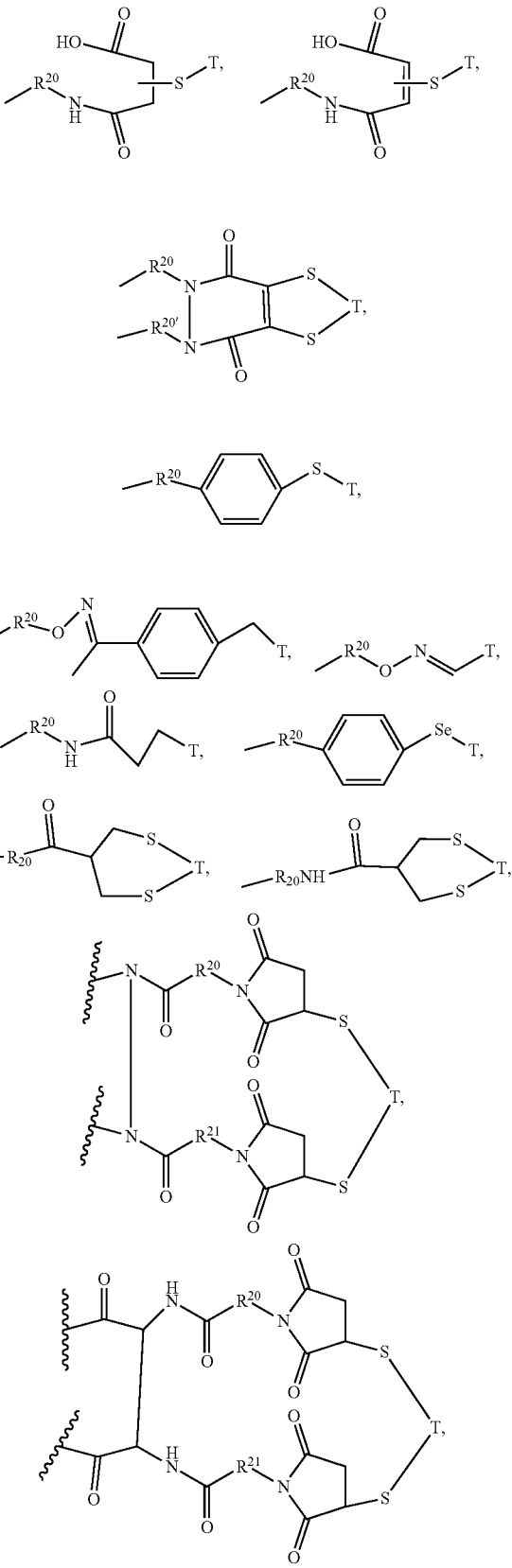

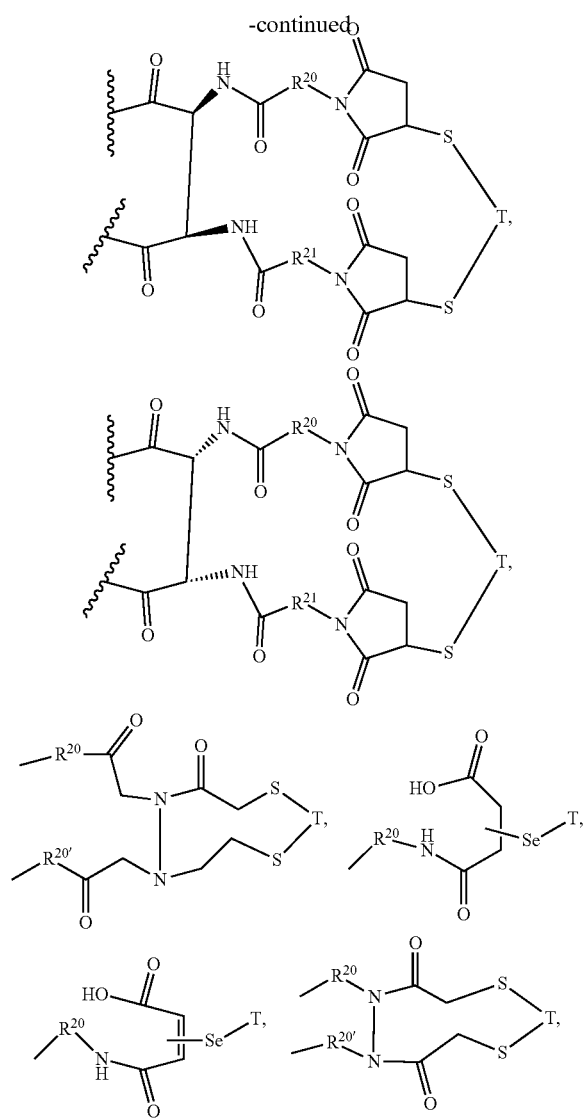

wherein $R^{20}$ and $R^{21}$ are independently $C_1$~$C_8$ alkyl; $C_2$~$C_8$ heteroalkyl, or heterocyclic; $C_3$~$C_8$ aryl, Ar-alkyl, cycloalkyl, alkylcycloalkyl, heterocycloalkyl, heteroalkylcycloalkyl, carbocyclic, or alkylcarbonyl; or $C_2$-$C_{100}$ polyethylene glycol having formula of $(CH_2CH_2O)_p$.

9. The composition according to claim 1, wherein the cell binding molecule is capable of targeting against a tumor cell, a virus infected cell, a microorganism infected cell, a parasite infected cell, an autoimmune disease cell, an activated tumor cells, a myeloid cell, an activated T-cell, an affecting B cell, or a melanocyte, or any cells expressing any one of the following antigens or receptors: CD1, CD1a, CD1b, CD1c, CD1d, CD1e, CD2, CD3, CD3d, CD3e, CD3g, CD4, CD5, CD6, CD7, CD8, CD8a, CD8b, CD9, CD10, CD11a, CD11b, CD11c, CD11d, CD12w, CD14, CD15, CD16, CD16a, CD16b, CDw17, CD18, CD19, CD20, CD21, CD22, CD23, CD24, CD25, CD26, CD27, CD28, CD29, CD30, CD31, CD32, CD32a, CD32b, CD33, CD34, CD35, CD36, CD37, CD38, CD39, CD40, CD41, CD42, CD42a, CD42b, CD42c, CD42d, CD43, CD44, CD45, CD46, CD47, CD48, CD49b, CD49c, CD49c, CD49d, CD49f, CD50, CD51, CD52, CD53, CD54, CD55, CD56, CD57, CD58, CD59, CD60, CD60a, CD60b, CD60c, CD61, CD62E, CD62L, CD62P, CD63, CD64, CD65, CD65s, CD66, CD66a, CD66b, CD66c, CD66d, CD66e, CD66f, CD67, CD68, CD69, CD70, CD71, CD72, CD73, CD74, CD75, CD75s, CD76, CD77, CD78, CD79, CD79a, CD79b, CD80, CD81, CD82, CD83, CD84, CD85, CD85a, CD85b, CD85c, CD85d, CD85e, CD85f, CD85g, CD85g, CD85i, CD85j, CD85k, CD85m, CD86, CD87, CD88, CD89, CD90, CD91, CD92, CD93, CD94, CD95, CD96, CD97, CD98, CD99, CD100, CD101, CD102, CD103, CD104, CD105, CD106, CD107, CD107a, CD107b, CD108, CD109, CD110, CD111, CD112, CD113, CD114, CD115, CD116, CD117, CD118, CD119, CD120, CD120a, CD120b, CD121, CD121a, CD121b, CD122, CD123, CD123a, CD124, CD125, CD126, CD127, CD128, CD129, CD130, CD131, CD132, CD133, CD134, CD135, CD136, CD137, CD138, CD139, CD140, CD140a, CD140b, CD141, CD142, CD143, CD144, CD145, CDw145, CD146, CD147, CD148, CD149, CD150, CD151, CD152, CD153, CD154, CD155, CD156, CD156a, CD156b, CD156c, CD156d, CD157, CD158, CD158a, CD158b1, CD158b2, CD158c, CD158d, CD158e1, CD158e2, CD158f2, CD158g, CD158h, CD158i, CD158j, CD158k, CD159, CD159a, CD159b, CD159c, CD160, CD161, CD162, CD163, CD164, CD165, CD166, CD167, CD167a, CD167b, CD168, CD169, CD170, CD171, CD172, CD172a, CD172b, CD172g, CD173, CD174, CD175, CD175s, CD176, CD177, CD178, CD179, CD179a, CD179b, CD180, CD181, CD182, CD183, CD184, CD185, CD186, CDw186, CD187, CD188, CD189, CD190, CD191, CD192, CD193, CD194, CD195, CD196, CD197, CD198, CD199, CDw198, CDw199, CD200, CD201, CD202, CD202(a,b), CD203, CD203c, CD204, CD205, CD206, CD207, CD208, CD209, CD210, CDw210a, CDw210b, CD211, CD212, CD213, CD213a1, CD213a2, CD214, CD215, CD216, CD217, CD218, CD218a, CD218, CD21b9, CD220, CD221, CD222, CD223, CD224, CD225, CD226, CD227, CD228, CD229, CD230, CD231, CD232, CD233, CD234, CD235, CD235a, CD235b, CD236, CD237, CD238, CD239, CD240, CD240ce, CD240d, CD241, CD242, CD243, CD244, CD245, CD246, CD247, CD248, CD249, CD250, CD251, CD252, CD253, CD254, CD255, CD256, CD257, CD258, CD259, CD260, CD261, CD262, CD263, CD264, CD265, CD266, CD267, CD268, CD269, CD270, CD271, CD272, CD273, CD274, CD275, CD276, CD277, CD278, CD279, CD281, CD282, CD283, CD284, CD285, CD286, CD287, CD288, CD289, CD290, CD291, CD292, CD293, CD294, CD295, CD296, CD297, CD298, CD299, CD300, CD300a, CD300b, CD300c, CD301, CD302, CD303, CD304, CD305, CD306, CD307, CD307a, CD307b, CD307c, CD307d, CD307e, CD307f, CD308, CD309, CD310, CD311, CD312, CD313, CD314, CD315, CD316, CD317, CD318, CD319, CD320, CD321, CD322, CD323, CD324, CD325, CD326, CD327, CD328, CD329, CD330, CD331, CD332, CD333, CD334, CD335, CD336, CD337, CD338, CD339, CD340, CD341, CD342, CD343, CD344, CD345, CD346, CD347, CD348, CD349, CD350, CD351, CD352, CD353, CD354, CD355, CD356, CD357, CD358, CD359, CD360, CD361, CD362, CD363, CD364, CD365, CD366, CD367, CD368, CD369, CD370, CD371, CD372, CD373, CD374, CD375, CD376, CD377, CD378, CD379, CD381, CD382, CD383, CD384, CD385, CD386, CD387, CD388, CD389, CRIPTO, CRIPTO, CR, CR1, CRGF, CRIPTO, CXCR5, LY64, TDGF1, 4-1BB, APO2, ASLG659, BMPR1B, 4-1BB, SAC, 5T4 (Trophoblastic glycoprotein, TPBG, 5T4, Wnt-Activated Inhibitory Factor 1 or WAIF1), Adenocarcinoma antigen, AGS-5, AGS-22M6, Activin receptor-like kinase 1, AFP, AKAP-4, ALK, Alpha integrin, Alpha v beta6, Amino-peptidase N, Amyloid beta, Androgen receptor, Angiopoietin 2, Angiopoietin 3, Annexin A1, Anthrax toxin protective antigen, Anti-transferrin receptor, AOC3 (VAP-1), B7-H3, *Bacillus anthracis* anthrax, BAFF (B-cell activating factor), BCMA, B-lymphoma cell, bcr-abl, Bombesin, BORIS, C5, C242 antigen, CA125 (carbohydrate antigen 125, MUC16), CA-IX (or CAIX, carbonic anhydrase 9), CALLA, CanAg, *Canis lupus familiaris* IL31, Carbonic anhydrase IX, Cardiac myosin, CCL11(C-C motif chemokine 11), CCR4 (C-C chemokine receptor type 4), CCR5, CD3E (epsilon), CEA (Carcinoembryonic antigen), CEACAM3, CEACAM5 (carcino-embryonic antigen), CFD (Factor D), Ch4D5, Cholecystokinin 2 (CCK2R), CLDN18 (Claudin-18), Clumping factor A, cMet, CRIPTO, FCSF1R (Colony stimulating factor 1 receptor), CSF2 (colony stimulating factor 2, Granulocyte-macrophage colony-stimulating factor (GM-CSF)), CSP4, CTLA4 (cytotoxic T-lymphocyte-associated protein 4), CTAA16.88 tumor antigen, CXCR4, C—X—C chemokine receptor type 4, cyclic ADP ribose hydrolase, Cyclin B1, CYP1B1, Cytomegalovirus, Cytomegalovirus glycoprotein B, Dabigatran, DLL3 (delta-like-ligand 3), DLL4 (delta-like-ligand 4), DPP4 (Dipeptidyl-peptidase 4), DR5 (Death receptor 5), *E. coli* shiga toxin type-1, *E. coli* shiga toxin type-2, ED-B, EGFL7 (EGF-like domain-containing protein 7), EGFR, EGFRII, EGFRvIII, Endoglin, Endothelin B receptor, Endotoxin, EpCAM (epithelial cell adhesion molecule), EphA2, Episialin, ERBB2 (Epidermal Growth Factor Receptor 2), ERBB3, ERG (TM-PRSS2 ETS fusion gene), *Escherichia coli*, ETV6-AML, FAP (Fibroblast activation protein alpha), FCGR1, alpha-Fetoprotein, Fibrin II, beta chain, Fibronectin extra domain-B, FOLR (folate receptor), Folate receptor alpha, Folate hydrolase, Fos-related antigen 1F protein of respiratory syncytial virus, Frizzled receptor, Fucosyl GM1, GD2 ganglioside, G-28 (a cell surface antigen glyvolipid), GD3 idiotype, GloboH, Glypican 3, N-glycolylneuraminic acid, GM3, GMCSF receptor a-chain, Growth differentiation factor 8, GP100, GPNMB (Trans-membrane glycoprotein NMB), GUCY2C (Guanylate cyclase 2C, guanylyl cyclase C(GC-C), intestinal Guanylate cyclase, Guanylate cyclase-C receptor, Heat-stable enterotoxin receptor (hSTAR)), Heat shock proteins, Hemagglutinin, Hepatitis B surface antigen, Hepatitis B virus, HER1 (human epidermal growth factor receptor 1), HER2, HER2/neu, HER3 (ERBB-3), IgG4, HGF/SF (Hepatocyte growth factor/scatter factor), HHGFR, HIV-1, Histone complex, HLA-DR (human leukocyte antigen), HLA-DR10, HLA-DRB, HMWMAA, Human chorionic gonadotropin, HNGF, Human scatter factor receptor kinase, HPV E6/E7, Hsp90, hTERT, ICAM-1 (Intercellular Adhesion Molecule 1), Idiotype, IGF1R (IGF-1, insulin-like growth factor 1 receptor), IGHE, IFN-γ, Influenza hemagglutinin, IgE, IgE Fc region, IGHE, interleukins (comprising IL-1, IL-2, IL-3, IL-4, IL-5, IL-6, IL-6R, IL-7, IL-8, IL-9, IL-10, IL-11, IL-12, IL-13, IL-15, IL-17, IL-17A, IL-18, IL-19, IL-20, IL-21, IL-22, IL-23, IL-27, or IL-28), IL31RA, ILGF2 (Insulin-like growth factor 2), Integrins (α4, $α_{IIb}β_3$, αvβ3, $α_4β_7$, α5β1, α6β4, α7β7, αIIβ3, α5β5, αvβ5), Interferon gamma-induced protein, ITGA2, ITGB2, KIR2D, Kappa Ig, LCK, Le, Legumain, Lewis-Y antigen, LFA-1 (Lymphocyte function-associated antigen 1, CD11 a), LHRH, LINGO-1, Lipoteichoic acid, LIV1A, LMP2, LTA, MAD-CT-1, MAD-CT-2, MAGE-1, MAGE-2, MAGE-3, MAGE A1, MAGE A3, MAGE 4, MART1, MCP-1, MIF (Macrophage migration inhibitory factor, or glycosylation-inhibiting factor (GIF)), MS4A1 (membrane-spanning 4-domains subfamily A member 1), MSLN (mesothelin), MUC1 (Mucin 1, cell surface associated (MUC1) or polymorphic epithelial mucin (PEM)), MUC1-KLH, MUC16 (CA125), MCP1(monocyte chemotactic protein 1), MelanA/MART1, ML-IAP, MPG, MS4A1 (membrane-spanning 4-domains subfamily A), MYCN, Myelin-associated glycoprotein, Myostatin, NA17, NARP-1, NCA-90 (granulocyte antigen), Nectin-4 (ASG-22ME), NGF, Neural apoptosis-regulated proteinase 1, NOGO-A, Notch receptor, Nucleolin, Neu oncogene product, NY-BR-1, NY-ESO-1, OX-40, OxLDL (Oxidized low-density lipoprotein), 0Y-TES1, P21, p53 nonmutant, P97, Page4, PAP, Paratope of anti-(N-glycolylneuraminic acid), PAX3, PAX5, PCSK9, PDCD1 (PD-1, Programmed cell death protein 1), PDGF-Ra (Alpha-type platelet-derived growth factor receptor), PDGFR-f3, PDL-1, PLAC1, PLAP-like testicular alkaline phosphatase, Platelet-derived growth factor receptor beta, Phosphate-sodium co-transporter, PMEL 17, Polysialic acid, Proteinase3 (PR1), Prostatic carcinoma, PS (Phosphatidyl-serine), Prostatic carcinoma cells, *Pseudomonas aeruginosa*, PSMA, PSA, PSCA, Rabies virus glycoprotein, RHD (Rh polypeptide 1 (RhPI)), Rhesus factor, RANKL, RhoC, Ras mutant, RGS5, ROBO4, Respiratory syncytial virus, RON, ROR1, Sarcoma translocation breakpoints, SART3, Sclerostin, SLAMF7 (SLAM family member 7), Selectin P, SDC1 (Syndecan 1), sLe(a), Somatomedin C, SIP (Sphingosine-l-phosphate), Somatostatin, Sperm protein 17, SSX2, STEAP1 (six-transmembrane epithelial antigen of the prostate 1), STEAP2, STn, TAG-72 (tumor associated glycoprotein 72), Survivin, T-cell receptor, T cell transmembrane protein, TEM1 (Tumor endothelial marker 1), TENB2, Tenascin C (TN-C), TGF-α, TGF-β (Transforming growth factor beta), TGF-β1, TGF-β2 (Transforming growth factor-beta 2), Tie (CD202b), Tie2, TIM-1 (CDX-014), Tn, TNF, TNF-α, TNFRSF8, TNFRSF10B (tumor necrosis factor receptor superfamily member 10B), TNFRSF-13B (tumor necrosis factor receptor superfamily member 13B), TPBG (trophoblast glycoprotein), TRAIL-R1 (Tumor necrosis apoptosis Inducing ligand Receptor 1), TRAILR2 (Death receptor 5 (DR5)), tumor-associated calcium signal transducer 2, tumor specific glycosylation of MUC1, TWEAK receptor, TYRP1 (glycoprotein 75), TRP-2, Tyrosinase, VCAM-1, VEGF, VEGF-A, VEGF-2, VEGFR-1, VEGFR2, or vimentin, WT1, XAGE 1, or cells expressing any insulin growth factor receptors, or any epidermal growth factor receptors.

10. The composition according to claim 9, wherein the tumor cell is selected from the group consisting of lymphoma cells, myeloma cells, renal cells, breast cancer cells, prostate cancer cells, ovarian cancer cells, colorectal cancer cells, gastric cancer cells, squamous cancer cells, small-cell lung cancer cells, none small-cell lung cancer cells, testicular cancer cells, malignant cells, or any cells that grow and divide at an unregulated, quickened pace to cause cancers.

11. A pharmaceutical composition comprising a therapeutically effective amount of the composition of claim 1, and a pharmaceutically acceptable salt, carrier, diluent, or excipient therefore, or a combination of the conjugates thereof, for the treatment or prevention of a cancer, or an autoimmune disease, or an infectious disease.

12. The pharmaceutical composition according to claim 11, either in a liquid formula or in a formulated lyophilized solid, comprising by weight of: 0.01%-99% of one or more the conjugate compound; 0.0%-20.0% of one or more polyols; 0.0%-2.0% of one or more surfactants; 0.0%-5.0% of one or more preservatives; 0.0%-30% of one or more amino acids; 0.0%-5.0% of one or more antioxidants; 0.0%-0.3% of one or more metal chelating agents; 0.0%-30.0% of one or more buffer salts for adjusting pH of the formulation to pH 4.5 to 7.5; and 0.0%-30.0% of one or more of isotonic agent for adjusting osmotic pressure between about 250 to 350 mOsm when reconstituted for administration to a patient;

- wherein the polyol is selected from fructose, mannose, maltose, lactose, arabinose, xylose, ribose, rhamnose, galactose, glucose, sucrose, trehalose, sorbose, melezitose, raffinose, mannitol, xylitol, erythritol, maltitol, lactitol, erythritol, threitol, sorbitol, glycerol, or L-gluconate and its metallic salts;
- wherein the surfactant is selected from polysorbate 20, polysorbate 40, polysorbate 65, polysorbate 80, polysorbate 81, or polysorbate 85, poloxamer, poly(ethylene oxide)-poly(propylene oxide), polyethylene-polypropylene, Triton; sodium dodecyl sulfate (SDS), sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (lauroamidopropyl); myristamidopropyl-, palmidopropyl-, or isostearamidopropyl-dimethylamine; sodium methyl cocoyl-, or disodium methyl oleyl-taurate; dodecyl betaine, dodecyl dimethylamine oxide, cocamidopropyl betaine and coco ampho glycinate; or isostearyl ethylimidonium ethosulfate; polyethyl glycol, polypropyl glycol, and copolymers of ethylene and propylene glycol;
- wherein the preservative is selected from benzyl alcohol, octadecyldimethylbenzyl ammonium chloride, hexamethonium chloride, benzalkonium chloride, benzethonium chloride, phenol, butyl and benzyl alcohol, alkyl parabens, catechol, resorcinol, cyclohexanol, 3-pentanol, or m-cresol;
- wherein the amino acid is selected from arginine, cystine, glycine, lysine, histidine, ornithine, isoleucine, leucine, alanine, glycine glutamic acid or aspartic acid;
- wherein the antioxidant is selected from ascorbic acid, glutathione, cystine or methionine;
- wherein the chelating agent is selected from EDTA or EGTA;
- wherein the buffer salt is selected from sodium, potassium, ammonium, or trihydroxyethylamino salts of citric acid, ascorbic acid, gluconic acid, carbonic acid, tartaric acid, succinic acid, acetic acid or phthalic acid; Tris or tromethamine hydrochloride, phosphate or sulfate; arginine, glycine, glycylglycine, or histidine with anionic acetate, chloride, phosphate, sulfate, or succinate salts;
- wherein the tonicity agent is selected from mannitol, sorbitol, sodium acetate, potassium chloride, sodium phosphate, potassium phosphate, trisodium citrate, or sodium chloride.

13. The pharmaceutical composition according to claim 11, is packed in a vial, bottle, pre-filled syringe, or pre-filled auto-injector syringe, in a form of a liquid or lyophilized solid.

14. The composition of claim 1, having in vitro, in vivo or ex vivo cell killing activity.

15. The pharmaceutical composition according to claim 11, administered concurrently with a chemotherapeutic agent, a radiation therapy, an immunotherapy agent, an autoimmune disorder agent, an anti-infectious agent or the other conjugates for synergistically treatment or prevention of a cancer, or an autoimmune disease, or an infectious disease.

16. The pharmaceutical composition according to claim 15, wherein the chemotherapeutic agent is selected from:
- (1). A). an alkylating agent: selected from nitrogen mustards: chlorambucil, chlornaphazine, cyclophosphamide, dacarbazine, estramustine, ifosfamide, mechlorethamine, mechlorethamine oxide hydrochloride, mannomustine, mitobronitol, melphalan, mitolactol, pipobroman, novembichin, phenesterine, prednimustine, thiotepa, trofosfamide, uracil mustard; CC-1065 and adozelesin, carzelesin, bizelesin or their synthetic analogues; duocarmycin and its synthetic analogues, KW-2189, CBI-TMI, or CBI dimers; benzodiazepine dimers or pyrrolobenzodiazepine (PBD) dimers, tomaymycin dimers, indolinobenzodiazepine dimers, imidazobenzothiadiazepine dimers, or oxazolidinobenzodiazepine dimers; Nitrosoureas: comprising carmustine, lomustine, chlorozotocin, fotemustine, nimustine, ranimustine; Alkyl sulphonates: including busulfan, treosulfan, improsulfan and piposulfan); Triazenes or dacarbazine; Platinum containing compounds: comprising carboplatin, cisplatin, and oxaliplatin; aziridines, benzodopa, carboquone, meturedopa, or uredopa; ethylenimines and methylamelamines including altretamine, triethylenemelamine, trietylenephosphoramide, triethylenethiophosphoramide and trimethylolomelamine];
- b). A plant alkaloid: selected from the group consisting of *Vinca* alkaloids: including vincristine, vinblastine, vindesine, vinorelbine, and navelbin; Taxoids: comprising paclitaxel, docetaxol and their analogs, Maytansinoids including DM1, DM2, DM3, DM4, DM5, DM6, DM7, maytansine, ansamitocins and their analogs, cryptophycins (including the group of cryptophycin 1 and cryptophycin 8); epothilones, eleutherobin, discodermolide, bryostatins, dolostatins, auristatins, tubulysins, cephalostatins; pancratistatin; a sarcodictyin; spongistatin;
- c). A DNA Topoisomerase Inhibitor: selected from the groups of Epipodophyllins: comprising 9-aminocamptothecin, camptothecin, crisnatol, daunomycin, etoposide, etoposide phosphate, irinotecan, mitoxantrone, novantrone, retinoic acids (or retinols), teniposide, topotecan, 9-nitrocamptothecin or RFS 2000; and mitomycins and their analogs;
- d). An antimetabolite: selected from the group consisting of {[Anti-folate: (DHFR inhibitors: comprising methotrexate, trimetrexate, denopterin, pteropterin, aminopterin (4-aminopteroic acid) or folic acid analogues); IMP dehydrogenase Inhibitors: (including mycophenolic acid, tiazofurin, ribavirin, EICAR); Ribonucleotide reductase Inhibitors: (including hydroxyurea, deferoxamine)]; [Pyrimidine analogs: Uracil analogs: (including ancitabine, azacitidine, 6-azauridine, capecitabine, carmofur, cytarabine, dideoxyuridine, doxifluridine, enocitabine, 5-Fluorouracil, floxuridine, ratitrexed); Cytosine analogs: (including cytarabine, cytosine arabinoside, fludarabine); Purine analogs: (including azathioprine, fludarabine, mercaptopurine, thiamiprine, thioguanine)]; folic acid replenisher, frolinic acid};
- e). A hormonal therapy: selected from Receptor antagonists: [Anti-estrogen: (including megestrol, raloxifene, tamoxifen); LHRH agonists: (including goscrclin, leuprolide acetate); Anti-androgens: (including bicalutamide, flutamide, calusterone, dromostanolone propionate, epitiostanol, goserelin, leuprolide, mepitiostane, nilutamide, testolactone, trilostane and other androgens inhibitors)]; Retinoids/Deltoids: [Vitamin D3 analogs: (including CB 1093, EB 1089 KH 1060, cholecalciferol, ergocalciferol); Photodynamic therapies: (including verteporfin, phthalocyanine, photosensitizer Pc4, demethoxyhypocrellin A); Cytokines: (comprising Interferon-alpha, Interferon-gamma, tumor necrosis factor (TNFs), human proteins containing a TNF domain)] I;

f). A kinase inhibitor, selected from the group consisting of BIBW 2992 (anti-EGFR/Erb2), imatinib, gefitinib, pegaptanib, sorafenib, dasatinib, sunitinib, erlotinib, nilotinib, lapatinib, axitinib, pazopanib. Vandetanib, E7080 (anti-VEGFR2), mubritinib, ponatinib, bafetinib, bosutinib, cabozantinib, vismodegib, iniparib, ruxolitinib, CYT387, axitinib, tivozanib, sorafenib, bevacizumab, cetuximab, Trastuzumab, Ranibizumab, Panitumumab, ispinesib;

g). A poly (ADP-ribose) polymerase (PARP) inhibitors selected from the group of olaparib, niraparib, iniparib, talazoparib, veliparib, CEP 9722, E7016, BGB-290, or 3-aminobenzamide;

h). An antibiotic, selected from the group consisting of an enediyne antibiotic (selected from the group of calicheamicin, calicheamicin yl, 61, al or (31; dynemicin, including dynemicin A and deoxydynemicin; esperamicin, kedarcidin, C-1027, maduropeptin, or neocarzinostatin chromophore and related chromoprotein enediyne antibiotic chromomophores), aclacinomycins, actinomycin, authramycin, azaserine, bleomycins, cactinomycin, carabicin, carminomycin, carzinophilin; chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin and deoxydoxorubicin, epirubicin, eribulin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin;

i). A polyketide (acetogenin), bullatacin and bullatacinone; gemcitabine, epoxomicins andcarfilzomib, bortezomib, thalidomide, lenalidomide, pomalidomide, tosedostat, zybrestat, PLX4032, STA-9090, Stimuvax, allovectin-7, Xegeva, Provenge, Yervoy, Isoprenylation inhibitors and Lovastatin, Dopaminergic neurotoxins andl-methyl-4-phenylpyridinium ion, Cell cycle inhibitors (including staurosporine), Actinomycins (including Actinomycin D, dactinomycin), amanitins, Bleomycins (including bleomycin A2, bleomycin B2, peplomycin), Anthracyclines (including daunorubicin, doxorubicin (adriamycin), idarubicin, epirubicin, pirarubicin, zorubicin, mtoxantrone, MDR inhibitors or verapamil, $Ca^{2+}$ ATPase inhibitors or thapsigargin, Histone deacetylase inhibitors ((including Vorinostat, Romidepsin, Panobinostat, Valproic acid, Mocetinostat (MGCD0103), Belinostat, PCI-24781, Entinostat, SB939, Resminostat, Givinostat, AR-42, CUDC-101, sulforaphane, Trichostatin A); Thapsigargin, Celecoxib, glitazones, epigallocatechin gallate, Disulfiram, Salinosporamide A.; Anti-adrenals, selected from the group of aminoglutethimide, mitotane, trilostane; aceglatone; aldophosphamide glycoside; aminolevulinic acid; amsacrine; arabinoside, bestrabucil; bisantrene; edatraxate; defofamine; demecolcine; diaziquone; eflornithine (DFMO), elfornithine; elliptinium acetate, etoglucid; gallium nitrate; gacytosine, hydroxyurea; ibandronate, lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2, 2',2"-trichlorotriethylamine; trichothecenes (including the group of T-2 toxin, verrucarin A, roridin A and anguidine); urethane, siRNA, antisense drugs;

(2). An anti-autoimmune disease agent: cyclosporine, cyclosporine A, aminocaproic acid, azathioprine, bromocriptine, chlorambucil, chloroquine, cyclophosphamide, corticosteroids (including the group consisting of amcinonide, betamethasone, budesonide, hydrocortisone, flunisolide, fluticasone propionate, fluocortolone danazol, dexamethasone, Triamcinolone acetonide, beclomethasone, dipropionate), DHEA, enanercept, hydroxychloroquine, infliximab, meloxicam, methotrexate, mofetil, mycophenylate, prednisone, sirolimus, tacrolimus;

(3). An anti-infectious disease agent comprising:
a). Aminoglycosides: amikacin, astromicin, gentamicin (netilmicin, sisomicin, isepamicin), hygromycin B, kanamycin (amikacin, arbekacin, bekanamycin, dibekacin, tobramycin), neomycin (framycetin, paromomycin, ribostamycin), netilmicin, spectinomycin, streptomycin, tobramycin, verdamicin;
b). Amphenicols: azidamfenicol, chloramphenicol, florfenicol, thiamphenicol;
c). Ansamycins: geldanamycin, herbimycin;
d). Carbapenems: biapenem, doripenem, ertapenem, imipenem, cilastatin, meropenem, panipenem;
e). Cephems: carbacephem (loracarbef), cefacetrile, cefaclor, cefradine, cefadroxil, cefalonium, cefaloridine, cefalotin or cefalothin, cefalexin, cefaloglycin, cefamandole, cefapirin, cefatrizine, cefazaflur, cefazedone, cefazolin, cefbuperazone, cefcapene, cefdaloxime, cefepime, cefminox, cefoxitin, cefprozil, cefroxadine, ceftezole, cefuroxime, cefixime, cefdinir, cefditoren, cefepime, cefetamet, cefmenoxime, cefodizime, cefonicid, cefoperazone, ceforanide, cefotaxime, cefotiam, cefozopran, cephalexin, cefpimizole, cefpiramide, cefpirome, cefpodoxime, cefprozil, cefquinome, cefsulodin, ceftazidime, cefteram, ceftibuten, ceftiolene, ceftizoxime, ceftobiprole, ceftriaxone, cefuroxime, cefuzonam, cephamycin (including cefoxitin, cefotetan, cefmetazole), oxacephem (flomoxef, latamoxef);
f). Glycopeptides: bleomycin, vancomycin (including oritavancin, telavancin), teicoplanin (dalbavancin), ramoplanin;
g). Glycylcyclines: tigecycline;
h). β-Lactamase inhibitors: penam (sulbactam, tazobactam), clavam (clavulanic acid);
i). Lincosamides: clindamycin, lincomycin;
j). Lipopeptides: daptomycin, A54145, calcium-dependent antibiotics (CDA);
k). Macrolides: azithromycin, cethromycin, clarithromycin, dirithromycin, erythromycin, flurithromycin, josamycin, ketolide (telithromycin, cethromycin), midecamycin, miocamycin, oleandomycin, rifamycins (rifampicin, rifampin, rifabutin, rifapentine), rokitamycin, roxithromycin, spectinomycin, spiramycin, tacrolimus (FK506), troleandomycin, telithromycin;
l). Monobactams: aztreonam, tigemonam;
m). Oxazolidinones: linezolid;

n). Penicillins: amoxicillin, ampicillin, pivampicillin, hetacillin, bacampicillin, metampicillin, talampicillin, azidocillin, azlocillin, benzylpenicillin, benzathine benzylpenicillin, benzathine phenoxymethylpenicillin, clometocillin, procaine benzylpenicillin, carbenicillin (carindacillin), cloxacillin, dicloxacillin, epicillin, flucloxacillin, mecillinam (pivmecillinam), mezlocillin, meticillin, nafcillin, oxacillin, penamecillin, penicillin, pheneticillin, phenoxymethylpenicillin, piperacillin, propicillin, sulbenicillin, temocillin, ticarcillin;

o). Polypeptides: bacitracin, colistin, polymyxin B;

p). Quinolones: alatrofloxacin, balofloxacin, ciprofloxacin, clinafloxacin, danofloxacin, difloxacin, enoxacin, enrofloxacin, floxin, garenoxacin, gatifloxacin, gemifloxacin, grepafloxacin, kano trovafloxacin, levofloxacin, lomefloxacin, marbofloxacin, moxifloxacin, nadifloxacin, norfloxacin, orbifloxacin, ofloxacin, pefloxacin, trovafloxacin, grepafloxacin, sitafloxacin, sparfloxacin, temafloxacin, tosufloxacin, trovafloxacin;

q). Streptogramins: pristinamycin, quinupristin/dalfopristin;

r). Sulfonamides: mafenide, prontosil, sulfacetamide, sulfamethizole, sulfanilimide, sulfasalazine, sulfisoxazole, trimethoprim, trimethoprim-sulfamethoxazole (co-trimoxazole);

s). Steroid antibacterials: selected from fusidic acid;

t). Tetracyclines: doxycycline, chlortetracycline, clomocycline, demeclocycline, lymecycline, meclocycline, metacycline, minocycline, oxytetracycline, penimepicycline, rolitetracycline, tetracycline, glycylcyclines (including tigecycline);

u). Other antibiotics: selected from the group consisting of annonacin, arsphenamine, bactoprenol inhibitors (Bacitracin), DADAL/AR inhibitors (cycloserine), dictyostatin, discodermolide, eleutherobin, epothilone, ethambutol, etoposide, faropenem, fusidic acid, furazolidone, isoniazid, laulimalide, metronidazole, mupirocin, mycolactone, NAM synthesis inhibitors (fosfomycin), nitrofurantoin, paclitaxel, platensimycin, pyrazinamide, quinupristin/dalfopristin, rifampicin (rifampin), tazobactam tinidazole, uvaricin;

(4). Anti-viral drugs comprising:

a). Entry/fusion inhibitors: aplaviroc, maraviroc, vicriviroc, gp41 (enfuvirtide), PRO 140, CD4 (ibalizumab);

b). Integrase inhibitors: raltegravir, elvitegravir, globoidnan A;

c). Maturation inhibitors: bevirimat, vivecon;

d). Neuraminidase inhibitors: oseltamivir, zanamivir, peramivir;

e). Nucleosides &nucleotides: abacavir, aciclovir, adefovir, amdoxovir, apricitabine, brivudine, cidofovir, clevudine, dexelvucitabine, didanosine (ddI), elvucitabine, emtricitabine (FTC), entecavir, famciclovir, fluorouracil (5-FU), 3'-fluoro-substituted 2',3'-dideoxynucleoside analogues (including the group consisting of 3'-fluoro-2',3'-dideoxythymidine (FLT) and 3'-fluoro-2',3'-dideoxyguanosine (FLG), fomivirsen, ganciclovir, idoxuridine, lamivudine (3TC), 1-nucleosides (including the group consisting of β-1-thymidine and β-1-2'-deoxycytidine), penciclovir, racivir, ribavirin, stampidine, stavudine (d4T), taribavirin (viramidine), telbivudine, tenofovir, trifluridine valaciclovir, valganciclovir, zalcitabine (ddC), zidovudine (AZT);

f). Non-nucleosides: amantadine, ateviridine, capravirine, diarylpyrimidines (etravirine, rilpivirine), delavirdine, docosanol, emivirine, efavirenz, foscarnet (phosphonoformic acid), imiquimod, interferon alfa, loviride, lodenosine, methisazone, nevirapine, NOV-205, peginterferon alfa, podophyllotoxin, rifampicin, rimantadine, resiquimod (R-848), tromantadine;

g). Protease inhibitors: amprenavir, atazanavir, boceprevir, darunavir, fosamprenavir, indinavir, lopinavir, nelfinavir, pleconaril, ritonavir, saquinavir, telaprevir (VX-950), tipranavir;

h). anti-virus drugs: abzyme, arbidol, calanolide a, ceragenin, cyanovirin-n, diarylpyrimidines, epigallocatechin gallate (EGCG), foscarnet, griffithsin, taribavirin (viramidine), hydroxyurea, KP-1461, miltefosine, pleconaril, portmanteau inhibitors, ribavirin, seliciclib;

(5). pharmaceutically acceptable salts, acids, derivatives, hydrate or hydrated salt; or a crystalline structure; or an optical isomer, racemate, di astereomer or enantiomer of any of the above drugs.

17. The pharmaceutical composition according to claim 15, comprising a synergistic agent selected from one or several of the following drugs: Abatacept, abemaciclib, Abiraterone acetate, Abraxane, Acetaminophen/hydrocodone, Acalabrutinib, aducanumab, Adalimumab, ADXS31-142, ADXS-HER2, afatinib dimaleate, aldesleukin, alectinib, alemtuzumab, Alitretinoin, ado-trastuzumab emtansine, Amphetamine/dextroamphetamine, anastrozole, Aripiprazole, anthracyclines, Aripiprazole, Atazanavir, Atezolizumab, Atorvastatin, Avelumab, Axicabtagene ciloleucel, axitinib, belinostat, BCG Live, Bevacizumab, bexarotene, blinatumomab, Bortezomib, bosutinib, brentuximab vedotin, brigatinib, Budesonide, Budesonide/formoterol, Buprenorphine, Cabazitaxel, Cabozantinib, capmatinib, Capecitabine, carfilzomib, chimeric antigen receptor-engineered T (CAR-T) cells, Celecoxib, ceritinib, Cetuximab, Chidamide, Ciclosporin, Cinacalcet, crizotinib, Cobimetinib, Cosentyx, crizotinib, CTL019, Dabigatran, dabrafenib, dacarbazine, daclizumab, dacomotinib, daptomycin, Daratumumab, Darbepoetin alfa, Darunavir, dasatinib, denileukin diftitox, Denosumab, Depakote, Dexlansoprazole, Dexmethylphenidate, Dexamethasone, DigniCap Cooling System, Dinutuximab, Doxycycline, Duloxetine, Duvelisib, durvalumab, elotuzumab, Emtricibine/Rilpivirine/Tenofovir, disoproxil fumarate, Emtricitbine/tenofovir/efavirenz, Enoxaparin, ensartinib, Enzalutamide, Epoetin alfa, erlotinib, Esomeprazole, Eszopiclone, Etanercept, Everolimus, exemestane, everolimus, exenatide ER, Ezetimibe, Ezetimibe/simvastatin, Fenofibrate, Filgrastim, fingolimod, Fluticasone propionate, Fluticasone/salmeterol, fulvestrant, gazyva, gefitinib, Glatiramer, Goserelin acetate, Icotinib, Imatinib, Ibritumomab tiuxetan, ibrutinib, idelalisib, ifosfamide, Infliximab, imiquimod, ImmuCyst, Immuno BCG, iniparib, Insulin aspart, Insulin detemir, Insulin glargine, Insulin lispro, Interferon alfa, Interferon alfa-1b, Interferon alfa-2a, Interferon alfa-2b, Interferon beta, Interferon beta 1a, Interferon beta 1b, Interferon gamma-1a, lapatinib, Ipilimumab, Ipratropium bromide/salbutamol, Ixazomib, Kanuma, Lanreotide acetate, lenalidomide, lenaliomide, lenvatinib mesylate, letrozole, Levothyroxine, Levothyroxine, Lidocaine, Linezolid, Liraglutide, Lisdexamfetamine, LN-144, lorlatinib, Memantine, Methylphenidate, Metoprolol, Mekinist, mericitabine/Rilpivirine/Tenofovir, Modafinil, Mometasone, Mycidac-C, Necitumumab, neratinib, Nilotinib, niraparib, Nivolumab, ofatumumab, obinutuzumab, olaparib, Olmesartan, Olmesartan/hydrochlorothiazide, Omalizumab, Omega-3 fatty acid ethyl esters, Oncorine, Oseltamivir, Osimertinib, Oxycodone, palbociclib, Palivizumab, panitumumab, panobinostat, pazopanib, pembrolizumab, PD-1 antibody, PD-L1 antibody, Pemetrexed, pertuzumab, Pneumococcal conjugate vaccine, pomalidomide, Pregabalin, ProscaVax, Propranolol, Quetiapine, Rabeprazole, radium 223 chloride, Raloxifene, Raltegravir, ramucirumab, Ranibizumab, regorafenib, ribociclib, Rituximab, Rivaroxaban, romidepsin, Rosuvastatin, ruxolitinib phosphate, Salbutamol, savolitinib, semaglutide, Sevelamer, Sildenafil, siltuximab, Sipuleucel-T, Sitagliptin, Sitagliptin/metformin, Solifenacin, solanezumab, Sonidegib, Sorafenib, Sunitinib, tacrolimus, tacrimus, Tadalafil, tamoxifen, Tafinlar, Talimogene laherparepvec, talazoparib, Telaprevir, talazoparib, Temozolomide, temsirolimus, Tenofovir/emtricitabine, tenofovir disoproxil fumarate, Testosterone gel, Thalidomide, TICE BCG, Tiotropium bromide, Tisagenlecleucel, toremifene, trametinib, Trastuzumab, Trabectedin (ecteinascidin 743), trametinib, tremelimumab, Trifluridine/tipiracil, Tretinoin, Uro-BCG, Ustekinumab, Valsartan, veliparib, vandetanib, vemurafenib, venetoclax, vorinostat, ziv-aflibercept, Zostavax, and their analogs, derivatives, pharmaceutically acceptable salts, carriers, diluents, or excipients thereof, or a combination above thereof.

18. The composition according to claim 1, wherein the antibody is a single chain antibody, an antibody fragment that binds to a target cell, a monoclonal antibody, a monoclonal antibody fragment that binds to the target cell, a chimeric antibody, a chimeric antibody fragment that binds to the target cell, a domain antibody, a domain antibody fragment that binds to the target cell.

19. The composition according to claim 1, wherein $Y^1$ is N, or $Y^2$, $Y^3$, $Y^4$, $Y^5$, $Y^6$ and $Y^7$ form an aromatic ring of benzene.

20. The composition according to claim 1, wherein the D/T ratio is 3.4 to 3.9.

* * * * *